(12) United States Patent
Michelotti et al.

(10) Patent No.: US 7,741,479 B2
(45) Date of Patent: Jun. 22, 2010

(54) UREA INHIBITORS OF MAP KINASES

(75) Inventors: Enrique Luis Michelotti, Fort Washington, PA (US); Eric Bruce Springman, East Norriton, PA (US); Duyan Nguyen, North Wales, PA (US); Rupa S. Shetty, King of Prussia, PA (US); Younghee Lee, Blue Bell, PA (US); Kristofer Kent Moffett, Blue Bell, PA (US); Jennifer Lee Ludington, Lansdale, PA (US); Ted Tsutomis Fujimoto, Churchville, PA (US); Zenon D. Konteatis, Chatham Twp, NJ (US); Bin Liu, Dayton, NJ (US); Frank Hollinger, Blue Bell, PA (US); Bruce D. Dorsey, Ambler, PA (US)

(73) Assignee: Locus Pharmaceuticals, Inc., Blue Bell, PA (US)

( * ) Notice: Subject to any disclaimer, the term of this patent is extended or adjusted under 35 U.S.C. 154(b) by 866 days.

(21) Appl. No.: 11/295,638

(22) Filed: Dec. 7, 2005

(65) Prior Publication Data
US 2006/0167247 A1 Jul. 27, 2006

Related U.S. Application Data

(60) Provisional application No. 60/633,739, filed on Dec. 7, 2004.

(51) Int. Cl.
C07D 273/06 (2006.01)
(52) U.S. Cl. ............... 540/545; 540/575; 544/59; 544/386; 549/69; 549/70
(58) Field of Classification Search .............. 549/69
See application file for complete search history.

(56) References Cited

U.S. PATENT DOCUMENTS

| | | | |
|---|---|---|---|
| 5,569,654 A | 10/1996 | Armour et al. | |
| 5,599,930 A | 2/1997 | Romero et al. | |
| 5,696,110 A | 12/1997 | Bourrain et al. | |
| 5,763,437 A | 6/1998 | Sato et al. | |
| 5,942,387 A | 8/1999 | Hollinshead | |
| 6,080,763 A | 6/2000 | Regan et al. | |
| 6,187,799 B1 | 2/2001 | Wood et al. | |
| 6,228,881 B1 | 5/2001 | Regan et al. | |
| 6,242,453 B1 | 6/2001 | Cirillo et al. | |
| 6,297,381 B1 | 10/2001 | Cirillo et al. | |
| 6,329,415 B1 | 12/2001 | Cirillo et al. | |
| 6,333,325 B1 | 12/2001 | Cirillo et al. | |
| 6,358,945 B1 | 3/2002 | Breitfelder et al. | |
| 6,372,773 B1 | 4/2002 | Regan | |
| 6,492,393 B1 | 12/2002 | Breitfelder et al. | |
| 6,506,747 B1 | 1/2003 | Betageri et al. | |
| 6,506,748 B2 | 1/2003 | Hickey et al. | |
| 6,525,046 B1 | 2/2003 | Cirillo et al. | |
| 6,627,629 B2 | 9/2003 | Ko et al. | |
| 6,656,933 B2 | 12/2003 | Hickey | |

| | | |
|---|---|---|
| 2003/0069284 A1 | 4/2003 | Keegan et al. |
| 2003/0212070 A1 | 11/2003 | Schwink et al. |
| 2003/0225053 A1 | 12/2003 | Gao et al. |
| 2004/0122235 A1 | 6/2004 | Polisetti et al. |
| 2004/0259912 A1 | 12/2004 | Matsumoto et al. |
| 2005/0239841 A1 | 10/2005 | Browning et al. |
| 2006/0009453 A1 | 1/2006 | Geuns-Meyer et al. |
| 2006/0014761 A1 | 1/2006 | Morgan et al. |
| 2006/0069102 A1 | 3/2006 | Leban et al. |

FOREIGN PATENT DOCUMENTS

| | | | |
|---|---|---|---|
| WO | WO 98/52558 A1 | | 11/1998 |
| WO | WO 98/52559 A1 | | 11/1998 |
| WO | WO 99/32111 | * | 1/1999 |
| WO | WO 99/32110 A1 | | 7/1999 |
| WO | WO 99/32111 A1 | | 7/1999 |

(Continued)

OTHER PUBLICATIONS

Attanasi, O.A., et al., "Conjugated Azoalkenes. Part 12. Synthesis of New 1-Amino0-3-cyanopyrrole, 1,2-Diaminopyrrole and Pyrrolo[2,3-b]pyrrole Derivatives by Reaction of Some Conjugated Azoalkenes with Activated Nitriles," *J. Chem. Soc. Perkin Trans.* 1:1009-1014, Journal of the Chemical Society (1992).

(Continued)

*Primary Examiner*—James O Wilson
*Assistant Examiner*—Brian McDowell
(74) *Attorney, Agent, or Firm*—Pepper Hamilton LLP

(57) ABSTRACT

The present invention is directed to a compound having the formula

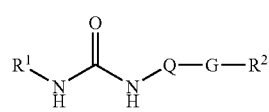

wherein $R^1$, $R^2$, G, and Q are defined herein. The compounds of the present invention are useful as inhibitors of protein kinases such as MAP kinases, in particular p38 kinases. The present invention is also directed to compositions comprising a compound according to the above formula. The compounds and compositions described herein are useful for treating and preventing an inflammatory condition or disease. The present invention is also directed to a method of treating or preventing a protein kinase-mediated condition.

19 Claims, No Drawings

FOREIGN PATENT DOCUMENTS

| | | |
|---|---|---|
| WO | WO 99/32463 A1 | 7/1999 |
| WO | WO 00/41698 A1 | 7/2000 |
| WO | WO 00/43384 A1 | 7/2000 |
| WO | WO 00/55139 A3 | 9/2000 |
| WO | WO 00/55152 * | 9/2000 |
| WO | WO 00/55152 A1 | 9/2000 |
| WO | WO 01/36403 A1 | 5/2001 |
| WO | 02/14311 A2 | 2/2002 |
| WO | WO 02/083628 A1 | 10/2002 |
| WO | WO 02/083642 A1 | 10/2002 |
| WO | WO 02/085859 A1 | 10/2002 |
| WO | WO 02/092576 A1 | 11/2002 |
| WO | WO 02/096876 A1 | 12/2002 |
| WO | WO 02/098869 A2 | 12/2002 |
| WO | WO 03/005999 A2 | 1/2003 |
| WO | WO 03/049742 A1 | 6/2003 |
| WO | WO 03/068229 A1 | 8/2003 |
| WO | WO 03/068746 A1 | 8/2003 |
| WO | WO 2004/056827 A2 | 7/2004 |
| WO | WO 2004/060305 A2 | 7/2004 |
| WO | WO 2004/060305 A3 | 7/2004 |
| WO | WO 2004/060306 A2 | 7/2004 |
| WO | WO 2004/060306 A3 | 7/2004 |
| WO | WO 2004/061084 A2 | 7/2004 |
| WO | WO 2004/061084 A3 | 7/2004 |
| WO | WO 2004/089929 A1 | 10/2004 |
| WO | WO 2004/111009 A1 | 12/2004 |
| WO | WO 2005/014554 A1 | 2/2005 |
| WO | WO 2005/023761 A2 | 3/2005 |
| WO | WO 2005/023761 A3 | 3/2005 |
| WO | 2006/018662 A2 | 2/2006 |
| WO | 2006/062982 A2 | 6/2006 |
| WO | 2006/078610 A1 | 7/2006 |

OTHER PUBLICATIONS

Burak, K., and Machon, Z., "Synthesis of isothiazole derivatives with potential biological activity," *Pharmazie* 47:492-495, Govi-Verlag, Pharmazeutischer Verlag GmbH (1992).

Watt, A.P., et al., "Use of chiral liquid chromatography—tandom mass spectrometry to investigate the metabolism of racemic cholecystokinin-B antagonists," *J. Chromatogr. A* 896:217-227, Elsevier Science B.V. (2000).

Search results of STN CHEMCATS Database, May 15, 2006 (American Chemical Society).

P38 Drug Discovery Program, Locus Pharmaceuticals, Nov. 2, 2004.

Wilson, K.P., et al., "Crystal Structure of p38 Mitogen-activated Protein Kinase," *J. Biol. Chem.* 44:27696-27700, American Society for Biochemistry & Molecular Biology, Inc. (1996).

Co-pending U.S. Appl. No. 11/295,433, inventors Michelotti, E.L., et al., filed Dec. 7, 2005 (Not Published).

Co-pending U.S. Appl. No. 11/649,363, inventors Michelotti, E.L., et al., filed Jan. 4, 2007 (Not Published).

Form PCT/ISA/220, Written Opinion and ISR from PCT/US2009/053959, Jan. 12, 2010.

* cited by examiner

UREA INHIBITORS OF MAP KINASES

The application claims the benefit of U.S. Provisional Application No. 60/633,739, filed Dec. 7, 2004, which is herein incorporated by reference in its entirety.

BACKGROUND OF THE INVENTION

1. Field of the Invention

The present invention relates to novel urea compounds of Formula I, compositions comprising said compounds, and the use of a compound of Formula I to treat a protein kinase-mediated disease or inhibit a protein kinase.

2. Background Art

Intracellular signal transduction is the means by which cells respond to extracellular stimuli. Protein kinases are involved in signal transduction. Protein kinases are usually categorized into five classes with the two major classes being, tyrosine kinases and serine/threonine kinases. For many biological responses, multiple intracellular kinases are involved, and an individual kinase can be involved in more than one signaling event. These kinases are often cytosolic and can translocate to the nucleus or the ribosomes where they can affect transcriptional and translational events, respectively.

Overproduction of cytokines such as interleukin-1 (IL-1) and tumor necrosis factor-alpha (TNF-α) is implicated in a wide variety of inflammatory diseases, including rheumatoid arthritis (RA), psoriasis, multiple sclerosis, inflammatory bowel disease, endotoxin shock, osteoporosis, Alzheimer's disease, and congestive heart failure, among others (see, e.g., Henry et al., *Drugs Future*, 24:1345-1354 (1999) Salituro et al., *Curr. Med. Chem.*, 6:807-823 (1999)). There is convincing evidence in human patients that protein antagonists of cytokines, such as, for example, monoclonal antibody to TNF-α, soluble TNF-α receptor-Fc fusion protein (etanercept, or Enbrel®) and IL-1 receptor antagonists, can provide effective treatment for chronic inflammatory diseases.

TNF-α is a protein whose synthesis occurs in many cell types in response to an external stimulus, such as, for example, a mitogen, an infectious organism, or trauma. Signaling from the cell surface to the nucleus proceeds via several intracellular mediators including kinases that catalyze phosphorylation of proteins downstream in the signaling cascade. Important mediators for the production of TNF-α include the mitogen-activated protein (MAP) kinases, and in particular, p38 kinase.

p38 kinases are activated in response to various stress stimuli, including, but not limited to, proinflammatory cytokines, endotoxin, ultraviolet light, and osmotic shock. Four isoforms of p38 have been described. The α and β forms are expressed in inflammatory cells and are considered to be key mediators of TNF-α production. Inhibition of the enzymes p38α and β in cells results in reduced levels of expression of TNF-α, and such inhibitors are effective in animal models of inflammatory disease.

Small molecule inhibitors of p38 are expected to have several advantages over protein inhibitors of TNF-α or IL-1. p38 inhibitors can not only block the production of TNF-α and IL-1, but can also directly interfere with many of their secondary biological effects. In addition, small molecule inhibitors are unlikely to induce immune reactions commonly associated with the administration of proteins. A small molecule inhibitor of p38 would have less chance of being inactivated after oral administration; a major drawback of peptides is their degradation upon oral administration. Thus, there remains a need for compounds which are inhibitors of a p38 kinase, in particular a p38α kinase.

SUMMARY OF THE INVENTION

A first aspect of the present invention is directed to a novel compound of Formula I.

A second aspect of the present invention is directed to a composition comprising a compound of Formula I and a suitable carrier or excipient.

A third aspect of the present invention is directed to a method of treating, inhibiting, or preventing an inflammatory, said method comprising administering to a subject in need thereof an effective amount of a compound of Formula I.

A fourth aspect of the present invention is directed to a method of inhibiting or modulating the activity of a p38 MAP kinase, comprising contacting the p38 MAP kinase with a compound of Formula I.

A fifth aspect of the present invention is directed to a method of treating, inhibiting, or preventing a p38-mediated condition, comprising administering to a patient in need thereof an effective amount of a compound of Formula I.

A sixth aspect of the present invention is directed to the use of a compound of Formula I for preparing a pharmaceutical composition to be used for inhibiting or modulating p38, for treating or preventing an inflammatory condition or disease, or for treating or preventing a p38-mediated condition.

A seventh aspect of the present invention is directed to a method of selectively inhibiting p38.

A eighth aspect of the present invention is directed to a method of preparing a compound of Formula I.

DETAILED DESCRIPTION OF THE INVENTION

The present invention provides novel compounds that are potent and selective inhibitors of p38 MAP kinase, including p38α, and, as such, are also potent inhibitors of TNF-α expression in human cells. Compounds of the present invention are useful in the treatment of p38 and TNF-α expression-mediated inflammatory and other disorders, including, but not limited to, bone resorption, graft vs. host reaction, atherosclerosis, arthritis, osteoarthritis, rheumatoid arthritis, gout, psoriasis, topical inflammatory disease states, adult respiratory distress syndrome, asthma, chronic pulmonary inflammatory disease, chronic obstructive pulmonary disorder, cardiac reperfusion injury, renal reperfusion injury, thrombus, glomerulonephritis, Crohn's disease, ulcerative colitis, inflammatory bowel disease, multiple sclerosis, endotoxin shock, osteoporosis, Alzheimer's disease, congestive heart failure, allergy, cancer, and cachexia.

A first aspect of the present invention is directed to a compound of Formula I:

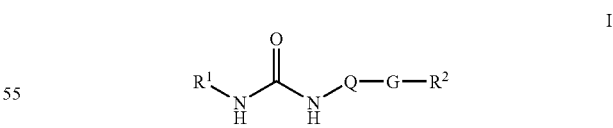

or a pharmaceutically acceptable salt thereof, wherein $R^1$ is aryl or heteroaryl, each of which is optionally substituted with one or more $R^3$ groups; ar($C_{1-3}$)alkyl; or $C_{1-4}$ alkyl;

Q is a diradical of phenyl or a 5 or 6-membered heteroaryl group, each of which is optionally substituted with one or more of $R^4$ and $R^5$;

G is a linker substituted from the group consisting of optionally substituted $C_{1-3}$ alkylene, —$CH_2NH$—, and a single bond;

$R^2$ is

or

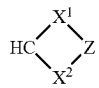

wherein $X^1$ and $X^2$ are independently $(CR^6R^7)_n$, wherein n is independently at each occurrence 1, 2, or 3; and Z is —$NR^8$—, —$NR^8$—S(O)$_2$—, —$NR^8$C(O)—, —S—, —S(O)—, —S(O)$_2$—, or —C(O)—; or $R^2$ is selected from the group consisting of —N(CH$_2$)$_m$—S—(CH$_2$)$_p$—CH$_3$, —(CH$_2$)$_m$—S(O)—(CH$_2$)$_p$—CH$_3$, —(CH$_2$)$_m$—S(O)$_2$—(CH$_2$)$_p$—CH$_3$, and C$_{1-6}$ alkyl-C(O)O—C$_{1-6}$ alkyl, wherein is m is an integer from 1 to 3 and p is 0 or an integer from 1 to 3; or $R^2$ is heteroarylamino or heteroarylalkylamino;

$R^3$ is independently C$_{1-4}$ alkyl, halogen, hydroxy, alkoxy, amino, C$_{1-4}$ alkylamino, di(C$_{1-4}$)alkylamino, optionally substituted phenyl, optionally substituted phenoxy, C$_{1-4}$ haloalkyl, CONR$^a$R$^b$, or COOR$^a$, wherein R$^a$ and R$^b$ are independently H or C$_{1-4}$ alkyl;

$R^4$ is independently C$_{3-10}$ alkyl or C$_{3-10}$ haloalkyl, each of which is optionally substituted with one to three phenyl groups; C$_{3-7}$ cycloalkyl, which is optionally substituted with one or more C$_{1-3}$ alkyl, halogen, hydroxy, oxo, or thioketo; C$_{3-10}$ optionally substituted cycloheteroalkyl; C$_{3-10}$ branched alkenyl which may optionally be partially or fully halogenated, and which is optionally substituted with one to three C$_{1-5}$ alkyl or a phenyl group; C$_{5-7}$ cycloalkenyl optionally substituted with one to three C$_{1-3}$ alkyl groups; cyano; or C$_{1-4}$ alkoxycarbonyl;

$R^5$ is hydrogen, alkyl, halogen, hydroxy, alkoxy, amino, alkylamino, dialkylamino, phenyl, or substituted phenyl;

$R^6$ and $R^7$ are independently at each occurrence hydrogen, C$_{1-4}$ alkyl, halogen, amino, C$_{1-4}$ alkylamino, C$_{1-4}$ hydroxyalkyl, NH—CO—(C$_{1-4}$)alkyl, —COO—(C$_{1-4}$)alkyl, —CONH$_2$, —CONH—(C$_{1-4}$)alkyl, —CH$_2$NH$_2$, —CH$_2$NH—(C$_{1-4}$)alkyl, CH$_2$NH—CO—(C$_{1-4}$)alkyl, CH$_2$COOH, CH$_2$COO—(C$_{1-4}$)alkyl, —C$_{1-4}$alkyl(C$_{6-10}$)aryl, or —C$_{1-4}$alkyl(5-6 membered)heteroaryl;

$R^6$ and $R^7$ together form a C$_{3-5}$ cycloalkyl group;

$R^8$ is a moiety having a molecular weight from about 1 to about 350.

In one embodiment, the present invention is directed to a compound according to Formula I wherein $R^1$ is phenyl, naphthyl, quinolinyl, isoquinolinyl, tetrahydronaphthyl, tetrahydroquiolinyl, tetrahydroisoquinolinyl, benzimidazolyl, benzofuranyl, benzodioxolyl, benzoxazolyl, pyrazolyl, pyridinyl, indanyl, indenyl, indazolyl, or indolyl, each of which is optionally substituted with one or more R$^3$ groups; ar(C$_{1-3}$)alkyl; or C$_{1-4}$ alkyl;

Q is a diradical of 5-membered heteroaryl optionally substituted with one or more of R$^4$ and R$^5$;

G is a linker substituted from the group consisting of optionally substituted C$_{1-3}$ alkylene and a single bond;

$R^2$ is

or

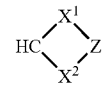

wherein $X^1$ and $X^2$ are independently $(CR^6R^7)_n$, wherein n is independently at each occurrence 1, 2, or 3; and Z is —HN—S(O)$_2$—, —NR$^8$C(O)—, —S—, —S(O)—, —S(O)$_2$—, or —C(O)—; or $R^2$ is selected from the group consisting of —N(CH$_2$)$_m$—S—(CH$_2$)$_p$—CH$_3$, —(CH$_2$)$_m$—S(O)—(CH$_2$)$_p$—CH$_3$, and —(CH$_2$)$_m$—S(O)$_2$—(CH$_2$)$_p$—CH$_3$, wherein is m is an integer from 1 to 3 and p is 0 or an integer from 1 to 3; or $R^2$ is heteroarylamino or heteroarylalkylamino;

$R^3$ is independently C$_{1-2}$ alkyl, halogen, hydroxy, alkoxy, amino, C$_{1-2}$ alkylamino, dialkylamino, optionally substituted phenyl, or optionally substituted phenoxy;

$R^4$ is independently C$_{3-10}$ alkyl or C$_{3-10}$ haloalkyl, each of which is optionally substituted with one to three phenyl groups; C$_{3-7}$ cycloalkyl, which is optionally substituted with one or more C$_{1-3}$ alkyl, halogen, hydroxy, oxo, or thioketo; C$_{3-10}$ optionally substituted cycloheteroalkyl; C$_{3-10}$ branched alkenyl which may optionally be partially or fully halogenated, and which is optionally substituted with one to three C$_{1-5}$ alkyl or a phenyl group; C$_{5-7}$ cycloalkenyl optionally substituted with one to three C$_{1-3}$ alkyl groups; cyano; or C$_{1-4}$ alkoxycarbonyl;

$R^5$ is alkyl, halogen, hydroxy, alkoxy, amino, alkylamino, dialkylamino, phenyl, or substituted phenyl;

$R^6$ and $R^7$ are independently at each occurrence hydrogen, C$_{1-4}$ alkyl, halogen, amino, C$_{1-4}$ alkylamino, NH—CO—(C$_{1-4}$) alkyl, COO—(C$_{1-4}$)alkyl, CONH$_2$, CONH—(C$_{1-4}$) alkyl, CH$_2$NH$_2$, CH$_2$NH—(C$_{1-4}$)alkyl, CH$_2$NH—CO—(C$_{1-4}$) alkyl, or CH$_2$OH; and $R^8$ is selected from the group consisting of H, C$_{1-6}$ alkyl In one embodiment, the present invention is directed to a compound of Formula I, wherein $R^1$ is phenyl, naphthyl, quinolinyl, isoquinolinyl, tetrahydronaphthyl, tetrahydroquiolinyl, tetrahydroisoquinolinyl, benzimidazolyl, benzofuranyl, benzodioxolyl, benzoxazolyl, pyrazolyl, pyridinyl, indanyl, indenyl, indazolyl, or indolyl, each of which is optionally substituted with one or more R$^3$ groups, In another embodiment, $R^1$ is phenyl substituted with one or more halogens. In another embodiment, $R^1$ is phenyl substituted in the 4 position. In another embodiment, $R^1$ is 4-bromophenyl, 4-chlorophenyl, or 4-fluorophenyl. Other examples of substituted phenyl are disclosed herein.

In another embodiment, $R^1$ is naphthyl substituted with an electron withdrawing group in the 4 position. In other embodiments, $R^1$ is selected from the group consisting of naphthyl substituted with a halogen, preferably in the 4-position; naphthyl substituted with a cyano, preferably in the 4-position; naphthyl substituted with a hydroxy or $C_{1-6}$ alkoxy, preferably in the 4-position; and 2-naphthyl.

In another embodiment, $R^1$ is quinolinyl or isoquinolinyl, each of which is optionally substituted with one or more of halogen, cyano, alkoxy, and hydroxy. In other embodiments, $R^1$ is quinolinyl or isoquinolinyl substituted with an electron withdrawing group, preferably in the 4 position.

In another embodiment, $R^1$ is methyl, ethyl, or propyl.

In another embodiment, $R^1$ is a 2-phenylisopropyl, or phenylcycloalkyl group.

In another embodiment, $R^1$ is pyridyl, optionally substituted with one or two $C_{1-4}$ alkyl groups, for example 4-pyridyl, or 2,6-dimethyl-4-pyridyl. Alternatively, $R^1$ is pyridyl substituted with a halogen, for example, chloro, such as 2-chloro-3-pyridyl.

Suitable values of $R^1$ include 4-chlorophenyl, 4-phenoxyphenyl, 1-naphthyl, 2-naphthyl, 1-(4-cyano)naphthyl, 1-(4-chloro)naphthyl, 1-(4-bromo)naphthyl, 1-(4-hydroxy)naphthyl, 4-quinolinyl, 8-quinolinyl, 1-indanyl, 7-(1H-indazolyl), 2-oxo-1,2,3,4-tetrahydroquinolin-7-yl, and 3H-benzimidazol-4-yl.

Other suitable values of $R^1$ include 3-indolyl, 2,3-dichlorophenyl, 3-chlorophenyl, 4-cyano-1-napthyl, 5-benzo[1,3]dioxyl, 2,2-difluoro-5-benzo[1,3]dioxyolyl, 4-cyano-3-chlorophenyl, 3,4-dichlorophenyl, 1-hydroxyisoquinolin-4-yl, 2-trifluoromethyl-4-cyano-phenyl, 3-trifluoromethyl-4-cyanophenyl, 3-methylphenyl, 3,5-dichlorophenyl, 1-methyl-1H-pyrazol-3-yl, 2,6-dimethyl-4-pyridyl, 5-benzoxazolyl, 6-benzoxazolyl, 2-chloro-4-cyanophenyl, and 4-methoxy-3-chlorophenyl.

Other suitable $R^1$ groups include 2,3,4-trichlorophenyl; 2,3-dichloro-4-hydroxyphenyl; 2,3-dichloro-4-methoxyphenyl; 1-naphthyl; 2,3-dichloro-4-fluorophenyl; 4-cyano-1-naphthyl; 2,3-dichloro-4-cyanophenyl; 2,3-dichloro-4-difluoromethoxyphenyl; 2,3-dichloro-4-methoxycarbonylphenyl; 2-chloro-4-fluorophenyl; 2,4-dichlorophenyl; 3-chloro-2-methylphenyl; 2-chloro-3,4-difluorophenyl; 3-chloro-2-methoxyphenyl; 3-fluoro-2-methylphenyl; 2-tert-butylphenyl; 2-methoxyphenyl; 4-fluorophenyl; 5-chlorobenzo[d][1,3]dioxol-4-yl; 2-ethylphenyl; 2-bromophenyl; 2-isopropylphenyl; 2-trifluoromethoxyphenyl; 2-iodophenyl; 2-trifluoromethylphenyl; 2-chlorophenyl; 2-chloro-3-methylphenyl; and 2-chloro-3-methoxyphenyl.

In each of the above embodiments, Q can be pyrrole, pyrazole, imidazole, oxazole, thiazole, furan, or thiophene, each of which is optionally substituted with one or more of $R^4$ and $R^5$. For example, in each of the above embodiments, Q is selected from the group consisting of thienyl, pyrazolyl, and thiazolyl, each of which is optionally substituted with one or more of $R^4$ and $R^5$. In certain embodiments, the 5-membered heterocycle is substituted with a $C_{1-5}$ alkyl group, preferably a tert-butyl group. Other substituents include, but are not limited to methyl, ethyl, and isopropyl.

In other embodiments, Q is a thienyl group in which the urea is bonded to the 2 position and G is bonded to the three position. Alternatively, Q is a thienyl group in which the urea is bonded to the 3 position and G is bonded to the 2 position.

In another embodiment, Q is a pyrazolyl group in which the urea is bonded to the 3 position and G is bonded to the 2 position.

In another embodiment, Q is a thiazolyl group in which the urea is bonded to the 5 position and G is bonded to the 4 position.

In another embodiment, Q is phenyl, optionally substituted a group selected from $C_{1-4}$ alkyl, $C_{1-4}$ haloalkyl, $C_{1-4}$ alkoxy, and halogen.

In one embodiment, $R^2$ is

In another embodiment, $R^2$ is

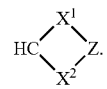

In other suitable embodiments, $X^1$ and $X^2$ are both unsubstituted $C_{1-3}$ alkylene groups. In other embodiments, $X^1$ and $X^2$ are both unsubstituted ethylene.

Suitable values of $R^2$ include morpholinyl, thiomorpholinyl, oxothiomorpholinyl, dioxothiomorpholinyl, oxopiperazinyl, oxodiazepanyl, and dioxothiadiazepanyl. Other suitable groups include, but are not limited to, 1-oxothiomorpholinyl, 1,1-dioxothiomorpholinyl, 4-morpholinyl, 3-oxopiperazinyl, 5-oxo-1,4-diazepanyl, and 1,1-dioxo[1,2,5]thiadiazepanyl.

Other suitable $R^2$ groups include:

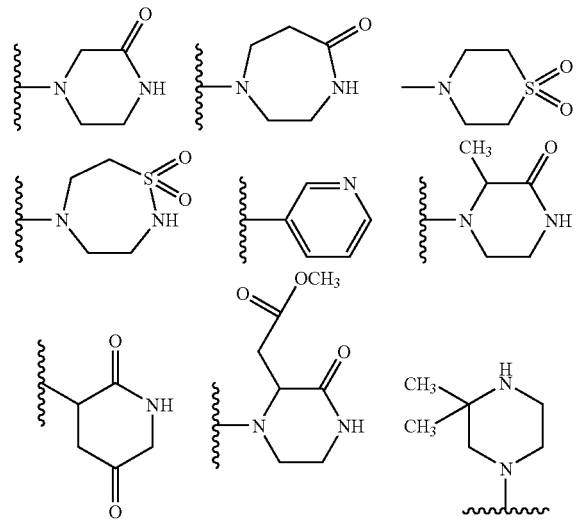

Other suitable $R^2$ groups include:

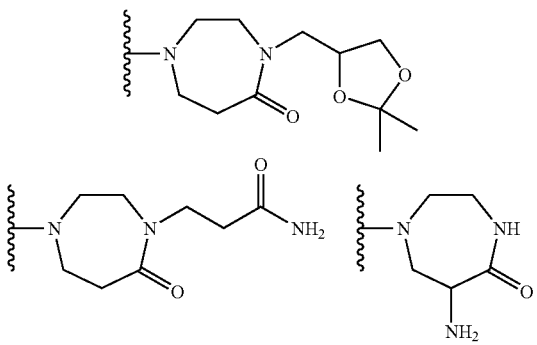

-continued
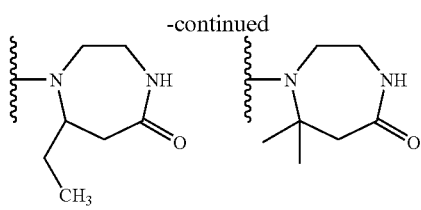
Other suitable R² groups include:
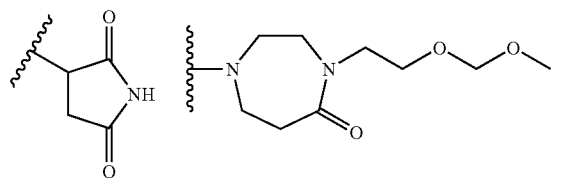
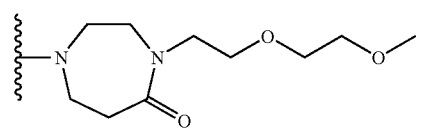
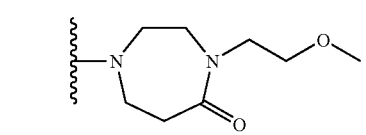
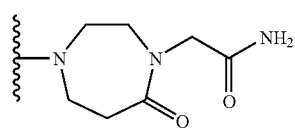
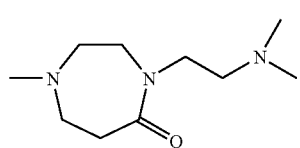
Other suitable R² groups include
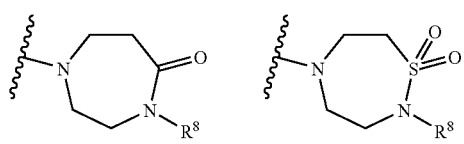
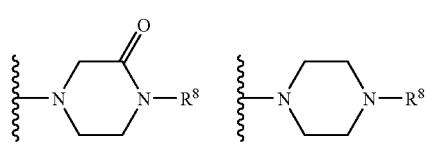
wherein R⁸ is as defined above.
In another embodiment, R² together with Q and G form
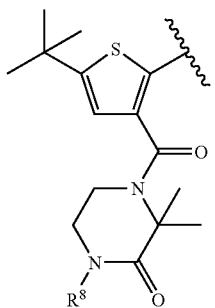 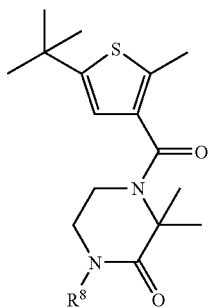
wherein R⁸ is as defined above, for example H.
In another embodiment, Q, together with G and R², forms a from the following:
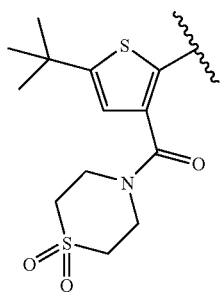 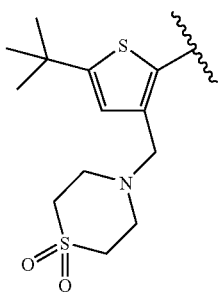
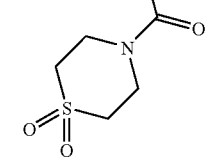 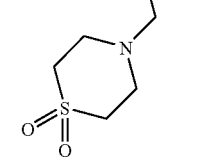
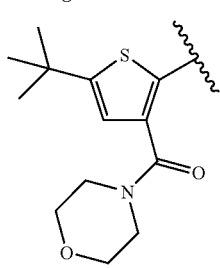 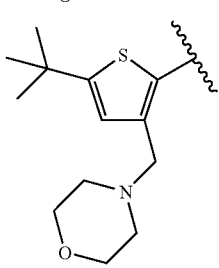
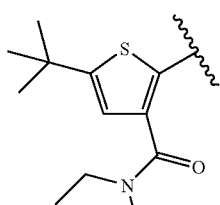 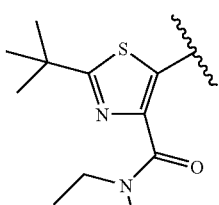
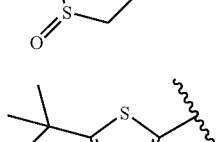 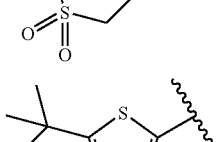
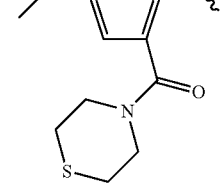 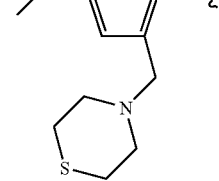

-continued

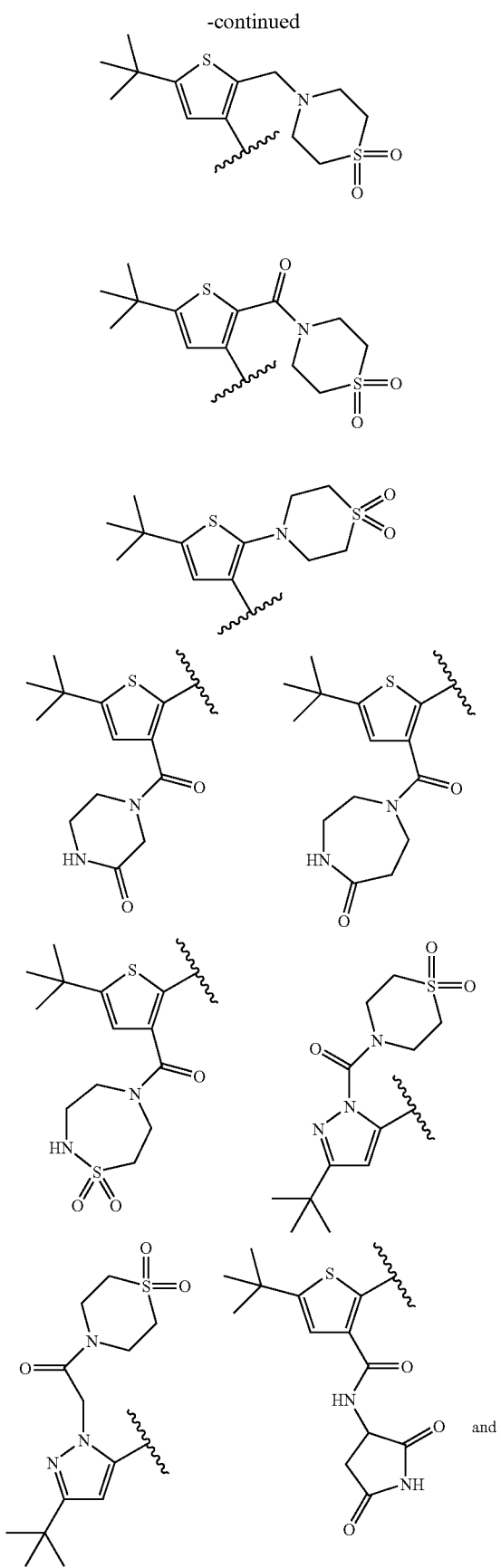

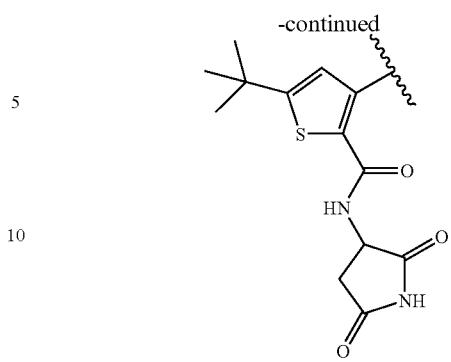

and

In one embodiment, the present invention is directed to a compound of Formula I, wherein $R^3$ is cyclopropyl, cyclobutyl, cyclopentanyl, cyclohexanyl, cycloheptanyl, bicyclopentanyl, bicyclohexanyl and bicycloheptanyl, each of which is optionally substituted.

Suitable values of $R^3$ include cyclopentenyl, cyclohexenyl, cyclohexadienyl, cycloheptenyl, cycloheptadienyl, bicyclohexenyl and bicycloheptenyl, each of which is optionally substituted with one to three $C_{1-3}$ alkyl groups.

In one embodiment, the present invention is directed to a compound of Formula I, wherein G is a single bond. In another embodiment, G is a $C_{1-3}$ unsubstituted alkylene group. In another embodiment, G is a $C_{1-3}$ alkylene linker substituted with an oxo group. Suitable linkers for G include, but not limited to, $CH_2$, $CH_2CH_2$, $C(O)$, $CH_2C(O)$, and $C(O)CH_2$.

In one embodiment, $R^4$ is selected from the group consisting of cyano, $C_{3-10}$ alkyl, and $C_{3-10}$ haloalkyl. Other suitable examples of $R^4$ groups include methoxycarbonyl, ethoxycarbonyl, and propoxycarbonyl.

In one embodiment, $R^5$ is $C_{1-6}$ alkyl. In another embodiment, $R^5$ is $C_{1-6}$ alkoxy. In another embodiment, $R^5$ is $C_{1-6}$ alkylamino or $C_{1-6}$ dialkyamino. In another embodiment, $R^5$ is phenyl, optionally substituted with 1 or 2 substituents selected from the group consisting of $C_{1-4}$ alkyl, hydroxy, amino, and $C_{1-4}$ alkoxy.

In one embodiment, the present invention is directed to a compound of Formula I, wherein $R^6$ and $R^7$ are independently $C_{1-4}$ alkyl, amino, $C_{1-4}$alkylamino, NH—CO—$C_{1-4}$alkyl, COO—$C_{1-4}$alkyl, $CONH_2$, CONH—$C_{1-4}$alkyl, $CH_2NH_2$, $CH_2NH$—$C_{1-4}$alkyl, $CH_2NH$—CO—$C_{1-4}$alkyl, and $CH_2OH$.

In another embodiment, the present invention is directed to a compound of Formula I, wherein $R^6$ and $R^7$ are independently $C_{1-6}$alkoxycarbonyl($C_{1-4}$)alkyl, such as —$CH_2COOCH_3$.

In another embodiment, $R^6$ and $R^7$ are both hydrogen. Alternatively, in another embodiment, at least one occurrence of $R^6$ is methyl. Other suitable $R^6$ and $R^7$ groups include ethyl and propyl.

Alternatively, $R^6$ and $R^7$ together form a 3-6 membered cycloalklyl ring, such as cyclopropyl, cyclobutyl, and cyclopentyl, with the resulting $R^2$ ring being a spiro ring system.

In one embodiment, $R^8$ is a moiety having a molecular weight from about 1 to about 350. The moiety is generally an organic moiety containing one or more carbon atoms. Of course, however, $R^8$ does include hydrogen. Alternatively, the moiety of $R^8$ is one selected from moieties having a molecular weight from about 1 to about 300, from about 1 to about 250, from about 1 to about 150, and from about 1 to about 100. In other embodiments, $R^8$ is a moiety having a molecular weight from about 100 to about 300, or from about 100 to about 200.

Any of the $R^8$ groups listed above can be hydrophobic in nature or hydrophilic in nature. For example, in one embodiment, $R^8$ is a hydrophilic group having a molecular weight of about 50 to about 300, or alternatively a hydrophobic group having a molecular weight of about 50 to about 300.

The $R^8$ moiety can contain one or more standard functional groups. Such functional groups include but are not limited to basic and acidic groups, and more specifically amino, hydroxy, carboxy, and the like. For example, in certain embodiments, $R^8$ is a moiety having at least one functional group that has a pKa of less than 7, preferably less than 5. In other embodiments, $R^8$ is a moiety having at least one functional group that has a pKa of greater than 7, preferably greater than 9. The $R^8$ moiety may also or alternatively contain one or more substituents selected from the group consisting of one or more halo, hydroxy, carboxyl, amino, nitro, cyano, $C_{1-6}$ acylamino, $C_{1-6}$ acyloxy, $C_{1-6}$ alkoxy, aryloxy, alkylthio, $C_{6-10}$ aryl, $C_{4-7}$ cycloalkyl, $C_{2-6}$ alkenyl, $C_{2-6}$ alkynyl, $C_{6-10}$ aryl($C_{2-6}$)alkenyl, $C_{6-10}$ aryl($C_{2-6}$)alkynyl, saturated and unsaturated heterocyclic, or heteroaryl.

Optional substituents on the aryl, arylalkyl and heteroaryl groups of $R^8$ include one or more halo, $C_{1-6}$ haloalkyl, $C_{6-10}$ aryl, heteroaryl, $C_{4-7}$ cycloalkyl, $C_{1-6}$ alkyl, $C_{2-6}$ alkenyl, $C_{2-6}$ alkynyl, $C_{6-10}$ aryl($C_{1-6}$)alkyl, $C_{6-10}$ aryl($C_{2-6}$)alkenyl, $C_{6-10}$ aryl($C_{2-6}$)alkynyl, $C_{1-6}$ hydroxyalkyl, nitro, amino, ureido, cyano, $C_{1-6}$ acylamino, hydroxy, thiol, $C_{1-6}$ acyloxy, azido, $C_{1-6}$ alkoxy, carboxy, ($C_{1-6}$)alkylsulfonyl and ($C_{1-6}$)alkylcarboxylate.

In another embodiment, $R^8$ is a group having a molecular weight of about 80 to about 250, preferably from about 80 to about 200, and containing an aryl, such as a phenyl group.

In another embodiment, $R^8$ is a group having a molecular weight of about 80 to about 250, preferably from about 80 to about 200, and containing a tetrazole group.

In another embodiment, $R^8$ is a group having a molecular weight of about 80 to about 250, preferably from about 80 to about 200, and containing a morpholine group.

In another embodiment, $R^8$ is a group having a molecular weight of about 15 to about 250, preferably from about 80 to about 200, and containing a piperazine group.

In another embodiment, $R^8$ is a group having a molecular weight of about 15 to about 250, preferably from about 80 to about 200, and containing a pyrrolidine group.

In another embodiment, $R^8$ is a group having a molecular weight of about 60 to about 250, preferably from about 80 to about 200, and containing a pyrrolidine group and an amide group.

In another embodiment, $R^8$ is a group having a molecular weight of about 15 to about 250, preferably from about 50 to about 200, and containing an amide group.

In another embodiment, $R^8$ is a group having a molecular weight of about 40 to about 250, preferably from about 50 to about 200, and containing an alkoxyamide group.

In another embodiment, $R^8$ is a group having a molecular weight of about 40 to about 250, preferably from about 50 to about 200, and containing a hydroxyamide group.

In another embodiment, $R^8$ is a group having a molecular weight of about 15 to about 250, preferably from about 50 to about 200, and containing a carboxy group In another embodiment, $R^8$ is a group having a molecular weight of about 45 to about 250, preferably from about 50 to about 200, and containing a 1,2-diol group.

In another embodiment, $R^8$ is a group having a molecular weight of about 15 to about 250, preferably from about 80 to about 200, and containing an ($C_{1-4}$)alkoxy($C_{1-4}$)alkoxy group.

More specific moieties from which $R^8$ can be selected include $C_{1-4}$ alkyl, $C_{1-4}$ alkenyl, or $C_{1-4}$ alkynyl, each of which is optionally substituted with one or more of hydroxy, halogen, halogen, hydroxy, cyano, amino, mono($C_{1-6}$)alkylamino, di($C_{1-6}$)alkylamino, $C_{1-6}$ alkoxy, aminocarbonyl, $C_{1-6}$ alkylaminocarbonyl, $C_{6-10}$ arylaminocarbonyl, aralkylaminocarbonyl, $C_{1-6}$ alkylcarbonylamino, arylcarbonylamino, and aralkylcarbonylamino, $C_{1-6}$ cycloalkyl, 3-7 membered cycloheteroalkyl, hydroxy($C_{1-6}$)alkyl, nitro, aminoalkyl, monoalkylaminoalkyl, dialkylaminoalkyl, formylamino, ($C_{1-6}$)alkylcarbonylamino, carboxy, ($C_{1-6}$)alkoxycarbonyl, aminocarbonyl, mono($C_{1-6}$)alkylaminocarbonyl, di($C_{1-6}$)alkylaminocarbonyl, carboxy($C_{1-6}$)alkyl, ($C_{1-6}$) alkoxycarbonyl($C_{1-6}$)alkyl, aminocarbonyl($C_{1-6}$)alkyl, mono ($C_{1-6}$)alkylaminocarbonyl($C_{1-6}$)alkyl, di($C_{1-6}$)alkylaminocarbonylalkyl($C_{1-6}$), sulfonylamino, ($C_{1-6}$) alkylsulfonylamino, aminosulfonyl, mono($C_{1-6}$) alkylaminosulfonyl, di($C_{1-6}$)alkylaminosulfonyl, ($C_{1-6}$) alkoxycarbonylamino, aminocarbonylamino, mono($C_{1-6}$) alkylaminocarbonylamino, di($C_{1-6}$) alkylaminocarbonylamino, $C_{6-10}$ aryl, 5-10 membered heteroaryl, N-hydroxyaminocarbonyl, N-alkoxyaminocarbonyl, and N-alkoxy-N-alkylaminocarbonyl. In certain embodiments, any ring substituents in the above list may be further optionally substituted.

$R^8$ may also be a group having a molecular weight from about 50 to about 250 and having one or more amino acid residues. Such amino acid residues include phenylalanine, tryptophan, tyrosine, histidine, leucine, isoleucine, valine, glutamine, asparagine, serine, cysteine, arginine, lysine, histidine, aspartic acid, glutamic acid, alanine, threonine, methionine, and glycine. Of course other amino acids may also be incorporated into a moiety in $R^8$.

Other suitable moieties include arylalkyl and heteroarylalkyl groups. The arylalkyl and heteroarylalkyl groups will generally have an alkyl group of 1 to 6 carbon atoms, preferably 1 to 4 carbon atoms. The heteroaryl group is preferably a nitrogen-containing heteroaryl group. Such groups include but are not limited to benzyl, phenethyl, and naphthylmethyl. Other suitable groups include tetrazolyl-($C_{1-6}$)alkyl.

$R^8$ may alternatively be a group having a molecular weight from about 100 to about 250 and having a biotin moiety.

In other embodiments, $R^8$ may be selected from the group consisting of —($C_{1-6}$)alkyl-C(O)NH$_2$; —($C_{1-6}$)alkyl-C(O) NH—($C_{1-6}$)alkyl; —($C_{1-6}$)alkyl-C(O)N—(($C_{1-6}$)alkyl)$_2$; and —($C_{1-6}$)alkyl-C(O)NH—($C_{1-6}$)hydroxyalkyl; ($C_{1-6}$)alkyl-C (O)N—(($C_{1-6}$)hydroxyalkyl)$_2$.

In other embodiments, $R^8$ may be selected from the group consisting of —($C_{1-6}$)alkyl-COOH; ($C_{1-6}$)alkyl-C(O)O— ($C_{1-6}$)alkyl; and —($C_{1-6}$)alkyl-C(O)O—($C_{1-6}$)hydroxyalkyl.

In other embodiments, $R^8$ may be a —($C_{1-6}$)alkyl-cycloheteroalkyl moiety, in which the cycloheteroalkyl moiety, such as morpholinyl or dioxalanyl, is optionally substituted.

In other embodiments, $R^8$ may be a —($C_{1-6}$)alkyl-oxadiazolyl moiety, in which the oxadiazolyl moiety is optionally substituted.

In another embodiment, $R^8$ is a moiety having a molecular weight of about 20 to about 100 and having 2, 3, or 4 hydrogen bond donor or acceptor groups. Such groups are known in the art.

Other suitable $R^8$ groups include —CH$_2$CH$_2$—N(CH$_3$)$_2$; —CH$_2$C(O)NHCH$_2$CH$_2$N(CH$_3$)$_2$; CH$_2$C(O)NHCH$_2$CH$_2$N (Et)$_2$; —CH$_2$C(O)N(CH$_3$)CH$_2$CH$_2$N(CH$_3$)$_2$; —C(O)-biotin;

—C(O)—CH₂CH₂—C₆H₄—OCH₃; —C(O)O-tert-butyl; —CH₂C(O)NH—CH₂-cycloalkyl; —CH₂C(O)NH—CH₂-cyclopropyl; (CH₂)₅—N(CH₃)₂; and —C(O)-morpholinyl; wherein any of the cyclo groups can be optionally substituted.

In certain embodiments, R⁸ can be a substituent selected from the group consisting of —CH₂CH₂NH₂; —CH₂CH₂N(CH₃)₂; —CH₂CH₂N(CH₃)₂; —CH₂CH₂C(O)NH₂; or —CH₂CH₂C(O)N(CH₃)₂.

Other suitable groups for R⁸ include —(C₁₋₆)alkyl-tetrazolyl.

Other suitable groups for R⁸ include

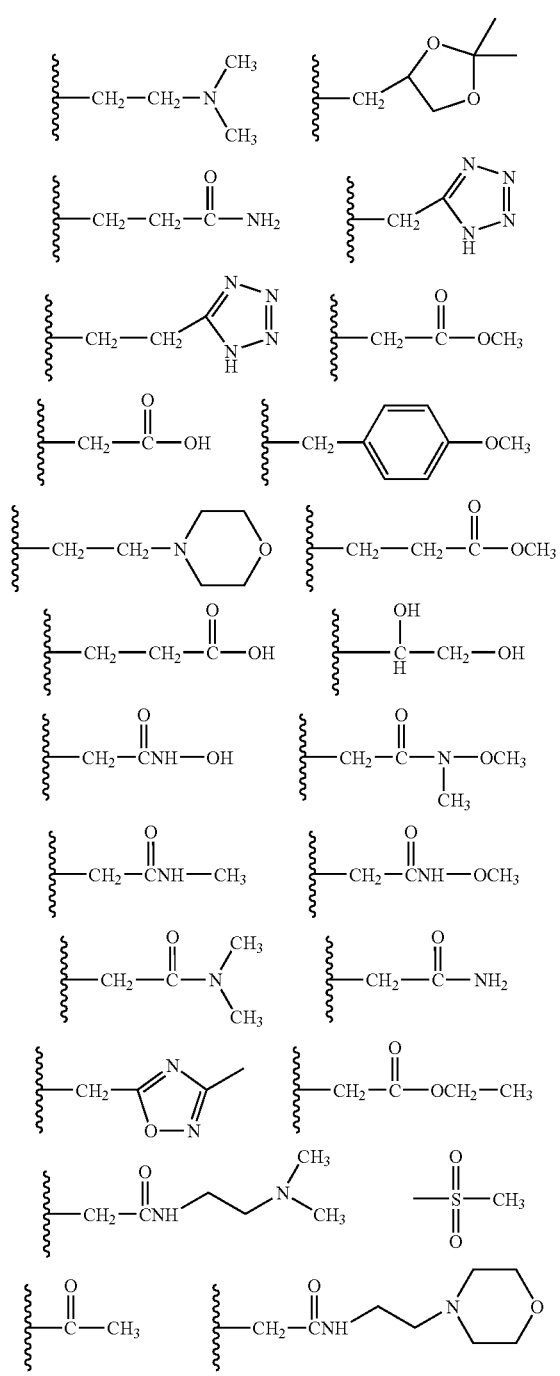

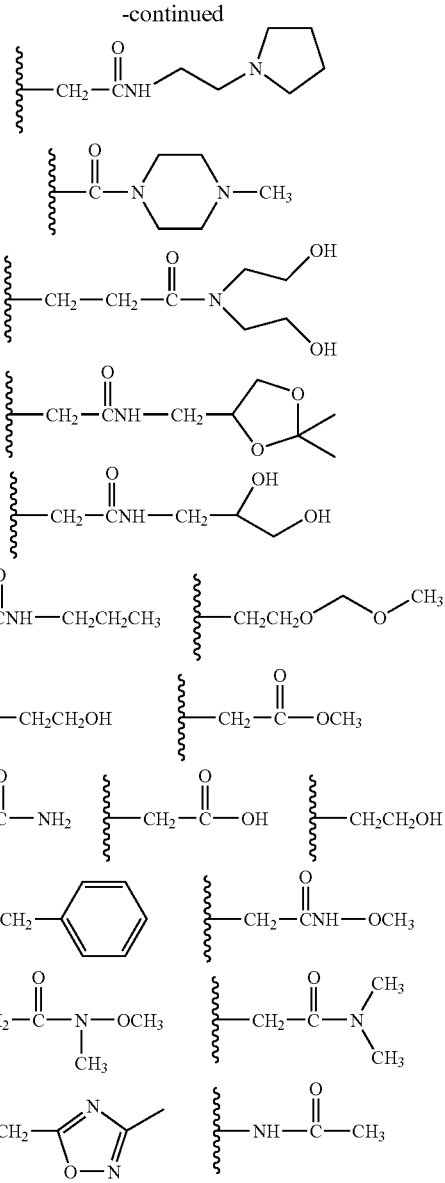

Another embodiment of the invention is directed to a compound of Formula I wherein Z is S, S(O), or S(O)₂; and X¹ and X² are both unsubstituted ethylene.

A first subclass of compounds falling within the scope of the present invention includes compounds of Formula I wherein R¹ is optionally substituted phenyl; and Q is optionally substituted thienyl.

In one embodiment within this first subclass of compounds, R¹ is phenyl substituted with one or more halogens. In another embodiment, R¹ is phenyl substituted in the 4 position. In another embodiment, R¹ is 4-bromophenyl, 4-chlorophenyl, or 4-fluorophenyl. In other embodiments, R¹ is phenyl substituted with a phenoxy group. Suitable R¹ groups include 4-chlorophenyl and 4-phenoxyphenyl.

In another embodiment within this first subclass, Q is unsubstituted thienyl. In certain embodiments, the thienyl group is bonded to N of the urea in the 2 or 3 position. In other embodiments, the thienyl group is substituted in the 5-position with a C₁₋₅ alkyl group, for example a tert-butyl group.

In another embodiment, $R^2$ is a group selected from the group consisting of morpholin-4-yl, thiomorpholin-4-yl, 1-oxothiomorpholin-4-yl, and 1,1-dioxothiomorpholin-4-yl, each of which is optionally substituted.

In another embodiment within this first subclass, G is selected from the group consisting of $CH_2$, $CH_2CH_2$, C(O), and $CH_2C(O)$.

A second subclass of compounds falling within the scope of the present invention includes compounds of Formula I wherein $R^1$ is optionally substituted phenyl; and Q is optionally substituted pyrazolyl.

In one embodiment within this second subclass of compounds, $R^1$ is phenyl substituted with one or more halogens. In another embodiment, $R^1$ is phenyl substituted in the 4 position. In another embodiment, $R^1$ is 4-bromophenyl, 4-chlorophenyl, or 4-fluorophenyl. In other embodiments, $R^1$ is phenyl substituted with a phenoxy group. Suitable $R^1$ groups include 4-chlorophenyl.

In another embodiment within this second subclass, Q is unsubstituted pyrazolyl. In another embodiment, Q is pyrazolyl bonded to the N of the urea in the 3-position. In another embodiment, the pyrazolyl group is substituted with a $C_{1-5}$ alkyl group, preferably a tert-butyl group, preferably in the 5-position.

In another embodiment, $R^2$ is a group selected from the group consisting of morpholin-4-yl, thiomorpholin-4-yl, 1-oxothiomorpholin-4-yl, and 1,1-dioxothiomorpholin-4-yl, each of which is optionally substituted.

In another embodiment within this second subclass, G is selected from the group consisting of $CH_2$, $CH_2CH_2$, C(O), and $CH_2C(O)$.

A third subclass of compounds falling within the scope of the present invention includes compounds of Formula I wherein $R_1$ is naphthyl, quinolinyl, or isoquinolinyl, each of which is optionally substituted; and Q is optionally substituted thienyl.

In one embodiment within this third subclass of compounds, $R^1$ is naphthyl substituted with an electron withdrawing group in the 4 position. In other embodiments, $R^1$ is selected from the group consisting of naphthyl substituted with a halogen, preferably in the 4-position; naphthyl substituted with a cyano, preferably in the 4-position; naphthyl substituted with a hydroxy or $C_{1-6}$ alkoxy, preferably in the 4-position; and 2-naphthyl. In another embodiment, $R^1$ is quinolinyl or isoquinolinyl, each of which is optionally substituted with one or more of halogen, cyano, alkoxy, and hydroxy. In other embodiments, $R^1$ is quinolinyl or isoquinolinyl substituted with an electron withdrawing group. Suitable $R^1$ groups include, but are not limited to, 1-naphthyl, 2-naphthyl, 1-(4-cyano)naphthyl, 1-(4-chloro)naphthyl, 1-(4-bromo)naphthyl, 1-(4-hydroxy)naphthyl, 4-quinolinyl, and 8-quinolinyl.

In another embodiment within this third subclass, Q is unsubstituted thienyl. In certain embodiments, the thienyl group is bonded to N of the urea in the 2 or 3 position. In other embodiments, the thienyl group is substituted in the 5-position with a $C_{1-5}$ alkyl group, for example a tert-butyl group.

In another embodiment, $R^2$ is a group selected from the group consisting of morpholin-4-yl, thiomorpholin-4-yl, 1-oxothiomorpholin-4-yl, and 1,1-dioxothiomorpholin-4-yl, each of which is optionally substituted.

In another embodiment within this third subclass, G is selected from the group consisting of $CH_2$, $CH_2CH_2$, C(O), and $CH_2C(O)$.

A fourth subclass of compounds falling within the scope of the present invention includes compounds of Formula I wherein $R^1$ is naphthyl, quinolinyl, or isoquinolinyl, each of which is optionally substituted; and Q is optionally substituted pyrazolyl.

In one embodiment within this third subclass of compounds, $R^1$ is naphthyl substituted with an electron withdrawing group in the 4 position. In other embodiments, $R^1$ is selected from the group consisting of naphthyl substituted with a halogen, preferably in the 4-position; naphthyl substituted with a cyano, preferably in the 4-position; naphthyl substituted with a hydroxy or $C_{1-6}$ alkoxy, preferably in the 4-position; and 2-naphthyl. In another embodiment, $R^1$ is quinolinyl or isoquinolinyl, each of which is optionally substituted with one or more of halogen, cyano, alkoxy, and hydroxy. In other embodiments, $R^1$ is quinolinyl or isoquinolinyl substituted with an electron withdrawing group. Suitable $R^1$ groups include, but are not limited to, 1-naphthyl, 2-naphthyl, 1-(4-cyano)naphthyl, 1-(4-chloro)naphthyl, 1-(4-bromo)naphthyl, 1-(4-hydroxy)naphthyl, 4-quinolinyl, and 8-quinolinyl.

In another embodiment within this fourth subclass, Q is unsubstituted pyrazolyl. In another embodiment, Q is pyrazolyl bonded to the N of the urea in the 3-position. In another embodiment, the pyrazolyl group is substituted with a $C_{1-5}$ alkyl group, preferably a tert-butyl group, preferably in the 5-position.

In another embodiment, $R^2$ is a group selected from the group consisting of morpholin-4-yl, thiomorpholin-4-yl, 1-oxothiomorpholin-4-yl, and 1,1-dioxothiomorpholin-4-yl, each of which is optionally substituted.

In another embodiment within this fourth subclass, G is selected from the group consisting of $CH_2$, $CH_2CH_2$, C(O), and $CH_2C(O)$.

A fifth subclass of compounds falling within the scope of the present invention includes compounds of Formula I wherein $R^1$ is optionally substituted phenyl; and Q is optionally substituted thiazolyl.

In one embodiment within this fifth subclass, $R^1$ is phenyl substituted with one or more halogens. In another embodiment, $R^1$ is phenyl substituted in the 4 position. In another embodiment, $R^1$ is 4-bromophenyl, 4-chlorophenyl, or 4-fluorophenyl.

In another embodiment within this fifth subclass, the pyrazolyl is substituted at the 2 position with a $C_{1-4}$ alkyl group, such a tert-butyl group. In other embodiments, the urea moiety is bonded to the 5 position of the pyrazole and G is bonded to the 4 position of the pyrazole.

A sixth subclass of compounds falling within the scope of the present invention includes compounds of Formula I wherein $R^1$ is optionally substituted naphthyl and Q is optionally substituted thiazolyl.

In one embodiment within this sixth subclass, $R^1$ is 1-naphthyl or 2-naphthyl. In certain embodiments, $R^1$ is unsubstituted.

In another embodiment within this fifth subclass, the pyrazole is substituted at the 2 position with a $C_{1-4}$ alkyl group, such a tert-butyl group. In other embodiments, the urea moiety is bonded to the 5 position of the pyrazole and G is bonded to the 4 position of the pyrazole.

Another group of compounds of the present invention includes a compound according to Formula I wherein $R^1$ is phenyl optionally substituted with 1-3 of $C_{1-4}$ alkyl, halogen, amino, hydroxy, cyano, $C_{1-4}$ haloakyl, and $C_{1-4}$ alkoxy; and $R^2$ is selected from the group consisting of 4-morpholinyl, 1-oxothiomorpholin-4-yl, 1,1-dioxothio-morpholin-4-yl, 3-oxopiperazin-1-yl, 5-oxo-1,4-diazepan-1-yl, and 1,1-dioxo[1,2,5]thiadiazepan-5-yl.

Another group of compounds of the present invention includes a compound according to Formula I wherein $R^1$ is naphthyl optionally substituted with 1-3 of $C_{1-4}$ alkyl, halogen, amino, hydroxy, cyano, $C_{1-4}$ haloalkyl, and $C_{1-4}$ alkoxy; and $R^2$ is selected from the group consisting of 4-morpholinyl, 1-oxothiomorpholin-4-yl, 1,1-dioxothio-morpholin-4-yl, 3-oxopiperazin-1-yl, 5-oxo-1,4-diazepan-1-yl, and 1,1-dioxo[1,2,5]thia-diazepan-5-yl.

A compound of the invention can be selected from a compound according to Formula I wherein $R^2$ is one of the following groups,

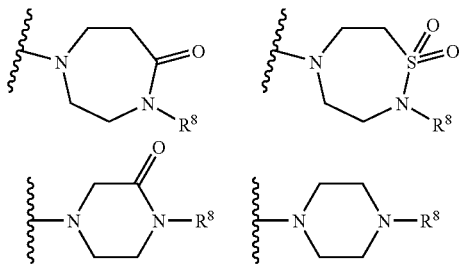

and wherein $R^8$ is a moiety selected from the group having a molecular weight from about 1 to about 300, from about 1 to about 250, from about 1 to about 150, and from about 1 to about 100. In another embodiment, when R 4 is an oxopiperazine ring, $R^8$ is —$CH_2C(O)NHCH_2CH_2N(CH_3)_2$ or —$CH_2C(O)N(CH_3)OCH_3$. In another embodiment, when R 4 is an oxopiperazine ring, $R^8$ is a C1-6 alkyl group substituted with a heteroaryl group, particularly a 5 membered heteroaryl ring.

A compound of the invention can be selected from a compound according to Formula I wherein $R^4$ is one of the following groups,

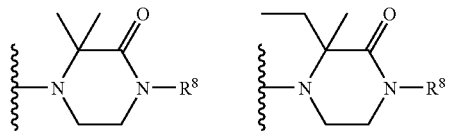

and wherein $R^8$ is a moiety selected from the group having a molecular weight from about 1 to about 300, from about 1 to about 250, from about 1 to about 150, and from about 1 to about 100.

In another embodiment, the invention is directed to a compound of Formula I wherein $R^2$ is a piperazine-$R^8$, wherein $R^8$ is acetyl or methylsulfonyl.

In other embodiments, a compound of the invention is a compound according to Formula I, wherein: $R^2$ is 1,1-dioxo-$1\lambda^6$-thiomorpholine and $R^1$ is 4-chlorophenyl; $R^2$ is 1,1-dioxo-$1\lambda^6$-thiomorpholine and $R^1$ is naphthalen-1-yl; $R^2$ is 1,1-dioxo-$1\lambda^6$-thiomorpholin-4-yl and $R^1$ is 4-chlorophenyl) urea; $R^2$ is 1,1-dioxo-$1\lambda^6$-thiomorpholine and $R^1$ is 2-naphthalenyl; $R^2$ is 1,1-dioxo-$1\lambda^6$-thiomorpholin-4-yl and $R^1$ is naphthalen-1-yl; $R^2$ is 1,1-dioxo-$1\lambda^6$-thiomorpholin-4-yl and $R^1$ is naphthalen-2-yl; $R^2$ is 1,1-dioxo-$1\lambda^6$-thiomorpholin-4-yl and $R^1$ is 4-chlorophenyl; $R^2$ is 1,1-dioxo-$1\lambda^6$-thiomorpholin-4-yl and $R^1$ is naphthalen-2-yl; $R^2$ is 1,1-dioxo-$1\lambda^6$-thiomorpholin-4-yl and $R^1$ is naphthalen-1-yl; $R^2$ is 1,1-dioxo-$1\lambda^6$-thiomorpholine and $R^1$ is 4-chlorophenyl; $R^2$ is 1,1-dioxo-$1\lambda^6$-thiomorpholine and $R^1$ is naphthalen-1-yl; $R^2$ is 1,1-dioxo-$1\lambda^6$-thiomorpholine and $R^1$ is naphthalen-2-yl; $R^2$ is 1,1-dioxo-$1\lambda^6$-thiomorpholin-4-yl and $R^1$ is naphthalen-2-yl; $R^2$ is 1,1-dioxo-$1\lambda^6$-thiomorpholin-4-yl and $R^1$ is naphthalen-1-yl; $R^2$ is 1,1-dioxo-$1\lambda^6$-thiomorpholin-4-yl and $R^1$ is 4-chlorophenyl; $R^1$ is 4-morpholinyl and $R^1$ is naphthalen-1-yl; $R^2$ is 1,1-dioxo-$1\lambda^6$-thiomorpholine and $R^1$ is 4-chlorophenyl; $R^2$ is thiomorpholine and $R^1$ is naphthalen-1-yl; $R^2$ is morpholin-4-yl and $R^1$ is naphthalen-1-yl; $R^2$ is thiomorpholin-4-yl and $R^1$ is naphthalen-1-yl; $R^2$ is 1,1-dioxo-$1\lambda^6$-thiomorpholine and $R^1$ is naphthalen-1-yl; $R^2$ is 1-oxo-$1\lambda^4$-thiomorpholine and $R^1$ is naphthalen-1-yl; $R^2$ is 1,1-dioxo-$1\lambda^6$-thiomorpholine and $R^1$ is naphthalen-2-yl; $R^2$ is 1,1-dioxo-$1\lambda^6$-thiomorpholin-4-yl and $R^1$ is naphthalen-1-yl; $R^2$ is 1,1-dioxo-$1\lambda^6$-thiomorpholine and $R^1$ is naphthalen-1-yl; $R^2$ is 1,1-dioxo-$1\lambda^6$-thiomorpholine and $R^1$ is naphthalen-2-yl; $R^2$ is 1,1-dioxo-$1\lambda^6$-thiomorpholin-4-yl and $R^1$ is naphthalen-2-yl; $R^2$ is 1,1-dioxo-$1\lambda^6$-thiomorpholine and $R^1$ is 4-phenoxyphenyl; $R^2$ is 1,1-dioxo-$1\lambda^6$ thiomorpholine and $R^1$ is quinolin-8-ylurea; $R^2$ is 1,1-dioxo-$1\lambda^6$-thiomorpholine and $R^1$ is indan-1-yl; $R^2$ is 1,1-dioxo-$1\lambda^6$-thiomorpholine and $R^1$ is quinolin-4-yl; $R^2$ is 1,1-dioxo-$1\lambda^6$-thiomorpholine and $R^1$ is 1H-indazol-7-yl; $R^2$ is 1,1-dioxo-$1\lambda^6$-thiomorpholine and $R^1$ is 2-oxo-1,2,3,4-tetrahydroquinolin-7-yl; $R^2$ is 1,1-dioxo-$1\lambda^6$-thiomorpholine and $R^1$ is 4-hydroxynaphthalen-1-yl; $R^2$ is 3-oxopiperazine and $R^1$ is naphthalen-1-yl; $R^2$ is 5-oxo[1,4]diazepane and $R^1$ is naphthalen-1-yl; $R^2$ is 1,1-dioxo-$1\lambda^6$-[1,2,5]thiadiazepane and $R^1$ is naphthalen-1-yl; $R^2$ is 1,1-dioxo-$1\lambda^6$-[1,2,5]thiadiazepane and $R^1$ is naphthalen-2-yl; $R^2$ is 1,1-dioxo-$1\lambda^6$-[1,2,5]thiadiazepane and $R^1$ is 4-chlorophenyl; $R^1$ is 4-bromonaphthalen-1-yl and $R^2$ is 1,1-dioxo-$1\lambda^6$-thiomorpholine; $R^2$ is 1,1-dioxo-$1\lambda^6$-thiomorpholine and $R^1$ is 4-chloronaphthalen-1-yl; $R^1$ is 3H-Benzimidazol-4-yl and $R^2$ is 1,1-dioxo-$1\lambda^6$-thiomorpholine; $R^2$ is 1,1-dioxo-$1\lambda^6$-thiomorpholine and $R^1$ is 4-cyanonaphthalen-1-yl; $R^2$ is 5-oxo[1,4]diazepane and $R^1$ is naphthalen-2-yl; $R^2$ is 2-(methylsulfonyl)ethylcarbamoyl and $R^1$ is naphthalen-1-yl)urea; $R^2$ is 5-oxo-[1,4]diazepane and $R^1$ is 4-chlorophenyl; $R^2$ is 3-oxopiperazine and $R^1$ is 4-chlorophenyl; $R^2$ is 3-oxopiperazine and $R^1$ is 2-naphthyl; $R^2$ is 1,1-dioxo-$1\lambda^6$-thiomorpholine and $R^1$ is 1H-indol-3-yl; $R^2$ is 5-oxo-[1,4]diazepane and $R^1$ is naphthalen-1-yl; $R^2$ is 1,1-dioxo-$1\lambda^6$-[1,2,5]thiadiazepane and $R^1$ is naphthalen-1-yl; $R^2$ is 3-oxopiperazine and $R^1$ is naphthalen-1-yl; $R^2$ is 5-oxo-[1,4]diazepane and $R^1$ is 2,3-dichlorophenyl; $R^2$ is 5-oxo-[1,4]diazepane and $R^1$ is 3-chlorophenyl; $R^2$ is 5-oxo-[1,4]diazepane and $R^1$ is 4-cyanonaphthyl; $R^2$ is 1,1-dioxo-$1\lambda^6$-[1,2,5]thiadiazepane and $R^1$ is 4-cyanonaphthalen-1-yl; $R^2$ is 3-oxopiperazine-1-carbonyl and $R^1$ is 4-cyano-naphthalen-1-yl; $R^2$ is 1,1-dioxo-$1\lambda^6$-thiomorpholine and $R^1$ is 2,3-dichlorophenyl; $R^2$ is 1,1-dioxo-$1\lambda^6$-thiomorpholine and $R^1$ is 3-chlorophenyl; $R^1$ is benzo[1,3]dioxol-5-yl and $R^2$ is 1,1-dioxo-$1\lambda^6$-thiomorpholine; $R^2$ is 1,1-dioxo-$1\lambda^6$-thiomorpholine and $R^1$ is 2,2-difluorobenzo[1,3]dioxol-5-yl; $R^2$ is 1,1-dioxo-$1\lambda^6$-thiomorpholine and $R^1$ is 3-chloro-4-methoxyphenyl; $R^2$ is 1,1-dioxo-$1\lambda^6$-thiomorpholine-4-carbonyl and $R^1$ is 3,4-dichlorophenyl; $R^2$ is 1,1-dioxo-$1\lambda^6$-thiomorpholine-4-carbonyl and $R^1$ is 4-cyanophenyl; $R^2$ is 1,1-dioxo-$1\lambda^6$-thiomorpholine and $R^1$ is 4-cyano-3-trifluoromethylphenyl; $R^2$ is 1,1-dioxo-$1\lambda^6$-thiomorpholine and $R^1$ is 1-methyl-1-phenylethyl; $R^2$ is 1,1-dioxo-$1\lambda^6$-thiomorpholine and $R^1$ is 3-tolyl; $R^2$ is 1,1-dioxo-$1\lambda^6$-thiomorpholine and $R^1$ is 3,5-dichlorophenyl; $R^2$ is 1,1-dioxo-$1\lambda^6$-thiomorpholine and $R^1$ is 1-methyl-1H-pyrazol-3-yl; $R^2$ is 1,1-dioxo-$1\lambda^6$-thiomorpholine and $R^1$ is 2,6-dimethylpyridin-4-yl; $R^1$ is 1-benzoxazol-5-yl and $R^2$ is 1,1-dioxo-$1\lambda^6$-thiomorpholine; $R^1$ is 1-benzoxazol-6-yl and $R^2$ is 1,1-dioxo-$1\lambda^6$-thiomorpholine; $R^1$ is 1-benzo[1,3]dioxol-5-yl and $R^2$ is 5-oxo-[1,4]diazepane; $R^2$ is 5-oxo-[1,4]diazepane and $R^1$ is 2,2-difluorobenzo[1,3]dioxol-5-yl; $R^2$ is 1,1-dioxo-1$\lambda^6$-thiomorpholine and $R^1$ is 2-chloro-4-cyanophenyl; $R^2$ is 1,1-dioxo-1$\lambda^6$-thiomorpholine and $R^1$ is phenyl; $R^2$ is 2-methyl-3-oxopiperazine and $R^1$ is 4-chlorophenyl; $R^2$ is 5-oxo-[1,4]diazepane and $R^1$ is naphthalen-1-yl; $R^2$ is 1,1-dioxo-1$\lambda^6$-[1,2,5]thiadiazepane and $R^1$ is naphthalen-1-yl; $R^2$ is 5-oxo-[1,4]diazepane and $R^1$ is methyl; $R^2$ is 3-oxopiperazine and $R^1$ is naphthalen-1-yl; $R^2$ is 1,1-dioxo-1$\lambda^6$-thiomorpholine and $R^1$ is 4-cyano-2-trifluoromethylphenyl; $R^2$ is 1,1-dioxo-1$\lambda^6$-thiomorpholine and $R^1$ is 1-hydroxyisoquinolin-4-yl; $R^2$ is 2-methyl-3-oxopiperazine and $R^1$ is naphthalen-1-yl; $R^1$ is naphthalen-1-yl and $R^2$ is 3-oxo-piperazin-2-yl}acetic acid methyl ester; $R^2$ is 5-oxo-[1,4]diazepane and $R^1$ is 4-cyano-2-trifluoromethylphenyl; $R^2$ is 5-oxo-[1,4]diazepane and $R^1$ is 2-chloro-4-cyanophenyl; $R^2$ is 1,1-dioxo-1$\lambda^6$-[1,2,5]thiadiazepane and $R^1$ is 4-cyano-2-trifluoromethylphenyl; $R^2$ is 1,1-dioxo-1$\lambda^6$-[1,2,5]thiadiazepane-5-carbonyl and $R^1$ is 4-cyano-2-chlorophenyl; $R^1$ is 1-benzo[1,3]dioxol-5-yl and $R^2$ is 1,1-dioxo-1$\lambda^6$-[1,2,5]thiadiazepane; $R^2$ is 1,1-dioxo-1$\lambda^6$-[1,2,5]thiadiazepane and $R^1$ is 2,2-difluorobenzo[1,3]dioxol-5-yl; $R^2$ is 1,1-dioxo-1$\lambda^6$-[1,2,5]thiadiazepane and $R^1$ is 3-chloro-4-methoxyphenyl; $R^2$ is 1,1-dioxo-1$\lambda^6$-[1,2,5]thiadiazepane and $R^1$ is 3,4-dichlorophenyl; $R^2$ is 1,1-dioxo-1$\lambda^6$-[1,2,5]thiadiazepane and $R^1$ is 1-methyl-1-phenylethyl; $R^2$ is 1,1-dioxo-1$\lambda^6$-[1,2,5]thiadiazepane and $R^1$ is 3-tolylyl; $R^2$ is 1,1-dioxo-1$\lambda^6$-[1,2,5]thiadiazepane and $R^1$ is 3,5-dichlorophenyl; $R^2$ is 1,1-dioxo-1$\lambda^6$-[1,2,5]thiadiazepane and $R^1$ is 1-methyl-1H-pyrazol-3-yl; $R^2$ is 5-oxo-[1,4]diazepane and $R^1$ is 3-chloro-4-methoxyphenyl; $R^1$ is 1-benzoxazol-5-yl and $R^2$ is 5-oxo-[1,4]diazepane; $R^2$ is 5-oxo-[1,4]diazepane and $R^1$ is 1-hydroxyisoquinolin-4-yl; $R^1$ is 1-benzoxazol-6-yl and $R^2$ is 5-oxo-[1,4]diazepane; $R^2$ is 1,1-dioxo-1$\lambda^6$-[1,2,5]thiadiazepane and $R^1$ is 3-chloro-4-cyanophenyl; $R^2$ is 5-oxo-[1,4]diazepane and $R^1$ is 3,4-dichlorophenyl; $R^1$ is 1-benzoxazol-5-yl and $R^2$ is 1,1-dioxo-1$\lambda^6$-[1,2,5]thiadiazepane; $R^2$ is 1,1-dioxo-1$\lambda^6$-[1,2,5]thiadiazepane and $R^1$ is 1-phenylcyclopropyl; $R^2$ is 1,1-dioxo-1$\lambda^6$-[1,2,5]thiadiazepane and $R^1$ is 1-hydroxyisoquinolin-4-yl; $R^1$ is 4-aminomethylphenyl and $R^2$ is 5-oxo-[1,4]diazepane; $R^1$ is 4-aminomethylnaphthalen-1-yl and $R^2$ is 5-oxo-[1,4]diazepane-1-carbonyl)thiophen-2-yl]urea; $R^1$ is naphthalen-2-yl and $R^2$ is 2,5-dioxopyrrolidin-3-yl; $R^2$ is 2-methyl-3-oxopiperazine and $R^1$ is naphthalen-2-yl; $R^2$ is 5-oxo-[1,4]diazepane and $R^1$ is m-tolylyl; $R^2$ is 5-oxo[1,4]diazepane and $R^1$ is 3-chloro-4-cyanophenyl; $R^2$ is 5-oxo-[1,4]diazepane and $R^1$ is 3,5-dichlorophenyl; $R^1$ is naphthalen-2-yl and $R^2$ is 3-oxopiperazin-2-ylacetic acid methyl ester; $R^2$ is 6-amino-5-oxo-[1,4]diazepane and $R^1$ is 2,3-dichlorophenyl; $R^2$ is 5-oxo-[1,4]diazepane and $R^1$ is 3-piperidin-4-yl; $R^2$ is 5-oxo-[1,4]diazepane and $R^1$ is 2,3-dichlorophenyl; $R^2$ is 5-oxo-[1,4]diazepane and $R^1$ is quinolin-4-yl; $R^2$ is 4-(2-methoxymethoxyethyl)-5-oxo-[1,4]diazepane and $R^1$ is 2,3-dichlorophenyl; $R^2$ is 2-(2-methoxyethoxy)ethyl]-5-oxo-[1,4]diazepane and $R^1$ is 2,3-dichlorophenyl; $R^1$ is 2,3-dichlorophenyl and $R^2$ is 7-oxo-[1,4]diazepan-1-yl; $R^2$ is 4-(2-dimethylaminoethyl)-5-oxo-[1,4]diazepane and $R^1$ is 2,3-dichlorophenyl; $R^2$ is 4-(2,2-dimethyl-[1,3]dioxolan-4-ylmethyl)-5-oxo-[1,4]diazepane and $R^1$ is 2,3-dichlorophenyl; $R^2$ is 1-(3-Amino-3-oxopropyl)-7-oxo-1,4-diazepane; R2 is 2-ethyl-3-oxopiperazine and R1 is 2,3-dichlorophenyl; $R^2$ is 2-methyl-3-oxopiperazine and $R^1$ is 2,3-dichlorophenyl; $R^2$ is 2,2-dimethyl-3-oxo-piperazine and $R^1$ is 2,3-dichlorophenyl; $R^2$ is 5-oxo-[1,4]diazepane and $R^1$ is 3,5-difluorophenyl; $R^2$ is 2-oxopiperazine-4-carbonyl and $R^1$ is 2,3-dichlorophenyl; $R^2$ is 1-(2-(dimethylamino)ethyl)-7-oxo-1,4-diazepane and $R^1$ is 2,3-dichlorophenyl; $R^2$ is 2-methyl-3-oxopiperazine and $R^1$ is 2,3-dichlorophenyl; $R^2$ is 1-((2,2-dimethyl-1,3-dioxolan-4-yl)methyl)-7-oxo-1,4-diazepane and $R^1$ is 2,3-dichlorophenyl; $R^2$ is 3-amino-3-oxopropyl-7-oxo-1,4-diazepane and $R^1$ is 2,3-dichlorophenyl; $R^2$ is 5-oxo-1,4-diazepane and $R^1$ is 2,3,4-trichlorophenyl; $R^2$ is 3-(1-((1H-Tetrazol-5-yl)methyl)-7-oxo-1,4-diazepane and $R^1$ is 2,3-dichlorophenyl; $R^2$ is spiro[2.5]-1,4-diazeocan-5-one and $R^1$ is 2,3-dichlorophenyl; $R^2$ is 5-oxo-1,4-diazepane and $R^1$ is 2,3-dichlorophenyl; $R^2$ is 2-oxopiperazine and $R^1$ is 2,3-dichlorophenyl; $R^2$ is 1,1-dioxy-1-thia-2,5-diazepan-1-one and $R^1$ is 2,3-dichlorophenyl; $R^2$ is 1-methyl-7-oxo-1,4-diazepane and $R^1$ is 2,3-dichlorophenyl; $R^2$ is 5-oxo-1,4-diazepane and $R^1$ is 2,3-dichloro-4-hydroxyphenyl; $R^1$ is 5-oxo-1,4-diazepane and $R^2$ is 2,3-dichloro-4-methoxyphenyl; $R^2$ is 2,2-dimethyl-3-oxopiperazine and $R^1$ is naphthalen-1-yl; $R^2$ is 6,6-dimethyl-5-oxo-1,4-diazepane and $R^2$ is 2,3-dichlorophenyl; $R^2$ is 2,2-dimethyl-3-oxopiperazine and $R^1$ is 2,3-dichloro-4-fluorophenyl; $R^2$ is 2,2-dimethyl-3-oxopiperazine and $R^1$ is 3,5-dichlorophenyl; $R^2$ is 5-methyl-7-oxo-1,4-diazepane and $R^1$ is 2,3-dichlorophenyl; $R^2$ is 2,2-dimethyl-3-oxopiperazine and $R^1$ is 4-cyanonaphthalen-1-yl; $R^2$ is 1-(2-(dimethylamino)ethyl)-6,6-dimethyl-7-oxo-1,4-diazepane and $R^1$ is 2,3-dichlorophenyl; $R^2$ is 2-oxopiperazine and $R^1$ is 2,3-dichloro-4-fluorophenyl; $R^2$ is 5-oxo-1,4-diazepane and $R^1$ is 2,3-dichloro-4-fluorophenyl; $R^1$ is 2,3-dichlorophenyl and $R^2$ is (7-oxo-1,4-diazepan-5-yl)acetate; $R^2$ is 2-(2-amino-2-oxoethyl)-3-oxopiperazine and $R^1$ is 2,3-dichlorophenyl; $R^2$ is 5-oxo-1,4-diazepane and $R^2$ is 2,3-dichloro-4-cyanopheny; $R^2$ is 5-oxo-1,4-diazepane and $R^1$ is 2,3-dichloro-4-(difluoromethoxy)phenyl; $R^2$ is 1-(2-(1H-Tetrazol-5-yl)ethyl)-7-oxo-1,4-diazepane and $R^1$ is 2,3-dichlorophenyl; $R^2$ is 2,2-dimethyl-3-oxopiperazine and $R^1$ is 2,3-dichlorophenyl; $R^2$ is 1-(2-(dimethylamino)ethyl)-7-oxo-1,4-diazepane and $R^1$ is 2,3-dichloro-4-fluorophenyl; $R^2$ is 1-(2-(dimethylamino)ethyl)-7-oxo-1,4-diazepane and $R^1$ is 2,3-dichloro-4-fluorophenyl; $R^2$ is 2,2-dimethyl-3-oxopiperazine and $R^1$ is 2-chloro-4-fluorophenyl; $R^2$ is 5-oxo-1,4-diazepane and $R^1$ is 2-chloro-4-fluorophenyl; $R^2$ is 2,2-dimethyl-3-oxopiperazine and $R^1$ is 2,3-dichloro-4-fluorophenyl; $R^2$ is 1-(2-(dimethylamino)ethyl)-3,3-dimethyl-2-oxopiperazine and $R^1$ is 2,3-dichlorophenyl; $R^2$ is 1-(2-(dimethylamino)ethyl)-3,3-dimethyl-2-oxopiperazine and $R^1$ is 2,3-dichloro-4-fluorophenyl; $R^2$ is 2,2-dimethyl-3-oxopiperazine and $R^1$ is 2,4-dichlorophenyl; $R^2$ is 5-oxo-1,4-diazepane and $R^1$ is 2,4-dichlorophenyl; $R^2$ is 1-(2-Aminoethyl)-7-oxo-1,4-diazepane and R1 is 2,3-dichlorophenyl; $R^2$ is 2-ethyl-2-methyl-3-oxopiperazine and $R^1$ is 2,3-dichlorophenyl; $R^1$ is 2,3-dichlorophenyl and $R^2$ is 3,3-dimethyl-2-oxopiperazin-1-yl)acetic acid; $R^2$ is 1-(2-(dimethylamino)ethyl)-3,3-dimethyl-2-oxopiperazine and $R^1$ is 2,3-dichloro-4-fluorophenyl; $R^2$ is 1-(2-(dimethylamino)ethyl)-3,3-dimethyl-2-oxopiperazine and $R^1$ is 2,3-dichlorophenyl; $R^2$ is 2,2-dimethyl-3-oxopiperazine and $R^1$ is 2,3-dichloro-4-cyanophenyl; $R^2$ is 2,2-dimethyl-3-oxopiperazine and $R^1$ is 2,3-dichloro-4-(difluoromethoxy)phenyl; $R^2$ is 1-(4-Methoxybenzyl)-3,3-dimethyl-2-oxopiperazine and $R^1$ is 2,3-dichlorophenyl; $R^1$ is 2,3-dichlorophenyl and $R^2$ is (2-methyl-3-oxopiperazin-2-yl)acetate; $R^2$ is 3,3-dimethyl-1-(2-morpholinoethyl)-2-oxopiperazine and $R^1$ is 2,3-dichlorophenyl; $R^2$ is 2-ethyl-2-methyl-3-oxopiperazine and $R^1$ is 2,3-dichloro-4-fluorophenyl; $R^1$ is 2,3-dichlorophenyl and $R^2$ is methyl (3,3-dimethyl-2-oxopiperazin-1-yl)propanoate; $R^1$ is 2,3-dichloro-4-fluorophenyl and $R^2$ is methyl (2-methyl-3-oxopiperazin-2-yl)acetate; $R^1$ is 2,3-dichlorophenyl and $R^2$ is (2-methyl-3-oxopiperazin-2-yl)acetic acid; $R^1$ is 3,5-dichloropyridin-4-yl and $R^2$ is 1-(2-(dimethylamino)ethyl)-7-oxo-1,4-diazepane-4-carbonyl)thiophen-2-yl; $R^1$ is 3,5-dichloropyridin-4-yl and $R^2$ is 1-(2-(dimethylamino)ethyl)-3,3-dimethyl-2-oxopiperazine-4-carbonyl)thiophen-2-yl; $R^1$ is 2-chloropyridin-3-yl and $R^2$ is 5-oxo-1,4-diazepane-1-carbonyl; $R^1$ is 2-chloropyridin-3-yl and $R^2$ is 2,2-dimethyl-3-oxopiperazine-1-carbonyl; $R^1$ is 2,3-dichloropheny and $R^2$ is thiomorpholine-1,1-dioxide-4-carbonyl; $R^1$ is 2,3-dichlorophenyl and $R^2$ is 1-(morpholine-4-carbonyl)piperazine; $R^1$ is 2,3-dichlorophenyl and $R^2$ is 1-(dimethylcarbamoyl)piperazine; $R^1$ is 2,3-dichlorophenyl and $R^2$ is methyl piperazine-1-carboxylate; $R^1$ is 2,3-dichlorophenyl and $R^2$ is 1-(2-(2-(dimethylamino)ethylamino)-2-oxoethyl)-3,3-dimethyl-2-oxopiperazine; $R^1$ is 2-(trifluoromethyl)phenyl and $R^2$ is 1-(2-(dimethylamino)ethyl)-3,3-dimethyl-2-oxopiperazine; $R^1$ is 2-chloro-4-fluorophenyl and $R^2$ is 1-(2-(2-(dimethylamino)ethylamino)-2-oxoethyl)-3-ethyl-3-methyl-2-oxopiperazine; $R^1$ is 2-chloro-3-methylphenyl and $R^2$ is 2,2-dimethyl-3-oxopiperazine; $R^1$ is 3-chloropyridin-4-yl and $R^2$ is 1-(2-(dimethylamino)ethyl)-3,3-dimethyl-2-oxopiperazine; $R^1$ is 3,5-dichloropyridin-4-yl and $R^2$ is 1-(2-(dimethylamino)ethyl)-7-oxo-1,4-diazepane-4-carbonyl)thiophen-2-yl; $R^1$ is 3,5-dichloropyridin-4-yl and $R^2$ is 2,2-dimethyl-3-oxopiperazine; $R^1$ is 2,3-dichloro-4-fluorophenyl and $R^2$ is 3,3-dimethyl-2-oxopiperazin-1-yl-N-(2-dimethylaminoethyl)acetamide; $R^1$ is 2-chloro-5-methoxyphenyl and $R^2$ is 2,2-dimethyl-3-oxopiperazine; $R^2$ is 2-(2-amino-2-oxoethyl)-2-methyl-3-oxopiperazine and $R^1$ is 2,3-dichlorophenyl; $R^2$ is 2-(2-hydroxyethyl)-2-methyl-3-oxopiperazine and $R^1$ is 2,3-dichloro-4-fluorophenyl; $R^1$ is 2,3-dichlorophenyl and $R^2$ is (3,3-dimethyl-2-oxopiperazin-1-yl)propanoic acid; $R^2$ is 1-((2,2-dimethyl-1,3-dioxolan-4-yl)methyl)-3,3-dimethyl-2-oxopiperazine and $R^1$ is 2,3-dichlorophenyl; $R^2$ is 1-(2,3-dihydroxypropyl)-3,3-dimethyl-2-oxopiperazine and $R^1$ is 2,3-dichlorophenyl; $R^2$ is 2-(methylcarbamoyl)pyrrolidine and $R^1$ is 2,3-dichloro-4-(difluoromethoxy)phenyl; $R^2$ is 2-oxo-3-phenethylpiperazine and $R^1$ is 2,3-dichlorophenyl; $R^2$ is 2-ethyl-3-oxopiperazine and $R^1$ is 2,3-dichloro-4-fluorophenyl; $R^2$ is 4,4-dioxy-4-thiomorpholine and $R^1$ is 2,3-dichloro-4-fluorophenyl; $R^2$ is 1,1-dioxy-1-thia-2,5-diazepan-1-one and $R^1$ is 2,3-dichloro-4-fluorophenyl; $R^2$ is 2-ethyl-2-methyl-3-oxopiperazine and $R^1$ is 2-chloro-4-fluorophenyl; $R^2$ is spiro[4.5]-1,4-diazedecan-5-one and $R^1$ is 2,3-dichlorophenyl; $R^2$ is 1-(2-(dimethylamino)ethyl)-3-ethyl-3-methyl-2-oxopiperazine and $R^1$ is 2,3-dichloro-4-fluorophenyl; $R^2$ is 1-(2-(dimethylamino)ethyl)-3,3-dimethyl-2-oxopiperazine and $R^1$ is 2-chloro-4-fluorophenyl; $R^2$ is spiro[3.5]-1,4-diazenon-5-one and $R^1$ is 2,3-dichloro-4-fluorophenyl; $R^2$ is 2-(hydroxymethyl)-6-oxopiperazine and $R^1$ is 2,3-dichlorophenyl; $R^2$ is 5-oxo-1,4-diazepane and $R^1$ is 2,3-dichlorophenyl; $R^2$ is 1-(2-(dimethylamino)ethyl)-7-oxo-1,4-diazepane and $R^1$ is 2,3-dichloro-4-fluorophenyl; $R^2$ is 1-(2-(dimethylamino)ethyl)-7-oxo-1,4-diazepane and $R^1$ is 2,3-dichlorophenyl; $R^2$ is 1-(2-(dimethylamino)ethyl)-7-oxo-1,4-diazepane and $R^1$ is 2-chloro-4-fluorophenyl; $R^2$ is 3-ethyl-1,3-dimethyl-2-oxopiperazine and $R^1$ is 2,3-dichlorophenyl; $R^1$ is 2,3-dichloro-4-fluorophenyl and $R^2$ is methyl (3,3-dimethyl-2-oxopiperazin-1-yl)acetate; $R^2$ is 1-(2-(hydroxyamino)-2-oxoethyl)-3,3-dimethyl-2-oxopiperazine and $R^1$ is 2,3-dichloro-4-fluorophenyl; $R^2$ is 5-oxo-1,4-diazepane and $R^1$ is 2-chloro-3,4-difluorophenyl; $R^1$ is 1-(2-(dimethylamino)ethyl)-3,3-dimethyl-2-oxopiperazine and $R^2$ is 2-chloro-3,4-difluorophenyl; $R^2$ is 1-(2-(methoxy(methyl)amino)-2-oxoethyl)-3,3-dimethyl-2-oxopiperazine and $R^1$ is 2,3-dichlorophenyl; $R^2$ is 2-(2-hydroxyethyl)-2-methyl-3-oxopiperazine and $R^1$ is 3-chloro-2-methylphenyl; $R^2$ is 1-(2-(methoxy(methyl)amino)-2-oxoethyl)-3,3-dimethyl-2-oxopiperazine and $R^1$ is 2,3-dichloro-4-fluorophenyl; $R^1$ is 2-chloro-3,4-difluorophenyl and $R^2$ is methyl (2-methyl-3-oxopiperazin-2-yl)acetate; $R^2$ is 2-(2-hydroxyethyl)-2-methyl-3-oxopiperazine and $R^1$ is 2-chloro-3,4-difluorophenyl; $R^2$ is 2-(2-hydroxyethyl)-2-methyl-3-oxopiperazine and $R^1$ is 2,3-dichloro-4-fluorophenyl; $R^2$ is 3,3-dimethyl-1-(2-(methylamino)-2-oxoethyl)-2-oxopiperazine and $R^1$ is 2,3-dichlorophenyl; $R^2$ is 1-(2-(methoxyamino)-2-oxoethyl)-3,3-dimethyl-2-oxopiperazine and $R^1$ is 2,3-dichlorophenyl; $R^2$ is 2-(2-(methoxyamino)-2-oxoethyl)-2-methyl-3-oxopiperazine and $R^1$ is 2,3-dichloro-4-fluorophenyl; $R^2$ is 2-(2-(methoxy(methyl)amino)-2-oxoethyl)-2-methyl-3-oxopiperazine and $R^1$ is 2,3-dichloro-4-fluorophenyl; $R^2$ is 1-(2-(dimethylamino)-2-oxoethyl)-3,3-dimethyl-2-oxopiperazine and $R^1$ is 2,3-dichlorophenyl; $R^2$ is 1-(2-amino-2-oxoethyl)-3,3-dimethyl-2-oxopiperazine and $R^1$ is 2,3-dichlorophenyl; $R^2$ is 2,2-dimethyl-3-oxopiperazine and $R^1$ is 2,3-dichloro-4-fluorophenyl; $R^2$ is 2,2-dimethyl-3-oxopiperazine and $R^1$ is 2,3-dichlorophenyl; $R^2$ is 3-hydroxypiperidine and $R^1$ is 2,3-dichlorophenyl; $R^2$ is 2-methyl-2-((3-methyl-1,2,4-oxadiazol-5-yl)methyl)-3-oxopiperazine and $R^1$ is 2,3-dichloro-4-fluorophenyl; R2 is 3-acetamidopiperidine and $R^1$ is 2,3-dichlorophenyl; $R^1$ is 2,3-dichloro-4-fluorophenyl and $R^2$ is 2,2-dimethyl-3-oxopiperazine; $R^2$ is 3,3-dimethyl-1-((3-methyl-1,2,4-oxadiazol-5-yl)methyl)-2-oxopiperazine and $R^1$ is 2,3-dichlorophenyl; $R^2$ is 1,3,3-trimethyl-2-oxopiperazine and $R^1$ is 2,3-dichlorophenyl; $R^2$ is 2-(2-hydroxyethyl)-2-methyl-3-oxopiperazine and $R^1$ is 2,3-dichlorophenyl; $R^2$ is 3,3-dimethyl-1-((3-methyl-1,2,4-oxadiazol-5-yl)methyl)-2-oxopiperazine and $R^1$ is 2,3-dichloro-4-fluorophenyl; $R^2$ is 1,1-dioxy-1-thia-2,5-diazepan-1-one and $R^1$ is 2,3-dichloro-4-fluorophenyl; $R^1$ is 1-(benzo[d][1,3]dioxol-5-yl and $R^2$ is 2-oxopiperazine; R2 is 2-(2-hydroxyethyl)-2-methyl-3-oxopiperazine and $R^1$ is 3-chloro-2-methoxyphenyl; $R^2$ is 2-(2-hydroxyethyl)-2-methyl-3-oxopiperazine and $R^1$ is 2,3-dichlorophenyl; $R^1$ is 2,3-dichloro-4-fluorophenyl and $R^2$ is methyl (2-methyl-3-oxo-4-ethylacetyl-piperazin-2-yl)acetate; $R^2$ is 1,3-bis(2-Amino-2-oxoethyl)-3-methyl-2-oxopiperazine and $R^1$ is 2,3-dichlorophenyl; $R^2$ is 1,3-bis(2-(Methoxyamino)-2-oxoethyl)-3-methyl-2-oxopiperazine and $R^1$ is 2,3-dichlorophenyl; $R^2$ is 2-(2-hydroxyethyl)-2-methyl-3-oxopiperazine and $R^1$ is 3-fluoro-2-methylphenyl; $R^2$ is 2-(2-hydroxyethyl)-2-methyl-3-oxopiperazine and $R^1$ is 3-fluoro-2-methylphenyl; $R^2$ is 2-(2-Amino-2-oxoethyl)-2-methyl-3-oxopiperazine and $R^1$ is 2,3-dichloro-4-fluorophenyl; $R^1$ is 2,3-Dichloro-4-fluorophenyl and $R^2$ is 2,2-dimethyl-3-oxopiperazine; $R^1$ is 2,3-dichlorophenyl and $R^2$ is dioxothiomorpholin-4-yl; $R^1$ is 1-(benzo[d][1,3]dioxol-4-yl)-3-(5-tert-butyl-3-(5-oxo-1,4-diazepane-1-carbonyl)thiophen-2-yl)urea; $R^2$ is 2,2-dimethyl-3-oxopiperazine and $R^1$ is 2-chloro-5-methoxyphenyl; $R^1$ is 2,3-dichloro-4-fluorophenyl and $R^2$ is (3,3-dimethyl-2-oxo-piperazin-1-yl)-N-(2-dimethylaminoethyl)acetamide; $R^2$ is 2,2-dimethyl-3-oxopiperazine and $R^1$ is 3,5-dichloropyridin-4-yl; $R^2$ is 2,2-dimethyl-3-oxopiperazine and $R^1$ is 3-chloropyridin-4-yl; $R^2$ is 1-(2-(dimethylamino)ethyl)-3,3-dimethyl-2-oxopiperazine and $R^1$ is 3-chloropyridin-4-yl; $R^2$ is 2,2-dimethyl-3-oxopiperazine and $R^1$ is 2-chloro-3-methylphenyl; $R^2$ is 1-(2-(2-(dimethylamino)ethylamino)-2-oxoethyl)-3-ethyl-3-methyl-2-oxopiperazine and $R^1$ is 2-chloro-4-fluorophenyl; $R^2$ is 1-(2-(2-(dimethylamino)ethylamino)-2-oxoethyl)-3-ethyl-3-methyl-2-oxopiperazine and $R^1$ is 2-(trifluoromethyl)phenyl; $R^2$ is 1-(2-(2-(dimethylamino)ethylamino)-2-oxoethyl)-3,3-dimethyl-2-oxopiperazine and $R^1$ is 2,3-dichlorophenyl; $R^2$ is thiomorpholine-1,1-dioxide and R2 is 2,3-dichlorophenyl; $R^2$ is 2,2-dimethyl-3-oxopiperazine and $R^1$ is 2-chloropyridin-3-yl; $R^2$ is 5-oxo-1,4-diazepane and $R^1$ is 2-chloropyridin-3-yl; $R^2$ is 1-(2-(dimethylamino)ethyl)-3,3-dimethyl-2- oxopiperazine and R¹ is 3,5-dichloropyridin-4-yl; R² is 1-(2-(dimethylamino)ethyl)-7-oxo-1,4-diazepane and R¹ is 3,5-dichloropyridin-4-yl.

In other embodiments, R2 is selected from methyl (3,3-dimethyl-2-oxopiperazin-1-yl)acetate; 1-(2-(methoxy(methyl)amino)-2-oxoethyl)-3,3-dimethyl-2-oxopiperazine; 2,2-dimethyl-3-oxopiperazine; and 2-oxopiperazine.

In another embodiment, the present invention is directed to a compound of Formula I having an inhibitory effect on a p38 of at least 60%, 70%, 80%, 90%, or 95% at a concentration of 2 µM, as determined according to the assay described herein. In another embodiment, the present invention is also directed to a compound of any one of the subclasses of compounds described above, wherein the compound has an inhibitory effect on a p38 of at least 60%, 70%, 80%, 90%, or 95% at a concentration of 10 µM, as determined according to the assay described herein. In another embodiment, the present invention is directed to a compound of Formula I having an inhibitory effect on a human p38 of at least 60%, 70%, 80%, 90%, or 95% at a concentration of 2 µM, as determined according to the assay described herein. In another embodiment, the present invention is directed to a compound of Formula I having an inhibitory effect on a human p38α or p38β of at least 60%, 70%, 80%, 90%, or 95% at a concentration of 2 µM, as determined according to the assay described herein.

By way of a non-limiting example, one embodiment of the invention is directed to a compound of Formula I wherein R¹ is optionally substituted phenyl; and Q is optionally substituted thienyl; and wherein said compound inhibits p38 by at least 80% at a concentration of 2 µM. In another embodiment, the present invention is directed to a compound according to Formula I wherein R¹ is naphthyl optionally substituted with 1-3 of $C_{1-4}$ alkyl, halogen, amino, hydroxy, cyano, $C_{1-4}$ haloakyl, and $C_{1-4}$ alkoxy; and R² is selected from the group consisting of 4-morpholinyl, 1-oxothiomorpholin-4-yl, 1,1-dioxothio-morpholin-4-yl, 3-oxopiperazin-1-yl, 5-oxo-1,4-diazepan-1-yl, and 1,1-dioxo[1,2,5]thia-diazepan-5-yl; and wherein said compound inhibits p38α by at least 75% at a concentration of 2 µM.

The present invention is also directed to a compound according to Formula I, or to any of the subclasses or specific embodiments described above, wherein the compound inhibits p38 selectively over one or more of the following kinases: c-RAF, Flt3, JNK2a2, JNK3, Lck, Lyn, Tie2, and TrkB. In another embodiment, the compound of Formula I inhibits p38 selectively over all of c-RAF, Flt3, JNK2a2, JNK3, Lck, Lyn, Tie2, and TrkB. In other embodiments, the compound of the invention can inhibit greater than 80% of the activity of a p38 kinase without inhibiting more than 5%, 10%, 20%, or 30% of the activity of one or more of the following kinases: c-RAF, Flt3, JNK2a2, JNK3, Lck, Lyn, Tie2, and TrkB. In another embodiment, the method of the present invention inhibits p38 selectively over all of c-RAF, Flt3, JNK2a2, JNK3, Lck, Lyn, Tie2, and TrkB.

In yet a further embodiment, the invention is directed to a compound of Formula I, or of any one of the subclasses described above, having the ability to inhibit p38α and p38β selectively over p38γ and p38δ. In another embodiment, the present invention is directed to a compound according to Formula I, or to any of the individual subclasses or embodiments described above, inhibiting a p38α or p38β kinase without inhibiting substantially the activity of a p38γ or p38δ kinase. In certain embodiments, the method of the invention can inhibit greater than 80% of the activity of a p38α or p38β kinase without inhibiting more than 30%, 40%, or 50% of the activity of a p38γ or p38δ kinase. In yet a further embodiment, the invention is directed to a compound of Formula I, or of any one of the subclasses described above, having the ability to inhibit p38α and p38β selectively over p38γ and p38δ.

The phrase "selective inhibition," and grammatical variants thereof, refers to inhibiting the activity of a first protein or first group of proteins without substantially inhibiting the activity of a second protein or a second group of proteins, at a given concentration of compound. In one embodiment, selective inhibition refers to inhibiting by at least 60% the activity of a first protein or first group of protein without inhibiting more than 40% of the activity of a second protein or a second group of proteins. In another embodiment, selective inhibition refers to inhibiting by at least 70% the activity of a first protein or first group of protein without inhibiting more than 30% of the activity of a second protein or a second group of proteins. In another embodiment, selective inhibition refers to inhibiting by at least 80% the activity of a first protein or first group of protein without inhibiting more than 20% of the activity of a second protein or a second group of proteins. In another embodiment, selective inhibition refers to inhibiting by at least 90% the activity of a first protein or first group of protein without inhibiting more than 30% of the activity of a second protein or a second group of proteins.

Examples of suitable compounds, which are useful in the methods and compositions disclosed herein, include:

1-[5-tert-butyl-3-(1,1-dioxo-1$\lambda^6$-thiomorpholine-4-carbonyl)thiophen-2-yl]-3-(4-chlorophenyl)urea;
1-[5-tert-butyl-3-(1,1-dioxo-1$\lambda^6$-thiomorpholine-4-carbonyl)thiophen-2-yl]-3-naphthalen-1-ylurea;
1-[5-tert-butyl-3-(1,1-dioxo-1$\lambda^6$-thiomorpholin-4-ylmethyl)thiophen-2-yl]-3-(4-chlorophenyl)urea;
1-[5-tert-butyl-3-(1,1-dioxo-1$\lambda^6$-thiomorpholine-4-carbonyl)thiophen-2-yl]-3-naphthalen-2-ylurea;
1-[5-tert-butyl-3-(1,1-dioxo-1$\lambda^6$-thiomorpholin-4-ylmethyl)thiophen-2-yl]-3-naphthalen-1-ylurea;
1-[5-tert-butyl-3-(1,1-dioxo-1$\lambda^6$-thiomorpholin-4-ylmethyl)thiophen-2-yl]-3-naphthalen-2-ylurea;
1-{5-tert-butyl-2-[2-(1,1-dioxo-1$\lambda^6$-thiomorpholin-4-yl)-2-oxoethyl]-2H-pyrazol-3-yl}-3-(4-chlorophenyl)urea;
1-{5-tert-butyl-2-[2-(1,1-dioxo-1$\lambda^6$-thiomorpholin-4-yl)-2-oxoethyl]-2H-pyrazol-3-yl}-3-naphthalen-2-ylurea;
1-{5-tert-butyl-2-[2-(1,1-dioxo-1$\lambda^6$-thiomorpholin-4-yl)-2-oxoethyl]-2H-pyrazol-3-yl}-3-naphthalen-1-ylurea;
1-[5-tert-butyl-2-(1,1-dioxo-1$\lambda^6$-thiomorpholine-4-carbonyl)thiophen-3-yl]-3-(4-chlorophenyl)urea;
1-[5-tert-butyl-2-(1,1-dioxo-1$\lambda^6$-thiomorpholine-4-carbonyl)thiophen-3-yl]-3-naphthalen-1-ylurea;
1-[5-tert-butyl-2-(1,1-dioxo-1$\lambda^6$-thiomorpholine-4-carbonyl)thiophen-3-yl]-3-naphthalen-2-ylurea;
1-[5-tert-butyl-2-(1,1-dioxo-1$\lambda^6$-thiomorpholin-4-ylmethyl)thiophen-3-yl]-3-naphthalen-2-ylurea;
1-[5-tert-butyl-2-(1,1-dioxo-1$\lambda^6$-thiomorpholin-4-ylmethyl)thiophen-3-yl]-3-naphthalen-1-ylurea;
1-[5-tert-butyl-2-(1,1-dioxo-1$\lambda^6$-thiomorpholin-4-ylmethyl)thiophen-3-yl]-3-(4-chlorophenyl)urea;
1-[5-tert-butyl-3-(morpholine-4-carbonyl)thiophen-2-yl]-3-naphthalen-1-yl-urea;
1-[5-tert-butyl-2-(1,1-dioxo-1$\lambda^6$-thiomorpholine-4-carbonyl)-2H-pyrazol-3-yl]-3-(4-chlorophenyl)urea;
1-[5-tert-butyl-3-(thiomorpholine-4-carbonyl)thiophen-2-yl]-3-naphthalen-1-ylurea;
1-(5-tert-butyl-3-morpholin-4-ylmethylthiophen-2-yl)-3-naphthalen-1-ylurea;
1-(5-tert-butyl-3-thiomorpholin-4-ylmethylthiophen-2-yl)-3-naphthalen-1-yl-urea;
1-[5-tert-butyl-2-(1,1-dioxo-1$\lambda^6$-thiomorpholine-4-carbonyl)-2H-pyrazol-3-yl]-3-naphthalen-1-ylurea;

1-[5-tert-butyl-3-(1-oxo-1λ$^4$-thiomorpholine-4-carbonyl)thiophen-2-yl]-3-naphthalen-1-ylurea;
1-[5-tert-butyl-2-(1,1-dioxo-1λ$^6$-thiomorpholine-4-carbonyl)-2H-pyrazol-3-yl]-3-naphthalen-2-ylurea;
1-[5-tert-butyl-3-(1,1-dioxo-1λ$^6$-thiomorpholin-4-yl)thiophen-3-yl]-3-naphthalen-1-ylurea;
1-[2-tert-butyl-4-(1,1-dioxo-1λ$^6$-thiomorpholine-4-carbonyl)thiazol-5-yl]-3-naphthalen-1-ylurea;
1-[2-tert-butyl-4-(1,1-dioxo-1λ$^6$-thiomorpholine-4-carbonyl)thiazol-5-yl]-3-naphthalen-2-ylurea;
1-[5-tert-butyl-2-(1,1-dioxo-1λ$^6$-thiomorpholin-4-yl)thiophen-3-yl]-3-naphthalen-2-ylurea;
1-[5-tert-butyl-3-(1,1-dioxo-1λ$^6$-thiomorpholine-4-carbonyl)thiophen-2-yl]-3-(4-phenoxyphenyl)urea;
1-[5-tert-butyl-3-(1,1-dioxo-1λ$^6$-thiomorpholine-4-carbonyl)thiophen-2-yl]-3-quinolin-8-ylurea;
1-[5-tert-butyl-3-(1,1-dioxo-1λ$^6$-thiomorpholine-4-carbonyl)thiophen-2-yl]-3-indan-1-ylurea;
1-[5-tert-butyl-3-(1,1-dioxo-1λ$^6$-thiomorpholine-4-carbonyl)thiophen-2-yl]-3-quinolin-4-ylurea;
1-[5-tert-butyl-3-(1,1-dioxo-1λ$^6$-thiomorpholine-4-carbonyl)thiophen-2-yl]-3-(1H-indazol-7-yl)urea;
1-[5-tert-butyl-3-(1,1-dioxo-1λ$^6$-thiomorpholine-4-carbonyl)thiophen-2-yl]-3-(2-oxo-1,2,3,4-tetrahydroquinolin-7-yl)urea;
1-[5-tert-butyl-3-(1,1-dioxo-1λ$^6$-thiomorpholine-4-carbonyl)thiophen-2-yl]-3-(4-hydroxynaphthalen-1-yl)urea;
1-[5-tert-butyl-3-(3-oxopiperazine-1-carbonyl)thiophen-2-yl]-3-naphthalen-1-ylurea;
1-[5-tert-butyl-3-(5-oxo[1,4]diazepane-1-carbonyl)thiophen-2-yl]-3-naphthalen-1-yl-urea;
1-[5-tert-butyl-3-(1,1-dioxo-1λ$^6$-[1,2,5]thiadiazepane-5-carbonyl)thiophen-2-yl]-3-naphthalen-1-ylurea;
1-[5-tert-butyl-3-(1,1-dioxo-1λ$^6$-[1,2,5]thiadiazepane-5-carbonyl)thiophen-2-yl]-3-naphthalen-2-ylurea;
1-[5-tert-butyl-3-(1,1-dioxo-1λ$^6$-[1,2,5]thiadiazepane-5-carbonyl)thiophen-2-yl]-3-(4-chlorophenyl)urea;
1-(4-Bromonaphthalen-1-yl)-3-[5-tert-butyl-3-(1,1-dioxo-1λ$^6$-thiomorpholine-4-carbonyl)thiophen-2-yl]urea;
1-[5-tert-butyl-3-(1,1-dioxo-1λ$^6$-thiomorpholine-4-carbonyl)thiophen-2-yl]-3-(4-chloronaphthalen-1-yl)urea;
1-(3H-Benzimidazol-4-yl)-3-[5-tert-butyl-3-(1,1-dioxo-1λ$^6$-thiomorpholine-4-carbonyl)thiophen-2-yl]urea;
1-[5-tert-butyl-3-(1,1-dioxo-1λ$^6$-thiomorpholine-4-carbonyl)thiophen-2-yl]-3-(4-cyanonaphthalen-1-yl)urea;
1-[5-tert-butyl-3-(5-oxo[1,4]diazepane-1-carbonyl)thiophen-2-yl]-3-naphthalen-2-ylurea;
1-(3-(2-(Methylsulfonyl)ethylcarbamoyl)-5-tert-butylthiophen-2-yl)-3-(naphthalen-1-yl)urea;
1-[5-tert-butyl-3-(5-oxo-[1,4]diazepane-1-carbonyl)thiophen-2-yl]-3-(4-chloro-phenyl)urea;
1-[5-tert-butyl-3-(3-oxopiperazine-1-carbonyl)thiophen-2-yl]-3-(4-chloro-phenyl)urea;
1-[5-tert-butyl-3-(3-oxopiperazine-1-carbonyl)thiophen-2-yl]-3-(2-naphthyl)urea;
1-[5-tert-butyl-3-(1,1-dioxo-1λ$^6$-thiomorpholine-4-carbonyl)thiophen-2-yl]-3-(1H-indol-3-yl)urea;
1-[5-tert-butyl-2-(5-oxo-[1,4]diazepane-1-carbonyl)thiophen-3'-yl]-3-naphthalen-1-ylurea;
1-[5-tert-butyl-2-(1,1-dioxo-1λ$^6$-[1,2,5]thiadiazepane-5-carbonyl)thiophen-3-yl]-3-naphthalen-1-ylurea;
1-[5-tert-butyl-2-(3-oxopiperazine-1-carbonyl)thiophen-3-yl]-3-naphthalen-1-ylurea;
1-[5-tert-butyl-3-(5-oxo-[1,4]diazepane-1-carbonyl)thiophen-2-yl]-3-(2,3-dichlorophenyl)urea;
1-[5-tert-butyl-3-(5-oxo-[1,4]diazepane-1-carbonyl)thiophen-2-yl]-3-(3-chlorophenyl)urea;
1-[5-tert-butyl-3-(5-oxo-[1,4]diazepane-1-carbonyl)thiophen-2-yl]-3-(4-cyanonaphthyl)urea;
1-[5-tert-butyl-3-(1,1-dioxo-1λ$^6$-[1,2,5]thiadiazepane-5-carbonyl)thiophen-2-yl]-3-(4-cyanonaphthalen-1-yl)urea;
1-[5-tert-butyl-3-(3-oxopiperazine-1-carbonyl)thiophen-2-yl]-3-(4-cyano-naphthalen-1-yl)urea;
1-[5-tert-butyl-3-(1,1-dioxo-1λ$^6$-thiomorpholine-4-carbonyl)thiophen-2-yl]-3-(2,3-dichlorophenyl)urea;
1-[5-tert-butyl-3-(1,1-dioxo-1λ$^6$-thiomorpholine-4-carbonyl)thiophen-2-yl]-3-(3-chlorophenyl)urea;
1-Benzo[1,3]dioxol-5-yl-3-[5-tert-butyl-3-(1,1-dioxo-1λ$^6$-thiomorpholine-4-carbonyl)thiophen-2-yl]urea;
1-[5-tert-butyl-3-(1,1-dioxo-1λ$^6$-thiomorpholine-4-carbonyl)thiophen-2-yl]-3-(2,2-difluorobenzo[1,3]dioxol-5-yl)urea;
1-[5-tert-butyl-3-(1,1-dioxo-1λ$^6$-thiomorpholine-4-carbonyl)thiophen-2-yl]-3-(3-chloro-4-methoxyphenyl)urea;
1-[5-tert-butyl-3-(1,1-dioxo-1λ$^6$-thiomorpholine-4-carbonyl)thiophen-2-yl]-3-(3,4-dichlorophenyl)urea;
1-[5-tert-butyl-3-(1,1-dioxo-1λ$^6$-thiomorpholine-4-carbonyl)thiophen-2-yl]-3-(3-chloro-4-cyanophenyl)urea;
1-[5-tert-butyl-3-(1,1-dioxo-1λ$^6$-thiomorpholine-4-carbonyl)thiophen-2-yl]-3-(4-cyano-3-trifluoromethylphenyl)urea;
1-[5-tert-butyl-3-(1,1-dioxo-1λ$^6$-thiomorpholine-4-carbonyl)thiophen-2-yl]-3-(1-methyl-1-phenylethyl)urea;
1-[5-tert-butyl-3-(1,1-dioxo-1λ$^6$-thiomorpholine-4-carbonyl)thiophen-2-yl]-3-(3-tolyl)urea;
1-[5-tert-butyl-3-(1,1-dioxo-1λ$^6$-thiomorpholine-4-carbonyl)thiophen-2-yl]-3-(3,5-dichlorophenyl)urea;
1-[5-tert-butyl-3-(1,1-dioxo-1λ$^6$-thiomorpholine-4-carbonyl)thiophen-2-yl]-3-(1-methyl-1H-pyrazol-3-yl)urea;
1-[5-tert-butyl-3-(1,1-dioxo-1λ$^6$-thiomorpholine-4-carbonyl)thiophen-2-yl]-3-(2,6-dimethylpyridin-4-yl)urea;
1-Benzoxazol-5-yl-3-[5-tert-butyl-3-(1,1-dioxo-1λ$^6$-thiomorpholine-4-carbonyl)thiophen-2-yl]urea;
1-Benzoxazol-6-yl-3-[5-tert-butyl-3-(1,1-dioxo-1λ$^6$-thiomorpholine-4-carbonyl)thiophen-2-yl]urea;
1-Benzo[1,3]dioxol-5-yl-3-[5-tert-butyl-3-(5-oxo-[1,4]diazepane-1-carbonyl)-thiophen-2-yl]urea;
1-[5-tert-butyl-3-(5-oxo-[1,4]diazepane-1-carbonyl)-thiophen-2-yl]-3-(2,2-difluoro-benzo[1,3]dioxol-5-yl)urea;
1-(3-(Pyridin-3-ylcarbamoyl)-5-tert-butylthiophen-2-yl)-3-(4-chlorophenyl)urea;
1-[5-tert-butyl-3-(1,1-dioxo-1λ$^6$-thiomorpholine-4-carbonyl)thiophen-2-yl]-3-(2-chloro-4-cyanophenyl)urea;
1-[5-tert-butyl-3-(1,1-dioxo-1λ$^6$-thiomorpholine-4-carbonyl)thiophen-2-yl]-3-(1-phenylcyclopropyl)urea;
1-[5-tert-butyl-3-(2-methyl-3-oxopiperazine-1-carbonyl)thiophen-2-yl]-3-(4-chlorophenyl)urea;
1-[2-tert-butyl-5-(5-oxo-[1,4]diazepane-1-carbonyl)thiazol-4-yl]-3-naphthalen-1-ylurea;
1-[2-tert-butyl-4-(1,1-dioxo-1λ$^6$-[1,2,5]thiadiazepane-5-carbonyl)thiazol-5-yl]-3-naphthalen-1-ylurea;
1-[5-tert-butyl-2-(5-oxo-[1,4]diazepane-1-carbonyl)thiophen-3-yl]-3-methyl-urea;
1-(3-(N-methyl-N-(2-(methylsulfonyl)ethyl)carbamoyl)-5-tert-butylthiophen-2-yl)-3-(naphthalen-1-yl)urea;
1-[2-tert-butyl-4-(3-oxopiperazine-1-carbonyl)thiazol-5-yl]-3-naphthalen-1-ylurea;
1-[5-tert-butyl-3-(1,1-dioxo-1λ$^6$-thiomorpholine-4-carbonyl)thiophen-2-yl]-3-(4-cyano-2-trifluoromethylphenyl)urea;
1-[5-tert-butyl-3-(1,1-dioxo-1λ$^6$-thiomorpholine-4-carbonyl)thiophen-2-yl]-3-(1-hydroxyisoquinolin-4-yl)urea;

5-tert-butyl-2-(3-naphthalen(-1-ylureido)thiophene-3-carboxylic acid (2,5-dioxo-pyrrolidin-3-yl)amide;
1-[5-tert-butyl-3-(2-methyl-3-oxopiperazine-1-carbonyl)thiophen-2-yl]-3-naphthalen-1-ylurea;
{1-[5-tert-butyl-2-(3-naphthalen-1-yl-ureido)thiophene-3-carbonyl]-3-oxo-piperazin-2-yl}-acetic acid methyl ester;
1-[5-tert-butyl-3-(5-oxo-[1,4]diazepane-1-carbonyl)thiophen-2-yl]-3-(4-cyano-2-trifluoromethylphenyl)urea;
1-[5-tert-Butyl-3-(5-oxo-[1,4]diazepane-1-carbonyl)thiophen-2-yl]-3-(2-chloro-4-cyanophenyl)urea;
1-[5-tert-Butyl-3-(1,1-dioxo-1$\lambda^6$-[1,2,5]thiadiazepane-5-carbonyl)thiophen-2-yl]-3-(4-cyano-2-trifluoromethylphenyl)urea;
1-[5-tert-Butyl-3-(1,1-dioxo-1$\lambda^6$-[1,2,5]thiadiazepane-5-carbonyl)thiophen-2-yl]-3-(4-cyano-2-chlorophenyl)urea;
1-Benzo[1,3]dioxol-5-yl-3-[5-tert-butyl-3-(1,1-dioxo-1$\lambda^6$-[1,2,5]thiadiazepane-5-carbonyl)thiophen-2-yl]urea;
1-[5-tert-Butyl-3-(1,1-dioxo-1$\lambda^6$-[1,2,5]thiadiazepane-5-carbonyl)thiophen-2-yl]-3-(2,2-difluorobenzo[1,3]dioxol-5-yl)urea;
1-[5-tert-Butyl-3-(1,1-dioxo-1$\lambda^6$-[1,2,5]thiadiazepane-5-carbonyl)thiophen-2-yl]-3-(3-chloro-4-methoxyphenyl)urea;
1-[5-tert-Butyl-3-(1,1-dioxo-1$\lambda^6$-[1,2,5]thiadiazepane-5-carbonyl)thiophen-2-yl]-3-(3,4-dichlorophenyl)urea;
1-[5-tert-Butyl-3-(1,1-dioxo-1$\lambda^6$-[1,2,5]thiadiazepane-5-carbonyl)thiophen-2-yl]-3-(1-methyl-1-phenylethyl)urea;
1-[5-tert-Butyl-3-(1,1-dioxo-1$\lambda^6$-[1,2,5]thiadiazepane-5-carbonyl)thiophen-2-yl]-3-(3-tolylyl)urea;
1-[5-tert-Butyl-3-(1,1-dioxo-1$\lambda^6$-[1,2,5]thiadiazepane-5-carbonyl)thiophen-2-yl]-3-(3,5-dichlorophenyl)urea;
1-[5-tert-Butyl-3-(1,1-dioxo-1$\lambda^6$-[1,2,5]thiadiazepane-5-carbonyl)thiophen-2-yl]-3-(1-methyl-1H-pyrazol-3-yl)urea;
5-tert-Butyl-2-[3-(4-chlorophenyl)ureido]thiophene-3-carboxylic acid (2,5-dioxopyrrolidin-3-yl)amide;
1-[5-tert-Butyl-3-(5-oxo-[1,4]diazepane-1-carbonyl)thiophen-2-yl]-3-(3-chloro-4-methoxyphenyl)urea;
1-Benzoxazol-5-yl-3-[5-tert-butyl-3-(5-oxo-[1,4]diazepane-1-carbonyl)-thiophen-2-yl]urea;
1-[5-tert-Butyl-3-(5-oxo-[1,4]diazepane-1-carbonyl)thiophen-2-yl]-3-(1-hydroxyisoquinolin-4-yl)urea;
1-Benzoxazol-6-yl-3-[5-tert-butyl-3-(5-oxo-[1,4]diazepane-1-carbonyl)-thiophen-2-yl]urea;
1-[5-tert-Butyl-3-(1,1-dioxo-1$\lambda^6$-[1,2,5]thiadiazepane-5-carbonyl)thiophen-2-yl]-3-(3-chloro-4-cyanophenyl)urea;
1-[5-tert-Butyl-2-(5-oxo-[1,4]diazepane-1-carbonyl)thiophen-3-yl]-3-(3,4-dichlorophenyl)urea;
1-Benzoxazol-5-yl-3-[5-tert-butyl-3-(1,1-dioxo-1$\lambda^6$-[1,2,5]thiadiazepane-5-carbonyl)thiophen-2-yl]urea;
1-[5-tert-Butyl-3-(1,1-dioxo-1$\lambda^6$-[1,2,5]thiadiazepane-5-carbonyl)thiophen-2-yl]-3-(1-phenylcyclopropyl)urea;
1-[5-tert-Butyl-3-(1,1-dioxo-1$\lambda^6$-[1,2,5]thiadiazepane-5-carbonyl)thiophen-2-yl]-3-(1-hydroxyisoquinolin-4-yl)urea;
1-(4-Aminomethylphenyl)-3-[5-tert-butyl-3-(5-oxo-[1,4]diazepane-1-carbonyl)thiophen-2-yl]urea;
1-(4-Aminomethylnaphthalen-1-yl)-3-[5-tert-butyl-3-(5-oxo-[1,4]diazepane-1-carbonyl)thiophen-2-yl]urea;
5-tert-Butyl-2-(3-naphthalen-2-ylureido)thiophene-3-carboxylic acid (2,5-dioxopyrrolidin-3-yl)-amide;
1-[5-tert-Butyl-3(2-methyl-3-oxopiperazine-1-carbonyl)thiophen-2-yl]-3-naphthalen-2-ylurea;
1-[5-tert-Butyl-3-(5-oxo-[1,4]diazepane-1-carbonyl)thiophen-2-yl]-3-m-tolylurea;
1-[5-tert-Butyl-3-(5-oxo[1,4]diazepane-1-carbonyl)thiophen-2-yl]-3-(3-chloro-4-cyanophenyl)urea;
1-[5-tert-Butyl-3-(5-oxo-[1,4]diazepane-1-carbonyl)thiophen-2-yl]-3-(3,5-dichlorophenyl)urea;
{1-[5-tert-Butyl-2-(3-naphthalen-2-ylureido)thiophene-3-carbonyl]-3-oxo-piperazin-2-yl}acetic acid methyl ester;
1-[3-(6-Amino-5-oxo-[1,4]diazepane-1-carbonyl)-5-tert-butylthiophen-2-yl]-3-(2,3-dichlorophenyl)urea;
1-[5-tert-Butyl-3-(5-oxo-[1,4]diazepane-1-carbonyl)thiophen-2-yl]-3-piperidin-4-ylurea;
1-[5-tert-Butyl-2-(5-oxo-[1,4]diazepane-1-carbonyl)thiophen-3-yl]-3-(2,3-dichlorophenyl)urea;
1-[5-tert-Butyl-3-(5-oxo-[1,4]diazepane-1-carbonyl)thiophen-2-yl]-3-quinolin-4-ylurea;
1-{5-tert-Butyl-3-[4-(2-methoxymethoxyethyl)-5-oxo-[1,4]diazepane-1-carbonyl]thiophen-2-yl}-3-(2,3-dichlorophenyl)urea;
1-(5-tert-butyl-3-{4-[2-(2-methoxyethoxy)ethyl]-5-oxo-[1,4]diazepane-1-carbonyl}thiophen-2-yl)-3-(2,3-dichlorophenyl)urea;
1-{5-tert-butyl-3-[4-(2-methoxyethyl)-5-oxo-[1,4]diazepane-1-carbonyl]-thiophen-2-yl}-3-(2,3-dichlorophenyl)urea;
2-(4-{5-tert-Butyl-2-[3-(2,3-dichlorophenyl)ureido]thiophene-3-carbonyl}-7-oxo-[1,4]diazepan-1-yl)acetamide;
1-{5-tert-Butyl-3-[4-(2-dimethylaminoethyl)-5-oxo-[1,4]diazepane-1-carbonyl]-thiophen-2-yl}-3-(2,3-dichlorophenyl)urea;
1-{5-tert-Butyl-3-[4-(2,2-dimethyl-[1,3]dioxolan-4-ylmethyl)-5-oxo-[1,4]diazepane-1-carbonyl]thiophen-2-yl}-3-(2,3-dichlorophenyl)urea;
1-(3-(1-(3-Amino-3-oxopropyl)-7-oxo-1,4-diazepane-4-carbonyl)-5-tert-butylthiophen-2-yl)-3-(2,3-dichlorophenyl)urea;
5-tert-butyl-2-[3-(2,3-dichlorophenyl)ureido]thiophene-3-carboxylic acid (pyridin-3-ylmethyl)amide;
5-tert-Butyl-2-(3-naphthalen-1-yl-ureido)thiophene-3-carboxylic acid (pyridin-3-ylmethyl)amide;
5-tert-Butyl-2-(3-naphthalen-2-yl-ureido)thiophene-3-carboxylic acid (pyridin-3-ylmethyl)amide;
5-tert-Butyl-2-[3-(2,3-dichlorophenyl)ureido]thiophene-3-carboxylic acid (3H-benzotriazol-5-yl)amide;
1-[5-tert-Butyl-3-(2-ethyl-3-oxopiperazine-1-carbonyl)thiophen-2-yl]-3-(2,3-dichlorophenyl)urea;
1-[5-tert-Butyl-3-(2-methyl-3-oxopiperazine-1-carbonyl)thiophen-2-yl]-3-(2,3-dichlorophenyl)urea;
1-[5-tert-Butyl-3-(2,2-dimethyl-3-oxo-piperazine-1-carbonyl)thiophen-2-yl]-3-(2,3-dichlorophenyl)urea;
1-[5-tert-butyl-3-(5-oxo-[1,4]diazepane-1-carbonyl)thiophen-2-yl]-3-(3,5-difluorophenyl)urea;
1-(5-tert-Butyl-3-(2-oxopiperazine-4-carbonyl)thiophen-2-yl)-3-(2,3-dichlorophenyl)urea;
1-(2-tert-Butyl-4-(1-(2-(dimethylamino)ethyl)-7-oxo-1,4-diazepane-4-carbonyl)thiazol-5-yl)-3-(2,3-dichlorophenyl)urea;
(R)-1-(5-tert-Butyl-3-(2-methyl-3-oxopiperazine-1-carbonyl)thiophen-2-yl)-3-(2,3-dichlorophenyl)urea;
1-(2-tert-Butyl-4-(1-((2,2-dimethyl-1,3-dioxolan-4-yl)methyl)-7-oxo-1,4-diazepane-4-carbonyl)thiazol-5-yl)-3-(2,3-dichlorophenyl)urea;
1-(4-(1-(3-Amino-3-oxopropyl)-7-oxo-1,4-diazepane-4-carbonyl)-2-tert-butylthiazol-5-yl)-3-(2,3-dichlorophenyl)urea;
1-(5-tert-Butyl-3-(5-oxo-1,4-diazepane-1-carbonyl)thiophen-2-yl)-3-(2,3,4-trichlorophenyl)urea;

1-(3-(1-((1H-Tetrazol-5-yl)methyl)-7-oxo-1,4-diazepane-4-carbonyl)-5-tert-butylthiophen-2-yl)-3-(2,3-dichlorophenyl)urea;
1-(5-tert-Butyl-3-(spiro[2.5]-1,4-diazeoctan-5-one-1-carbonyl)thiophen-2-yl)-3-(2,3-dichlorophenyl)urea;
1-(2-tert-Butyl-4-(5-oxo-1,4-diazepane-1-carbonyl)thiazol-5-yl)-3-(2,3-dichlorophenyl)urea;
1-(2-tert-Butyl-4-(2-oxopiperazine-4-carbonyl)thiazole-5-yl)-3-(2,3-dichlorophenyl)urea;
1-(2-tert-Butyl-4-(1,1-dioxy-1-thia-2,5-diazepan-1-one-5-carbonyl)thiazole-5-yl)-3-(2,3-dichlorophenyl)urea;
1-(5-tert-Butyl-3-(1-methyl-7-oxo-1,4-diazepane-4-carbonyl)thiophen-2-yl)-3-(2,3-dichlorophenyl)urea;
1-(5-tert-Butyl-3-(5-oxo-1,4-diazepane-1-carbonyl)thiophen-2-yl)-3-(2,3-dichloro-4-hydroxyphenyl)urea;
1-(5-tert-Butyl-3-(5-oxo-1,4-diazepane-1-carbonyl)thiophen-2-yl)-3-(2,3-dichloro-4-methoxyphenyl)urea;
1-(5-tert-Butyl-3-(2,2-dimethyl-3-oxopiperazine-1-carbonyl)thiophen-2-yl)-3-(naphthalen-1-yl)urea;
1-(5-tert-Butyl-3-(6,6-dimethyl-5-oxo-1,4-diazepane-1-carbonyl)thiophen-2-yl)-3-(2,3-dichlorophenyl)urea;
1-(5-tert-Butyl-3-(2,2-dimethyl-3-oxopiperazine-1-carbonyl)thiophen-2-yl)-3-(2,3-dichloro-4-fluorophenyl)urea;
1-(5-tert-Butyl-3-(2,2-dimethyl-3-oxopiperazine-1-carbonyl)thiophen-2-yl)-3-(3,5-dichlorophenyl)urea;
1-(5-tert-Butyl-3-(5-methyl-7-oxo-1,4-diazepane-4-carbonyl)thiophen-2-yl)-3-(2,3-dichlorophenyl)urea;
1-(5-tert-Butyl-3-(2,2-dimethyl-3-oxopiperazine-1-carbonyl)thiophen-2-yl)-3-(4-cyanonaphthalen-1-yl)urea;
1-(5-tert-Butyl-3-(1-(2-(dimethylamino)ethyl)-6,6-dimethyl-7-oxo-1,4-diazepane-4-carbonyl)thiophen-2-yl)-3-(2,3-dichlorophenyl)urea;
1-(5-tert-Butyl-3-(2-oxopiperazine-4-carbonyl)thiophen-2-yl)-3-(2,3-dichloro-4-fluorophenyl)urea;
1-(5-tert-Butyl-3-(5-oxo-1,4-diazepane-1-carbonyl)thiophen-2-yl)-3-(2,3-dichloro-4-fluorophenyl)urea;
Methyl 2-(4-(2-tert-butyl-5-(3-(2,3-dichlorophenyl)ureido)thiophene-4-carbonyl)-7-oxo-1,4-diazepan-5-yl)acetate;
1-(3-(2-(2-amino-2-oxoethyl)-3-oxopiperazine-1-carbonyl)-5-tert-butylthiophen-2-yl)-3-(2,3-dichlorophenyl)urea;
1-(5-tert-Butyl-3-(5-oxo-1,4-diazepane-1-carbonyl)thiophen-2-yl)-3-(2,3-dichloro-4-cyanophenyl)urea;
1-(5-tert-Butyl-3-(5-oxo-1,4-diazepane-1-carbonyl)thiophen-2-yl)-3-(2,3-dichloro-4-(difluoromethoxy)phenyl)urea;
Methyl 4-(3-(5-tert-butyl-3-(5-oxo-1,4-diazepane-1-carbonyl)thiophen-2-yl)ureido)-2,3-dichlorobenzoate;
1-(3-(1-(2-(1H-Tetrazol-5-yl)ethyl)-7-oxo-1,4-diazepane-4-carbonyl)-5-tert-butylthiophen-2-yl)-3-(2,3-dichlorophenyl)urea;
1-(5-tert-Butyl-2-(2,2-dimethyl-3-oxopiperazine-1-carbonyl)thiophen-3-yl)-3-(2,3-dichlorophenyl)urea;
1-(5-tert-Butyl-2-(1-(2-(dimethylamino)ethyl)-7-oxo-1,4-diazepane-4-carbonyl)thiophen-3-yl)-3-(2,3-dichloro-4-fluorophenyl)urea;
1-(5-tert-Butyl-3-(1-(2-(dimethylamino)ethyl)-7-oxo-1,4-diazepane-4-carbonyl)thiophen-2-yl)-3-(2,3-dichloro-4-fluorophenyl)urea;
1-(5-tert-Butyl-3-(2,2-dimethyl-3-oxopiperazine-1-carbonyl)thiophen-2-yl)-3-(2-chloro-4-fluorophenyl)urea;
1-(5-tert-Butyl-3-(5-oxo-1,4-diazepane-1-carbonyl)thiophen-2-yl)-3-(2-chloro-4-fluorophenyl)urea;
1-(2-tert-Butyl-4-(2,2-dimethyl-3-oxopiperazine-1-carbonyl)thiazol-5-yl)-3-(2,3-dichloro-4-fluorophenyl)urea;
1-(5-tert-Butyl-3-(1-(2-(dimethylamino)ethyl)-3,3-dimethyl-2-oxopiperazine-4-carbonyl)thiophen-2-yl)-3-(2,3-dichlorophenyl)urea;
1-(5-tert-Butyl-3-(1-(2-(dimethylamino)ethyl)-3,3-dimethyl-2-oxopiperazine-4-carbonyl)thiophen-2-yl)-3-(2,3-dichloro-4-fluorophenyl)urea;
1-(5-tert-Butyl-3-(2,2-dimethyl-3-oxopiperazine-1-carbonyl)thiophen-2-yl)-3-(2,4-dichlorophenyl)urea;
1-(5-tert-Butyl-3-(5-oxo-1,4-diazepane-1-carbonyl)thiophen-2-yl)-3-(2,4-dichlorophenyl)urea;
1-(4-(1-(2-Aminoethyl)-7-oxo-1,4-diazepane-4-carbonyl)-2-tert-butylthiazol-5-yl)-3-(2,3-dichlorophenyl)urea;
1-(3-(1-(2-aminoethyl)-7-oxo-1,4-diazepane-4-carbonyl)-5-tert-butylthiophen-2-yl)-3-(2,3-dichlorophenyl)urea;
1-(5-tert-Butyl-3-(2-ethyl-2-methyl-3-oxopiperazine-1-carbonyl)thiophen-2-yl)-3-(2,3-dichlorophenyl)urea;
Methyl 2-(4-(2-tert-butyl-5-(3-(2,3-dichlorophenyl)ureido)thiophene-4-carbonyl)-3,3-dimethyl-2-oxopiperazin-1-yl)acetate;
2-(4-(2-tert-Butyl-5-(3-(2,3-dichlorophenyl)ureido)thiophene-4-carbonyl)-3,3-dimethyl-2-oxopiperazin-1-yl)acetic acid;
1-(5-tert-Butyl-2-(1-(2-(dimethylamino)ethyl)-3,3-dimethyl-2-oxopiperazine-4-carbonyl)thiophen-3-yl)-3-(2,3-dichloro-4-fluorophenyl)urea;
1-(5-tert-Butyl-2-(1-(2-(dimethylamino)ethyl)-3,3-dimethyl-2-oxopiperazine-4-carbonyl)thiophen-3-yl)-3-(2,3-dichlorophenyl)urea;
1-(5-tert-Butyl-3-(2,2-dimethyl-3-oxopiperazine-1-carbonyl)thiophen-2-yl)-3-(2,3-dichloro-4-cyanophenyl)urea;
1-(5-tert-Butyl-3-(2,2-dimethyl-3-oxopiperazine-1-carbonyl)thiophen-2-yl)-3-(2,3-dichloro-4-(difluoromethoxy)phenyl)urea;
1-(3-(1-(4-Methoxybenzyl)-3,3-dimethyl-2-oxopiperazine-4-carbonyl)-5-tert-butylthiophen-2-yl)-3-(2,3-dichlorophenyl)urea;
Methyl 2-(1-(2-tert-butyl-5-(3-(2,3-dichlorophenyl)ureido)thiophene-4-carbonyl)-2-methyl-3-oxopiperazin-2-yl)acetate;
1-(5-tert-Butyl-3-(3,3-dimethyl-1-(2-morpholinoethyl)-2-oxopiperazine-4-carbonyl)thiophen-2-yl)-3-(2,3-dichlorophenyl)urea;
1-(5-tert-Butyl-3-(2-ethyl-2-methyl-3-oxopiperazine-1-carbonyl)thiophen-2-yl)-3-(2,3-dichloro-4-fluorophenyl)urea;
Methyl 3-(4-(2-tert-butyl-5-(3-(2,3-dichlorophenyl)ureido)thiophene-4-carbonyl)-3,3-dimethyl-2-oxopiperazin-1-yl)propanoate;
Methyl 2-(1-(2-tert-butyl-5-(3-(2,3-dichloro-4-fluorophenyl)ureido)thiophene-4-carbonyl)-2-methyl-3-oxopiperazin-2-yl)acetate;
2-(1-(2-tert-Butyl-5-(3-(2,3-dichlorophenyl)ureido)thiophene-4-carbonyl)-2-methyl-3-oxopiperazin-2-yl)acetic acid;
1-(3-(2-(2-Amino-2-oxoethyl)-2-methyl-3-oxopiperazine-1-carbonyl)-5-tert-butylthiophen-2-yl)-3-(2,3-dichlorophenyl)urea;
1-(5-tert-Butyl-3-(2-(2-hydroxyethyl)-2-methyl-3-oxopiperazine-1-carbonyl)thiophen-2-yl)-3-(2,3-dichloro-4-fluorophenyl)urea;
3-(4-(2-tert-Butyl-5-(3-(2,3-dichlorophenyl)ureido)thiophene-4-carbonyl)-3,3-dimethyl-2-oxopiperazin-1-yl)propanoic acid;
1-(5-tert-Butyl-3-(1-((2,2-dimethyl-1,3-dioxolan-4-yl)methyl)-3,3-dimethyl-2-oxopiperazine-4-carbonyl)thiophen-2-yl)-3-(2,3-dichlorophenyl)urea;
1-(5-tert-Butyl-3-(1-(2,3-dihydroxypropyl)-3,3-dimethyl-2-oxopiperazine-4-carbonyl)thiophen-2-yl)-3-(2,3-dichlorophenyl)urea;

(S)-1-(5-tert-Butyl-3-(2-(methylcarbamoyl)pyrrolidine-1-carbonyl)thiophen-2-yl)-3-(2,3-dichloro-4-(difluoromethoxy)phenyl)urea;

(S)-1-(5-tert-Butyl-3-(2-oxo-3-phenethylpiperazine-4-carbonyl)thiophen-2-yl)-3-(2,3-dichlorophenyl)urea;

1-(5-tert-Butyl-3-(2-ethyl-3-oxopiperazine-1-carbonyl)thiophen-2-yl)-3-(2,3-dichloro-4-fluorophenyl)urea;

1-(5-tert-Butyl-3-(4,4-dioxy-4-thiomorpholine-1-carbonyl)thiophen-2-yl)-3-(2,3-dichloro-4-fluorophenyl)urea;

1-(5-tert-Butyl-3-(1,1-dioxy-1-thia-2,5-diazepan-1-one-5-carbonyl)thiophen-2-yl)-3-(2,3-dichloro-4-fluorophenyl)urea;

1-(5-tert-butyl-3-(2-ethyl-2-methyl-3-oxopiperazine-1-carbonyl)thiophen-2-yl)-3-(2-chloro-4-fluorophenyl)urea;

1-(5-tert-butyl-3-(spiro[4.5]-1,4-diazedecan-5-one-1-carbonyl)thiophen-2-yl)-3-(2,3-dichlorophenyl)urea;

1-(5-tert-Butyl-3-(1-(2-(dimethylamino)ethyl)-3-ethyl-3-methyl-2-oxopiperazine-4-carbonyl)thiophen-2-yl)-3-(2,3-dichloro-4-fluorophenyl)urea;

1-(5-tert-Butyl-3-(1-(2-(dimethylamino)ethyl)-3,3-dimethyl-2-oxopiperazine-4-carbonyl)thiophen-2-yl)-3-(2-chloro-4-fluorophenyl)urea;

1-(5-tert-Butyl-3-(spiro[3.5]-1,4-diazenon-5-one-1-carbonyl)thiophen-2-yl)-3-(2,3-dichloro-4-fluorophenyl)urea;

1-(5-tert-Butyl-3-(2-(hydroxymethyl)-6-oxopiperazine-4-carbonyl)thiophen-2-yl)-3-(2,3-dichlorophenyl)urea;

1-(5-tert-Butyl-2-(5-oxo-1,4-diazepane-1-carbonyl)-1H-pyrrol-3-yl)-3-(2,3-dichlorophenyl)urea;

1-(5-tert-Butyl-2-(1-(2-(dimethylamino)ethyl)-7-oxo-1,4-diazepane-4-carbonyl)-1H-pyrrol-3-yl)-3-(2,3-dichloro-4-fluorophenyl)urea;

1-(5-tert-Butyl-2-(1-(2-(dimethylamino)ethyl)-7-oxo-1,4-diazepane-4-carbonyl)-1H-pyrrol-3-yl)-3-(2,3-dichlorophenyl)urea;

1-(5-tert-Butyl-3-(1-(2-(dimethylamino)ethyl)-7-oxo-1,4-diazepane-4-carbonyl)thiophen-2-yl)-3-(2-chloro-4-fluorophenyl)urea;

1-(5-tert-Butyl-3-(3-ethyl-1,3-dimethyl-2-oxopiperazine-4-carbonyl)thiophen-2-yl)-3-(2,3-dichlorophenyl)urea;

Methyl 2-(4-(2-tert-butyl-5-(3-(2,3-dichloro-4-fluorophenyl)ureido)thiophene-4-carbonyl)-3,3-dimethyl-2-oxopiperazin-1-yl)acetate;

1-(5-tert-Butyl-3-(1-(2-(hydroxyamino)-2-oxoethyl)-3,3-dimethyl-2-oxopiperazine-4-carbonyl)thiophen-2-yl)-3-(2,3-dichloro-4-fluorophenyl)urea;

1-(5-tert-Butyl-3-(5-oxo-1,4-diazepane-1-carbonyl)thiophen-2-yl)-3-(2-chloro-3,4-difluorophenyl)urea;

1-(5-tert-Butyl-2-(1-(2-(dimethylamino)ethyl)-3,3-dimethyl-2-oxopiperazine-4-carbonyl)thiophen-3-yl)-3-(2-chloro-3,4-difluorophenyl)urea;

1-(5-tert-Butyl-3-(1-(2-(methoxy(methyl)amino)-2-oxoethyl)-3,3-dimethyl-2-oxopiperazine-4-carbonyl)thiophen-2-yl)-3-(2,3-dichlorophenyl)urea;

1-(5-tert-Butyl-3-(2-(2-hydroxyethyl)-2-methyl-3-oxopiperazine-1-carbonyl)thiophen-2-yl)-3-(3-chloro-2-methylphenyl)urea;

1-(5-tert-Butyl-3-(1-(2-(methoxy(methyl)amino)-2-oxoethyl)-3,3-dimethyl-2-oxopiperazine-4-carbonyl)thiophen-2-yl)-3-(2,3-dichloro-4-fluorophenyl)urea;

Ethyl 2-(2-tert-butyl-5-(3-(2,3-dichlorophenyl)ureido)thiophene-4-carboxamido)-2-methylbutanoate;

Methyl 2-(1-(2-tert-butyl-4-(3-(2-chloro-3,4-difluorophenyl)ureido)thiophene-5-carbonyl)-2-methyl-3-oxopiperazin-2-yl)acetate;

1-(5-tert-Butyl-2-(2-(2-hydroxyethyl)-2-methyl-3-oxopiperazine-1-carbonyl)thiophen-3-yl)-3-(2-chloro-3,4-difluorophenyl)urea;

1-(5-tert-Butyl-2-(2-(2-hydroxyethyl)-2-methyl-3-oxopiperazine-1-carbonyl)thiophen-3-yl)-3-(2,3-dichloro-4-fluorophenyl)urea;

1-(5-tert-Butyl-3-(3,3-dimethyl-1-(2-(methylamino)-2-oxoethyl)-2-oxopiperazine-4-carbonyl)thiophen-2-yl)-3-(2,3-dichlorophenyl)urea;

1-(5-tert-Butyl-3-(1-(2-(methoxyamino)-2-oxoethyl)-3,3-dimethyl-2-oxopiperazine-4-carbonyl)thiophen-2-yl)-3-(2,3-dichlorophenyl)urea;

1-(5-tert-Butyl-3-(2-(2-(methoxyamino)-2-oxoethyl)-2-methyl-3-oxopiperazine-1-carbonyl)thiophen-2-yl)-3-(2,3-dichloro-4-fluorophenyl)urea;

1-(5-tert-Butyl-3-(2-(2-(methoxy(methyl)amino)-2-oxoethyl)-2-methyl-3-oxopiperazine-1-carbonyl)thiophen-2-yl)-3-(2,3-dichloro-4-fluorophenyl)urea;

1-(5-tert-Butyl-3-(1-(2-(dimethylamino)-2-oxoethyl)-3,3-dimethyl-2-oxopiperazine-4-carbonyl)thiophen-2-yl)-3-(2,3-dichlorophenyl)urea;

1-(3-(1-(2-amino-2-oxoethyl)-3,3-dimethyl-2-oxopiperazine-4-carbonyl)-5-tert-butylthiophen-2-yl)-3-(2,3-dichlorophenyl)urea;

1-(5-tert-Butyl-2-(2,2-dimethyl-3-oxopiperazine-1-carbonyl)furan-3-yl)-3-(2,3-dichloro-4-fluorophenyl)urea;

1-(5-tert-Butyl-2-(2,2-dimethyl-3-oxopiperazine-1-carbonyl)furan-3-yl)-3-(2,3-dichloro-4-fluorophenyl)urea;

1-(5-tert-butyl-3-(3-hydroxypiperidine-1-carbonyl)thiophen-2-yl)-3-(2,3-dichlorophenyl)urea;

1-(5-tert-Butyl-3-(2-methyl-2-((3-methyl-1,2,4-oxadiazol-5-yl)methyl)-3-oxopiperazine-1-carbonyl)thiophen-2-yl)-3-(2,3-dichloro-4-fluorophenyl)urea;

1-(3-(3-Acetamidopiperidine-1-carbonyl)-5-tert-butylthiophen-2-yl)-3-(2,3-dichlorophenyl)urea;

1-(2,3-Dichloro-4-fluorophenyl)-3-(2-(2,2-dimethyl-3-oxopiperazine-1-carbonyl)-5-(trifluoromethyl)furan-3-yl)urea;

1-(5-tert-Butyl-2-(2,2-dimethyl-3-oxopiperazine-1-carbonyl)-1H-pyrrol-3-yl)-3-(2,3-dichloro-4-fluorophenyl)urea;

1-(5-tert-Butyl-3-(3,3-dimethyl-1-((3-methyl-1,2,4-oxadiazol-5-yl)methyl)-2-oxopiperazine-4-carbonyl)thiophen-2-yl)-3-(2,3-dichlorophenyl)urea;

1-(5-tert-Butyl-2-(2,2-dimethyl-3-oxopiperazine-1-carbonyl)-1H-pyrrol-2-yl)-3-(2,3-dichlorophenyl)urea;

1-(5-tert-Butyl-3-(1,3,3-trimethyl-2-oxopiperazine-4-carbonyl)thiophen-2-yl)-3-(2,3-dichlorophenyl)urea;

Methyl 2-(1-(2-tert-butyl-5-(3-(2,3-dichlorophenyl)ureido)-1H-pyrrole-4-carbonyl)-2-methyl-3-oxopiperazin-2-yl)acetate;

1-(5-tert-Butyl-3-(2-(2-hydroxyethyl)-2-methyl-3-oxopiperazine-1-carbonyl)-1H-pyrrol-2-yl)-3-(2,3-dichlorophenyl)urea;

1-(5-tert-Butyl-3-(3,3-dimethyl-1-((3-methyl-1,2,4-oxadiazol-5-yl)methyl)-2-oxopiperazine-4-carbonyl)thiophen-2-yl)-3-(2,3-dichloro-4-fluorophenyl)urea;

1-(5-tert-Butyl-2-(1,1-dioxy-1-thia-2,5-diazepan-1-one-5-carbonyl)-1H-pyrrol-2-yl)-3-(2,3-dichloro-4-fluorophenyl)urea;

Methyl 2-(1-(2-tert-butyl-4-(3-(2,3-dichloro-4-fluorophenyl)ureido)-1H-pyrrole-5-carbonyl)-2-methyl-3-oxopiperazin-2-yl)acetate;

1-(5-tert-Butyl-1-methyl-3-(1,3,3-trimethyl-2-oxopiperazine-4-carbonyl)-1H-pyrrol-3-yl)-3-(2,3-dichlorophenyl)urea;

1-(Benzo[d][1,3]dioxol-5-yl)-3-(5-tert-butyl-3-(2-oxopiperazine-4-carbonyl)thiophen-2-yl)urea;

1-(5-tert-Butyl-3-(2-(2-hydroxyethyl)-2-methyl-3-oxopiperazine-1-carbonyl)thiophen-2-yl)-3-(3-chloro-2-methoxyphenyl)urea;

1-(5-tert-Butyl-3-(2-(2-hydroxyethyl)-2-methyl-3-oxopiperazine-1-carbonyl)thiophen-2-yl)-3-(2,3-dichlorophenyl)urea;

Methyl 2-(1-(2-tert-butyl-3-(3-(2,3-dichloro-4-fluorophenyl)ureido)-thiophene-5-carbonyl)-2-methyl-3-oxo-4-ethylacetyl-piperazin-2-yl)acetate;

1-(3-(1,3-bis(2-Amino-2-oxoethyl)-3-methyl-2-oxopiperazine-4-carbonyl)-5-tert-butylthiophen-2-yl)-3-(2,3-dichlorophenyl)urea;

1-(3-(1,3-bis(2-(Methoxyamino)-2-oxoethyl)-3-methyl-2-oxopiperazine-4-carbonyl)-5-tert-butylthiophen-2-yl)-3-(2,3-dichlorophenyl)urea;

1-(5-tert-Butyl-3-(2-(2-hydroxyethyl)-2-methyl-3-oxopiperazine-1-carbonyl)thiophen-2-yl)-3-(3-fluoro-2-methylphenyl)urea;

1-(5-tert-Butyl-3-(2-(2-hydroxyethyl)-2-methyl-3-oxopiperazine-1-carbonyl)thiophen-2-yl)-3-(3-fluoro-2-methylphenyl)urea;

1-(3-(2-(2-Amino-2-oxoethyl)-2-methyl-3-oxopiperazine-1-carbonyl)-5-tert-butylthiophen-2-yl)-3-(2,3-dichloro-4-fluorophenyl)urea;

1-(2,3-Dichloro-4-fluorophenyl)-3-(2-(2,2-dimethyl-3-oxopiperazine-1-carbonyl)-5-tert-pentyl-1H-pyrrol-3-yl)urea;

1-(2,3-Dichlorophenyl)-3-(2-(2,2-dimethyl-3-oxopiperazine-1-carbonyl)-5-tert-pentyl-1H-pyrrol-3-yl)urea;

1-(2,3-Dichlorophenyl)-3-(2-(dioxothiomorpholine-4-carbonyl)-5-(trifluoromethyl)phenyl)urea;

1-(2,3-Dichlorophenyl)-3-(3-(dioxothiomorpholine-4-carbonyl)-5-(trifluoromethyl)phenyl)urea;

1-(5-tert-Butyl-3-(5-oxo-1,4-diazepane-1-carbonyl)thiophen-2-yl)-3-(2-tert-butylphenyl)urea;

1-(5-tert-Butyl-3-(5-oxo-1,4-diazepane-1-carbonyl)thiophen-2-yl)-3-(2-methoxyphenyl)urea;

Methyl 2-(4-(2-tert-Butyl-4-(3-(2,3-dichlorophenyl)ureido)-1H-pyrrole-5-carbonyl)-3,3-dimethyl-2-oxopiperazin-1-yl)acetate;

1-(5-tert-Butyl-2-(1-(2-(methoxy(methyl)amino)-2-oxoethyl)-3,3-dimethyl-2-oxopiperazine-4-carbonyl)-1H-pyrrol-3-yl)-3-(2,3-dichlorophenyl)urea;

1-(5-tert-Butyl-2-(2,2-dimethyl-3-oxopiperazine-1-carbonyl)-1-methyl-1H-pyrrol-3-yl)-3-(2,3-dichlorophenyl)urea;

1-(Benzo[d][1,3]dioxol-4-yl)-3-(5-tert-butyl-3-(2-oxopiperazine-4-carbonyl)thiophen-2-yl)urea;

1-(Benzo[d][1,3]dioxol-4-yl)-3-(5-tert-butyl-3-(5-oxo-1,4-diazepane-1-carbonyl)thiophen-2-yl)urea;

1-(5-tert-Butyl-3-(1-(2-(dimethylamino)ethyl)-3-ethyl-3-methyl-2-oxopiperazine-4-carbonyl)thiophen-2-yl)-3-(4-fluorophenyl)urea;

1-(5-tert-Butyl-3-(4,4-dioxy-4-thiomorpholine-1-carbonyl)thiophen-2-yl)-3-(benzo[d][1,3]dioxol-4-yl)urea;

1-(5-tert-Butyl-3-(1-(2-(methoxy(methyl)amino)-2-oxoethyl)-3,3-dimethyl-2-oxopiperazine-4-carbonyl)thiophen-2-yl)-3-(2-chloro-4-fluorophenyl)urea;

1-(5-tert-Butyl-2-(1,1-dioxy-1-thia-2,5-diazepan-1-one-5-carbonyl)furan-3-yl)-3-(2,3-dichlorophenyl)urea;

1-(5-tert-Butyl-3-(2,2-dimethyl-3-oxopiperazine-1-carbonyl)thiophen-2-yl)-3-(4-chlorobenzo[d][1,3]dioxol-5-yl)urea;

1-(Benzo[d][1,3]dioxol-4-yl)-3-(5-tert-butyl-3-(2,2-dimethyl-3-oxopiperazine-1-carbonyl)thiophen-2-yl)urea;

1-(Benzo[d][1,3]dioxol-5-yl)-3-(5-tert-butyl-3-(2,2-dimethyl-3-oxopiperazine-1-carbonyl)thiophen-2-yl)urea;

1-(5-tert-Butyl-3-(3-ethyl-1-(2-(methoxy(methyl)amino)-2-oxoethyl)-3-methyl-2-oxopiperazine-4-carbonyl)thiophen-2-yl)-3-(2,3-dichlorophenyl)urea;

1-(2-(4,4-Dioxy-4-thiomorpholine-1-carbonyl)-4-chloro-5-trifluoromethylphenyl)-3-(2,3-dichlorophenyl)urea;

1-(2-(1-(2-Amino-2-oxoethyl)-3,3-dimethyl-2-oxopiperazine-4-carbonyl)-5-tert-butyl-1H-pyrrol-3-yl)-3-(2,3-dichlorophenyl)urea;

1-(5-tert-Butyl-2-(2-dimethylaminoethyl-1,1-dioxy-1-thia-2,5-diazepan-1-one-5-carbonyl)furan-3-yl)-3-(2,3-dichlorophenyl)urea;

1-(5-tert-Butyl-3-(4,4-dioxy-4-thiomorpholine-1-carbonyl)thiophen-2-yl)-3-(5-chlorobenzo[d][1,3]dioxol-4-yl)urea;

1-(5-tert-Butyl-3-(5-oxo-1,4-diazepane-1-carbonyl)thiophen-2-yl)-3-(4-chlorobenzo[d][1,3]dioxol-5-yl)urea;

Methyl 2-(4-(2-tert-butyl-5-(3-(2,3-dichlorophenyl)ureido)thiophene-4-carbonyl)-3-ethyl-3-methyl-2-oxopiperazin-1-yl)acetate;

1-(5-tert-Butyl-3-(1-(2-(2-(dimethylamino)ethylamino)-2-oxoethyl)-3-ethyl-3-methyl-2-oxopiperazine-4-carbonyl)thiophen-2-yl)-3-(2,3-dichlorophenyl)urea;

1-(5-tert-Butyl-2-(1-(2-(dimethylamino)ethyl)-3,3-dimethyl-2-oxopiperazine-4-carbonyl)-1H-pyrrol-3-yl)-3-(2,3-dichlorophenyl)urea;

1-(5-tert-Butyl-3-(1-(2-(methoxy(methyl)amino)-2-oxoethyl)-3,3-dimethyl-2-oxopiperazine-4-carbonyl)thiophen-2-yl)-3-(2-chloro-3,4-difluorophenyl)urea;

1-(3-(3-(2-Amino-2-oxoethyl)-1,3-dimethyl-2-oxopiperazine-4-carbonyl)-5-tert-butylthiophen-2-yl)-3-(2,3-dichlorophenyl)urea;

1-(3-(3-(2-Amino-2-oxoethyl)-3-methyl-1-((3-methyl-1,2,4-oxadiazol-5-yl)methyl)-2-oxopiperazine-4-carbonyl)-5-tert-butylthiophen-2-yl)-3-(2,3-dichlorophenyl)urea;

1-(4-Chloro-2-(5-oxo-1,4-diazepane-1-carbonyl)-5-(trifluoromethyl)phenyl)-3-(2,3-dichlorophenyl)urea;

1-(5-tert-Butyl-3-(5-oxo-1,4-diazepane-1-carbonyl)thiophen-2-yl)-3-(2-ethylphenyl)urea;

1-(5-tert-Butyl-3-(5-oxo-1,4-diazepane-1-carbonyl)thiophen-2-yl)-3-o-tolylurea;

1-(2-Bromophenyl)-3-(5-tert-butyl-3-(5-oxo-1,4-diazepane-1-carbonyl)thiophen-2-yl)urea;

1-(5-tert-Butyl-3-(5-oxo-1,4-diazepane-1-carbonyl)thiophen-2-yl)-3-(2-isopropylphenyl)urea;

1-(5-tert-Butyl-3-(5-oxo-1,4-diazepane-1-carbonyl)thiophen-2-yl)-3-(2-(trifluoromethoxy)phenyl)urea;

1-(5-tert-Butyl-3-(5-oxo-1,4-diazepane-1-carbonyl)thiophen-2-yl)-3-(2-iodophenyl)urea;

1-(5-tert-Butyl-3-(5-oxo-1,4-diazepane-1-carbonyl)thiophen-2-yl)-3-(2-chlorophenyl)urea;

1-(5-tert-Butyl-3-(5-oxo-1,4-diazepane-1-carbonyl)thiophen-2-yl)-3-(2-(trifluoromethyl)phenyl)urea;

1-(5-tert-Butyl-3-(2,2-dimethyl-3-oxopiperazine-1-carbonyl)thiophen-2-yl)-3-(2-chlorophenyl)urea;

1-(5-tert-Butyl-3-(1-(2-(dimethylamino)ethyl)-3,3-dimethyl-2-oxopiperazine-4-carbonyl)thiophen-2-yl)-3-(2-tert-butylphenyl)urea;

1-(5-tert-Butyl-3-(1-(2-(dimethylamino)ethyl)-3,3-dimethyl-2-oxopiperazine-4-carbonyl)thiophen-2-yl)-3-ortho-tolylurea;

1-(5-tert-Butyl-3-(1-(2-(dimethylamino)ethyl)-3,3-dimethyl-2-oxopiperazine-4-carbonyl)thiophen-2-yl)-3-(2-ethylphenyl)urea;

1-(5-tert-Butyl-3-(1-(2-(dimethylamino)ethyl)-3,3-dimethyl-2-oxopiperazine-4-carbonyl)thiophen-2-yl)-3-(2-(trifluoromethyl)phenyl)urea;

1-(5-tert-Butyl-3-(1-(2-(dimethylamino)ethyl)-3,3-dimethyl-2-oxopiperazine-4-carbonyl)thiophen-2-yl)-3-(2-methoxyphenyl)urea;
1-(5-tert-Butyl-3-(1-(2-(dimethylamino)ethyl)-7-oxo-1,4-diazepane-4-carbonyl)thiophen-2-yl)-3-ortho-tolylurea;
1-(5-tert-Butyl-3-(1-(2-(dimethylamino)ethyl)-7-oxo-1,4-diazepane-4-carbonyl)thiophen-2-yl)-3-(2-ethylphenyl)urea;
1-(5-tert-Butyl-3-(1-(2-(dimethylamino)ethyl)-7-oxo-1,4-diazepane-4-carbonyl)thiophen-2-yl)-3-(2-tert-butylphenyl)urea;
1-(5-tert-Butyl-3-(1-(2-(dimethylamino)ethyl)-7-oxo-1,4-diazepane-4-carbonyl)thiophen-2-yl)-3-(2-methoxyphenyl)urea;
1-(5-tert-Butyl-3-(1-(2-(dimethylamino)ethyl)-7-oxo-1,4-diazepane-4-carbonyl)thiophen-2-yl)-3-(2-chlorophenyl)urea;
1-(5-tert-Butyl-3-(1-(2-(dimethylamino)ethyl)-7-oxo-1,4-diazepane-4-carbonyl)thiophen-2-yl)-3-(2-(trifluoromethyl)phenyl)urea;
1-(5-tert-Butyl-3-(1-(methylsulfonyl)piperazine-4-carbonyl)thiophen-2-yl)-3-(2,3-dichlorophenyl)urea;
1-(3-(1-Acetylpiperazine-4-carbonyl)-5-tert-butylthiophen-2-yl)-3-(2,3-dichlorophenyl)urea;
1-(3-(1-Acetyl-1,4-diazepane-4-carbonyl)-5-tert-butylthiophen-2-yl)-3-(2,3-dichlorophenyl)urea;
1-(5-tert-Butyl-3-(1-(methylsulfonyl)-1,4-diazepane-4-carbonyl)thiophen-2-yl)-3-(2,3-dichlorophenyl)urea;
1-(5-tert-Butyl-3-(3-ethyl-3-methyl-1-(2-(2-morpholinoethylamino)-2-oxoethyl)-2-oxopiperazine-4-carbonyl)thiophen-2-yl)-3-(2,3-dichlorophenyl)urea;
1-(5-tert-Butyl-3-(1-(2-(2-(dimethylamino)ethylamino)-2-oxoethyl)-3-ethyl-3-methyl-2-oxopiperazine-4-carbonyl)thiophen-2-yl)-3-(2,3-dichloro-4-fluorophenyl)urea;
1-(5-tert-Butyl-2-(2-methyl-1,1-dioxy-1-thia-2,5-diazepan-1-one-5-carbonyl)furan-3-yl)-3-(2,3-dichlorophenyl)urea;
1-(5-tert-Butyl-3-(1-(2-(2-(dimethylamino)ethylamino)-2-oxoethyl)-3,3-dimethyl-2-oxopiperazine-4-carbonyl)thiophen-2-yl)-3-(2,3-dichlorophenyl)urea;
1-(5-tert-Butyl-3-(1-(2-(2-(dimethylamino)ethylamino)-2-oxoethyl)-3,3-dimethyl-2-oxopiperazine-4-carbonyl)thiophen-2-yl)-3-(2,3-dichloro-4-fluorophenyl)urea;
1-(5-tert-Butyl-3-(3-ethyl-3-methyl-2-oxo-1-(2-oxo-2-(2-(pyrrolidin-1-yl)ethylamino)ethyl)piperazine-4-carbonyl)thiophen-2-yl)-3-(2,3-dichlorophenyl)urea;
1-(5-tert-Butyl-3-(3-ethyl-3-methyl-1-(2-(4-methylpiperazin-1-yl)-2-oxoethyl)-2-oxopiperazine-4-carbonyl)thiophen-2-yl)-3-(2,3-dichlorophenyl)urea;
Ethyl 1-(2-tert-butyl-5-(3-(2,3-dichlorophenyl)ureido)thiophene-4-carbonyl)-2-methyl-3-oxopiperazine-2-carboxylate;
1-(3-(1-(3-(Bis(2-hydroxyethyl)amino)-3-oxopropyl)-3,3-dimethyl-2-oxopiperazine-4-carbonyl)-5-tert-butylthiophen-2-yl)-3-(2,3-dichlorophenyl)urea;
2-(4-{5-tert-Butyl-2-[3-(2-chloro-4-fluorophenyl)ureido]thiophene-3-carbonyl}-7-oxo-[1,4]diazepan-1-yl)-N-methoxy-N-methylacetamide;
2-(4-{5-tert-Butyl-2-[3-(2-chloro-3,4-difluorophenyl)ureido]thiophene-3-carbonyl}-7-oxo-[1,4]diazepan-1-yl)-N-methoxy-N-methylacetamide;
2-(4-{5-tert-Butyl-2-[3-(2-chloro-3,4-difluorophenyl)ureido]thiophene-3-carbonyl}-7-oxo-[1,4]diazepan-1-yl)-N-(2-dimethylaminoethyl)acetamide;
1-(5-tert-Butyl-3-(1-(2-(dimethylamino)ethyl)-3,3-dimethyl-2-oxopiperazine-4-carbonyl)thiophen-2-yl)-3-(2-chloropyridin-3-yl)urea;
1-(5-tert-Butyl-3-(1-(2-(dimethylamino)ethyl)-7-oxo-1,4-diazepane-4-carbonyl)thiophen-2-yl)-3-(2-chloropyridin-3-yl)urea;
1-(5-tert-Butyl-3-(1-(2-(dimethylamino)ethyl)-3,3-dimethyl-2-oxopiperazine-4-carbonyl)thiophen-2-yl)-3-(2-chloro-3-methylphenyl)urea;
1-(5-tert-Butyl-3-(1-(2-(dimethylamino)ethyl)-7-oxo-1,4-diazepane-4-carbonyl)thiophen-2-yl)-3-(2-chloro-3-methylphenyl)urea;
1-(5-tert-butyl-3-(2,2-dimethyl-3-oxopiperazine-1-carbonyl)thiophen-2-yl)-3-o-tolylurea;
1-(5-tert-butyl-3-(2,2-dimethyl-3-oxopiperazine-1-carbonyl)thiophen-2-yl)-3-(2-ethylphenyl)urea;
1-(5-tert-Butyl-3-(2,2-dimethyl-3-oxopiperazine-1-carbonyl)thiophen-2-yl)-3-(2-tert-butylphenyl)urea;
1-(5-tert-Butyl-3-(1-(2-(dimethylamino)ethyl)-3,3-dimethyl-2-oxopiperazine-4-carbonyl)thiophen-2-yl)-3-(2-chloro-3-methoxyphenyl)urea;
1-(5-tert-Butyl-3-(1-(2-(dimethylamino)ethyl)-7-oxo-1,4-diazepane-4-carbonyl)thiophen-2-yl)-3-(2-chloro-3-methoxyphenyl)urea;
1-(5-tert-Butyl-3-(1-(2-((2,2-dimethyl-1,3-dioxolan-4-yl)methylamino)-2-oxoethyl)-3,3-dimethyl-2-oxopiperazine-4-carbonyl)thiophen-2-yl)-3-(2,3-dichlorophenyl)urea;
1-(5-tert-Butyl-3-(1-(2-(2,3-dihydroxypropylamino)-2-oxoethyl)-3,3-dimethyl-2-oxopiperazine-4-carbonyl)thiophen-2-yl)-3-(2,3-dichlorophenyl)urea;
1-(5-tert-Butyl-2-(1-(2-(2-(dimethylamino)ethylamino)-2-oxoethyl)-3-ethyl-3-methyl-2-oxopiperazine-4-carbonyl)thiophen-3-yl)-3-(2,3-dichlorophenyl)urea;
1-(5-tert-Butyl-2-(1-(2-(2-(dimethylamino)ethylamino)-2-oxoethyl)-3,3-dimethyl-2-oxopiperazine-4-carbonyl)thiophen-3-yl)-3-(2,3-dichlorophenyl)urea;
1-(5-tert-Butyl-3-(3,3-dimethyl-2-oxo-1-(2-oxo-2-(propylamino)ethyl)piperazine-4-carbonyl)thiophen-2-yl)-3-(2,3-dichlorophenyl)urea;
1-(5-tert-Butyl-3-(1-(2-(methoxymethoxy)ethyl)-3,3-dimethyl-2-oxopiperazine-4-carbonyl)thiophen-2-yl)-3-(2,3-dichlorophenyl)urea;
1-(5-tert-Butyl-3-(1-(2-hydroxyethyl)-3,3-dimethyl-2-oxopiperazine-4-carbonyl)thiophen-2-yl)-3-(2,3-dichlorophenyl)urea;
1-(5-tert-Butyl-3-(1,3,3-trimethylpiperazine-4-carbonyl)thiophen-2-yl)-3-(2,3-dichlorophenyl)urea;
1-(5-tert-butyl-3-(5-oxo-1,4-diazepane-1-carbonyl)thiophen-2-yl)-3-(3,5-dichloropyridin-4-yl)urea;
1-(5-tert-Butyl-3-(1-(2-(2-(dimethylamino)ethylamino)-2-oxoethyl)piperazine-4-carbonyl)thiophen-2-yl)-3-(2,3-dichlorophenyl)urea;
1-(2-tert-Butyl-4-(2,2-dimethyl-3-oxopiperazine-1-carbonyl)thiazol-5-yl)-3-(2,3-dichlorophenyl)urea;
1-(5-tert-butyl-3-(1-(2-(3-(dimethylamino)propylamino)-2-oxoethyl)-3,3-dimethyl-2-oxopiperazine-4-carbonyl)thiophen-2-yl)-3-(2,3-dichlorophenyl)urea;
1-(5-tert-butyl-3-(5-oxo-1,4-diazepane-1-carbonyl)-1H-pyrrol-2-yl)-3-(2,3-dichlorophenyl)urea;
2-(4-{5-tert-Butyl-2-[3-(2-chloro-4-fluoro-phenyl)-ureido]-thiophene-3-carbonyl}-3,3-dimethyl-2-oxo-piperazin-1-yl)-N-(2-dimethylamino-ethyl)-acetamide;
Methyl 2-(4-(2-tert-butyl-5-(3-(2,3-dichlorophenyl)ureido)thiazole-4-carbonyl)-3,3-dimethyl-2-oxopiperazin-1-yl)acetate;
Methyl 4-(3-(5-tert-butyl-2-(2,2-dimethyl-3-oxopiperazine-1-carbonyl)thiophen-3-yl)ureido)-3-chlorobenzoate;

(2-(4-{5-tert-Butyl-3-[3-(2-chloro-3,4-difluoro-phenyl)-ureido]-thiophene-2-carbonyl}-3,3-dimethyl-2-oxo-piperazin-1-yl)-N-(2-dimethylamino-ethyl)-acetamide);

2-(4-{5-tert-Butyl-3-[3-(2,3-dichloro-pyridin-4-yl)-ureido]-thiophene-2-carbonyl}-3,3-dimethyl-2-oxo-piperazin-1-yl)-N-(2-dimethylamino-ethyl)-acetamide;

1-(5-tert-butyl-2-(2,2-dimethyl-3-oxopiperazine-1-carbonyl)thiophen-3-yl)-3-(2-chloro-6-methylphenyl)urea;

1-(5-tert-butyl-3-(1-(3-(4-methoxyphenyl)propanoyl)-piperazine-4-carbonyl)thiophen-2-yl)-3-(2,3-dichlorophenyl)urea;

1-(5-tert-butyl-3-(1-(2-(4-methoxyphenyl)acetyl)piperazine-4-carbonyl)thiophen-2-yl)-3-(2,3-dichlorophenyl)urea;

tert-butyl 4-(2-tert-butyl-5-(3-(2,3-dichlorophenyl)ureido)-thiophene-4-carbonyl)piperazine-1-carboxylate;

tert-butyl 4-(2-tert-butyl-5-(3-(2,3-dichlorophenyl)ureido)-thiophene-4-carbonyl)-3,3-dimethylpiperazine-1-carboxylate;

1-(5-tert-butyl-3-(piperazine-4-carbonyl)thiophen-2-yl)-3-(2,3-dichlorophenyl)urea;

methyl 2-(4-(2-tert-butyl-5-(3-(2,3-dichlorophenyl)ureido)-thiophene-4-carbonyl)piperazin-1-yl)acetate;

1-(5-tert-butyl-3-(1-(2-(2-(diethylamino)ethylamino)-2-oxoethyl)-3,3-dimethyl-2-oxopiperazine-4-carbonyl)thiophen-2-yl)-3-(2,3-dichlorophenyl)urea;

1-(5-tert-butyl-3-(1-(2-((2-(dimethylamino)ethyl)(methyl)amino)-2-oxoethyl)-3,3-dimethyl-2-oxopiperazine-4-carbonyl)thiophen-2-yl)-3-(2,3-dichlorophenyl)urea;

1-(5-tert-butyl-3-(1-(2-(cyclopropylmethylamino)-2-oxoethyl)-3,3-dimethyl-2-oxopiperazine-4-carbonyl)thiophen-2-yl)-3-(2,3-dichlorophenyl)urea;

1-(2-tert-butyl-4-(1-(2-(2-(dimethylamino)ethylamino)-2-oxoethyl)-3,3-dimethyl-2-oxopiperazine-4-carbonyl)thiazol-5-yl)-3-(2,3-dichlorophenyl)urea;

1-(5-tert-butyl-3-((2,2,2-trifluoroethyl)carbamoyl)thiophen-2-yl)-3-(2,3-dichlorophenyl)urea;

1-(5-tert-butyl-3-(1-(5-(dimethylamino)pentyl)-3,3-dimethyl-2-oxopiperazine-4-carbonyl)thiophen-2-yl)-3-(2,3-dichlorophenyl)urea;

1-(5-tert-butyl-3-(3,3-dimethyl-2-oxo-1-(2-oxo-2-(2,2,2-trifluoroethylamino)ethyl)piperazine-4-carbonyl)thiophen-2-yl)-3-(2,3-dichlorophenyl)urea;

1-(5-tert-butyl-2-(2,2-dimethyl-3-oxopiperazine-1-carbonyl)thiophen-3-yl)-3-(2-chloro-5-methoxyphenyl)urea;

2-(4-{5-tert-Butyl-3-[3-(2,3-dichloro-4-fluoro-phenyl)-ureido]-thiophene-2-carbonyl}-3,3-dimethyl-2-oxo-piperazin-1-yl)-N-(2-dimethylamino-ethyl)-acetamide;

1-(5-tert-Butyl-3-(2,2-dimethyl-3-oxopiperazine-1-carbonyl)thiophen-2-yl)-3-(3,5-dichloropyridin-4-yl)urea;

1-(5-tert-Butyl-3-(2,2-dimethyl-3-oxopiperazine-1-carbonyl)thiophen-2-yl)-3-(3-chloropyridin-4-yl)urea;

1-(5-tert-Butyl-3-(1-(2-(dimethylamino)ethyl)-3,3-dimethyl-2-oxopiperazine-4-carbonyl)thiophen-2-yl)-3-(3-chloropyridin-4-yl)urea;

1-(5-tert-Butyl-3-(2,2-dimethyl-3-oxopiperazine-1-carbonyl)thiophen-2-yl)-3-(2-chloro-3-methylphenyl)urea;

1-(5-tert-Butyl-3-(1-(2-(2-(dimethylamino)ethylamino)-2-oxoethyl)-3-ethyl-3-methyl-2-oxopiperazine-4-carbonyl)thiophen-2-yl)-3-(2-chloro-4-fluorophenyl)urea;

1-(5-tert-Butyl-3-(1-(2-(2-(dimethylamino)ethylamino)-2-oxoethyl)-3-ethyl-3-methyl-2-oxopiperazine-4-carbonyl)thiophen-2-yl)-3-(2-(trifluoromethyl)phenyl)urea;

1-(5-tert-Butyl-3-(1-(2-(2-(dimethylamino)ethylamino)-2-oxoethyl)-3,3-dimethyl-2-oxopiperazine-4-carbonyl)-1H-pyrrol-2-yl)-3-(2,3-dichlorophenyl)urea;

methyl 4-(2-tert-butyl-5-(3-(2,3-dichlorophenyl)ureido)-thiophene-4-carbonyl)piperazine-1-carboxylate;

1-(5-tert-butyl-3-(1-(dimethylcarbamoyl)piperazine-4-carbonyl)thiophen-2-yl)-3-(2,3-dichlorophenyl)urea;

1-(5-tert-butyl-3-(1-(morpholine-4-carbonyl)piperazine-4-carbonyl)thiophen-2-yl)-3-(2,3-dichlorophenyl)urea;

N-(5-tert-Butyl-3-(thiomorpholine-1,1-dioxide-4-carbonyl)thiophen-2-yl)-2-(2,3-dichlorophenyl)acetamide;

1-(5-tert-Butyl-3-(2,2-dimethyl-3-oxopiperazine-1-carbonyl)thiophen-2-yl)-3-(2-chloropyridin-3-yl)urea;

1-(5-tert-Butyl-3-(5-oxo-1,4-diazepane-1-carbonyl)thiophen-2-yl)-3-(2-chloropyridin-3-yl)urea;

1-(5-tert-Butyl-3-(1-(2-(dimethylamino)ethyl)-3,3-dimethyl-2-oxopiperazine-4-carbonyl)thiophen-2-yl)-3-(3,5-dichloropyridin-4-yl)urea;

1-(5-tert-Butyl-3-(1-(2-(dimethylamino)ethyl)-7-oxo-1,4-diazepane-4-carbonyl)thiophen-2-yl)-3-(3,5-dichloropyridin-4-yl)urea;

and pharmaceutically acceptable salts thereof.

The present invention also includes a salt of a compound according to Formula I. The term salt refers to an acid- and/or base-addition salt of a compound according to Formula I. Acid-addition salts can be formed by adding an appropriate acid to the compound according to Formula I. Base-addition salts can be formed by adding an appropriate base to the compound according to Formula I. Said acid or base does not substantially degrade, decompose, or destroy said compound according to Formula I. Examples of suitable salts include hydrochloride, hydrobromide, acetate, fumrate, maleate, oxalate, and succinate salts. Other suitable salts include sodium, potassium, carbonate, and tromethamine salts.

It is also to be understood that the present invention is considered to encompass stereoisomers as well as optical isomers, e.g., mixtures of enantiomers as well as individual enantiomers and diastereomers, which arise as a consequence of structural asymmetry in selected compounds of the present series.

The compounds of Formula I may also be solvated, including hydrated. Hydration may occur during manufacturing of the compounds or compositions comprising the compounds, or the hydration may occur over time due to the hygroscopic nature of the compounds.

Certain compounds within the scope of Formula I may be derivatives referred to as "prodrugs." The expression "prodrug" denotes a derivative of a known direct acting drug, which derivative has enhanced delivery characteristics and therapeutic value as compared to the drug, and is transformed into the active drug by an enzymatic or chemical process. Prodrugs are derivatives of the compounds of the invention which have metabolically cleavable groups and become by solvolysis or under physiological conditions the compounds of the invention which are pharmaceutically active in vivo. For example, ester derivatives of compounds of this invention are often active in vivo, but not in vitro. Other derivatives of the compounds of this invention have activity in both their acid and acid derivative forms, but the acid derivative form often offers advantages of solubility, tissue compatibility, or delayed release in the mammalian organism (see, Bundgard, H., *Design of Prodrugs*, pp. 7-9, 21-24, Elsevier, Amsterdam 1985). Prodrugs include acid derivatives well known to practitioners of the art, such as, for example, esters prepared by reaction of the parent acid with a suitable alcohol, or amides prepared by reaction of the parent acid compound with an amine. Simple aliphatic or aromatic esters derived from acidic groups pendent on the compounds of this invention are preferred prodrugs. In some cases, it is desirable to prepare double ester type prodrugs such as (acyloxy) alkyl esters or ((alkoxycarbonyl)oxy)alkyl esters.

When any variable occurs more than one time in any constituent or in Formula I, its definition on each occurrence is independent of its definition at every other occurrence, unless otherwise indicated. Also, combinations of substituents and/or variables are permissible only if such combinations result in stable compounds.

The term "alkyl," as used herein by itself or as part of another group, refers to both straight and branched chain radicals of up to 10 carbons, unless the chain length is limited thereto, such as methyl, ethyl, propyl, isopropyl, butyl, 1-methylpropyl, 2-methylpropyl, pentyl, 1-methylbutyl, isobutyl, pentyl, t-amyl ($CH_3CH_2(CH_3)_2C-$), hexyl, isohexyl, heptyl, octyl, or decyl.

The term "alkenyl," as used herein by itself or as part of another group, refers to a straight or branched chain radical of 2-10 carbon atoms, unless the chain length is limited thereto, including, but not limited to, ethenyl, 1-propenyl, 2-propenyl, 2-methyl-1-propenyl, 1-butenyl, 2-butenyl, 3-butenyl, pentenyl, 1-hexenyl, and 2-hexenyl.

The term "alkynyl," as used herein by itself or as part of another group, refers to a straight or branched chain radical of 2-10 carbon atoms, unless the chain length is limited thereto, wherein there is at least one triple bond between two of the carbon atoms in the chain, including, but not limited to, ethynyl, 1-propynyl, 2-propynyl, 1-butynyl, 2-butynyl, 1-methyl-2-butynyl, 1-methyl-3-butynyl, 2-methyl-3-pentynyl, hexynyl, and heptynyl.

In instances herein where there is an alkenyl or alkynyl moiety as a substituent group, the unsaturated linkage, i.e., the vinylenyl or acetylenyl linkage, is preferably not directly attached to a nitrogen, oxygen or sulfur moiety.

The term "cycloalkyl," as used herein by itself or as part of another group, refers to cycloalkyl groups containing 3 to 14, preferably 3 to 10, carbon atoms. Typical examples are cyclopropyl, cyclobutyl, cyclopentyl, cyclohexyl, and bicyclo[2.2.2]octyl.

The term "cycloalkenyl," as used herein by itself or as part of another group, refers to cycloalkenyl groups containing 3 to 14, preferably 3 to 10, carbon atoms and 1 to 3 carbon-carbon double bonds. Typical examples include cyclopropenyl, cyclobutenyl, cyclopentenyl, cyclohexenyl, cycloheptenyl, and cyclohexdienyl.

The term "alkylene," as used herein by itself or as a part of another group, refers to a diradical of an unbranched saturated hydrocarbon chain, having, unless otherwise indicated, from 1 to 15 carbon atoms, preferably 1 to 10 carbon atoms and more preferably 1 to 6 carbon atoms. This term is exemplified by groups such as methylene ($-CH_2-$), ethylene ($-CH_2CH_2-$), propylene ($-CH_2CH_2CH_2-$), butylene, and the like.

The term "alkenylene," as used herein by itself or part of another group, refers to a diradical of an unbranched, unsaturated hydrocarbon chain, having, unless otherwise indicated, from 2 to 15 carbon atoms, preferably 1 to 10 carbon atoms, more preferably 1 to 6 carbon atoms, and having at least 1 and preferably from 1 to 6 sites of vinyl unsaturation. saturation. This term is exemplified by groups such as ethenylene ($-CH=CH-$), propenylene ($-CH_2CH=CH-$, $-CH=CHCH_2-$), and the like.

The term "alkoxy," as used herein by itself or as part of another group, refers to any of the above alkyl groups linked to an oxygen atom. Typical examples are methoxy, ethoxy, isopropyloxy, sec-butyloxy, and t-butyloxy.

The term "alkenyloxy," as used herein by itself or as part of another group, refers to any of the above alkenyl groups linked to an oxygen atom. Typical examples include ethenyloxy, propenyloxy, butenyloxy, pentenyloxy, and hexenyloxy.

The term "aryl," as used herein by itself or as part of another group, refers to monocyclic or bicyclic aromatic groups containing from 6 to 14 carbons in the ring portion, preferably 6-10 carbons in the ring portion. Typical examples include phenyl, naphthyl, anthracenyl, or fluorenyl.

The term "aralkyl" or "arylalkyl," as employed herein by itself or as part of another group, refers to $C_{1-6}$ alkyl groups as defined above having an aryl substituent, such as benzyl, phenylethyl, or 2-naphthylmethyl.

The term "heteroaryl," as used herein as used herein by itself or as part of another group, refers to groups having 5 to 14 ring atoms; 6, 10, or 14 π electrons shared in a cyclic array; and containing carbon atoms and 1, 2, 3, or 4 oxygen, nitrogen, or sulfur atoms. Examples of heteroaryl groups are: thienyl, benzo[b]thienyl, naphtho[2,3-b]thienyl, thianthrenyl, furyl, pyranyl, isobenzofuranyl, benzoxazolyl, chromenyl, xanthenyl, phenoxathinyl, 2H-pyrrolyl, pyrrolyl, imidazolyl, pyrazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalazinyl, naphthyridinyl, quinazolinyl, cinnolinyl, pteridinyl, 4αH-carbazolyl, carbazolyl, β-carbolinyl, phenanthridinyl, acridinyl, perimidinyl, phenanthrolinyl, phenazinyl, isothiazolyl, phenothiazinyl, isoxazolyl, furazanyl, phenoxazinyl, and tetrazolyl groups. Further heteroaryls are described in A. R. Katritzky and C. W. Rees, eds., *Comprehensive Heterocyclic Chemistry: The Structure, Reactions, Synthesis and Use of Heterocyclic Compounds*, Vol. 1-8, Pergamon Press, NY (1984).

The term "alkylenedioxy," as used herein by itself or as part of another group, refers for a ring and is especially $C_{1-4}$ alkylenedioxy. Alkylenedioxy groups may optionally be substituted with halogen (especially fluorine). Typical examples include methylenedioxy ($-OCH2O-$) or difluoromethylenedioxy ($-OCF_2O-$).

The term "halogen" or "halo," as used herein by itself or as part of another group, refers to chlorine, bromine, fluorine or iodine.

The term "monoalkylamine" or "monoalkylamino," as used herein by itself or as part of another group, refers to the group $NH_2$ wherein one hydrogen has been replaced by an alkyl group, as defined above.

The term "dialkylamine" or "dialkylamino," as used herein by itself or as part of another group refers to the group, $NH_2$ wherein both hydrogens have been replaced by alkyl groups, as defined above.

The term "hydroxyalkyl," as used herein as used herein by itself or as part of another group, refers to any of the above alkyl groups wherein one or more hydrogens thereof are substituted by one or more hydroxyl moieties.

The term "acylamino," as used herein refers to a moiety of the formula $-NR^aC(O)R^b$, wherein $R^a$ and $R^b$ are independently hydrogen or alkyl groups is defined above.

The term "haloalkyl," as used herein as used herein by itself or as part of another group, refers to any of the above alkyl groups wherein one or more hydrogens thereof are substituted by one or more halo moieties. Typical examples include fluoromethyl, trifluoromethyl, trichloroethyl, and trifluoroethyl.

The term "haloalkenyl," as used herein as used herein by itself or as part of another group, refers to any of the above alkenyl groups wherein one or more hydrogens thereof are substituted by one or more halo moieties. Typical examples include fluoroethenyl, difluoroethenyl, and trichloroethenyl.

The term "haloalkynyl," as used herein as used herein by itself or as part of another group, refers to any of the above alkynyl groups wherein one or more hydrogens thereof are substituted by one or more halo moieties. Typical examples include fluoroethynyl, trifluoroethynyl, and trichloroethynyl.

The term "carboxyalkyl," as used herein as used herein by itself or as part of another group, refers to any of the above alkyl groups wherein one or more hydrogens thereof are substituted by one or more carboxylic acid moieties.

The term "heteroatom" is used herein to mean an oxygen atom ("O"), a sulfur atom ("S") or a nitrogen atom ("N"). It will be recognized that when the heteroatom is nitrogen, it may form an $NR^aR^b$ moiety, wherein $R^a$ and $R^b$ are, independently from one another, hydrogen or alkyl, or together with the nitrogen to which they are bound, form a saturated or unsaturated 5-, 6-, or 7-membered ring.

The term "oxy" means an oxygen (O) atom.

The term "thio" means a sulfur (S) atom.

Generally and unless defined otherwise, the phrase "optionally substituted" used herein refers to a group or groups being optionally substituted with one or more substituents independently selected from the group consisting of amino, hydroxy, nitro, halogen, cyano, thiol, $C_{1-6}$ alkyl, $C_{2-6}$ alkenyl, $C_{2-6}$ alkynyl, $C_{3-6}$ cycloalkyl, $C_{3-6}$ cycloalkenyl, $C_{3-6}$ cycloheteralkyl, $C_{3-6}$ cycloheteroalkenyl, $C_{6-10}$ aryl, 5-10 membered heteroaryl, $C_{1-6}$ alkoxy, $C_{3-6}$ alkenyloxy, $C_{1-6}$ alkylthio, $C_{1-6}$ alkylenedioxy, $C_{1-6}$ alkoxy($C_{1-6}$)alkyl, $C_{6-10}$ aryl($C_{1-6}$)alkyl, $C_{6-10}$ aryl($C_{2-6}$)alkenyl, $C_{6-10}$ aryl($C_{1-6}$) alkoxy, $C_{1-6}$ aminoalkyl, $C_{1-6}$ aminoalkoxy, $C_{1-6}$ hydroxyalkyl, $C_{2-6}$ hydroxyalkoxy, mono($C_{1-4}$)alkylamino, di($C_{1-4}$) alkylamino, $C_{2-6}$ alkylcarbonylamino, $C_{2-6}$ alkoxycarbonylamino, $C_{2-6}$ alkoxycarbonyl, carboxy, ($C_{1-6}$) alkoxy($C_{2-6}$)alkoxy, mono($C_{1-4}$)alkylamino($C_{2-6}$)alkoxy, di($C_{1-4}$)alkylamino($C_{2-6}$)alkoxy $C_{2-10}$ mono(carboxyalkyl) amino, bis($C_{2-10}$ carboxyalkyl)amino, aminocarbonyl, $C_{6-14}$ aryl($C_{1-6}$)alkoxycarbonyl, $C_{2-6}$ alkynylcarbonyl, $C_{1-6}$ alkylsulfonyl, $C_{2-6}$ alkynylsulfonyl, $C_{6-10}$ arylsulfonyl, $C_{6-10}$ aryl ($C_{1-6}$)alkylsulfonyl, $C_{1-6}$ alkylsulfinyl, $C_{1-6}$ alkylsulfonamido, $C_{6-10}$ arylsulfonamido, $C_{6-10}$ aryl($C_{1-6}$) alkylsulfonamido, amidino, guanidino, $C_{1-6}$ alkyliminoamino, formyliminoamino, $C_{2-6}$ carboxyalkoxy, $C_{2-6}$ carboxyalkyl, and carboxy($C_{1-6}$)alkylamino.

When the phrase "optionally substituted" is used with reference to an alkyl, alkenyl, or alkynyl group, the phrase "optionally substituted" herein refers to said group or groups being optionally substituted with one or more substituents independently selected from the group consisting of amino, hydroxy, nitro, halogen, cyano, thiol, $C_{3-6}$ cycloalkyl, $C_{3-6}$ cycloalkenyl, $C_{3-6}$ cycloheteralkyl, $C_{3-6}$ cycloheteroalkenyl, $C_{6-10}$ aryl, 5-10 membered heteroaryl, $C_{1-6}$ alkoxy, $C_{3-6}$ alkenyloxy, $C_{1-6}$ alkylthio, $C_{1-6}$alkylenedioxy, $C_{1-6}$ alkoxy($C_{1-6}$) alkyl, $C_{6-10}$ aryl($C_{1-6}$)alkyl, $C_{6-10}$ aryl($C_{2-6}$)alkenyl, $C_{6-10}$ aryl($C_{1-6}$)alkoxy, $C_{1-6}$ aminoalkyl, $C_{1-6}$ aminoalkoxy, $C_{1-6}$ hydroxyalkyl, $C_{2-6}$ hydroxyalkoxy, mono($C_{1-4}$)alkylamino, di($C_{1-4}$)alkylamino, $C_{2-6}$ alkylcarbonylamino, $C_{2-6}$ alkoxycarbonylamino, $C_{2-6}$ alkoxycarbonyl, carboxy, ($C_{1-6}$)alkoxy ($C_{2-6}$)alkoxy, mono($C_{1-4}$)alkylamino($C_{2-6}$)alkoxy, di($C_{1-4}$) alkylamino($C_{2-6}$)alkoxy $C_{2-10}$ mono(carboxyalkyl)amino, bis($C_{2-10}$ carboxyalkyl) amino, $C_{6-14}$ aryl($C_{1-6}$)alkoxycarbonyl, $C_{2-6}$ alkynylcarbonyl, $C_{1-6}$ alkylsulfonyl, $C_{2-6}$ alkynylsulfonyl, $C_{6-10}$ arylsulfonyl, $C_{6-10}$ aryl($C_{1-6}$)alkylsulfonyl, $C_{1-6}$ alkylsulfinyl, $C_{1-6}$ alkylsulfonamido, $C_{6-10}$ arylsulfonamido, $C_{6-10}$ aryl($C_{1-6}$)alkylsulfonamido, amidino, guanidino, $C_{1-6}$ alkyliminoamino, formyliminoamino, $C_{2-6}$ carboxyalkoxy, $C_{2-6}$ carboxyalkyl, and carboxy($C_{1-6}$)alkylamino.

Although detailed definitions have not been provided for every term used above, each term is understood by one of ordinary skill in the art.

Compositions

A composition according to the present invention includes a pharmaceutical composition comprising a compound of Formula I, as defined above, and one or more pharmaceutically acceptable excipients. Preferred compositions of the present invention are pharmaceutical compositions comprising a compound selected from one or more embodiments listed above, and one or more pharmaceutically acceptable excipients. In another embodiment, a composition according to the present invention comprises a compound selected from one of the subgroups recited above, and one or more pharmaceutically acceptable excipients. Pharmaceutical compositions that comprise one or more compounds of Formula I may be formulated, as is well known in the prior art, such as by reference to known compilations as Remington's Pharmaceutical Sciences, Mack Publishing Co., Easton, Pa., USA.

In one embodiment of the invention, the composition comprises a compound selected from one or more of the individual embodiments listed above. In another embodiment, the composition comprises a compound selected from any of the specific compounds listed above, and pharmaceutically acceptable salts thereof.

In one embodiment, the compositions of the invention comprise from about 0.001 mg to about 1000 mg of a compound of Formula I. In another embodiment, the compositions of the invention comprise from about 0.01 mg to about 10 mg of a compound of Formula I. In another embodiment, the composition comprises an amount of a compound of Formula I in an amount sufficient to treat or prevent an inflammatory condition, an inflammatory disease, rheumatoid arthritis, psoriatic arthritis, or cancer. The amount of compound in each composition may vary depending upon the particular purpose of the pharmaceutical composition. In general, but not always, a composition used to prevent a disease or condition will have a lower amount of compound than a composition used to treat a disease or condition.

The pharmaceutical compositions of the invention can be administered to any animal that can experience the beneficial effects of the compounds of the invention. Foremost among such animals are humans, although the invention is not intended to be so limited. Other suitable animals include canines, felines, dogs, cats, livestock, horses, cattle, sheep, and the like.

The pharmaceutical compositions of the present invention can be administered by any means that achieve their intended purpose. For example, administration can be by subcutaneous, intravenous, intramuscular, intraperitoneal, buccal, or ocular routes, rectally, parenterally, intrasystemically, intravaginally, topically (as by powders, ointments, drops or transdermal patch), or as an oral or nasal spray. The dosage administered will be dependent upon the age, health, and weight of the recipient, kind of concurrent treatment, if any, frequency of treatment, and the nature of the effect desired.

In addition to the pharmacologically active compounds, the new pharmaceutical preparations can contain suitable pharmaceutically acceptable carriers comprising excipients and auxiliaries that facilitate processing of the active compounds into preparations that can be used pharmaceutically.

The pharmaceutical preparations of the present invention are manufactured in a manner that is, itself, known, for example, by means of conventional mixing, granulating, dragée-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

Pharmaceutical excipients are well known in the art. Suitable excipients include fillers such as saccharides, for example, lactose or sucrose, mannitol or sorbitol, cellulose preparations and/or calcium phosphates, for example, tricalcium phosphate or calcium hydrogen phosphate, as well as binders, such as, starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents can be added, such as, the above-mentioned starches and also carboxymethylstarch, cross-linked polyvinyl pyrrolidone, agar, or alginic acid or a salt thereof, such as, sodium alginate. Auxiliaries are, above all, flow-regulating agents and lubricants, for example, silica, talc, stearic acid or salts thereof, such as, magnesium stearate or calcium stearate, and/or polyethylene glycol. Dragée cores are provided with suitable coatings that, if desired, are resistant to gastric juices. For this purpose, concentrated saccharide solutions can be used, which may optionally contain gum arabic, talc, polyvinyl pyrrolidone, polyethylene glycol, and/or titanium dioxide, lacquer solutions and suitable organic solvents or solvent mixtures. In order to produce coatings resistant to gastric juices, solutions of suitable cellulose preparations, such as, acetylcellulose phthalate or hydroxypropylmethyl-cellulose phthalate, are used. Dye stuffs or pigments can be added to the tablets or dragee coatings, for example, for identification or in order to characterize combinations of active compound doses.

Other pharmaceutical preparations which can be used orally include push-fit capsules made of gelatin, as well as soft, sealed capsules made of gelatin and a plasticizer, such as, glycerol or sorbitol. The push-fit capsules can contain the active compounds in the form of granules that may be mixed with fillers such as lactose, binders such as starches, and/or lubricants such as talc or magnesium stearate and, optionally, stabilizers. In soft capsules, the active compounds are preferably dissolved or suspended in suitable liquids, such as, fatty oils or liquid paraffin. In addition, stabilizers may be added.

Suitable formulations for parenteral administration include aqueous solutions of the active compounds in water-soluble form, for example, water-soluble salts, alkaline solutions, and cyclodextrin inclusion complexes. Especially preferred alkaline salts are ammonium salts prepared, for example, with Tris, choline hydroxide, Bis-Tris propane, N-methylglucamine, or arginine.

The compounds of this invention may also be administered parenterally as an injectable dosage form in a physiologically acceptable diluent such as sterile liquids or mixtures thereof, including water, saline, aqueous dextrose and other pharmaceutically acceptable sugar solutions, alcohols such as ethanol, isopropanol, or hexadecyl alcohol, glycols such as propylene glycol or polyethylene glycol, glycerol ketals such as 2,2-dimethyl-1,3-dioxolane-4-methanol, ethers such as poly(ethyleneglycol)400, a pharmaceutically acceptable oil, fatty acid, fatty acid ester or glyceride, or an acetylated fatty acid glyceride with or without the addition of a pharmaceutically acceptable surfactant, such as a soap or detergent, suspending agent such as pectin, carbomers, methylcellulose, hydroxypropylmethylcellulose, or carboxymethylcellulose, an emulsifying agent or pharmaceutical adjuvants. In all cases, the form should be sterile and should be fluid to the extent that easy syringability exists. It should be stable under the conditions of manufacture and storage and should be preserved against the contaminating action of microorganisms such as bacteria and fungi.

Pharmaceutically acceptable oils which are useful in the formulation herein include those of petroleum, animal, vegetable or synthetic origin, including peanut oil, soybean oil, sesame oil, cottonseed oil, olive oil, sunflower oil, petrolatum, and mineral oil. Fatty acids which may be used include oleic acid, stearic acid, and isostearic acid, while the fatty acid esters useful herein may include ethyl oleate and isopropyl myristate. Suitable soaps include fatty acid alkali metal, ammonium, and triethanolamine salts. Acceptable detergents include cationic detergents, for example, dimethyl dialkyl ammonium halides, alkyl pyridinium halides, and alkylamine acetates and anionic detergents, such as alkyl, aryl, and olefin sulfonates, alkyl, olefin, ether and monoglyceride sulfates, and sulfosuccinates. Useful non-ionic detergents may include fatty amine oxides, fatty acid alkanolamides and polyoxyethylenepolypropylene copolymers. Amphoteric detergents may include alkyl-β-aminopropionates and 2-alkylimidazoline quaternary salts, and mixtures thereof.

The parenteral compositions of this invention contain, in one embodiment, from about 0.5 to about 25% by weight of the active compounds described herein in solution. The parenteral formulations in the form of sterile injectable solutions or suspensions will also preferably contain from about 0.05% to about 5% suspending agent in an isotonic medium. Buffers and preservatives may be added. A suitable surfactant may also be added. These surfactants may include polyethylene sorbitan fatty acid esters, such as sorbitan monooleate, and the high molecular weight adducts of ethylene oxide with a hydrophobic base, formed by the condensation of propylene oxide with propylene glycol.

In addition, suspensions of the active compounds as appropriate oily injection suspensions can be administered. Suitable lipophilic solvents or vehicles include fatty oils, for example, sesame oil, or synthetic fatty acid esters, for example, ethyl oleate or triglycerides or polyethylene glycol-400. Aqueous injection suspensions can contain substances that increase the viscosity of the suspension, for example, sodium carboxymethyl cellulose, sorbitol, and/or dextran. Optionally, the suspension may also contain stabilizers.

Liquid dosage forms for oral administration include pharmaceutically acceptable emulsions, solutions, suspensions, syrups, and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

Topical administration includes administration to the skin or mucosa, including surfaces of the lung and eye. Compositions for topical administration, including those for inhalation, may be prepared as a dry powder which may be pressurized or non-pressurized. In nonpressurized powder compositions, the active ingredients in finely divided form may be used in admixture with a larger-sized pharmaceutically acceptable inert carrier comprising particles having a size, for example, of up to 100 micrometers in diameter.

Suitable inert carriers include sugars such as lactose. Desirably, at least 95% by weight of the particles of the active ingredient have an effective particle size in the range of 0.01 to 10 micrometers.

Alternatively, the composition may be pressurized and contain a compressed gas, such as nitrogen or a liquefied gas propellant. The liquefied propellant medium and indeed the total composition are preferably such that the active ingredients do not dissolve therein to any substantial extent. The pressurized composition may also contain a surface-active agent. The surface-active agent may be a liquid or solid non-ionic surface-active agent or may be a solid anionic surface-active agent. It is preferred to use the solid anionic surface-active agent in the form of a sodium salt.

A further form of topical administration is to the eye. The compounds and compositions of the present invention are delivered in a pharmaceutically acceptable ophthalmic vehicle, such that the compounds are maintained in contact with the ocular surface for a sufficient time period to allow the compounds to penetrate the corneal and internal regions of the eye, as for example the anterior chamber, posterior chamber, vitreous body, aqueous humor, vitreous humor, cornea, iris/ciliary, lens, choroid/retina and sclera. The pharmaceutically acceptable ophthalmic vehicle may, for example, be an ointment, vegetable oil or an encapsulating material.

Compositions for rectal or vaginal administration are preferably suppositories which can be prepared by mixing the compounds of the present invention with suitable non-irritating excipients or carriers such as cocoa butter, polyethylene glycol or a suppository wax which are solid at room temperature but liquid at body temperature and therefore melt in the rectum or vaginal cavity and release the drugs.

The compositions of the present invention can also be administered in the form of liposomes. As is known in the art, liposomes are generally derived from phospholipids or other lipid substances. Liposomes are formed by mono- or multilamellar hydrated liquid crystals that are dispersed in an aqueous medium. Any non-toxic, physiologically acceptable and metabolizable lipid capable of forming liposomes can be used. The present compositions in liposome form can contain, in addition to the compounds of the present invention, stabilizers, preservatives, excipients, and the like. The preferred lipids are the phospholipids and the phosphatidyl cholines (lecithins), both natural and synthetic. Methods to form liposomes are known in the art (see, for example, Prescott, Ed., *Meth. Cell Biol.* 14:33 (1976)).

In another embodiment, the present invention is directed to a composition comprising a compound of Formula I and a carrier, wherein said carrier is suitable for an assay. Such carriers may include solid carriers and liquid carriers. A composition suitable for an assay may, but not necessarily, be sterile. Examples of suitable carriers for assays include dimethylsulfoxide, ethanol, dicloromethane, methanol, and the like. In another embodiment, a composition comprises a compound of Formula I and a carrier, wherein the compound is in an amount suitable for inhibiting p38.

Use of the Compounds and Compositions

A further aspect of the present invention is directed to a method of using a compound of Formula I. A compound according to Formula I is useful for the treatment or prevention of a p38-mediated condition. In one embodiment, the present invention is directed to a method treating, preventing, or ameliorating a p38-mediated condition comprising administering to a subject in need of such treatment an effective amount of a compound according to Formula I. In one embodiment of the invention, the method uses a compound selected from one or more of the individual embodiments listed above.

In one embodiment, the condition or disease is mediated by p38α.

Another embodiment of the present invention is directed to the treatment or prevention of an inflammatory condition. In one embodiment, the present invention is directed to a method treating, preventing, or ameliorating an inflammatory condition or disease comprising administering to a subject in need of such treatment an effective amount of a compound according to Formula I. In one embodiment of the invention, the method uses a compound selected from one or more of the individual embodiments listed above.

The subject of the method disclosed herein is preferably an animal, including, but not limited, a cow, horse, sheep, pig, chicken, turkey, quail, cat, dog, mouse, rat, rabbit, and guinea pig, and is more preferably a mammal, and most preferably a human.

The term "p38-mediated condition", as used herein means any disease or other deleterious condition in which p38 is known to play a role. This includes conditions known to be caused by interleukins or TNFs, in particular TNF-α, overproduction. Such conditions include, without limitation, inflammatory diseases, autoimmune diseases, chronic obstructive pulmonary disorder, destructive bone disorders, proliferative disorders, cancer, infectious diseases, neurodegenerative diseases, allergies, reperfusion/ischemia in stroke, heart attacks, angiogenic disorders, organ hypoxia, vascular hyperplasia, cardiac hypertrophy, thrombin-induced platelet aggregation, and conditions associated with prostaglandin endoperoxidase synthase-2.

Inflammatory diseases which may be treated or prevented include, but are not limited to acute pancreatitis, chronic pancreatitis, asthma, allergies, and adult respiratory distress syndrome.

Autoimmune diseases which may be treated or prevented include, but are not limited to, glomerulonephritis, rheumatoid arthritis, systemic lupus erythematosus, scleroderma, chronic thyroiditis, Graves' disease, autoimmune gastritis, diabetes, autoimmune hemolytic anemia, autoimmune neutropenia, thrombocytopenia, atopic dermatitis, chronic active hepatitis, myasthenia gravis, multiple sclerosis, inflammatory bowel disease, ulcerative colitis, Crohn's disease, psoriasis, or graft vs. host disease.

Destructive bone disorders which may be treated or prevented include, but are not limited to, osteoporosis, osteoarthritis and multiple myeloma-related bone disorder.

Proliferative diseases which may be treated or prevented include, but are not limited to, acute myelogenous leukemia, chronic myelogenous leukemia, metastatic melanoma, Kaposi's sarcoma, and multiple myeloma.

Angiogenic disorders which may be treated or prevented include solid tumors, ocular neovasculization, infantile haemangiomas.

Infectious diseases which may be treated or prevented include, but are not limited to, sepsis, septic shock, and Shigellosis.

Viral diseases which may be treated or prevented include, but are not limited to, acute hepatitis infection (including hepatitis A, hepatitis B and hepatitis C), and CMV retinitis.

Neurodegenerative diseases which may be treated or prevented by the compounds of this invention include, but are not limited to, Alzheimer's disease, Parkinson's disease, and cerebral ischemias or neurodegenerative disease caused by traumatic injury.

A compound and composition of the present invention can be used for the treatment and/or prevention of allergies. In one embodiment, the compound or composition is used to treat or prevent inflammatory symptoms of an allergic reaction. In another embodiment, the compound or composition is used to treat or prevent a respiratory inflammatory response evoked by an allergan.

In another embodiment, a compound or composition of the present invention is used to treat cancer. In one embodiment, the compound or composition is used to treat a cancer that is associate with chronic inflammation, including but not limited to colorectal cancer, colon cancer, esophageal cancer, mesothelioma, ovarian cancer, and gastric cancer. In another embodiment, the compound or composition is used to treat cancer by blocking tumorigenesis. In another embodiment, the compound or composition is used to treat cancer by inhibiting metastasis. In another embodiment, the compound or composition is used to treat cancer by inducing apoptosis.

A "p38-mediated condition" also includes ischemia/reperfusion in stroke, heart attacks, myocardial ischemia, organ hypoxia, vascular hyperplasia, cardiac hypertrophy, and thrombin-induced platelet aggregation.

A compound of Formula I may further be administered to a subject to inhibit or prevent a healthy subject from developing an inflammatory condition or a p38-mediated condition. A subject, who does not have an inflammatory or p38-mediated condition but may develop one, may be administered a compound according to Formula I to prevent or inhibit the. In other words, a compound of Formula I may be used as a prophylactic agent that prevents or inhibits the development of an inflammatory or p38-mediated condition or disease. According to the method, a compound according to Formula I is administered at an effective dose to significant onset of the inflammatory or p38-mediated condition or disease. The presence of the compound of Formula I in or on the subject's body prevents or inhibits the development of the inflammatory or p38-mediated condition or disease.

The compounds of the present invention may be administered in an effective amount within the dosage range of about 0.01 mg/kg to about 300 mg/kg, preferably between 0.1 mg/kg to 100 mg/kg body weight, more preferably from 0.1 mg/kg to 10 mg/kg body weight. Compounds of the present invention may be administered in a single daily dose, or the total daily dosage may be administered in divided doses of, e.g., two, three or four times daily. Those of skill in the treatment of inflammatory conditions and p38-mediated conditions could determine the effective daily amount from the test results presented here. The exact dosage and frequency of administration depends on the particular compound of Formula I used, the particular condition being treated, the severity of the condition being treated, and the age, weight, and general physical condition of the particular patient, as well as other medication the individual may be taking, as is well known to those skilled in the art. The dosages may be varied depending upon the requirements of the patient, the severity of the condition being treated, and the compound being employed. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day, if desired.

A therapeutically effective amount is understood to mean the amount of a compound that, when administered to a mammal for treating a disease, is sufficient to effect such treatment for the disease. The therapeutically effective amount will vary depending on the compound, the disease and its severity and the age, weight, etc., of the mammal to be treated.

Furthermore, the dosages may vary according to the particular usage. For example, a higher amount of a compound of Formula I may be used when treating a subject having a well-developed inflammatory condition, compared to the amount used to prevent a subject from developing the inflammatory condition.

In all cases of administration, it is understood that the compound of Formula I can be administered as a pharmaceutical composition comprising said compound and a pharmaceutically acceptable excipient, as described herein. Alternatively, the compound of Formula I may be administered as a pure material if appropriate.

In an additional aspect of the present invention, a compound of Formula I may be used alone or in combination with one or more additional anti-inflammatory agents. When a compound of the present invention is used along with one or more additional anti-inflammatory agents, the compound of the present invention may be formulated with the other anti-inflammatory agent or agents so that a pharmaceutical composition comprising a compound of Formula I and one or more additional anti-inflammatory agents is administered to an animal. Alternatively, the compound of Formula I can be administered as a separate pharmaceutical composition from the composition comprising the one or more additional anti-inflammatory agents.

The compounds of the present invention are also useful in drug discovery assays. The compounds of Formula I may be used in assays to determine the efficacy and/or potency of other compounds as anti-inflammatory agents or as inhibitors of a p38 kinase. These assays include in vivo and in vitro assays. The compounds of the present invention can be used as controls or can be used as lead compounds to discover new, useful anti-inflammatory compounds or new, useful inhibitors of a p38 kinase. Additionally, a compound of Formula I may be used to form a crystallized complex with a p38 protein.

The compounds may also be used in inhibiting p38 in vitro or in vivo. The amount of the compound of Formula I used to inhibit p38 is not necessarily the same when used in vivo compared to in vivo. Factors such as pharmacokinetics and pharmacodynamics of the particular compound may require that a large or smaller amount of the compound of Formula I be used when inhibiting p38 in vivo. Accordingly, an additional aspect of the present invention is a method of inhibiting p38, comprising contacting a p38 kinase with a compound according to Formula I. In one embodiment of this aspect of the present invention, the method comprises contacting a cell with a compound of Formula I, wherein said cell has a p38 kinase. In another embodiment of the present invention, the method comprises administering a compound of Formula I to a subject in an amount sufficient to inhibit a p38 kinase, wherein said subject has or expresses the p38 kinase.

In another embodiment, the present invention is directed to a method of selectively inhibiting a p38 kinase, comprising contacting the p38 kinase with a compound according to Formula I. In this embodiment, the compound of Formula I can be administered to a composition comprising a p38 kinase, along with other kinases, and the compound inhibits the activity of p38 without interfering with the activity of the other kinases. For example, the compound of Formula I can be administered to a cell that contains a p38 kinase along with one or more of the following kinases: c-RAF, Flt3, JNK2α2, JNK3, Lck, Lyn, Tie2, TrkB, IGF-IR, ERK1, ERK2, MEK1, PRAK, Yeo, and ZAP-70. When practiced as described herein, the method inhibits the activity of the p38 kinase without interfering with the activity of one or more of the following kinases: c-RAF, Flt3, JNK2a2, JNK3, Lck, Lyn, Tie2, and TrkB. In another embodiment, the present invention is directed to selectively inhibiting a p38α or p38β kinase without inhibiting substantially the activity of a p38γ or p38δ kinase. In certain embodiments, the method of the invention can inhibit greater than 80% of the activity of a p38α or p38β kinase without inhibiting more than 30%, 40%, or 50% of the activity of a p38γ or p38δ kinase. In other embodiments, the method of the invention can inhibit greater than 80% of the activity of a p38 kinase without inhibiting more than 5%, 10%, 20%, or 30% of the activity of one or more of the following kinases: c-RAF, Flt3, JNK2a2, JNK3, Lck, Lyn, Tie2, and TrkB. In another embodiment, the method of the present invention inhibits p38 selectively over all of c-RAF, Flt3, JNK2a2, JNK3, Lck, Lyn, Tie2, and TrkB. In yet a further embodiment, the invention is directed to a compound of Formula I, or of any one of the subclasses described above, having the ability to inhibit p38α and p38β selectively over p38γ and p38δ.

In another embodiment of the present invention, a compound of Formula I can be used for preparing a pharmaceutical composition to be used for inhibiting or modulating p38, for treating or preventing an inflammatory condition or disease, or for treating or preventing a p38-mediated condition.

In another embodiment, any one of the methods described herein uses a compound selected from the group consisting of any of the specific compounds listed above, and pharmaceutically acceptable salts thereof.

The biological activity of a compound according to Formula I can be determined by testing said compound using methods known in the art. For example, one can evaluate the ability of a compound to prevent, treat, or inhibit an inflammatory condition by one or more known assays. Additionally, one can evaluate the ability of a compound to inhibit or modulate the activity of a p38 kinase using one or more known assays. One known assay is to test for the inhibition of the p38-catalyzed phosphorylation of EGF receptor peptide by a test compound. EGF receptor peptide is described in published U.S. Patent Application Pub. No. 2003/0149037 (Salituro et al.) and is a phosphoryl acceptor in a p38-catalyzed kinase reaction. The inhibitory activity of the test compound can be determined by comparing the extent of phosphorylation of the EGF receptor peptide in the presence of test compound and in the absence of test compound.

A second assay for testing the p38-inhibitory activity of a compound is a test for inhibition of ATPase activity. This assay determines the ability of a compound to inhibit the ATPase activity of activated p38. The product of p38 ATPase activity, ADP, is quantified by HPLC analysis.

A third assay is another that tests a compound's ability to inhibit p38's kinase activity. This assay, as described in detail in the examples section below, measures the incorporation of $^{33}$P from γ-[$^{33}$P]ATP into the GST-ATF-2 substrate, amino acids 19-96 (Upstate, NY USA). This incorporation is catalyzed by p38. In the presence of an inhibitory compound, the p38-catalyzed the incorporation of $^{33}$P from γ-[$^{33}$P]ATP into the GST-ATF-2 substrate is lower.

Another assay which can be used to test a compounds ability to inhibit p38 is one which measures the activation kinetics of p38 by MKK6. The activation of p38 by upstream kinase MKK6 is characterized using, e.g., ELISA. A test compound is preincubated with p38 kinase.

An assay which tests a compound's ability to inhibit TNFα secretion caused by lipopolysaccharide (LPS) can also be used. Such assays are known to one of skill in the art, and an example is described in detail below.

It is further understood that the p38 MAP kinase family of proteins includes at least four different isoforms: α, β, γ, and δ. Other names of p38 MAP kinase include, but are not limited to, cytokine suppressive anti-inflammatory drug-binding protein (CSBP), CSBP kinase, and stress activated protein kinase (SAPK). The sequences of p38 MAP kinases have been disclosed in the following U.S. Pat. Nos. 5,783,664; 5,777,097; 5,955,366; 6,033,873; 5,869,043; 6,444,455 B1; 5,948,885; and 6,376,214 B1.

Methods of Preparation of Compounds

In another aspect, the present invention is directed to a method of making a compound according to Formula I. The compound for use in the present invention can be synthesized according to methods outlined in the following descriptions. The compounds for use in the present invention can be synthesized using procedures known in the art. The following general schemes illustrate synthetic methods used to prepare compounds of the present invention.

The compounds of the present invention can be prepared using at least one of the methods described below. A compound of Formula I, wherein G is C(O) or CH$_2$, can be prepared according to general Method I, shown in the following scheme:

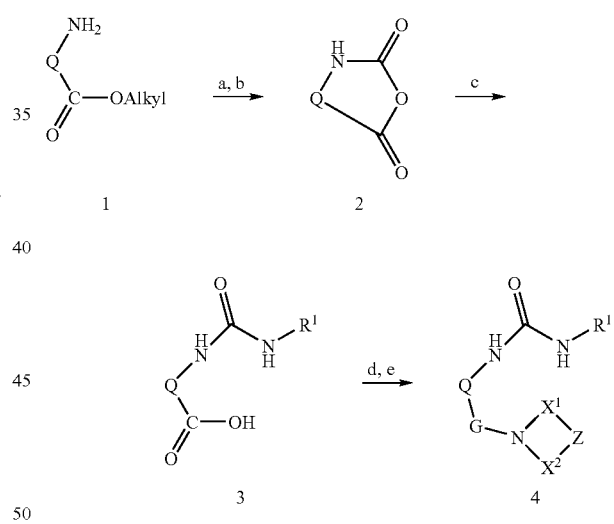

wherein G is CH$_2$ or C(O), and Q, R$^1$, X$^1$, X$^2$, and Z are as defined above. Step a uses a base such as sodium hydroxide or potassium hydroxide to hydrolyze the ester. The resulting acid is then reacted in Step b with phosgene to form Compound 2. Compound 2 is then reacted with a suitable amine, R$^1$—NH$_2$, to form Compound 3, which is further coupled with a suitable amine to form Compound 4, wherein G is C(O). If desired, Compound 4 can be further reacted with a reducing agent, such as BH$_3$ THF, to reduce the C(O) to CH$_2$ so that G is CH$_2$. Compound 4, whether G is CH$_2$ or C(O), in a exemplary compound of Formula I. In certain, embodiments, a coupling agent may be used in Step d. Suitable coupling agents include, for example, EDCI and 1-hydroxybenzotriazole.

For example, a compound according to Formula I, wherein G is either C(O) or CH$_2$, can be prepared according to the following scheme:

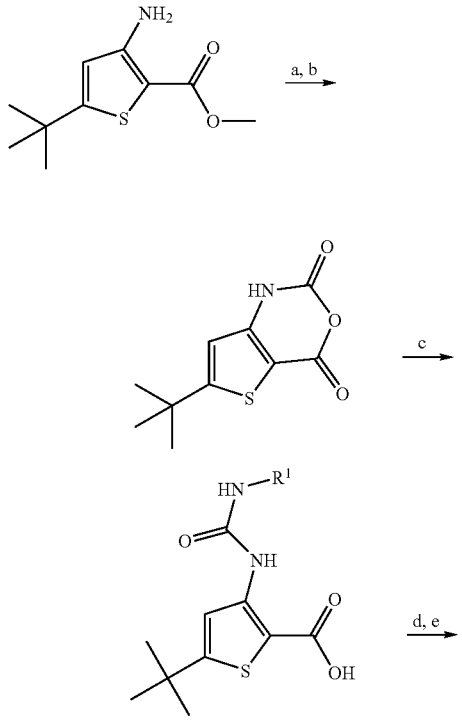

wherein R$^1$, X$^1$, X$^2$, and Z are defined as above. Step (a) converts the ester to an acid and uses a base such as potassium hydroxide. Step (b) uses COCl$_2$. Step (c) uses a suitable amine R$^1$—NH$_2$. Step (d) uses an amine of the formula

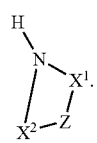

Step (e) uses a reducing agent, for example, BH$_3$-THF. An appropriate catalyst or coupling agent, e.g., EDCI or 1-hydroxybenzotriazole (HOBt), can be used to effect the formation of the amide in Step (d).

By way of another example of Method I, a compound according to Formula I, wherein G is either C(O) or CH$_2$, can similarly be prepared according to the following scheme:

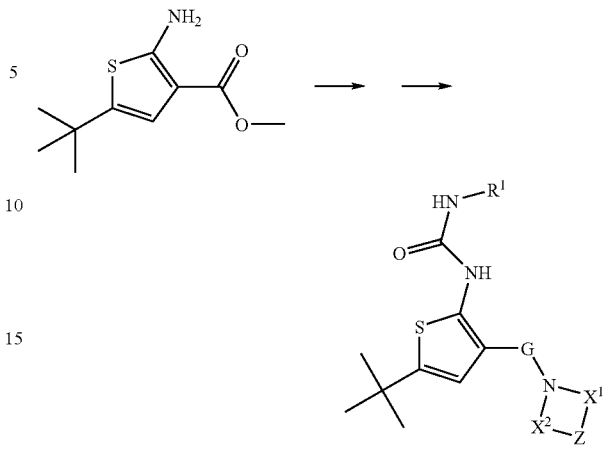

wherein R$^1$, X$^1$, X$^2$, and Z are defined as above.

In another method, Method II, a compound according to Formula I wherein G is C(O) and R$^2$ is

can be prepared as shown in the following scheme:

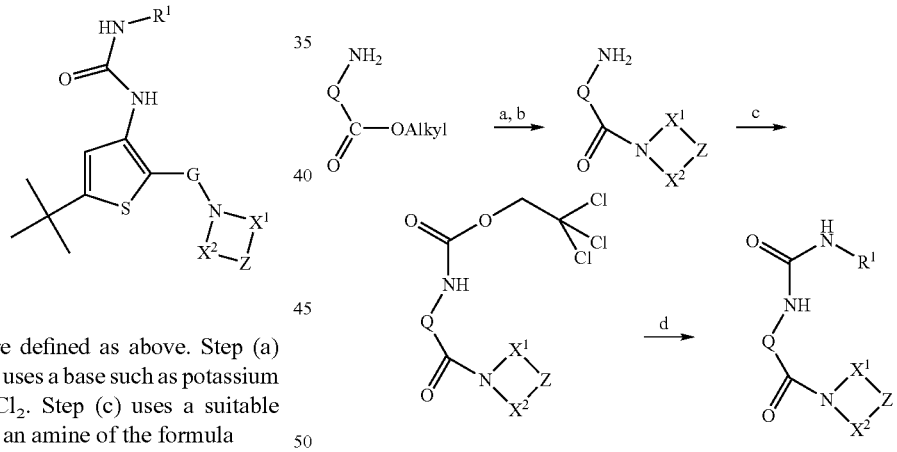

wherein Q, R$^1$, X$^1$, and X$^2$ are as defined for Formula I. In Method II, Step a comprises reacting the compound with a base, e.g., NaOH or K$_2$CO$_3$ to form the acid, which is then reacted with an appropriate amine

to form the amide. The amide is then reacted with 2,2,2-trifluoroethylchloroformate to form the carbamate. The carbamate is then reacted with amine R$^1$—NH$_2$ to form a compound of Formula I.

For example, a compound according to Formula I can be prepared according to Method II as follows:

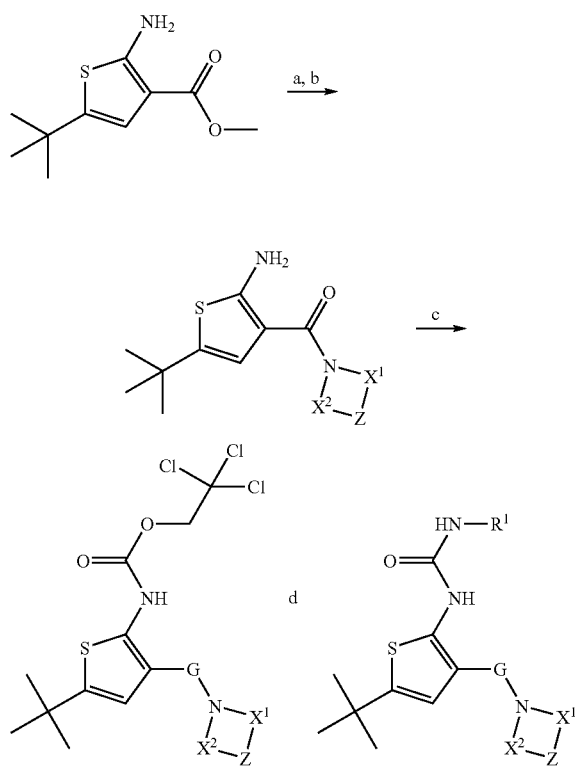

wherein Step a reacts the amino ester with KOH; then the resulting amino acid is reacted with EDCI and HOBt; followed by reacting the amino amide with

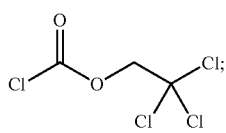

and then forming the urea by reacting $R^1$—$NH_2$ with the carbamate.

Alternatively, a compound according to Formula I can be prepared as shown in Method III:

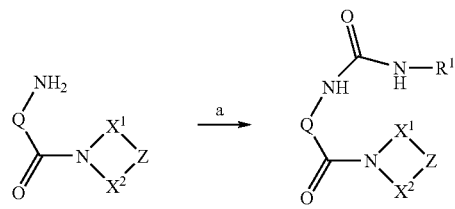

wherein Q, $X^1$, $X^2$, Z, and $R^1$ are as defined for Formula I. Step a comprises reacting the amine shown with an appropriate isocyanate $R^1$—NCO under microwave conditions.

For example, a compound of Formula I can be prepared according to Method III as shown in the following scheme:

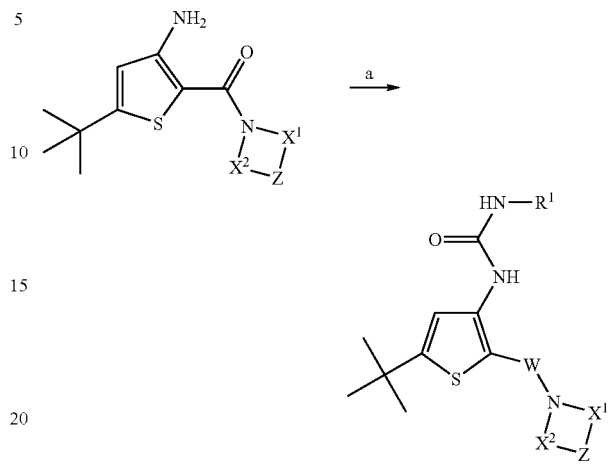

wherein $R^1$, $X^1$, $X^2$, and Z are defined as above and wherein Step a reacts a compound $R^1$—NCO with the thiophene shown while subjecting the reaction components to microwave conditions.

An additional method, Method IVa, of preparing certain compounds of Formula I comprises a solid phase method as shown in the following scheme.

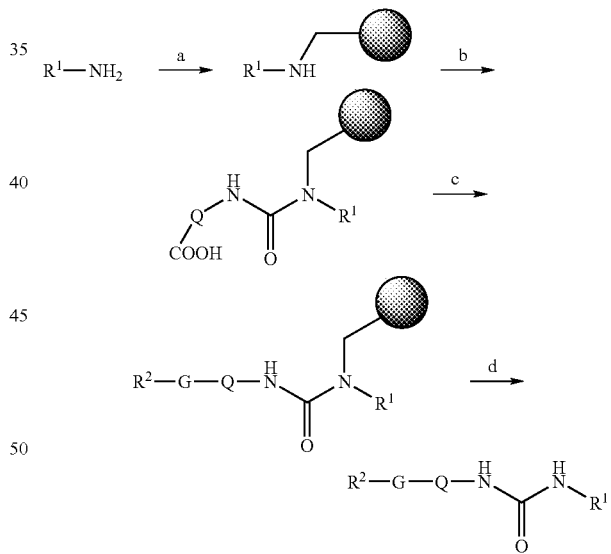

wherein $R^1$, $R^2$, G, and Q are as defined for Formula I. Step (a) comprises reacting an amine $R^1$—$NH_2$ with a solid-phase resin to form the resin bound amine. Step (b) comprises reacting the resin-bound amine with an appropriate compound to form the resin-bound urea. The resin-bound urea is further functionalized and then removed from the resin in Steps (c) and (d) to form a compound according to Formula I.

In another embodiment, the invention is directed to a method of preparing a compound according to Formula I, wherein Q is a thienyl group, said method comprising (a) reacting $R^1$—$NH_2$ with a BAL resin and NaBH(OAc)$_3$ to form a solid-phase aniline, wherein $R^1$ is as defined above for Formula I; (b) reacting the solid-phase aniline with

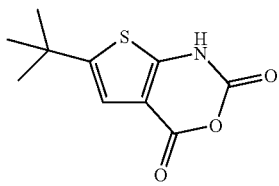

to form a urea; (c) reacting the urea with EDCI (1-(3-dimethylaminopropyl)-3-ethylcarbodiimide hydrochloride) and thio-morpholine-1,1-dioxide to form a solid-phase amide; (d) removing the resin; thereby forming the compound according to Formula I. An example of this embodiment is shown in Method IVa as follows:

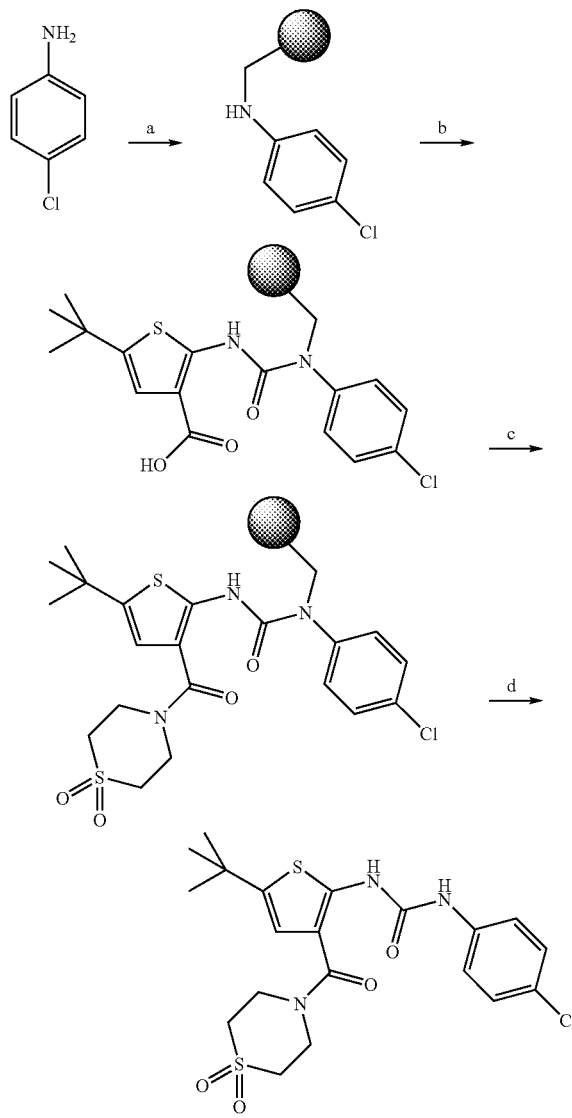

wherein 4-chloroaniline is reacted with a BAL resin (backbone amide link resin, such as 4-(4-formyl-3,5-dimethoxyphenoxy)butyryl AM resin or polystyrene-indole-CHO resin, and NaBH(OAc)$_3$. The resin is shown as a sphere. Step b comprises reacting the solid-phase aniline with

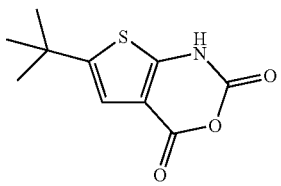

to form the urea. The urea is then reacted with EDCI (1-(3-dimethylaminopropyl)-3-ethylcarbodiimide hydrochloride) and thio-morpholine-1,1-dioxide to form the amide. Step d comprises removal of the urea from the resin with, for example, 50% trifluoroacetic acid in dichloromethane.

An alternative solid phase method comprises a method of preparing a compound according to Formula I,

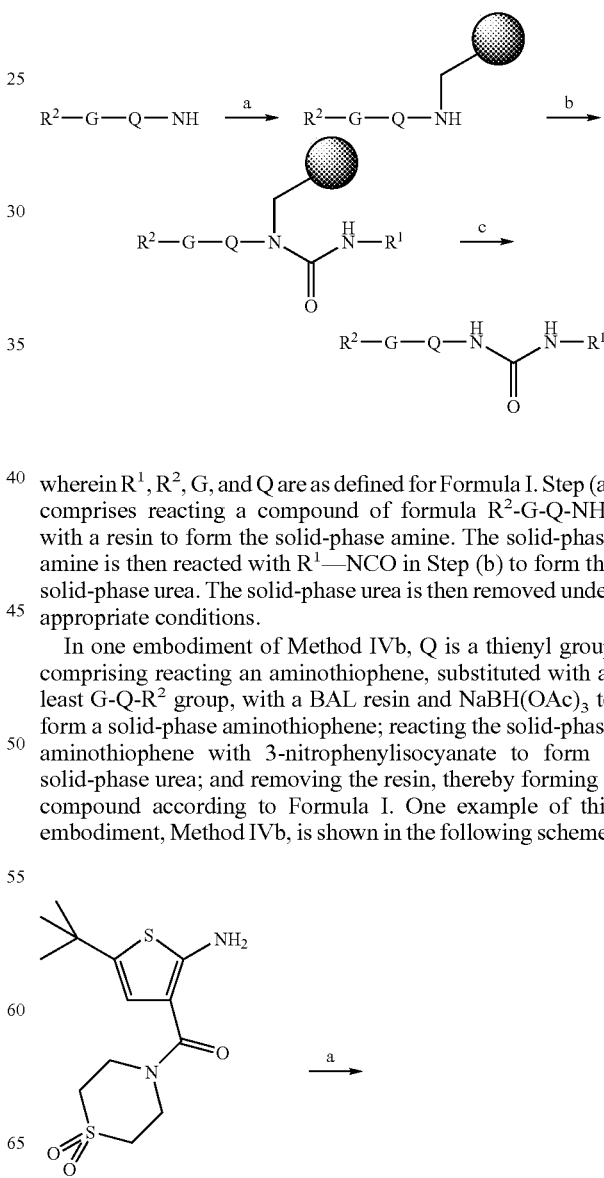

wherein $R^1$, $R^2$, G, and Q are as defined for Formula I. Step (a) comprises reacting a compound of formula $R^2$-G-Q-NH$_2$ with a resin to form the solid-phase amine. The solid-phase amine is then reacted with $R^1$—NCO in Step (b) to form the solid-phase urea. The solid-phase urea is then removed under appropriate conditions.

In one embodiment of Method IVb, Q is a thienyl group comprising reacting an aminothiophene, substituted with at least G-Q-$R^2$ group, with a BAL resin and NaBH(OAc)$_3$ to form a solid-phase aminothiophene; reacting the solid-phase aminothiophene with 3-nitrophenylisocyanate to form a solid-phase urea; and removing the resin, thereby forming a compound according to Formula I. One example of this embodiment, Method IVb, is shown in the following scheme:

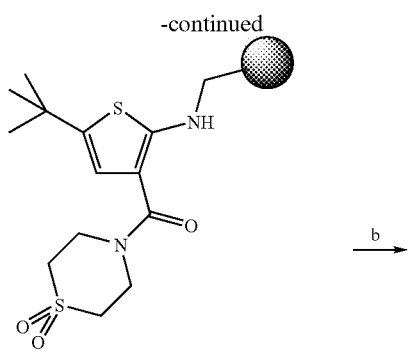

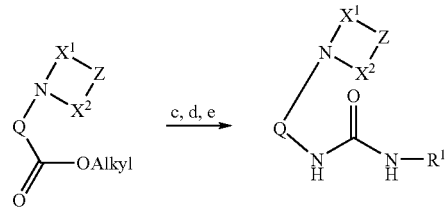

wherein Q, $X^1$, $X^2$, Z and $R^1$ are as defined as for Formula I. Starting with the amino ester, if this compound is reacted in Step a with $NaNO_2/CuBr_2$. The resulting halogen containing compound is reacting with an appropriate amine

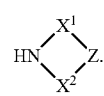

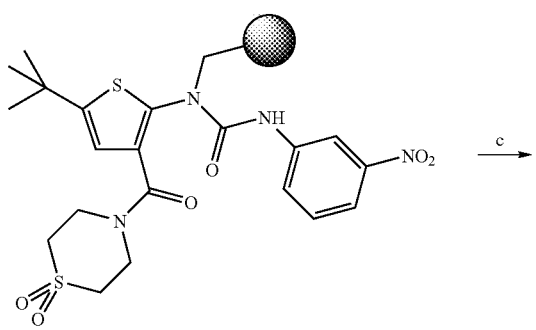

The resulting compound is the hydrolyzed with a base to form the corresponding acid. The resulting acid is then reacted with DPPA/TEA in Step d, followed by reaction with amine $R^1$—$NH_2$.

In another method, certain compounds of Formula I can be prepared according to Method VI shown in the following scheme:

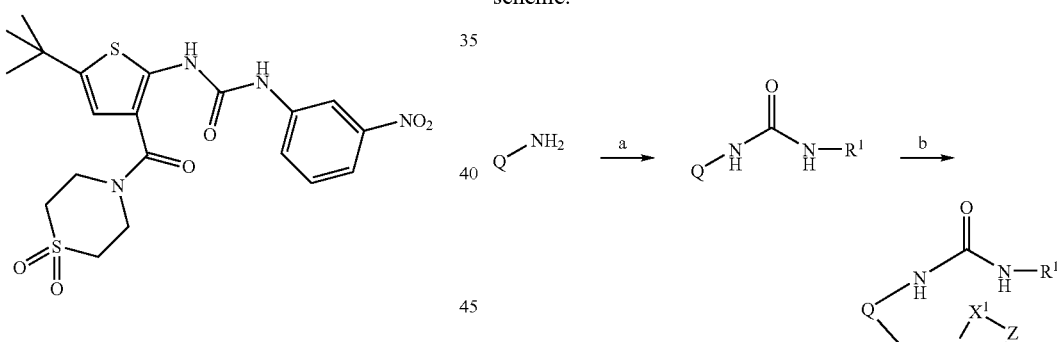

wherein the aminothiophene is reached with a BAL resin (backbone amide link resin, 4-(4-formyl-3,5-dimethoxyphenoxy)butyryl AM resin) and then $NaBH(OAc)_3$ to form the solid-phase thiophene. The solid-phase thiophene is then reacted with 3-nitrophenylisocyanate to form the urea. The urea is then released from the resin with, for example, 50% trifluoroacetic acid in dichloromethane, to produce a compound of Formula I In another method, certain compounds of Formula I can be prepared according to Method V shown in the following scheme:

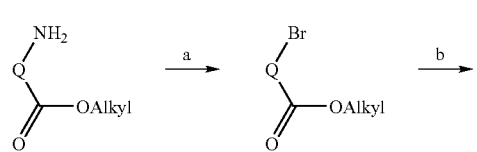

wherein Q is a nitrogen-containing heteroaryl, and $X^1$, $X^2$, Z, and $R^1$ are as defined for Formula I. Method VI comprises reacting the initial amine with isocyanate $R^1$—NCO in Step a. The resulting urea is reacted with a compound of formula

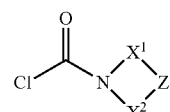

in Step b, such that the carbonyl form a bond with the nitrogen atom of Q, thereby forming a compound according to Formula I.

For example, a compound of Formula I can be prepared according to Method VI as shown in the following scheme:

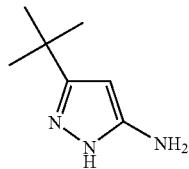

a →

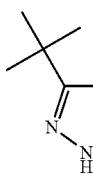

b →

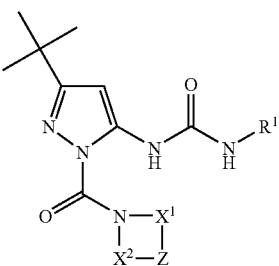

wherein $R^1$, $X^1$, $X^2$, and Z are defined as above, and wherein Step a comprises reaction $R^1$—NCO with the compounds shown, followed by addition of a compound of formula

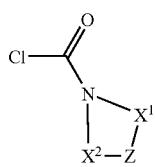

in Step b.

In another embodiment, certain compounds of Formula I can be prepared according to the following scheme:

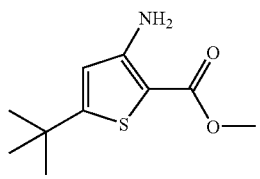

a →

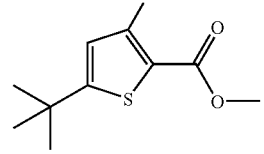

b →

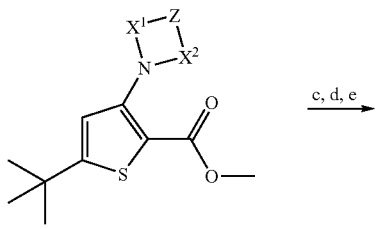

c, d, e →

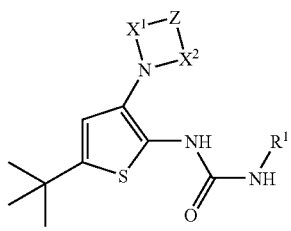

wherein $R^1$, $X^1$, $X^2$, and Z are defined as above, and wherein Step a comprises reacting the thiophene with $NaNO_2/CuBr_2$, followed by addition of

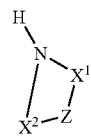

in Step b, followed by hydrolysis of the ester with a base, such as NaOH, in Step c, addition of DPPA/TEA, and finally addition of the amine $R^1NH_2$ in Step e.

In another embodiment, certain compounds according to Formula I can be prepared according to the following scheme:

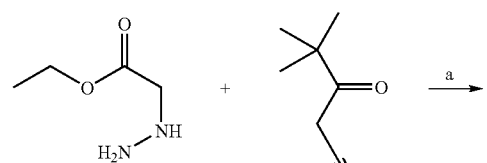

a →

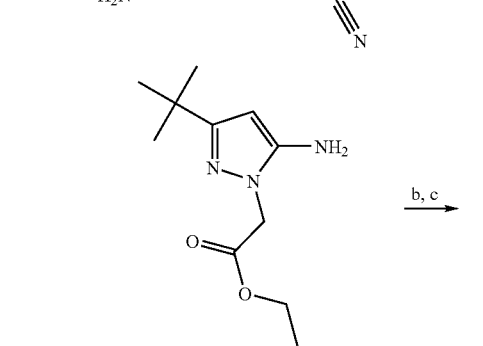

b, c →

-continued

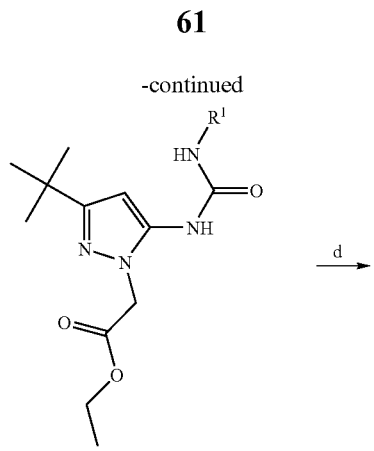

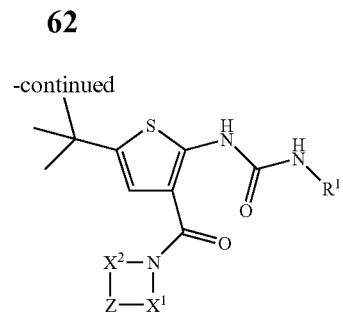

wherein $R^1$, $X^1$, $X^2$, and Z are defined as above. Step (a) comprises reacting the aminothiophene with $R^1$—NCO to form the urea, and then reacting the urea with an amine of the formula

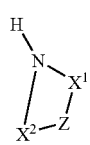

in the presence of EDCI and HOBt to form a compound according to Formula I.

In another embodiment, a compound of Formula I, wherein Q is 2-aminopyrrole and G is C(O) can be prepared according to the general shown in the following scheme:

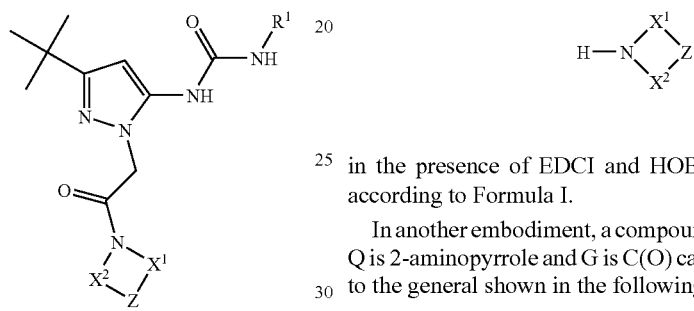

wherein $R^1$, $X^1$, $X^2$, and Z are defined as above. Step a comprises heating in toluene. Step b comprises reacting the product of Step a with $R^1$—NCO followed by addition of a base such as NaOH. Step d comprises reacting the product of Step c with an amine of the formula

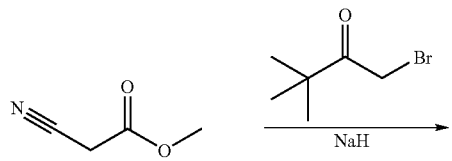

in the presence of DIEA/EDCI.

In another embodiment, certain compounds of Formula I can be prepared according to the following scheme:

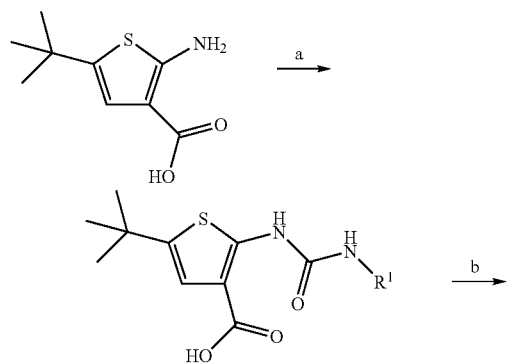

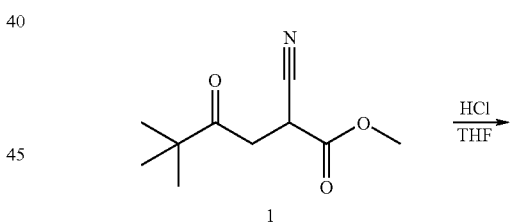

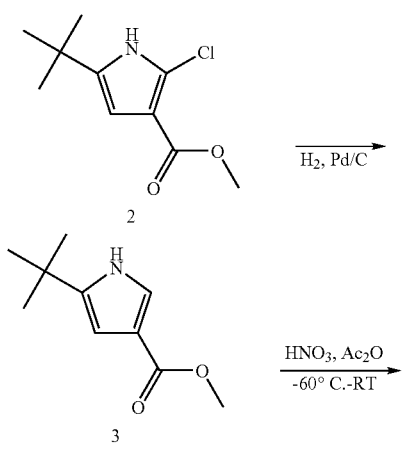

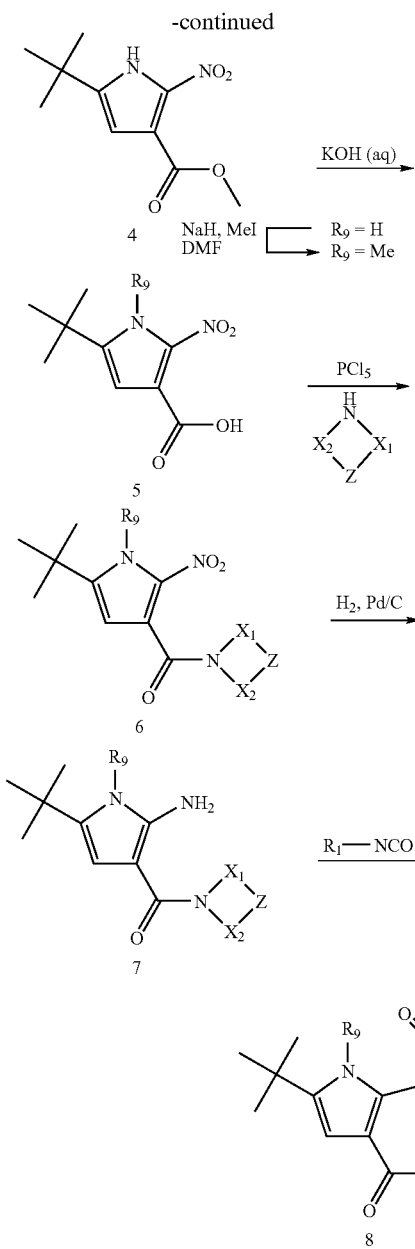

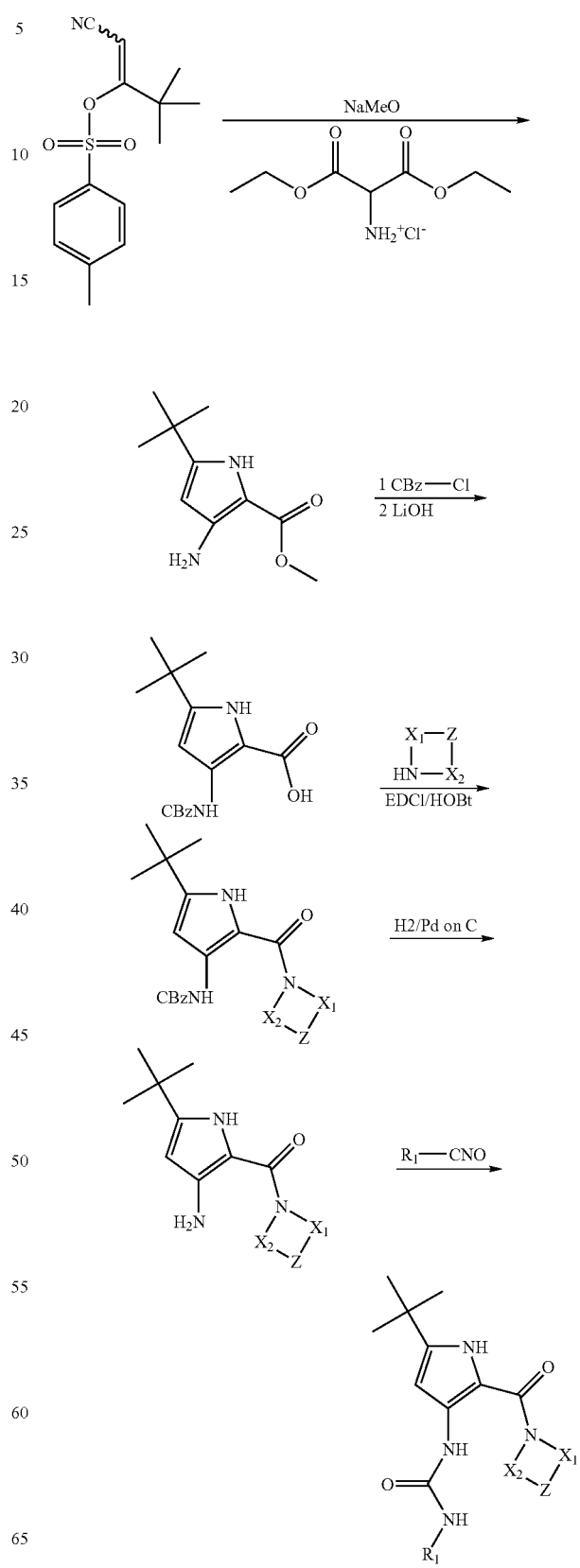

wherein $R^1$, $X^1$, $X^2$, and Z are as defined above and $R^9$ is either H or methyl. 2-Chloropyrrole 2 can be converted in 2 steps to 2-nitropyrrole. The ester moiety can be hydrolyzed, using KOH for example, to the corresponding carboxylic acid 5, which is then reacted with the appropriate amine to yield amide 6 which can be further reacted with a reducing agent, such as hydrogen, to reduce the nitro group to an amine. The amine can then be reacted with the appropriate isocyanate to yield compound 8, which is an exemplary compound of Formula I.

In another embodiment, certain compounds for Formula I can be prepared according to the following scheme:

wherein $X^1$, $X^2$, Z, and $R^1$ are defined as above. The 3-aminopyrrole is protected first as the benzylcarbamate and the ester hydrolyzed to the amide 3 using LiOH. The acid is then reacted with appropriate amine to yield amide 4 which is then deprotected using H2/Pd-c to give the amine 5. The amine can then be reacted with the appropriate isocyanate to yield compound 6, which is an exemplary compound of Formula I.

For example, 2-benzyloxyacetic acid can be reacted with the appropriate amine to yield the amide, which is then reacted with ammonium formate and Pd on carbon to remove benzyl group to give the appropriate tosylate to give the aminofuran, which is further reacted with the appropriate iscocyanate to give an exemplary compound of Formula I.

In another embodiment, certain compounds of Formula I can be prepared according to the following scheme.

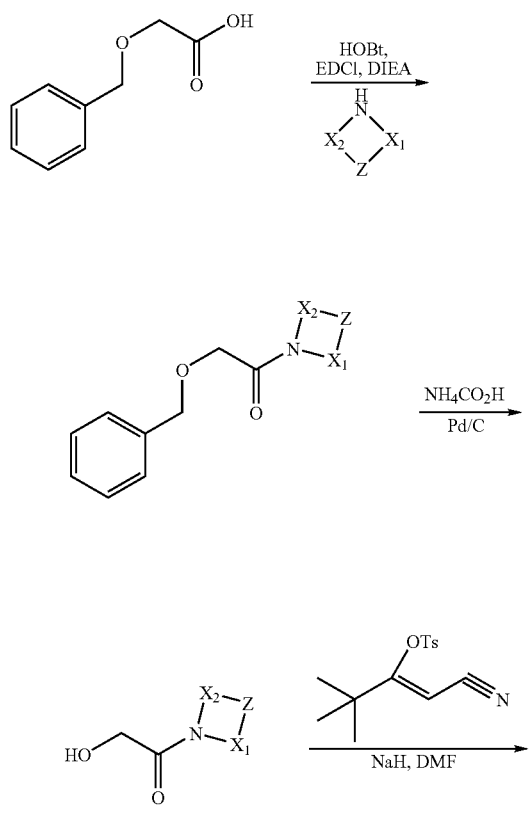

wherein $X^1$, $X^2$, Z, and $R^1$ are defined as above.

In another embodiment, certain compounds according to Formula I can be prepared according to the following scheme

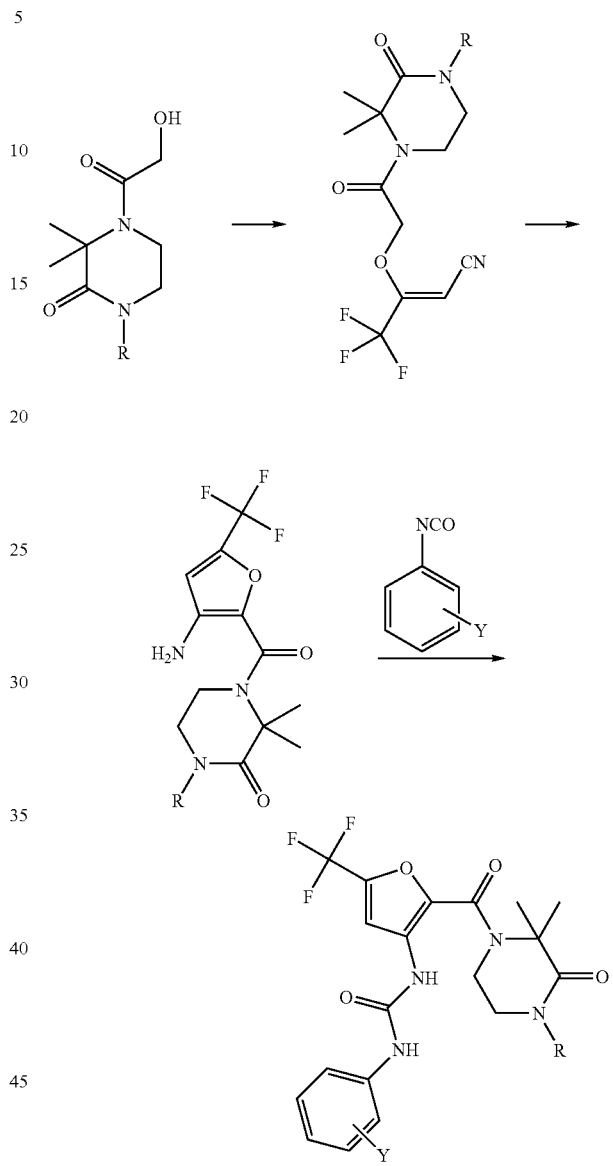

wherein R is defined above. The acid is converted to the ester using NaH, DMF and then heated to give the furan. The aminofuran is then reacted with an appropriate isocyanate to give the final compound which is an exemplary compound of Formula I.

In another embodiment, certain compounds according to Formula I can be prepared according to the following scheme

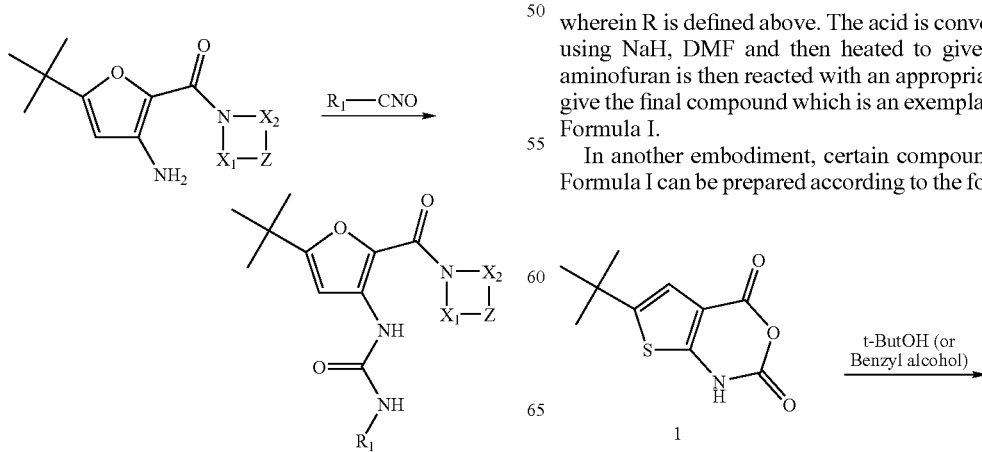

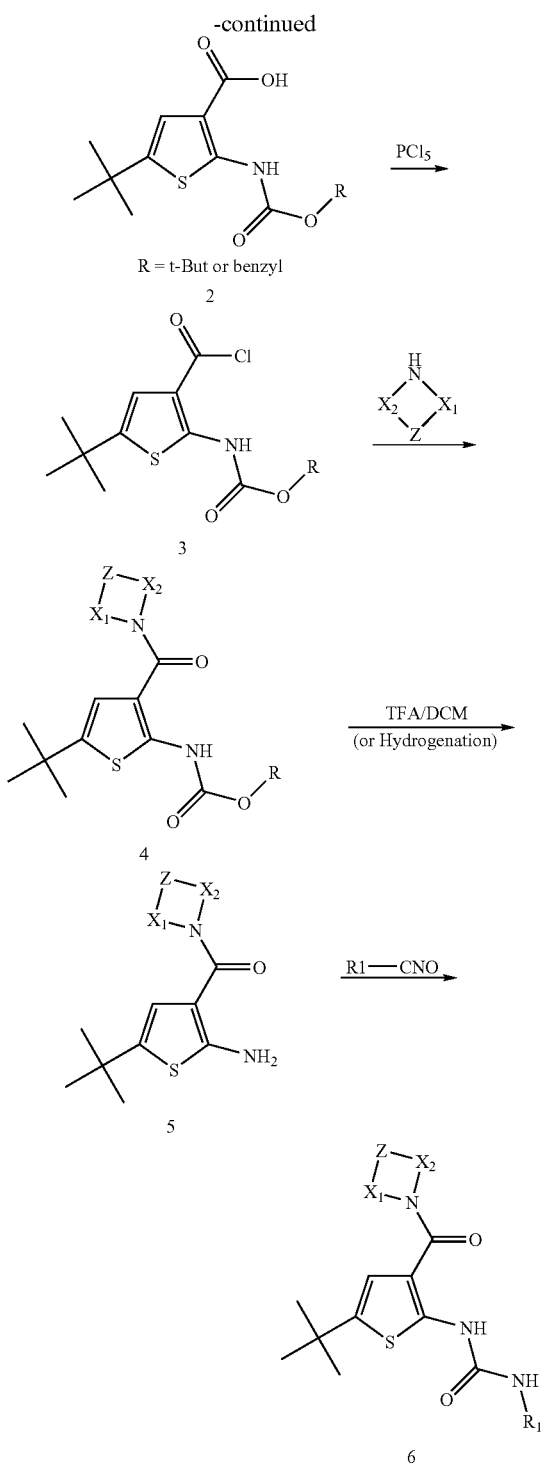

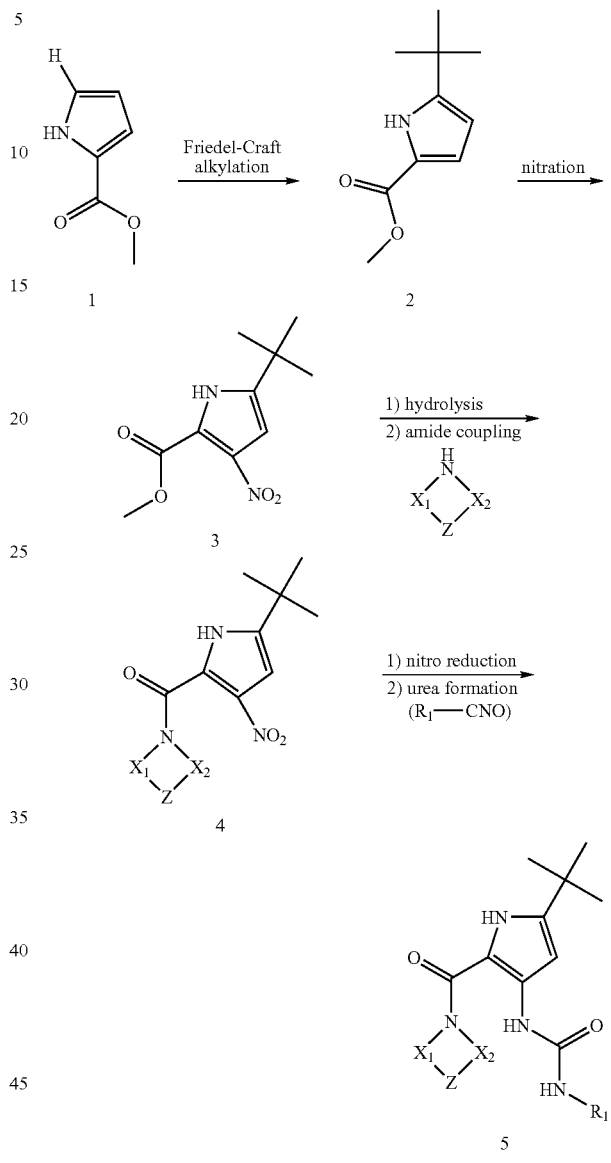

wherein $X^1$, $X^2$, Z, and $R^1$ are as defined above. The compound 1 can be reacted either with t-butanol or benzyl alcohol to give 2 where the amine is either t-Boc or benzylcarbamate protected. The acid is then converted to acid chloride 3, which is then reacted with the appropriate amine to give amide 4. The Boc or the Cbz group is then removed, and the amine 5 is reacted with appropriate isocyanate to give 6 which is an exemplary compound of Formula I.

In another embodiment, certain compounds according to Formula I can be prepared according to the following scheme wherein $X^1$, $X^2$, Z, and $R^1$ are as defined above. The pyrrole can reacted with t-butylchloride under Friedel-Craft alkylation condition to give the tert-butylpyrrole 2, which can then be nitrated. The ester is then hydrolyzed, e.g., with LiOH, and coupled to give amide 4. Compound 4 is then reduced to give the amine which is reacted with isocyanate to give compound 5, which is an exemplary compound of Formula I.

The corresponding starting amines are either commercially available or can be prepared by methods reported in the literature. Other non commercially available starting materials are described below. Of course, other methods and procedures well known in the art may be used to prepare certain compounds of Formula I.

The following examples are illustrative, but not limiting, of the method, compounds, and compositions of the present invention. Other suitable modifications and adaptations of the variety of conditions and parameters normally encountered and obvious to those skilled in the art are within the spirit and scope of the invention.

$^1$H-NMR spectra were recorded according to standard procedures. Significant peaks are tabulated in the order: number of protons, multiplicity (s, singlet; d, doublet; t, triplet; q, quartet; m, multiplet; br s, broad singlet) and coupling constant(s) in Hertz.

EXAMPLES

The following description provides procedures that were used to prepare certain compounds according to Formula I and certain intermediates to prepare those compounds.

The following provides a procedure used for the preparation of 6-tert-butyl-1H-thieno[2,3-d][1,3]oxazine-2,4-dione or 6-tert-butyl-1H-thieno[3,2-d][1,3]oxazine-2,4-dione.

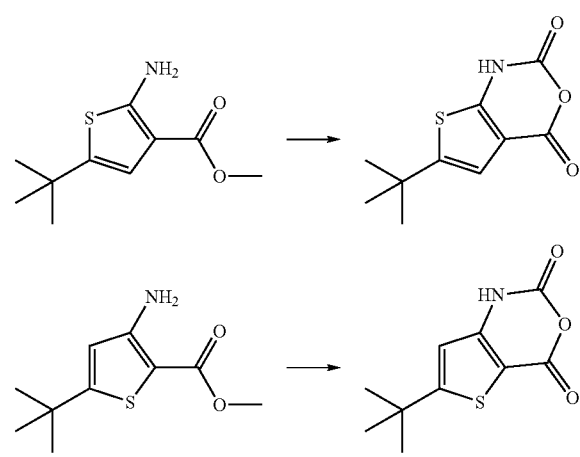

or

To a vial containing methyl 5-tert-butyl-2-aminothiophene-3-carboxylate (0.643 g) in 1:1 methanol:H₂O (6 mL) was added KOH (0.5069 g). The vial was capped and the mixture was stirred at 80° C. for 6 h. The solvent was removed under vacuum and the crude product was dissolved in water (50 mL) and transferred to a 100 mL round bottom flask. To the vigorously stirred aqueous solution was added at room temperature drop wise phosgene (2M toluene, 6 mL) over a 15 minute period. The resulting mixture was stirred at room temperature overnight. The crude reaction mixture was filtered; the precipitate was washed with water, dried and dissolved in ethyl acetate (10 mL). The organic solution was dried over anhydrous sodium sulfate, filtered and the solvent was removed under vacuum to give 654.9 mg (96%) of the expected 6-tert-butyl-1H-thieno[2,3-d][1,3]oxazine-2,4-dione.

In similar way, 6-tert-butyl-1H-thieno[3,2-d][1,3]oxazine-2,4-dione was prepared from methyl 5-tert-butyl-3-aminothiophene-2-carboxylate.

The following provides a procedure that was used for the ring opening of 6-tert-butyl-1H-thieno[2,3-d][1,3]oxazine-2,4-dione or 6-tert-butyl-1H-thieno[3,2-d][1,3]oxazine-2,4-dione by the corresponding amine or aniline.

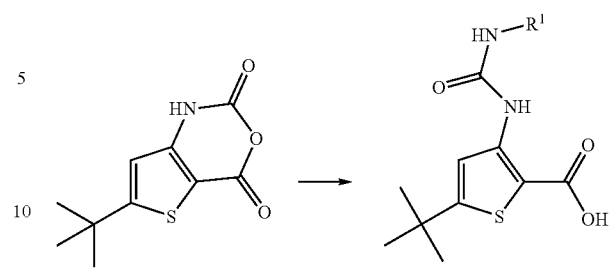

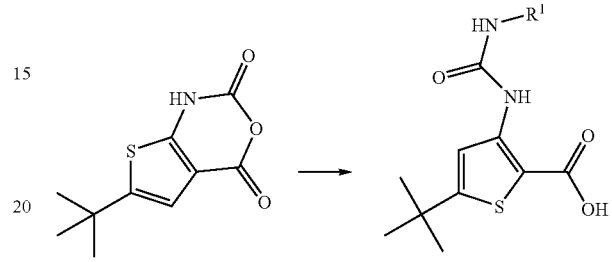

or

A solution of 6-tert-butyl-1H-thieno[2,3-d][1,3]oxazine-2,4-dione (0.597 g, 2.65 mmol), the corresponding amine (2.9 mmol) in THF (20 mL) was stirred at 70° C. overnight. The reaction mixture was allowed to cool down to room temperature. If the product had precipitated the reaction mixture was filtered and the solids were washed with a minimal amount of dichloromethane and dried under vacuum. If the reaction mixture was homogeneous the solvent was eliminated under vacuum and the product was purified by flash chromatography.

The following provides a general procedure that was used to prepare the amides, wherein G is —C(O)—.

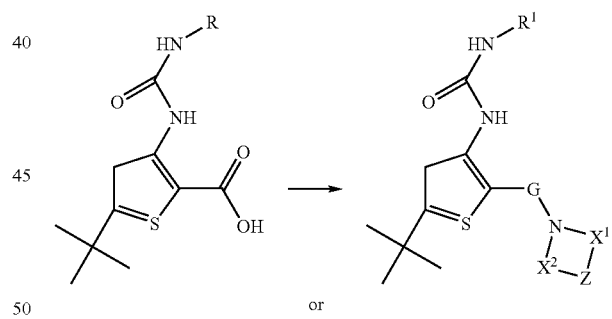

or

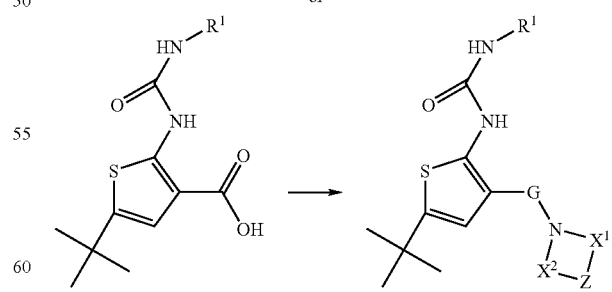

A solution of the previously prepared urea acid (1 mmol), EDCI (1.2 mmol) and HOBt (1.1 mmol) in DCM (5 mL), DMF (5 mL), and the corresponding amine (1 mmol) was stirred at room temperature for 27 h. The reaction mixture was diluted with ethyl acetate (30 mL) and washed with water (3×15 mL) and with brine (15 mL). The organic layer was dried over anhydrous sodium sulfate, filtered and concentrated under vacuum. Purification by flash column yielded the desired product.

Compounds prepared using the preceding method include those of Examples 1, 2, 4, 10-12, 16, 18, 22, 36, and 37.

The following provides a general procedure that was used for the reduction of the amide to prepare a compound as shown below wherein G is $CH_2$.

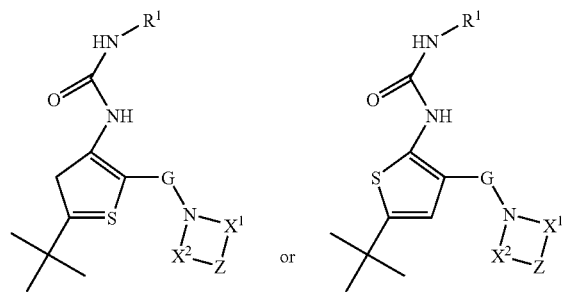

To the previously prepared amide (0.18 mmol) was added $BH_3$:THF (1M solution, 0.18 mL, 0.18 mmol). The resulting mixture was stirred at 60° C. for 8 h. The reaction was cooled to room temperature, quenched by slow addition of methanol (1 mL) and stirred room temperature for 18 h. The solvent was removed under vacuum; the residue was dissolved in MeOH (1 mL) and then passed through an ion exchange column (2.5 g Dowex 50WX2-200 resin, eluted with 20 mL methanol followed by 30 mL of 10% $NH_4OH$ in methanol and 20 mL of methanol). Fractions containing the product were combined and the solvent removed under vacuum. Final purification by flash chromatography (silica gel, eluted with 500 mL of a 96:4 dichloromethane:methanol) gave the expected product.

Compounds prepared using this method include those of Examples 3, 5, 6, 13-15, 19, and 20.

The following provides a general procedure that was used for the preparation of certain compounds according to Formula I.

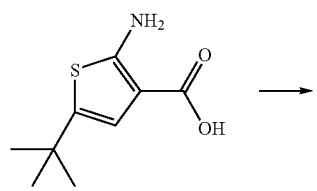

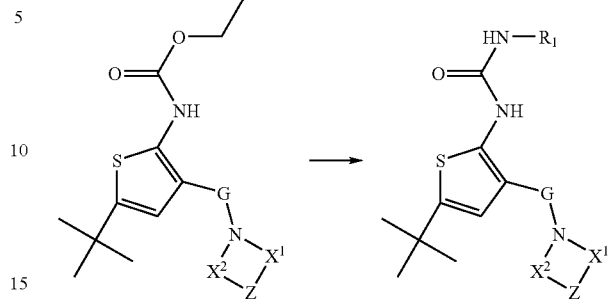

1) Amide Formation: A solution of 5-tert-butyl-2-aminothiophene-3-carboxylic acid (0.75 mmol), EDCI (0.83 mmol) and HOBt (0.83 mmol) in dichloromethane (3 mL) and the corresponding amine (0.9 mmol) was stirred at room temperature overnight. The reaction mixture was diluted with ethyl acetate and washed with water and with brine. The organic layer was dried over anhydrous sodium sulfate, filtered and concentrated under vacuum. Purification by flash column (silica gel) yielded the desired product.

2) Carbamate Formation: To a stirred solution of the previously formed amide (1 mmol) and sodium hydroxide (2.5 mmol) in water (2 mL) and ethyl acetate (4 mL) was added 2,2,2-trichloroethyl chloroformate (1.4 mmol) over 1 hour period keeping the reaction temperature between 5-15° C. The mixture was gradually warmed to room temperature and stirred for an additional 2 hours. To the resulting mixture was added 50% aqueous sodium hydroxide (0.5 mL) and stirred at 80° C. for 1 hour. The reaction was cooled down to room temperature diluted with water and extracted with ethyl acetate (3×10 mL). The combined organic layers were dried over anhydrous sodium sulfate and the solvent eliminated under vacuum yielding the expected compound 3) Urea Formation: A mixture of the previously prepared carbamate (0.086 mmol), the amine (0.1 mmol), DIEA (0.33 mmol), and DMSO (1 mL) was placed in a crimp-top microwave vial and heated in a microwave (to about 85° C.) for 20 minutes. The reaction was cooled and poured into water (30 mL) and extracted with ethyl acetate (3×25 mL). The combined organic layers were washed with water (20 mL), brine (20 mL), dried over anhydrous sodium sulfate, concentrated under vacuum and purified by preparative thin layer chromatography (eluted with 95:5 dichloromethane:methanol) yielding the expected compound.

The same set of reactions can be carried out starting with 5-tert-butyl-3-aminothiophene-2-carboxylic acid to produce additional compounds according to Formula I as shown in the following scheme.

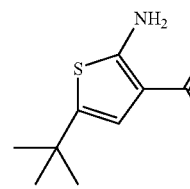

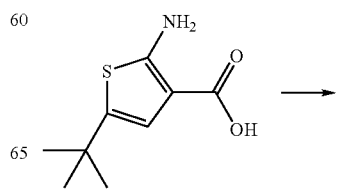

-continued

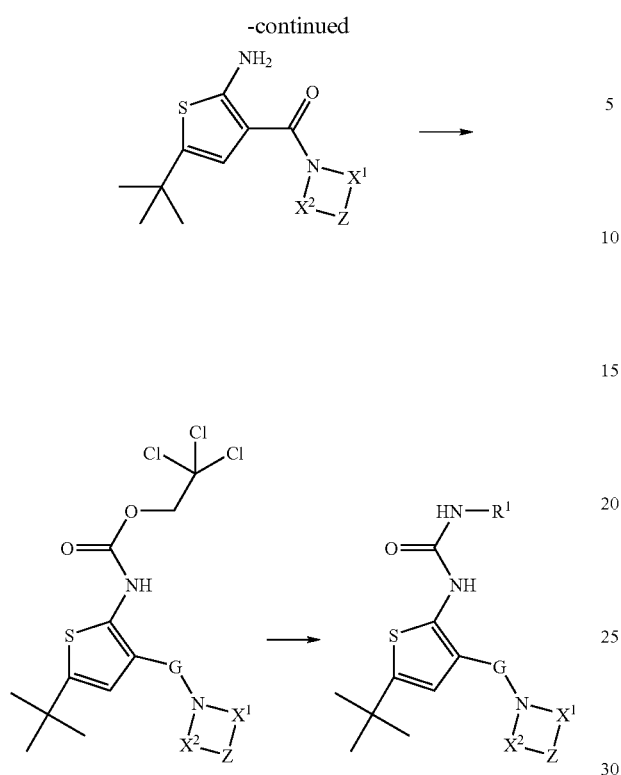

Compounds prepared using this method include those of Examples 29-35 and 41-44.

The following provides a procedure that was used to form the urea for certain compounds according to Formula I.

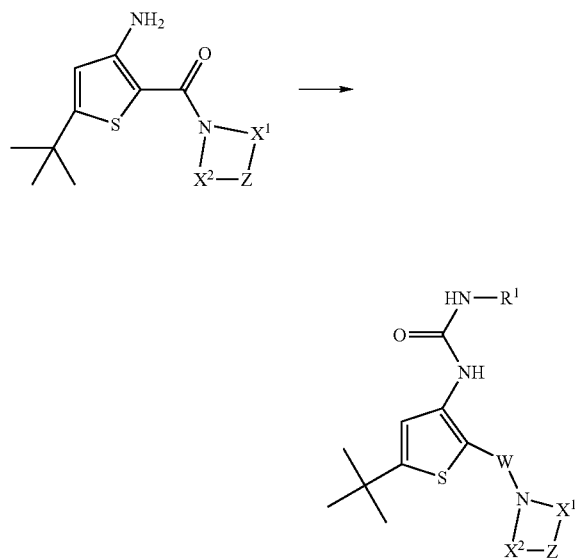

A solution of the amine (0.1358 mmol) and isocyanate (0.152 mmol) in toluene (1 mL) was heated in the microwave at 80° C. for 40 minutes. The solvent was removed under vacuum and the crude mixture was purified by preparative thin layer chromatography (silica gel 95:5 dichloromethane: methanol) to afford the desired compound.

Compounds prepared using this method include those of Examples 38-40 and 45.

The following provides procedure used to prepare certain compounds of Formula I.

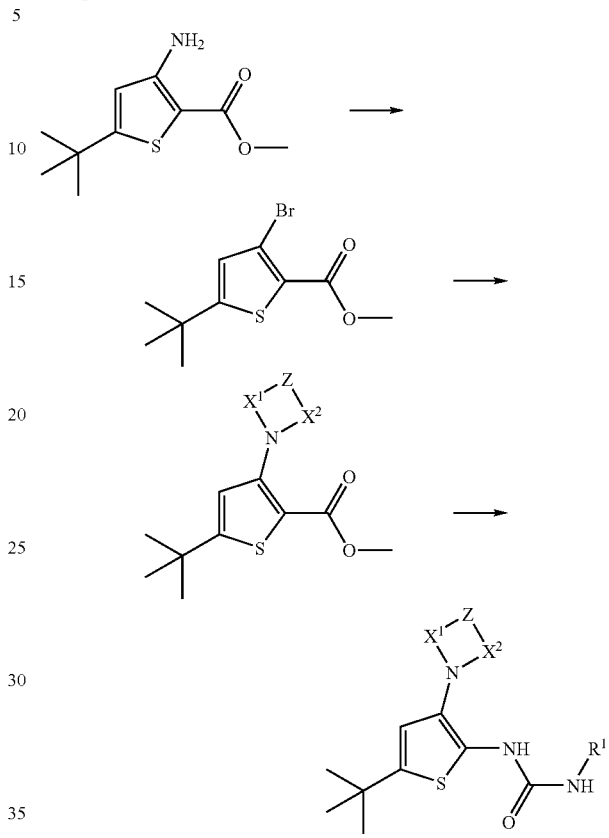

1) Bromide Preparation: To a solution of methyl 5-tert-butyl-3-aminothiophene-2-carboxylate (9.38 mmol) in a mixture of concentrated hydrochloric acid (3 mL) and water (3 mL) cooled to 0° C. (ice bath) was slowly added an aqueous solution of sodium nitrite (11.25 mmol in 2 mL) and stirred for 15 minutes. A solution of cuprous bromide (11.3 mmol) in water (2 mL) was added, and the reaction was heated at 100° C. for 2 hours. The reaction mixture was cooled down to room temperature and basified with aqueous ammonium hydroxide. The resulting precipitate was filtered, dried and purified by column chromatography (silica gel, 1:1 dichloromethane: hexane) to afford the desired bromide product.

2) Bromide displacement: A solution of the previously prepared bromide (1.66 mmol), the amine (1.73 mmol), cesium carbonate (2.02 mmol), and xantphos (0.1443 mmol) in dioxane (2 mL) was added $Pd_2(dba)_3$ (0.072 mmol) and heated at 85° C. overnight. The reaction was cooled down to room temperature, and treated with 1N aqueous hydrogen chloride (30 mL), and extracted with ethyl acetate (3×30 mL). The crude product was purified by chromatographic column (silica gel, 95:5 dichloromethane:methanol) to afford the desired amine.

3) Ester Hydrolysis: A solution of the amine (from the previous step) and sodium hydroxide (50%, 0.5 mL) methanol (4 mL) was heated at 80° C. for 2 hours. The reaction mixture was cooled down to room temperature, treated with aqueous 1N hydrogen chloride (30 mL), and extracted with ethyl acetate (3×30 mL). The combined organic layers were washed with brine, dried over anhydrous magnesium sulfate, and concentrated under vacuum to yield the expected acid.

4) Curtius Reaction: A solution of the acid (0.315 mmol) (from the above step) and triethylamine (0.473 mmol) in toluene (1 mL) was stirred at room temperature for 15 minutes. DPPA (0.4095 mmol) was added, and the reaction mixture was stirred at 100° C. for 2 hours. The reaction was cooled down to room temperature, the amine (1.58 mmol) was added and the resulting mixture was heated at 100° C. for an additional 1 hour. The solvent was removed under vacuum, and the residue was dissolved in methanol (3 mL) and purified by the preparative Supercritical Fluid Chromatography (amino column, 5-50% methanol:carbon dioxide gradient) to afford the desired compound.

Compounds prepared using this method include those of Examples 24 and 27.

Other compounds of Formula I were prepared using the following procedure shown in the following scheme and described as follows.

1) Pyrazole Synthesis: A solution of ethyl hydrazinyl acetate hydrochloride (7.49 mmol) and DIEA (6.51 mmol) in toluene was stirred at room temperature for 15 minutes. 4,4-Dimethyl-3-oxopentanenitrile (7.49 mmol) was added, and the reaction was refluxed overnight. The reaction mixture was quenched with water and the resulting mixture was extracted with ethyl acetate (3×30 mL). The combined organic layers were dried over anhydrous magnesium sulfate and concentrated under vacuum to afford the desired aminopyrazole as a brown solid. This material was used in the next step without further purification.

2) Urea Formation: To a refluxing solution of the previous prepared aminopyrazole (0.4439 mmol) in toluene (4 mL) was added drop wise a solution of the corresponding isocyanate (0.497 mmol) in toluene (1 mL) over a period of 1 hour. The reaction mixture was heated at 50° C. for 18 h, and then cooled down to room temperature. The solvent was removed under vacuum. The crude product was purified by preparative thin layer chromatography (silica gel, 95:5 dichloromethane:methanol) to afford the desired urea.

3) Ester hydrolysis: A solution of the previously prepared urea (0.3296 mmol) and sodium hydroxide (50% aqueous solution, 1.06 mL, 1.32 mmol) in 2:1:1 THF:methanol:$H_2O$ (2 mL) was stirred at room temperature for 2 h. The resulting solution was diluted with brine and extracted with ethyl acetate (3×30 mL). The organic layers were combined, dried, and evaporated under vacuum yielding the desired compound.

4) Amide Formation: A solution of the previously prepared acid (0.2729 mmol), EDCI (0.2729 mmol), HOBt (0.2729 mmol), and appropriate amine (0.30 mmol) in dichloromethane (3 mL) was stirred at room temperature overnight. Water was added, and the mixture extracted with dichloromethane (3×30 mL). The combined organic layers were dried over anhydrous magnesium sulfate, concentrated under vacuum, and purified by preparative thin layer chromatography (silica gel, 95:5 dichloromethane:methanol) to yield the expected compound.

Compounds prepared using this method include those of Examples 7-9.

Certain compounds of Formula I wherein Q is a pyrazole group were prepared using the procedure described as follows.

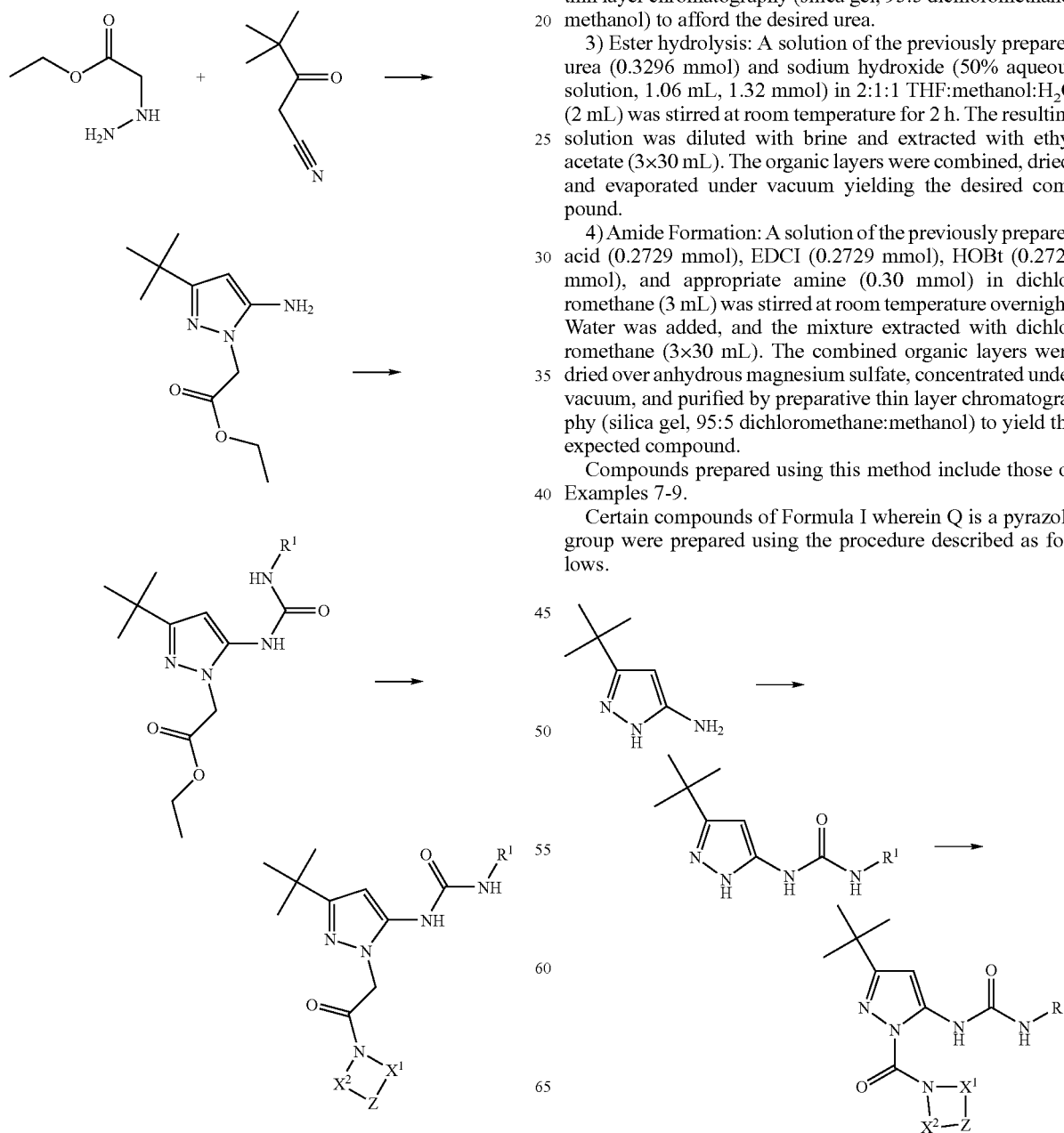

1) Urea Formation: To a solution of 5-tert-butyl-3-amino-2H-pyrazole (5 mmol) in toluene (25 mL) under nitrogen was added the isocyanate (5 mmol). The resulting mixture was refluxed for 26 h. The reaction mixture was cooled down to room temperature and filtered. The filtrate was concentrated and purified by flash column; (5×14 cm silica gel column; 97:3 dichloromethane:methanol 1600 mL) yielding the desired urea.

2) Pyrazole N-derivatization: A mixture of the carbamoyl chloride of the amine (0.9 mmol), DIEA (1.0 mmol), and the previous pyrazole (1.0 mmol) in 1,4-dioxane (5 mL) was heated at 70° C. for 15 h. The reaction mixture was cooled down to room temperature, the solvent was removed under vacuum, and the crude product was purified by flash column (4×15 cm silica, 97:3 dichloromethane:methanol). A final purification was carried out by preparative Supercritical Fluid Chromatography yielding the expected compound.

Compounds prepared using this method include those of Examples 17, 21, and 23.

Certain compounds of Formula I were prepared using the solid phase synthetic method described as follows.

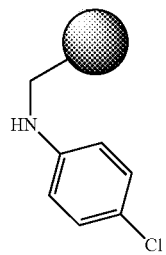

1) BAL resin (backbone amide link resin): 4-(4-formyl-3,5-dimethoxyphenoxy)butyryl AM resin (2 g, 1.0 mmol/g, 2.0 mmol) was placed in a 50 mL syringe. A solution of 4-chloroaniline (1.02 g, 8.0 mmol) in 5% acetic acid in DMF (20 mL) was charged to the syringe, and the syringe was shaken for 2 h. A solution of NaBH(OAc)₃ (1.37 g, 6.5 mmol) in 5% acetic acid in DMF (15 mL) was prepared and added to the resin. After shaking at room temperature for 16 h, the resin was sequentially washed with 5% acetic acid in DMF (2×20 mL), methanol (2×20 mL), dichloromethane (2×20 mL), 10% diisopropylethylamine in dichloromethane (3×20 mL), dichloromethane (4×20 mL), and dried under vacuum.

1.

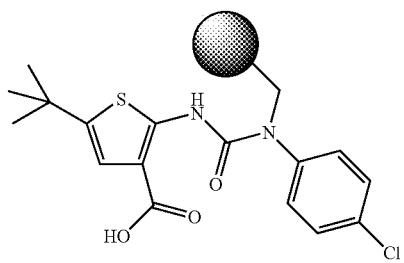

2) The previously prepared secondary amine resin (0.3 mmol) was treated with a solution of 1H-thieno[2,3-d][1,3]oxazine-2,4-dione (168 mg, 0.75 mmol) in tetrahydrofuran (5 mL), and the reaction mixture was heated to 75° C. for 16 h. The resin was washed with THF (2×5 mL) and dichloromethane (4×5 mL), and dried under vacuum.

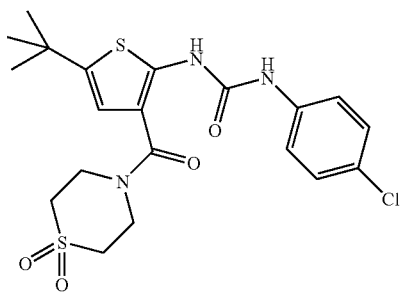

3) Amide Formation and Removal of Resin: The previously prepared acid intermediate on resin was treated with EDCI (172 mg, 0.9 mmol), HOBt (122 mg, 0.9 mmol) and thiomorpholine 1,1-dioxide (121 mg, 0.9 mmol) in dichloromethane at room temperature for 16 h, washed with dichloromethane (2×5 mL), methanol (2×5 mL), dichloromethane (3×5 mL), and dried under vacuum.

An aliquot of resin prepared above (0.1 mmol) was treated with 50% TFA/dichloromethane (2 mL) for 3 min in a 5 mL syringe, and the cleavage solution was filtered. The resin was washed with dichloromethane (1 mL), and the combined solution was evaporated by nitrogen blowing under mild heating to give the product which was extracted with ethyl acetate and 1 N aqueous hydrochloric acid. The organic layer was separated, dried over anhydrous sodium sulfate and concentrated under vacuum to give the desired product (12 mg, 0.025 mmol) as a solid.

¹H NMR (400 MHz, CD₃OD) δ 7.43 (d, J=8.8 Hz, 2H), 7.26 (d, J=8.8 Hz, 2H), 6.65 (s, 1H), 4.09 (m, 4H), 3.21 (m, 4H), 1.35 (s, 9H)

An alternative solid-phase procedure was also used for certain compounds of Formula I as described below.

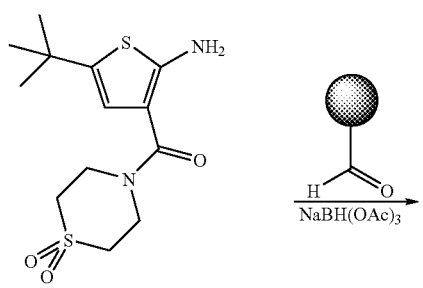

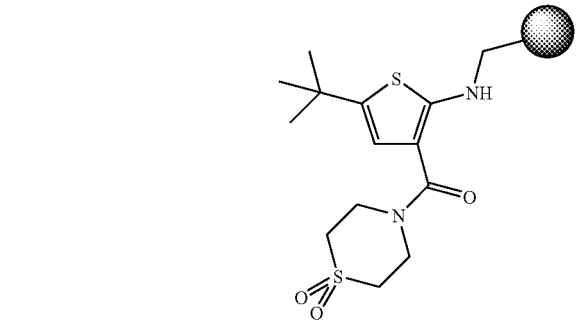

1) BAL resin (backbone amide link resin, 4-(4-formyl-3,5-dimethoxyphenoxy)butyryl AM resin (0.2 g, 1.0 mmol/g, 0.2 mmol) was placed in a 10 mL syringe. A solution of the corresponding substituted thiopheneamine (126 mg, 0.4 mmol) in 5% acetic acid in DMF (3 mL) was charged to the syringe, and the syringe was shaken for 2 h. A solution of NaBH(OAc)$_3$ (127 mg, 0.6 mmol) in 5% acetic acid in DMF (2 mL) was prepared and added to the resin. After shaking at room temperature for 16 h, the resin was sequentially washed with 5% acetic acid in DMF (2×5 mL), methanol (2×5 mL), dichloromethane (2×5 mL), 10% diisopropylethylamine in dichloromethane (3×5 mL), dichloromethane (4×5 mL), and dried under vacuum.

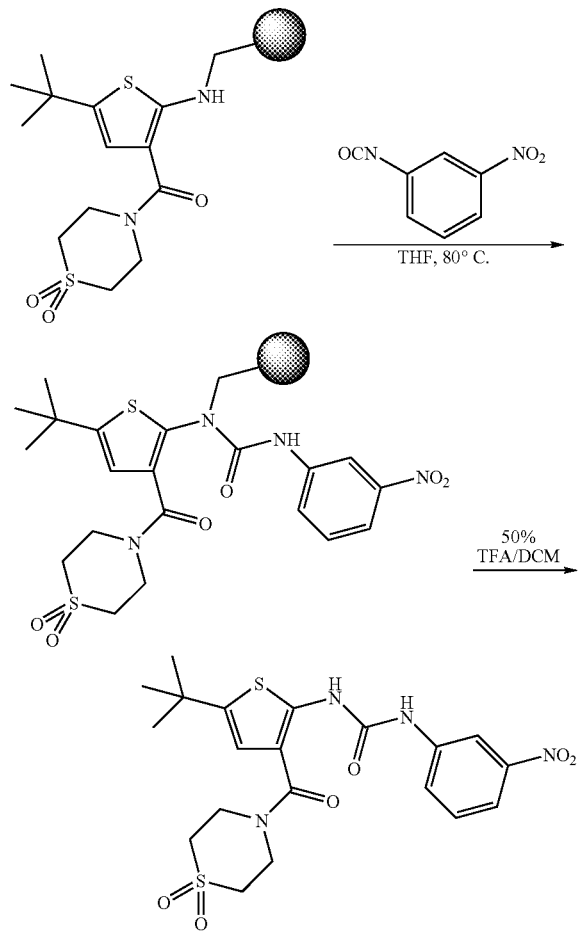

2) Preparation of Resin-linked Urea and Removal of Resin: An aliquot of the resin prepared above (0.1 mmol) was treated with 3-nitrophenyl isocyanate (66 mg, 0.4 mmol) in tetrahydrofuran (3 mL) at 80° C. for 8 h. The resin was sequentially washed with dichloromethane (2×5 mL), methanol (2×5 mL), dichloromethane (3×5 mL), and then treated with 50% TFA/dichloromethane (2 mL) for 3 minutes in a 5 mL syringe, and the cleavage solution was filtered. The resin was washed with dichloromethane (1 mL), and the combined solution was evaporated to dryness by nitrogen blowing under mild heating to give the desired product (22 mg, 0.045 mmol) as a solid.

$^1$H NMR (400 MHz, DMSO-d$_6$) δ 10.22 (s, 1H), 9.67 (s, 1H), 8.48 (t, J=2.2 Hz, 1H), 7.76 (m, 1H), 7.61 (m, 1H), 7.52 (t, J=8.0 Hz, 1H), 6.62 (s, 1H), 3.87 (m, 4H), 3.21 (m, 4H), 1.25 (s, 9H)

Example 1

1-[5-tert-butyl-3-(1,1-dioxo-1λ$^6$-thiomorpholine-4-carbonyl)thiophen-2-yl]-3-(4-chlorophenyl)urea

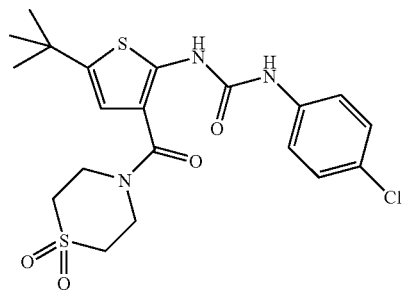

$^1$H NMR (400 MHz, acetone-d$_6$): δ 9.77 (s, 1H), 9.26 (s, 1H), 7.58 (d, J=8.8 Hz, 2H), 7.30 (d, J=9.0 Hz, 2H), 6.73 (s, 1H), 4.14 (t, J=4.9 Hz, 4H), 3.25 (t, J=5.2 Hz, 4H), 1.35 (s, 9H).

Example 2

1-[5-tert-butyl-3-(1,1-dioxo-1λ$^6$-thiomorpholine-4-carbonyl)thiophen-2-yl]-3-naphthalen-1-ylurea

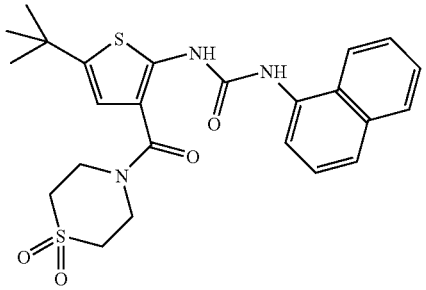

$^1$H NMR (400 MHz, acetone-d$_6$): δ 10.03 (s, 1H), 9.23 (s, 1H), 8.11 (d, J=8.4 Hz, 1H), 8.00 (d, J=7.2 Hz, 1H), 7.86 (d, J=8.0 Hz, 1H), 7.67 (d, J=8.2 Hz, 1H), 7.49-7.41 (m, 2H), 7.40-7.34 (m, 1H), 6.70 (s, 1H), 4.14-4.05 (m, 4H), 3.20 (t, J=4.8 Hz, 4H), 1.30 (s, 9H).

Example 3

1-[5-tert-butyl-3-(1,1-dioxo-1λ$^6$-thiomorpholin-4-ylmethyl)thiophen-2-yl]-3-(4-chlorophenyl)urea

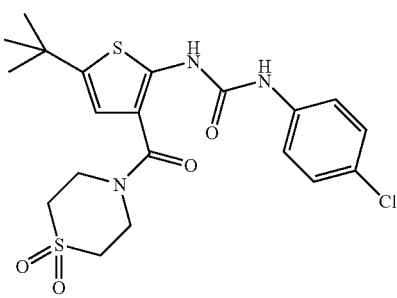

¹H NMR (400 MHz, acetone-d₆): δ 8.87 (s, 1H), 8.47 (s, 1H), 7.52 (d, J=9.0 Hz, 2H), 7.29 (d, J=9.0 Hz, 2H), 6.50 (s, 1H), 3.65 (s, 2H), 3.14-3.08 (m, 4H), 3.00-2.93 (m, 4H), 1.34 (s, 10H).

Example 4

1-[5-tert-butyl-3-(1,1-dioxo-1λ⁶-thiomorpholine-4-carbonyl)thiophen-2-yl]-3-naphthalen-2-ylurea

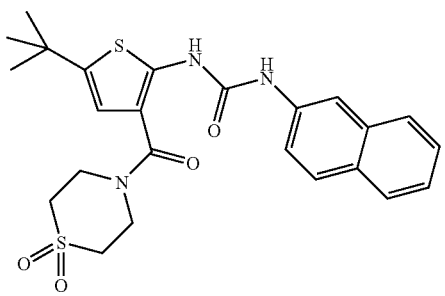

¹H NMR (400 MHz, acetone-d₆): δ 9.85 (s, 1H), 9.41 (s, 1H), 8.27 (d, J=2.0 Hz, 1H), 7.84-7.79 (m, 3H), 7.56 (dd, J=8.9, 2.2 Hz, 1H), 7.48-7.43 (m, 1H), 7.39-7.33 (m, 1H), 6.75 (s, 1H), 4.18-4.11 (m, 4H), 3.25 (t, J=5.3 Hz, 4H), 1.37 (s, 9H).

Example 5

1-[5-tert-butyl-3-(1,1-dioxo-1λ⁶-thiomorpholin-4-ylmethyl)thiophen-2-yl]-3-naphthalen-1-ylurea

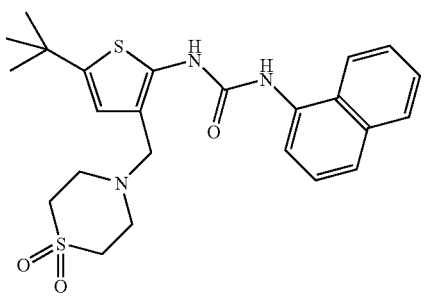

¹H NMR (400 MHz, CD₃OD): δ 8.00-7.93 (m, 1H), 7.87-7.80 (m, 1H), 7.71 (d, J=8.2 Hz, 1H), 7.60 (d, J=7.2 Hz, 1H), 7.49-7.38 (m, 3H), 6.33 (d, J=12.9 Hz, 1H), 3.29 (s, 2H), 2.60 (s, 8H), 1.27 (s, 9H).

Example 6

1-[5-tert-butyl-3-(1,1-dioxo-1λ⁶-thiomorpholin-4-ylmethyl)thiophen-2-yl]-3-naphthalen-2-ylurea

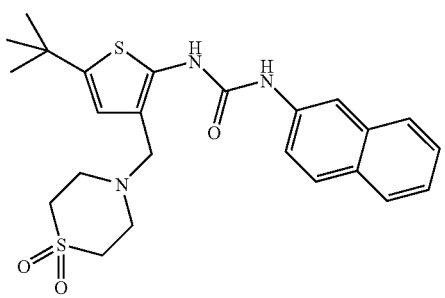

¹H NMR (400 MHz, CD₃OD): δ 8.00 (d, J=2.0 Hz, 1H), 7.77-7.68 (m, 3H), 7.43-7.36 (m, 2H), 7.35-7.30 (m, 1H), 6.40 (s, 1H), 3.52 (s, 2H), 3.00-2.93 (m, 4H), 2.93-2.87 (m, 4H), 1.31 (s, 10H).

Example 7

1-{5-tert-butyl-2-[2-(1,1-dioxo-1λ⁶-thiomorpholin-4-yl)-2-oxoethyl]-2H-pyrazol-3-yl}-3-(4-chlorophenyl)urea

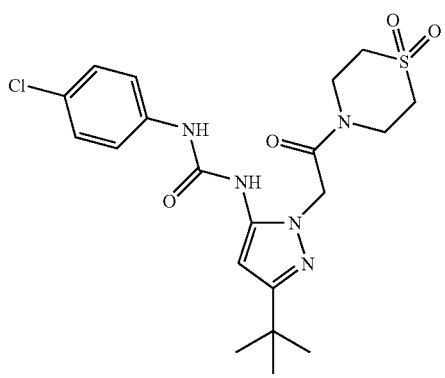

¹H NMR (400 MHz, acetone-d₆): δ 8.70 (s, 1H), 7.88 (s, 1H), 7.53 (dd, J=7.1, 4.6 Hz, 2H), 7.26 (dd, J=7.1, 4.7 Hz, 2H), 6.18 (s, 1H), 5.12 (s, 2H), 0.00 (m, 2H), 4.02 (s, 2H), 0.00 (m, 4H), 0.00 (s, 9H).

Example 8

1-{5-tert-butyl-2-[2-(1,1-dioxo-1λ⁶-thiomorpholin-4-yl)-2-oxoethyl]-2H-pyrazol-3-yl}-3-naphthalen-2-ylurea

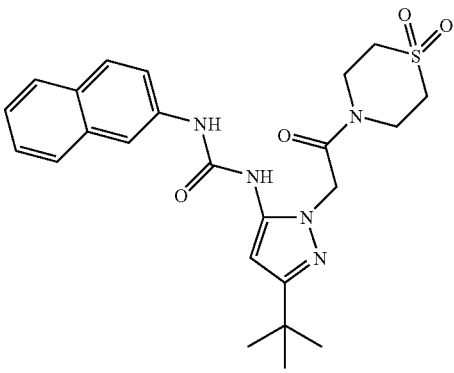

¹H NMR (400 MHz, acetone-d₆): δ 8.86 (s, 1H), 8.15 (d, J=2.0 Hz, 1H), 8.05 (s, 1H), 0.00 (m, 3H), 7.57 (dd, J=8.7, 4.5 Hz, 1H), 7.42 (m, 1H), 7.34 (m, 1H), 6.24 (s, 1H), 5.15 (s, 2H), 0.00 (m, 2H), 0.00 (m, 2H), 3.13 (q, J=5.2 Hz, 4H), 1.27 (s, 9H).

Example 9
1-{5-tert-butyl-2-[2-(1,1-dioxo-1λ⁶-thiomorpholin-4-yl)-2-oxoethyl]-2H-pyrazol-3-yl}-3-naphthalen-1-ylurea

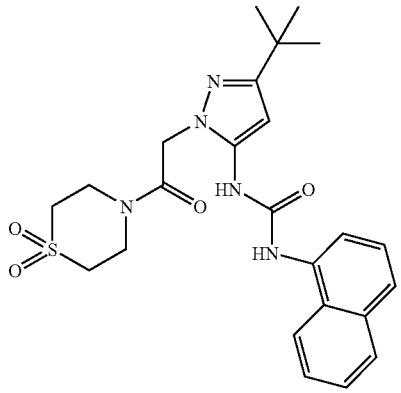

¹H NMR (400 MHz, acetone-$d_6$): δ 8.62 (s, 1H), 8.22 (s, 1H), 8.15 (m, 1H), 7.97 (d, J=11.7 Hz, 1H), 7.89 (m, 1H), 7.67 (d, J=8.2 Hz, 1H), 2.43 (m, 3H), 6.22 (s, 1H), 5.12 (d, J=7.0 Hz, 2H), 4.10 (m, 2H), 3.99 (m, 2H), 3.15 (m, 4H), 1.26 (s, 9H).

Example 10
1-[5-tert-butyl-2-(1,1-dioxo-1λ⁶-thiomorpholine-4-carbonyl)thiophen-3-yl]-3-(4-chlorophenyl)urea

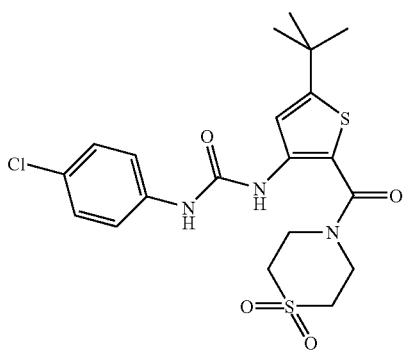

¹H NMR (400 MHz, acetone-$d_6$): δ 9.70 (s, 1H), 9.24 (s, 1H), 7.82 (s, 1H), 7.62 (d, J=14.4 Hz, 2H), 7.30 (d, J=15.3 Hz, 2H), 4.20 (m, 4H), 3.27-3.23 (m, 4H), 1.40 (s, 9H).

Example 11
1-[5-tert-butyl-2-(1,1-dioxo-1λ⁶-thiomorpholine-4-carbonyl)thiophen-3-yl]-3-naphthalen-1-ylurea

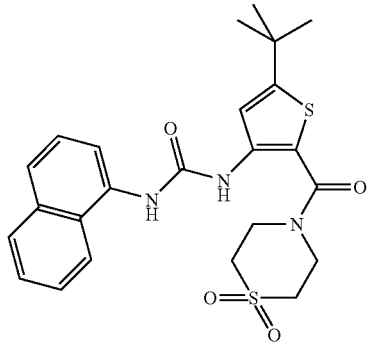

¹H NMR (400 MHz, acetone-$d_6$): δ 9.72 (s, 1H), 9.03 (s, 1H), 8.21 (m, 1H), 7.93 (m, 2H), 7.82 (s, 1H), 7.72 (d, J=8.2 Hz, 1H), 7.50 (m, 3H), 4.20 (m, 4H), 3.22 (m, 4H), 1.38 (s, 9H).

Example 12
1-[5-tert-butyl-2-(1,1-dioxo-1λ⁶-thiomorpholine-4-carbonyl)thiophen-3-yl]-3-naphthalen-2-ylurea

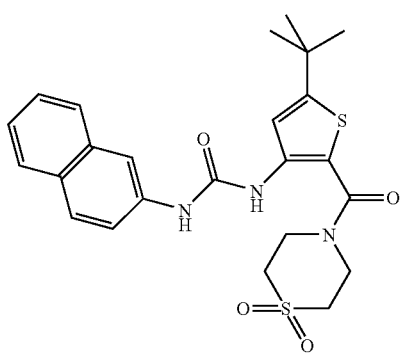

¹H NMR (400 MHz, acetone-$d_6$): δ 9.72 (s, 1H), 9.28 (s, 1H), 8.29 (d, J=2.1 Hz, 1H), 7.86 (s, 1H), 7.81 (m, 3H), 7.59 (dd, J=8.9, 4.4 Hz, 1H), 7.45 (m, 1H), 7.36 (m, 1H), 4.26-4.22 (m, 4H), 3.27 (t, J=5.5 Hz, 4H), 1.41 (s, 9H).

Example 13
1-[5-tert-butyl-2-(1,1-dioxo-1λ⁶-thiomorpholin-4-ylmethyl)thiophen-3-yl]-3-naphthalen-2-ylurea

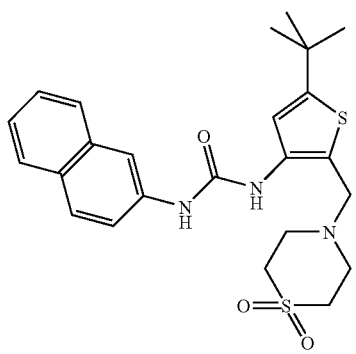

¹H NMR (400 MHz, acetone-$d_6$): δ 9.16 (s, 1H), 8.53 (s, 1H), 8.22 (d, J=2.0 Hz, 1H), 7.78 (d, J=14.2 Hz, 2H), 7.62 (dd, J=8.9, 5.1 Hz, 1H), 7.49 (s, 1H), 7.42 (t, J=7.9 Hz, 1H), 7.32 (t, J=7.2 Hz, 1H), 3.87 (s, 2H), 3.11-3.08 (m, 4H), 3.07-3.04 (m, 4H), 1.37 (s, 9H).

Example 14

1-[5-tert-butyl-2-(1,1-dioxo-1λ⁶-thiomorpholin-4-ylmethyl)thiophen-3-yl]-3-naphthalen-1-ylurea

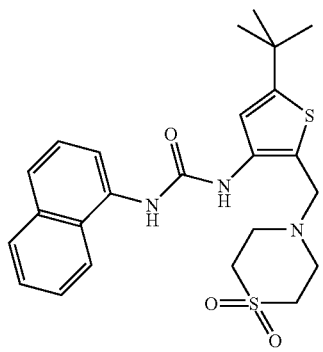

¹H NMR (400 MHz, acetone-d₆): δ 8.29 (s, 1H), 8.19 (s, 1H), 8.10 (m, 1H), 7.96-7.90 (m, 2H), 7.74 (d, J=8.2 Hz, 1H), 7.55-7.49 (m, 3H), 7.45 (s, 1H), 3.71 (s, 2H), 2.89 (d, J=21.3 Hz, 8H), 1.35 (s, 9H).

Example 15

1-[5-tert-butyl-2-(1,1-dioxo-1λ⁶-thiomorpholin-4-ylmethyl)thiophen-3-yl]-3-(4-chlorophenyl)urea

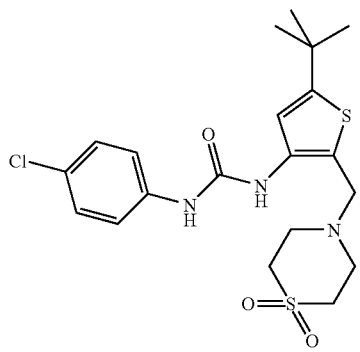

¹H NMR (400 MHz, acetone-d₆): δ 8.88 (s, 1H), 8.40 (s, 1H), 7.57 (d, J=12.6 Hz, 2H), 7.38 (s, 1H), 7.25 (d, J=12.1 Hz, 2H), 3.81 (s, 2H), 3.09-3.09 (m, 4H), 3.04-3.00 (m, 4H), 1.35 (s, 9H).

Example 16

1-[5-tert-butyl-3-(morpholine-4-carbonyl)thiophen-2-yl]-3-naphthalen-1-yl-urea

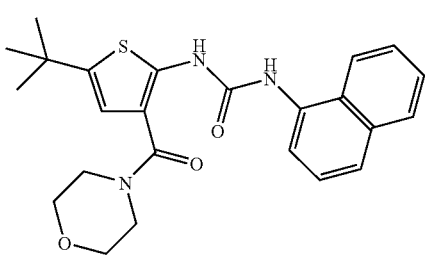

¹H NMR (400 MHz, CDCl₃): δ 10.17 (s, 1H), 8.82-8.74 (m, 1H), 7.92 (d, J=8.6 Hz, 1H), 7.88 (d, J=7.4 Hz, 1H), 7.80 (d, J=8.2 Hz, 1H), 7.64 (d, J=8.2 Hz, 1H), 7.45 (t, J=7.9 Hz, 1H), 7.40 (t, J=7.5 Hz, 1H), 7.27 (t, J=7.6 Hz, 1H), 6.30 (s, 1H), 3.58 (s, 8H), 1.20 (s, 9H).

Example 17

1-[5-tert-butyl-2-(1,1-dioxo-1λ⁶-thiomorpholine-4-carbonyl)-2H-pyrazol-3-yl]-3-(4-chlorophenyl)urea

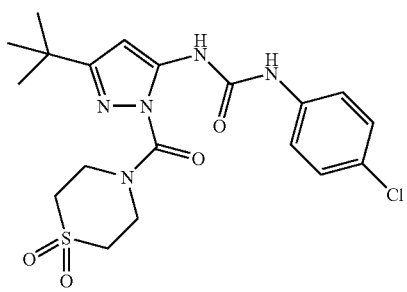

¹H NMR (400 MHz, DMSO-d₆): δ 9.91 (s, 1H), 9.31 (s, 1H), 7.46 (d, J=9.0 Hz, 2H), 7.30 (d, J=8.8 Hz, 2H), 6.46 (s, 1H), 4.07 (s, 4H), 3.34 (s, 4H), 1.22 (s, 9H).

Example 18

1-[5-tert-butyl-3-(thiomorpholine-4-carbonyl)thiophen-2-yl]-3-naphthalen-1-ylurea

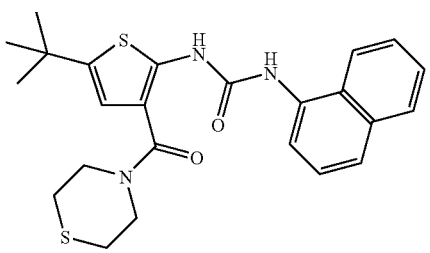

¹H NMR (400 MHz, DMSO-d₆): δ 10.09 (s, 1H), 8.62 (s, 1H), 7.89 (t, J=8.0 Hz, 2H), 7.80 (d, J=8.0 Hz, 1H), 7.64 (d, J=8.2 Hz, 1H), 7.48-7.37 (m, 2H), 7.27 (t, J=7.8 Hz, 1H), 6.29 (s, 1H), 3.87-3.79 (m, 4H), 2.59-2.53 (m, 4H), 1.22 (s, 9H).

Example 19

1-(5-tert-butyl-3-morpholin-4-ylmethylthiophen-2-yl)-3-naphthalen-1-ylurea

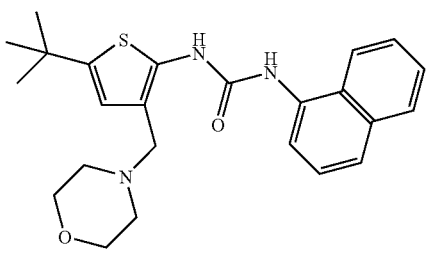

¹H NMR (400 MHz, CDCl₃): δ 9.17 (s, 1H), 8.13-8.07 (m, 1H), 7.88-7.82 (m, 1H), 7.76 (d, J=8.2 Hz, 1H), 7.68 (s, 1H), 7.56 (d, J=7.0 Hz, 1H), 7.52-7.42 (m, 3H), 6.23 (s, 1H), 3.11 (s, 2H), 2.85 (s, 4H), 1.90 (s, 4H), 1.28 (s, 9H).

Example 20

1-(5-tert-butyl-3-thiomorpholin-4-ylmethylthiophen-2-yl)-3-naphthalen-1-yl-urea

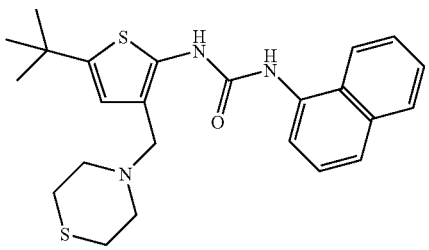

¹H NMR (400 MHz, CDCl₃): δ 8.97 (s, 1H), 8.11-8.05 (m, 1H), 7.93-7.88 (m, 1H), 7.84 (d, J=8.0 Hz, 1H), 7.58-7.48 (m, 4H), 6.92 (s, 1H), 6.21 (s, 1H), 3.12 (s, 2H), 2.19-2.11 (m, 4H), 1.80 (t, J=4.2 Hz, 4H), 1.30 (s, 9H).

Example 21

1-[5-tert-butyl-2-(1,1-dioxo-1$\lambda^6$-thiomorpholine-4-carbonyl)-2H-pyrazol-3-yl]-3-naphthalen-1-ylurea

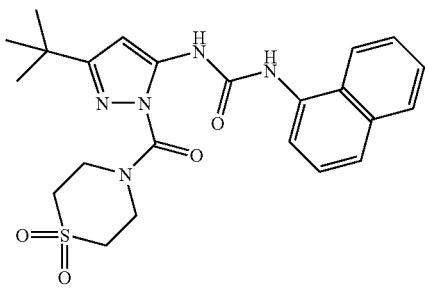

¹H NMR (400 MHz, acetone-d₆): δ 9.45 (s, 1H), 9.16 (s, 1H), 8.21-8.16 (m, 1H), 8.00-7.90 (m, 2H), 7.74 (d, J=8.2 Hz, 1H), 7.56-7.48 (m, 3H), 6.64 (s, 1H), 4.28 (s, 4H), 3.34 (s, 4H), 1.30 (s, 9H).

Example 22

1-[5-tert-butyl-3-(1-oxo-1$\lambda^4$-thiomorpholine-4-carbonyl)thiophen-2-yl]-3-naphthalen-1-ylurea

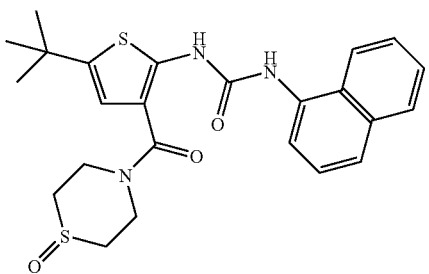

¹H NMR (400 MHz, CDCl₃): δ 9.94 (s, 1H), 9.02 (s, 1H), 8.01 (d, J=8.4 Hz, 1H), 7.83 (d, J=7.4 Hz, 1H), 7.77 (d, J=8.2 Hz, 1H), 7.62 (d, J=8.2 Hz, 1H), 7.42 (t, J=7.9 Hz, 1H), 7.37 (t, J=7.4 Hz, 1H), 7.28 (t, J=7.5 Hz, 1H), 6.31 (s, 1H), 4.01 (d, J=14.4 Hz, 2H), 3.89 (t, J=12.4 Hz, 2H), 2.74 (d, J=13.5 Hz, 2H), 2.56 (t, J=10.8 Hz, 2H), 1.18 (s, 9H).

Example 23

1-[5-tert-butyl-2-(1,1-dioxo-1$\lambda^6$-thiomorpholine-4-carbonyl)-2H-pyrazol-3-yl]-3-naphthalen-2-ylurea

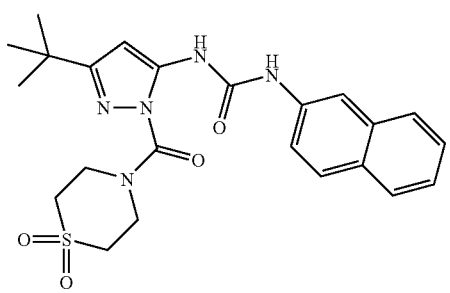

¹H NMR (400 MHz, DMSO-d₆): δ 9.99 (s, 1H), 9.39 (s, 1H), 8.15 (d, J=1.8 Hz, 1H), 7.84-7.74 (m, 3H), 7.46-7.40 (m, 2H), 7.37-7.31 (m, 1H), 6.52 (s, 1H), 4.09 (s, 4H), 3.36 (s, 4H), 1.24 (s, 9H).

Example 24

1-[5-tert-butyl-2-(1,1-dioxo-1$\lambda^6$-thiomorpholin-4-yl)thiophen-3-yl]-3-naphthalen-1-ylurea

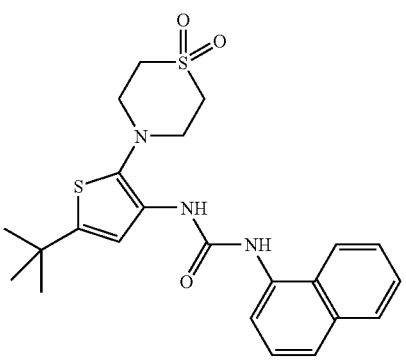

¹H NMR (400 MHz, acetone-d₆): δ 9.12 (s, 1H), 8.64 (s, 1H), 8.31 (m, 1H), 8.02 (d, J=6.8 Hz, 1H), 7.86 (m, 1H), 7.62 (d, J=8.2 Hz, 1H), 7.55 (s, 1H), 7.48-7.42 (m, 3H), 3.35-3.24 (m, 8H), 1.34 (s, 9H).

Example 25

1-[2-tert-butyl-4-(1,1-dioxo-1λ⁶-thiomorpholine-4-carbonyl)thiazol-5-yl]-3-naphthalen-1-ylurea

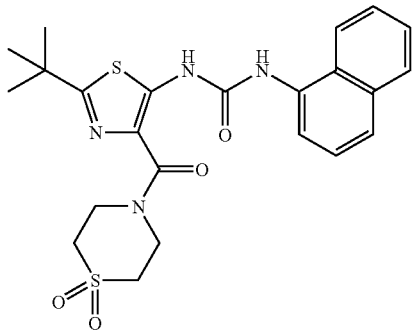

$^1$H NMR (400 MHz, CDCl$_3$): δ 10.96 (s, 1H), 8.92 (s, 1H), 8.06 (d, J=8.4 Hz, 1H), 7.85 (d, J=8.0 Hz, 1H), 7.78-7.71 (m, 2H), 7.53-7.37 (m, 3H), 4.58 (s, 2H), 3.85 (s, 2H), 3.10 (s, 2H), 2.76 (s, 2H), 1.14 (s, 9H).

Example 26

1-[2-tert-butyl-4-(1,1-dioxo-1λ⁶-thiomorpholine-4-carbonyl)thiazol-5-yl]-3-naphthalen-2-ylurea

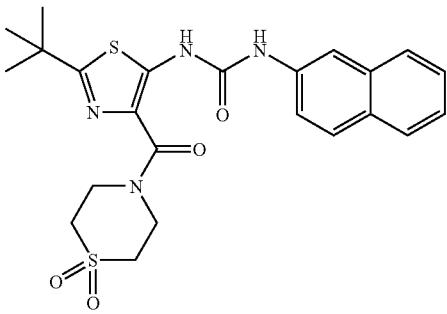

$^1$H NMR (400 MHz, THF-d$_8$): δ 10.95 (s, 1H), 9.50 (s, 1H), 8.23 (s, 1H), 7.78-7.72 (m, 3H), 7.51 (dd, J=8.8, 2.0 Hz, 1H), 7.40 (t, J=7.5 Hz, 1H), 7.32 (t, J=7.6 Hz, 1H), 4.76 (s, 2H), 4.15 (s, 2H), 3.20 (s, 2H), 3.12 (s, 2H), 1.43 (s, 9H).

Example 27

1-[5-tert-butyl-2-(1,1-dioxo-1λ⁶-thiomorpholin-4-yl)thiophen-3-yl]-3-naphthalen-2-ylurea

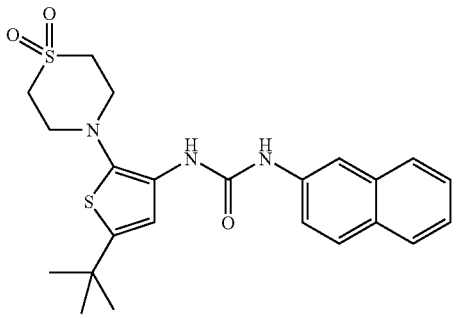

$^1$H NMR (400 MHz, acetone-d$_6$): δ 8.77 (s, 1H), 8.19 (d, J=1.6 Hz, 1H), 8.06 (s, 1H), 7.81-7.75 (m, 3H), 7.58-7.54 (m, 2H), 7.43 (t, J=7.5 Hz, 1H), 7.34 (t, J=7.4 Hz, 1H), 3.40 (t, J=5.0 Hz, 4H), 3.31 (t, J=4.8 Hz, 4H), 1.37 (s, 9H).

Example 28

1-[5-tert-butyl-3-(1,1-dioxo-1λ⁶-thiomorpholine-4-carbonyl)thiophen-2-yl]-3-(4-phenoxyphenyl)urea

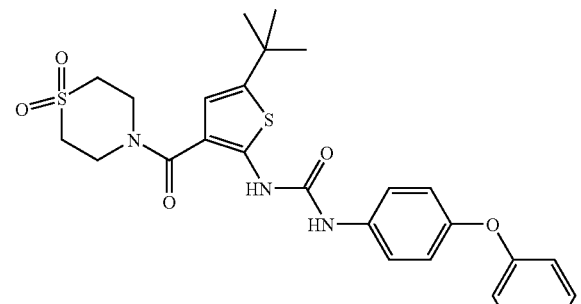

$^1$H NMR (400 MHz, acetone-d$_6$): δ 9.77 (s, 1H), 9.24 (s, 1H), 7.60 (d, J=8.9 Hz, 2H), 7.36 (t, J=7.8 Hz, 2H), 7.09 (t, J=7.4 Hz, 1H), 7.02-6.96 (m, 4H), 6.73 (s, 1H), 4.13 (t, J=5.0 Hz, 4H), 3.23 (t, J=5.3 Hz, 4H), 1.36 (s, 9H).

Example 29

1-[5-tert-butyl-3-(1,1-dioxo-1λ⁶-thiomorpholine-4-carbonyl)thiophen-2-yl]-3-quinolin-8-ylurea

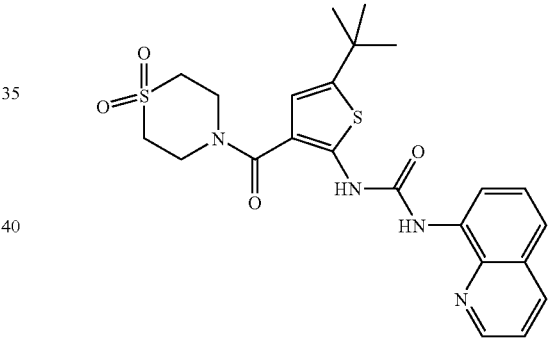

$^1$H NMR (400 MHz, acetone-d$_6$): δ 10.07 (s, 1H), 9.96 (s, 1H), 8.84 (dd, J=4.1, 1.6 Hz, 1H), 8.67 (m, 1H), 8.34 (dd, J=8.4, 1.6 Hz, 1H), 7.59-7.54 (m, 3H), 6.74 (s, 1H), 4.13 (t, J=5.2 Hz, 4H), 3.21 (t, J=5.3 Hz, 4H), 1.39 (s, 9H).

Example 30

1-[5-tert-butyl-3-(1,1-dioxo-1λ⁶-thiomorpholine-4-carbonyl)thiophen-2-yl]-3-indan-1-ylurea

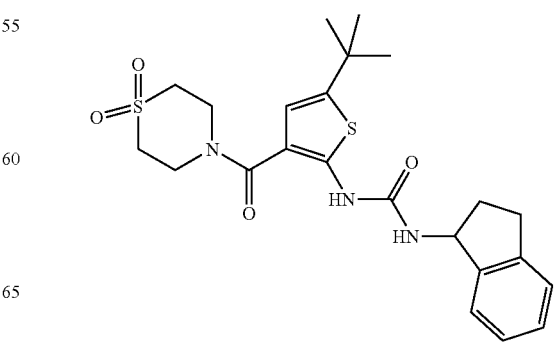

$^1$H NMR (400 MHz, acetone-$d_6$): δ 9.49 (s, 1H), 7.35 (m, 1H), 7.26-7.16 (m, 4H), 6.67 (s, 1H), 5.33 (q, J=7.7 Hz, 1H), 4.08 (t, J=5.1 Hz, 4H), 3.19 (t, J=5.3 Hz, 4H), 2.98 (m, 1H), 2.87 (t, J=8.1 Hz, 1H), 2.54 (m, 1H), 1.88 (m, 1H), 1.36 (s, 9H).

Example 31

1-[5-tert-butyl-3-(1,1-dioxo-1λ$^6$-thiomorpholine-4-carbonyl)thiophen-2-yl]-3-quinolin-4-ylurea

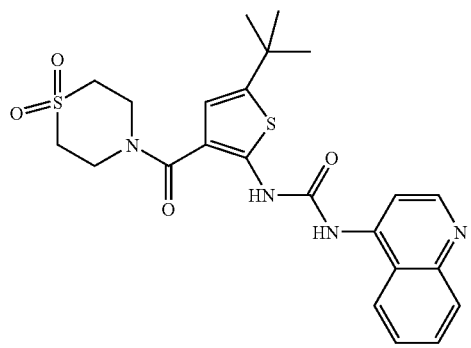

$^1$H NMR (400 MHz, acetone-$d_6$): δ 8.78 (d, J=5.1 Hz, 1H), 8.36-8.28 (m, 2H), 8.02 (d, J=8.4 Hz, 1H), 7.73 (m, 1H), 7.56 (m, 1H), 6.77 (s, 1H), 4.15 (t, J=5.1 Hz, 4H), 3.25 (t, J=5.3 Hz, 4H), 1.39 (s, 9H).

Example 32

1-[5-tert-butyl-3-(1,1-dioxo-1λ$^6$-thiomorpholine-4-carbonyl)thiophen-2-yl]-3-(1H-indazol-7-yl)urea

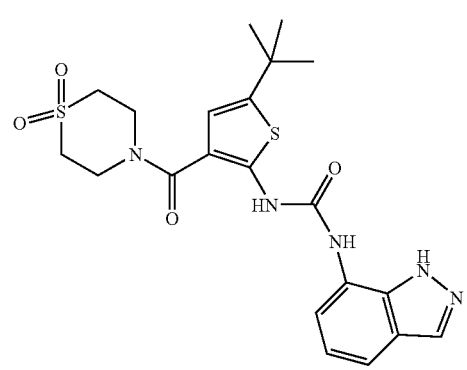

$^1$H NMR (400 MHz, acetone-$d_6$): δ 10.21 (s, 2H), 8.04 (s, 1H), 7.54-7.48 (m, 2H), 7.08 (t, J=7.7 Hz, 1H), 6.74 (s, 1H), 4.15 (t, J=4.9 Hz, 4H), 3.25 (t, J=5.2 Hz, 4H), 1.38 (s, 9H).

Example 33

1-[5-tert-butyl-3-(1,1-dioxo-1λ$^6$-thiomorpholine-4-carbonyl)thiophen-2-yl]-3-(2-oxo-1,2,3,4-tetrahydro-quinolin-7-yl)urea

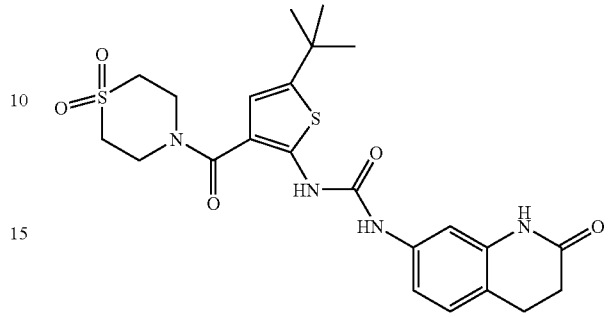

$^1$H NMR (400 MHz, THF-$d_8$): ) 9.73 (s, 1H), 9.01 (s, 1H), 8.90 (s, 1H), 7.10 (s, 1H), 6.90-6.80 (m, 2H), 6.49 (s, 1H), 3.95 (s, 4H), 2.99 (d, J=4.9 Hz, 4H), 2.72 (t, J=7.4 Hz, 2H), 2.33 (t, J=7.1 Hz, 2H), 1.26 (s, 9H).

Example 34

1-[5-tert-butyl-3-(1,1-dioxo-1λ$^6$-thiomorpholine-4-carbonyl)thiophen-2-yl]-3-(4-hydroxynaphthalen-1-yl)urea

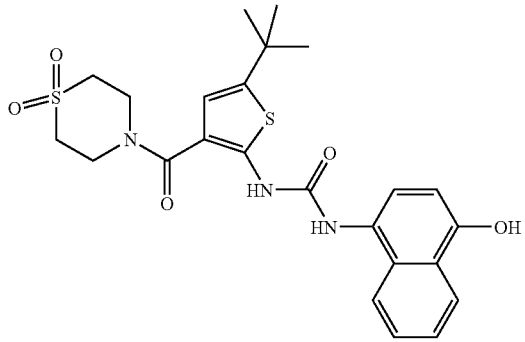

$^1$H NMR (400 MHz, acetone-$d_6$): δ 9.80 (s, 2H), 8.80 (s, 1H), 8.29 (d, J=8.0 Hz, 1H), 8.06 (d, J=8.2 Hz, 1H), 7.57-7.46 (m, 3H), 6.94 (d, J=8.0 Hz, 1H), 6.69 (s, 1H), 4.07 (s, 4H), 3.17 (t, J=4.8 Hz, 4H), 1.34 (s, 9H).

Example 35

1-[5-tert-butyl-3-(3-oxopiperazine-1-carbonyl)thiophen-2-yl]-3-naphthalen-1-ylurea

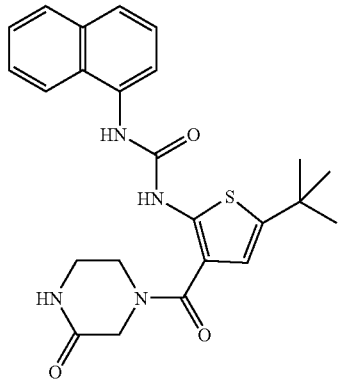

¹H NMR (400 MHz, acetone-d₆): δ 10.23 (s, 1H), 9.48 (s, 1H), 8.20 (d, J=8.0 Hz, 1H), 8.04 (d, J=7.4 Hz, 1H), 7.89 (d, J=6.8 Hz, 1H), 7.69-7.64 (m, 2H), 7.51-7.41 (m, 3H), 6.70 (s, 1H), 4.32 (s, 2H), 3.89 (t, J=5.3 Hz, 2H), 3.47 (s, 2H), 1.34 (s, 9H).

Example 36

1-[5-tert-butyl-3-(5-oxo[1,4]diazepane-1-carbonyl)thiophen-2-yl]-3-naphthalen-1-yl-urea

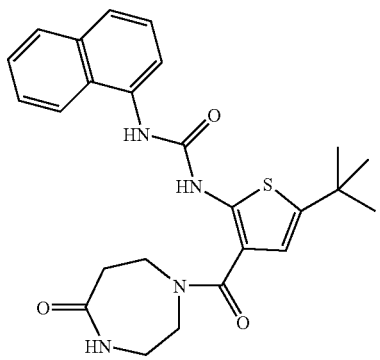

¹H NMR (400 MHz, acetone-d₆): δ 10.29 (s, 1H), 9.55 (s, 1H), 8.18 (d, J=8.2 Hz, 1H), 8.02 (d, J=7.4 Hz, 1H), 7.88 (d, J=8.2 Hz, 1H), 7.66 (d, J=8.2 Hz, 1H), 7.50-7.38 (m, 3H), 7.32 (s, 1H), 6.62 (s, 1H), 3.77 (s, 4H), 3.41 (s, 2H), 2.72 (t, J=5.0 Hz, 2H), 1.34 (s, 9H).

Example 37

1-[5-tert-butyl-3-(1,1-dioxo-1λ⁶-[1,2,5]thiadiazepane-5-carbonyl)thiophen-2-yl]-3-naphthalen-1-ylurea

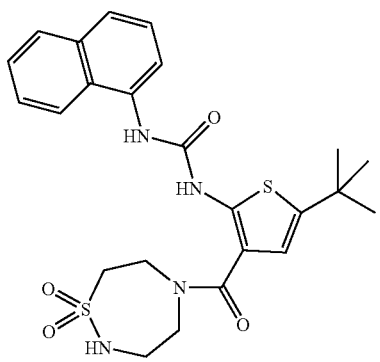

¹H NMR (400 MHz, acetone-d₆): δ 9.19 (s, 1H), 8.15 (m, 1H), 7.97 (d, J=7.6 Hz, 1H), 7.92 (m, 1H), 7.72 (d, J=8.2 Hz, 1H), 7.54-7.47 (m, 3H), 6.73 (s, 1H), 6.57 (s, 1H), 3.99 (t, J=6.0 Hz, 2H), 3.93 (t, J=5.3 Hz, 2H), 3.50 (m, 2H), 3.44 (t, J=5.9 Hz, 2H), 1.35 (s, 9H), 10.08 (s, 1H).

Example 38

1-[5-tert-butyl-3-(1,1-dioxo-1λ⁶-[1,2,5]thiadiazepane-5-carbonyl)thiophen-2-yl]-3-naphthalen-2-ylurea

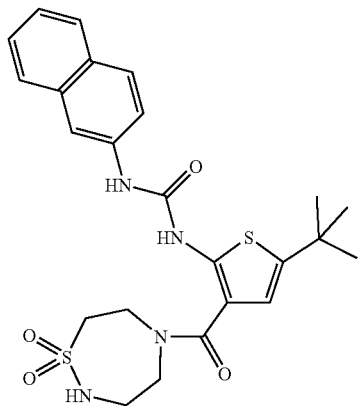

¹H NMR (400 MHz, acetone-d₆): δ 10.05 (s, 1H), 9.45 (s, 1H), 8.26 (d, J=1.8 Hz, 1H), 7.85-7.79 (m, 3H), 7.57 (dd, J=8.9, 2.0 Hz, 1H), 7.46 (t, J=7.6 Hz, 1H), 7.37 (t, J=7.5 Hz, 1H), 6.76 (s, 1H), 6.59 (s, 1H), 4.02 (t, J=6.1 Hz, 2H), 3.95 (t, J=5.3 Hz, 2H), 3.53 (m, 2H), 3.45 (t, J=6.0 Hz, 2H), 1.37 (s, 9H).

Example 39

1-[5-tert-butyl-3-(1,1-dioxo-1λ⁶-[1,2,5]thiadiazepane-5-carbonyl)thiophen-2-yl]-3-(4-chlorophenyl)urea

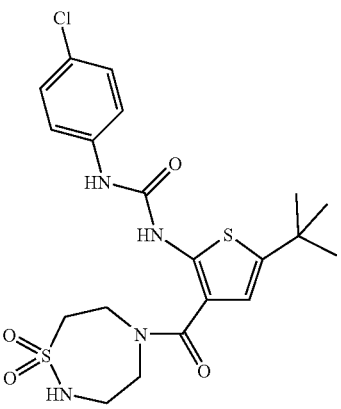

¹H NMR (400 MHz, acetone-d₆): δ 9.41 (s, 1H), 7.61 (d, J=8.8 Hz, 2H), 7.31 (d, J=9.0 Hz, 2H), 6.75 (s, 1H), 6.58 (s, 1H), 4.01 (t, J=6.1 Hz, 2H), 3.93 (t, J=5.3 Hz, 2H), 3.50 (m, 2H), 3.43 (t, J=6.0 Hz, 2H), 1.36 (s, 9H), 10.01 (s, 1H).

Example 40
1-(4-Bromonaphthalen-1-yl)-3-[5-tert-butyl-3-(1,1-dioxo-1λ⁶-thiomorpholine-4-carbonyl)thiophen-2-yl]urea

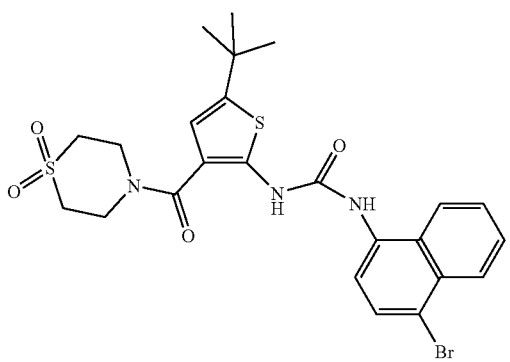

¹H NMR (400 MHz, acetone-d₆): δ 9.96 (s, 1H), 9.42 (s, 1H), 8.28-8.22 (m, 2H), 7.96 (d, J=8.2 Hz, 1H), 7.86 (d, J=8.2 Hz, 1H), 7.69 (t, J=7.6 Hz, 1H), 7.62 (t, J=7.7 Hz, 1H), 6.75 (s, 1H), 4.13 (t, J=5.2 Hz, 4H), 3.24 (t, J=5.3 Hz, 4H), 1.36 (s, 9H).

Example 41
1-[5-tert-butyl-3-(1,1-dioxo-1λ⁶-thiomorpholine-4-carbonyl)thiophen-2-yl]-3-(4-chloronaphthalen-1-yl)urea

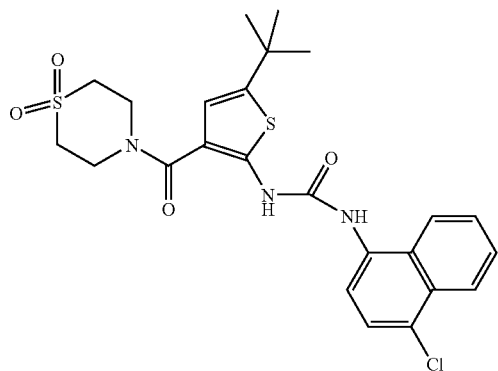

¹H NMR (400 MHz, acetone-d₆): δ 9.88 (s, 1H), 9.49 (s, 1H), 8.27 (d, J=8.4 Hz, 2H), 8.00 (d, J=8.2 Hz, 1H), 7.73-7.60 (m, 3H), 6.74 (s, 1H), 4.13 (t, J=5.1 Hz, 4H), 3.23 (t, J=5.3 Hz, 4H), 1.36 (s, 9H).

Example 42
1-(3H-Benzimidazol-4-yl)-3-[5-tert-butyl-3-(1,1-dioxo-1λ⁶-thiomorpholine-4-carbonyl)thiophen-2-yl]urea

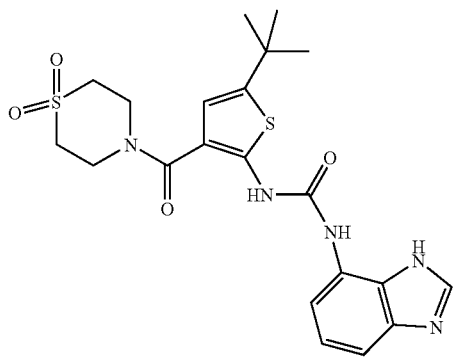

¹H NMR (400 MHz, acetone-d₆): δ 10.02 (s, 1H), 9.43 (s, 1H), 8.11 (s, 1H), 7.96-7.80 (m, 1H), 7.26 (d, J=8.0 Hz, 1H), 7.17 (t, J=7.7 Hz, 1H), 6.71 (s, 1H), 4.11 (s, 4H), 3.21 (s, 4H), 1.38 (s, 9H).

Example 43
1-[5-tert-butyl-3-(1,1-dioxo-1λ⁶-thiomorpholine-4-carbonyl)thiophen-2-yl]-3-(4-cyanonaphthalen-1-yl)urea

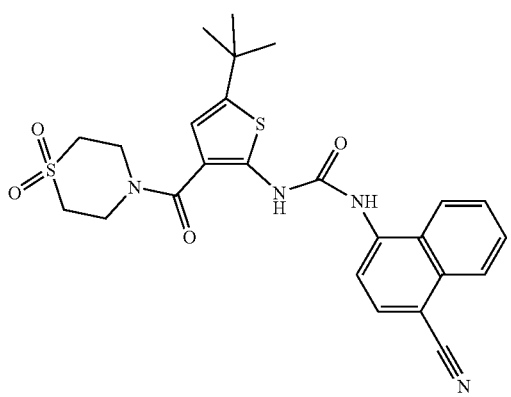

¹H NMR (400 MHz, acetone-d₆): δ 10.12 (s, 1H), 9.93 (s, 1H), 8.46 (d, J=8.6 Hz, 1H), 8.41 (d, J=8.2 Hz, 1H), 8.20 (d, J=8.0 Hz, 1H), 8.06 (d, J=8.2 Hz, 1H), 7.81 (t, J=7.1 Hz, 1H), 7.71 (t, J=7.8 Hz, 1H), 6.76 (s, 1H), 4.15 (t, J=5.0 Hz, 4H), 3.25 (t, J=5.3 Hz, 4H), 1.38 (s, 9H).

Example 44
1-[5-tert-butyl-3-(5-oxo[1,4]diazepane-1-carbonyl)thiophen-2-yl]-3-naphthalen-2-ylurea

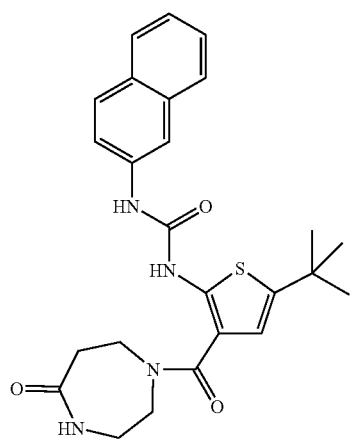

¹H NMR (400 MHz, acetone-d₆): δ 9.94 (s, 1H), 9.56 (s, 1H), 8.29 (s, 1H), 7.86-7.79 (m, 3H), 7.59 (dd, J=8.7, 1.5 Hz, 1H), 7.46 (t, J=7.5 Hz, 1H), 7.37 (t, J=7.5 Hz, 1H), 7.02 (t, J=5.2 Hz, 1H), 6.67 (s, 1H), 3.86-3.77 (m, 4H), 3.47 (q, J=4.7 Hz, 2H), 2.74 (t, J=5.5 Hz, 2H), 1.39 (s, 9H).

Example 45

1-(3-(2-(Methylsulfonyl)ethylcarbamoyl)-5-tert-butylthiophen-2-yl)-3-(naphthalen-1-yl)urea

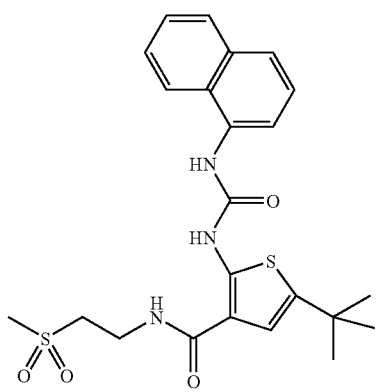

¹H NMR (400 MHz, acetone-d₆): δ 11.36 (s, 1H), 9.41 (s, 1H), 8.28 (m, 1H), 7.99-7.91 (m, 2H), 7.78 (s, 1H), 7.75 (d, J=8.4 Hz, 1H), 7.57-7.50 (m, 3H), 6.99 (s, 1H), 3.83 (q, J=6.5 Hz, 2H), 3.40 (t, J=6.8 Hz, 2H), 3.01 (s, 3H), 1.35 (s, 9H).

Example 46

1-[5-tert-butyl-3-(5-oxo-[1,4]diazepane-1-carbonyl)thiophen-2-yl]-3-(4-chloro-phenyl)urea

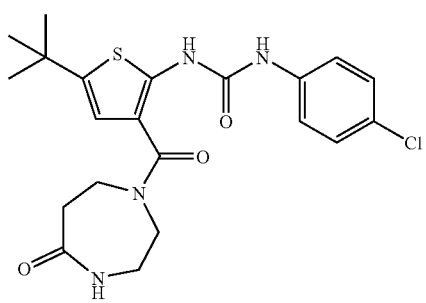

¹H NMR (400 MHz, DMSO-d₆): δ 9.87 (s, 1H), 9.67 (s, 1H), 7.66 (t, J=5.4 Hz, 1H), 7.45 (d, J=8.8 Hz, 2H), 7.30 (d, J=8.8 Hz, 2H), 6.55 (s, 1H), 3.65-3.58 (m, 4H), 3.26-3.19 (m, 2H), 2.60-2.53 (m, 2H), 1.29 (s, 9H).

Example 47

1-[5-tert-butyl-3-(3-oxopiperazine-1-carbonyl)thiophen-2-yl]-3-(4-chloro-phenyl)urea

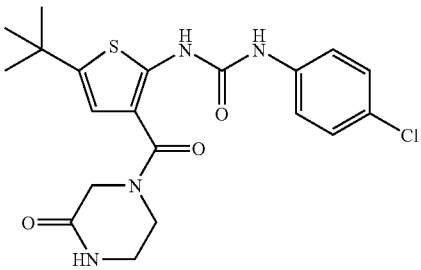

¹H NMR (400 MHz, DMSO-d₆): δ 9.91 (s, 1H), 9.80 (s, 1H), 8.10 (s, 1H), 7.45 (d, J=8.8 Hz, 2H), 7.30 (d, J=8.8 Hz, 2H), 6.64 (s, 1H), 4.07 (s, 2H), 3.70 (t, =5.3 Hz, 2H), 3.25 (s, 2H), 1.30 (s, 9H).

Example 48

1-[5-tert-butyl-3-(3-oxopiperazine-1-carbonyl)thiophen-2-yl]-3-(2-naphthyl)urea

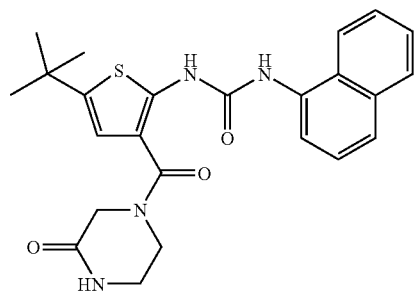

¹H NMR (400 MHz, CDCl₃): δ 9.97 (s, 1H), 9.00 (s, 1H), 8.16 (s, 1H), 7.71-7.62 (m, 3H), 7.56 (s, 1H), 7.40-7.26 (m, 3H), 6.42 (s, 1H), 4.32 (s, 2H), 3.69 (s, 2H), 3.24 (s, 2H), 1.29 (s, 9H).

Example 49

1-[5-tert-butyl-3-(1,1-dioxo-1$\lambda^6$-thiomorpholine-4-carbonyl)thiophen-2-yl]-3-(1H-indol-3-yl)urea

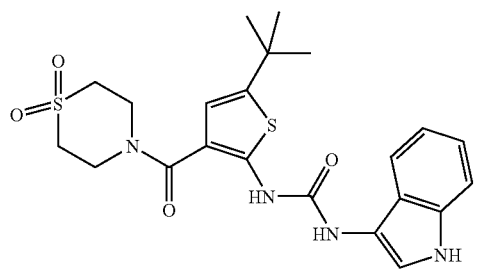

¹H NMR (400 MHz, acetone-d₆): δ 10.05 (s, 1H), 9.78 (s, 1H), 9.08 (s, 1H), 7.71 (s, 1H), 7.63 (d, J=8.0 Hz, 1H), 7.41 (d, J=8.2 Hz, 1H), 7.13 (t, J=7.6 Hz, 1H), 7.02 (t, J=7.4 Hz, 1H), 6.70 (s, 1H), 4.10 (s, 4H), 3.20 (s, 4H), 1.36 (s, 9H).

Example 50

1-[5-tert-butyl-2-(5-oxo-[1,4]diazepane-1-carbonyl)thiophen-3-yl]-3-naphthalen-1-ylurea

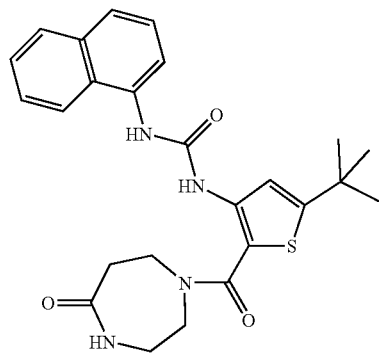

$^1$H NMR (400 MHz, acetone-d$_6$): δ 9.83 (s, 1H), 9.10 (s, 1H), 8.23 (m, 1H), 7.96-7.89 (m, 2H), 7.88 (s, 1H), 7.70 (d, J=8.2 Hz, 1H), 7.53-7.47 (m, 3H), 3.88 (m, 4H), 3.45 (q, J=4.7 Hz, 2H), 2.70 (t, J=5.4 Hz, 2H), 1.39 (s, 9H).

Example 51

1-[5-tert-butyl-2-(1,1-dioxo-1λ$^6$-[1,2,5]thiadiazepane-5-carbonyl)thiophen-3-yl]-3-naphthalen-1-ylurea

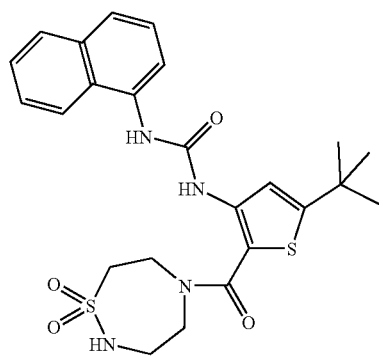

$^1$H NMR (400 MHz, acetone-d$_6$): δ 10.03 (s, 1H), 9.19 (s, 1H), 8.25 (m, 1H), 7.97-7.87 (m, 3H), 7.70 (d, J=8.2 Hz, 1H), 7.53-7.45 (m, 3H), 7.38 (s, 1H), 4.31 (s, 2H), 4.00 (t, J=5.0 Hz, 2H), 3.49 (s, H), 1.39 (s, 9H).

Example 52

1-[5-tert-butyl-2-(3-oxopiperazine-1-carbonyl)thiophen-3-yl]-3-naphthalen-1-ylurea

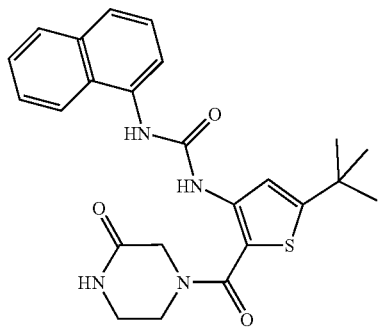

$^1$H NMR (400 MHz, acetone-d$_6$): δ 10.03 (s, 1H), 9.19 (s, 1H), 8.25 (m, 1H), 7.97-7.87 (m, 3H), 7.70 (d, J=8.2 Hz, 1H), 7.53-7.45 (m, 3H), 7.38 (s, 1H), 4.31 (s, 2H), 4.00 (t, J=5.0 Hz, 2H), 3.49 (s, 2H), 1.39 (s, 9H).

Example 53

1-[5-tert-butyl-3-(5-oxo-[1,4]diazepane-1-carbonyl)thiophen-2-yl]-3-(2,3-dichlorophenyl)urea

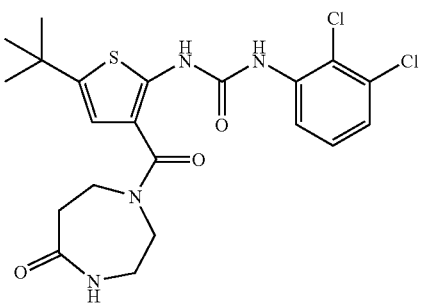

$^1$H NMR (400 MHz, CD3OD): δ 7.99 (dd, J=7.1, 2.6 Hz, 1H), 7.25-7.19 (m, 2H), 6.59 (s, 1H), 3.79-3.71 (m, 4H), 3.39-3.33 (m, 2H), 2.75-2.68 (m, 2H), 1.33 (s, 9H).

Example 54

1-[5-tert-butyl-3-(5-oxo-[1,4]diazepane-1-carbonyl)thiophen-2-yl]-3-(3-chlorophenyl)urea

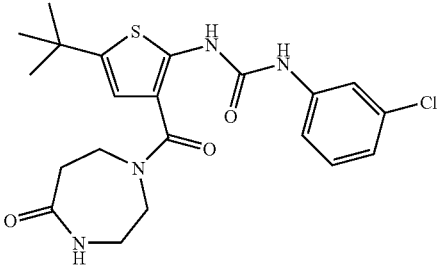

¹H NMR (400 MHz, DMSO-d₆): δ 9.95 (s, 1H), 9.71 (s, 1H), 7.70-7.63 (m, 2H), 7.28 (t, J=8.0 Hz, 1H), 7.24-7.19 (m, 1H), 7.01 (ddd, J=7.8, 1.9, 1.1 Hz, 1H), 6.56 (s, 1H), 3.66-3.58 (m, 4H), 3.26-3.20 (m, 2H), 2.61-2.54 (m, 2H), 1.30 (s, 9H).

Example 55

1-[5-tert-butyl-3-(5-oxo-[1,4]diazepane-1-carbonyl)thiophen-2-yl]-3-(4-cyanonaphthyl)urea

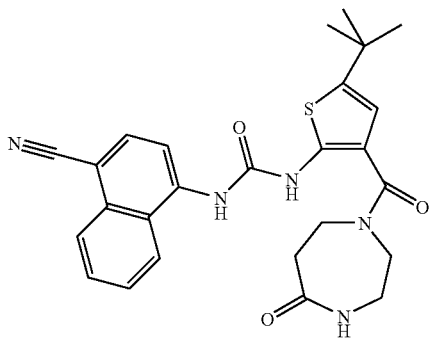

¹H NMR (400 MHz, acetone-d₆): δ 8.41 (d, J=8.0 Hz, 2H), 8.19 (d, J=8.4 Hz, 1H), 8.05 (d, J=8.2 Hz, 1H), 7.79 (t, J=7.6 Hz, 1H), 7.68 (t, J=7.7 Hz, 1H), 7.08 (s, 1H), 6.69 (s, 1H), 3.83 (m, 4H), 3.48 (t, J=4.1 Hz, 2H), 2.75 (m, 2H), 1.38 (s, 9H).

Example 56

1-[5-tert-butyl-3-(1,1-dioxo-1λ⁶-[1,2,5]thiadiazepane-5-carbonyl)thiophen-2-yl]-3-(4-cyanonaphthalen-1-yl)urea

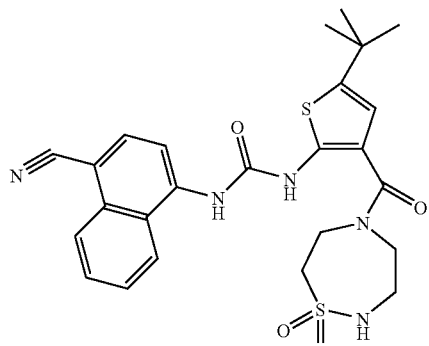

¹H NMR (400 MHz, acetone-d₆): δ 8.43-8.37 (m, 2H), 8.19 (d, J=8.4 Hz, 1H), 8.05 (d, J=8.2 Hz, 1H), 7.80 (t, J=7.6 Hz, 1H), 7.70 (t, J=7.7 Hz, 1H), 6.77 (s, 1H), 4.00 (t, J=6.1 Hz, 2H), 3.95 (t, J=5.4 Hz, 2H), 3.52 (t, J=5.3 Hz, 2H), 3.44 (t, J=6.1 Hz, 2H), 1.38 (s, 9H).

Example 57

1-[5-tert-butyl-3-(3-oxopiperazine-1-carbonyl)thiophen-2-yl]-3-(4-cyano-naphthalen-1-yl)urea

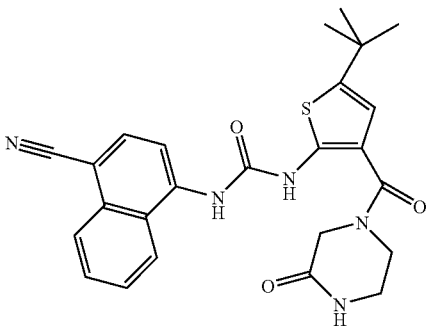

¹H NMR (400 MHz, acetone-d₆): δ 10.28 (s, 1H), 10.17 (s, 1H), 8.41 (d, J=8.4 Hz, 1H), 8.27 (d, J=8.2 Hz, 1H), 8.14-8.04 (m, 3H), 7.80 (t, J=7.3 Hz, 1H), 7.74 (t, J=7.4 Hz, 1H), 6.66 (s, 1H), 4.10 (s, 2H), 3.71 (t, J=5.2 Hz, 2H), 3.26 (s, 2H), 1.31 (s, 9H).

Example 58

1-[5-tert-butyl-3-(1,1-dioxo-1λ⁶-thiomorpholine-4-carbonyl)thiophen-2-yl]-3-(2,3-dichlorophenyl)urea

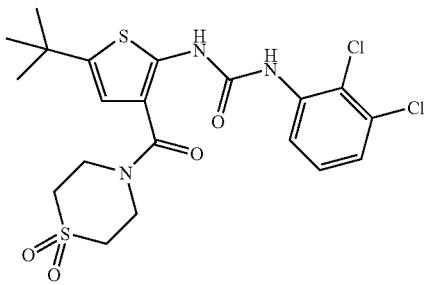

¹H NMR (400 MHz, DMSO-d₆): δ 10.00 (s, 1H), 9.32 (s, 1H), 7.95-7.88 (m, 1H), 7.27-7.23 (m, 2H), 6.62 (s, 1H), 3.85 (s, 4H), 3.23-3.17 (m, 4H), 1.23 (s, 9H).

Example 59

1-[5-tert-butyl-3-(1,1-dioxo-1λ⁶-thiomorpholine-4-carbonyl)thiophen-2-yl]-3-(3-chlorophenyl)urea

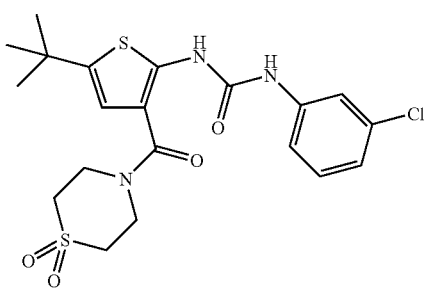

$^1$H NMR (400 MHz, DMSO-d$_6$): δ 9.94 (s, 1H), 9.63 (s, 1H), 7.69 (t, J=2.0 Hz, 1H), 7.28 (t, J=8.0 Hz, 1H), 7.23 (ddd, J=8.2, 1.9, 1.1 Hz, 1H), 7.02 (ddd, J=7.7, 1.9, 1.1 Hz, 1H), 6.66 (s, 1H), 3.92 (s, 4H), 3.29-3.23 (m, 4H), 1.30 (s, 9H).

Example 60

1-Benzo[1,3]dioxol-5-yl-3-[5-tert-butyl-3-(1,1-dioxo-1λ$^6$-thiomorpholine-4-carbonyl)thiophen-2-yl]urea

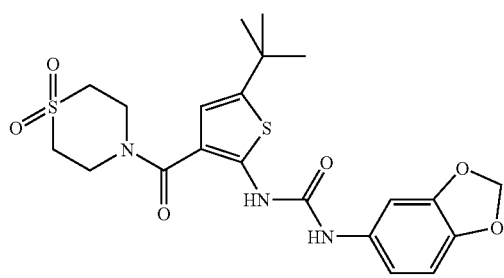

$^1$H NMR (400 MHz, acetone-d$_6$): δ 9.74 (s, 1H), 9.22 (s, 1H), 7.32 (d, J=2.1 Hz, 1H), 6.90 (dd, J=8.4, 2.1 Hz, 1H), 6.77 (d, J=8.4 Hz, 1H), 6.71 (s, 1H), 5.96 (s, 2H), 4.12 (t, J=5.2 Hz, 4H), 3.23 (t, J=5.3 Hz, 4H), 1.36 (s, 9H)

Example 61

1-[5-tert-butyl-3-(1,1-dioxo-1λ$^6$-thiomorpholine-4-carbonyl)thiophen-2-yl]-3-(2,2-difluorobenzo[1,3]dioxol-5-yl)urea

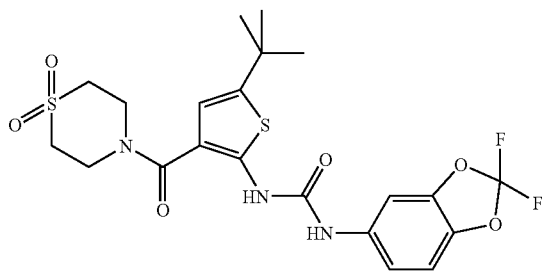

The compound of the Example 61 was prepared according to Method II using suitable reactants.

$^1$H NMR (400 MHz, acetone-d$_6$): δ 9.83 (s, 1H), 9.55 (s, 1H), 7.77 (s, 1H), 7.20 (s, 2H), 6.74 (s, 1H), 4.13 (t, J=5.1 Hz, 4H), 3.23 (t, J=5.2 Hz, 4H), 1.37 (s, 9H).

Example 62

1-[5-tert-butyl-3-(1,1-dioxo-1λ$^6$-thiomorpholine-4-carbonyl)thiophen-2-yl]-3-(3-chloro-4-methoxyphenyl)urea

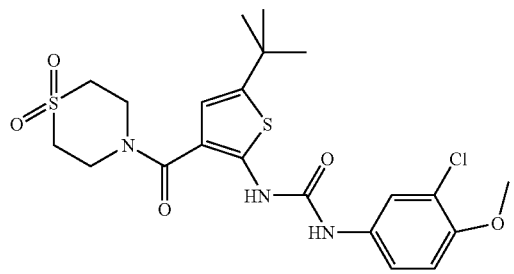

$^1$H NMR (400 MHz, acetone-d$_6$): δ 9.78 (s, 1H), 9.27 (s, 1H), 7.78 (d, J=2.5 Hz, 1H), 7.40 (dd, J=9.0, 2.5 Hz, 1H), 7.07 (d, J=9.0 Hz, 1H), 6.72 (s, 1H), 4.13 (t, J=5.2 Hz, 4H), 3.87 (s, 3H), 3.23 (t, J=5.3 Hz, 4H), 1.37 (s, 9H).

Example 63

1-[5-tert-butyl-3-(1,1-dioxo-1λ$^6$-thiomorpholine-4-carbonyl)thiophen-2-yl]-3-(3,4-dichlorophenyl)urea

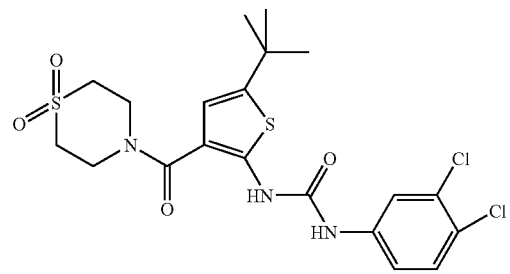

$^1$H NMR (400 MHz, acetone-d$_6$): δ 9.88 (s, 1H), 9.64 (s, 1H), 8.00 (d, J=2.1 Hz, 1H), 7.50-7.43 (m, 2H), 6.74 (s, 1H), 4.13 (t, J=5.0 Hz, 4H), 3.24 (t, J=5.3 Hz, 4H), 1.37 (s, 9H).

Example 64

1-[5-tert-butyl-3-(1,1-dioxo-1λ$^6$-thiomorpholine-4-carbonyl)thiophen-2-yl]-3-(3-chloro-4-cyanophenyl)urea

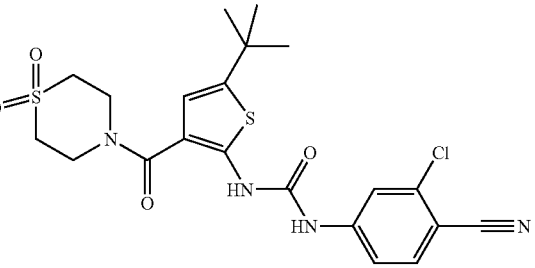

¹H NMR (400 MHz, acetone-d₆): δ 10.15 (s, 2H), 8.08 (d, J=2.0 Hz, 1H), 7.76 (d, J=8.6 Hz, 1H), 7.60 (dd, J=8.6, 2.0 Hz, 1H), 6.74 (d, J=6.8 Hz, 1H), 4.13 (t, J=5.2 Hz, 4H), 3.24 (t, J=5.3 Hz, 4H), 1.38 (s, 9H).

Example 65

1-[5-tert-butyl-3-(1,1-dioxo-1λ⁶-thiomorpholine-4-carbonyl)thiophen-2-yl]-3-(4-cyano-3-trifluoromethylphenyl)urea

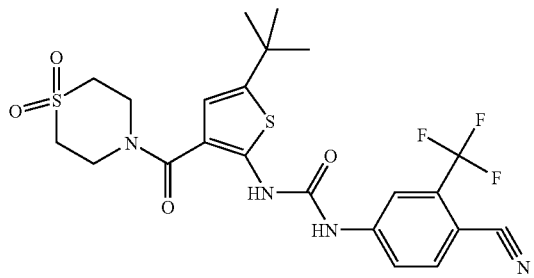

¹H NMR (400 MHz, acetone-d₆): δ 10.19 (s, 2H), 8.33 (d, J=1.8 Hz, 1H), 7.99-7.91 (m, 2H), 6.77 (s, 1H), 4.13 (t, J=5.3 Hz, 4H), 3.24 (t, J=5.4 Hz, 4H), 1.38 (s, 9H).

Example 66

1-[5-tert-butyl-3-(1,1-dioxo-1λ⁶-thiomorpholine-4-carbonyl)thiophen-2-yl]-3-(1-methyl-1-phenylethyl)urea

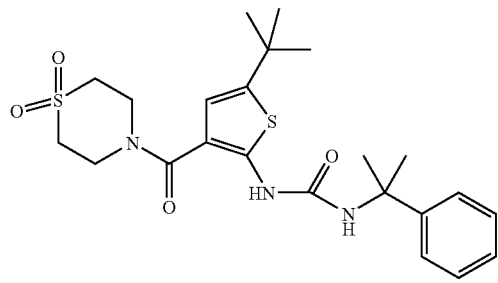

¹H NMR (400 MHz, acetone-d₆): δ 9.48 (s, 1H), 7.48 (d, J=7.6 Hz, 2H), 7.36 (s, 1H), 7.30 (t, J=7.8 Hz, 2H), 7.18 (t, J=7.3 Hz, 1H), 6.63 (s, 1H), 4.09 (t, J=5.1 Hz, 4H), 3.20 (t, J=5.2 Hz, 4H), 1.70 (s, 6H), 1.30 (s, 9H).

Example 67

1-[5-tert-butyl-3-(1,1-dioxo-1λ⁶-thiomorpholine-4-carbonyl)thiophen-2-yl]-3-(3-tolyl)urea

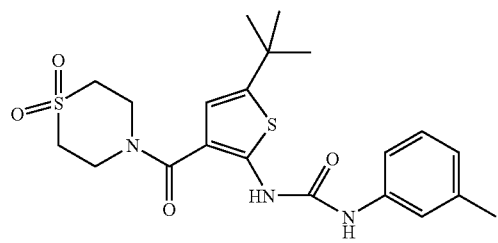

¹H NMR (400 MHz, acetone-d₆): δ 9.73 (s, 1H), 9.18 (s, 1H), 7.46 (s, 1H), 7.36 (d, J=8.2 Hz, 1H), 7.17 (t, J=7.8 Hz, 1H), 6.85 (d, J=7.4 Hz, 1H), 6.72 (s, 1H), 4.13 (t, J=5.1 Hz, 4H), 3.23 (t, J=5.2 Hz, 4H), 2.31 (s, 3H), 1.37 (s, 9H).

Example 68

1-[5-tert-butyl-3-(1,1-dioxo-1λ⁶-thiomorpholine-4-carbonyl)thiophen-2-yl]-3-(3,5-dichlorophenyl)urea

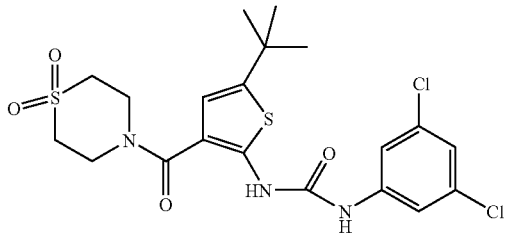

¹H NMR (400 MHz, acetone-d₆): δ 9.93 (s, 1H), 9.76 (s, 1H), 7.65 (d, J=1.8 Hz, 2H), 7.10 (t, J=1.6 Hz, 1H), 6.75 (s, 1H), 4.13 (t, J=5.0 Hz, 4H), 3.24 (t, J=5.3 Hz, 4H), 1.37 (s, 9H).

Example 69

1-[5-tert-butyl-3-(1,1-dioxo-1λ⁶-thiomorpholine-4-carbonyl)thiophen-2-yl]-3-(1-methyl-1H-pyrazol-3-yl)urea

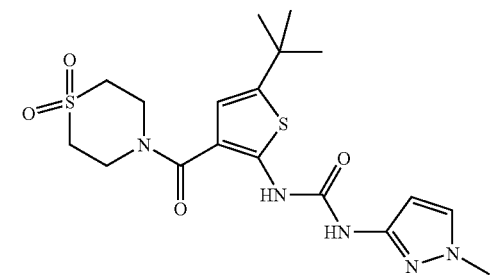

¹H NMR (400 MHz, acetone-d₆): δ 9.04 (s, 1H), 7.48 (d, J=2.0 Hz, 1H), 6.72 (s, 1H), 6.14 (s, 1H), 4.12 (t, J=5.1 Hz, 4H), 3.85 (s, 3H), 3.22 (t, J=5.3 Hz, 4H), 1.36 (s, 9H).

Example 70

1-[5-tert-butyl-3-(1,1-dioxo-1λ⁶-thiomorpholine-4-carbonyl)thiophen-2-yl]-3-(2,6-dimethylpyridin-4-yl)urea

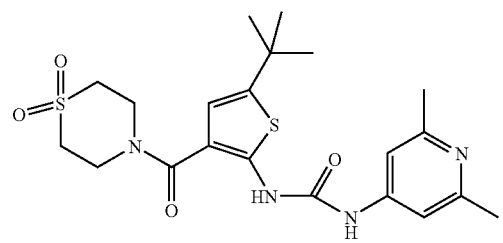

¹H NMR (400 MHz, acetone-d₆): δ 9.84 (s, 1H), 9.51 (s, 1H), 7.23 (s, 2H), 6.75 (s, 1H), 4.13 (t, J=5.0 Hz, 4H), 3.23 (t, J=5.2 Hz, 4H), 2.38 (s, 6H), 1.37 (s, 9H).

Example 71

1-Benzoxazol-5-yl-3-[5-tert-butyl-3-(1,1-dioxo-1λ⁶-thiomorpholine-4-carbonyl)thiophen-2-yl]urea

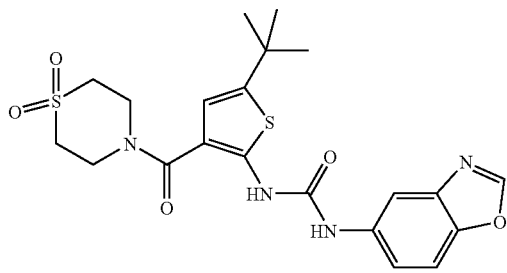

¹H NMR (400 MHz, acetone-d₆): δ 9.89 (s, 1H), 9.71 (s, 1H), 8.36 (s, 1H), 8.24 (d, J=2.0 Hz, 1H), 7.65 (d, J=8.6 Hz, 1H), 7.37 (dd, J=8.6, 2.0 Hz, 1H), 6.74 (s, 1H), 4.14 (t, J=5.1 Hz, 4H), 3.25 (t, J=5.3 Hz, 4H), 1.38 (s, 9H).

Example 72

1-Benzoxazol-6-yl-3-[5-tert-butyl-3-(1,1-dioxo-1λ⁶-thiomorpholine-4-carbonyl)thiophen-2-yl]urea

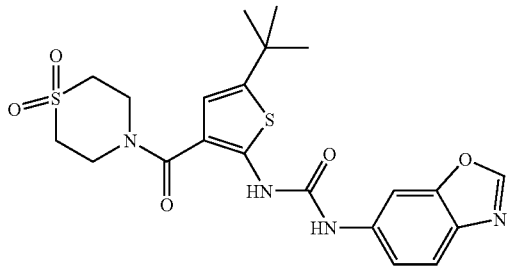

¹H NMR (400 MHz, acetone-d₆): δ 9.84 (s, 1H), 9.51 (s, 1H), 8.42 (s, 1H), 8.14 (d, J=2.0 Hz, 1H), 7.61 (d, J=8.8 Hz, 1H), 7.54 (dd, J=8.8, 2.1 Hz, 1H), 6.73 (s, 1H), 4.14 (t, J=5.2 Hz, 4H), 3.24 (t, J=5.4 Hz, 4H), 1.38 (s, 9H).

Example 73

1-Benzo[1,3]dioxol-5-yl-3-[5-tert-butyl-3-(5-oxo-[1,4]diazepane-1-carbonyl)-thiophen-2-yl]urea

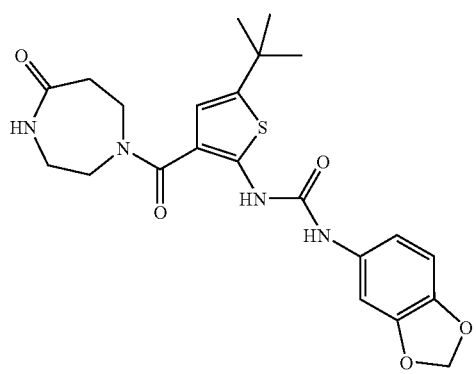

¹H NMR (400 MHz, acetone-d₆): δ 9.79 (s, 1H), 9.30 (s, 1H), 7.32 (d, J=1.8 Hz, 1H), 7.04 (t, J=5.2 Hz, 1H), 6.90 (dd, J=8.4, 1.8 Hz, 1H), 6.76 (d, J=8.4 Hz, 1H), 6.64 (s, 1H), 5.96 (s, 2H), 3.84-3.75 (m, 4H), 3.45 (q, J=4.7 Hz, 2H), 2.72 (t, J=5.4 Hz, 2H), 1.36 (s, 9H).

Example 74

1-[5-tert-butyl-3-(5-oxo-[1,4]diazepane-1-carbonyl)-thiophen-2-yl]-3-(2,2-difluoro-benzo[1,3]dioxol-5-yl)urea

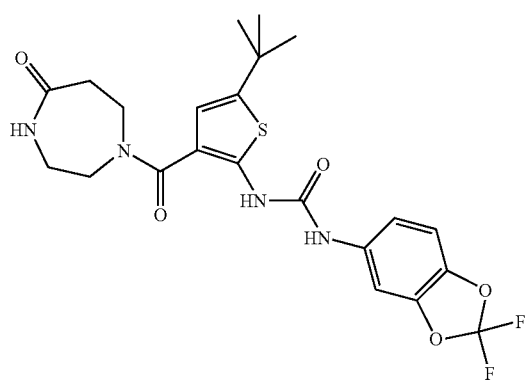

¹H NMR (400 MHz, DMSOd₆): δ 10.28 (s, 1H), 9.97 (s, 1H), 7.65 (s, 2H), 7.27 (d, J=8.8 Hz, 1H), 7.07 (dd, J=8.8, 2.0 Hz, 1H), 6.53 (s, 1H), 3.61 (s, 4H), 3.23 (s, 2H), 2.57 (s, 2H), 1.29 (s, 9H).

Example 75

1-(3-(Pyridin-3-ylcarbamoyl)-5-tert-butylthiophen-2-yl)-3-(4-chlorophenyl)urea

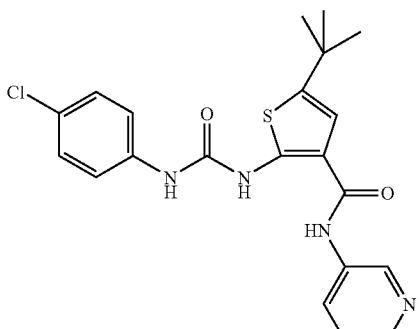

¹H NMR (400 MHz, acetone-d₆): δ 9.50 (s, 2H), 8.86 (d, J=2.5 Hz, 1H), 8.32 (dd, J=4.6, 1.3 Hz, 1H), 8.13 (m, 1H), 7.67 (d, J=9.0 Hz, 2H), 7.38-7.31 (m, 3H), 7.21 (s, 1H), 1.38 (s, 9H).

Example 76

1-[5-tert-butyl-3-(1,1-dioxo-1λ⁶-thiomorpholine-4-carbonyl)thiophen-2-yl]-3-(2-chloro-4-cyanophenyl)urea

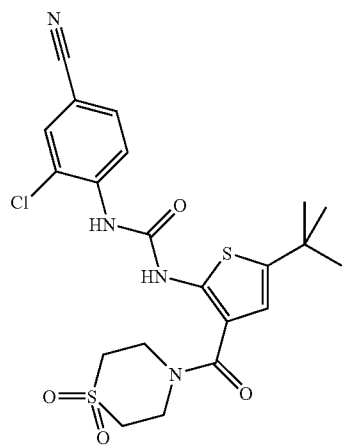

¹H NMR (400 MHz, acetone-d₆): δ 9.63 (s, 2H), 8.55 (d, J=8.8 Hz, 1H), 7.88 (d, J=1.8 Hz, 1H), 7.73 (dd, J=8.7, 1.7 Hz, 1H), 6.76 (s, 1H), 4.11 (t, J=4.9 Hz, 4H), 3.23 (t, J=5.2 Hz, 4H), 1.38 (s, 9H).

Example 77

1-[5-tert-butyl-3-(1,1-dioxo-1λ⁶-thiomorpholine-4-carbonyl)thiophen-2-yl]-3-(1-phenylcyclopropyl)urea

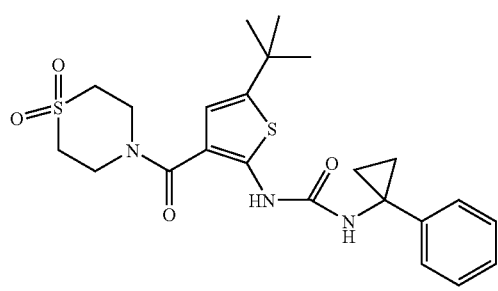

¹H NMR (400 MHz, acetone-d₆): δ 9.94 (s, 2H), 7.35 (d, J=7.6 Hz, 2H), 7.29 (t, J=7.5 Hz, 2H), 7.17 (t, J=7.0 Hz, 1H), 6.65 (s, 1H), 4.07 (s, 4H), 3.14 (s, 4H), 1.32 (s, 13H).

Example 78
1-[5-tert-butyl-3-(2-methyl-3-oxopiperazine-1-carbonyl)thiophen-2-yl]-3-(4-chlorophenyl)urea

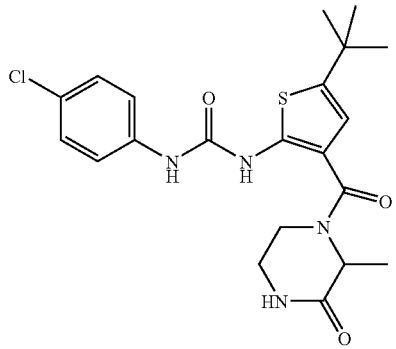

¹H NMR (400 MHz, acetone-d₆): δ 9.99 (s, 1H), 9.58 (s, 1H), 7.62 (d, J=8.8 Hz, 2H), 7.31 (d, J=8.8 Hz, 2H), 7.27 (s, 1H), 6.70 (s, 1H), 4.87 (q, J=6.9 Hz, 1H), 4.34-4.25 (m, 1H), 3.62-3.51 (m, 2H), 3.38 (m, 1H), 1.52 (d, J=7.2 Hz, 3H), 1.38 (s, 9H).

Example 79
1-[2-tert-butyl-5-(5-oxo-[1,4]diazepane-1-carbonyl)thiazol-4-yl]-3-naphthalen-1-ylurea

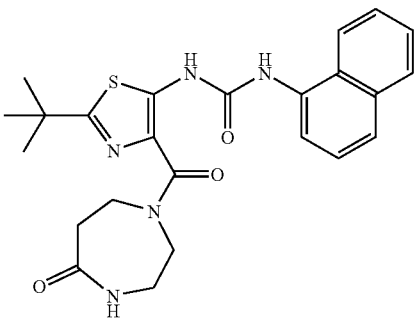

¹H NMR (400 MHz, DMSO-d₆): δ 10.83 (s, 1H), 10.06 (s, 1H), 8.15 (d, J=8.2 Hz, 1H), 7.91 (d, J=7.4 Hz, 1H), 7.84 (d, J=7.6 Hz, 1H), 7.71-7.62 (m, 2H), 7.58-7.49 (m, 2H), 7.46 (t, J=7.9 Hz, 1H), 4.12 (s, 1H), 4.06 (s, 1H), 3.74 (s, 2H), 3.29-3.25 (m, 2H), 2.66 (s, 1H), 2.56 (s, 1H), 1.34 (s, 9H).

Example 80
1-[2-tert-butyl-4-(1,1-dioxo-1λ⁶-[1,2,5]thiadiazepane-5-carbonyl)thiazol-5-yl]-3-naphthalen-1-ylurea

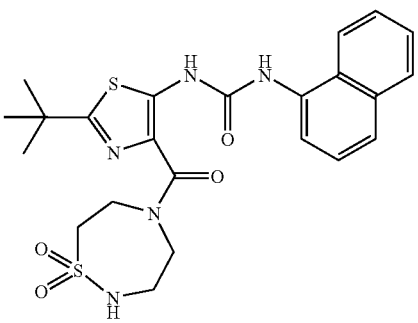

¹H NMR (400 MHz, acetone-d₆): δ 11.31-11.22 (m, 1H), 9.52 (s, 1H), 8.25-8.19 (m, 1H), 7.97-7.89 (m, 2H), 7.75 (d, J=8.2 Hz, 1H), 7.54-7.47 (m, 3H), 6.51-6.44 (m, 1H), 4.52 (t, J=6.0 Hz, 1H), 4.48 (t, J=5.4 Hz, 1H), 4.00-3.92 (m, 2H), 3.60 (t, J=5.5 Hz, 1H), 3.47-3.40 (m, 2H), 3.30 (q, J=5.9 Hz, 1H), 1.38 (s, 9H).

Example 81

1-[5-tert-butyl-2-(5-oxo-[1,4]diazepane-1-carbonyl)thiophen-3-yl]-3-methyl-urea

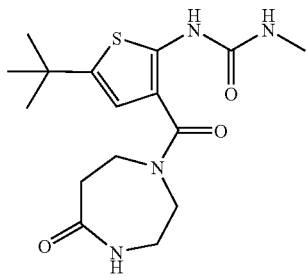

¹H NMR (400 MHz, acetone-d₆): δ 9.51 (s, 1H), 7.18 (t, J=5.2 Hz, 1H), 6.78 (s, 1H), 6.58 (s, 1H), 3.80-3.71 (m, 4H), 3.42 (q, J=4.9 Hz, 2H), 2.78 (d, J=4.5 Hz, 3H), 2.72-2.66 (m, 2H), 1.34 (s, 9H).

Example 82

1-(3-(N-methyl-N-(2-(methylsulfonyl)ethyl)carbamoyl)-5-tert-butylthiophen-2-yl)-3-(naphthalen-1-yl)urea

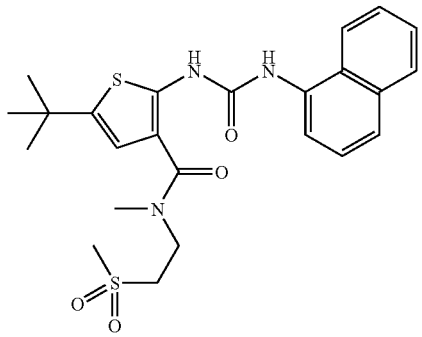

¹H NMR (400 MHz, acetone-d₆): δ 10.07 (s, 1H), 9.09 (s, 1H), 8.13 (d, J=7.8 Hz, 1H), 8.02 (d, J=7.4 Hz, 1H), 7.89 (dd, J=7.3, 2.0 Hz, 1H), 7.69 (d, J=8.4 Hz, 1H), 7.52-7.42 (m, 3H), 6.74 (s, 1H), 3.97 (t, J=7.0 Hz, 2H), 3.52 (t, J=7.0 Hz, 2H), 3.21 (s, 3H), 3.03 (s, 3H), 1.34 (s, 9H)

Example 83

1-[2-tert-butyl-4-(3-oxopiperazine-1-carbonyl)thiazol-5-yl]-3-naphthalen-1-ylurea

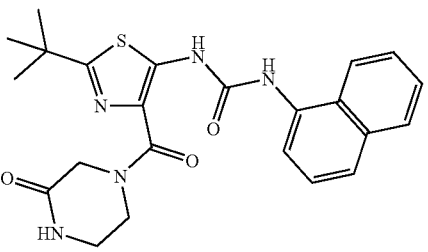

¹H NMR (400 MHz, DMSO-d₆): δ 11.00-10.82 (m, 1H), 10.09 (s, 1H), 8.16 (d, J=8.0 Hz, 1H), 8.07 (s, 1H), 7.91 (dd, J=7.3, 1.8 Hz, 1H), 7.84 (d, J=7.4 Hz, 1H), 7.69 (d, J=8.2 Hz, 1H), 7.58-7.49 (m, 2H), 7.46 (t, J=7.9 Hz, 1H), 4.75 (s, 1H), 4.30 (s, 1H), 4.14 (s, 1H), 3.81 (s, 1H), 3.32 (s, 2H), 1.34 (s, 9H).

Example 84

1-[5-tert-butyl-3-(1,1-dioxo-1λ⁶-thiomorpholine-4-carbonyl)thiophen-2-yl]-3-(4-cyano-2-trifluoromethylphenyl)urea

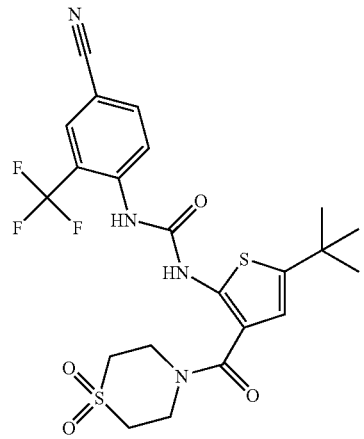

¹H NMR (400 MHz, acetone-d₆): δ 9.51 (s, 2H), 8.40 (d, J=8.8 Hz, 1H), 8.12 (s, 1H), 8.04 (d, J=8.6 Hz, 1H), 6.76 (s, 1H), 4.11 (t, J=4.8 Hz, 4H), 3.23 (t, J=5.1 Hz, 4H), 1.36 (s, 9H).

Example 85

1-[5-tert-butyl-3-(1,1-dioxo-1λ⁶-thiomorpholine-4-carbonyl)thiophen-2-yl]-3-(1-hydroxyisoquinolin-4-yl)urea

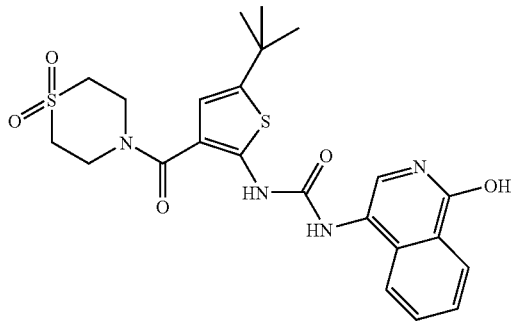

¹H NMR (400 MHz, acetone-d₆): δ 10.31 (s, 1H), 9.94 (s, 1H), 8.52 (s, 1H), 8.34 (d, J=7.8 Hz, 1H), 7.81 (d, J=8.0 Hz, 1H), 7.76 (t, J=7.6 Hz, 1H), 7.55 (t, J=8.1 Hz, 1H), 7.52 (s, 1H), 6.70 (s, 1H), 4.08 (s, 4H), 3.19 (s, 4H), 1.34 (s, 9H).

Example 86

5-tert-butyl-2-(3-naphthalen(-1-ylureido)thiophene-3-carboxylic acid (2,5-dioxo-pyrrolidin-3-yl)amide

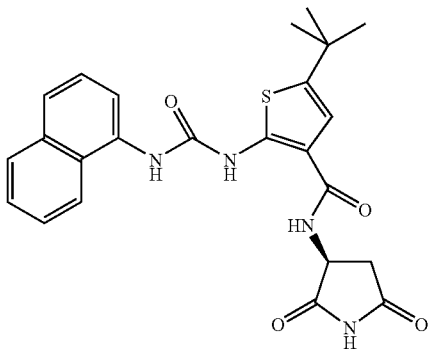

¹H NMR (400 MHz, acetone-d₆): δ 11.16 (s, 1H), 10.19 (s, 1H), 9.51 (s, 1H), 8.26-8.15 (m, 2H), 7.97-7.90 (m, 2H), 7.73 (d, J=8.2 Hz, 1H), 7.55-7.49 (m, 3H), 7.01 (s, 1H), 4.72 (m, 1H), 3.07 (dd, J=17.8, 9.4 Hz, 1H), 2.88 (dd, J=17.7, 5.9 Hz, 1H), 1.35 (s, 9H).

Example 87

1-[5-tert-butyl-3-(2-methyl-3-oxopiperazine-1-carbonyl)thiophen-2-yl]-3-naphthalen-1-ylurea

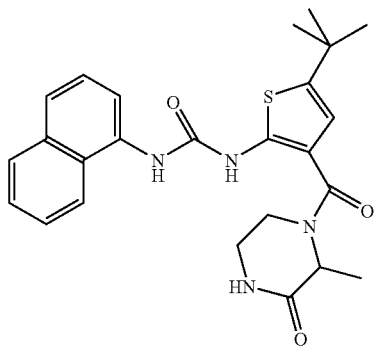

¹H NMR (400 MHz, acetone-d₆): δ 10.15 (s, 1H), 9.38 (s, 1H), 8.21 (m, 1H), 8.00 (d, J=7.4 Hz, 1H), 7.92 (m, 1H), 7.72 (d, J=8.2 Hz, 1H), 7.55-7.48 (m, 3H), 7.17 (s, 1H), 6.70 (s, 1H), 4.82 (q, J=6.9 Hz, 1H), 4.29 (d, J=9.6 Hz, 1H), 3.61-3.50 (m, 2H), 3.38 (m, 1H), 1.51 (d, J=7.0 Hz, 3H), 1.38 (s, 9H).

Example 88

{1-[5-tert-butyl-2-(3-naphthalen-1-yl-ureido)thiophene-3-carbonyl]-3-oxo-piperazin-2-yl}-acetic acid methyl ester

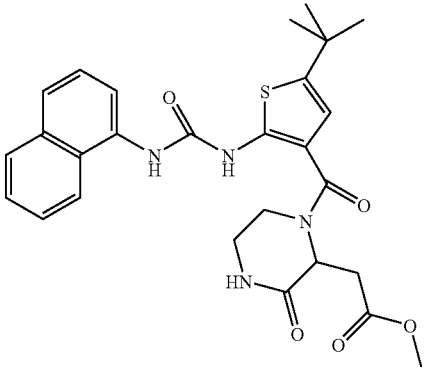

¹H NMR (400 MHz, acetone-d₆): δ 10.04 (s, 1H), 9.36 (s, 1H), 8.23 (m, 1H), 8.03 (d, J=7.4 Hz, 1H), 7.93 (m, 1H), 7.71 (d, J=8.2 Hz, 1H), 7.56-7.48 (m, 3H), 7.38 (s, 1H), 6.68 (s, 1H), 5.23 (t, J=5.9 Hz, 1H), 4.27 (d, J=13.9 Hz, 1H), 3.82 (t, J=10.5 Hz, 1H), 3.63 (s, 3H), 3.52 (dt, J=11.9, 3.7 Hz, 1H), 3.40 (m, 1H), 2.99 (m, 2H), 1.38 (s, 9H).

Example 89

1-[5-tert-butyl-3-(5-oxo-[1,4]diazepane-1-carbonyl)thiophen-2-yl]-3-(4-cyano-2-trifluoromethylphenyl)urea

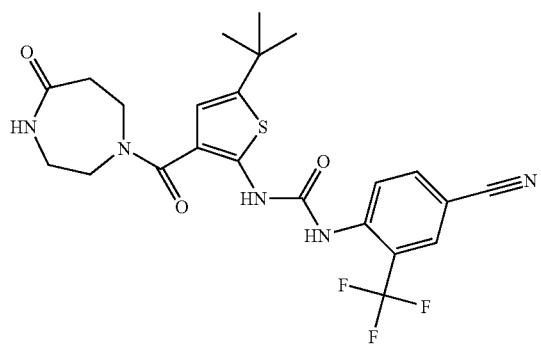

¹H NMR (400 MHz, acetone-d₆): δ 9.31 (s, 1H), 8.41 (d, J=8.8 Hz, 1H), 8.11 (s, 1H), 8.04 (d, J=8.2 Hz, 1H), 6.93 (s, 1H), 6.67 (s, 1H), 3.77 (m, 4H), 3.44 (q, J=4.8 Hz, 2H), 2.69 (m, 2H), 1.37 (s, 9H), 9.89 (s, 1H).

Example 90

1-[5-tert-Butyl-3-(5-oxo-[1,4]diazepane-1-carbonyl)thiophen-2-yl]-3-(2-chloro-4-cyanophenyl)urea

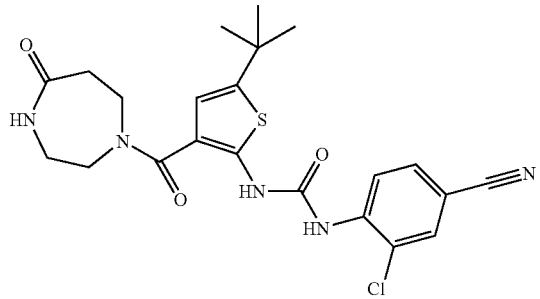

¹H NMR (400 MHz, acetone-d₆): δ 8.55 (d, J=8.8 Hz, 1H), 7.87 (d, J=1.6 Hz, 1H), 7.72 (dd, J=8.8, 1.8 Hz, 1H), 6.96 (s, 1H), 6.67 (s, 1H), 3.78 (m, 4H), 3.44 (q, J=4.5 Hz, 2H), 2.69 (t, J=5.5 Hz, 2H), 1.38 (s, 9H), 9.54 (s, 2H

Example 91

1-[5-tert-Butyl-3-(1,1-dioxo-1λ⁶-[1,2,5]thiadiazepane-5-carbonyl)thiophen-2-yl]-3-(4-cyano-2-trifluoromethylphenyl)urea

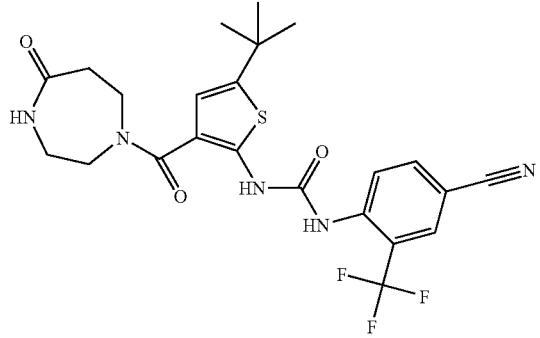

¹H NMR (400 MHz, CDCl₃): δ (ppm) 10.17 (s, 1H), 8.82-8.74 (m, 1H), 7.92 (d, J=8.6 Hz, 1H), 7.88 (d, J=7.4 Hz, 1H), 7.80 (d, J=8.2 Hz, 1H), 7.64 (d, J=8.2 Hz, 1H), 7.45 (t, J=7.9 Hz, 1H), 7.40 (t, J=7.5 Hz, 1H), 7.27 (t, J=7.6 Hz, 1H), 6.30 (s, 1H), 3.58 (s, 8H), 1.20 (s, 9H).

Example 92

1-[5-tert-Butyl-3-(1,1-dioxo-1λ⁶-[1,2,5]thiadiazepane-5-carbonyl)thiophen-2-yl]-3-(4-cyano-2-chlorophenyl)urea

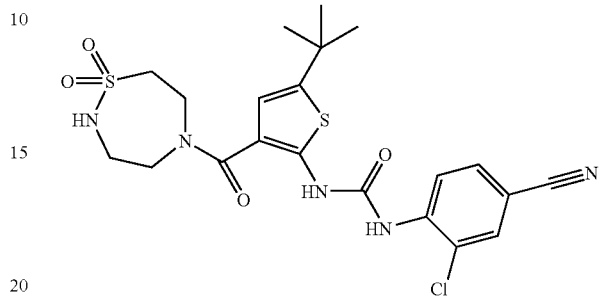

¹H NMR (400 MHz, DMSO-d₆): δ (ppm) 9.91 (s, 1H), 9.31 (s, 1H), 7.46 (d, J=9.0 Hz, 2H), 7.30 (d, J=8.8 Hz, 2H), 6.46 (s, 1H), 4.07 (s, 4H), 3.34 (s, 4H), 1.22 (s, 9H).

Example 93

1-Benzo[1,3]dioxol-5-yl-3-[5-tert-butyl-3-(1,1-dioxo-1λ⁶-[1,2,5]thiadiazepane-5-carbonyl)thiophen-2-yl]urea

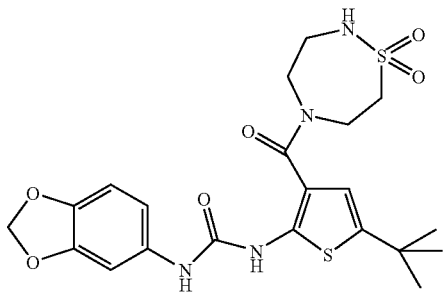

¹H NMR (400 MHz, acetone-d₆): δ (ppm) 9.96 (s, 1H), 9.21 (s, 1H), 7.31 (d, J=2.0 Hz, 1H), 6.89 (dd, J=8.3, 2.0 Hz, 1H), 6.77 (d, J=8.4 Hz, 1H), 6.73 (s, 1H), 6.63 (s, 1H), 5.96 (s, 2H), 4.00 (t, J=6.1 Hz, 2H), 3.90-3.94 (m, 2H), 3.48-3.52 (m, 2H), 3.43 (t, J=5.9 Hz, 2H), 1.36 (s, 9H).

Example 94

1-[5-tert-Butyl-3-(1,1-dioxo-1λ⁶-[1,2,5]thiadiazepane-5-carbonyl)thiophen-2-yl]-3-(2,2-difluorobenzo[1,3]dioxol-5-yl)urea

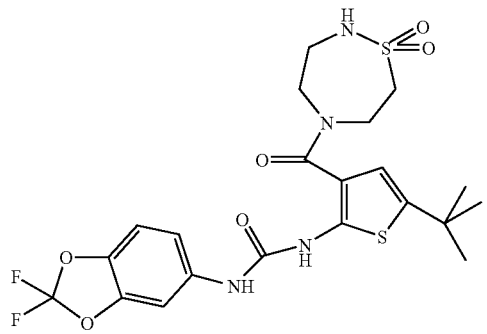

¹H NMR (400 MHz, acetone-d₆): δ (ppm) 10.06 (s, 1H), 9.60 (s, 1H), 7.77 (s, 1H), 7.16-7.21 (m, 2H), 6.75 (s, 1H), 6.66 (s, 1H), 4.00 (t, J=6.0 Hz, 2H), 3.91-3.94 (m, 2H), 3.48-3.51 (m, 2H), 3.42 (t, J=6.0 Hz, 2H), 1.37 (s, 9H).

Example 95

1-[5-tert-Butyl-3-(1,1-dioxo-1λ⁶-[1,2,5]thiadiazepane-5-carbonyl)thiophen-2-yl]-3-(3-chloro-4-methoxyphenyl)urea

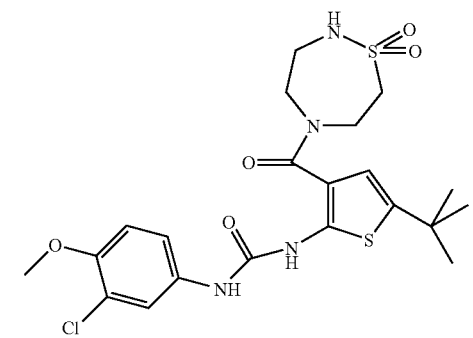

¹H NMR (400 MHz, acetone-d₆): δ (ppm) 10.02 (s, 1H), 9.25 (s, 1H), 7.78 (d, J=2.5 Hz, 1H), 7.39 (dd, J=9.0, 2.5 Hz, 1H), 7.06 (d, J=8.8 Hz, 1H), 6.74 (s, 1H), 6.61 (s, 1H), 4.02 (q, J=7.3 Hz, 2H), 3.91-3.94 (m, 2H), 3.87 (s, 3H), 3.48-3.52 (m, 2H), 3.43 (t, J=6.0 Hz, 2H), 1.36 (s, 9H).

Example 96

1-[5-tert-Butyl-3-(1,1-dioxo-1λ⁶-[1,2,5]thiadiazepane-5-carbonyl)thiophen-2-yl]-3-(3,4-dichlorophenyl)urea

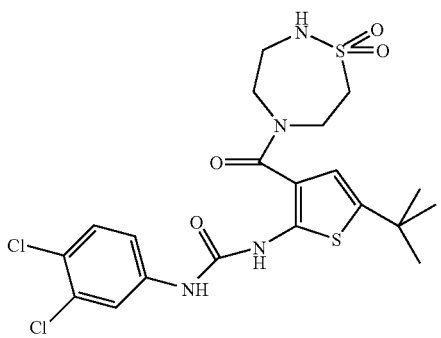

¹H NMR (400 MHz, acetone-d₆): δ (ppm) 10.14 (s, 1H), 9.68 (s, 1H), 8.00 (d, J=2.1 Hz, 1H), 7.42-7.49 (m, 2H), 6.76 (s, 1H), 6.65 (s, 1H), 4.00 (t, J=6.0 Hz, 2H), 3.91-3.94 (m, 2H), 3.48-3.51 (m, 2H), 3.42 (t, J=5.9 Hz, 2H), 1.37 (s, 9H).

Example 97

1-[5-tert-Butyl-3-(1,1-dioxo-1λ⁶-[1,2,5]thiadiazepane-5-carbonyl)thiophen-2-yl]-3-(1-methyl-1-phenylethyl)urea

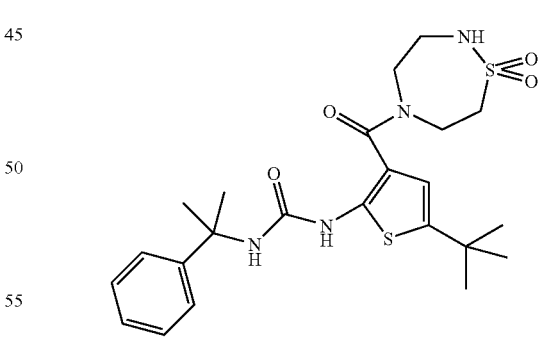

¹H NMR (400 MHz, acetone-d₆): δ (ppm) 9.69 (s, 1H), 7.47 (d, J=7.8 Hz, 2H), 7.28-7.32 (m, 3H), 7.18 (t, J=7.3 Hz, 1H), 6.64 (s, 1H), 6.57 (s, 1H), 3.97 (t, J=6.1 Hz, 2H), 3.88-3.92 (m, 2H), 3.48-3.51 (m, 2H), 3.44 (t, J=5.8 Hz, 2H), 1.68 (s, 6H), 1.29 (s, 9H).

Example 98

1-[5-tert-Butyl-3-(1,1-dioxo-1λ⁶-[1,2,5]thiadiaz-epane-5-carbonyl)thiophen-2-yl]-3-(3-tolylyl)urea

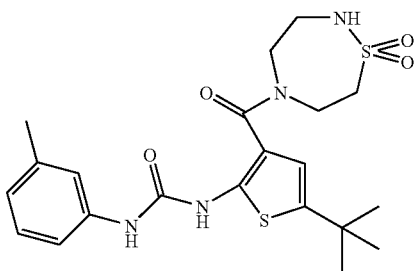

¹H NMR (400 MHz, acetone-d₆): δ (ppm) 9.96 (s, 1H), 9.17 (s, 1H), 7.45 (s, 1H), 7.34 (d, J=8.0 Hz, 1H), 7.17 (t, J=7.8 Hz, 1H), 6.85 (d, J=7.6 Hz, 1H), 6.74 (s, 1H), 6.57 (s, 1H), 4.01 (t, J=6.0 Hz, 2H), 3.91-3.94 (m, 2H), 3.49-3.52 (m, 2H), 3.44 (t, J=5.9 Hz, 2H), 2.31 (s, 3H), 1.36 (s, 9H).

Example 99

1-[5-tert-Butyl-3-(1,1-dioxo-1λ⁶-[1,2,5]thiadiaz-epane-5-carbonyl)thiophen-2-yl]-3-(3,5-dichlorophe-nyl)urea

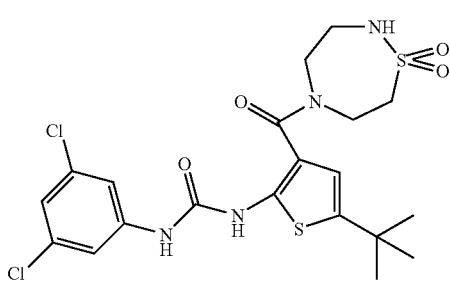

¹H NMR (400 MHz, acetone-d₆): δ (ppm) 10.17 (s, 1H), 9.80 (s, 1H), 7.65 (d, J=1.8 Hz, 2H), 7.09 (t, J=1.8 Hz, 1H), 6.77 (s, 1H), 6.64 (s, 1H), 4.01 (t, J=6.0 Hz, 2H), 3.91-3.95 (m, 2H), 3.48-3.52 (m, 2H), 3.42 (t, J=6.0 Hz, 2H), 1.37 (s, 9H).

Example 100

1-[5-tert-Butyl-3-(1,1-dioxo-1λ⁶-[1,2,5]thiadiaz-epane-5-carbonyl)thiophen-2-yl]-3-(1-methyl-1H-pyrazol-3-yl)urea

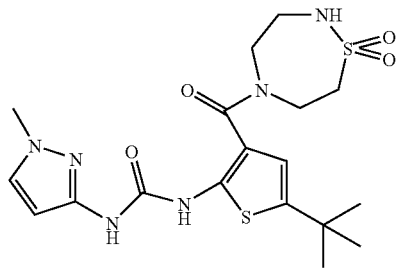

¹H NMR (400 MHz, acetone-d₆): δ (ppm) 11.02 (s, 1H), 9.05 (s, 1H), 7.48 (d, J=2.0 Hz, 1H), 6.72 (s, 1H), 6.66 (s, 1H), 6.14 (s, 1H), 3.98 (q, J=7.2 Hz, 2H), 3.90-3.94 (m, 2H), 3.84 (s, 3H), 3.50-3.53 (m, 2H), 3.41 (t, J=5.7 Hz, 2H), 1.36 (s, 9H).

Example 101

5-tert-Butyl-2-[3-(4-chlorophenyl)ureido]thiophene-3-carboxylic acid (2,5-dioxopyrrolidin-3-yl)amide

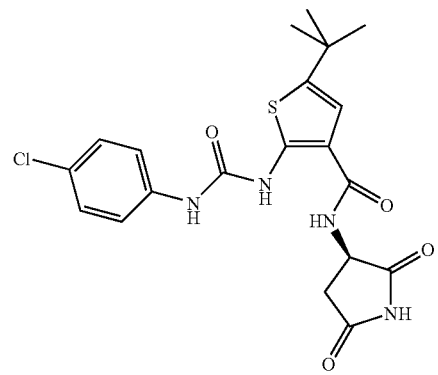

¹H NMR (400 MHz, acetone-d₆): δ (ppm) 11.04 (s, 1H), 10.21 (s, 1H), 9.61 (s, 1H), 8.23 (d, J=7.0 Hz, 1H), 7.63 (d, J=8.8 Hz, 2H), 7.32 (d, J=9.0 Hz, 2H), 7.01 (s, 1H), 4.67-4.74 (m, 1H), 3.07 (dd, J=17.8, 9.4 Hz, 1H), 2.88 (dd, J=17.7, 5.9 Hz, 1H), 1.35 (s, 9H).

Example 102

1-[5-tert-Butyl-3-(5-oxo-[1,4]diazepane-1-carbonyl)thiophen-2-yl]-3-(3-chloro-4-methoxyphenyl)urea

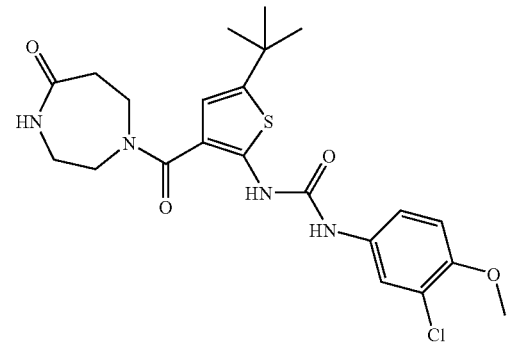

121

¹H NMR (400 MHz, acetone-d₆): δ (ppm) 9.85 (s, 1H), 9.36 (s, 1H), 7.78 (d, J=2.5 Hz, 1H), 7.39 (dd, J=8.8, 2.5 Hz, 1H), 7.05 (d, J=9.0 Hz, 1H), 7.02 (s, 1H), 6.65 (s, 1H), 3.86 (s, 3H), 3.76-3.83 (m, 4H), 3.43-3.48 (m, 2H), 2.70-2.74 (m, 2H), 1.36 (s, 9H).

Example 103

1-Benzoxazol-5-yl-3-[5-tert-butyl-3-(5-oxo-[1,4]diazepane-1-carbonyl)-thiophen-2-yl]urea

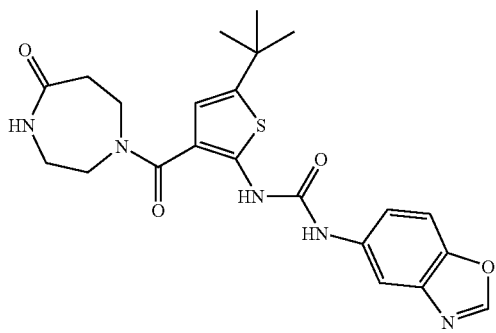

¹H NMR (400 MHz, acetone-d₆): δ (ppm) 9.93 (s, 1H), 9.67 (s, 1H), 8.35 (s, 1H), 8.24 (d, J=1.6 Hz, 1H), 7.64 (d, J=8.6 Hz, 1H), 7.36 (dd, J=8.6, 1.8 Hz, 1H), 7.06 (s, 1H), 6.67 (s, 1H), 3.78-3.85 (m, 4H), 3.45-3.49 (m, 2H), 2.72-2.76 (m, 2H), 1.38 (s, 9H).

Example 104

1-[5-tert-Butyl-3-(5-oxo-[1,4]diazepane-1-carbonyl)thiophen-2-yl]-3-(1-hydroxyisoquinolin-4-yl)urea

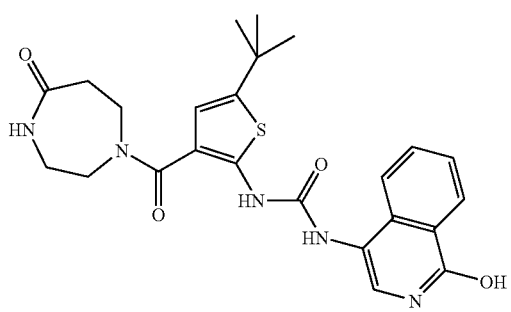

¹H NMR (400 MHz, acetone-d₆): δ (ppm) 10.34 (s, 1H), 10.02 (s, 1H), 8.51 (s, 1H), 8.34 (d, J=8.0 Hz, 1H), 7.84 (d, J=8.0 Hz, 1H), 7.76 (t, J=7.6 Hz, 1H), 7.54 (t, J=7.5 Hz, 1H), 7.50 (s, 1H), 6.93 (s, 1H), 6.62 (s, 1H), 3.71-3.78 (m, 4H), 3.39-3.43 (m, 2H), 2.65-2.69 (m, 2H), 1.35 (s, 9H).

122

Example 105

1-Benzoxazol-6-yl-3-[5-tert-butyl-3-(5-oxo-[1,4]diazepane-1-carbonyl)-thiophen-2-yl]urea ¹H NMR (400 MHz, acetone-d₆): δ (ppm) 9.89 (s, 1H), 9.50 (s, 1H), 8.41 (s, 1H), 8.14 (d, J=1.6 Hz, 1H), 7.60 (d, J=8.8 Hz, 1H), 7.54 (dd, J=8.8, 1.8 Hz, 1H), 7.00 (s, 1H), 6.66 (s, 1H), 3.77-3.84 (m, 4H), 3.44-3.49 (m, 2H), 2.71-2.75 (m, 2H), 1.38 (s, 9H).

Example 106

1-[5-tert-Butyl-3-(1,1-dioxo-1λ⁶-[1,2,5]thiadiazepane-5-carbonyl)thiophen-2-yl]-3-(3-chloro-4-cyanophenyl)urea ¹H NMR (400 MHz, acetone-d₆): δ (ppm) 10.56 (s, 1H), 8.10 (d, J=1.6 Hz, 1H), 7.74 (d, J=8.6 Hz, 1H), 7.61 (dd, J=8.5, 1.7 Hz, 1H), 6.74 (s, 1H), 6.49 (s, 1H), 6.14 (s, 1H), 3.89-4.00 (m, 4H), 3.44-3.48 (m, 2H), 3.35-3.40 (m, 2H), 1.37 (s, 9H).

Example 107

1-[5-tert-Butyl-2-(5-oxo-[1,4]diazepane-1-carbonyl)thiophen-3-yl]-3-(3,4-dichlorophenyl)urea ¹H NMR (400 MHz, acetone-d₆): δ (ppm) 10.17 (s, 1H), 9.84 (s, 1H), 7.86 (s, 1H), 7.66 (s, 1H), 7.49 (d, J=8.6 Hz, 1H), 7.28 (dd, J=8.8, 2.5 Hz, 1H), 6.55 (s, 1H), 3.60-3.63 (m, 4H), 3.21-3.24 (m, 2H), 2.55-2.59 (m, 2H), 1.29 (s, 9H).

Example 108

1-Benzoxazol-5-yl-3-[5-tert-butyl-3-(1,1-dioxo-1λ⁶-[1,2,5]thiadiazepane-5-carbonyl)thiophen-2-yl]urea

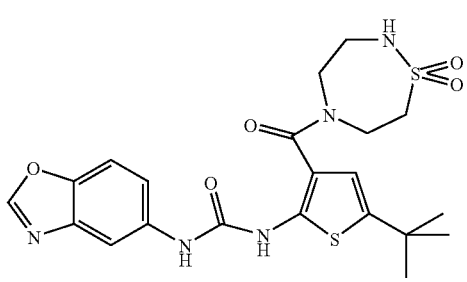

¹H NMR (400 MHz, acetone-d₆): δ (ppm) 10.10 (s, 1H), 9.70 (s, 1H), 8.35 (s, 1H), 8.24 (s, 1H), 7.64 (d, J=8.6 Hz, 1H), 7.37 (d, J=8.6 Hz, 1H), 6.76 (s, 1H), 6.68 (s, 1H), 4.01 (t, J=6.0 Hz, 2H), 3.92-3.95 (m, 2H), 3.49-3.53 (m, 2H), 3.43 (t, J=5.6 Hz, 2H), 1.38 (s, 9H).

Example 109

1-[5-tert-Butyl-3-(1,1-dioxo-1λ⁶-[1,2,5]thiadiazepane-5-carbonyl)thiophen-2-yl]-3-(1-phenylcyclopropyl)urea

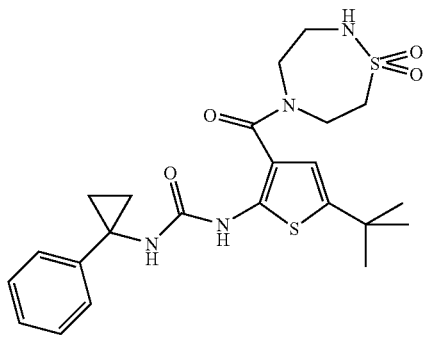

¹H NMR (400 MHz, acetone-d₆): δ (ppm) 10.48 (s, 1H), 9.76 (s, 1H), 7.38 (d, J=7.0 Hz, 2H), 7.30 (t, J=7.6 Hz, 2H), 7.17 (t, J=7.3 Hz, 1H), 6.69 (s, 1H), 6.51 (s, 1H), 3.96 (t, J=6.0 Hz, 2H), 3.87-3.90 (m, 2H), 3.46-3.49 (m, 2H), 3.39-3.44 (m, 2H), 1.32 (s, 13H).

Example 110

1-[5-tert-Butyl-3-(1,1-dioxo-1λ⁶-[1,2,5]thiadiazepane-5-carbonyl)thiophen-2-yl]-3-(1-hydroxyisoquinolin-4-yl)urea

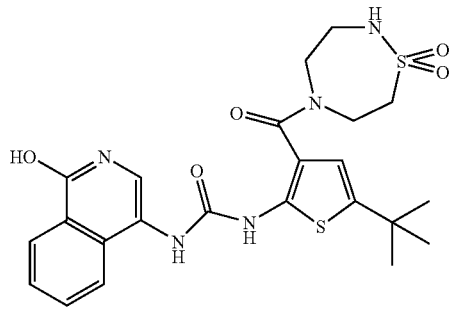

¹H NMR (400 MHz, acetone-d₆): δ (ppm) 10.27 (s, 1H), 10.13 (s, 1H), 8.53 (s, 1H), 8.34 (d, J=8.0 Hz, 1H), 7.82 (d, J=8.2 Hz, 1H), 7.76 (t, J=7.6 Hz, 1H), 7.54 (t, J=7.5 Hz, 1H), 7.50 (s, 1H), 6.71 (s, 1H), 6.68 (s, 1H), 3.96 (t, J=5.7 Hz, 2H), 3.86-3.90 (m, 2H), 3.38-3.46 (m, 4H), 1.34 (s, 9H).

Example 111

1-(4-Aminomethylphenyl)-3-[5-tert-butyl-3-(5-oxo-[1,4]diazepane-1-carbonyl)thiophen-2-yl]urea

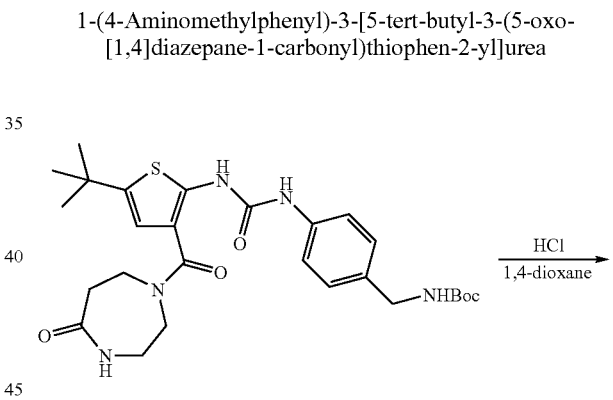

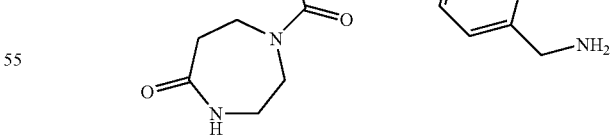

To a vial containing the previously prepared Boc protected amine ca. 0.15 mmol) was added 4M HCl in dioxane (2 mL), the vial was capped and the reaction mixture was swirled at room temperature for 4 hours. The solvent was removed under vacuum, 1M aqueous sodium hydroxide was added and the resulting mixture extracted 3 times with ethyl acetate. The combined organic layers were washed with brine, dried over anhydrous sodium sulfate, filtered and the solvent removed

Example 112

1-(4-Aminomethylnaphthalen-1-yl)-3-[5-tert-butyl-3-(5-oxo-[1,4]diazepane-1-carbonyl)thiophen-2-yl]urea

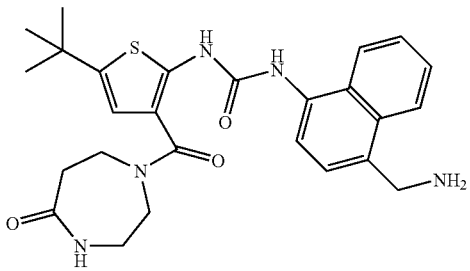

¹H NMR (400 MHz, CD₃OD): δ 8.03 (t, J=8.3 Hz, 2H), 7.69 (d, J=7.8 Hz, 1H), 7.55-7.49 (m, 1H), 7.45 (t, J=7.6 Hz, 2H), 6.58 (s, 1H), 4.25 (s, 2H), 3.75-3.68 (m, 4H), 3.34-3.30 (m, 2H), 2.71-2.65 (m, 2H), 1.32 (s, 9H).

Preparation of 4-(aminomethyl)naphthalen-1-amine

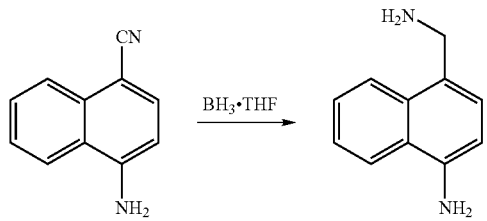

To a vial containing 4-aminonaphthalene-1-carbonitrile (0.59 mmol) was added BH₃.THF (1M solution (1.2 mmol). The vial was capped and stirred at 70° C. for 19.5 hours. The reaction was cooled down to room temperature and quenched by drop wise addition of methanol (2 mL), stirred at room temperature for 30 minutes, filtered and stirred with Dowex 50WX2-200 resin (1 g) for 26.5 hours. The resin was filtered, washed with methanol (20 mL) and 10% aqueous ammonia (50 mL). The solvent was removed under vacuum. The material was used without any further purification in the next step.

Preparation of tert-butyl-(1-aminonaphthalen-4-yl)methylcarbamate

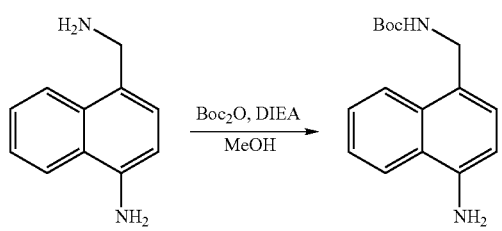

To a vial containing 4-(aminomethyl)naphthalen-1-amine (0.41 mmol) in methanol (2 mL) was added (Boc)₂O (0.41 mmol) and DIEA (0.46 mmol). The vial was loosely capped and the resulting solution stirred at room temperature for 28 hours. The reaction mixture was diluted with ethyl acetate and washed with saturated aqueous sodium bicarbonate. The combined aqueous layers were extracted once with ethyl acetate. The combined organic layers were washed with brine, dried over anhydrous sodium sulfate, filtered and solvent removed under vacuum. Purification by preparative super critical fluid chromatography gave the desired product (59.6 mg, 53%).

The title compound was prepared using the above prepared amine in a process analogous to that used for Example 111.

Example 113

5-tert-Butyl-2-(3-naphthalen-2-ylureido)thiophene-3-carboxylic acid (2,5-dioxopyrrolidin-3-yl)-amide

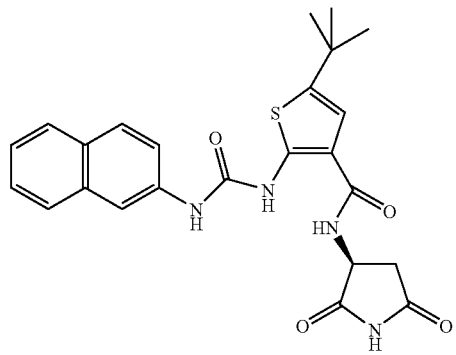

¹H NMR (400 MHz, acetone-d₆): δ 9.75 (s, 1H), 8.32 (s, 1H), 8.21 (m, 1H), 7.83 (m, 3H), 7.61 (dd, 1H), 7.47 (t, 1H), 7.19 (t, 1H), 7.01 (s, 1H), 4.75 (q, 1H), 3.14 (m, 1H), 2.90 (m, 1H), 1.94 (s, 9H).

Example 114

1-[5-tert-Butyl-3(2-methyl-3-oxopiperazine-1-carbonyl)thiophen-2-yl]-3-naphthalen-2-ylurea

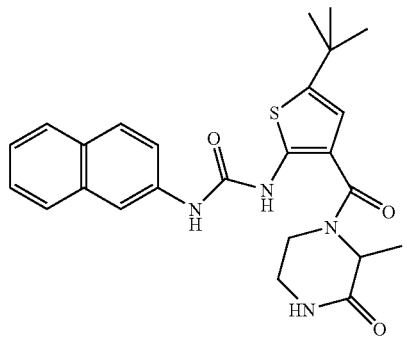

¹H NMR (400 MHz, acetone-d₆): δ 10.02 (s, 1H), 9.57 (s, 1H), 8.25 (s, 1H), 7.81 (m, 3H), 7.60 (dd, 1H), 7.32 (t, 1H), 7.18 (t, 1H), 7.17 (s, 1H), 6.72 (s, 1H), 4.80 (m, 1H), 4.32 (m, 1H), 3.60 (m, 2H), 3.39 (m, 1H), 1.50 (d, 3H), 1.42 (s, 9H)

Example 115

1-[5-tert-Butyl-3-(5-oxo-[1,4]diazepane-1-carbonyl)thiophen-2-yl]-3-m-tolylurea

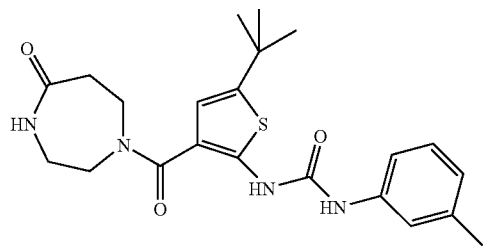

¹H NMR (400 MHz, acetone-d₆): δ 9.83 (s, 1H), 9.30 (s, 1H), 7.45 (s, 1H), 7.38 (d, 1H), 7.18 (t, 1H), 6.92 (m, 1H), 6.81 (d, 1H), 6.61 (s, 1H), 3.78 (m, 4H), 3.42 (m, 2H), 2.65 (m, 2H), 2.30 (s, 3H), 1.40 (s, 9H)

Example 116

1-[5-tert-Butyl-3-(5-oxo[1,4]diazepane-1-carbonyl)thiophen-2-yl]-3-(3-chloro-4-cyanophenyl)urea

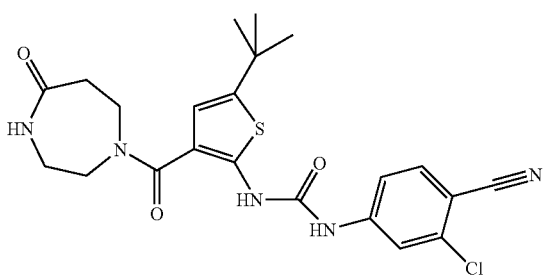

¹H NMR (400 MHz, DMSO): δ 10.42 (s, 1H), 9.90 (s, 1H), 7.88 (s, 1H), 7.78 (d, 1H), 7.60 (t, 1H), 7.36 (dd, 1H), 6.55 (s, 1H), 3.60 (m, 4H), 3.22 (m, 2H), 2.50 (m, 2H), 1.23 (s, 9H)

Example 117

1-[5-tert-Butyl-3-(5-oxo-[1,4]diazepane-1-carbonyl)thiophen-2-yl]-3-(3,5-dichlorophenyl)urea

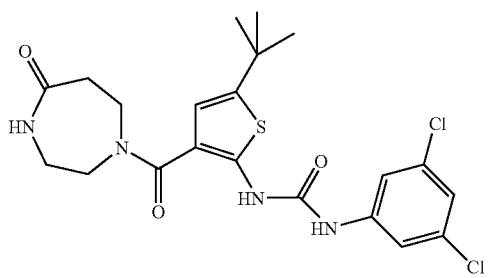

¹H NMR (400 MHz, acetone-d₆): δ 7.68 (s, 2H), 7.08 (s, 1H), 6.90 (t, 1H), 6.05 (s, 1H), 3.78 (m, 4H), 3.42 (m, 2H), 2.70 (m, 2H), 2.30 (s, 3H), 1.40 (s, 9H)

Example 118

{1-[5-tert-Butyl-2-(3-naphthalen-2-ylureido)thiophene-3-carbonyl]-3-oxo-piperazin-2-yl}acetic acid methyl ester

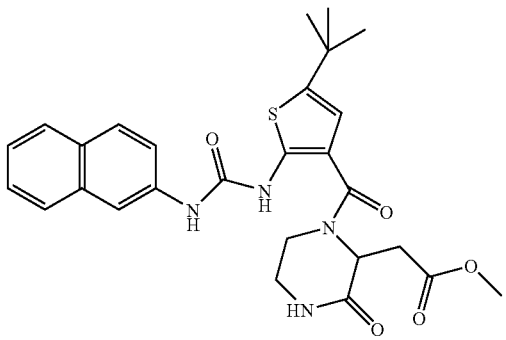

¹H NMR (400 MHz, DMSO): δ 10.00 (s, 1H), 9.60 (s, 1H), 8.28 (s, 1H), 7.80 (m, 3H), 7.60 (dd, 1H), 7.52 (t, 1H), 7.38 (m, 2H), 6.70 (s, 1H), 5.22 (d, 1H), 4.30 (d, 1H), 3.80 (m, 1H), 3.62 (s, 3H), 3.51 (m, 2H), 3.01 (m, 2H), 1.40 (s, 9H)

Example 119

1-[3-(6-Amino-5-oxo-[1,4]diazepane-1-carbonyl)-5-tert-butylthiophen-2-yl]-3-(2,3-dichlorophenyl)urea

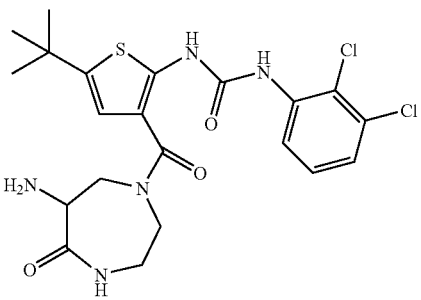

¹H NMR (400 MHz, CD₃OD): δ 7.93-7.87 (m, 1H), 7.20-7.14 (m, 2H), 6.53 (s, 1H), 4.14-3.93 (m, 2H), 3.85-3.77 (m, 1H), 3.56 (s, 2H), 3.40-3.31 (m, 1H), 3.24-3.17 (m, 1H), 1.27 (s, 9H).

Example 120

1-[5-tert-Butyl-3-(5-oxo-[1,4]diazepane-1-carbonyl)thiophen-2-yl]-3-piperidin-4-ylurea

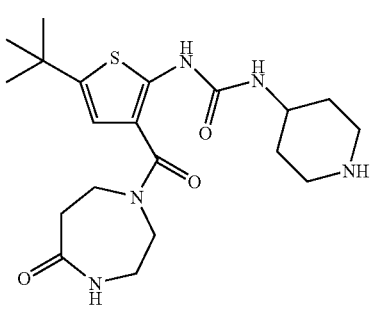

¹H NMR (400 MHz, CD₃OD): δ 6.54 (s, 1H), 3.76-3.70 (m, 4H), 3.68-3.58 (m, 1H), 3.36 (t, J=4.4 Hz, 2H), 3.02 (dt, J=8.3, 4.3 Hz, 2H), 2.74-2.69 (m, 2H), 2.65 (dt, J=12.1, 2.5 Hz, 2H), 1.90 (dd, J=13.0, 3.3 Hz, 2H), 1.44-1.34 (m, 2H), 1.33 (s, 9H).

Example 121

1-[5-tert-Butyl-2-(5-oxo-[1,4]diazepane-1-carbonyl)thiophen-3-yl]-3-(2,3-dichlorophenyl)urea

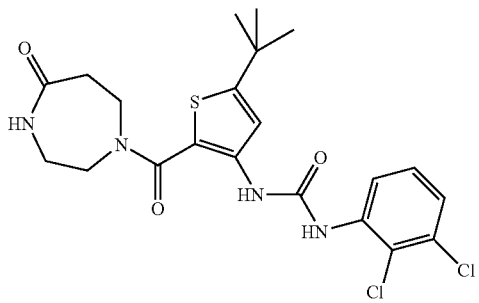

¹H NMR (400 MHz, acetone-d₆): δ 9.65 (s, 1H), 9.18 (s, 1H), 7.93 (m, 1H), 7.63 (m, 1H), 7.40 (s, 1H), 7.25 (m, 1H), 6.40 (s, 1H), 3.65 (m, 4H), 3.22 (m, 2H), 2.52 (m, 2H), 1.35 (s, 9H)

Example 122

1-[5-tert-Butyl-3-(5-oxo-[1,4]diazepane-1-carbonyl)thiophen-2-yl]-3-quinolin-4-ylurea

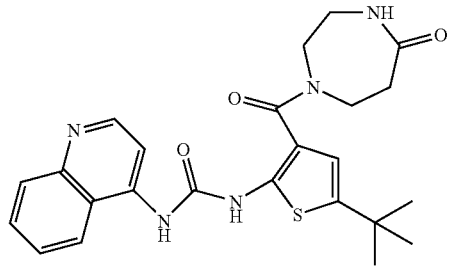

¹H NMR (400 MHz, acetone-d₆): δ 8.78 (d, 1H), 8.35 (d, 1H), 8.00 (d, 1H), 7.73 (t, 1H), 7.56 (t, 1H), 6.92 (bs, 1H), 6.68 (s, 1H), 3.80 (m, 4H), 3.42 (m, 2H), 2.70 (m, 2H), 1.40 (s, 9H)

Example 123

1-{5-tert-Butyl-3-[4-(2-methoxymethoxyethyl)-5-oxo-[1,4]diazepane-1-carbonyl]thiophen-2-yl}-3-(2,3-dichloro-phenyl)urea

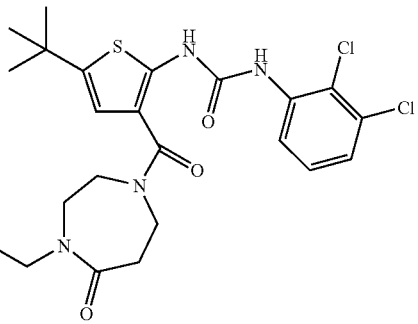

¹H NMR (400 MHz, CD₃OD): δ 8.02-7.96 (m, 1H), 7.25-7.22 (m, 2H), 6.59 (s, 1H), 4.50 (s, 2H), 3.83-3.78 (m, 2H), 3.74 (t, J=5.8 Hz, 2H), 3.70-3.65 (m, 2H), 3.58 (s, 4H), 3.28 (s, 3H), 2.81 (t, J=5.7 Hz, 2H), 1.35 (s, 9H).

Intermediate 5-tert-butyl-2-aminothiophene-3-carboxylic acid was prepared as follows for synthesis of Examples 123-153 and other suitable example:

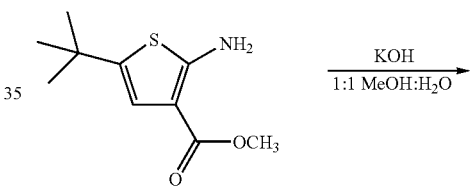

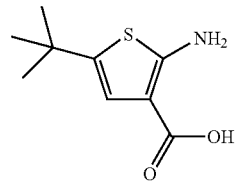

To a vial containing methyl 5-tert-butyl-2-aminothiophene-3-carboxylate (1.0 mmol) in a 1:1 methanol:water (3 mL) mixture was added potassium hydroxide (3 mmol). The vial was capped and the resulting mixture was stirred at 80° C. for 5 hours. The reaction was cooled down to room temperature and the solvent removed under vacuum. The crude product was dissolved in water, acidified with 1M HCl and the resulting mixture extracted 2 times with ethyl acetate. The combined organic layers were washed with brine, dried over anhydrous sodium sulfate, filtered and solvent removed under vacuum. This material was used without further purification.

Preparation of 5-tert-butyl-2-(3-(2,3-dichlorophenyl)ureido)thiophene-3-carboxylic acid

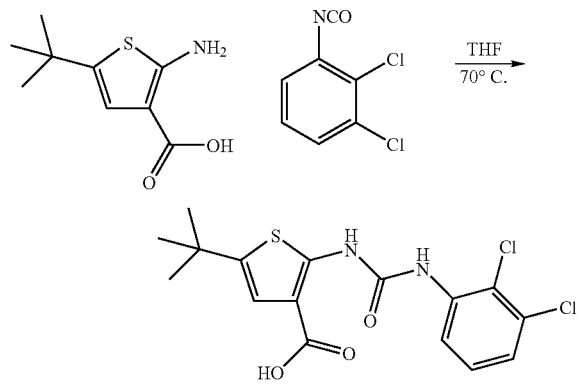

To a vial containing 5-tert-butyl-2-aminothiophene-3-carboxylic acid (1 mmol) in THF (7 mL) was added 2,3-dichlorophenyl isocyanate (1 mmol). The vial was capped and the solution was stirred at 70° C. for 21 hours. The reaction was cooled down to room temperature and the solvent was removed under vacuum. The oil residue was treated with dichloromethane and the resulting mixture was left to stand at room temperature for 1 hour. The solids were filtered, washed with minimal amount of dichloromethane and dried under vacuum to yield the expected 5-tert-butyl-2-(3-(2,3-dichlorophenyl)ureido)thiophene-3-carboxylic acid (317.2 mg, 83%). Coupling with the appropriate amine was performed as described above for Example 1.

Example 124

1-(5-tert-butyl-3-{4-[2-(2-methoxyethoxy)ethyl]-5-oxo-[1,4]diazepane-1-carbonyl}thiophen-2-yl)-3-(2,3-dichloro-phenyl)urea

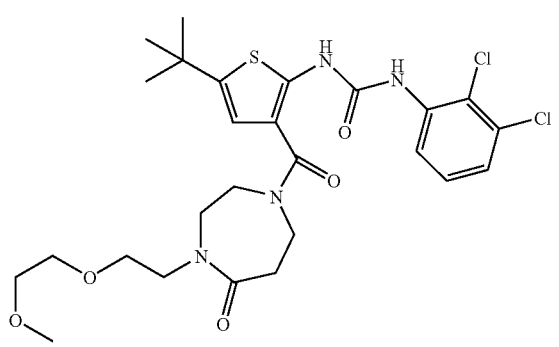

$^1$H NMR (400 MHz, CD$_3$OD): δ 8.02-7.96 (m, 1H), 7.27-7.21 (m, 2H), 6.59 (s, 1H), 3.83-3.78 (m, 2H), 3.74 (t, J=5.7 Hz, 2H), 3.69-3.64 (m, 2H), 3.58-3.51 (m, 4H), 3.50-3.42 (m, 4H), 3.29 (s, 3H), 2.80 (t, J=5.6 Hz, 2H), 1.35 (s, 9H)

Example 125

1-{5-tert-butyl-3-[4-(2-methoxyethyl)-5-oxo-[1,4]diazepane-1-carbonyl]-thiophen-2-yl}-3-(2,3-dichlorophenyl)urea

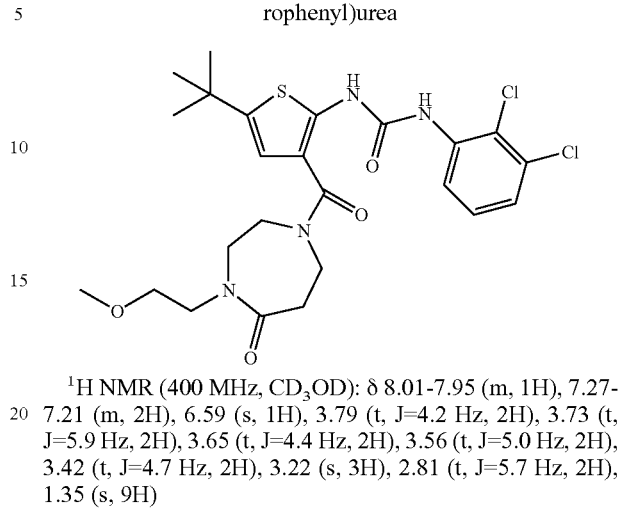

$^1$H NMR (400 MHz, CD$_3$OD): δ 8.01-7.95 (m, 1H), 7.27-7.21 (m, 2H), 6.59 (s, 1H), 3.79 (t, J=4.2 Hz, 2H), 3.73 (t, J=5.9 Hz, 2H), 3.65 (t, J=4.4 Hz, 2H), 3.56 (t, J=5.0 Hz, 2H), 3.42 (t, J=4.7 Hz, 2H), 3.22 (s, 3H), 2.81 (t, J=5.7 Hz, 2H), 1.35 (s, 9H)

Example 126

2-(4-{5-tert-Butyl-2-[3-(2,3-dichlorophenyl)ureido]thiophene-3-carbonyl}-7-oxo-[1,4]diazepan-1-yl)acetamide

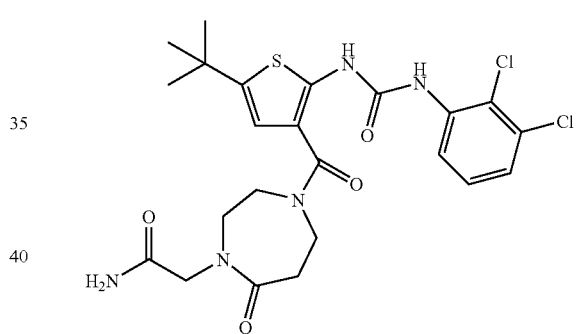

$^1$H NMR (400 MHz, CD$_3$OD): δ 8.03-7.97 (m, 1H), 7.26-7.19 (m, 2H), 6.58 (s, 1H), 4.11 (s, 2H), 3.90-3.85 (m, 2H), 3.81-3.75 (m, 2H), 3.64 (t, J=3.9 Hz, 2H), 2.81 (t, J=5.4 Hz, 2H), 1.34 (s, 9H)

Example 127

1-{5-tert-Butyl-3-[4-(2-dimethylaminoethyl)-5-oxo-[1,4]diazepane-1-carbonyl]-thiophen-2-yl}-3-(2,3-dichlorophenyl)urea

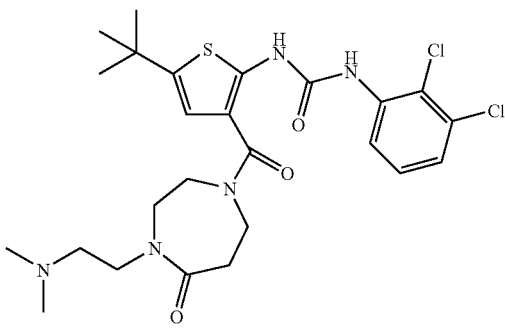

¹H NMR (400 MHz, CD₃OD): δ 8.01-7.96 (m, 1H), 7.28-7.22 (m, 2H), 6.60 (s, 1H), 3.82-3.77 (m, 2H), 3.75 (t, J=5.9 Hz, 2H), 3.64 (s, 4H), 3.55 (t, J=6.8 Hz, 2H), 2.82 (t, J=5.8 Hz, 2H), 2.54 (t, J=6.0 Hz, 2H), 2.33 (s, 6H), 1.36 (s, 9H)

Example 128

1-{5-tert-Butyl-3-[4-(2,2-dimethyl-[1,3]dioxolan-4-ylmethyl)-5-oxo-[1,4]diazepane-1-carbonyl]thiophen-2-yl}-3-(2,3-dichlorophenyl)urea

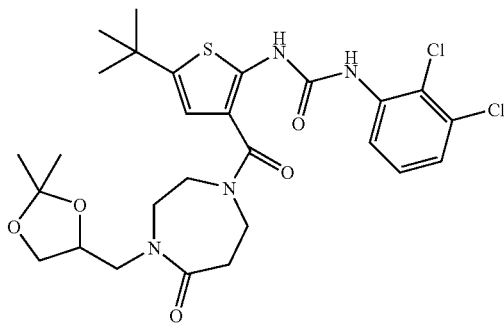

¹H NMR (400 MHz, CD₃OD): δ 8.02-7.96 (m, 1H), 7.28-7.22 (m, 2H), 6.60 (s, 1H), 4.26-4.18 (m, 1H), 3.99 (dd, J=8.4, 6.4 Hz, 1H), 3.87-3.62 (m, 8H), 3.56 (dd, J=8.2, 6.6 Hz, 1H), 2.83 (q, J=5.6 Hz, 2H), 1.35 (s, 12H), 1.24 (s, 3H)

Example 129

1-(3-(1-(3-Amino-3-oxopropyl)-7-oxo-1,4-diazepane-4-carbonyl)-5-tert-butylthiophen-2-yl)-3-(2,3-dichlorophenyl)urea

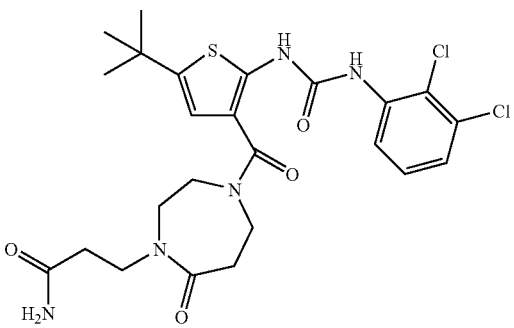

¹H NMR (400 MHz, CD₃OD): δ 8.03-7.96 (m, 1H), 7.28-7.21 (m, 2H), 6.58 (s, 1H), 3.81-3.76 (m, 2H), 3.76-3.70 (m, 2H), 3.68-3.61 (m, 4H), 2.77 (t, J=5.6 Hz, 2H), 2.45 (t, J=6.7 Hz, 2H), 1.35 (s, 9H)

Example 130

5-tert-butyl-2-[3-(2,3-dichlorophenyl)ureido]thiophene-3-carboxylic acid (pyridin-3-ylmethyl)amide

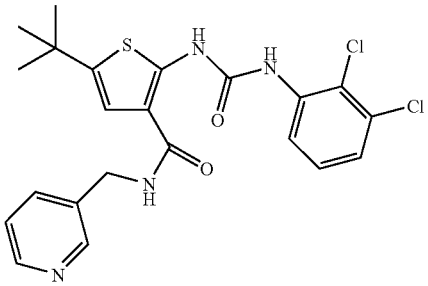

¹H NMR (400 MHz, CD₃OD): δ 8.50 (d, J=1.0 Hz, 1H), 8.35 (d, J=3.9 Hz, 1H), 7.80-7.73 (m, 2H), 7.30 (dd, J=7.8, 4.9 Hz, 1H), 7.23-7.14 (m, 2H), 6.98 (s, 1H), 4.50 (s, 2H), 1.30 (s, 9H)

Example 131

5-tert-Butyl-2-(3-naphthalen-1-yl-ureido)thiophene-3-carboxylic acid (pyridin-3-ylmethyl)amide

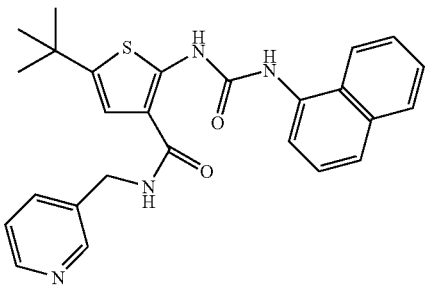

¹H NMR (400 MHz, CD₃OD): δ 8.45 (s, 1H), 8.35 (d, J=3.9 Hz, 1H), 8.05-7.99 (m, 1H), 7.84-7.79 (m, 1H), 7.72-7.66 (m, 2H), 7.61 (d, J=7.4 Hz, 1H), 7.46-7.39 (m, 3H), 7.28 (dd, J=7.8, 4.9 Hz, 1H), 6.96 (s, 1H), 4.44 (s, 2H), 1.30 (s, 9H)

Example 132

5-tert-Butyl-2-(3-naphthalen-2-yl-ureido)thiophene-3-carboxylic acid (pyridin-3-ylmethyl)amide

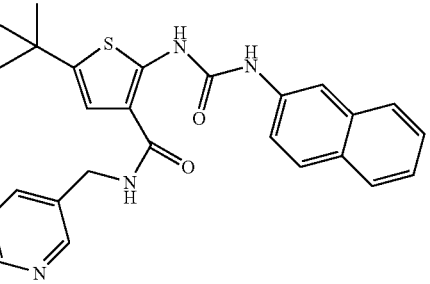

¹H NMR (400 MHz, CD₃OD): δ 8.48 (s, 1H), 8.32 (d, J=4.1 Hz, 1H), 8.00 (d, J=1.2 Hz, 1H), 7.75-7.61 (m, 4H), 7.45 (dd, J=8.8, 2.0 Hz, 1H), 7.33 (t, J=7.1 Hz, 1H), 7.29-7.22 (m, 2H), 6.99 (s, 1H), 4.48 (s, 2H), 1.30 (s, 9H)

Example 133

5-tert-Butyl-2-[3-(2,3-dichlorophenyl)ureido]thiophene-3-carboxylic acid (3H-benzotriazol-5-yl) amide

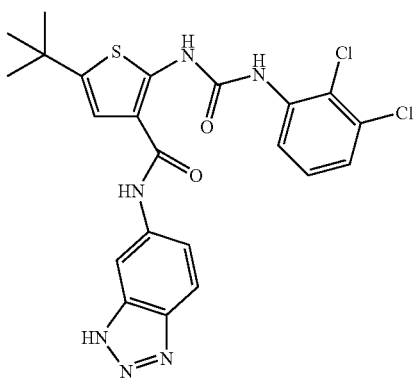

¹H NMR (400 MHz, CD₃OD/CDCl₃): δ 8.24 (d, J=1.2 Hz, 1H), 7.92-7.86 (m, 1H), 7.79 (d, J=9.0 Hz, 1H), 7.54 (dd, J=9.0, 1.8 Hz, 1H), 7.20-7.14 (m, 3H), 1.37 (s, 9H)

Example 134

1-[5-tert-Butyl-3-(2-ethyl-3-oxopiperazine-1-carbonyl)thiophen-2-yl]-3-(2,3-dichlorophenyl)urea

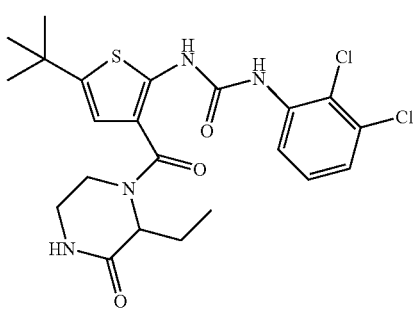

¹H NMR (400 MHz, DMSO-d₆): δ 10.03-9.98 (m, 1H), 9.30 (s, 1H), 7.96-7.86 (m, 2H), 7.27-7.21 (m, 2H), 6.52 (s, 1H), 4.57 (s, 1H), 3.88 (s, 1H), 3.36 (s, 1H), 3.19-3.11 (m, 1H), 3.10-3.02 (m, 1H), 1.90-1.69 (m, 2H), 1.24 (s, 9H), 0.83 (t, J=7.4 Hz, 3H)

Example 135

1-[5-tert-Butyl-3-(2-methyl-3-oxopiperazine-1-carbonyl)thiophen-2-yl]-3-(2,3-dichlorophenyl)urea

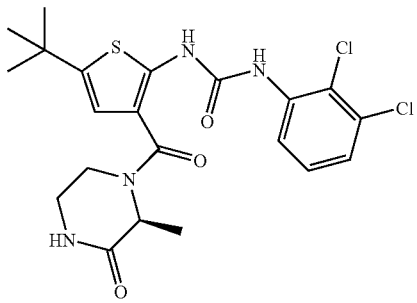

¹H NMR (400 MHz, DMSO-d₆): δ 10.06 (s, 1H), 9.36 (s, 1H), 8.02-7.94 (m, 2H), 7.33-7.26 (m, 2H), 6.57 (s, 1H), 4.57 (s, 1H), 3.91 (s, 1H), 3.46-3.24 (m, 2H), 3.18-3.09 (m, 1H), 1.37 (t, J=10.9 Hz, 3H), 1.29 (s, 9H)

Example 136

1-[5-tert-Butyl-3-(2,2-dimethyl-3-oxo-piperazine-1-carbonyl)thiophen-2-yl]-3-(2,3-dichlorophenyl)urea

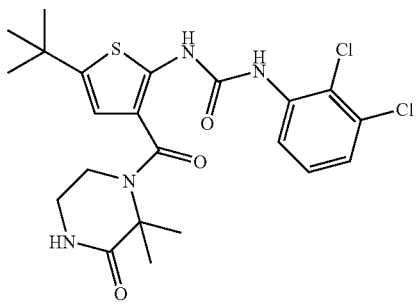

¹H-NMR (400 MHz DMSO-d₆) δ 10.12 (s, 1H); 9.60 (s, 1H); 8.15 (t, 1H); 7.91 (dd, 1H); 7.30 (m, 2H); 6.59 (s, 1H); 3.51 (t, 1H); 3.27 (bs, 3H); 1.65 (s, 6H); 1.28 (s, 9H).

Example 137

1-[5-tert-butyl-3-(5-oxo-[1,4]diazepane-1-carbonyl)thiophen-2-yl]-3-(3,5-difluorophenyl)urea

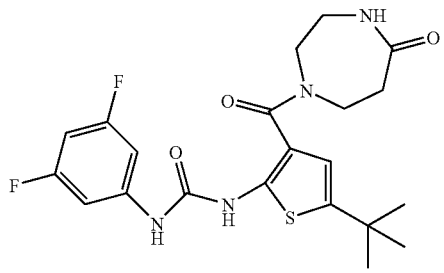

$^1$H-NMR (400 MHz DMSO-d$_6$) δ 9.96 (s, 1H), 9.66 (s, 1H), 7.23-7.30 (m, 2H), 6.93 (s, 1H), 6.68 (s, 1H), 6.64 (t, t J=9.3, 2.3 Hz, 1H), 3.77-3.84 (m, 4H), 3.43-3.48 (m, 2H), 2.69-2.73 (m, 2H), 1.38 (s, 9H).

Example 138

1-(5-tert-Butyl-3-(2-oxopiperazine-4-carbonyl)thiophen-2-yl)-3-(2,3-dichlorophenyl)urea

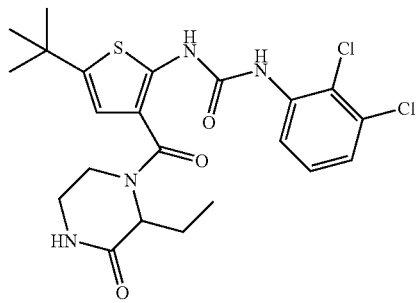

$^1$H-NMR (400 MHz DMSO-d$_6$) δ 10.09 (s, 1H), 9.37 (s, 1H), 8.05 (s, 1H), 7.94-7.88 (m, 1H), 7.27-7.21 (m, 2H), 6.56 (s, 1H), 4.00 (s, 2H), 3.61 (t, J=5.0 Hz, 2H), 3.22-3.16 (m, 2H), 1.24 (s, 9H).

Example 139

1-(2-tert-Butyl-4-(1-(2-(dimethylamino)ethyl)-7-oxo-1,4-diazepane-4-carbonyl)thiazol-5-yl)-3-(2,3-dichlorophenyl)urea

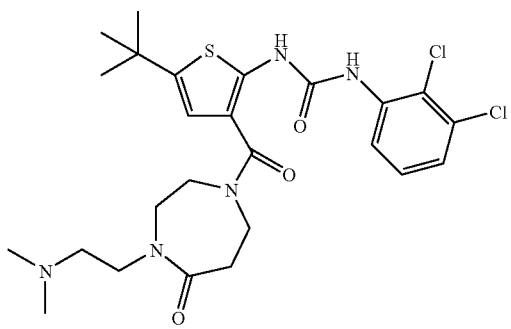

$^1$H NMR (400 MHz, CD$_3$OD/CDCl$_3$): δ 7.88 (dd, J=6.7, 2.8 Hz, 1H), 7.17-7.10 (m, 2H), 4.17 (d, J=25.2 Hz, 2H), 3.79 (d, J=15.8 Hz, 2H), 3.60-3.53 (m, 2H), 3.47 (s, 2H), 2.78 (d, J=32.8 Hz, 2H), 2.38 (d, J=24.2 Hz, 2H), 2.22 (s, 3H), 2.19 (s, 3H), 1.33 (s, 9H)

Example 140

(R)-1-(5-tert-Butyl-3-(2-methyl-3-oxopiperazine-1-carbonyl)thiophen-2-yl)-3-(2,3-dichlorophenyl)urea

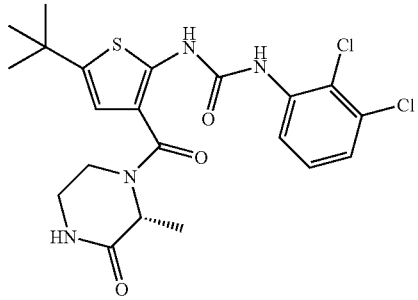

$^1$H NMR (400 MHz, CD$_3$OD): δ 7.99 (dd, J=7.3, 2.4 Hz, 1H), 7.24-7.17 (m, 2H), 6.58 (s, 1H), 4.16 (s, 1H), 3.52-3.38 (m, 2H), 3.30-3.23 (m, 2H), 1.53 (d, J=7.0 Hz, 3H), 1.33 (s, 9H).

Example 141

1-(2-tert-Butyl-4-(1-((2,2-dimethyl-1,3-dioxolan-4-yl)methyl)-7-oxo-1,4-diazepane-4-carbonyl)thiazol-5-yl)-3-(2,3-dichlorophenyl)urea

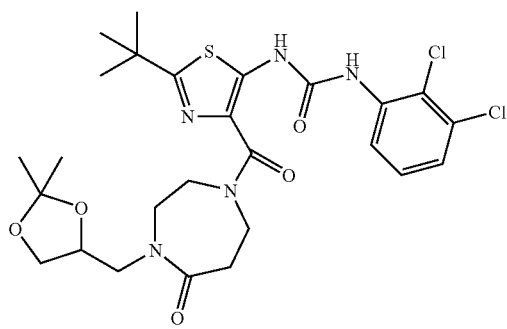

$^1$H NMR (400 MHz, DMSO-d$_6$): δ 10.76 (s, 1H), 9.87 (s, 1H), 7.84-7.79 (m, 1H), 7.32-7.22 (m, 2H), 4.16-3.80 (m, 4H), 3.78-3.42 (m, 6H), 3.33-3.24 (m, 1H), 2.72 (s, 1H), 2.63 (s, 1H), 1.30-1.21 (m, 12H), 1.16 (d, J=17.4 Hz, 3H)

Example 142

1-(4-(1-(3-Amino-3-oxopropyl)-7-oxo-1,4-diazepane-4-carbonyl)-2-tert-butylthiazol-5-yl)-3-(2,3-dichlorophenyl)urea

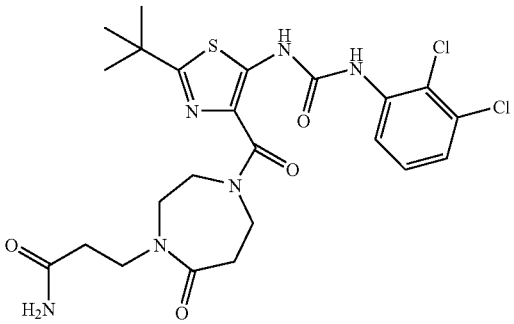

¹H NMR (400 MHz, CD₃OD/CDCl₃): δ 7.89 (dd, J=7.0, 2.7 Hz, 1H), 7.22-7.14 (m, 2H), 4.22 (s, 1H), 4.15 (s, 1H), 3.83 (s, 2H), 3.66 (s, 4H), 2.86 (s, 1H), 2.75 (s, 1H), 2.46 (s, 2H), 1.36 (s, 9H).

Example 143

1-(5-tert-Butyl-3-(5-oxo-1,4-diazepane-1-carbonyl)thiophen-2-yl)-3-(2,3,4-trichlorophenyl)urea

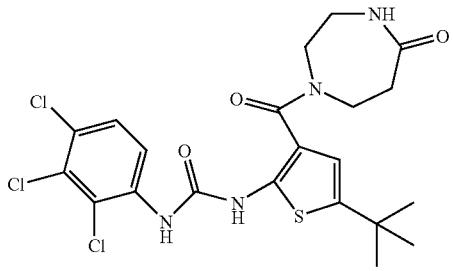

¹H NMR (400 MHz, acetone-d6): δ (ppm) 8.20 (d, 1H); 7.58 (d, 1H); 6.92 (bs, 1H); 6.65 (s, 1H); 3.79 (m, 4H); 3.43 (m, 2H); 2.72 (m, 2H); 1.38 (s, 9H).

Example 144

1-(3-(1-((1H-Tetrazol-5-yl)methyl)-7-oxo-1,4-diazepane-4-carbonyl)-5-tert-butylthiophen-2-yl)-3-(2,3-dichlorophenyl)urea

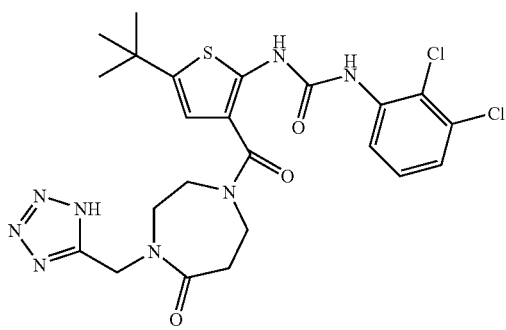

¹H NMR (400 MHz, acetone-d₆): δ (ppm) 9.40 (s, 1H); 7.95 (s, 1H); 7.23 (d, 2H); 6.50 (bs, 1H); 4.58 (s, 2H); 3.58 (m, 2H); 3.46 (s, 2H); 3.21 (s, 2H); 2.60 (m, 2H); 1.20 (s, 9H).

Example 145

1-(5-tert-Butyl-3-(spiro[2.5]-1,4-diazeoctan-5-one-1-carbonyl)thiophen-2-yl)-3-(2,3-dichlorophenyl)urea

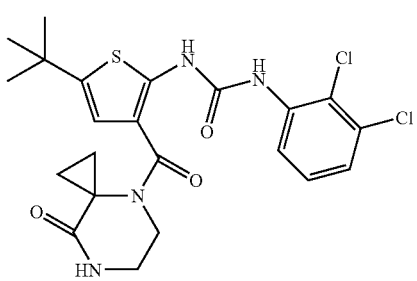

¹H NMR (400 MHz, DMSO): δ (ppm) 10.40 (s, 1H); 9.60 (s, 1H); 7.85 (m, 1H); 7.78 (s, 1H); 7.22 (m, 2H), 6.50 (s, 1H); 3.80 (m, 2H); 3.20 (m, 2H); 1.34 (m, 2H); 1.23 (s, 9H); 0.95 (m, 2H).

Example 146

1-(2-tert-Butyl-4-(5-oxo-1,4-diazepane-1-carbonyl)thiazol-5-yl)-3-(2,3-dichlorophenyl)urea

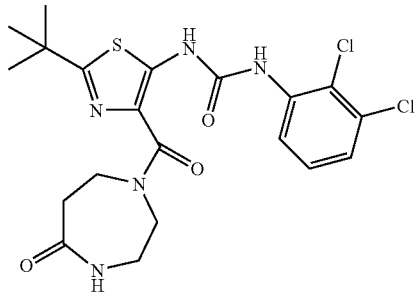

¹H NMR (400 MHz, DMSO-d₆): δ 10.82 (s, 1H), 9.92 (s, 1H), 7.87 (dd, J=8.0, 1.8 Hz, 1H), 7.65 (t, J=5.1 Hz, 1H), 7.37-7.28 (m, 2H), 4.03 (s, 1H), 3.98 (s, 1H), 3.79-3.65 (m, 2H), 3.27-3.22 (m, 2H), 2.64 (s, 1H), 2.54 (s, 1H), 1.33 (s, 9H).

Example 147

1-(2-tert-Butyl-4-(2-oxopiperazine-4-carbonyl)thiazole-5-yl)-3-(2,3-dichlorophenyl)urea

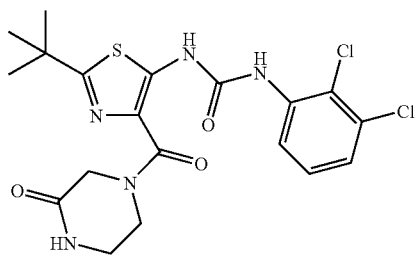

¹H NMR (400 MHz, DMSO-D₆): δ 10.93-10.78 (m, 1H), 9.97-9.86 (m, 1H), 8.01 (s, 1H), 7.81 (d, J=7.4 Hz, 1H), 7.33-7.22 (m, 2H), 4.62 (s, 1H), 4.16 (s, 1H), 4.07 (s, 1H), 3.74 (s, 1H), 3.29-3.18 (m, 2H), 1.28 (s, 9H).

Example 148

1-(2-tert-Butyl-4-(1,1-dioxy-1-thia-2,5-diazepan-1-one-5-carbonyl)thiazole-5-yl)-3-(2,3-dichlorophenyl)urea

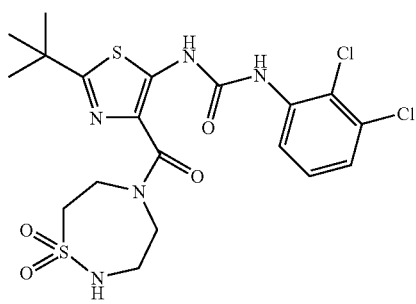

¹H NMR (400 MHz, DMSO-d₆): δ 11.12-11.09 (m, 1H), 10.08-10.04 (m, 1H), 7.83 (ddd, J=8.0, 3.3, 1.6 Hz, 1H), 7.43 (q, J=5.5 Hz, 1H), 7.39-7.28 (m, 2H), 4.28-4.18 (m, 2H), 3.89-3.81 (m, 2H), 3.59-3.53 (m, 1H), 3.45-3.39 (m, 1H), 3.27-3.20 (m, 1H), 3.15 (q, J=5.8 Hz, 1H), 1.34-1.31 (m, 9H)

Example 149

1-(5-tert-Butyl-3-(1-methyl-7-oxo-1,4-diazepane-4-carbonyl)thiophen-2-yl)-3-(2,3-dichlorophenyl)urea

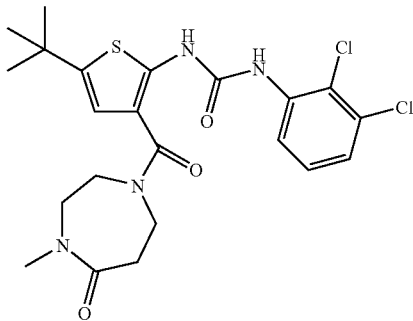

¹H NMR (400 MHz, acetone-d6): δ (ppm) 9.90 (s, 1H); 9.10 (s, 1H); 8.21 (d, 1H); 7.30 (m, 2H); 6.63 (s, 1H); 3.82 (m, 2H); 3.75 (m, 2H); 3.63 (m, 2H); 2.96 (s, 3H); 2.75 (m, 2H); 1.39 (s, 9H).

Example 150

1-(5-tert-Butyl-3-(5-oxo-1,4-diazepane-1-carbonyl)thiophen-2-yl)-3-(2,3-dichloro-4-hydroxyphenyl)urea

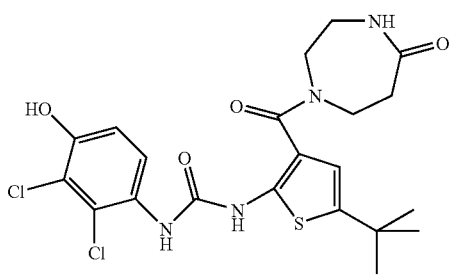

¹H NMR (400 MHz, CD₃OD): δ (ppm) 7.40 (d, 1H); 6.80 (d, 1H); 6.59 (s, 1H); 3.76 (m, 4H); 3.38 (m, 2H), 2.70 (m, 2H); 1.38 (s, 9H).

Example 151

1-(5-tert-Butyl-3-(5-oxo-1,4-diazepane-1-carbonyl)thiophen-2-yl)-3-(2,3-dichloro-4-methoxyphenyl)urea

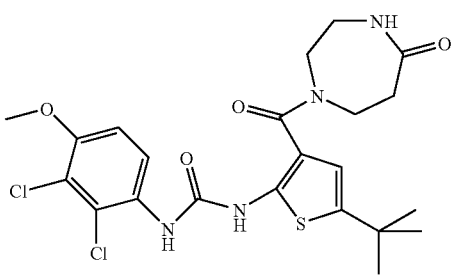

¹H NMR (400 MHz, acetone-d₆): δ (ppm) 9.95 (s, 1H); 9.0 (s, 1H); 7.98 (d, 1H); 7.16 (m, 2H); 6.62 (s, 1H), 3.92 (s, 3H); 3.80 (m, 4H); 3.43 (m, 2H); 2.72 (m, 2H); 1.37 (s, 9H).

Example 152

1-(5-tert-Butyl-3-(2,2-dimethyl-3-oxopiperazine-1-carbonyl)thiophen-2-yl)-3-(naphthalen-1-yl)urea

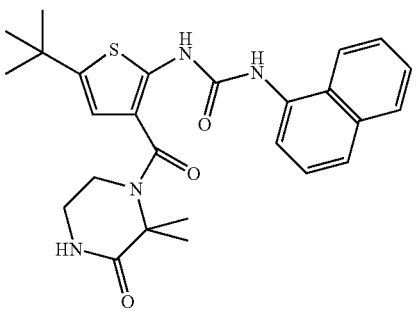

¹H NMR (400 MHz, DMSO-d₆): δ 9.97 (s, 1H), 9.82 (s, 1H), 8.16 (d, J=8.2 Hz, 1H), 8.05 (s, 1H), 7.89 (dd, J=11.3, 7.6 Hz, 2H), 7.65 (d, J=8.0 Hz, 1H), 7.58-7.49 (m, 2H), 7.45 (t, J=7.9 Hz, 1H), 3.56 (t, J=4.6 Hz, 2H), 3.31 (s, 2H), 1.70 (s, 6H), 1.29 (s, 9H).

Example 153

1-(5-tert-Butyl-3-(6,6-dimethyl-5-oxo-1,4-diazepane-1-carbonyl)thiophen-2-yl)-3-(2,3-dichlorophenyl)urea

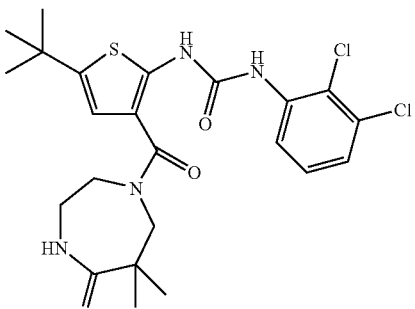

¹H NMR (400 MHz, CD₂Cl₂): δ (ppm) 11.51 (s, 1H), 8.17 (d, J=8.2 Hz, 1H), 7.49 (s, 1H), 7.26 (br s, 1H), 7.24-7.20 (m, 2H), 6.78 (s, 1H), 3.60-3.56 (m, 2H), 3.35-3.32 (m, 2H), 3.12 (s, 2H), 1.37 (s, 9H), 1.26 (s, 6H).

Example 154

1-(5-tert-Butyl-3-(2,2-dimethyl-3-oxopiperazine-1-carbonyl)thiophen-2-yl)-3-(2,3-dichloro-4-fluorophenyl)urea

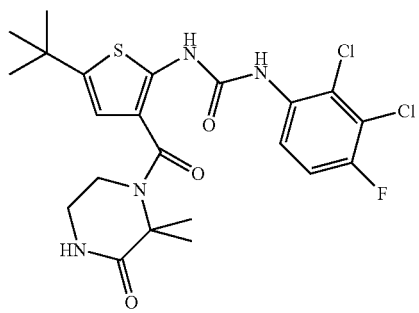

The compound of this example was prepared using a procedure analogous to the procedure described in Example 179. $^1$H NMR (400 MHz, CD$_3$OD/CDCl$_3$): δ (ppm) 7.89 (dd, J=9.4, 5.3 Hz, 1H), 7.09 (t, J=8.8 Hz, 1H), 6.44 (s, 1H), 3.67 (t, J=4.9 Hz, 2H), 3.40 (t, J=4.9 Hz, 2H), 1.78 (s, 6H), 1.31 (s, 9H).

Example 155

1-(5-tert-Butyl-3-(2,2-dimethyl-3-oxopiperazine-1-carbonyl)thiophen-2-yl)-3-(3,5-dichlorophenyl)urea

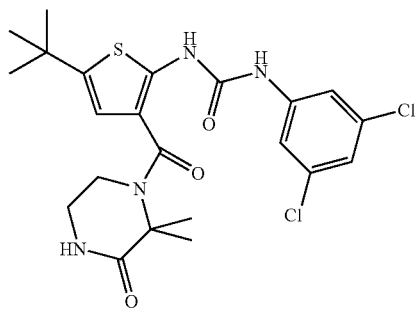

The compound of this example was prepared using a procedure analogous to the procedure described in Example 179. $^1$H NMR (400 MHz, CD$_3$OD/CDCl$_3$): δ (ppm) 7.44 (d, J=1.8 Hz, 2H), 6.95 (t, J=1.7 Hz, 1H), 6.42 (s, 1H), 3.68 (t, J=4.9 Hz, 2H), 3.42 (t, J=4.9 Hz, 2H), 1.76 (s, 6H), 1.31 (s, 9H).

Example 156

1-(5-tert-Butyl-3-(5-methyl-7-oxo-1,4-diazepane-4-carbonyl)thiophen-2-yl)-3-(2,3-dichlorophenyl)urea

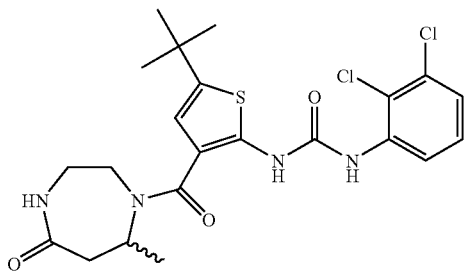

The compound of this example was prepared using a procedure analogous to the procedure described in Example 179. $^1$H NMR (400 MHz, acetone-d$_6$): δ (ppm) 9.81 (s, 1H), 9.09 (s, 1H), 8.22 (d, J=6.8 Hz, 1H), 7.27-7.38 (m, 2H), 6.95 (s, 1H), 6.62 (s, 1H), 4.79 (s, 1H), 4.29 (s, 1H), 3.44-3.54 (m, 1H), 3.24-3.42 (m, 2H), 2.93 (dd, J=14.2, 3.0 Hz, 1H), 2.46 (dd, J=14.4, 6.4 Hz, 1H), 1.37 (s, 9H), 1.31 (d, J=6.8 Hz, 3H).

Example 157

1-(5-tert-Butyl-3-(2,2-dimethyl-3-oxopiperazine-1-carbonyl)thiophen-2-yl)-3-(4-cyanonaphthalen-1-yl)urea

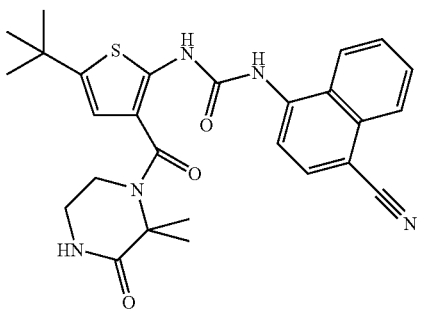

The compound of this example was prepared using a procedure analogous to the procedure described in Example 179. $^1$H NMR (400 MHz, CD$_3$OD/CDCl$_3$): δ (ppm) 8.24-8.10 (m, 4H), 7.88 (d, J=8.2 Hz, 1H), 7.68 (td, J=10.3, 3.8 Hz, 1H), 7.62 (ddd, J=8.3, 7.0, 1.2 Hz, 1H), 3.70 (t, J=4.9 Hz, 2H), 3.42 (t, J=4.8 Hz, 2H), 1.79 (s, 6H), 1.33 (s, 9H).

Example 158

1-(5-tert-Butyl-3-(1-(2-(dimethylamino)ethyl)-6,6-dimethyl-7-oxo-1,4-diazepane-4-carbonyl)thiophen-2-yl)-3-(2,3-dichlorophenyl)urea

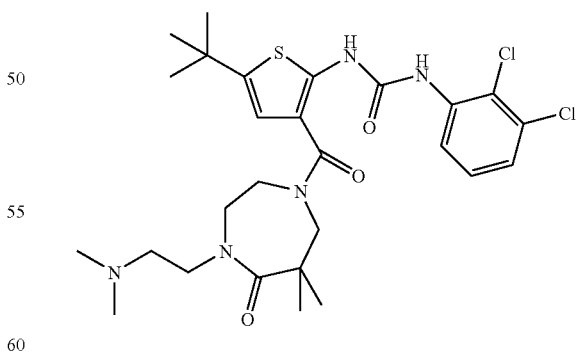

The compound of this example was prepared using a procedure analogous to the procedure described in Example 138. $^1$H NMR (400 MHz, CD$_2$Cl$_2$): δ (ppm) 9.03 (s, 1H), 8.88 (s, 1H), 8.29 (d, J=8.2 Hz, 1H), 7.22-7.06 (m, 2H), 6.48 (s, 1H), 3.64 (d, J=3.7 Hz, 2H), 3.51 (d, J=3.5 Hz, 2H), 3.41 (t, J=6.7 Hz, 2H), 3.27 (s, 2H), 2.32 (t, J=6.2 Hz, 2H), 2.04 (s, 6H), 1.36 (s, 9H), 1.29 (s, 6H).

Example 159

1-(5-tert-Butyl-3-(2-oxopiperazine-4-carbonyl)thiophen-2-yl)-3-(2,3-dichloro-4-fluorophenyl)urea

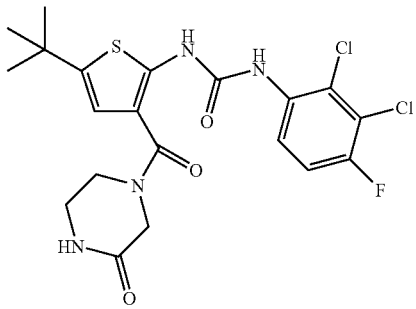

The compound of this example was prepared using a procedure analogous to the procedure described in Example 138. ¹H NMR (400 MHz, CD₃OD/CDCl₃): δ (ppm) 7.99 (dd, J=9.4, 5.3 Hz, 1H), 7.03 (dd, J=9.3, 8.3 Hz, 1H), 6.44 (s, 1H), 4.25 (s, 2H), 3.79 (t, J=5.3 Hz, 2H), 3.38 (t, J=5.3 Hz, 2H), 1.29 (s, 9H).

Example 160

1-(5-tert-Butyl-3-(5-oxo-1,4-diazepane-1-carbonyl)thiophen-2-yl)-3-(2,3-dichloro-4-fluorophenyl)urea

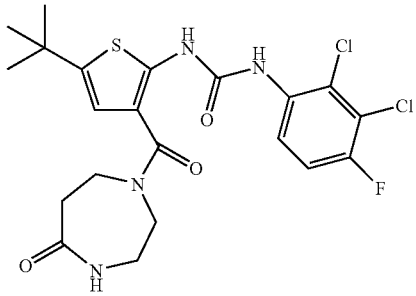

The compound of this example was prepared using a procedure analogous to the procedure described in Example 138. ¹H NMR (400 MHz, CD₃OD/CDCl₃): δ (ppm) 7.94 (dd, J=9.3, 5.2 Hz, 1H), 7.07 (dd, J=9.2, 8.3 Hz, 1H), 6.46 (s, 1H), 3.78-3.71 (m, 4H), 3.36-3.31 (m, 2H), 2.72-2.65 (m, 2H), 1.31 (s, 9H).

Example 161

Methyl 2-(4-(2-tert-butyl-5-(3-(2,3-dichlorophenyl)ureido)thiophene-4-carbonyl)-7-oxo-1,4-diazepan-5-yl)acetate

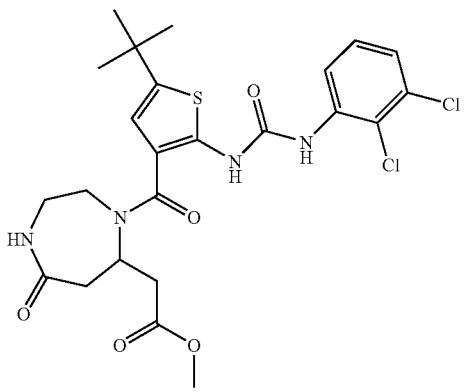

The compound of this example was prepared using a procedure analogous to the procedure described in Example 138. ¹H NMR (400 MHz, acetone-d₆): δ (ppm) 9.90 (s, 1H), 9.14 (s, 1H), 8.22 (dd, J=8.2, 1.6 Hz, 1H), 7.27-7.37 (m, 2H), 7.01 (s, 1H), 6.64 (s, 1H), 5.10 (s, 1H), 4.30 (s, 1H), 3.65 (s, 3H), 3.46-3.56 (m, 1H), 3.26-3.42 (m, 2H), 3.02 (dd, J=14.4, 3.1 Hz, 1H), 2.70-2.88 (m, 2H), 2.61 (dd, J=14.4, 6.2 Hz, 1H), 1.37 (s, 9H).

Example 162

1-(3-(2-(2-amino-2-oxoethyl)-3-oxopiperazine-1-carbonyl)-5-tert-butylthiophen-2-yl)-3-(2,3-dichlorophenyl)urea

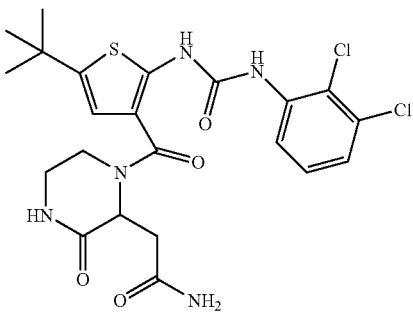

The compound of this example was prepared using a procedure analogous to the procedure described in Example 138. ¹H NMR (400 MHz, acetone-d₆): δ (ppm) 10.40 (s, 1H); 8.90 (s, 1H); 8.38 (d, 1H); 7.65 (bs, 1H); 7.40 (bs, 1H), 7.36 (t, 1H); 7.25 (d, 1H); 7.00 (bs, 1H); 6.62 (s, 1H); 5.22 (m, 1H); 3.85 (m, 2H); 3.38 (m, 2H); 3.00 (m, 2H); 1.40 (s, 9H).

Example 163

1-(5-tert-Butyl-3-(5-oxo-1,4-diazepane-1-carbonyl)thiophen-2-yl)-3-(2,3-dichloro-4-cyanophenyl)urea

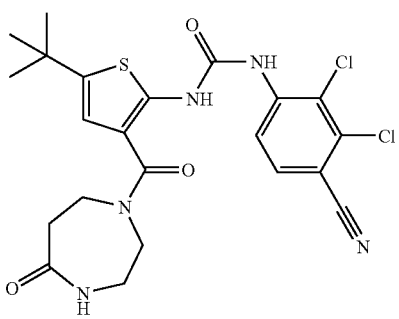

The compound of this example was prepared using a procedure analogous to the procedure described in Example 138. δ ¹H NMR (400 MHz, CD₃OD): δ (ppm) 8.40 (d, 1H); 7.70 (d, 1H); 6.60 (s, 1H); 3.78 (m, 4H); 3.38 (m, 2H), 2.73 (m, 2H); 1.38 (s, 9H).

Example 164

1-(5-tert-Butyl-3-(5-oxo-1,4-diazepane-1-carbonyl)thiophen-2-yl)-3-(2,3-dichloro-4-(difluoromethoxy)phenyl)urea

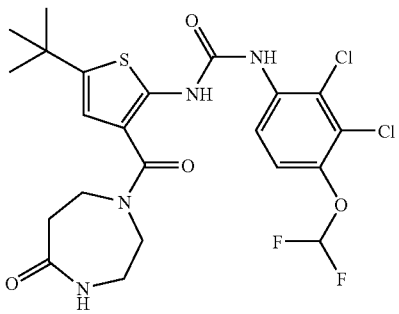

The compound of this example was prepared using a procedure analogous to the procedure described in Example 138. ¹H NMR (400 MHz, acetone-d₆): δ (ppm) 10.0 (s, 1H); 9.20 (s, 1H); 8.21 (d, 1H); 7.39 (d, 1H); 7.20 (m, 1H), 6.95 (d, 1H); 6.65 (s, 1H); 3.82 (m, 4H); 3.49 (m, 2H); 2.77 (m, 2H); 1.39 (s, 9H).

Example 165

Methyl 4-(3-(5-tert-butyl-3-(5-oxo-1,4-diazepane-1-carbonyl)thiophen-2-yl)ureido)-2,3-dichlorobenzoate

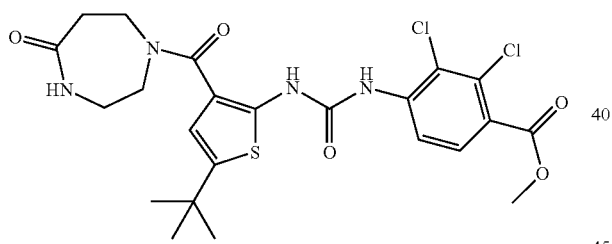

The compound of this example was prepared using a procedure analogous to the procedure described in Example 138. ¹H NMR (400 MHz, CD₃OD): δ (ppm) 8.27 (d, 1H); 7.78 (d, 1H); 6.60 (s, 1H); 3.88 (s, 2H); 3.78 (m, 4H); 3.38 (m, 2H), 2.72 (m, 2H); 1.39 (s, 9H).

Example 166

1-(3-(1-(2-(1H-Tetrazol-5-yl)ethyl)-7-oxo-1,4-diazepane-4-carbonyl)-5-tert-butylthiophen-2-yl)-3-(2,3-dichlorophenyl)urea

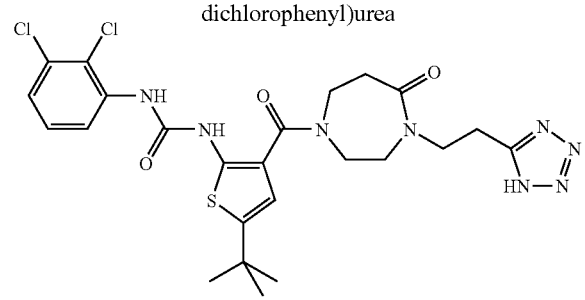

The compound of this example was prepared using a procedure analogous to the procedure described in Example 138. ¹H NMR (400 MHz, CDCl₃): δ (ppm) 9.98 (s, 1H), 8.28 (s, 1H), 8.06 (dd, J=8.0, 2.2 Hz, 1H), 7.09-7.00 (m, 2H), 6.29 (s, 1H), 3.83 (s, 2H), 3.69 (d, J=21.8 Hz, 4H), 3.54 (s, 2H), 3.19 (s, 2H), 2.70 (s, 2H), 1.23 (s, 9H).

Example 167

1-(5-tert-Butyl-2-(2,2-dimethyl-3-oxopiperazine-1-carbonyl)thiophen-3-yl)-3-(2,3-dichlorophenyl)urea

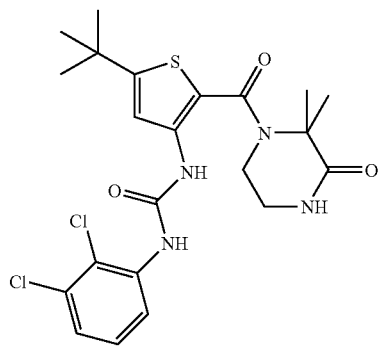

The compound of this example was prepared using a procedure analogous to the procedure described in Example 183. ¹H NMR (400 MHz, acetone-d₆): δ (ppm) 9.55 (s, 1H); 8.87 (s, 1H); 8.17 (d, 1H); 7.70 (s, 1H); 7.32 (m, 2H), 7.15 (bs, 1H); 3.92 (m, 2H); 3.55 (m, 2H); 1.70 (s, 6H); 1.40 (s, 9H).

Example 168

1-(5-tert-Butyl-2-(1-(2-(dimethylamino)ethyl)-7-oxo-1,4-diazepane-4-carbonyl)thiophen-3-yl)-3-(2,3-dichloro-4-fluorophenyl)urea

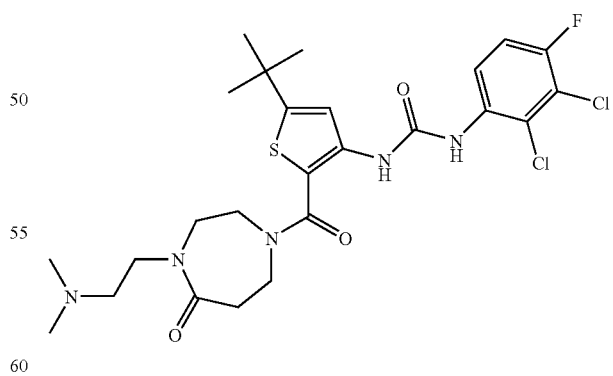

The compound of this example was prepared using a procedure analogous to the procedure described in Example 183. ¹H NMR (400 MHz, acetone-d6): δ (ppm) 9.78 (s, 1H); 8.99 (s, 1H); 8.08 (m, 1H); 7.70 (s, 1H); 7.32 (t, 1H); 3.92 (m, 2H); 3.80 (m, 2H); 3.65 (m, 2H); 3.47 (m, 2H); 2.78 (m, 2H); 2.37 (m, 2H); 2.16 (s, 6H); 1.40 (s, 9H).

Example 169
1-(5-tert-Butyl-3-(1-(2-(dimethylamino)ethyl)-7-oxo-1,4-diazepane-4-carbonyl)thiophen-2-yl)-3-(2,3-dichloro-4-fluorophenyl)urea

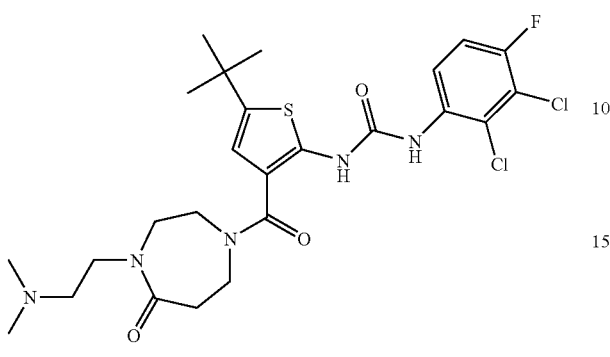

The compound of this example was prepared using a procedure analogous to the procedure described in Example 138.
¹H NMR (400 MHz, acetone-d₆): δ (ppm) 10.05 (bs, 1H); 9.30 (bs, 1H); 8.08 (m, 1H); 7.33 (t, 1H); 6.61 (s, 1H); 3.80 (m, 2H); 3.70 (m, 2H); 3.62 (m, 2H); 3.47 (m, 2H); 2.78 (m, 2H); 2.37 (m, 2H); 2.16 (s, 6H); 1.38 (s, 9H).

Example 170
1-(5-tert-Butyl-3-(2,2-dimethyl-3-oxopiperazine-1-carbonyl)thiophen-2-yl)-3-(2-chloro-4-fluorophenyl)urea

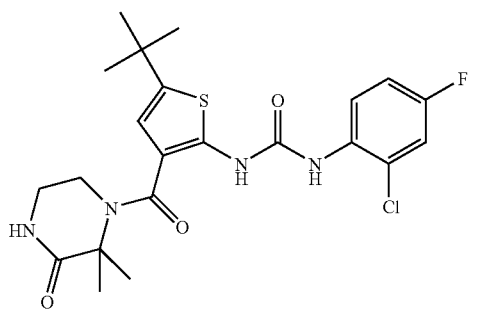

The compound of this example was prepared using a procedure analogous to the procedure described in Example 179.
¹H NMR (400 MHz, CD₃OD): δ (ppm) 7.88 (dd, J=9.1, 5.6 Hz, 1H), 7.25 (dd, J=8.3, 2.8 Hz, 1H), 7.07 (dt, J=8.5, 2.8 Hz, 1H), 6.56 (s, 1H), 3.67 (t, J=4.8 Hz, 2H), 3.41 (t, J=4.9 Hz, 2H), 1.80 (s, 6H), 1.35 (s, 9H).

Example 171
1-(5-tert-Butyl-3-(5-oxo-1,4-diazepane-1-carbonyl)thiophen-2-yl)-3-(2-chloro-4-fluorophenyl)urea

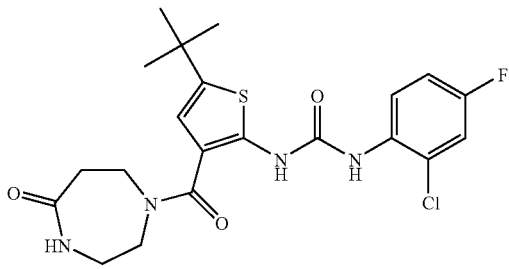

The compound of this example was prepared using a procedure analogous to the procedure described in Example 138.
¹H NMR (400 MHz, CD₃OD): δ (ppm) 7.93 (dd, J=9.2, 5.7 Hz, 1H), 7.23 (dd, J=8.2, 2.9 Hz, 1H), 7.05 (dt, J=8.5, 2.5 Hz, 1H), 6.59 (s, 1H), 3.71-3.80 (m, 4H), 3.37 (t, J=4.2 Hz, 2H), 2.72 (t, J=5.3 Hz, 2H), 1.34 (s, 9H).

Example 172
1-(2-tert-Butyl-4-(2,2-dimethyl-3-oxopiperazine-1-carbonyl)thiazol-5-yl)-3-(2,3-dichloro-4-fluorophenyl)urea

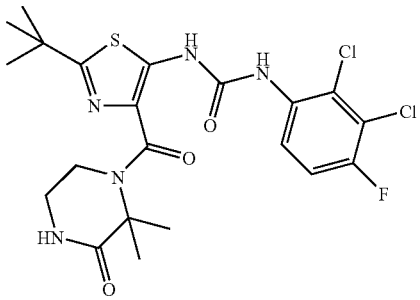

The compound of this example was prepared using a procedure analogous to the procedure described in Example 179.
¹H NMR (400 MHz, CD₃OD): δ (ppm) 7.82 (q, J=4.8 Hz, 1H), 7.11 (q, J=5.9 Hz, 1H), 3.97 (t, J=4.8 Hz, 2H), 3.51 (t, J=4.6 Hz, 2H), 1.79 (s, 6H), 1.35 (m, 9H).

Example 173
1-(5-tert-Butyl-3-(1-(2-(dimethylamino)ethyl)-3,3-dimethyl-2-oxopiperazine-4-carbonyl)thiophen-2-yl)-3-(2,3-dichlorophenyl)urea

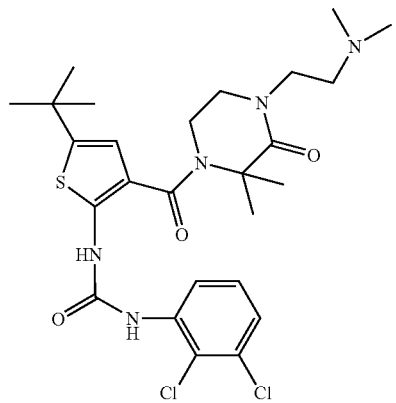

The compound of this example was prepared using a procedure analogous to the procedure described in Example 179.
¹H NMR (400 MHz, CDCl₃): δ (ppm) 8.18 (dd, J=7.5, 2.3 Hz, 1H), 7.77 (s, 1H), 7.18-7.12 (m, 2H), 6.43 (s, 1H), 3.75 (t, J=4.9 Hz, 2H), 3.55-3.50 (m, 4H), 2.49 (t, J=6.6 Hz, 2H), 2.25 (s, 6H), 1.78 (s, 6H), 1.35 (s, 9H), 10.22 (s, 1H).

Example 174

1-(5-tert-Butyl-3-(1-(2-(dimethylamino)ethyl)-3,3-dimethyl-2-oxopiperazine-4-carbonyl)thiophen-2-yl)-3-(2,3-dichloro-4-fluorophenyl)urea

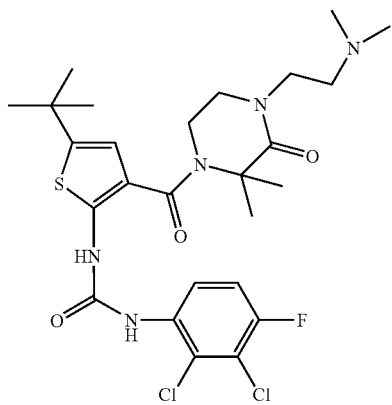

The compound of this example was prepared using a procedure analogous to the procedure described in Example 179. ¹H NMR (400 MHz, CDCl₃): δ (ppm) 10.21 (s, 1H), 8.14 (dd, J=9.4, 5.2 Hz, 1H), 7.88 (s, 1H), 7.04 (dd, J=9.3, 8.2 Hz, 1H), 6.42 (s, 1H), 3.75 (t, J=5.0 Hz, 2H), 3.55-3.47 (m, 4H), 2.48 (t, J=6.6 Hz, 2H), 2.25 (s, 6H), 1.77 (s, 6H), 1.34 (s, 9H).

Example 175

1-(5-tert-Butyl-3-(2,2-dimethyl-3-oxopiperazine-1-carbonyl)thiophen-2-yl)-3-(2,4-dichlorophenyl)urea

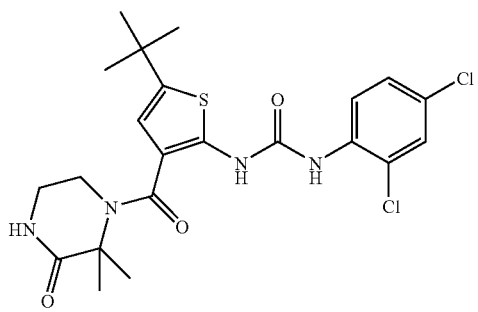

The compound of this example was prepared using a procedure analogous to the procedure described in Example 179. ¹H NMR (400 MHz, DMSO-d₆): δ (ppm) 10.00 (s, 1H), 9.52 (s, 1H), 8.04 (s, 1H), 7.96 (d, J=9.0 Hz, 1H), 7.59 (d, J=2.5 Hz, 1H), 7.36 (dd, J=9.0, 2.5 Hz, 1H), 6.55 (s, 1H), 3.51 (t, J=4.6 Hz, 2H), 3.25-3.30 (m, 2H), 1.68 (s, 6H), 1.28 (s, 9H).

Example 176

1-(5-tert-Butyl-3-(5-oxo-1,4-diazepane-1-carbonyl)thiophen-2-yl)-3-(2,4-dichlorophenyl)urea

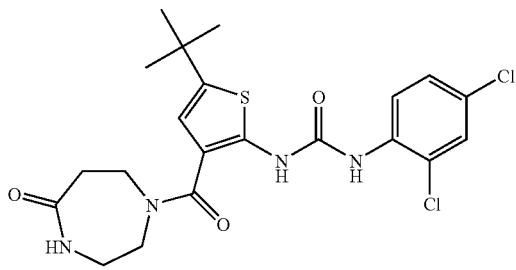

The compound of this example was prepared using a procedure analogous to the procedure described in Example 138. ¹H NMR (400 MHz, DMSO-d₆): δ (ppm) 10.01 (s, 1H), 9.32 (s, 1H), 8.02 (d, J=9.0 Hz, 1H), 7.67 (t, J=5.4 Hz, 1H), 7.59 (d, J=2.3 Hz, 1H), 7.36 (dd, J=9.0, 2.3 Hz, 1H), 6.55 (s, 1H), 3.60 (s, 4H), 3.22 (t, J=6.6 Hz, 2H), 2.56 (t, J=5.3 Hz, 2H), 1.29 (s, 9H).

Example 177

1-(4-(1-(2-Aminoethyl)-7-oxo-1,4-diazepane-4-carbonyl)-2-tert-butylthiazol-5-yl)-3-(2,3-dichlorophenyl)urea

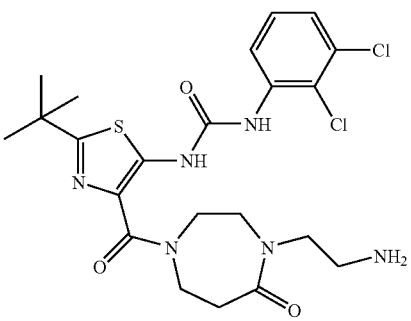

The compound of this example was prepared using a procedure analogous to the procedure described in Example 138. ¹H NMR (400 MHz, CD₃OD): δ (ppm) 7.87-7.83 (m, 1H), 7.24-7.20 (m, 2H), 4.24-4.16 (m, 2H), 3.90-3.83 (m, 2H), 3.70-3.64 (m, 2H), 3.53-3.47 (m, 2H), 2.95-2.77 (m, 4H), 1.38 (s, 9H).

Example 178

1-(3-(1-(2-aminoethyl)-7-oxo-1,4-diazepane-4-carbonyl)-5-tert-butylthiophen-2-yl)-3-(2,3-dichlorophenyl)urea

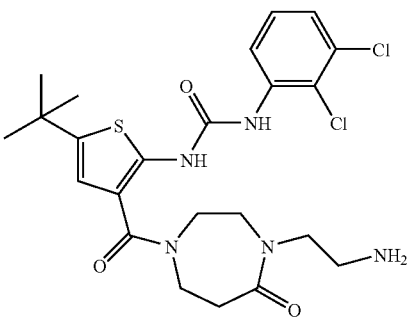

The compound of this example was prepared using a procedure analogous to the procedure described in Example 138. ¹H NMR (400 MHz, CD₃OD): δ (ppm) 8.14 (d, J=8.0 Hz, 1H), 7.24-7.20 (m, 2H), 6.44 (s, 1H), 4.81-74 (m, 4H), 3.55-5.52 (m, 2H), 3.44-3.40 (m, 2H), 2.84-2.80 (m, 2H), 2.78-2.53 (m, 2H), 1.32 (s, 9H).

Example 179

1-(5-tert-Butyl-3-(2-ethyl-2-methyl-3-oxopiperazine-1-carbonyl)thiophen-2-yl)-3-(2,3-dichlorophenyl)urea

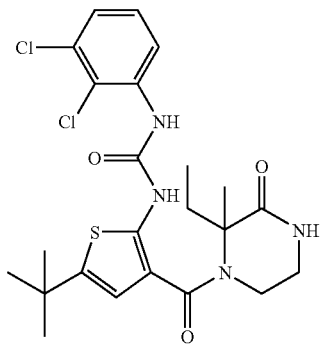

The compound of this example was prepared as follows.

A) 2-(tert-Butoxycarbonyl)-5-tert-butylthiophene-3-carboxylic acid

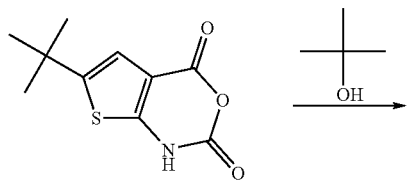

To 6-tert-butyl-1H-thieno[2,3-d][1,3]oxazine-2,4-dione (20 mg, 0.089 mmol) in a vial was added 2 mL of t-BuOH. The resulting reaction mixture was stirred at 90° C. for overnight. The solvent was removed and the residue (26 mg, 98%) was carried on to the next step without further purification.

B) tert-Butyl 5-tert-butyl-3-(2-ethyl-2-methyl-3-oxopiperazine-1-carbonyl)thiophen-2-ylcarbamate

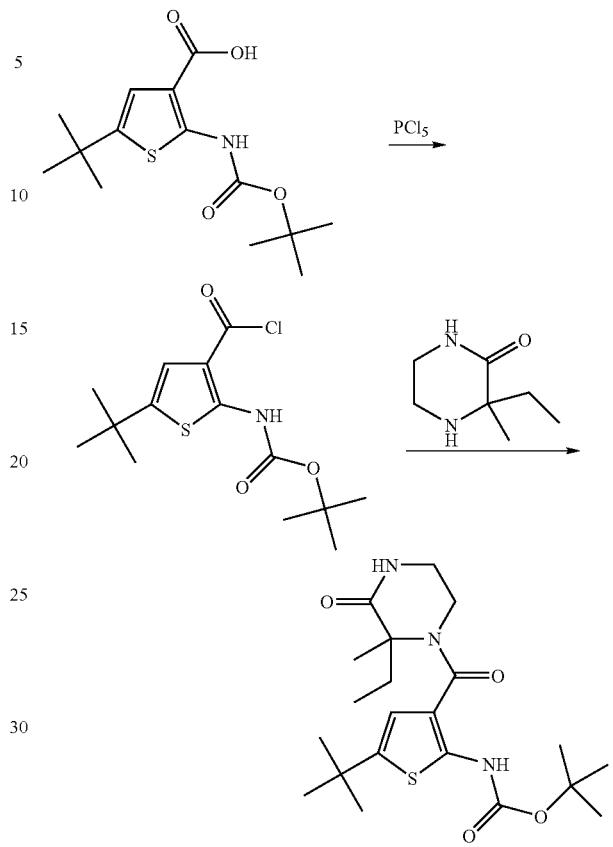

To 2-(tert-butoxycarbonyl)-5-tert-butylthiophene-3-carboxylic acid (100 mg, 0.33 mmol) in benzene (2 mL) was added PCl$_5$ (90.0 mg, 0.43 mmol). After the reaction mixture was stirred at room temperature for 20 min, it was added to a solution of 3-ethyl-3-methyl-piperazin-2-one (95.0 mg, 0.65 mmol) and DIEA (170 µL, 1.0 mmol) in DCM (3 mL) at room temperature. The resulting reaction mixture was then stirred at same temperature for 1 h. The reaction was diluted with EtOAc and the organic phase was washed with saturated aqueous NaHCO$_3$ and brine. The solvent was then dried over Na$_2$SO$_4$ powder and concentrated in vacuo. The crude product was purified by preparative TLC to afford of tert-butyl 5-tert-butyl-3-(2-ethyl-2-methyl-3-oxopiperazine-1-carbonyl)thiophen-2-ylcarbamate as yellow oil (95.0 mg, 67%).

C) 1-(5-tert-Butyl-3-(2-ethyl-2-methyl-3-oxopiperazine-1-carbonyl)-thiophen-2-yl)-3-(2,3-dichlorophenyl)urea

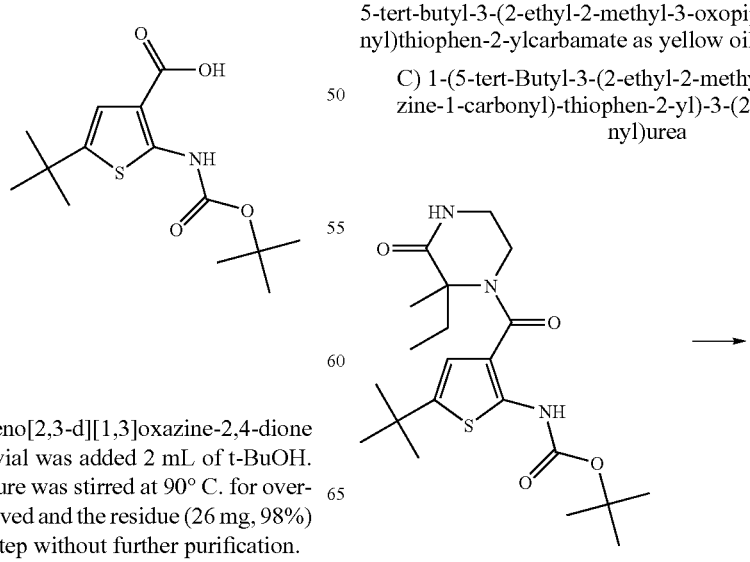

-continued

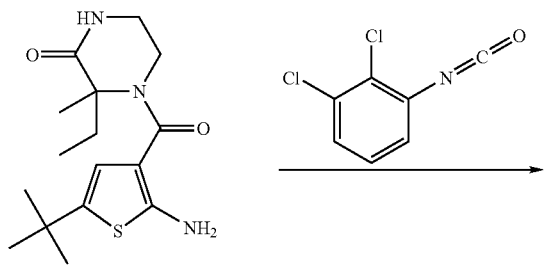

To tert-butyl 5-tert-butyl-3-(2-ethyl-2-methyl-3-oxopiperazine-1-carbonyl)thiophen-2-ylcarbamate (95.0 mg, 0.22 mmol) in DCM (2 mL) was added TFA (2 mL). The resulting reaction mixture was stirred at room temperature for 30 min, at which time SFC-MS indicated the completion of the reaction. The reaction mixture was then diluted with EtOAc and the organic phase was washed with excess 1N NaOH and brine, dried and concentrated. The product 4-(2-amino-5-tert-butylthiophene-3-carbonyl)-3-ethyl-3-methylpiperazin-2-one (72.0 mg, 99%) was carried on to the next step without further purification.

To 4-(2-amino-5-tert-butylthiophene-3-carbonyl)-3-ethyl-3-methylpiperazin-2-one (72.0 mg, 0.22 mmol) in THF (2 mL) was added 1,2-dichloro-3-isocyanatobenzene (50.0 mg, 0.27 mmol). The resulting reaction mixture was stirred at room temperature and the reaction progress monitored by SFC-MS. When the reaction was completed, solvent was removed under reduced pressure and the crude product purified by preparative TLC to afford 1-(5-tert-butyl-3-(2-ethyl-2-methyl-3-oxopiperazine-1-carbonyl)thiophen-2-yl)-3-(2,3-dichlorophenyl)urea (50 mg, 44%) as pale yellow solid. $^1$H NMR (400 MHz, DMSO-d$_6$): δ (ppm) 9.93 (s, 1H), 9.52 (s, 1H), 8.10 (s, 1H), 7.86 (d, J=8.2 Hz, 1H), 7.26-7.22 (m, 2H), 6.46 (s, 1H), 3.62-3.58 (m, 1H), 3.40-3.35 (m, 1H), 3.30-3.23 (m, 1H), 3.19-3.13 (m, 1H), 2.65-2.61 (m, 1H), 1.89-1.85 (m, 1H), 1.58 (s, 3H), 1.22 (s, 9H), 0.69 (t, J=7.4 Hz, 3H).

Example 180

Methyl 2-(4-(2-tert-butyl-5-(3-(2,3-dichlorophenyl)ureido)thiophene-4-carbonyl)-3,3-dimethyl-2-oxopiperazin-1-yl)acetate

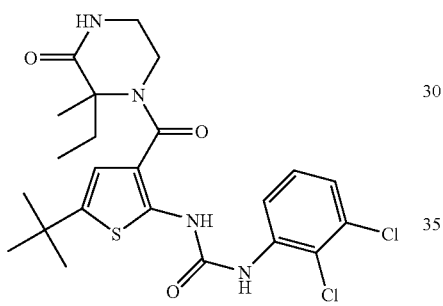

The compound of this example was prepared using a procedure analogous to the procedure described in Example 179. $^1$H NMR (400 MHz, CDCl$_3$): δ (ppm) 10.16 (s, 1H), 8.12 (dd, J=7.0, 2.9 Hz, 1H), 7.62 (s, 1H), 7.14-7.07 (m, 2H), 6.39 (s, 1H), 4.11 (s, 2H), 3.79 (t, J=4.9 Hz, 2H), 3.70 (s, 3H), 3.50 (t, J=4.8 Hz, 2H), 1.76 (s, 6H), 1.29 (s, 9H).

Example 181

2-(4-(2-tert-Butyl-5-(3-(2,3-dichlorophenyl)ureido)thiophene-4-carbonyl)-3,3-dimethyl-2-oxopiperazin-1-yl)acetic acid

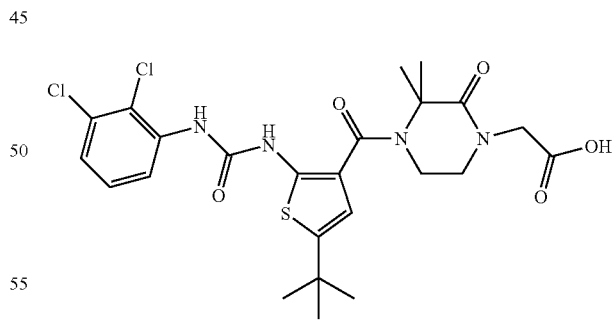

The compound of this example was prepared using a procedure analogous to the procedure described in Example 179. $^1$H NMR (400 MHz, CD$_3$OD): δ (ppm) 8.00-7.94 (m, 1H), 7.71 (s, 1H), 7.21-7.18 (m, 2H), 6.54 (s, 1H), 3.98 (s, 2H), 3.78-3.71 (m, 2H), 3.58-3.51 (m, 2H), 1.81 (s, 6H), 1.34 (s, 9H).

Example 182

1-(5-tert-Butyl-2-(1-(2-(dimethylamino)ethyl)-3,3-dimethyl-2-oxopiperazine-4-carbonyl)thiophen-3-yl)-3-(2,3-dichloro-4-fluorophenyl)urea

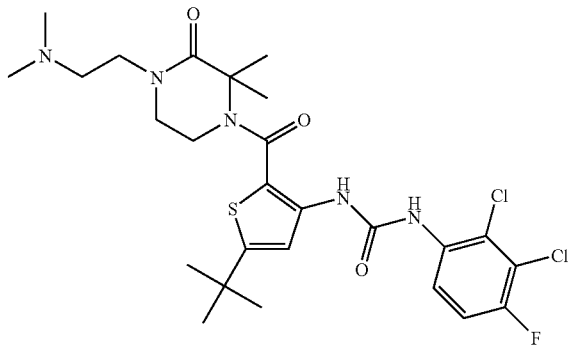

The compound of this example was prepared using a procedure analogous to the procedure described in Example 183. $^{1}$H NMR (400 MHz, acetone-$d_6$): δ (ppm) 9.42 (bs, 1H); 9.20 (bs, 1H); 7.88 (m, 1H); 7.40 (t, 1H); 7.38 (s, 1H); 3.69 (m, 2H); 3.45 (m, 2H); 3.39 (m, 2H); 2.30 (m, 2H); 2.08 (s, 6H); 1.60 (s, 6H); 1.30 (s, 9H).

Example 183

1-(5-tert-Butyl-2-(1-(2-(dimethylamino)ethyl)-3,3-dimethyl-2-oxopiperazine-4-carbonyl)thiophen-3-yl)-3-(2,3-dichlorophenyl)urea

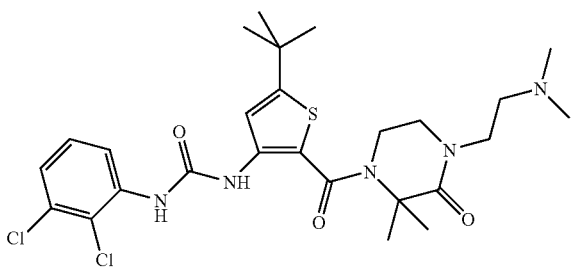

The compound of this example was prepared as follows.

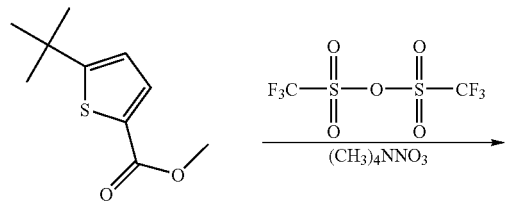

-continued

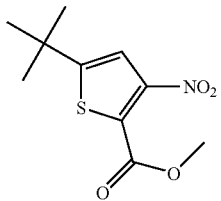

A) Methyl 5-tert-butyl-3-nitrothiophene-2-carboxylate

Triflic anhydride (1.99 g, 7.06 mmol) was added drop-wise to a solution of tetramethylammonium nitrate (0.96 g, 7.06 mmol) in dichloromethane (20 mL) at room temperature, under nitrogen and the resulting mixture was stirred for 1.5 h. The suspension was cooled to −78° C. and added dropwise methyl 5-tert-butylthiophene-2-carboxylate (1.0 g, 5.04 mmol). The cooling bath was removed and the reaction was gradually warmed to room temperature and stirred at 25° C. overnight. The mixture was quenched with saturated sodium bicarbonate, the organic layer was separated and the aqueous extracted with dichloromethane. The combined organic layers was dried, the solvent eliminated under vacuum and the crude product purified by chromatographic column (silicagel, hexane:ethyl acetate 95:5) to afford 0.490 g of methyl 5-tert-butyl-3-nitrothiophene-2-carboxylate as a yellow solid.

B) 5-tert-Butyl-3-nitrothiophene-2-carboxylic acid

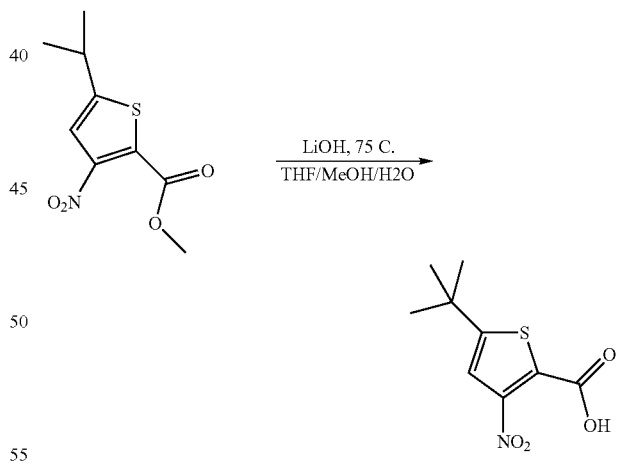

LiOH monohydrate (0.122 g, 2.90 mmol) was dissolved in 1 mL water and added to methyl 5-tert-butyl-3-nitrothiophene-2-carboxylate (0.235 g, 0.966 mmol) in 3 ml of a 3:1 mixture of THF:MeOH. The resulting mixture was heated at 75° C. for 5 hours. The reaction was cooled down to room temperature, acidified with 1N HCl, extracted with ethyl acetate, and the crude product was recrystallized from dichloromethane:hexane to afford 0.214 g of 5-tert-butyl-3-nitrothiophene-2-carboxylic acid as a yellow solid.

C) 4-(2-tert-Butyl-4-nitrothiophene-5-carbonyl)-1-(2-(dimethylamino)-ethyl)-3,3-dimethylpiperazin-2-one

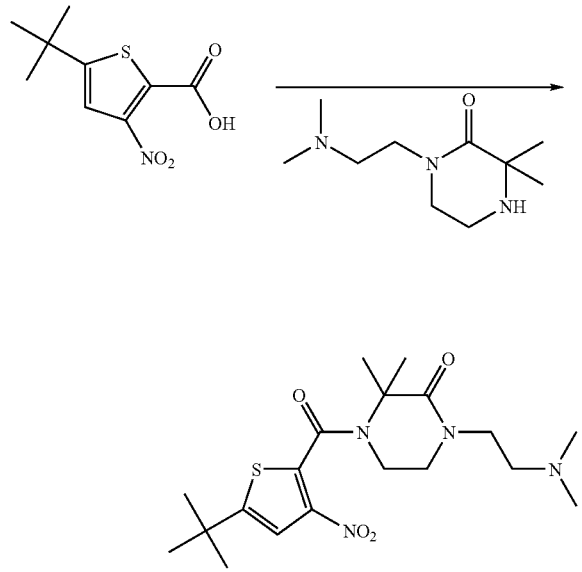

A stirred solution of 5-tert-butyl-3-nitrothiophene-2-carboxylic acid (0.214 g, 0.933 mmol) in 2 ml thionyl chloride was warmed at 45° C. for 1 h and then concentrated under vacuum. The residue was dissolved in 2 ml THF and added to a 3 ml THF solution of 1-(2-(dimethylamino)ethyl)-3,3-dimethylpiperazin-2-one (0.242 g, 1.21 mmol) and DIEA (0.362 g, 2.80 mmol). The resulting mixture was stirred at room temperature for 5 minutes, diluted with ethyl acetate, washed with 1N HCl, water, brine, dried and the solvent eliminated under vacuum to yield 0.300 g, (~85% purity) of 4-(2-tert-butyl-4-nitrothiophene-5-carbonyl)-1-(2-(dimethylamino)ethyl)-3,3-dimethyl-piperazin-2-one that was used as-is for the next step.

D) 4-(4-Amino-2-tert-butylthiophene-5-carbonyl)-1-(2-(dimethyl-amino)ethyl)-3,3-dimethylpiperazin-2-one

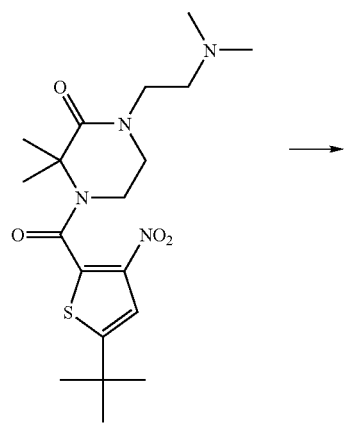

A mixture of 4-(2-tert-butyl-4-nitrothiophene-5-carbonyl)-1-(2-(dimethylamino)ethyl)-3,3-dimethylpiperazin-2-one (0.200 g, 0.49 mmol) and tin chloride dihydrate (0.55 g, 2.4 mmol) dissolved in 4 mL MeOH was stirred at 70° C. overnight. The reaction mixture was cooled down to room temperature, quenched with saturated NaHCO$_3$ (40 mL), and extracted with ethyl acetate. The combined organic layers was dried, the solvent eliminated under vacuum and the residue purified by chromatographic column (silica gel, dichloromethane) to afford 0.090 g of 4-(4-amino-2-tert-butylthiophene-5-carbonyl)-1-(2-(dimethylamino)ethyl)-3,3-dimethylpiperazin-2-one as a tan solid.

E) 1-(5-tert-Butyl-2-(1-(2-(dimethylamino)ethyl)-3,3-dimethyl-2-oxo-piperazine-4-carbonyl)thiophen-3-yl)-3-(2,3-dichlorophenyl)urea

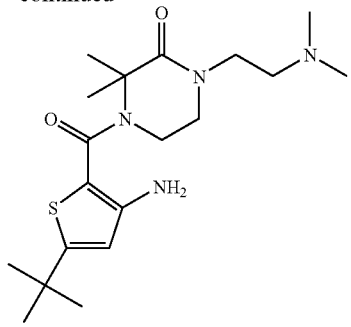

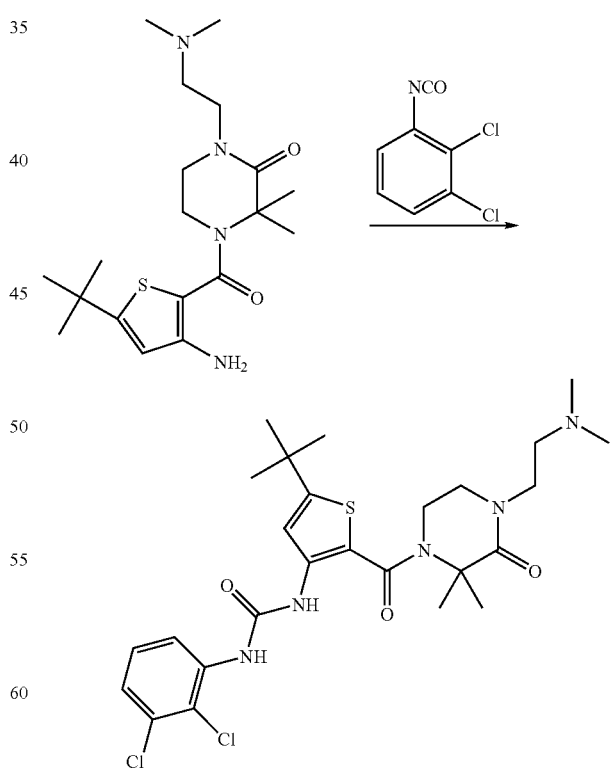

A mixture of 4-(4-amino-2-tert-butylthiophene-5-carbonyl)-1-(2-(dimethylamino)ethyl)-3,3-dimethylpiperazin-2-one (0.035 g, 0.092 mmol), dichlorophenyl isocyanate (0.019 g, 0.10 mmol), and THF (2 mL) was heated at 75° C. for 2 hours. The reaction mixture was diluted with ethyl acetate, washed with saturated sodium bicarbonate, dried, the solvent eliminated under vacuum and the crude product was purified by preparative thin layer chromatography (dichloromethane: methanol, 95:5) to afford 0.035 g of 1-(5-tert-butyl-2-(1-(2-(dimethylamino)ethyl)-3,3-dimethyl-2-oxopiperazine-4-carbonyl)thiophen-3-yl)-3-(2,3-dichlorophenyl)urea. ¹H NMR (400 MHz, acetone-d₆): δ (ppm) 9.57 (bs, 1H); 8.86 (bs, 1H); 8.17 (d, 1H); 7.65 (s, 1H); 7.30 (m, 2H); 3.90 (m, 2H); 3.60 (m, 2H); 3.50 (t, 2H); 2.43 (t, 2H); 2.20 (s, 6H); 1.70 (s, 6H); 1.40 (s, 9H).

Example 184

1-(5-tert-Butyl-3-(2,2-dimethyl-3-oxopiperazine-1-carbonyl)thiophen-2-yl)-3-(2,3-dichloro-4-cyanophenyl)urea

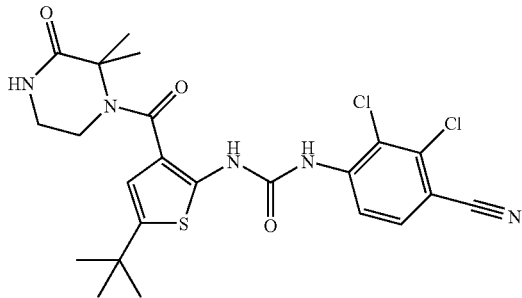

The compound of this example was prepared using a procedure analogous to the procedure described in Example 179. ¹H NMR (400 MHz, acetone-d₆): δ (ppm) 10.31 (bs, 1H); 9.80 (bs, 1H); 8.26 (d, 1H); 8.05 (s, 1H); 7.87 (bs, 1H); 6.59 (s. 1H); 3.50 (m, 2H); 3.25 (m, 2H); 1.64 (s, 6H); 1.27 (s, 9H).

Example 185

1-(5-tert-Butyl-3-(2,2-dimethyl-3-oxopiperazine-1-carbonyl)thiophen-2-yl)-3-(2,3-dichloro-4-(difluoromethoxy)phenyl)urea

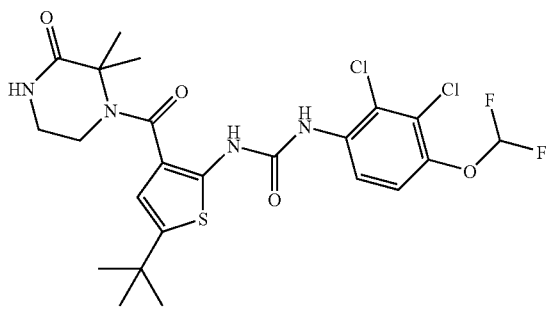

The compound of this example was prepared using a procedure analogous to the procedure described in Example 179. ¹H NMR (400 MHz, acetone-d₆): δ (ppm) 10.00 (bs, 1H); 9.60 (bs, 1H); 8.03 (bs, 1H); 7.93 (d, 1H); 7.0-7.40 (m, 2H); 6.55 (s, 1H); 3.50 (m, 2H); 3.25 (m, 2H); 1.64 (s, 6H); 1.27 (s, 9H).

Example 186

1-(3-(1-(4-Methoxybenzyl)-3,3-dimethyl-2-oxopiperazine-4-carbonyl)-5-tert-butylthiophen-2-yl)-3-(2,3-dichlorophenyl)urea

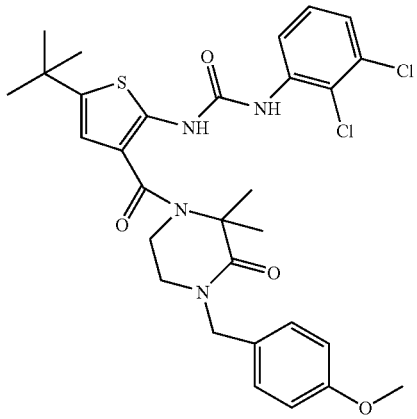

The compound of this example was prepared using a procedure analogous to the procedure described in Example 179. ¹H NMR (400 MHz, CD₂Cl₂): δ (ppm) 10.30 (s, 1H), 8.16 (dd, J=7.9, 1.9 Hz, 1H), 7.86 (s, 1H), 7.22-7.17 (m, 4H), 6.88 (d, J=8.6 Hz, 2H), 6.42 (s, 1H), 4.55 (s, 2H), 3.79 (s, 3H), 3.70-3.66 (m, 2H), 3.39-3.35 (m, 2H), 1.80 (s, 6H), 1.33 (s, 9H).

Example 187

Methyl 2-(1-(2-tert-butyl-5-(3-(2,3-dichlorophenyl)ureido)thiophene-4-carbonyl)-2-methyl-3-oxopiperazin-2-yl)acetate

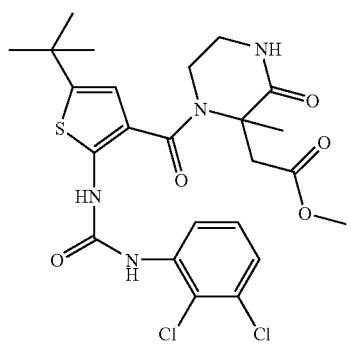

The compound of this example was prepared using a procedure analogous to the procedure described in Example 179. ¹H NMR (400 MHz, CDCl₃): δ (ppm) 9.29 (s, 1H), 8.26 (dd, J=7.9, 2.0 Hz, 1H), 7.94 (s, 1H), 7.22-7.14 (m, 2H), 6.61 (s, 1H), 6.37 (s, 1H), 4.12 (d, J=18.0 Hz, 1H), 4.06-4.00 (m, 1H), 3.70 (s, 3H), 3.68-3.62 (m, 2H), 3.41-3.36 (m, 1H), 3.32 (d, J=18.0 Hz, 1H), 1.83 (s, 3H), 1.34 (s, 9H).

Example 188

1-(5-tert-Butyl-3-(3,3-dimethyl-1-(2-morpholinoethyl)-2-oxopiperazine-4-carbonyl)thiophen-2-yl)-3-(2,3-dichlorophenyl)urea

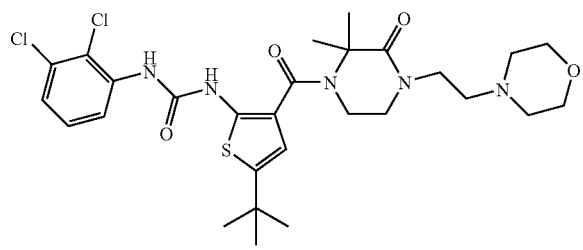

The compound of this example was prepared using a procedure analogous to the procedure described in Example 179. $^1$H NMR (400 MHz, CDCl$_3$): δ (ppm) 10.12 (s, 1H), 8.14-7.98 (m, 2H), 7.13-7.04 (m, 2H), 6.37 (s, 1H), 3.75-3.58 (m, 10H), 2.65-2.37 (m, 6H), 1.73 (s, 6H), 1.28 (s, 9H).

Example 189

1-(5-tert-Butyl-3-(2-ethyl-2-methyl-3-oxopiperazine-1-carbonyl)thiophen-2-yl)-3-(2,3-dichloro-4-fluorophenyl)urea

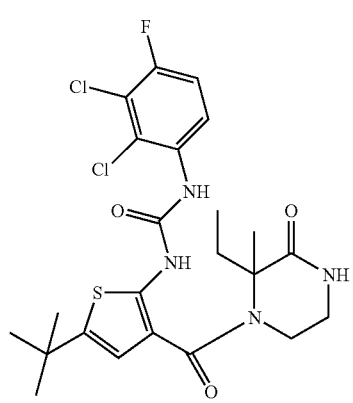

The compound of this example was prepared using a procedure analogous to the procedure described in Example 179 $^1$H NMR (400 MHz, DMSO-d$_6$): δ (ppm) 9.93 (s, 1H), 9.55 (s, 1H), 8.10 (s, 1H), 7.84-7.80 (m, 1H), 7.26-7.22 (m, 2H), 6.42 (s, 1H), 3.62-3.58 (m, 1H), 3.40-3.35 (m, 1H), 3.30-3.23 (m, 1H), 3.19-3.13 (m, 1H), 2.62-2.58 (m, 1H), 1.89-1.85 (m, 1H), 1.58 (s, 3H), 1.24 (s, 9H), 0.69 (t, J=7.4 Hz, 3H).

Example 190

Methyl 3-(4-(2-tert-butyl-5-(3-(2,3-dichlorophenyl)ureido)thiophene-4-carbonyl)-3,3-dimethyl-2-oxopiperazin-1-yl)propanoate

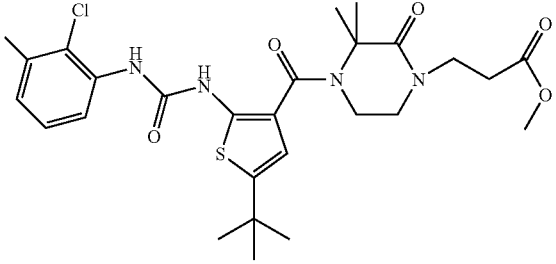

The compound of this example was prepared using a procedure analogous to the procedure described in Example 179. $^1$H NMR (400 MHz, CDCl$_3$): δ (ppm) 10.20 (s, 1H), 8.14 (dd, J=7.8, 2.0 Hz, 1H), 7.84 (s, 1H), 7.12-7.04 (m, 2H), 6.35 (s, 1H), 3.73-3.47 (m, 9H), 2.61 (t, J=6.5 Hz, 2H), 1.70 (s, 6H), 1.28 (s, 9H).

Example 191

Methyl 2-(1-(2-tert-butyl-5-(3-(2,3-dichloro-4-fluorophenyl)ureido)thiophene-4-carbonyl)-2-methyl-3-oxopiperazin-2-yl)acetate

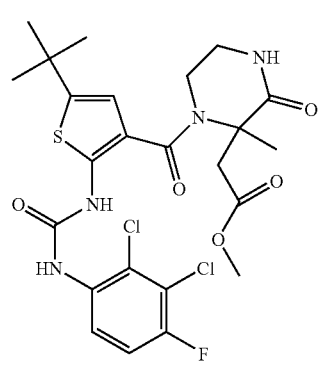

The compound of this example was prepared using a procedure analogous to the procedure described in Example 179. $^1$H NMR (400 MHz, CDCl$_3$): δ (ppm) 9.25 (s, 1H), 8.22 (q, J=4.9 Hz, 1H), 7.80 (s, 1H), 7.10 (q, J=5.8 Hz, 1H), 6.61 (s, 1H), 6.20 (s, 1H), 4.13 (d, J=17.3 Hz, 1H), 4.07-3.97 (m, 1H), 3.70 (s, 3H), 3.66-3.60 (m, 1H), 3.43-3.37 (m, 1H), 3.33 (d, J=17.7 Hz, 1H), 1.84 (s, 3H), 1.34 (s, 9H).

Example 192

2-(1-(2-tert-Butyl-5-(3-(2,3-dichlorophenyl)ureido)thiophene-4-carbonyl)-2-methyl-3-oxopiperazin-2-yl)acetic acid

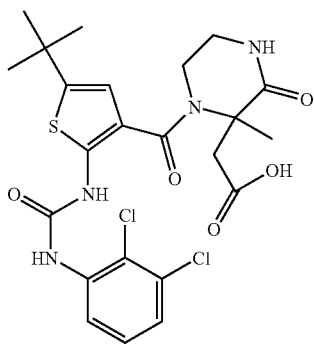

The compound of this example was prepared from Example 188 by hydrolysis of the ester being lithium hydroxide. ¹H NMR (400 MHz, CD₃COCD₃): δ (ppm) 9.66 (s, 1H), 8.71 (s, 1H), 8.22 (m, 1H), 7.45 (s, 1H), 7.36-7.27 (m, 2H), 6.60 (s, 1H), 4.03-3.97 (m, 1H), 3.94 (d, J=17.3 Hz, 1H), 3.81-3.74 (m, 1H), 3.64-3.57 (m, 1H), 3.51-3.44 (m, 1H), 3.27 (d, J=17.3 Hz, 1H), 1.78 (s, 3H), 1.36 (m, 9H).

Example 193

1-(3-(2-(2-Amino-2-oxoethyl)-2-methyl-3-oxopiperazine-1-carbonyl)-5-tert-butylthiophen-2-yl)-3-(2,3-dichlorophenyl)urea

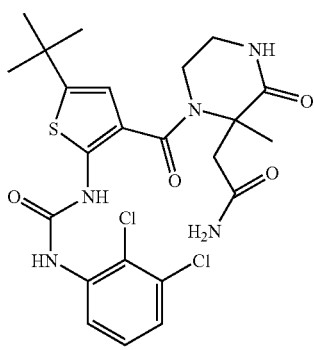

The compound of this example was prepared from Example 193 by coupling in presence of EDCI/HOBt using NH₄OH.

hydrolysis of the ester being lithium hydroxide. ¹H NMR (400 MHz, CD₃OD): δ (ppm) 8.08 (q, J=3.3 Hz, 1H), 7.22-7.14 (m, 2H), 6.57 (s, 1H), 3.94-3.83 (m, 2H), 3.79-3.64 (m, 1H), 3.52-3.45 (m, 1H), 3.37-3.27 (m, 4H), 3.03 (d, J=15.9 Hz, 1H), 1.82 (s, 3H), 1.33 (s, 9H).

Example 194

1-(5-tert-Butyl-3-(2-(2-hydroxyethyl)-2-methyl-3-oxopiperazine-1-carbonyl)thiophen-2-yl)-3-(2,3-dichloro-4-fluorophenyl)urea

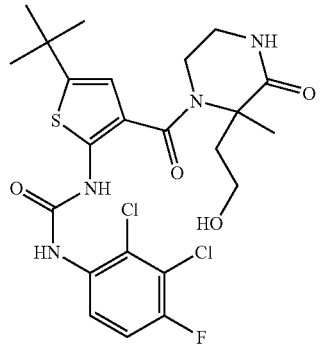

The compound of this example was prepared from the compound of Example 191 by reduction using DIBAL in IKM. ¹H NMR (400 MHz, CDCl₃): δ (ppm) 9.95 (s, 1H), 8.21 (dd, J=9.2, 5.5 Hz, 1H), 7.75 (s, 1H), 7.08 (dd, J=9.2, 8.2 Hz, 1H), 6.49 (s, 1H), 3.88-3.78 (m, 1H), 3.74-3.67 (m, 1H), 3.63-3.56 (m, 1H), 3.51-3.43 (m, 1H), 3.36-3.29 (m, 1H), 3.07-3.00 (m, 1H), 2.45-2.38 (m, 1H), 1.79 (s, 3H), 1.27 (s, 9H).

Example 195

3-(4-(2-tert-Butyl-5-(3-(2,3-dichlorophenyl)ureido)thiophene-4-carbonyl)-3,3-dimethyl-2-oxopiperazin-1-yl)propanoic acid

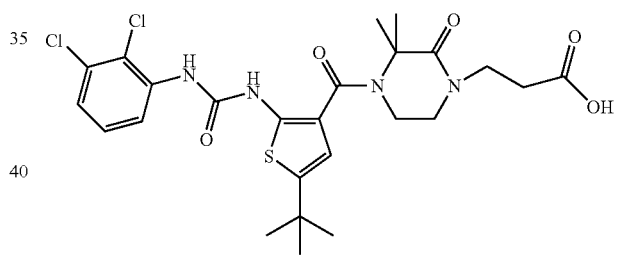

The compound of this example was prepared using a procedure analogous to the procedure described in Example 179. ¹H NMR (400 MHz, CDCl₃): δ (ppm) 10.32 (s, 1H), 8.55 (s, 1H), 8.24 (d, J=8.1 Hz, 1H), 7.08-6.96 (m, 2H), 6.33 (s, 1H), 3.79-3.53 (m, 4H), 3.39 (s, 2H), 2.41 (s, 2H), 1.64 (s, 6H), 1.30 (s, 9H).

Example 196

1-(5-tert-Butyl-3-(1-((2,2-dimethyl-1,3-dioxolan-4-yl)methyl)-3,3-dimethyl-2-oxopiperazine-4-carbonyl)thiophen-2-yl)-3-(2,3-dichlorophenyl)urea

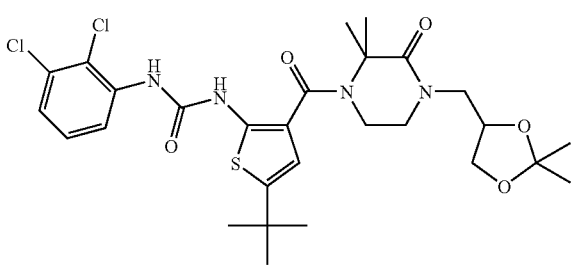

The compound of this example was prepared using a procedure analogous to the procedure described in Example 179. $^1$H NMR (400 MHz, CDCl$_3$): δ (ppm) 10.20 (s, 1H), 8.13 (q, J=3.3 Hz, 1H), 7.66 (s, 1H), 7.13-7.06 (m, 2H), 6.37 (s, 1H), 4.33-4.25 (m, 1H), 4.04-3.97 (m, 1H), 3.80-3.53 (m, 6H), 3.40-3.32 (m, 1H), 1.74 (d, J=4.2 Hz, 6H), 1.37 (s, 3H), 1.30-1.27 (m, 12H).

Example 197

1-(5-tert-Butyl-3-(1-(2,3-dihydroxypropyl)-3,3-dimethyl-2-oxopiperazine-4-carbonyl)thiophen-2-yl)-3-(2,3-dichlorophenyl)urea

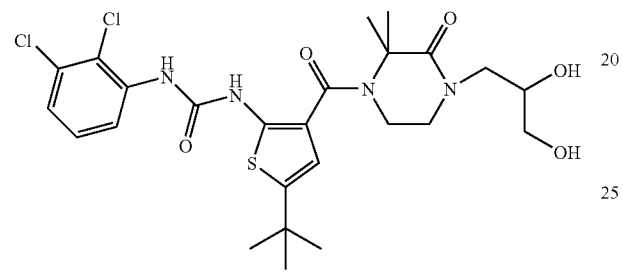

The compound of this example was prepared from the compound of Example 196 by hydrolysis in the presence of acid. $^1$H NMR (400 MHz, CDCl$_3$): δ (ppm) 10.17 (s, 1H), 8.11 (dd, J=6.8, 2.8 Hz, 1H), 7.37 (s, 1H), 7.14-7.10 (m, 2H), 6.37 (s, 1H), 3.90-3.83 (m, 1H), 3.72 (t, J=4.9 Hz, 2H), 3.63-3.42 (m, 6H), 1.76 (d, J=4.7 Hz, 6H), 1.29 (s, 9H).

Example 198

(S)-1-(5-tert-Butyl-3-(2-(methylcarbamoyl)pyrrolidine-1-carbonyl)thiophen-2-yl)-3-(2,3-dichloro-4-(difluoromethoxy)phenyl)urea

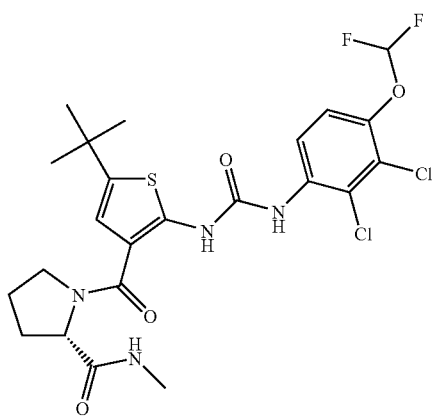

The compound of this example was prepared using a procedure analogous to the procedure described in Example 29. $^1$H NMR (400 MHz, CDCl$_3$) δ (ppm) 1.22 (s, 9H), 2.03 (s, 6H), 2.26 (t, J=7.2 Hz, 2H), 3.21 (t, J=8.0 Hz, 2H), 3.42 (m, 4H), 3.63 (qrt, J=7.2 Hz, 2H), 3.92-4.23 (m brd, 4H), 7.02 (s, 1H), 7.14 (m, 2H), 8.06 (d, J=8.8 Hz, 1H), 9.73 (s, 1H).

Example 199

(S)-1-(5-tert-Butyl-3-(2-oxo-3-phenethylpiperazine-4-carbonyl)thiophen-2-yl)-3-(2,3-dichlorophenyl)urea

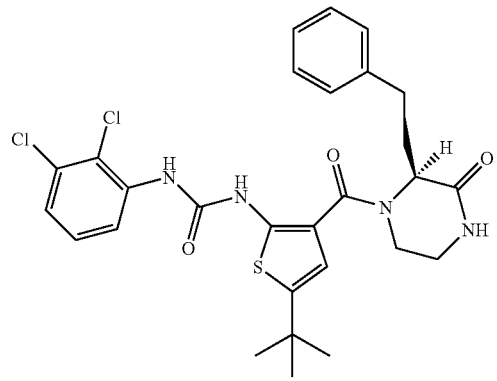

The compound of this example was prepared using a procedure analogous to the procedure described in Example 130. $^1$H NMR (400 MHz, CDCl$_3$): δ (ppm) 10.17 (d, J=7.3 Hz, 1H), 8.37-8.29 (m, 1H), 8.19-8.13 (m, 1H), 7.11-6.96 (m, 8H), 6.27 (s, 1H), 5.10-4.95 (m, 1H), 4.24-4.10 (m, 1H), 3.50-3.12 (m, 3H), 2.69-2.58 (m, 2H), 2.38-2.24 (m, 1H), 2.13-2.01 (m, 1H), 1.31 (d, J=2.7 Hz, 9H).

Example 200

1-(5-tert-Butyl-3-(2-ethyl-3-oxopiperazine-1-carbonyl)thiophen-2-yl)-3-(2,3-dichloro-4-fluorophenyl)urea

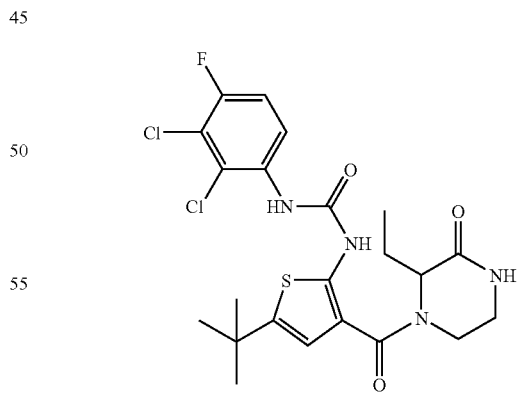

The compound of this example was prepared using a procedure analogous to the procedure described in Example 138. $^1$H NMR (400 MHz, CD$_6$SO): δ (ppm) 10.1 (s, 1H), 9.20 (s, 1H), 8.01-7.98 (m, 2H), 7.42-7.39 (m, 1H), 6.64 (s, 1H), 4.65-4.46 (m, 1H), 4.01-3.88 (m, 1H), 3.40-3.10 (m, 3H), 2.00-1.80 (m, 2H), 1.30 (s, 9H), 0.90 (t, J=6.6 Hz, 3H).

Example 201
1-(5-tert-Butyl-3-(4,4-dioxy-4-thiomorpholine-1-carbonyl)thiophen-2-yl)-3-(2,3-dichloro-4-fluorophenyl)urea

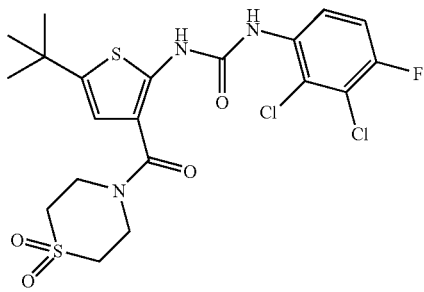

The compound of this example was prepared using a procedure analogous to the procedure described in Example 138. $^1$H NMR (400 MHz, CDCl$_3$): δ (ppm) 9.87 (s, 1H), 7.99 (dd, J=9.2, 5.1 Hz, 1H), 7.60 (m, 1H), 7.01 (dd, J=9.3, 8.1 Hz, 1H), 6.38 (s, 1H), 4.09 (t, J=4.9 Hz, 4H), 3.69 (m, 1H), 3.08 (t, J=5.2 Hz, 4H), 1.78 (m, 1H), 1.25 (s, 9H).

Example 202
1-(5-tert-Butyl-3-(1,1-dioxy-1-thia-2,5-diazepan-1-one-5-carbonyl)thiophen-2-yl)-3-(2,3-dichloro-4-fluorophenyl)urea

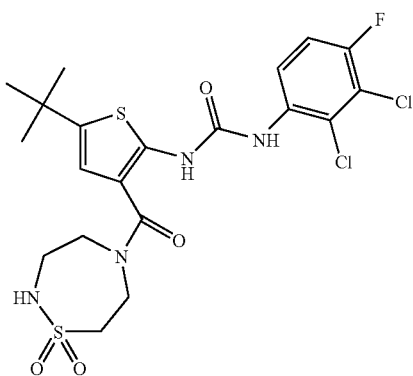

The compound of this example was prepared using a procedure analogous to the procedure described in Example 138. $^1$H NMR (400 MHz, CDCl$_3$): δ (ppm) 9.67 (s, 1H), 7.96 (dd, J=9.4, 5.2 Hz, 1H), 7.76 (s, 1H), 7.05 (dd, J=9.1, 8.3 Hz, 1H), 6.48 (s, 1H), 5.94 (s, 1H), 3.95-3.87 (m, 4H), 3.56-3.46 (m, 4H), 1.19 (s, 9H).

Example 203
1-(5-tert-butyl-3-(2-ethyl-2-methyl-3-oxopiperazine-1-carbonyl)thiophen-2-yl)-3-(2-chloro-4-fluorophenyl)urea

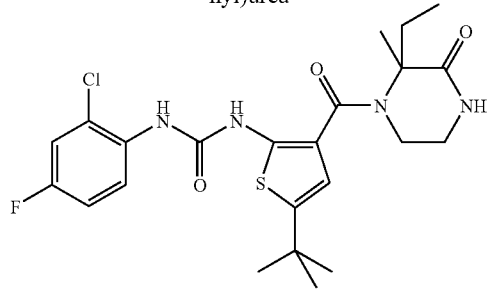

The compound of this example was prepared using a procedure analogous to the procedure described in Example 179. $^1$H NMR (400 MHz, CD$_3$OD): δ (ppm) 7.95-7.89 (m, 1H), 7.09-7.04 (m, 1H), 6.95-6.89 (m, 1H), 6.35 (s, 1H), 3.96-3.84 (m, 2H), 3.51-3.39 (m, 2H), 2.79-2.69 (m, 1H), 2.07-1.95 (m, 1H), 1.68 (s, 3H), 1.28 (s, 9H), 0.80 (t, J=7.0 Hz, 3H).

Example 204
1-(5-tert-butyl-3-(spiro[4.5]-1,4-diazedecan-5-one-1-carbonyl)thiophen-2-yl)-3-(2,3-dichlorophenyl)urea

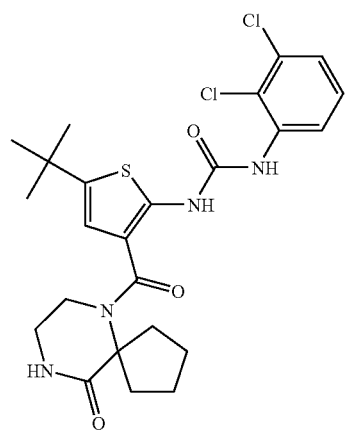

The compound of this example was prepared using a procedure analogous to the procedure described in Example 179. $^1$H NMR (400 MHz, CD$_2$Cl$_2$): δ (ppm) 10.36 (s, 1H), 8.11 (q, J=3.3 Hz, 1H), 7.69 (s, 1H), 7.23-7.19 (m, 2H), 6.55 (s, 1H), 6.06 (s, 1H), 3.82 (t, J=5.5 Hz, 2H), 3.43 (s, 2H), 2.38-2.19 (m, 4H), 2.00-1.95 (m, 2H), 1.86-1.82 (m, 2H), 1.29 (s, 9H).

Example 205
1-(5-tert-Butyl-3-(1-(2-(dimethylamino)ethyl)-3-ethyl-3-methyl-2-oxopiperazine-4-carbonyl)thiophen-2-yl)-3-(2,3-dichloro-4-fluorophenyl)urea

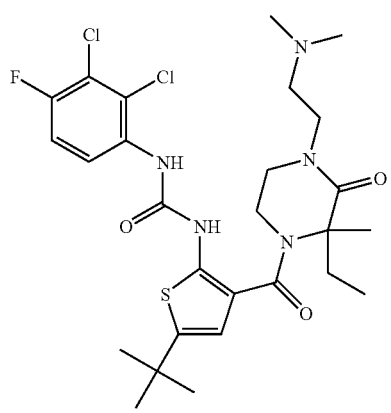

The compound of this example was prepared using a procedure analogous to the procedure described in Example 179.
¹H NMR (400 MHz, CD₃OD): δ (ppm) 7.90 (q, J=4.9 Hz, 1H), 7.14 (t, J=8.9 Hz, 1H), 6.48 (s, 1H), 3.90-3.86 (m, 1H), 3.62-3.38 (m, 5H), 2.84-2.80 (m, 1H), 2.5302.47 (m, 2H), 2.26 (s, 6H), 2.06-2.02 (m, 1H), 1.72 (s, 3H), 1.33 (s, 9H), 0.81 (t, J=7.4 Hz, 3H).

Example 206

1-(5-tert-Butyl-3-(1-(2-(dimethylamino)ethyl)-3,3-dimethyl-2-oxopiperazine-4-carbonyl)thiophen-2-yl)-3-(2-chloro-4-fluorophenyl)urea

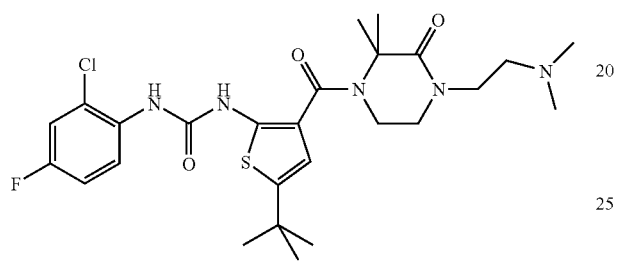

The compound of this example was prepared using a procedure analogous to the procedure described in Example 179.
¹H NMR (400 MHz, CD₃OD): δ (ppm) 7.83 (dd, J=9.1, 5.5 Hz, 1H), 7.09 (dd, J=8.1, 2.9 Hz, 1H), 6.96-6.89 (m, 1H), 6.43 (s, 1H), 3.69-3.64 (m, 2H), 3.56-3.46 (m, 4H), 2.66 (t, J=6.8 Hz, 2H), 2.38 (s, 6H), 1.73 (s, 6H), 1.28 (s, 9H).

Example 207

1-(5-tert-Butyl-3-(spiro[3.5]-1,4-diazenon-5-one-1-carbonyl)thiophen-2-yl)-3-(2,3-dichloro-4-fluorophenyl)urea

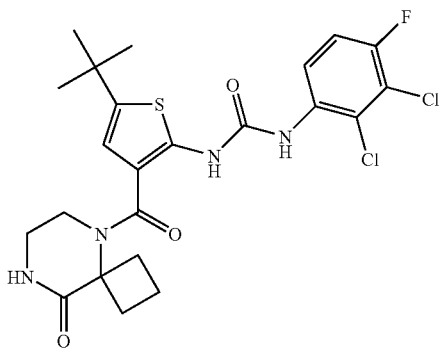

The compound of this example was prepared using a procedure analogous to the procedure described in Example 179.
¹H NMR (400 MHz, CD₂Cl₂): δ (ppm) 10.50 (s, 1H), 8.25 (s, 1H), 7.99 (dd, J=9.4, 5.3 Hz, 1H), 7.11 (t, J=8.8 Hz, 1H), 6.94 (s, 1H), 6.61 (s, 1H), 3.72 (t, J=5.8 Hz, 2H), 3.26 (t, J=4.9 Hz, 2H), 2.65 (t, J=9.7 Hz, 2H), 2.36-2.31 (m, 2H), 1.97 (q, J=9.7 Hz, 1H), 1.82-1.76 (m, 1H), 1.36 (s, 9H).

Example 208

1-(5-tert-Butyl-3-(2-(hydroxymethyl)-6-oxopiperazine-4-carbonyl)thiophen-2-yl)-3-(2,3-dichlorophenyl)urea

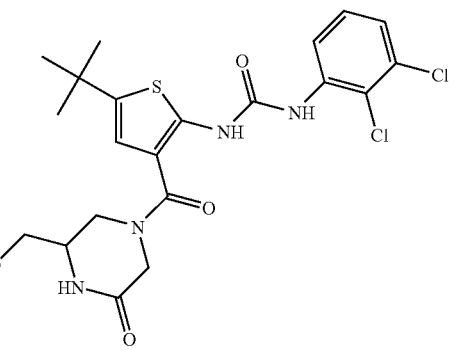

The compound of this example was prepared using a procedure analogous to the procedure described in Example 138.
¹H NMR (400 MHz, CDCl₃): δ (ppm) 10.18 (s, 1H), 8.18 (dd, J=7.8, 1.8 Hz, 2H), 7.17-7.09 (m, 2H), 6.46 (s, 1H), 4.59 (d, J=17.4 Hz, 1H), 4.20-4.08 (m, 1H), 3.95 (d, J=13.7 Hz, 1H), 3.82 (dd, J=13.6, 3.1 Hz, 1H), 3.62-3.52 (m, 3H), 1.35 (s, 9H).

Example 209

1-(5-tert-Butyl-2-(5-oxo-1,4-diazepane-1-carbonyl)-1H-pyrrol-3-yl)-3-(2,3-dichlorophenyl)urea

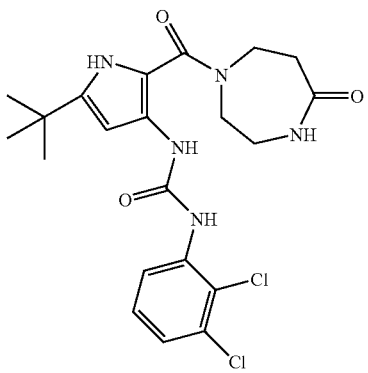

The compound of this example was prepared as follows:

A) Methyl 3-amino-5-tert-butyl-1H-pyrrole-2-carboxylate

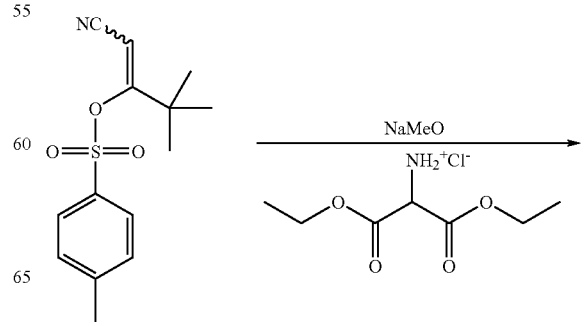

-continued

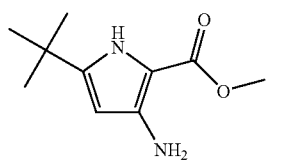

To a stirred sodium methoxide solution (15% by weight, 80 mL total) was added drop-wise a solution of 1-cyano-3,3-dimethylbut-1-en-2-yl 4-methylbenzenesulfonate (10.0 g, 36 mmol) and diethyl aminomalonate hydrochloride salt (9.0 g, 43 mmol) in methanol (50 mL). After the addition was completed, the reaction was stirred at room temperature for 2 hours, the solvent was removed under vacuum and the crude product was dissolved in water and extracted with ethyl acetate. The combined organic layers was washed with brine, dried and the solvent removed under vacuum. The crude product was purified by column chromatography (silicagel, dichloromethane:methanol 95:5) to afford 2.4 g of the desired methyl 3-amino-5-tert-butyl-1H-pyrrole-2-carboxylate used as such in the next step.

B) Methyl 3-(benzyloxycarbonyl)-5-tert-butyl-1H-pyrrole-2-carboxylate

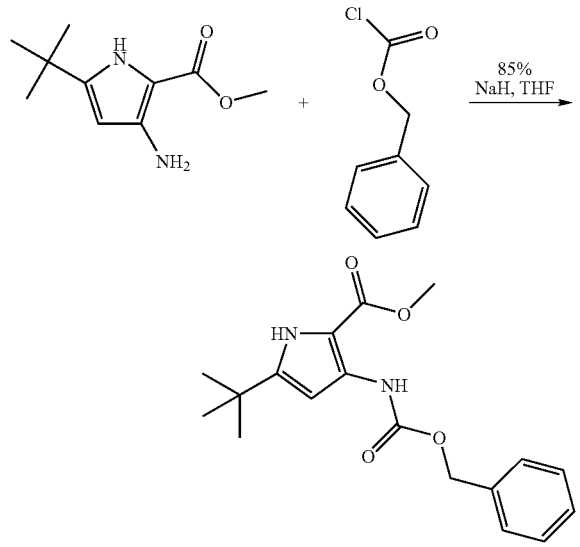

A mixture of the previously prepared methyl 3-amino-5-tert-butyl-1H-pyrrole-2-carboxylate (0.400 g, 2.0 mmol) and NaH (60% w/w, 0.760 g, 4.5 mmol) in THF (4 mL) was stirred at room temperature for 30 min. To the resulting mixture was added benzyl carbonochloridate drop wise and stirred at room temperature overnight. The reaction mixture was diluted with ethyl acetate and washed with saturated sodium bicarbonate solution. The crude product was recrystallized from dichloromethane:hexane to afford the desired methyl 3-(benzyloxycarbonyl)-5-tert-butyl-1H-pyrrole-2-carboxylate (0.560 g) as a white solid.

C) 3-(Benzyloxycarbonyl)-5-tert-butyl-1H-pyrrole-2-carboxylic acid

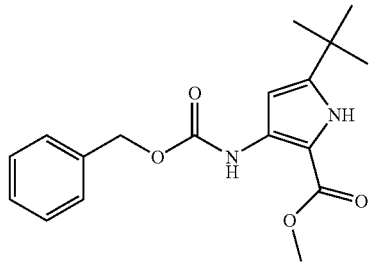

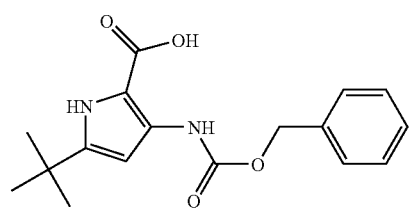

A mixture of the previously prepared 3-(benzyloxycarbonyl)-5-tert-butyl-1H-pyrrole-2-carboxylic acid (150 mg, 0.454 mmol), LiOH.H$_2$O (57 mg, 1.36 mmol), water (0.5 mL) and dioxane (4 mL) was heated at 75° C. for 5 hours. The reaction mixture was cooled down and concentrated under vacuum. The residue was taken up in 20 mL brine solution, acidified with 1N aqueous HCl, extracted with ethyl acetate. The combined organic layers were washed with brine, dried and the solvent removed under vacuum. The crude product was recrystallized from a mixture of dichloromethane:hexane to afford 112 mg of the desired 3-(benzyloxycarbonyl)-5-tert-butyl-1H-pyrrole-2-carboxylic acid as a white solid.

D) Benzyl 5-tert-butyl-2-(5-oxo-1,4-diazepane-1-carbonyl)-1H-pyrrol-3-ylcarbamate

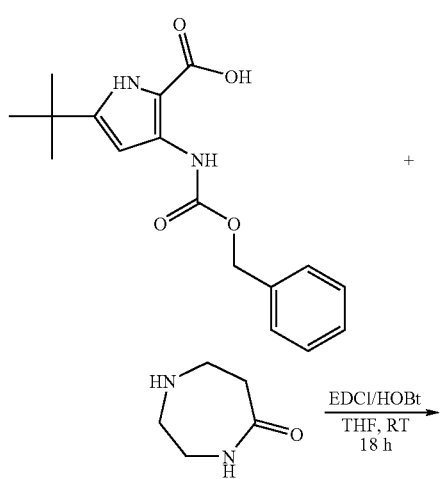

175

-continued

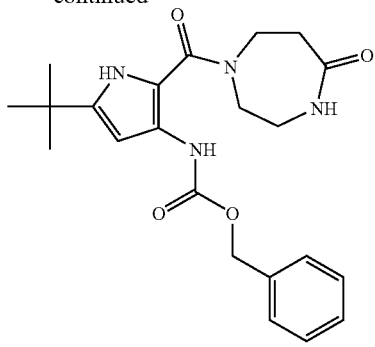

The previously prepared 3-(benzyloxycarbonyl)-5-tert-butyl-1H-pyrrole-2-carboxylic acid (112 mg, 0.35 mmol), 1,4-diazepan-5-one (48 mg, 0.42 mmol), EDCI (78 mg, 0.41 mmol), and HOBt (50 mg, 0.37 mmol) were stirred in dichloromethane (3 mL) at room temperature overnight. Water was added and the resulting mixture was extracted with dichloromethane. The combined organic layers were washed sequentially with water, brine, dried (anhydrous MgSO₄) and concentrated under vacuum. The crude product was purified by preparative thin layer chromatography using a mixture of dichloromethane:methanol 9:1 as elution solvent to afford 75 mg of the desired benzyl 5-tert-butyl-2-(5-oxo-1,4-diazepane-1-carbonyl)-1H-pyrrol-3-ylcarbamate.

E) 1-(4-Amino-2-tert-butyl-1H-pyrrole-5-carbonyl)-1,4-diazepan-5-one

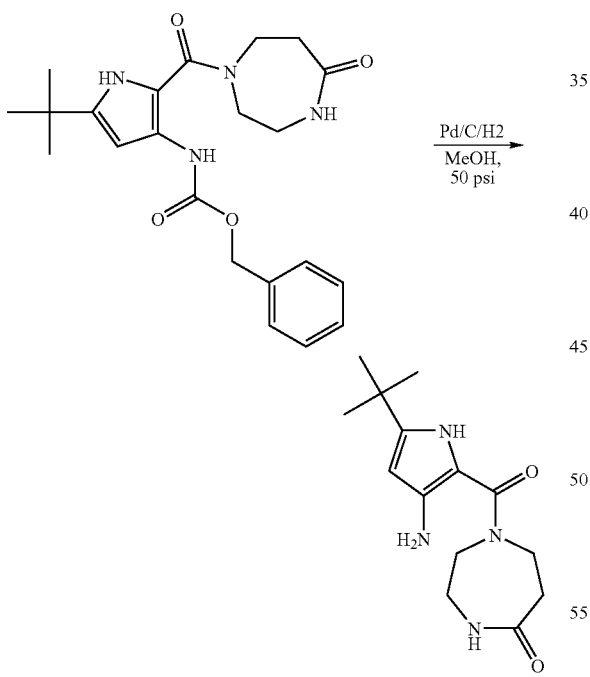

A mixture of the previously benzyl 5-tert-butyl-2-(5-oxo-1,4-diazepane-1-carbonyl)-1H-pyrrol-3-ylcarbamate (40 mg, 0.097 mmol), Pd on charcoal (10% w/w, 20 mg) and methanol (2 mL) was shaken in a Parr shaker under hydrogen (50 psi) for 18 hours. The reaction mixture was filtered through celite and the residue was concentrated under vacuum to afford 20 mg of the desired 1-(4-amino-2-tert-butyl-1H-pyrrole-5-carbonyl)-1,4-diazepan-5-one as a clear oil.

176

F) 1-(5-tert-Butyl-2-(5-oxo-1,4-diazepane-1-carbonyl)-1H-pyrrol-3-yl)-3-(2,3-dichlorophenyl)urea

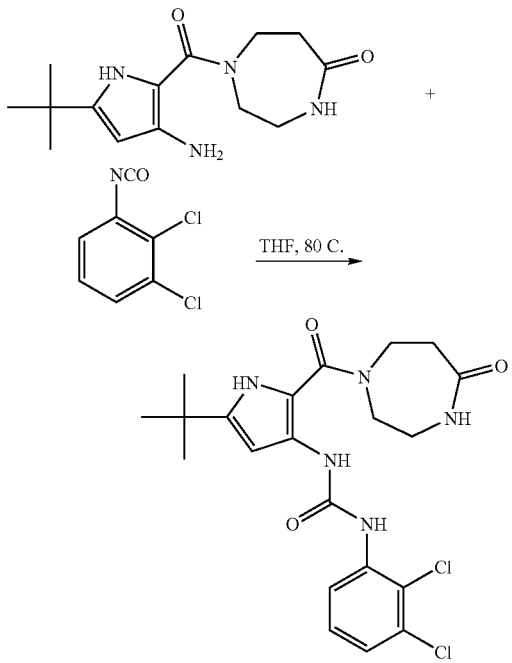

The previously prepared 1-(4-amino-2-tert-butyl-1H-pyrrole-5-carbonyl)-1,4-diazepan-5-one (8 mg, 0.03 mmol) and 2,3 dichlorophenyl isocyanate (5 mg, 0.03 mmol) were dissolved in THF (2 mL) and heated at 70° C. for 2 hours. The reaction mixture was cooled down to room temperature, diluted with ethyl acetate, washed with saturated aqueous sodium bicarbonate, dried and the solvent eliminated under vacuum. The crude product was purified by preparative thin layer chromatography using a mixture of dichloromethane:methanol 9:1 as elution solvent to afford 7.0 mg of 1-(5-tert-butyl-2-(5-oxo-1,4-diazepane-1-carbonyl)-1H-pyrrol-3-yl)-3-(2,3-dichloro-phenyl)urea as a white solid. $^1$H NMR (400 MHz, acetone-$d_6$): δ (ppm) 9.60 (bs, 1H); 8.60 (d, 2H); 8.26 (d, 1H); 7.30 (t, 1H); 7.20 (d, 1H); 6.84 (t, 1H); 6.59 (d, 1H); 3.76 (m, 2H); 3.70 (m, 2H); 3.40 (m, 2H); 2.61 (m, 2H); 1.37 (s, 9H).

Example 210

1-(5-tert-Butyl-2-(1-(2-(dimethylamino)ethyl)-7-oxo-1,4-diazepane-4-carbonyl)-1H-pyrrol-3-yl)-3-(2,3-dichloro-4-fluorophenyl)urea

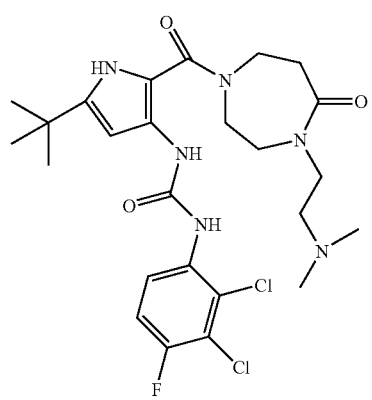

The compound of this example was prepared using a procedure analogous to the procedure described in Example 209. ¹H NMR (400 MHz, acetone-$d_6$): δ (ppm) 9.60 (bs, 1H); 8.67 (bs, 1H); 8.60 (bs, 1H); 8.20 (m, 1H); 7.30 (t, 1H); 6.59 (d, 1H); 3.80 (m, 2H); 3.65 (m, 2H); 3.60 (m, 2H); 3.43 (m, 2H); 2.74 (m, 2H); 2.35 (m, 2H); 2.17 (s, 6H); 1.32 (s, 9H).

Example 211

1-(5-tert-Butyl-2-(1-(2-(dimethylamino)ethyl)-7-oxo-1,4-diazepane-4-carbonyl)-1H-pyrrol-3-yl)-3-(2,3-dichlorophenyl)urea

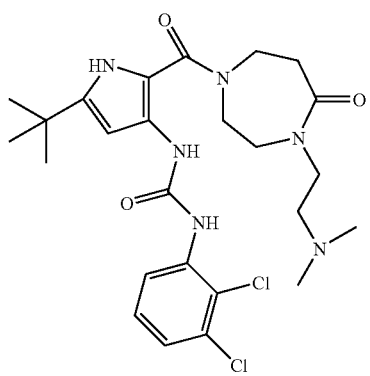

The compound of this example was prepared using a procedure analogous to the procedure described in Example 209. ¹H NMR (400 MHz, acetone-$d_6$): δ (ppm) 9.60 (bs, 1H); 8.67 (bs, 1H); 8.60 (bs, 1H); 8.27 (d, 1H); 7.30 (t, 1H); 7.20 (d, 1H); 6.59 (d, 1H); 3.80 (m, 2H); 3.65 (m, 2H); 3.60 (m, 2H); 3.45 (m, 2H); 2.74 (m, 2H); 2.38 (m, 2H); 2.17 (s, 6H); 1.37 (s, 9H).

Example 212

1-(5-tert-Butyl-3-(1-(2-(dimethylamino)ethyl)-7-oxo-1,4-diazepane-4-carbonyl)thiophen-2-yl)-3-(2-chloro-4-fluorophenyl)urea

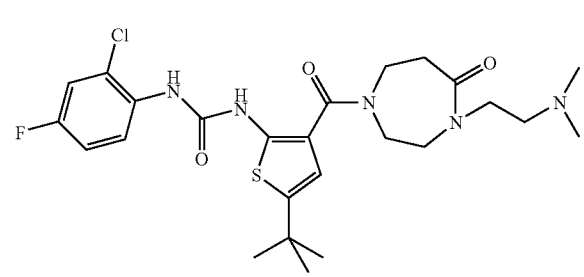

The compound of this example was prepared using a procedure analogous to the procedure described in Example 138. ¹H NMR (400 MHz, CDCl₃): δ (ppm) 9.97 (s, 1H), 8.09 (dd, J=9.0, 5.6 Hz, 1H), 7.98 (s, 1H), 7.04 (dd, J=7.9, 2.9 Hz, 1H), 6.97-6.90 (m, 1H), 6.38 (s, 1H), 3.83-3.71 (m, 4H), 3.55-3.48 (m, 4H), 2.78 (t, J=5.6 Hz, 2H), 2.42 (t, J=6.3 Hz, 2H), 2.22 (s, 6H), 1.29 (s, 9H).

Example 213

1-(5-tert-Butyl-3-(3-ethyl-1,3-dimethyl-2-oxopiperazine-4-carbonyl)thiophen-2-yl)-3-(2,3-dichlorophenyl)urea

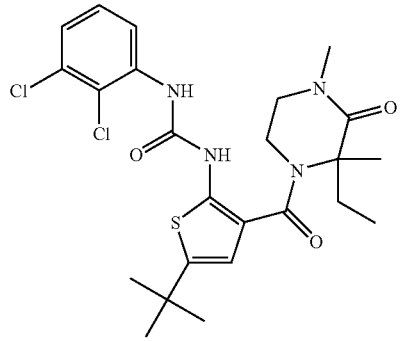

The compound of this example was prepared using a procedure analogous to the procedure described in Example 179. ¹H NMR (400 MHz, CD₃OD): δ (ppm) 8.07 (q, J=3.3 Hz, 1H), 7.23-7.20 (m, 2H), 6.45 (s, 1H), 3.95-3.90 (m, 1H), 3.62-3.56 (m, 3H), 2.98 (s, 3H), 2.82-2.77 (m, 1H), 2.12-2.06 (m, 1H), 1.70 (s, 3H), 1.37 (s, 9H), 0.80 (t, J=7.4 Hz, 3H).

Example 214

Methyl 2-(4-(2-tert-butyl-5-(3-(2,3-dichloro-4-fluorophenyl)ureido)thiophene-4-carbonyl)-3,3-dimethyl-2-oxopiperazin-1-yl)acetate

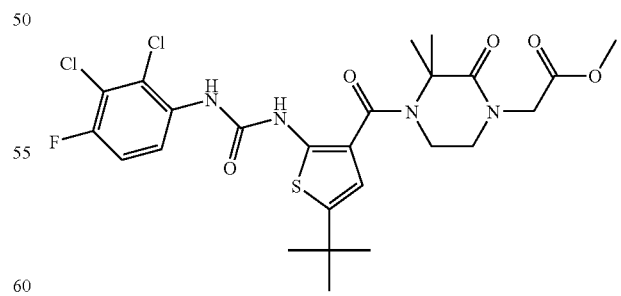

The compound of this example was prepared using a procedure analogous to the procedure described in Example 179. ¹H NMR (400 MHz, CDCl₃): δ (ppm) 7.88 (q, J=4.9 Hz, 1H), 7.04 (q, J=5.9 Hz, 1H), 6.40 (s, 1H), 4.09 (s, 2H), 3.74-3.67 (m, 5H), 3.51-3.46 (m, 2H), 1.75 (s, 6H), 1.27 (s, 9H).

Example 215

1-(5-tert-Butyl-3-(1-(2-(hydroxyamino)-2-oxoethyl)-3,3-dimethyl-2-oxopiperazine-4-carbonyl)thiophen-2-yl)-3-(2,3-dichloro-4-fluorophenyl)urea

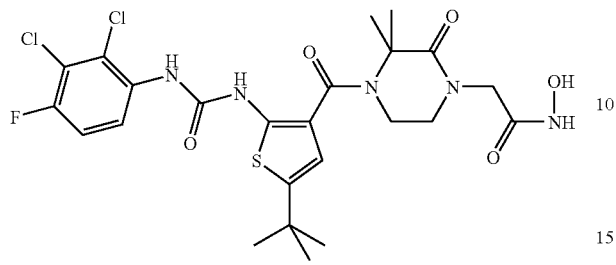

The compound of this example was prepared from the compound of Example 214 by hydrolysis of the ester followed by amide formation using EOLS and hydroxyamine hydrochloride. $^1$H NMR (400 MHz, CDCl$_3$): δ (ppm) 7.83 (q, J=4.8 Hz, 1H), 7.15 (q, J=6.0 Hz, 1H), 6.51 (s, 1H), 3.92 (s, 2H), 3.71-3.65 (m, 2H), 3.56-3.49 (m, 2H), 1.73 (s, 6H), 1.27 (s, 9H).

Example 216

1-(5-tert-Butyl-3-(5-oxo-1,4-diazepane-1-carbonyl)thiophen-2-yl)-3-(2-chloro-3,4-difluorophenyl)urea

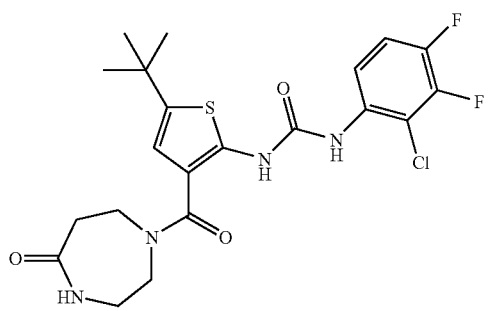

The compound of this example was prepared using a procedure analogous to the procedure described in Example 313. $^1$H NMR (400 MHz, acetone-d$_6$): δ (ppm) 9.90 (bs, 1H); 9.09 (bs, 1H); 8.00 (m, 1H); 7.35 (m, 1H); 7.00 (t, 1H); 6.65 (s, 1H); 3.80 (m, 4H); 3.43 (m, 2H); 2.70 (m, 2H); 1.39 (s, 9H).

Example 217

1-(5-tert-Butyl-2-(1-(2-(dimethylamino)ethyl)-3,3-dimethyl-2-oxopiperazine-4-carbonyl)thiophen-3-yl)-3-(2-chloro-3,4-difluorophenyl)urea

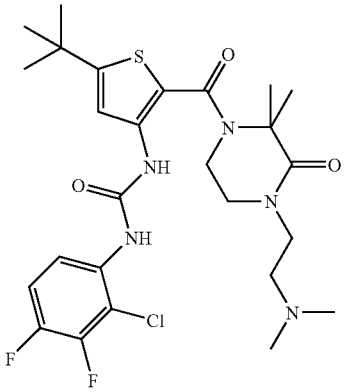

The compound of this example was prepared using a procedure analogous to the procedure described in Example 179. $^1$H NMR (400 MHz, acetone-d$_6$): δ (ppm) 9.58 (bs, 1H); 8.90 (bs, 1H); 7.95 (m, 1H); 7.70 (s, 1H); 7.38 (m, 1H); 3.95 (m, 2H); 3.63 (m, 2H); 3.50 (t, 2H); 2.42 (t, 2H); 2.20 (s, 6H); 1.70 (s, 6H); 1.40 (s, 9H).

Example 218

1-(5-tert-Butyl-3-(1-(2-(methoxy(methyl)amino)-2-oxoethyl)-3,3-dimethyl-2-oxopiperazine-4-carbonyl)thiophen-2-yl)-3-(2,3-dichlorophenyl)urea

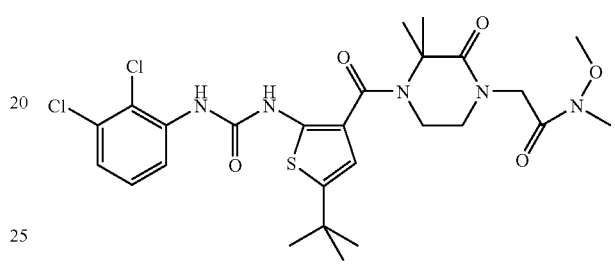

The compound of this example was prepared from the compound of Example 180 by hydrolysis of the ester followed by amide formation using EDCI and N,O-dimethylhydroxylamine hydrochloride. $^1$H NMR (400 MHz, CDCl$_3$): δ (ppm) 7.94-7.88 (m, 1H), 7.15-7.11 (m, 2H), 6.45 (s, 1H), 4.26 (s, 2H), 3.72-3.68 (m, 5H), 3.48-3.43 (m, 2H), 3.12 (s, 3H), 1.74 (s, 6H), 1.27 (s, 9H).

Example 219

1-(5-tert-Butyl-3-(2-(2-hydroxyethyl)-2-methyl-3-oxopiperazine-1-carbonyl)thiophen-2-yl)-3-(3-chloro-2-methylphenyl)urea

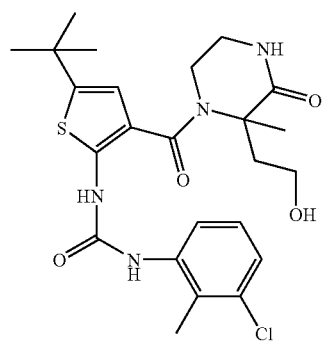

The compound of this example was prepared using a procedure analogous to the procedure of Example 194. $^1$H NMR (400 MHz, CD$_3$COCD$_3$): δ (ppm) 9.89 (s, 1H), 8.53 (s, 1H), 7.74-7.69 (m, 2H), 7.36 (s, 1H), 6.63 (s, 1H), 3.96-3.88 (m, 2H), 3.69-3.56 (m, 4H), 3.56-3.40 (m, 1H), 2.93-2.81 (m, 5H), 2.38-2.31 (m, 4H), 1.73 (s, 3H), 1.35 (s, 9H).

Example 220

1-(5-tert-Butyl-3-(1-(2-(methoxy(methyl)amino)-2-oxoethyl)-3,3-dimethyl-2-oxopiperazine-4-carbonyl)thiophen-2-yl)-3-(2,3-dichloro-4-fluorophenyl)urea

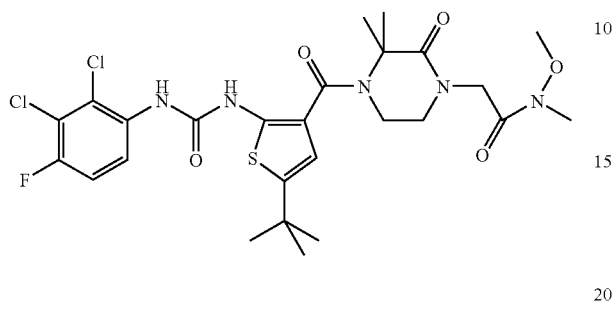

The compound of this example was prepared using a procedure analogous to the procedure of Example 218. $^1$H NMR (400 MHz, CDCl$_3$): δ (ppm) 7.92 (q, J=4.7 Hz, 1H), 7.13 (q, J=6.0 Hz, 1H), 6.51 (s, 1H), 4.33 (s, 2H), 3.79-3.74 (m, 5H), 3.52 (t, J=4.9 Hz, 2H), 3.18 (s, 3H), 1.80 (s, 6H), 1.33 (s, 9H).

Example 221

Ethyl 2-(2-tert-butyl-5-(3-(2,3-dichlorophenyl)ureido)thiophene-4-carboxamido)-2-methylbutanoate

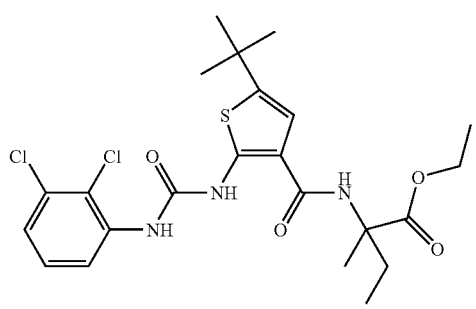

The compound of this example was prepared using a procedure analogous to the procedure described in Example 179. $^1$H NMR (400 MHz, CD$_2$Cl$_2$): δ (ppm) 11.5 (s, 1H), 8.16 (d, J=7.6 Hz, 1H), 7.33 (s, 1H), 7.2607.18 (m, 2H), 6.66 (s, 1H), 6.64 (s, 1H), 4.22 (q, J=7.1 Hz, 2H), 2.34-2.22 (m, 1H), 2.03-1.80 (m, 1H), 1.63 (s, 3H), 1.39 (s, 9H), 1.22 (t, J=7.1 Hz, 3H), 0.84 (t, J=7.4 Hz, 3H).

Example 222

Methyl 2-(1-(2-tert-butyl-4-(3-(2-chloro-3,4-difluorophenyl)ureido)thiophene-5-carbonyl)-2-methyl-3-oxopiperazin-2-yl)acetate

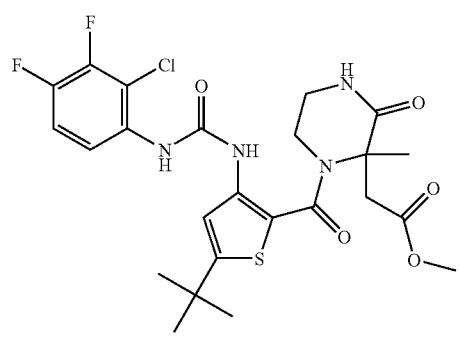

The compound of this example was prepared using a procedure analogous to the procedure described in Example 183. $^1$H NMR (400 MHz, CD$_2$Cl$_2$): δ (ppm) 8.78 (s, 1H), 8.00-7.94 (m, 1H), 7.69 (s, 1H), 7.61 (s, 1H), 7.13 (q, J=9.2 Hz, 1H), 6.62 (s, 1H), 4.12-4.00 (m, 1H), 3.95 (d, J=17.8 Hz, 1H), 3.81-3.74 (m, H), 3.61 (s, 3H), 3.60-3.58 (m, 1H), 3.43-3.35 (m, 1H), 3.26 (d, J=17.8 Hz, 1H), 1.78 (s, 3H), 1.38 (s, 9H).

Example 223

1-(5-tert-Butyl-2-(2-(2-hydroxyethyl)-2-methyl-3-oxopiperazine-1-carbonyl)thiophen-3-yl)-3-(2-chloro-3,4-difluorophenyl)urea

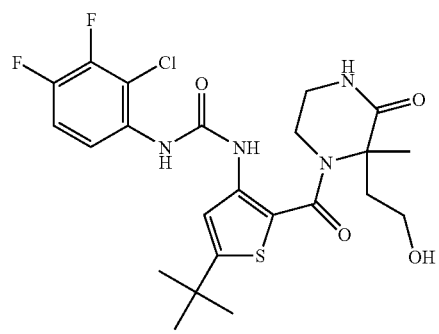

The compound of this example was prepared from compound of Example 222 by treatment with DIBAL-H in dichloromethane. $^1$H NMR (400 MHz, CD$_3$OD): δ (ppm) 7.79-7.74 (m, 1H), 7.38 (s, 1H), 7.26-7.18 (m, 1H), 4.12-3.97 (m, 1H), 3.73-3.58 (m, 4H), 3.52-3.44 (m, 1H), 3.01-2.93 (m, 1H), 2.36-2.28 (m, 1H), 1.76 (s, 3H), 1.37 (s, 9H).

Example 224

1-(5-tert-Butyl-2-(2-(2-hydroxyethyl)-2-methyl-3-oxopiperazine-1-carbonyl)thiophen-3-yl)-3-(2,3-dichloro-4-fluorophenyl)urea

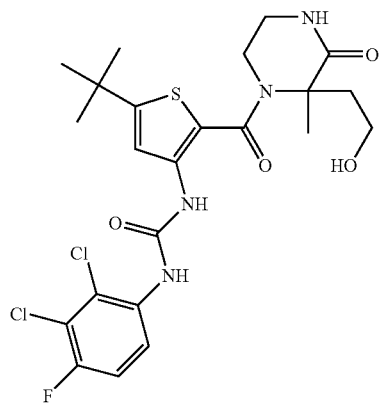

The compound of this example was prepared using the procedure of Example 223, except that 2,3-dichloro-4-fluorophenylisocyanate was used instead of 2-chloro-3,4-difluorophenylisocyanate. $^1$H NMR (400 MHz, CD$_3$OD): δ (ppm) 7.91 (dd, J=9.3, 5.2 Hz, 1H), 7.38 (s, 1H), 7.22 (dd, J=9.2, 8.4 Hz, 1H), 4.12-3.96 (m, 1H), 3.72-3.58 (m, 4H), 3.52-3.44 (m, 1H), 3.01-2.93 (m, 1H), 2.36-2.28 (m, 1H), 1.76 (s, 3H), 1.37 (s, 9H).

Example 225

1-(5-tert-Butyl-3-(3,3-dimethyl-1-(2-(methylamino)-2-oxoethyl)-2-oxopiperazine-4-carbonyl)thiophen-2-yl)-3-(2,3-dichlorophenyl)urea

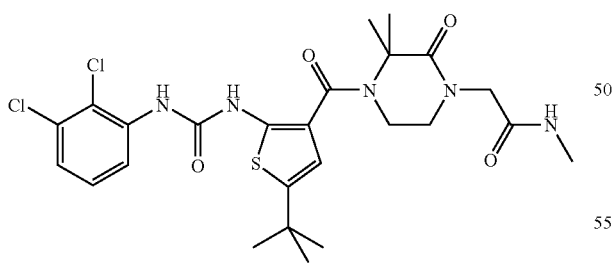

The compound of this example was prepared using a procedure analogous to the procedure described in Example 193. $^1$H NMR (400 MHz, CDCl$_3$): δ (ppm) 10.16 (s, 1H), 8.12 (dd, J=7.3, 2.2 Hz, 1H), 7.68 (s, 1H), 7.14-7.07 (m, 2H), 6.38 (s, 1H), 6.17 (d, J=4.9 Hz, 1H), 3.94 (s, 2H), 3.74 (t, J=5.0 Hz, 2H), 3.59 (t, J=4.9 Hz, 2H), 2.75 (d, J=5.1 Hz, 3H), 1.74 (s, 6H), 1.28 (s, 9H).

Example 226

1-(5-tert-Butyl-3-(1-(2-(methoxyamino)-2-oxoethyl)-3,3-dimethyl-2-oxopiperazine-4-carbonyl)thiophen-2-yl)-3-(2,3-dichlorophenyl)urea

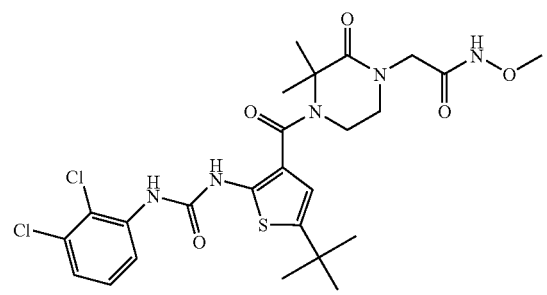

The compound of this example was prepared using a procedure analogous to the procedure described in Example 218. $^1$H NMR (400 MHz, CDCl$_3$): δ (ppm) 10.15 (s, 1H), 9.19 (s, 1H), 8.12 (dd, J=7.1, 3.1 Hz, 1H), 7.46 (s, 1H), 7.09-7.15 (m, 2H), 6.38 (s, 1H), 3.94-3.55 (m, 9H), 1.74 (s, 6H), 1.29 (s, 9H).

Example 227

1-(5-tert-Butyl-3-(2-(2-(methoxyamino)-2-oxoethyl)-2-methyl-3-oxopiperazine-1-carbonyl)thiophen-2-yl)-3-(2,3-dichloro-4-fluorophenyl)urea

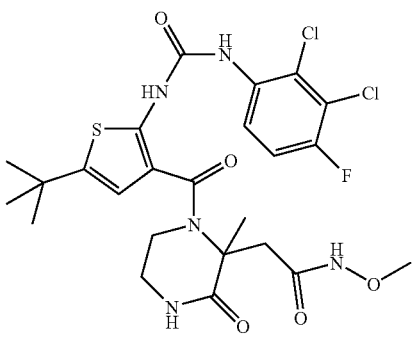

The compound of this example was made from compound of Example 191 by first hydrolysis with LiOH to give the corresponding acid followed by coupling with N-methoxyamine using EDCI, HOBt and DIEA to give the expected amide. $^1$H NMR (400 MHz, CD$_3$COCD$_3$): δ (ppm) 10.53 (s, 1H), 10.31 (s, 1H), 8.56 (s, 1H), 8.27 (dd, J=9.2, 5.3 Hz, 1H), 7.35 (s, 1H), 7.17 (dd, J=9.1, 8.4 Hz, 1H), 6.62 (d, J=8.6 Hz, 1H), 4.11-4.01 (m, 1H), 3.96-3.89 (m, 1H), 3.85 (d, J=15.1 Hz, 1H), 3.76-3.71 (m, 1H), 3.69 (s, 3H), 3.62-3.54 (m, 1H), 3.47-3.40 (m, 1H), 1.86 (s, 3H), 1.37 (s, 9H).

Example 228

1-(5-tert-Butyl-3-(2-(2-(methoxy(methyl)amino)-2-oxoethyl)-2-methyl-3-oxopiperazine-1-carbonyl)thiophen-2-yl)-3-(2,3-dichloro-4-fluorophenyl)urea

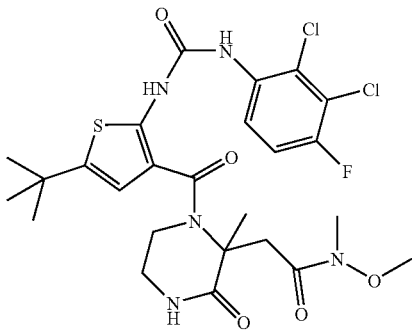

The compound of this example was using the procedure described in Example 218, except N-methoxy-N-methylamine was used instead of N-methoxyamine. $^1$H NMR (400 MHz, CD$_3$COCD$_3$): δ (ppm) 9.83 (s, 1H), 8.40 (s, 1H), 8.25 (dd, J=9.4, 5.2 Hz, 1H), 7.37-7.31 (m, 2H), 6.60 (s, 1H), 4.09-3.96 (m, 2H), 3.80 (s, 3H), 3.69 (d, J=10.3 Hz, 2H), 3.52-3.41 (m, 2H), 3.24 (s, 3H), 1.81 (s, 3H), 1.36 (s, 9H).

Example 229

1-(5-tert-Butyl-3-(1-(2-(dimethylamino)-2-oxoethyl)-3,3-dimethyl-2-oxopiperazine-4-carbonyl)thiophen-2-yl)-3-(2,3-dichlorophenyl)urea

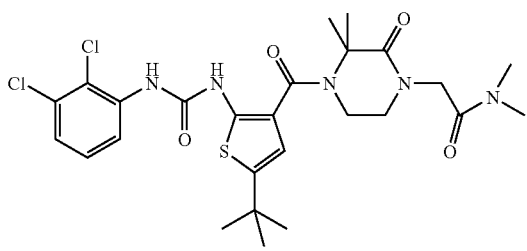

The compound of this example was prepared using a procedure analogous to the procedure described in Example 193. $^1$H NMR (400 MHz, CDCl$_3$): δ (ppm) 10.10 (s, 1H), 8.11 (dd, J=6.8, 3.2 Hz, 1H), 7.42-7.40 (m, 1H), 7.14-7.11 (m, 2H), 6.43 (s, 1H), 4.16 (s, 2H), 3.81 (t, J=4.9 Hz, 2H), 3.53 (t, J=4.9 Hz, 2H), 2.98 (s, 3H), 2.91 (s, 3H), 1.77 (s, 6H), 1.50 (s, 9H).

Example 230

1-(3-(1-(2-amino-2-oxoethyl)-3,3-dimethyl-2-oxopiperazine-4-carbonyl)-5-tert-butylthiophen-2-yl)-3-(2,3-dichlorophenyl)urea

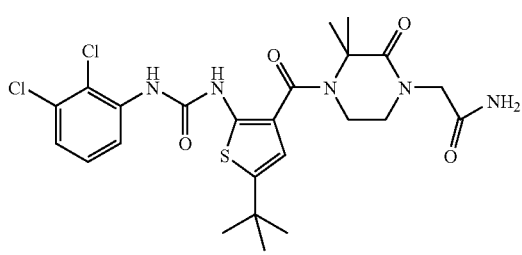

The compound of this example was prepared using a procedure analogous to the procedure described in Example 193. $^1$H NMR (400 MHz, CDCl$_3$): δ (ppm) 10.22 (s, 1H), 8.18 (dd, J=7.5, 2.5 Hz, 1H), 7.76 (s, 1H), 7.20-7.12 (m, 2H), 6.43 (s, 1H), 6.19 (s, 1H), 5.70 (d, J=54.5 Hz, 1H), 4.05 (s, 2H), 3.81 (t, J=4.7 Hz, 2H), 3.62 (t, J=4.9 Hz, 2H), 1.80 (s, 6H), 1.34 (s, 9H).

Example 231

1-(5-tert-Butyl-2-(2,2-dimethyl-3-oxopiperazine-1-carbonyl)furan-3-yl)-3-(2,3-dichloro-4-fluorophenyl)urea

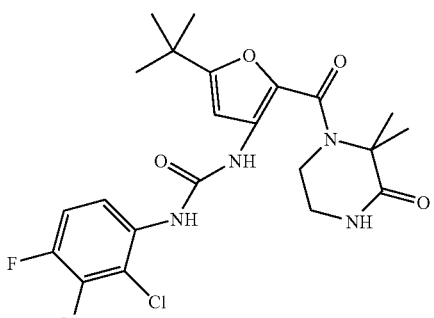

The compound of this example was prepared using a procedure analogous to the procedure of Example 273. $^1$H NMR (400 MHz, acetone-d$_6$): δ (ppm) 9.37 (bs, 1H); 9.12 (bs, 1H); 8.15 (m, 1H); 7.38 (t, 1H); 7.18 (bs, 1H); 7.03 (s, 1H); 3.95 (m, 2H); 3.60 (m, 2H); 1.72 (s, 6H); 1.30 (s, 9H).

Example 232

1-(5-tert-Butyl-2-(2,2-dimethyl-3-oxopiperazine-1-carbonyl)furan-3-yl)-3-(2,3-dichlorophenyl)urea

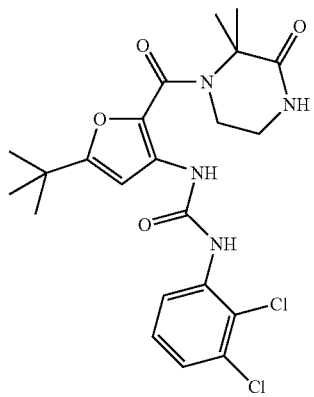

The compound of this example was prepared using a procedure analogous to the procedure of Example 273. $^1$H NMR (400 MHz, acetone-d$_6$): δ (ppm) 9.57 (bs, 1H); 9.50 (bs, 1H); 8.00 (t, 1H); 7.80 (d, 1H); 7.22 (m, 2H); 6.82 (s, 1H); 3.68 (m, 2H); 3.30 (m, 2H); 1.60 (s, 6H); 1.20 (s, 9H).

Example 233

1-(5-tert-butyl-3-(3-hydroxypiperidine-1-carbonyl)thiophen-2-yl)-3-(2,3-dichlorophenyl)urea

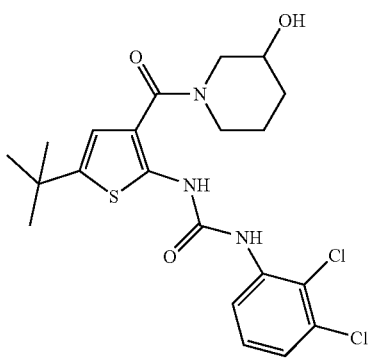

The compound of this example was prepared using a procedure analogous to the procedure described in Example 138.
¹H NMR (400 MHz, CD₂Cl₂): δ (ppm) 10.11 (s, 1H), 8.23 (s, 1H), 8.15 (m, 1H), 7.25-7.10 (m, 2H), 6.50 (s, 1H), 3.92 (s, 1H), 3.79-3.70 (m, 2H), 3.67-3.60 (m, 1H), 3.46 (m, 1H), 1.90-1.47 (m, 4H), 1.28 (m, 9H).

Example 234

1-(5-tert-Butyl-3-(2-methyl-2-((3-methyl-1,2,4-oxadiazol-5-yl)methyl)-3-oxopiperazine-1-carbonyl)thiophen-2-yl)-3-(2,3-dichloro-4-fluorophenyl)urea

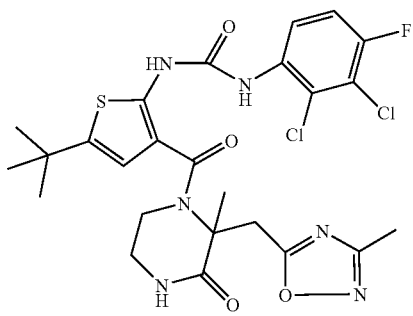

The compound of this example was prepared using the procedure as shown below.

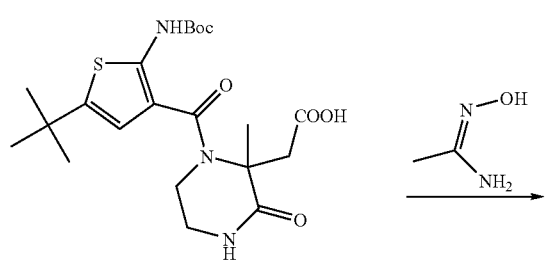

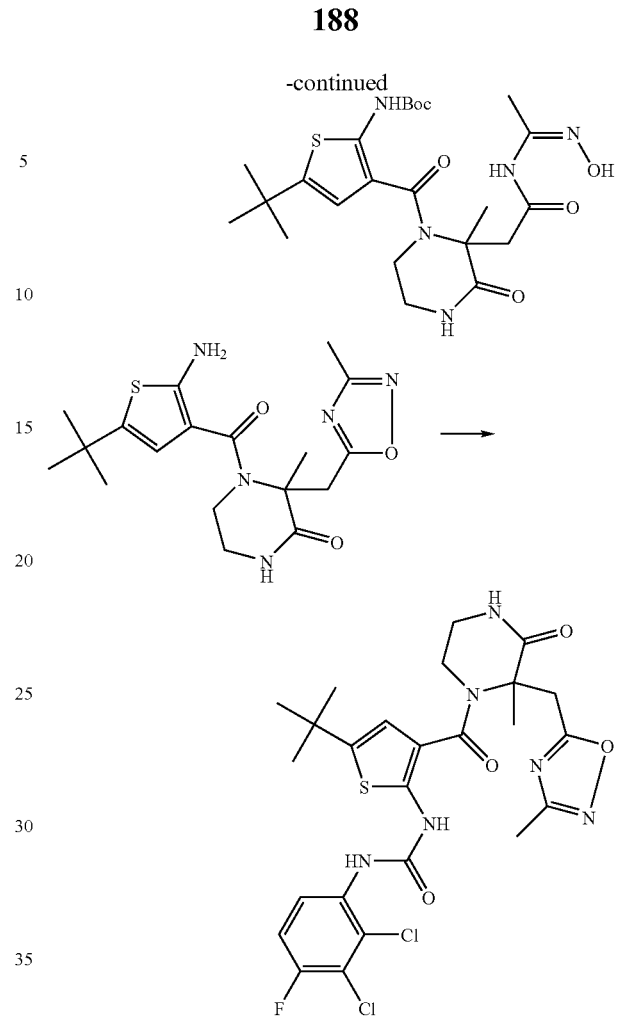

To a solution of 2-(1-(2-(tert-butoxycarbonyl)-5-tert-butylthiophene-3-carbonyl)-2-methyl-3-oxopiperazin-2-yl)acetic acid (0.14 g, 0.44 mmol), HOBt (0.088 mmol) and DIEA (0.28 g, 2.2 mmol) in DMF (5.0 mL) was added TBTU (0.44 mmol), the reaction mixture was stirred at room temperature for 1 h, N-hydroxyl-acetamidine (0.049 mg, 0.66 mmol) was added in one portion and the reaction mixture stirred at room temperature for 14 h. The reaction mixture was neutralized to pH 7.0 with 1N aqueous HCl, extracted with ethyl acetate, washed with water, brine, dried over anhydrous Na₂SO₄, filtered and concentrated under vacuum to give 220 mg of crude tert-butyl 5-tert-butyl-3-(2-(2-(N'-hydroxyacetamidino)-2-oxoethyl)-2-methyl-3-oxopiperazine-1-carbonyl)thiophen-2-ylcarbamate used in next step without further purification.

The previously prepared tert-butyl 5-tert-butyl-3-(2-(2-(N'-hydroxyacetamidino)-2-oxoethyl)-2-methyl-3-oxopiperazine-1-carbonyl)-thiophen-2-ylcarbamate (0.050 g, 0.098 mmol) was dissolved in DMF (3.0 mL) and heated at 140° C. for 3 h. The reaction mixture was cooled to room temperature, diluted with ethyl acetate, washed with water followed by brine and dried over anhydrous Na₂SO₄. The crude product was purified on preparative SFC to give 20 mg of 2-amino-5-tert-butyl-3-(2-methyl-2-((3-methyl-1,2,4-oxadiazol-5-yl)methyl)-3-oxopiperazine-1-carbonyl)thiophene used as such in the next step.

To 2-amino-5-tert-butyl-3-(2-methyl-2-((3-methyl-1,2,4-oxadiazol-5-yl)methyl)-3-oxopiperazine-1-carbonyl)thiophene (0.020 g, 0.05 mmol) in anhydrous THF (2.0 mL) was added 2,3-dichloro-4-fluoroisocyanate (0.020 g, 0.08 mmol) and stirred for 1 h. The reaction mixture was concentrated under vacuum and the crude product was purified preparative thin layer chromatography (silica gel, ethyl acetate:hexane 4:1) to give 9 mg 1-(5-tert-butyl-3-(2-methyl-2-((3-methyl-1,2,4-oxadiazol-5-yl)methyl)-3-oxo-piperazine-1-carbonyl)thiophen-2-yl)-3-(2,3-dichloro-4-fluorophenyl)urea. $^1$H NMR (400 MHz, CD$_3$COCD$_3$): δ (ppm) 9.80 (s, 1H), 9.01 (s, 1H), 8.15 (dd, J=9.3, 5.3 Hz, 1H), 7.43 (s, 1H), 7.35 (t, J=9.0 Hz, 1H), 6.49 (s, 1H), 4.30 (d, J=15.6 Hz, 1H), 3.90-3.83 (m, 1H), 3.79-3.72 (m, 2H), 3.48 (dd, J=8.6, 4.4 Hz, 2H), 2.29 (s, 3H), 1.91 (s, 3H), 1.35 (s, 9H).

Example 235

1-(3-(3-Acetamidopiperidine-1-carbonyl)-5-tert-butylthiophen-2-yl)-3-(2,3-dichlorophenyl)urea

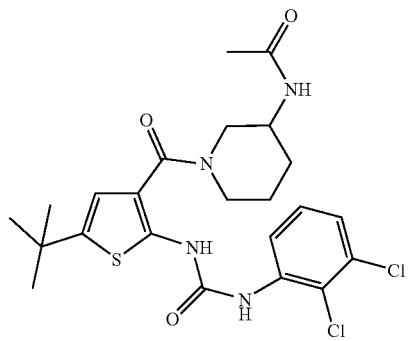

The compound of this example was prepared using the procedure described in Example 138. $^1$H NMR (400 MHz, CD$_3$OD): δ (ppm) 7.99 (dd, J=6.7, 2.9 Hz, 1H), 7.27-7.21 (m, 2H), 6.60 (s, 1H), 3.95-3.79 (m, 2H), 3.31-3.28 (m, 2H), 3.07 (br s, 1H), 1.99 (m, 4H), 1.86-1.80 (m, 1H), 1.62-1.51 (m, 2H), 1.35 (s, 9H).

Example 236

1-(2,3-Dichloro-4-fluorophenyl)-3-(2-(2,2-dimethyl-3-oxopiperazine-1-carbonyl)-5-(trifluoromethyl)furan-3-yl)urea

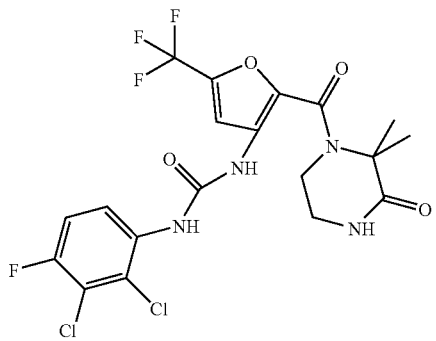

The compound of this example was prepared as follows.

A) 3-Cyano-1,1,1-trifluoroprop-2-en-2-yl-4-methyl-benzene-sulfonate

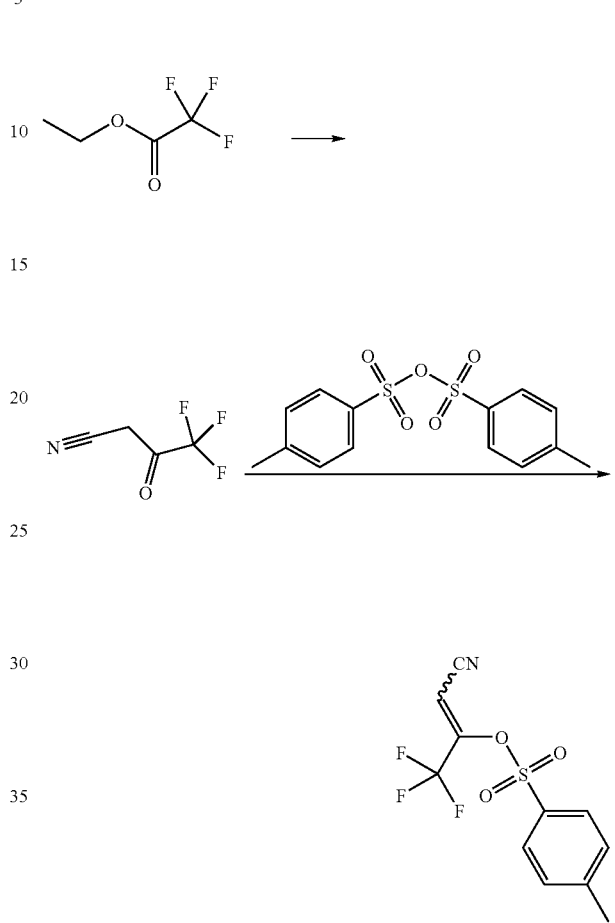

To a cooled (−78° C.) solution of LDA (2M, 15 g, 39 mmol) in anhydrous THF (50 mL) was added drop-wise a solution of ethyl trifluoroacetate (2.5 g, 18 mmol) and acetonitrile (1.4 g, 35 mmol) in 15 ml THF. The reaction was kept at −78° C. for 45 min, warmed up to room temperature over 1 hour period and quenched with ice water. The reaction was concentrated under vacuum, the residue extracted with ethyl ether, the pH brought to 1 with concentrated HCl, extracted with dichloromethane. The aqueous solution was extracted with ethyl ether, the combined organic layers dried over anhydrous sodium sulfate, and the solvent was removed under vacuum to afford 1.4 g of 4,4,4-trifluoro-3-oxobutanenitrile as a yellow oil, which was used as such in the next step.

To a solution of 4,4,4-trifluoro-3-oxobutanenitrile (1.40 g, 10.2 mmol) and p-toluensulfonic anhydride (4 g, 12.3 mmol) in 15 mL dichloromethane was added dropwise triethylamine (1.55 g, 15.3 mmol), and the resulting mixture stirred at room temperature overnight. The reaction mixture was quenched with water; the aqueous layer was back-extracted with dichloromethane. The combined organic layers were dried, and the solvent eliminated under vacuum. The crude product was purified by chromatographic column (silica gel, hexane:ethyl acetate 9:1) to afford 1.6 g of 3-cyano-1,1,1-trifluoroprop-2-en-2-yl 4-methylbenzenesulfonate as a yellow oil.

B) 4-(4-Amino-2-(trifluoromethyl)furan-5-carbonyl)-3,3-dimethyl-piperazin-2-one

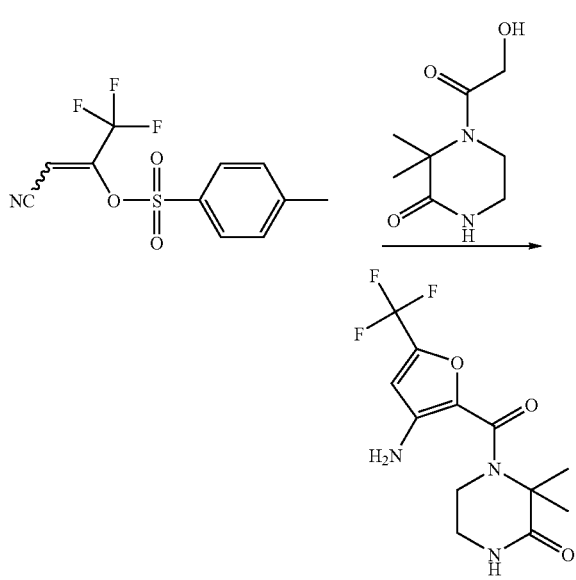

4-(2-Hydroxyacetyl)-3,3-dimethylpiperazin-2-one (0.090 g, 0.48 mmol) and sodium hydride (60%, 0.040 g, 0.97 mmol) were dissolved in 3 mL DMF and stirred at 25° C. for 30 min. To the resulting, cooled (0° C.) mixture was added drop-wise 3-cyano-1,1,1-trifluoroprop-2-en-2-yl 4-methylbenzenesulfonate (0.16 g, 0.56 mmol). The reaction was gradually warmed up to 25° C., stirred for an additional 2 hours, 2 additional equivalents of sodium hydride were added and the mixture stirred for another additional 4 hours. The reaction mixture was quenched with water, extracted with ethyl acetate, the combined organic layers dried, the solvent eliminated under vacuum and the crude product purified by preparative thin layer chromatography. (silicagel, dichloromethane:methanol 95:5) to afford 0.010 g of 4-(4-amino-2-(trifluoromethyl)furan-5-carbonyl)-3,3-dimethylpiperazin-2-one.

C) 1-(2,3-Dichloro-4-fluorophenyl)-3-(2-(2,2-dimethyl-3-oxo-piperazine-1-carbonyl)-5-(trifluoromethyl)furan-3-yl)urea

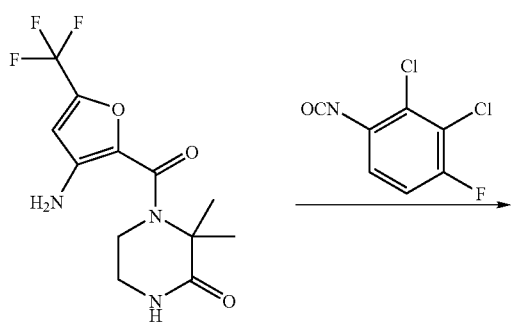

A solution of 4-(4-amino-2-(trifluoromethyl)furan-5-carbonyl)-3,3-dimethylpiperazin-2-one (0.010 g, 0.034 mmol) and 4-fluoro-2,3-dichloroisocyanate (0.015 g, 0.051 mmol) in THF (2 mL) was heated at 75° C. for 2 hours. The reaction mixture was diluted with ethyl acetate, washed with saturated sodium bicarbonate, dried and the solvent eliminated under vacuum. The crude product was purified by preparative thin layer chromatography (dichloromethane:methanol 95:5) to afford 0.012 g of 1-(2,3-dichloro-4-fluorophenyl)-3-(2-(2,2-dimethyl-3-oxopiperazine-1-carbonyl)-5-(trifluoromethyl)furan-3-yl)urea.

$^1$H NMR (400 MHz, acetone-d$_6$): δ (ppm) 9.43 (bs, 1H); 8.60 (bs, 2H); 8.20 (m, 1H); 7.30 (t, 1H); 7.03 (bs, 1H); 6.56 (d, 1H); 3.75 (m, 2H); 3.58 (m, 2H); 1.69 (s, 6H); 1.37 (s, 9H).

Example 237

1-(5-tert-Butyl-2-(2,2-dimethyl-3-oxopiperazine-1-carbonyl)-1H-pyrrol-3-yl)-3-(2,3-dichloro-4-fluorophenyl)urea

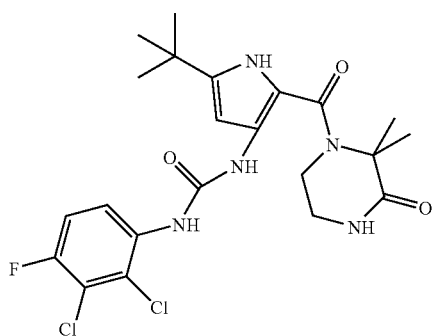

The compound of this example was prepared according to the following procedure:

A) Methyl 5-tert-butyl-1H-pyrrole-2-carboxylate

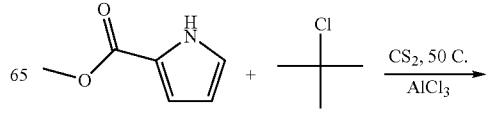

-continued

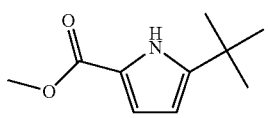

A mixture of the methylpyrrole-2-carboxylate (1.0 g, 7.99 mmol) and aluminum trichloride (2.13 g, 16.0 mmol) was dissolved in carbon disulfide (20 mL) and stirred at 50° C. for 1 hour. Tert-butyl chloride (0.740 g, 7.99 mmol) in carbon disulfide (5 mL) was added in one portion and the mixture stirred at room temperature for an additional 20 hours. The reaction mixture was quenched with ice and extracted with dichloromethane. The solvent was removed under vacuum and the resulting solid was washed with cold hexane to afford 0.850 g of the expected methyl 5-tert-butyl-1H-pyrrole-2-carboxylate as a tan solid.

B) Methyl 5-tert-butyl-3-nitro-1H-pyrrole-2-carboxylate

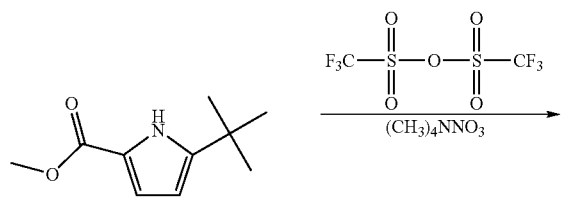

Triflic anhydride (0.545 g, 1.93 mmol) was added dropwise under nitrogen atmosphere to a stirred solution of tetramethylammonium nitrate (0.263 g, 1.93 mmol) in dichloromethane (5 mL) at room temperature and stirred for 1.5 h. The reaction mixture was cooled down to −78° C., methyl 5-tert-butyl-1H-pyrrole-2-carboxylate (0.250 g, 1.38 mmol) in methylene chloride (5 mL) was added drop wise. The cooling bath was removed and the reaction was gradually warmed up to room temperature and stirred at 25° C. overnight. The mixture was quenched with saturated sodium bicarbonate (pH equals about 8), and the dichloromethane layer was separated. The aqueous layer was extracted with dichloromethane. The organic layers were combined, dried and the solvent removed under vacuum to afford 0.238 mg of the expected methyl 5-tert-butyl-3-nitro-1H-pyrrole-2-carboxylate (~85% pure), which was used as such in the next step.

C) 5-tert-Butyl-3-nitro-1H-pyrrole-2-carboxylic acid

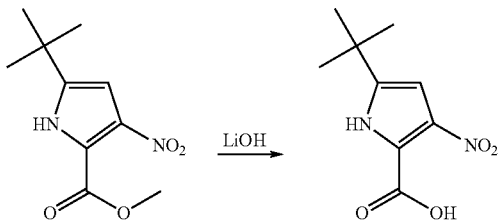

A solution of LiOH monohydrate (0.083 g, 2.0 mmol) in water (1 mL) was added to a solution of methyl 5-tert-butyl-3-nitro-1H-pyrrole-2-carboxylate (0.150 mL, 0.66 mmol) in THF:MeOH (3:1, 3 mL) and the resulting mixture heated at 75° C. for 5 hours. The reaction was cooled down to room temperature and acidified with 1N aqueous HCl, extracted with ethyl acetate. The combined organic layers were dried, the solvent eliminated under vacuum and the crude product recrystallized from dichloromethane:hexane to afford 90 mg of expected 5-tert-butyl-3-nitro-1H-pyrrole-2-carboxylic acid as a yellow solid.

D) 4-(2-tert-Butyl-4-nitro-1H-pyrrole-5-carbonyl)-3,3-dimethyl-piperazin-2-one

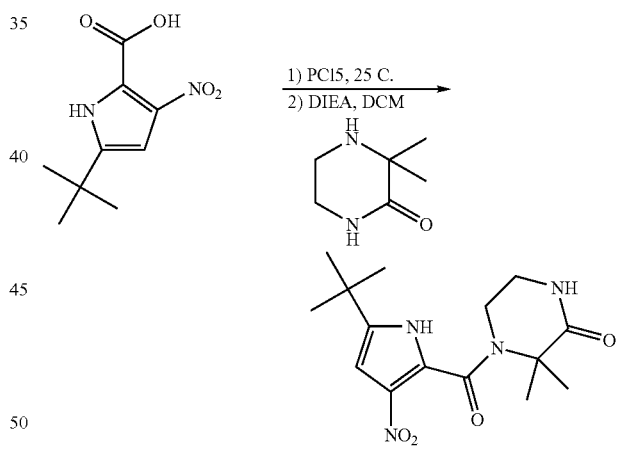

The previously prepared 5-tert-butyl-3-nitro-1H-pyrrole-2-carboxylic acid (0.203 g, 1.11 mmol) and PCl5 (0.232 g, 1.11 mmol) were dissolved in dichloromethane (4 mL) and stirred at room temperature for 5 minutes. The resulting solution was added in one portion to a solution of 3,3-dimethylpiperazin-2-one (0.214 g, 1.67 mmol) and DIEA (0.288 g, 2.23 mmol) in dichloromethane (3 mL) and stirred at room temperature for 5 minutes. The reaction mixture was diluted with dichloromethane and washed sequentially with 1N aqueous HCl, saturated sodium bicarbonate, dried and the solvent removed under vacuum. The crude product was purified by chromatographic column (silica gel, dichloromethane:methanol, 95:5) to afford 0.190 g of expected 4-(2-tert-butyl-4-nitro-1H-pyrrole-5-carbonyl)-3,3-dimethylpiperazin-2-one.

E) 4-(4-Amino-2-tert-butyl-1H-pyrrole-5-carbonyl)-3,3-dimethyl-piperazin-2-one

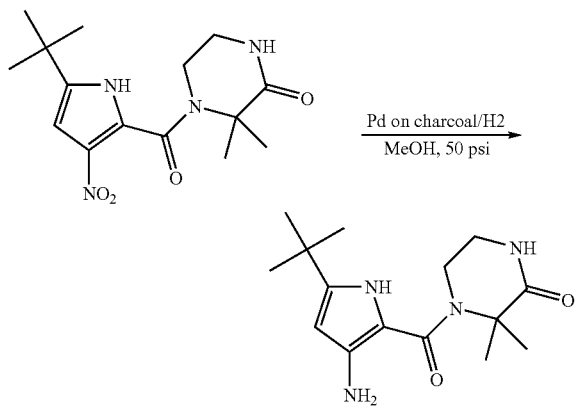

A mixture of the previously prepared 4-(2-tert-butyl-4-nitro-1H-pyrrole-5-carbonyl)-3,3-dimethylpiperazin-2-one (80 mg, 0.25 mmol) dissolved in methanol (2 mL) and Pd on charcoal (10% w/w, 20 mg) was shaken under hydrogen atmosphere in a Parr shaker at 50 psi for 18 hours. The reaction was filtered through celite, the residue concentrated under vacuum to afford 68 mg of the desired 4-(4-amino-2-tert-butyl-1H-pyrrole-5-carbonyl)-3,3-dimethylpiperazin-2-one as a yellow oil.

E) 1-(5-tert-Butyl-2-(2,2-dimethyl-3-oxopiperazine-1-carbonyl)-1H-pyrrol-3-yl)-3-(2,3-dichloro-4-fluorophenyl)urea

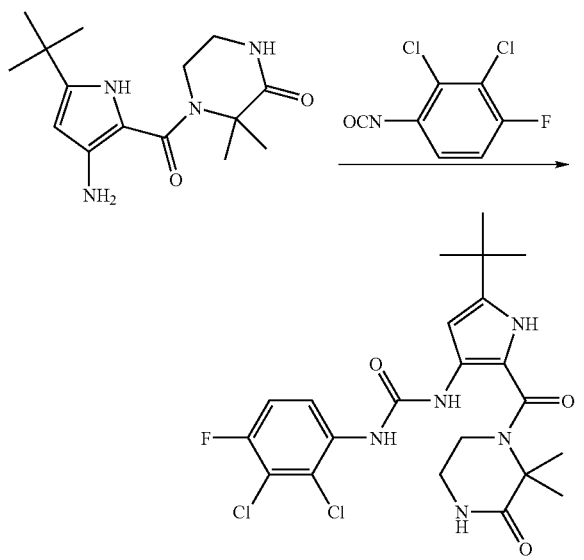

The 4-(4-amino-2-tert-butyl-1H-pyrrole-5-carbonyl)-3,3-dimethylpiperazin-2-one (21 mg, 0.072 mmol) and isocyanate (17 mg, 0.080 mmol) were dissolved in THF (2 mL) and heated at 75° C. for 10 min. The reaction mixture was cooled down to room temperature, diluted with ethyl acetate, washed with saturated sodium bicarbonate, dried, and the solvent eliminated under vacuum. The crude product was purified by preparative thin layer chromatography (dichloromethane:methanol, 9:1) to afford 19 mg of 1-(5-tert-butyl-2-(2,2-dimethyl-3-oxopiperazine-1-carbonyl)-1H-pyrrol-3-yl)-3-(2,3-dichloro-4-fluorophenyl)urea. $^1$H NMR (400 MHz, acetone-$d_6$): δ (ppm) 9.43 (bs, 1H); 8.60 (bs, 2H); 8.20 (m, 1H); 7.30 (t, 1H); 7.03 (bs, 1H); 6.56 (d, 1H); 3.75 (m, 2H); 3.58 (m, 2H); 1.69 (s, 6H); 1.37 (s, 9H).

Example 238

1-(5-tert-Butyl-3-(3,3-dimethyl-1-((3-methyl-1,2,4-oxadiazol-5-yl)methyl)-2-oxopiperazine-4-carbonyl)thiophen-2-yl)-3-(2,3-dichlorophenyl)urea

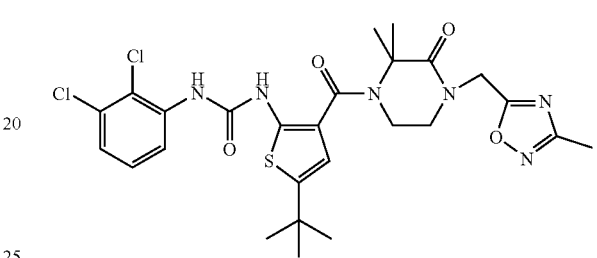

The compound of this example was prepared according to the following scheme and as described below.

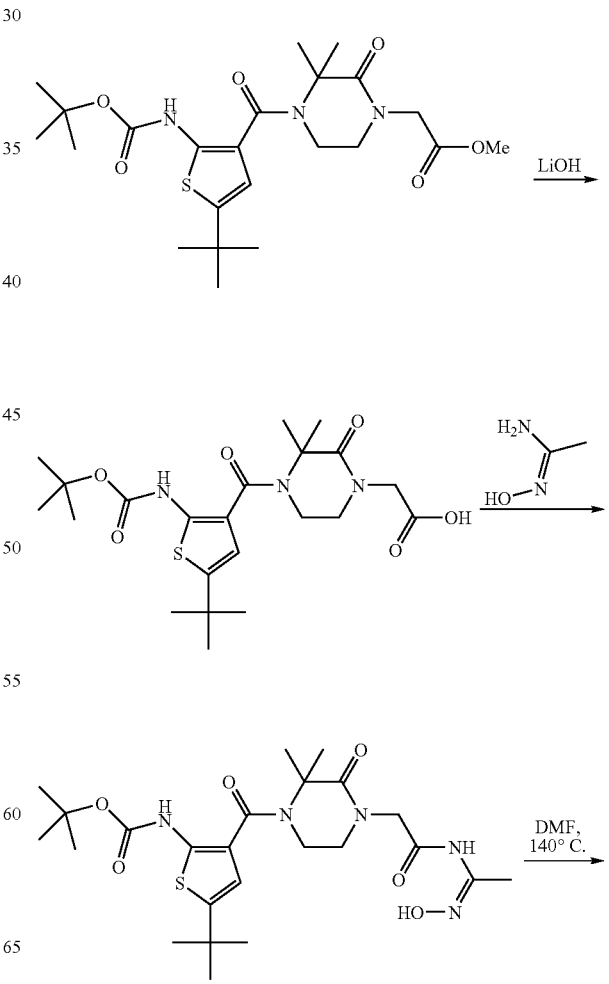

-continued

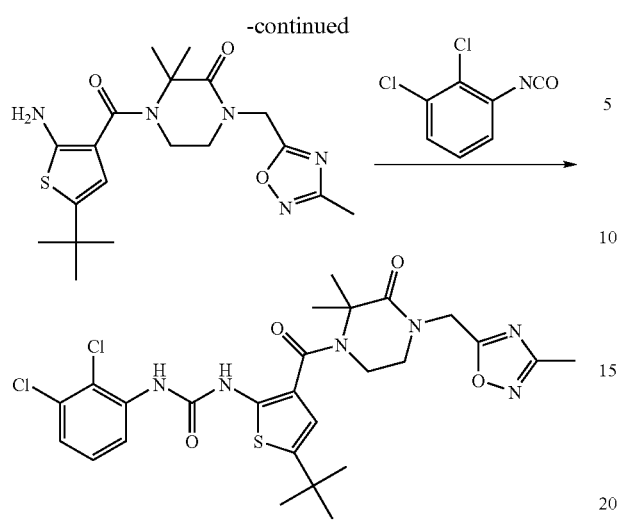

A solution of methyl 2-(4-(2-(tert-butoxycarbonyl)-5-tert-butylthiophene-3-carbonyl)-3,3-dimethyl-2-oxopiperazin-1-yl)acetate (100 mg, 0.21 mmol) and LiOH (0.52 mg) in MeOH (1 mL) was stirred at 75° C. for 3 h. The solvent was removed under vacuum, the residue dissolved in ethyl acetate, dried over anhydrous $Na_2SO_4$, and concentrated under vacuum. A solution of the residue, TBTU (1.0 equiv), DIEA (1.5 eqiv.), and catalytic amount of HOBt dissolved in DMF (1 mL) was stirred at room temperature overnight and then stirred at 140° C. for 9 h. The mixture was diluted with ethyl acetate and washed with water. The organic phase was dried over $Na_2SO_4$, concentrated under vacuum, the crude product dissolved in 1,4-dioxane (1 mL) and aryl isocyanate (50 mg) was added. The reaction mixture was stirred at room temperature overnight. The solvent was removed under vacuum and the crude product was purified by thin layer chromatography eluting with 10% MeOH in dichloromethane to give 1-(5-tert-butyl-3-(3,3-dimethyl-1-((3-methyl-1,2,4-oxadiazol-5-yl)methyl)-2-oxopiperazine-4-carbonyl)thiophen-2-yl)-3-(2,3-dichlorophenyl)urea as a yellow solid. $^1$H NMR (400 MHz, $CDCl_3$): δ (ppm) 10.21 (s, 1H), 8.18 (dd, J=7.4, 2.6 Hz, 1H), 7.81 (s, 1H), 7.18-7.11 (m, 2H), 6.43 (s, 1H), 4.81 (s, 2H), 3.86 (t, J=4.8 Hz, 2H), 3.69-3.64 (m, 2H), 2.38 (s, 3H), 1.82 (s, 6H), 1.34 (s, 9H).

Example 239

1-(5-tert-Butyl-3-(2,2-dimethyl-3-oxopiperazine-1-carbonyl)-1H-pyrrol-2-yl)-3-(2,3-dichlorophenyl)urea

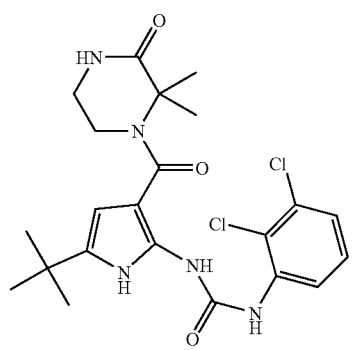

The compound of this example was prepared as follows:

A) Methyl 5-tert-butyl-2-nitro-1H-pyrrole-3-carboxylate

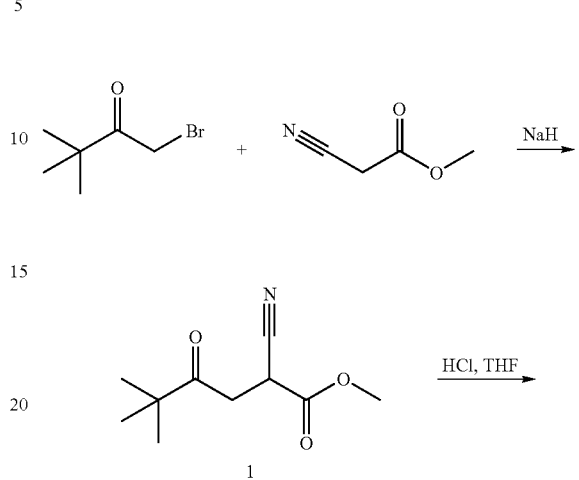

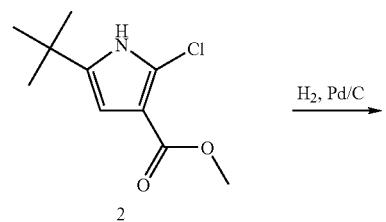

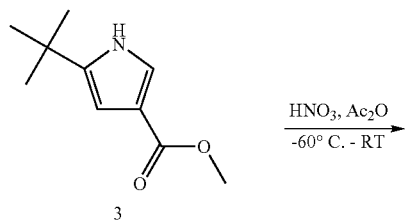

Compound 2 was prepared as reported in *Tetrahedron Lett.* 35, 5989-5922 (1994). To compound 2 in MeOH was added Pd (10% on carbon) and $NH_4OH$. The vial was placed in a Parr shaker under hydrogen at 60 psi and shaken at room temperature over night. The resulting mixture was filtered through celite, eluting with MeOH, the solvent was removed under vacuum to afford compound 3 in a quantitative yield.

To compound 3 (651 mg, 3.59 mmol) in Ac₂O (5 mL) was added concentrated nitric acid (271 mg, 4.30 mmol) in acetic anhydride (3 mL) at −60° C., the reaction mixture was allowed to slowly warm up to 0° C. and kept at that temperature for 2 h. The reaction mixture was then poured into ice-cold saturated aqueous sodium bicarbonate and stirred for 1 h. The product was extracted with ethyl acetate, the organic combined, dried and the solvent eliminated under vacuum. The crude product was flash chromatographed (Hexane:ethyl acetate 4:1) to afford methyl 5-tert-butyl-2-nitro-1H-pyrrole-3-carboxylate (compound 4) (590 mg, 73%) as yellow solid.

B) 5-tert-Butyl-2-nitro-1H-pyrrole-3-carboxylic acid

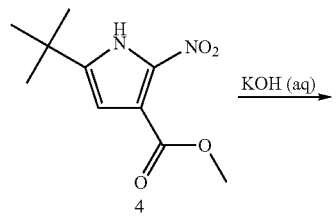

To methyl 5-tert-butyl-2-nitro-1H-pyrrole-3-carboxylate (900 mg, 3.98 mmol) was added 12% aqueous KOH (5 mL), and the resulting reaction mixture was stirred at 80° C. for 30 min. The reaction mixture was poured into 1N aqueous HCl (excess), the aqueous phase was extracted 3 times with dichloromethane, the combined organic layers was dried and concentrated under vacuum to afford 5-tert-butyl-2-nitro-1H-pyrrole-3-carboxylic acid (5) as yellow solid (750 mg, 89%).

C) 4-(2-tert-Butyl-5-nitro-1H-pyrrole-4-carbonyl)-3,3-dimethyl-piperazin-2-one

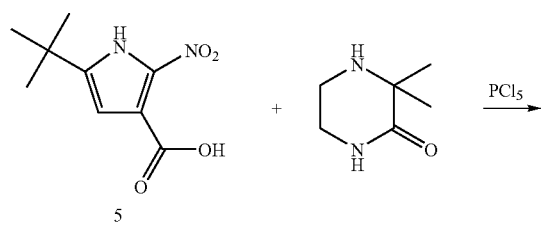

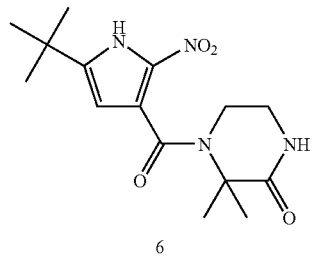

To 5-tert-butyl-2-nitro-1H-pyrrole-3-carboxylic acid (100 mg, 0.47 mmol) in benzene (2 mL) was added solid PCl₅ (120 mg, 0.57 mmol). The resulting reaction mixture was stirred at RT until all the PCl₅ went into the solution. This reaction mixture was then added to 3,3-dimethylpiperazin-2-one (120 mg, 0.94 mmol) and diethylamine (280 ml, 0.94 mmol) in dichloromethane (DCM) (3 mL). After 30 min, the reaction was diluted with DCM (10 mL) and followed by addition of sat. NaHCO₃. The organic phase was then washed with 1N HCl and brine, dried, and concentrated in vacuo. This crude product was further purified using flash chromatography (EtOAc/Hexane: 1/4) to provide 4-(2-tert-butyl-5-nitro-1H-pyrrole-4-carbonyl)-3,3-dimethylpiperazin-2-one 6 (74 mg, 49%) as yellow foam.

D) 4-(2-Amino-5-tert-butyl-1H-pyrrole-3-carbonyl)-3,3-dimethyl-piperazin-2-one

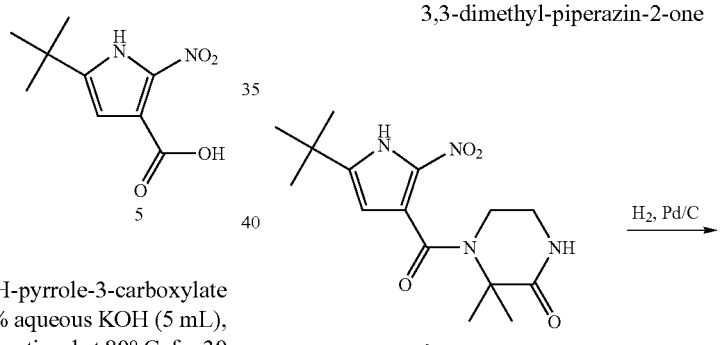

To 4-(2-tert-butyl-5-nitro-1H-pyrrole-4-carbonyl)-3,3-dimethylpiperazin-2-one (120 mg) in methanol (10 mL) was added Pd catalyst (10% on carbon, 60 mg) and the resulting reaction mixture was stirred under H₂ at 60 psi for overnight. After the solids were removed by filtration over Celite, the solvent was removed in vacuo to afford 4-(2-amino-5-tert-butyl-1H-pyrrole-3-carbonyl)-3,3-dimethylpiperazin-2-one 7 as a yellow film (100 mg, 92%).

E) 1-(5-tert-Butyl-3-(2,2-dimethyl-3-oxopiperazine-1-carbonyl)-1H-pyrrol-2-yl)-3-(2,3-dichlorophenyl)urea

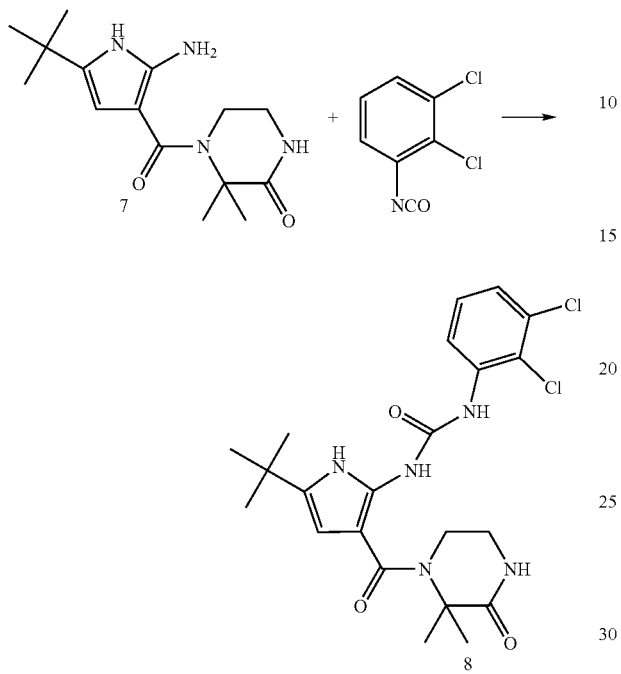

To 4-(2-amino-5-tert-butyl-1H-pyrrole-3-carbonyl)-3,3-dimethyl-piperazin-2-one 7 (60 mg, 0.21 mmol) in THF (1 mL) was added 1,2-dichloro-3-isocyanatobenzene (58 mg, 0.31 mmol) in THF (1 mL). The resulting reaction mixture was stirred at room temperature for 1 h, at which time, TLC indicated the completion of the reaction. The solvent was then removed in vacuo, and the residue was purified by prep. TLC (EtOAc/MeOH: 9.5/0.5) to provide 1-(5-tert-butyl-3-(2,2-dimethyl-3-oxopiperazine-1-carbonyl)-1H-pyrrol-2-yl)-3-(2,3-dichlorophenyl)urea (14.6 mg, 15%) as off-white solid. $^1$H NMR (400 MHz, CD$_3$OD): δ (ppm) 7.93 (t, J=4.9 Hz, 1H), 7.20 (q, J=1.9 Hz, 2H), 5.68 (s, 1H), 3.87 (t, J=5.1 Hz, 2H), 3.44 (t, J=5.0 Hz, 2H), 1.75 (s, 6H), 1.25 (s, 9H).

Example 240

1-(5-tert-Butyl-3-(1,3,3-trimethyl-2-oxopiperazine-4-carbonyl)thiophen-2-yl)-3-(2,3-dichlorophenyl)urea

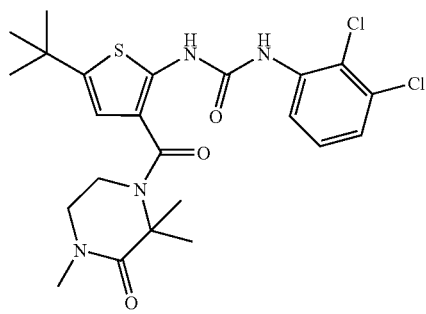

The compound of this example was prepared using the procedure described in Example 179 except that 1,3,3-trimethyl-piperazin-4-one was used instead of 3-ethyl-3-methyl-piperazin-2-one. $^1$H NMR (400 MHz, CDCl$_3$/CD$_3$OD): δ (ppm) 8.01-7.95 (m, 1H), 7.16-7.12 (m, 2H), 6.42 (s, 1H), 3.69 (t, J=4.9 Hz, 2H), 3.46 (t, J=4.9 Hz, 2H), 2.99 (s, 3H), 1.76 (s, 6H), 1.31 (s, 9H).

Example 241

Methyl 2-(1-(2-tert-butyl-5-(3-(2,3-dichlorophenyl)ureido)-1H-pyrrole-4-carbonyl)-2-methyl-3-oxopiperazin-2-yl)acetate

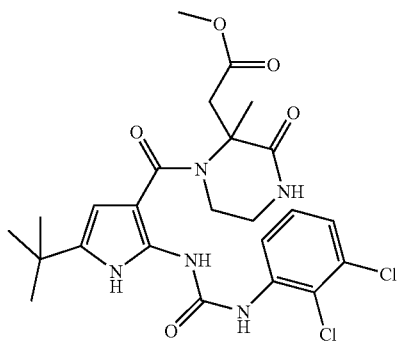

The compound of this example was prepared using the procedure described in Example 243, except that (2-methyl-3-oxo-piperazin-2-yl)-acedit acid methyl ester was used instead of 3,3-dimethyl-piperazin-2-one. $^1$H NMR (400 MHz, CD$_3$OD): δ (ppm) 8.02-7.96 (m, 1H), 7.27-7.20 (m, 2H), 5.76 (s, 1H), 4.82 (s, 17H), 4.10-4.03 (m, 1H), 4.00-3.92 (m, 2H), 3.57 (s, 3H), 3.51-3.44 (m, 1H), 3.41-3.34 (m, 1H), 3.18 (d, J=17.0 Hz, 1H), 1.79 (s, 3H), 1.27 (m, 9H).

Example 242

1-(5-tert-Butyl-3-(2-(2-hydroxyethyl)-2-methyl-3-oxopiperazine-1-carbonyl)-1H-pyrrol-2-yl)-3-(2,3-dichlorophenyl)urea

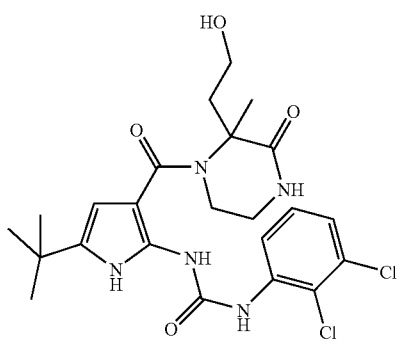

The compound of this example was prepared using the procedure described in Example 239, except that 3-(2-hydroxy-ethyl)-3-methyl-piperazin-2-one was used instead of 3,3-dimethyl-piperazin-2-one. $^1$H NMR (400 MHz, CD$_3$OD): δ (ppm) 8.01-7.95 (m, 1H), 7.25-7.22 (m, 2H), 5.79

(s, 1H), 4.10-4.01 (m, 1H), 3.77-3.69 (m, 1H), 3.64-3.43 (m, 4H), 3.02-2.93 (m, 1H), 2.37 (dt, J=10.7, 5.6 Hz, 1H), 1.75 (s, 3H), 1.25 (s, 9H).

Example 243

1-(5-tert-Butyl-3-(3,3-dimethyl-1-((3-methyl-1,2,4-oxadiazol-5-yl)methyl)-2-oxopiperazine-4-carbonyl)thiophen-2-yl)-3-(2,3-dichloro-4-fluorophenyl)urea

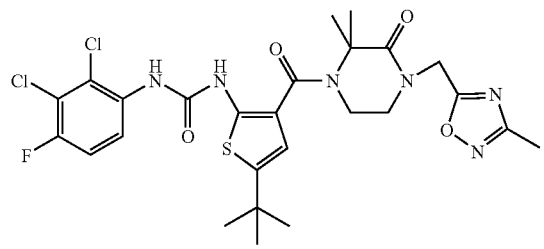

The compound of this example was prepared using the procedure described in Example 242 except that 2,3-dichloro-1-fluoro-4-isocyanatobenzene was used instead of 1,2-dichloro-3-isocyanato-benzene. $^1$H NMR (400 MHz, CDCl$_3$): δ (ppm) 10.19 (s, 1H), 8.12 (q, J=4.8 Hz, 1H), 7.75 (s, 1H), 7.06 (dd, J=9.4, 8.1 Hz, 1H), 6.43 (s, 1H), 4.81 (s, 2H), 3.86 (t, J=5.0 Hz, 2H), 3.66 (t, J=5.0 Hz, 2H), 2.38 (s, 3H), 1.81 (s, 6H), 1.34 (s, 9H).

Example 244

1-(5-tert-Butyl-2-(1,1-dioxy-1-thia-2,5-diazepan-1-one-5-carbonyl)-1H-pyrrol-2-yl)-3-(2,3-dichloro-4-fluorophenyl)urea

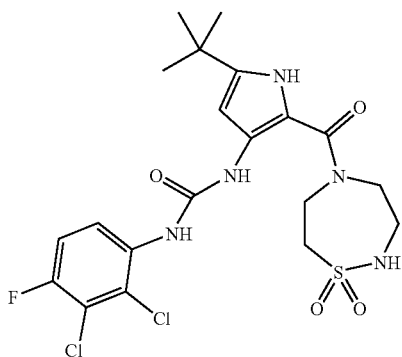

The compound of this example was prepared using the procedure described in Example 237, except that [1,2,5]-thiadiazepane-1,1-dioxide was used instead of 3,3-dimethyl-piperazin-2-one. $^1$H NMR (400 MHz, acetone-d$_6$): δ (ppm) 8.20 (m, 1H); 7.28 (t, 1H); 6.50 (s, 1H); 4.00 (m, 2H); 3.80 (m, 2H); 3.50 (m, 2H); 3.40 (m, 2H); 1.37 (s, 9H).

Example 245

Methyl 2-(1-(2-tert-butyl-4-(3-(2,3-dichloro-4-fluorophenyl)ureido)-1H-pyrrole-5-carbonyl)-2-methyl-3-oxopiperazin-2-yl)acetate

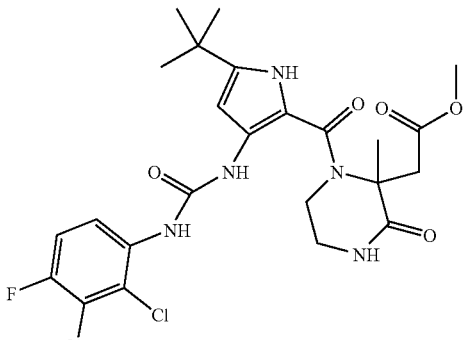

The compound of this example was prepared using the procedure described in Example 237, except that (2-methyl-3-oxo-piperazin-2-yl)-acetic acid methyl ester was used instead of 3,3-dimethyl-piperazin-2-one. $^1$H NMR (400 MHz, acetone-d$_6$): δ (ppm) 9.60 (bs, 1H); 8.30 (m, 2H); 8.03 (bs, 1H); 7.35 (m, 2H); 6.48 (d, 1H); 4.08 (m, 1H); 3.83 (m, 1H); 3.79 (d, 1H); 3.68 (m, 4H); 3.48 (m, 1H); 3.20 (d, 1H); 1.79 (s, 6H); 1.38 (s, 9H).

Example 246

1-(5-tert-Butyl-1-methyl-3-(1,3,3-trimethyl-2-oxopiperazine-4-carbonyl)-1H-pyrrol-2-yl)-3-(2,3-dichlorophenyl)urea

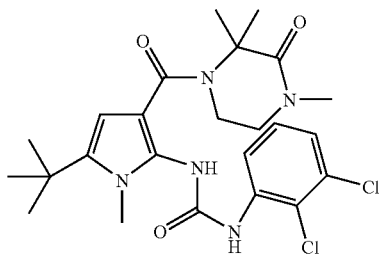

The compound of this example was prepared using the procedure described in Example 239, except that the pyrrole was N-methylated using NaH/MeI. $^1$H NMR (400 MHz, CD$_3$OD): δ (ppm) 7.90 (dd, J=6.7, 3.2 Hz, 1H), 7.07-7.10 (m, 2H), 5.80 (s, 1H), 3.63-3.60 (m, 2H), 3.44 (s, 3H), 3.24-3.28 (m, 2H), 2.80 (s, 3H), 1.80 (s, 6H), 1.26 (s, 9H).

Example 247

1-(Benzo[d][1,3]dioxol-5-yl)-3-(5-tert-butyl-3-(2-oxopiperazine-4-carbonyl)thiophen-2-yl)urea

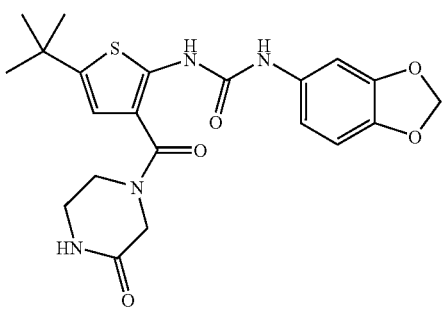

The compound of this example was prepared using the procedure described in Example 58, except that piperazin-2-one was used instead of 1,1-dioxothiomorpholine. ¹H NMR (400 MHz, DMSO-d₆): δ (ppm) 9.66 (s, 1H), 9.64 (s, 1H), 8.04 (s, 1H), 7.10 (d, J=2.0 Hz, 1H), 6.75 (d, J=8.4 Hz, 1H), 6.69 (dd, J=8.4, 2.0 Hz, 1H), 6.56 (s, 1H), 5.89 (s, 2H), 4.01 (s, 2H), 3.64 (t, J=5.3 Hz, 2H), 3.21-3.16 (m, 2H), 1.24 (s, 9H).

Example 248

1-(5-tert-Butyl-3-(2-(2-hydroxyethyl)-2-methyl-3-oxopiperazine-1-carbonyl)thiophen-2-yl)-3-(3-chloro-2-methoxyphenyl)urea

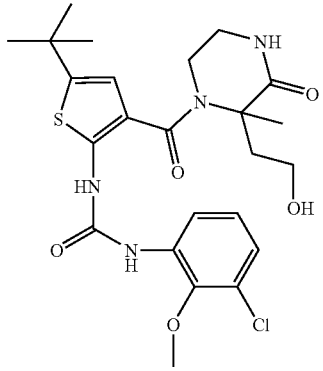

The compound of this example was prepared using the procedure described in Example 194, except that 2-methoxy-3-chlorophenylisocyanate was used instead of 2,3-dichloro-4-fluorophenylisocyanate. ¹H NMR (400 MHz, CDCl₃): δ (ppm) 9.60 (s, 1H), 8.17-8.13 (m, 2H), 6.98-6.91 (m, 2H), 6.51 (s, 1H), 3.87-3.78 (m, 2H), 3.76 (s, 3H), 3.69-3.60 (m, 1H), 3.58-3.42 (m, 2H), 3.27-3.21 (m, 1H), 2.81-2.72 (m, 1H), 2.52-2.45 (m, 1H), 1.71 (s, 3H), 1.28 (s, 9H).

Example 249

1-(5-tert-Butyl-3-(2-(2-hydroxyethyl)-2-methyl-3-oxopiperazine-1-carbonyl)thiophen-2-yl)-3-(2,3-dichlorophenyl)urea

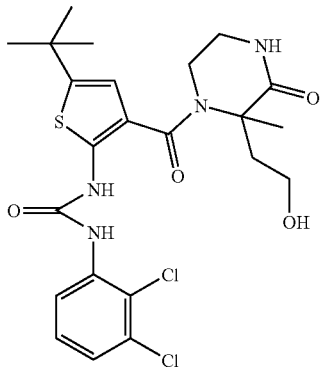

The compound of this example was prepared using the procedure described in Example 194, except that 2,3-dichlorophenylisocyanate was used instead of 2,3-dichloro-4-fluorophenylisocyanate. ¹H NMR (400 MHz, CD₃COCD₃): δ (ppm) 10.09 (s, 1H), 8.77 (s, 1H), 8.24 (dd, J=8.0, 1.7 Hz, 1H), 7.38-7.26 (m, 3H), 6.64 (s, 1H), 4.22 (s, 1H), 3.93-3.86 (m, 1H), 3.73-3.54 (m, 4H), 3.46-3.40 (m, 1H), 2.98-2.90 (m, 1H), 2.38-2.30 (m, 1H), 1.74 (s, 3H), 1.36 (s, 9H).

Example 250

Methyl 2-(1-(2-tert-butyl-3-(3-(2,3-dichloro-4-fluorophenyl)ureido)-thiophene-5-carbonyl)-2-methyl-3-oxo-4-ethylacetyl-piperazin-2-yl)acetate

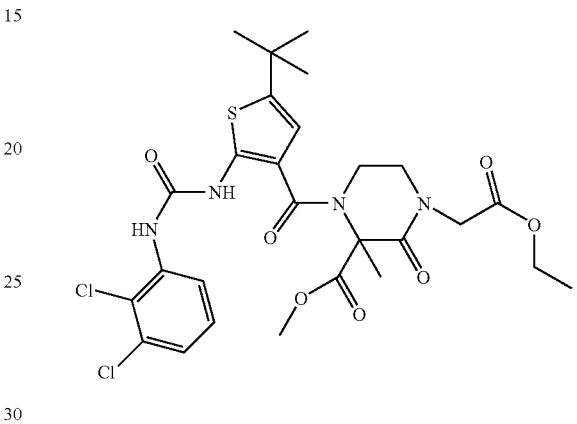

The compound of this example was prepared using the procedure described in Example 187, except that 1-(ethyl-2-aminoacetyl)-methyl-2-(2-methyl-3-oxopiperazin-2-yl)acetate was used instead of methyl-2-(2-methyl-3-oxopiperazin-2-yl)acetate. ¹H NMR (400 MHz, CDCl₃): δ (ppm) 9.38 (s, 1H), 8.27 (dd, J=7.9, 2.0 Hz, 1H), 7.95 (s, 1H), 7.19 (s, 1H), 7.18-7.16 (m, 2H), 6.62 (s, 1H), 4.30 (d, J=17.3 Hz, 1H), 4.18-4.14 (m, 1H), 4.12-4.05 (m, 2H), 3.99 (d, J=17.3 Hz, 1H), 3.81-3.74 (m, 1H), 3.71 (s, 3H), 3.66-3.60 (m, 1H), 3.55-3.48 (m, 1H), 3.31 (d, J=17.3 Hz, 1H), 1.85 (s, 3H), 1.34 (s, 9H), 1.23 (t, J=7.1 Hz, 3H).

Example 251

1-(3-(1,3-bis(2-Amino-2-oxoethyl)-3-methyl-2-oxopiperazine-4-carbonyl)-5-tert-butylthiophen-2-yl)-3-(2,3-dichlorophenyl)urea

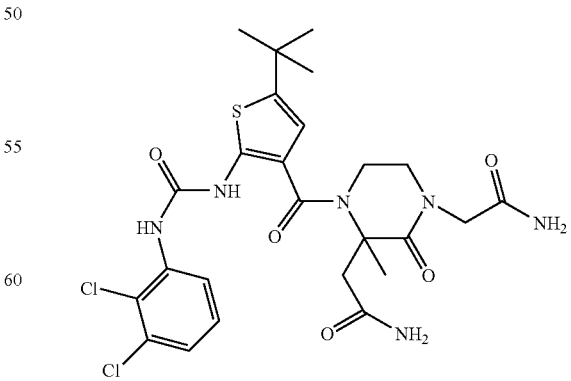

The compound of this example was made from compound of Example 250 by first hydrolysis with LiOH to give the corresponding acid followed by coupling with ammonia using EDCI and HOBt to give the expected amide. $^1$H NMR (400 MHz, CD$_3$OD): δ (ppm) 8.04 (dd, J=7.1, 2.7 Hz, 1H), 7.27-7.21 (m, 2H), 6.58 (s, 1H), 4.16 (s, 1H), 4.09 (d, J=21.8 Hz, 2H), 4.03-3.97 (m, 1H), 3.92 (d, J=16.1 Hz, 1H), 3.73-3.67 (m, 2H), 3.55-3.48 (m, 1H), 3.15 (d, J=16.0 Hz, 1H), 1.82 (s, 3H), 1.35 (s, 9H).

Example 252

1-(3-(1,3-bis(2-(Methoxyamino)-2-oxoethyl)-3-methyl-2-oxopiperazine-4-carbonyl)-5-tert-butylthiophen-2-yl)-3-(2,3-dichlorophenyl)urea

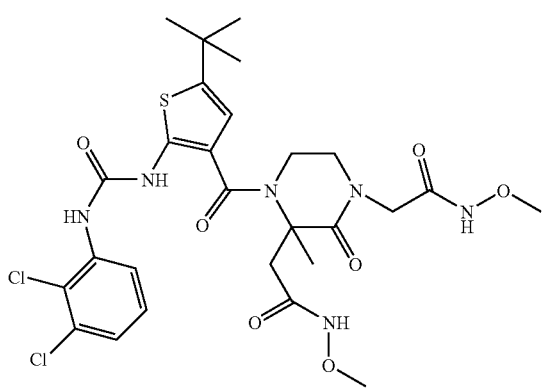

The compound of this example was prepared using the procedure described in Example 251, except that N-methoxyamine was used instead of ammonia. $^1$H NMR (400 MHz, CD$_3$OD): δ (ppm) 8.04 (dd, J=6.6, 3.1 Hz, 1H), 7.23-7.18 (m, 2H), 6.55 (s, 1H), 4.09-3.96 (m, 3H), 3.75-3.70 (m, 2H), 3.68 (s, 3H), 3.61 (s, 3H), 3.58-3.46 (m, 1H), 1.83 (s, 3H), 1.33 (s, 9H).

Example 253

1-(5-tert-Butyl-3-(2-(2-hydroxyethyl)-2-methyl-3-oxopiperazine-1-carbonyl)thiophen-2-yl)-3-(3-fluoro-2-methylphenyl)urea

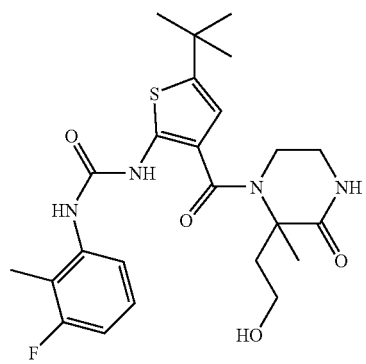

The compound of this example was prepared using the procedure described in Example 194, except that 3-fluoro-2-methylphenylisocyanate was used instead of 2,3-dichloro-4-thiosophenylisocyanate. $^1$H NMR (400 MHz, CDCl$_3$): δ (ppm) 9.97 (s, 1H), 7.72 (d, J=8.4 Hz, 1H), 7.34 (s, 1H), 7.12 (q, J=7.6 Hz, 1H), 6.79 (t, J=8.7 Hz, 1H), 6.65 (s, 1H), 6.45 (s, 1H), 4.99 (s, 1H), 3.84-3.77 (m, 1H), 3.67-3.54 (m, 3H), 3.48-3.40 (m, 1H), 3.30-3.23 (m, 1H), 2.83-2.75 (m, 1H), 1.68 (s, 3H), 1.29 (s, 9H).

Example 254

1-(5-tert-Butyl-3-(2-(2-hydroxyethyl)-2-methyl-3-oxopiperazine-1-carbonyl)thiophen-2-yl)-3-(3-fluoro-2-methylphenyl)urea

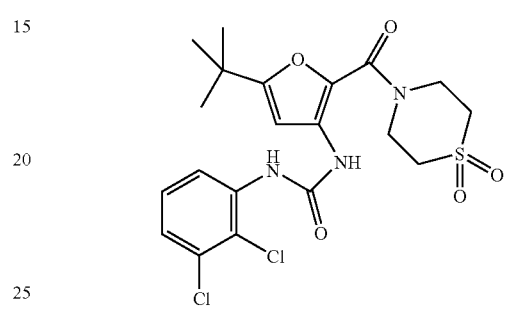

The compound of this example was prepared using the procedure described in Example 273. $^1$H NMR (400 MHz, CD$_3$OD) δ (ppm) 1.34 (s, 9H), 3.23 (m, 4H), 4.27 (m, 4H), 6.97 (s, 1H), 7.15 (m, 2H), 7.83 (d, J=8 Hz, 1H).

Example 255

1-(3-(2-(2-Amino-2-oxoethyl)-2-methyl-3-oxopiperazine-1-carbonyl)-5-tert-butylthiophen-2-yl)-3-(2,3-dichloro-4-fluorophenyl)urea

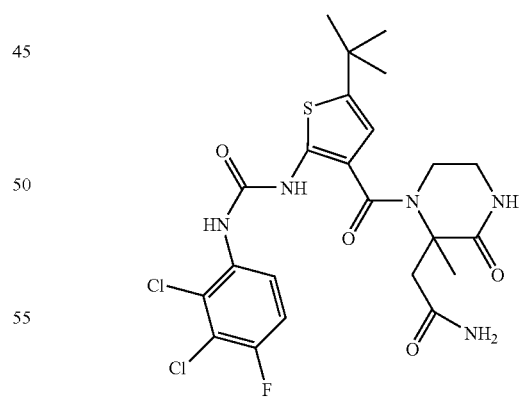

The compound of this example was prepared using the procedure described in Example 225, except that ammonia was used instead of N-methyoxyamine. $^1$H NMR (400 MHz, CD$_3$OD): δ (ppm) 8.02 (dd, J=9.2, 5.3 Hz, 1H), 7.17 (t, J=8.9 Hz, 1H), 6.58 (s, 1H), 3.94-3.89 (m, 1H), 3.86 (d, J=16.2 Hz, 1H), 3.71-3.65 (m, 1H), 3.52-3.46 (m, 1H), 3.37-3.31 (m, 1H), 3.05 (d, J=16.0 Hz, 1H), 1.82 (s, 3H), 1.34 (s, 9H).

Example 256

1-(2,3-Dichloro-4-fluorophenyl)-3-(2-(2,2-dimethyl-3-oxopiperazine-1-carbonyl)-5-tert-pentyl-1H-pyrrol-3-yl)urea

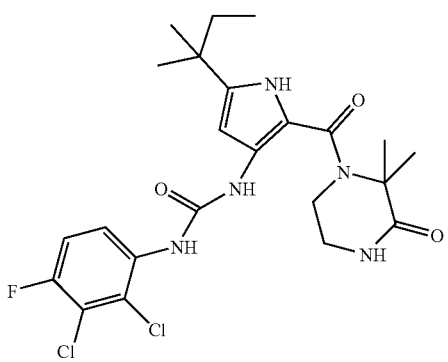

The compound of this example was prepared using the procedure described in Example 240, except that 2-chloro-2-methylbutane was used instead of t-butylchloride. $^1$H NMR (400 MHz, acetone-$d_6$): δ (ppm) 9.40 (bs, 1H); 8.60 (d, 2H); 8.20 (m, 1H); 7.30 (t, 1H); 7.13 (bs, 1H); 6.55 (d, 1H); 3.77 (m, 2H); 3.58 (m, 2H); 1.70 (s, 6H); 1.30 (m, 2H); 0.80 (t, 3H).

Example 257

1-(2,3-Dichlorophenyl)-3-(2-(2,2-dimethyl-3-oxopiperazine-1-carbonyl)-5-tert-pentyl-1H-pyrrol-3-yl)urea

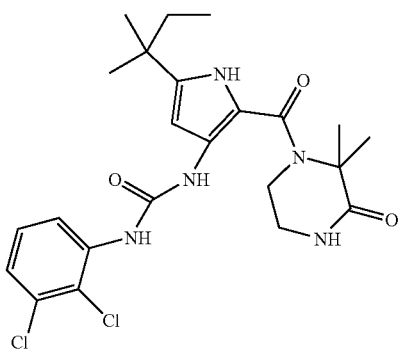

The compound of this example was prepared using the procedure described in Example 256, except that 2,3-dichloroaniline was used instead of 2,3-dichloro-4-fluoroaniline. $^1$H NMR (400 MHz, acetone-$d_6$): δ (ppm) 9.40 (bs, 1H); 8.60 (bs, 2H); 8.28 (d, 1H); 7.30 (t, 1H); 7.20 (d, 1H); 7.04 (bs, 1H); 6.52 (d, 1H); 3.77 (m, 2H); 3.58 (m, 2H); 1.68 (s, 6H); 1.30 (m, 2H); 0.80 (t, 3H).

Example 258

1-(2,3-Dichlorophenyl)-3-(2-(dioxothiomorpholine-4-carbonyl)-5-(trifluoromethyl)phenyl)urea

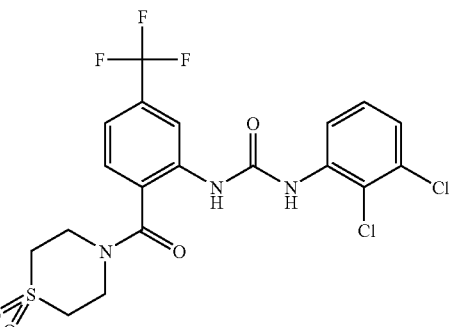

The compound of this example was prepared as shown in the following scheme and described below.

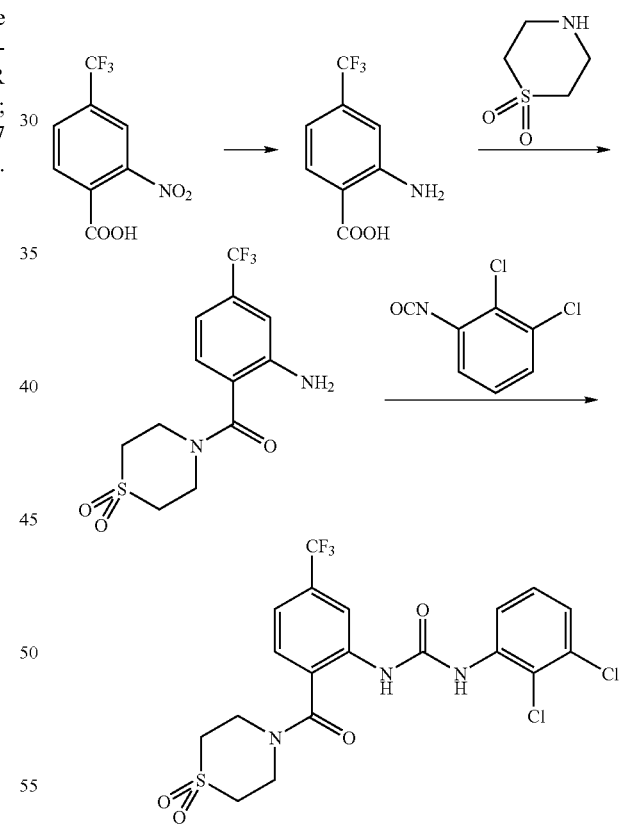

To a 100 mL flask containing 2-nitro-4-(trifluoromethyl)benzoic acid (940.5 mg, 4 mmol) in 30 mL MeOH was added 100 mg of 10% Pd on charcoal After flushing with hydrogen three times, the reaction mixture was agitated under hydrogen atmosphere for 2 h. The mixture was filtered through a plug of Celite, and the filtrate was concentrated to afford 2-amino-4-(trifluoromethyl)benzoic acid (740 mg, 3.6 mmol, 90%).

To a solution of 2-amino-4-(trifluoromethyl)benzoic acid (410 mg, 2 mmol) in dichloromethane (5 mL) were added thiomorpholine 1,1-dioxide (405 mg, 3 mmol), HOBt (340 mg, 2.5 mmol), EDCI (479 mg, 2.5 mmol), and the mixture was stirred at room temperature for 16 h. The volatiles were evaporated by under reduced pressure to give the crude product which was extracted twice with ethyl acetate:aqueous NaHCO$_3$. The organic layer was dried, concentrated, and the residue was used as such in the next reaction (580 mg).

To a solution of the previously prepared aniline (32 mg, 0.1 mmol) in dichloromethane (3 mL) was added 1,2-dichloro-3-isocyanatobenzene (18.8 mg, 0.1 mmol), and the reaction mixture was stirred for 2 h. After removal of volatiles, the crude product was purified by chromatographic column using a gradient of MeOH in dichloromethane as eluent to give 1-(2,3-dichlorophenyl)-3-(2-(dioxothiomorpholine-4-carbonyl)-5-(trifluoro-methyl)-phenyl)urea as a white solid (12.4 mg). $^1$H NMR (400 MHz, CD$_3$OD) δ (ppm) 8.07 (dd, J=6.8, 2.8 Hz, 1H), 7.83 (s, 1H), 7.58 (d, J=8.0 Hz, 1H), 7.46 (m, 1H), 7.25-7.20 (2H), 4.20 (m, 2H), 3.93 (m, 2H), 3.24 (m, 4H).

Example 259

1-(2,3-Dichlorophenyl)-3-(3-(dioxothiomorpholine-4-carbonyl)-5-(trifluoromethyl)phenyl)urea

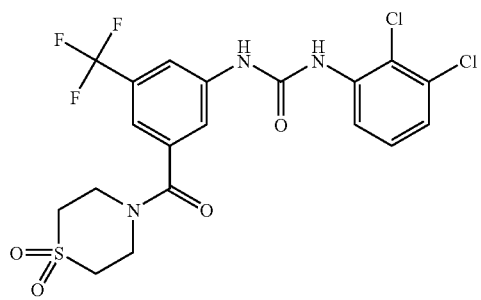

The compound of this example was prepared as shown in the following scheme and described below.

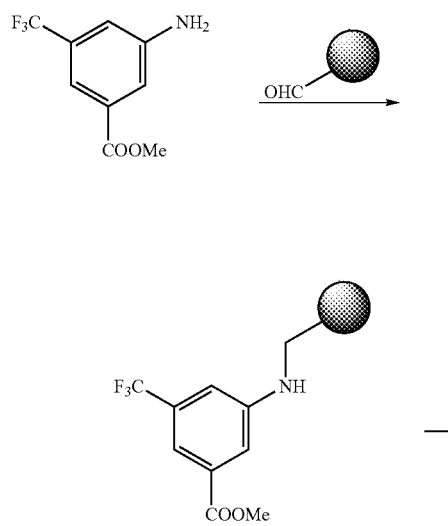

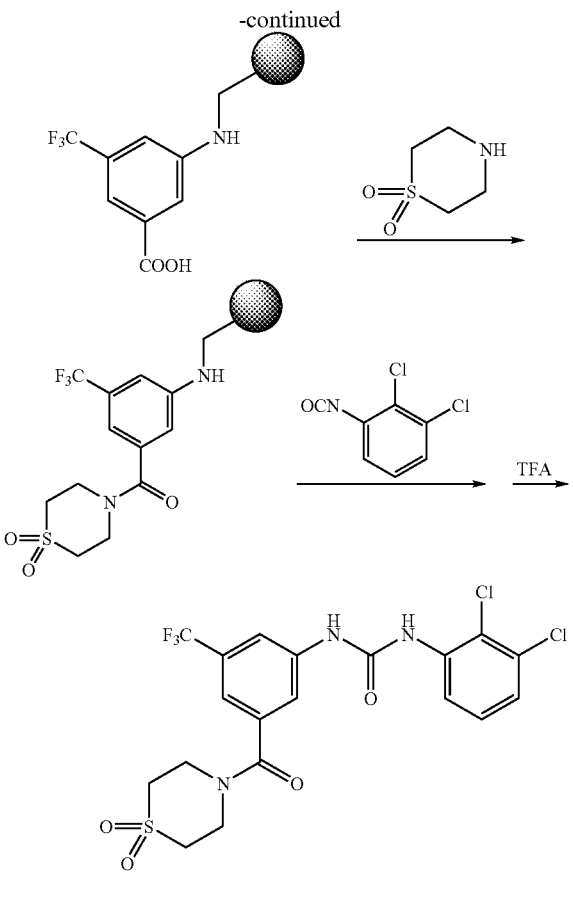

Indole aldehyde resin (0.9 g, 1.1 mmol/g, 1 mmol) was placed into a 20 mL syringe reactor. Methyl 3-amino-5-(trifluoromethyl)benzoate (440 mg, 1.0 mmol) in 5% AcOH in DMF (10 mL) was charged to the syringe, and the syringe was shaken for 2 h. A solution of NaBH(OAc)$_3$ (212 mg, 1.0 mmol) in 5% AcOH in DMF (3 mL) was added to the syringe. After shaking at room temperature for 2 h, additional solution of NaBH(OAc)$_3$ (212 mg, 1.0 mmol) in 5% AcOH in DMF (2 mL) was added to the syringe and the reaction was shaken at room temperature overnight. The resin was washed with 5% AcOH in DMF (2×20 mL), DMF (2×20 mL), dichloromethane (2×20 mL), 10% diisopropylethylamine in dichloromethane (2×20 mL), dichloromethane (4×20 mL), and dried under vacuum.

A heterogeneous suspension of the resin prepared above (1 mmol), LiOH hydrate (200 mg) in THF:water (4:1, 3 mL) was vigorously stirred at room temperature for 3 days. The resin was washed with THF (4×20 mL), water (4×20 mL), dichloromethane (4×20 mL), and dried under high vacuum. An aliquot of acid intermediate prepared as described above (0.1 mmol) was treated with EDCI (96 mg, 0.5 mmol), HOBt (68 mg, 0.5 mmol) and thiomorpholine 1,1-dioxide (68 mg, 0.5 mmol) in dichloromethane (2 mL) at room temperature for 12 h, and washed with dichloromethane (2×3 mL), MeOH (2×3 mL), dichloromethane (3×3 mL), and dried under vacuum.

The resin prepared above (0.1 mmol) in dichloromethane (2 mL) was treated with 1,2-dichloro-3-isocyanatobenzene (94 mg, 0.5 mmol) for 16 h, then washed with dichloromethane (2×3 mL), MeOH (2×3 mL), dichloromethane (3×3 mL), and treated with 50% TFA: dichloromethane (2 mL) for 1 min in a 5 mL syringe, and the cleavage solution was filtered. The resin was washed with dichloromethane (1 mL), and the combined solution was evaporated by nitrogen blowing under mild heating to give the product which was extracted with ethyl acetate:aqueous NaHCO$_3$. The desired 1-(2,3-dichlorophenyl)-3-(3-(dioxothiomorpholine-4-carbonyl)-5-(trifluoromethyl)phenyl)urea was crystallized from MeOH (3 day-standing at room temp, 17.4 mg). $^1$H NMR (400 MHz, CD$_3$OD) δ 8.12 (m, 1H), 7.88 (m, 2H), 7.47 (s, 1H), 7.28-7.21 (2H), 4.18 (m, 2H), 3.90 (m, 2H), 3.23 (m, 4H).

Example 260

1-(5-tert-Butyl-3-(5-oxo-1,4-diazepane-1-carbonyl)thiophen-2-yl)-3-(2-tert-butylphenyl)urea

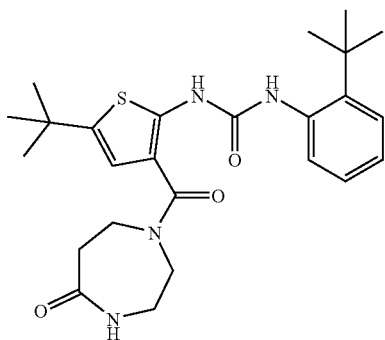

The compound of this example was prepared using the solid phase procedure described above. $^1$H NMR (400 MHz, CD$_3$OD) δ 7.43 (m, 1H), 7.23-7.17 (3H), 6.56 (s, 1H), 3.73 (m, 4H), 3.33 (m, 2H), 2.69 (m, 2H), 1.37 (s, 9H), 1.32 (s, 9H).

Example 261

1-(5-tert-Butyl-3-(5-oxo-1,4-diazepane-1-carbonyl)thiophen-2-yl)-3-(2-methoxyphenyl)urea

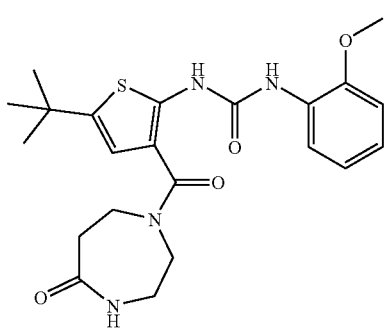

The compound of this example was prepared using the solid state procedure described above. $^1$H NMR (400 MHz, CD$_3$OD) δ 7.98 (dd, j 8.0, 1.6 Hz, 1H), 7.12-6.93 (2H), 6.88 (m, 1H), 6.56 (s, 1H), 3.85 (s, 3H), 3.74 (m, 4H), 3.34 (m, 2H), 2.70 (m, 2H), 1.34 (s, 9H).

Example 262

Methyl 2-(4-(2-tert-Butyl-4-(3-(2,3-dichlorophenyl)ureido)-1H-pyrrole-5-carbonyl)-3,3-dimethyl-2-oxopiperazin-1-yl)acetate

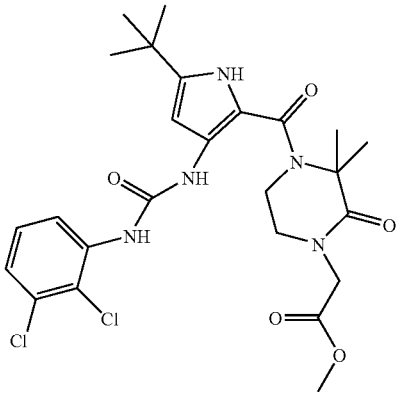

The compound of this example was prepared using the procedure described in Example 237, except that methyl-2-(3,3-dimethyl-2-oxopiperazin-1-yl)acetate was used instead of 3,3-dimethylpiperazin-2-one and the corresponding aniline. $^1$H NMR (400 MHz, acetone-d$_6$): δ (ppm) 9.60 (bs, 1H); 8.60 (d, 2H); 8.26 (d, 1H); 7.30 (t, 1H); 7.20 (d, 1H); 6.56 (d, 1H); 4.18 (s, 2H); 3.81 (m, 2H); 3.68 (m, 2H); 1.70 (s, 6H); 1.37 (s, 9H).

Example 263

1-(5-tert-Butyl-2-(1-(2-(methoxy(methyl)amino)-2-oxoethyl)-3,3-dimethyl-2-oxopiperazine-4-carbonyl)-1H-pyrrol-3-yl)-3-(2,3-dichlorophenyl)urea

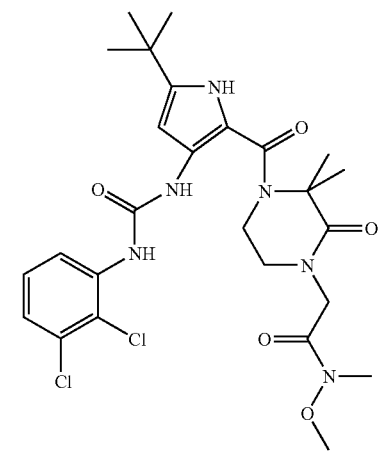

The compound of this example was prepared from compound 262 using the procedure described for compound 251, using N-methoxy-N-methylamine. $^1$H NMR (400 MHz, acetone-d$_6$): δ (ppm) 9.60 (bs, 1H); 8.62 (d, 2H); 8.26 (d, 1H);

7.30 (t, 1H); 7.20 (d, 1H); 6.56 (d, 1H); 4.35 (s, 2H); 3.81 (m, 2H); 3.79 (s, 3H); 3.62 (m, 2H); 3.18 (s, 3H); 1.72 (s, 6H); 1.37 (s, 9H).

Example 264

1-(5-tert-Butyl-2-(2,2-dimethyl-3-oxopiperazine-1-carbonyl)-1-methyl-1H-pyrrol-3-yl)-3-(2,3-dichlorophenyl)urea

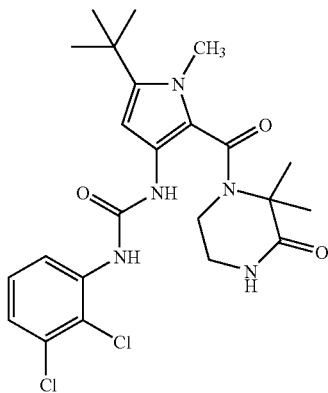

The compound of this example was prepared using the procedure described in Example 209, except that the pyrrole nitrogen was N-methylated using NaH/MeI. $^1$H NMR (400 MHz, CD$_3$OD): δ (ppm) 8.00 (d, 1H); 7.20 (m, 2H); 6.98 (s, 1H); 3.80 (m, 1H); 3.44 (m, 2H); 3.24 (m, 1H); 1.80 (d, 6H); 1.40 (s, 9H).

Example 265

1-(Benzo[d][1,3]dioxol-4-yl)-3-(5-tert-butyl-3-(2-oxopiperazine-4-carbonyl)thiophen-2-yl)urea

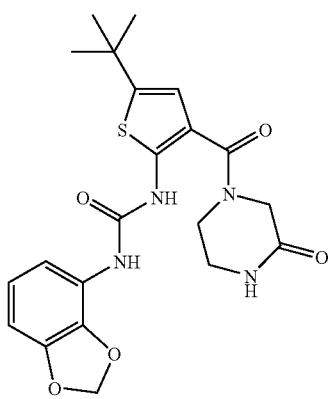

The compound of this example was prepared using the procedure described in Example 179. $^1$H NMR (400 MHz, CDCl$_3$/CD$_3$OD): δ (ppm) 7.31 (d, J=8.4 Hz, 1H), 6.75 (t, J=8.2 Hz, 1H), 6.55 (d, J=7.8 Hz, 1H), 6.50 (s, 1H), 5.92 (s, 2H), 4.25 (s, 2H), 3.81 (t, J=5.4 Hz, 2H), 3.38 (t, J=5.3 Hz, 2H), 1.31 (s, 9H).

Example 266

1-(Benzo[d][1,3]dioxol-4-yl)-3-(5-tert-butyl-3-(5-oxo-1,4-diazepane-1-carbonyl)thiophen-2-yl)urea

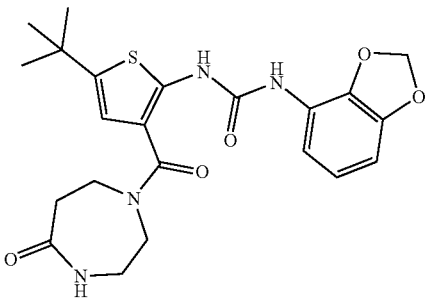

The compound of this example was prepared using the procedure described in Example 179. $^1$H NMR (400 MHz, CD$_3$OD): δ (ppm) 7.28 (d, J=8.4 Hz, 1H), 6.76 (t, J=8.1 Hz, 1H), 6.57 (dd, J=7.8, 0.9 Hz, 1H), 6.57 (s, 1H), 5.93 (s, 2H), 3.77-3.70 (m, 4H), 3.38-3.33 (m, 2H), 2.75-2.68 (m, 2H), 1.33 (s, 9H).

Example 267

1-(5-tert-Butyl-3-(1-(2-(dimethylamino)ethyl)-3-ethyl-3-methyl-2-oxopiperazine-4-carbonyl)thiophen-2-yl)-3-(4-fluorophenyl)urea

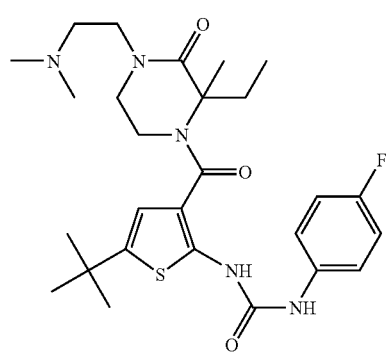

The compound of this example was prepared using the procedure described in Example 179. $^1$H NMR (400 MHz, CD$_2$Cl$_2$): δ (ppm) 9.73 (s, 1H), 7.83 (s, 1H), 7.32-7.27 (m, 2H), 6.97 (t, J=8.7 Hz, 2H), 6.46 (s, 1H), 3.96 (d, J=12.4 Hz, 1H), 3.67-3.51 (m, 3H), 3.42-3.34 (m, 2H), 2.71-2.61 (m, 1H), 2.45 (t, J=6.3 Hz, 2H), 2.22 (s, 6H), 2.10-2.03 (m, 1H), 1.70 (s, 3H), 1.36 (s, 9H), 0.75 (t, J=7.4 Hz, 3H).

Example 268

1-(5-tert-Butyl-3-(4,4-dioxy-4-thiomorpholine-1-carbonyl)thiophen-2-yl)-3-(benzo[d][1,3]dioxol-4-yl)urea

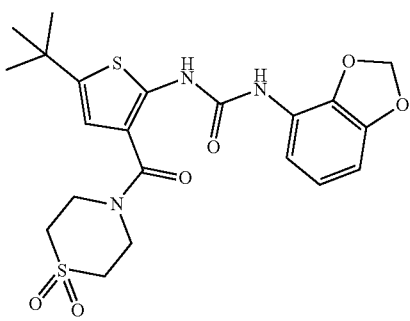

The compound of this example was prepared using the procedure described in Example 179. ¹H NMR (400 MHz, CDCl₃/CD₃OD): δ (ppm) 7.29 (d, J=8.4 Hz, 1H), 6.75 (t, J=8.1 Hz, 1H), 6.56 (d, J=7.8 Hz, 1H), 6.53 (s, 1H), 5.93 (d, J=5.9 Hz, 2H), 4.07 (t, J=4.9 Hz, 4H), 3.15 (t, J=5.1 Hz, 4H), 1.32 (s, 9H).

Example 269

1-(5-tert-Butyl-3-(1-(2-(methoxy(methyl)amino)-2-oxoethyl)-3,3-dimethyl-2-oxopiperazine-4-carbonyl)thiophen-2-yl)-3-(2-chloro-4-fluorophenyl)urea

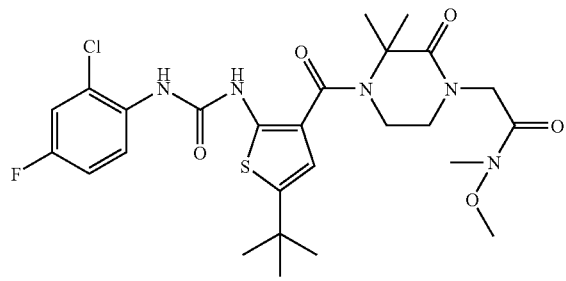

The compound of this example was prepared using the procedure described in Example 263. ¹H NMR (400 MHz, CDCl₃): δ (ppm) 10.14 (s, 1H), 8.14 (dd, J=9.2, 5.6 Hz, 1H), 7.84 (s, 1H), 7.03 (dd, J=8.1, 3.0 Hz, 1H), 6.97-6.90 (m, 1H), 6.42 (s, 1H), 4.31 (s, 2H), 3.85 (t, J=4.8 Hz, 2H), 3.76 (s, 3H), 3.54 (t, J=4.8 Hz, 2H), 3.19 (s, 3H), 1.79 (s, 6H), 1.32 (s, 9H).

Example 270

1-(5-tert-Butyl-2-(1,1-dioxy-1-thia-2,5-diazepan-1-one-5-carbonyl)furan-3-yl)-3-(2,3-dichlorophenyl)urea

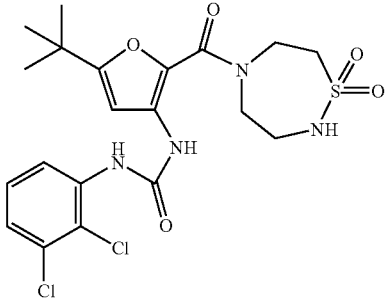

The compound of this example was prepared using the procedure described in Example 276. ¹H NMR (400 MHz, CD₃OD) δ (ppm) 1.20 (s, 9H), 3.25-3.39 (m, 4H), 3.82-4.33 (s brd, 4H), 4.72 (s brd, 1H), 6.98 (s, 1H), 7.17 (m, 2H), 8.03 (d, J=8 Hz, 1H), 8.64 (s brd, 1H).

Example 271

1-(5-tert-Butyl-3-(2,2-dimethyl-3-oxopiperazine-1-carbonyl)thiophen-2-yl)-3-(4-chlorobenzo[d][1,3]dioxol-5-yl)urea

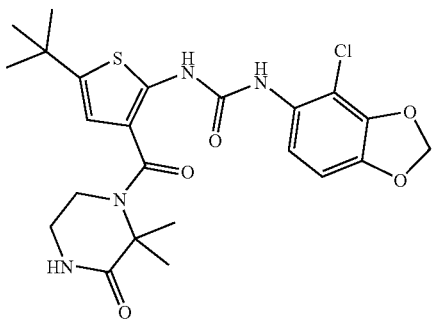

The compound of this example was prepared as follows.

A) 2-Chloro-3,4-dihydroxybenzoic acid: To a round-bottom flask containing 2-chloro-3,4-dimethoxybenzoic acid (1.00 g, 4.6 mmol, 1 equiv.) in DCM (25 mL) at 0° C. under nitrogen was added 1M solution of BBr₃ in DCM (9.5 mL, 2.0 equiv.) slowly dropwise over a 10-minute period. The solution was stirred at 0° C. and allowed to warm slowly to room temperature and stirred for. 8 h, the mixture was cooled in an ice bath and quenched by dropwise addition of water (5 mL) followed by addition of 2M NaOH (ca. 15 mL). The organic layer was extracted once with water. The combined aqueous layers were acidified with concentrated HCl, extracted with ethyl acetate. The combined organic layers, dried over anhydrous Na₂SO₄, filtered and solvent was removed under vacuum to give quantitative yield of 2-chloro-3,4-dihydroxybenzoic acid as a light brown solid.

B) Methyl 2-chloro-3,4-dihydroxybenzoate: To a vial containing 2-chloro-3,4-dihydroxybenzoic acid (0.873 g, 4.6 mmol, 1 equiv.) in 4.5 mL MeOH at 0° C. was added SOCl$_2$ (0.68 mL, 9.35 mmol, 2.0 equiv.) slowly dropwise. The vial was capped and the stirred solution was allowed to warm to room temperature and stirred for 24 h. The solvent eliminated under vacuum, the residue dissolved in ethyl acetate, washed with saturated NaHCO$_3$, brine, dried over anhydrous Na$_2$SO$_4$, filtered and the solvent removed under vacuum to give 899.8 mg (96%) of methyl 2-chloro-3,4-dihydroxybenzoate as a brown solid.

C) Methyl 4-chlorobenzo[d][1,3]dioxole-5-carboxylate

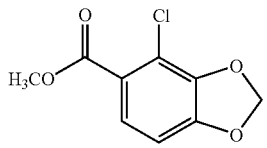

To a heavy walled vial containing methyl 2-chloro-3,4-dihydroxybenzoate (899.8 mg, 4.4 mmol, 1 equiv.) in 13 mL DMF was added KF (1.29 g, 22.2 mmol, 5 equiv.) and the mixture was stirred at room temperature for 30 min. Dibromomethane (0.375 mL, 5.3 mmol, 1.2 equiv.) was added and the mixture was heated to 120° C. for 4 h. The mixture was cooled down to room temperature, diluted with water, and extracted with ethyl ether. The combined ether layers were washed with 1M NaOH, water, brine, dried over anhydrous Na$_2$SO$_4$, filtered and solvent removed under vacuum. The crude product was absorbed onto silica and purified by flash column (silicagel, hexane:ethyl acetate 8 Å to give 395.8 mg (42%) of methyl 4-chlorobenzo[d][1,3]dioxole-5-carboxylate as a colorless crystalline solid. See *Tetrahedron Lett.* 38: 3361-3364 (1978); U.S. Patent Appl. Publication No. 20050009867.

D) 4-Chlorobenzo[d][1,3]dioxole-5-carboxylic acid

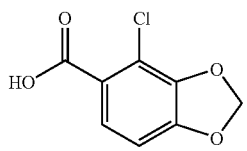

To a vial containing methyl 4-chlorobenzo[d][1,3]dioxole-5-carboxylate (395.8 mg, 1.8 mmol, 1 equiv.) in 3:1 THF:H$_2$O (15 mL) was added LiOH.H$_2$O (153.3 mg, 3.7 mmol, 2 equiv.). The vial was capped and the mixture was stirred at 70° C. for 2 h, diluted with water, acidified with 1M HCl to pH <3, and extracted with ethyl acetate. The combined organic layers was dried over anhydrous Na$_2$SO$_4$, filtered and the solvent was removed under vacuum to give a quantitative yield of 4-chlorobenzo[d][1,3]dioxole-5-carboxylic acid as a white solid.

E) tert-Butyl 4-chlorobenzo[d][1,3]dioxol-5-ylcarbamate

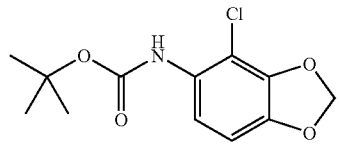

To a vial containing 4-chlorobenzo[d][1,3]dioxole-5-carboxylic acid (349 mg, 1.7 mmol, 1 equiv.) in t-BuOH (9 mL) was added TEA (0.61 mL, 4.4 mmol, 2.5 equiv.) and DPPA (0.49 mL, 2.3 mmol, 1.3 equiv.). The vial was capped and heated to 80° C. for 5.5 h. The mixture was cooled down to room temperature and the solvent eliminated under vacuum. The crude product was taken up in ethyl acetate and washed with 10% aqueous citric acid, water, saturated NaHCO$_3$, brine. The combined organic layers was dried over anhydrous Na$_2$SO$_4$, filtered and the solvent removed under vacuum. The crude product was absorbed onto silica and purified by flash column (silica, hexanes:ethyl acetate 9:1) to give 307.2 mg (65%) of tert-butyl 4-chlorobenzo[d][1,3]dioxol-5-ylcarbamate as a white solid.

F) 4-Chlorobenzo[d][1,3]dioxol-5-amine

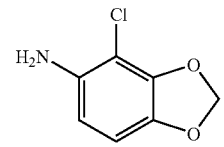

To a vial containing tert-butyl 4-chlorobenzo[d][1,3]dioxol-5-ylcarbamate (307.2 mg, 1.1 mmol, 1 equiv.) was added 5.5 mL of 4N HCl in dioxane (22 mmol, 20 equiv.). The mixture was stirred at room temperature for 5.5 h, the solvent removed under vacuum, the residue dissolved in ethyl acetate, washed with saturated NaHCO$_3$, and brine. The combined organic layers was dried over anhydrous Na$_2$SO$_4$, filtered and the solvent removed under to give a quantitative yield 4-chlorobenzo[d][1,3]dioxol-5-amine.

G) 4-Chloro-5-isocyanatobenzo[d][1,3]dioxole

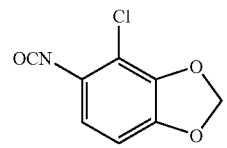

To a vial containing 4-chlorobenzo[d][1,3]dioxol-5-amine (28.8 mg, 0.168 mmol, 1 equiv.) in 1 mL THF was added 4M HCl in 1,4-dioxane (0.042 mL, 1 equiv.) followed by phosgene (20% in toluene; 0.360 mL, 0.684 mmol, 4 equiv.). The vial was capped and heated to 70° C. for 1 h, the solvent was removed under, the residue redissolved in toluene and solvent was again removed under vacuum to eliminate any remaining phosgene yielding 4-chloro-5-isocyanatobenzo[d][1,3]dioxole used as such in the next step.

H) The 4-chloro-5-isocyanatobenzo[d][1,3]dioxole was then used in a procedure analogous to that described for Example 179 to prepare the title compound. $^1$H NMR (400 MHz, CDCl$_3$): δ (ppm) 9.99 (s, 1H), 7.88 (s, 1H), 7.39 (s, 1H), 7.35 (d, J=8.6 Hz, 1H), 6.69 (d, J=8.4 Hz, 1H), 6.37 (s, 1H), 5.99 (s, 2H), 3.71 (t, J=4.6 Hz, 2H), 3.49-3.43 (m, 2H), 1.75 (s, 6H), 1.30 (s, 9H).

Example 272

1-(Benzo[d][1,3]dioxol-4-yl)-3-(5-tert-butyl-3-(2,2-dimethyl-3-oxopiperazine-1-carbonyl)thiophen-2-yl) urea

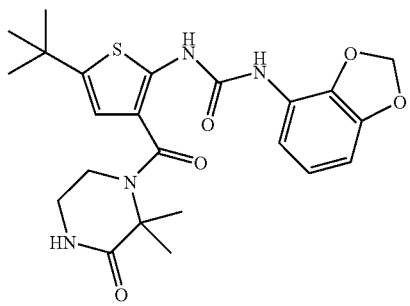

The compound of this example was prepared using the procedure described in Example 179. $^1$H NMR (400 MHz, CDCl$_3$/CD$_3$OD): δ (ppm) 7.28 (d, J=8.4 Hz, 1H), 6.75 (t, J=8.1 Hz, 1H), 6.56 (dd, J=7.8, 0.7 Hz, 1H), 6.45 (s, 1H), 5.93 (s, 2H), 3.67 (t, J=4.9 Hz, 2H), 3.40 (t, J=4.9 Hz, 2H), 1.77 (s, 6H), 1.32 (s, 9H).

Example 273

1-(Benzo[d][1,3]dioxol-5-yl)-3-(5-tert-butyl-3-(2,2-dimethyl-3-oxopiperazine-1-carbonyl)thiophen-2-yl) urea

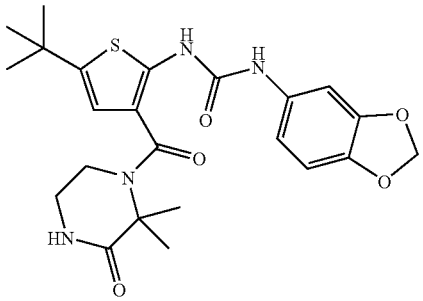

The compound of this example was prepared using the procedure described in Example 179. $^1$H NMR (400 MHz, CDCl$_3$/CD$_3$OD): δ (ppm) 7.08 (d, J=1.8 Hz, 1H), 6.74 (dd, J=8.4, 2.1 Hz, 1H), 6.68 (d, J=8.4 Hz, 1H), 6.40 (s, 1H), 5.87 (s, 2H), 3.67 (t, J=4.8 Hz, 2H), 3.41 (t, J=4.8 Hz, 2H), 1.75 (s, 6H), 1.30 (s, 9H).

Example 274

1-(5-tert-Butyl-3-(3-ethyl-1-(2-(methoxy(methyl) amino)-2-oxoethyl)-3-methyl-2-oxopiperazine-4-carbonyl)thiophen-2-yl)-3-(2,3-dichlorophenyl)urea

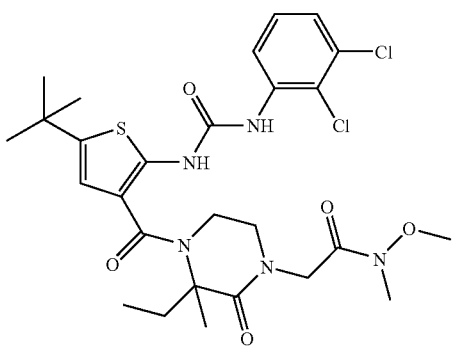

$^1$H NMR (400 MHz, CD$_2$Cl$_2$): δ (ppm) 10.20 (s, 1H), 8.17 (d, J=8.3 Hz, 1H), 8.05 (s, 1H), 7.22-7.12 (m, 2H), 6.51 (s, 1H), 4.38-4.27 (m, 2H), 4.12-4.06 (m, 1H), 3.75 (s, 3H), 3.74-3.63 (m, 2H), 3.43-3.34 (m, 1H), 3.17 (s, 3H), 2.71-2.60 (m, 1H), 2.10-2.00 (m, 1H), 1.75 (s, 3H), 1.38 (s, 9H), 0.78 (t, J=7.3 Hz, 3H).

Example 275

1-(2-(4,4-Dioxy-4-thiomorpholine-1-carbonyl)-4-chloro-5-trifluoromethylphenyl)-3-(2,3-dichlorophenyl)urea

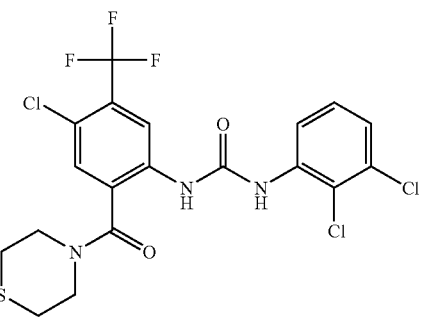

The compound of this example was prepared using a procedure analogous to the procedure described in Example 262. $^1$H NMR (400 MHz, CD$_3$OD): δ (ppm) 8.04 (dd, J=7.9, 2.0 Hz, 1H), 7.67 (s, 1H), 7.46 (s, 1H), 7.18-7.10 (m, 2H), 3.98 (s, 4H), 3.19 (s, 4H).

Example 276

1-(2-(1-(2-Amino-2-oxoethyl)-3,3-dimethyl-2-ox-opiperazine-4-carbonyl)-5-tert-butyl-1H-pyrrol-3-yl)-3-(2,3-dichlorophenyl)urea

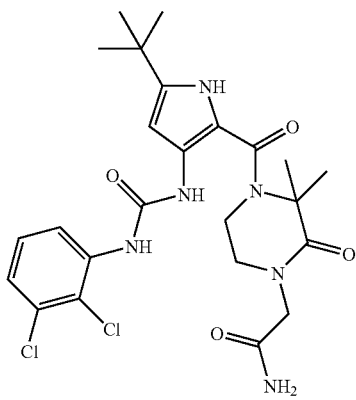

The compound of this example was prepared using a procedure analogous to the procedure described in Example 210. ¹H NMR (400 MHz, CD₃OD): δ (ppm) 8.00 (d, 1H); 7.20 (m, 2H); 6.28 (s, 1H); 3.95 (s, 3H); 3.74 (m, 2H); 3.59 (m, 2H); 1.80 (s, 6H); 1.30 (s, 9H).

Example 277

1-(5-tert-Butyl-2-(2-dimethylaminoethyl-1,1-dioxy-1-thia-2,5-diazepan-1-one-5-carbonyl)furan-3-yl)-3-(2,3-dichlorophenyl)urea

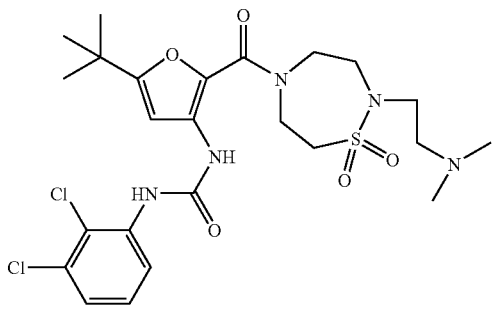

The compound of this example was prepared as follows.

A) 5-(2-(Benzyloxy)acetyl)-1,1-dioxy-1,2,5-thiadi-azepan-1-one

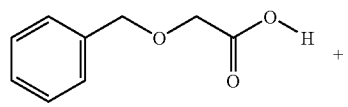

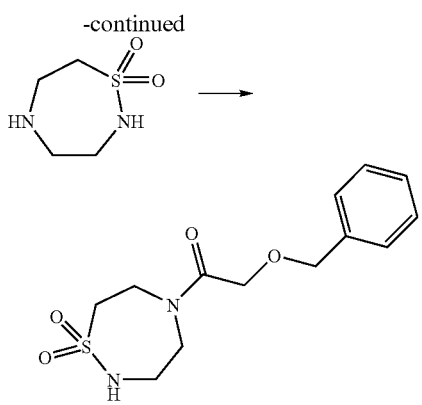

A 100 mL round-bottomed flask was charged with benzyloxyacetic acid (1.00 g, 6.1 mmol) and 20 mL DCM. The solution was stirred on an ice-water bath under nitrogen and treated with HOBt (0.83 g, 6.1 mmol). After 10 minutes, EDCI (1.30 g, 6.9 mmol) was added and the bath was removed. After 1 h, the solution was cooled and treated with DIEA (1.6 g, 12 mmol) and dioxythiadiazepine (0.80 g, 5.3 mmol). The mixture was allowed to stir for 17 h and diluted with 40 mL dichloromethane, washed with water (2×40 mL), dried over anhydrous sodium sulfate, and the solvent eliminated under vacuum yielding the expected 5-(2-(benzyloxy)acetyl)-1,1-dioxy-1,2,5-thiadiazepan-1-one (1.60 g) which was used as such in the next step.

B) 2-(Dimethylaminoethyl)-5-(2-hydroxyacetyl)-1,1-dioxy-1,2,5-thiadiazepan-1-one

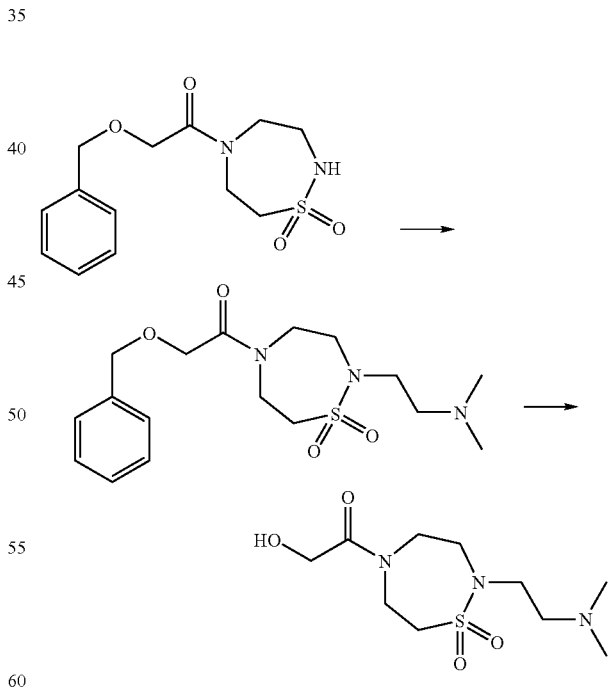

A vial containing the previously prepared 5-(2-(benzyloxy)acetyl)-1,1-dioxy-1,2,5-thiadiazepan-1-one (0.660 g, 2.21 mmol), DMF (3 mL) was stirred on ice water. NaH (0.30 g, 7.5 mmol) and the amine salt (0.40 g, 3.0 mmol) were added to the vial and the resulting mixture warmed to room temperature, stirred for 16 h, and diluted with saturated aqueous. NaHCO₃ The reaction mixture was extracted with ethyl acetate (2×20 mL), the combined organic layers was washed with brine, dried over anhydrous Na₂SO₄, and concentrated under vacuum. The crude product, ammonium formate (0.41 g, 7.3 mmol), and Pd/C (0.50, 0.20 mmol), and methanol (15 mL) were placed in a round-bottomed flask and the resulting mixture refluxed for 2 h, cooled and filtered through a pad celite. Concentration provided 0.45 g of the expected 2-(dimethylaminoethyl)-5-(2-hydroxyacetyl)-1,1-dioxy-1,2,5-thiadiazepan-1-one.

C) 5-tert-Butyl-2-(2-dimethylaminoethyl-1,1-dioxy-1-thia-2,5-diazepan-1-one-5-carbonyl)-3-aminofuran

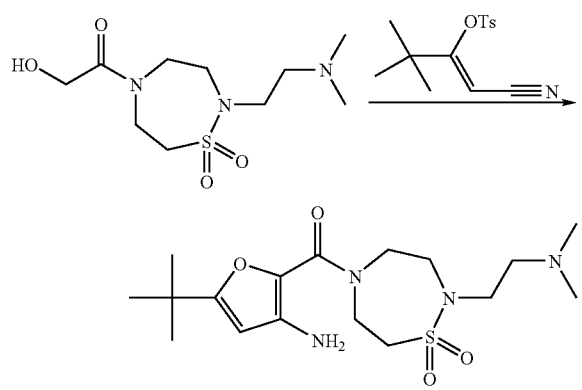

A 50 mL round-bottomed flask was charged with the previously prepared 2-(dimethylaminoethyl)-5-(2-hydroxyacetyl)-1,1-dioxy-1,2,5-thiadiazepan-1-one (0.450 g, 1.6 mmol) and DMF (25 mL). The solution was cooled on ice-water bath, treated with NaH (83 mg, 1.9 mmol) and was warmed to room temperature. After 20 minutes, the mixture was cooled down to 0° C. and treated with the enol ether in DMF (3 mL) solution and the ice-water bath was removed. After 2.5 h the reaction mixture was cooled down to 0° C., treated with NaH (167 mg, 3.8 mmol), and stirred for 16 h. The reaction mixture was extracted with methylene chloride (2×200 mL), the organic layers were combined, dried and the solvent eliminated under vacuum yielding 36 mg of the expected 5-tert-butyl-2-(2-dimethylaminoethyl-1,1-dioxy-1-thia-2,5-diazepan-1-one-5-carbonyl)-3-aminofuran which was used as such in the next step.

D) 1-(5-tert-Butyl-2-(2-dimethylaminoethyl-1,1-dioxy-1-thia-2,5-diazepan-1-one-5-carbonyl)furan-3-yl)-3-(2,3-dichlorophenyl)urea

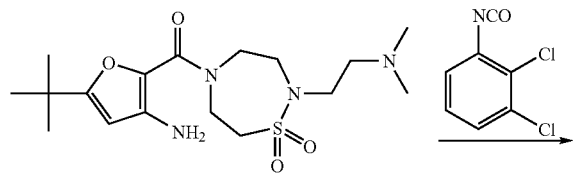

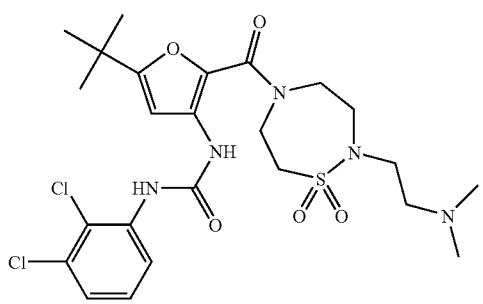

A vial containing the previously prepared (5-tert-butyl-3-(amino)furan-2-yl)(2-(dimethylaminoethyl)-1,1-dioxy-1,2,5-thiadiazepan-1-one-5-yl)methanone (0.030 g, 0.078 mmol) was charged with THF (2 mL) and nitrogen was bubbled through the solution for 2 min. The isocyanate (0.029 g, 0.16 mmol) was added and the vial capped and heated at 40° C. for 16 h. The mixture was cooled down, diluted with 5 volumes of dichloromethane, washed with 2 volumes of saturated aqueous NaHCO₃, dried over anhydrous Na₂SO₄ and purified by preparative thin layer chromatography eluting with a mixture of ethyl acetate:dichloromethane:methanol (5:2:1) to yield 4.8 mg of the desired (5-tert-butyl-3-(3-(2,3-dichlorophenyl)urea-1-yl)furan-2-yl)(2-(dimethylaminoethyl)-1,1-dioxy-1,2,5-thiadiazepan-1-one-5-yl)methanone.

Example 278

1-(5-tert-Butyl-3-(4,4-dioxy-4-thiomorpholine-1-carbonyl)thiophen-2-yl)-3-(5-chlorobenzo[d][1,3]dioxol-4-yl)urea

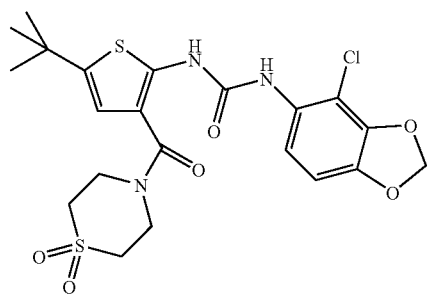

4-Chloro-5-isocyanatobenzo[d][1,3]dioxole was prepared as described in Example 276 and then used in a procedure analogous to that described for Example 58 to prepare the title compound. ¹H NMR (400 MHz, CDCl₃): δ (ppm) 9.80 (s, 1H), 7.66 (s, 1H), 7.33 (d, J=8.6 Hz, 1H), 6.68 (d, J=8.4 Hz, 1H), 6.39 (s, 1H), 5.99 (s, 2H), 4.11-4.03 (m, 4H), 3.08 (t, J=4.7 Hz, 4H), 1.26 (s, 9H).

Example 279

1-(5-tert-Butyl-3-(5-oxo-1,4-diazepane-1-carbonyl)thiophen-2-yl)-3-(4-chlorobenzo[d][1,3]dioxol-5-yl)urea

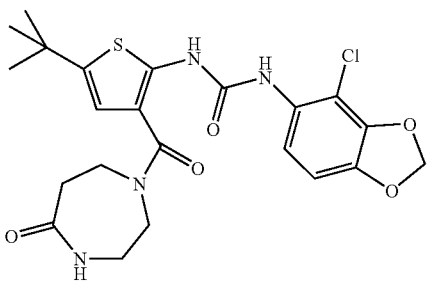

4-Chloro-5-isocyanatobenzo[d][1,3]dioxole was prepared as described in Example 275 and then used in a procedure analogous to that described for Example 58 to prepare the title compound. $^1$H NMR (400 MHz, CDCl$_3$): δ (ppm) 9.90 (s, 1H), 8.10 (s, 1H), 7.43 (d, J=8.6 Hz, 1H), 7.34 (br s, 1H), 6.66 (d, J=8.6 Hz, 1H), 6.36 (s, 1H), 5.96 (s, 2H), 3.73 (br s, J=2.5 Hz, 4H), 3.32 (br s, 2H), 2.68 (br s, 2H), 1.27 (s, 9H):

Example 280

Methyl 2-(4-(2-tert-butyl-5-(3-(2,3-dichlorophenyl)ureido)thiophene-4-carbonyl)-3-ethyl-3-methyl-2-oxopiperazin-1-yl)acetate

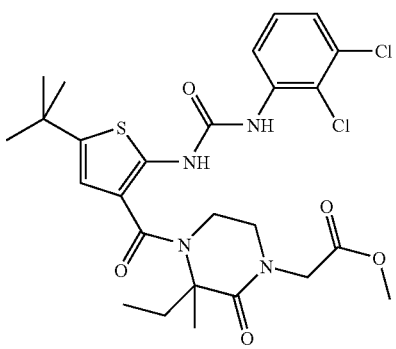

The compound of this example was prepared using a procedure analogous to the procedure described in Example 214. $^1$H NMR (400 MHz, CD$_2$Cl$_2$): δ (ppm) 10.10 (s, 1H), 8.14 (dd, J=7.7, 2.3 Hz, 1H), 7.42 (s, 1H), 7.26-7.19 (m, 2H), 6.51 (s, 1H), 6.49 (s, 1H), 4.22 (d, J=17.1 Hz, 1H), 4.12 (d, J=17.1 Hz, 1H), 4.09-4.01 (m, 1H), 3.78 (s, 3H), 3.70-3.60 (m, 2H), 3.45-3.33 (m, 1H), 2.76-2.69 (m, 1H), 2.13-2.03 (m, 1H), 1.75 (s, 3H), 1.38 (s, 9H), 0.83 (t, J=7.3 Hz, 3H).

Example 281

1-(5-tert-Butyl-3-(1-(2-(2-(dimethylamino)ethylamino)-2-oxoethyl)-3-ethyl-3-methyl-2-oxopiperazine-4-carbonyl)thiophen-2-yl)-3-(2,3-dichlorophenyl)urea

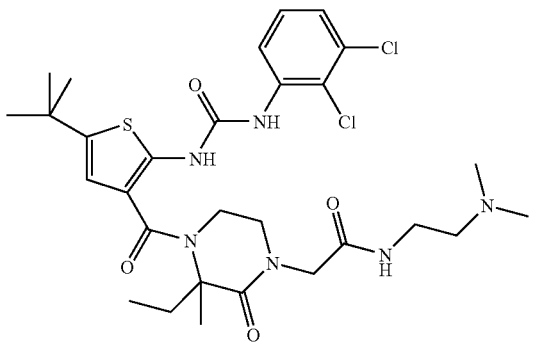

The compound of this example was prepared using a procedure analogous to the procedure described in Example 179. $^1$H NMR (400 MHz, CD$_2$Cl$_2$): δ (ppm) 10.13 (s, 1H), 8.13 (dd, J=7.7, 2.3 Hz, 1H), 7.92 (s, 1H), 7.22-7.11 (m, 2H), 6.51 (s, 1H), 6.49 (s, 1H), 4.05-4.01 (m, 4H), 3.71-3.59 (m, 2H), 3.47-3.41 (m, 1H), 3.33-3.25 (m, 2H), 2.74-2.64 (m, 1H), 2.38 (t, J=5.3 Hz, 2H), 2.19 (s, 6H), 2.15-1.94 (m, 1H), 1.74 (s, 3H), 1.35 (s, 9H), 0.78 (t, J=7.3 Hz, 3H).

Example 282

1-(5-tert-Butyl-2-(1-(2-(dimethylamino)ethyl)-3,3-dimethyl-2-oxopiperazine-4-carbonyl)-1H-pyrrol-3-yl)-3-(2,3-dichlorophenyl)urea

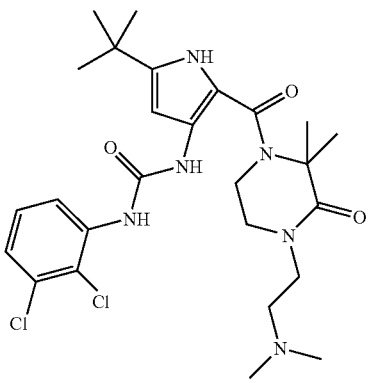

The compound of this example was prepared using a procedure analogous to the procedure described in Example 210. $^1$H NMR (400 MHz, acetone-d$_6$): δ (ppm) 9.58 (bs, 1H); 8.60 (bs, 2H); 8.26 (d, 1H); 7.30 (t, 1H); 7.20 (d, 1H); 6.50 (d, 1H); 3.78 (m, 2H); 3.65 (m, 2H); 3.50 (t, 2H); 2.40 (t, 2H); 1.70 (s, 6H); 1.35 (s, 9H).

Example 283

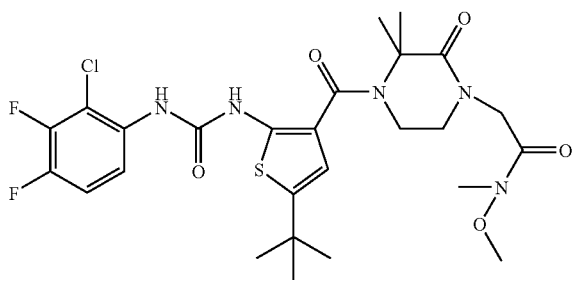

The compound of this example was prepared using a procedure analogous to the procedure described in Example 267. ¹H NMR (400 MHz, CDCl₃): δ (ppm) 10.21 (s, 1H), 8.02-7.96 (m, 1H), 7.75 (s, 1H), 7.05 (q, J=9.1 Hz, 1H), 6.45 (s, 1H), 4.32 (s, 2H), 3.86 (t, J=4.9 Hz, 2H), 3.77 (s, 3H), 3.56 (t, J=4.8 Hz, 2H), 3.20 (s, 3H), 1.80 (s, 6H), 1.34 (s, 9H).

Example 284

1-(3-(3-(2-Amino-2-oxoethyl)-1,3-dimethyl-2-oxopiperazine-4-carbonyl)-5-tert-butylthiophen-2-yl)-3-(2,3-dichlorophenyl)urea

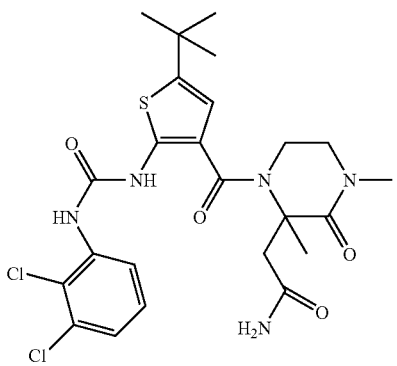

The compound of this example was prepared using a procedure analogous to the procedure described in Example 228. ¹H NMR (400 MHz, CD₃COCD₃): δ (ppm) 10.43 (s, 1H), 8.74 (s, 1H), 8.33 (dd, J=8.3, 1.4 Hz, 1H), 7.33 (t, J=8.0 Hz, 1H), 7.25 (dd, J=7.9, 1.5 Hz, 1H), 6.58 (s, 1H), 3.95-3.89 (m, 2H), 3.67 (d, J=9.5 Hz, 2H), 3.47 (dd, J=9.6, 5.9 Hz, 1H), 3.09 (d, J=15.5 Hz, 1H), 2.97 (s, 3H), 1.76 (s, 3H), 1.34 (s, 9H).

Example 285

1-(3-(3-(2-Amino-2-oxoethyl)-3-methyl-1-((3-methyl-1,2,4-oxadiazol-5-yl)methyl)-2-oxopiperazine-4-carbonyl)-5-tert-butylthiophen-2-yl)-3-(2,3-dichlorophenyl)urea

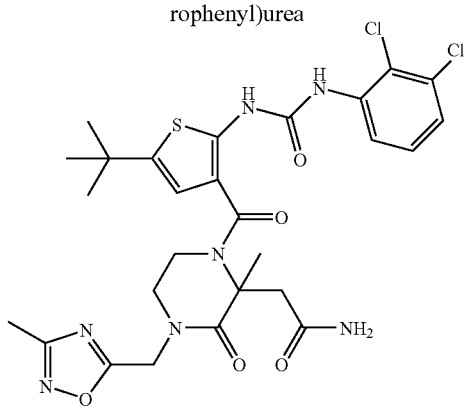

The compound of this example was prepared using a procedure analogous to the procedure described in Example 247. ¹H NMR (400 MHz, CDCl₃): δ (ppm) 10.09 (s, 1H), 8.44 (s, 1H), 8.29 (dd, J=8.0, 1.7 Hz, 1H), 7.20-7.11 (m, 2H), 6.59 (s, 1H), 6.13 (s, 1H), 5.50 (s, 1H), 4.96 (d, J=16.6 Hz, 1H), 4.64 (d, J=16.6 Hz, 1H), 4.04-3.97 (m, 2H), 3.84-3.77 (m, 1H), 3.66-3.56 (m, 1H), 3.03 (d, J=15.2 Hz, 1H), 2.28 (s, 3H), 1.90 (s, 3H), 1.34 (s, 9H).

Example 286

1-(4-Chloro-2-(5-oxo-1,4-diazepane-1-carbonyl)-5-(trifluoromethyl)phenyl)-3-(2,3-dichlorophenyl)urea

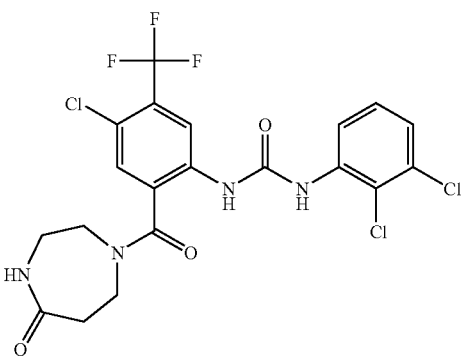

The compound of this example was prepared using the procedure described in Example 258 except that 2-amino-5-chloro-4-(trifluoromethyl)benzoic acid was used instead of 2-amino-4-(trifluoromethyl)benzoic acid. ¹H NMR (400 MHz, CD₃OD): δ (ppm) 7.84 (d, J=4.9 Hz, 1H), 7.68-7.62 (m, 1H), 7.11 (s, 1H), 6.85-6.82 (m, 2H), 3.54 (s, 2H), 3.22-3.13 (m, 2H), 3.07 (s, 1H), 2.96 (s, 1H), 2.39 (s, 1H), 2.29 (s, 1H).

Example 287

1-(5-tert-Butyl-3-(5-oxo-1,4-diazepane-1-carbonyl)thiophen-2-yl)-3-(2-ethylphenyl)urea

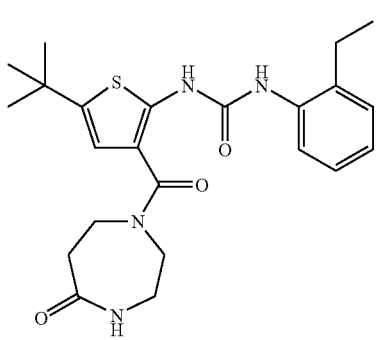

The compound of this example was prepared using a procedure analogous to the procedure described in Example 58. ¹H NMR (400 MHz, CD₃OD) δ (ppm) 7.47 (dd, J=8.0, 1.2 Hz, 1H), 7.21 (dd, J=7.6, 1.2 Hz, 1H), 7.16 (td, J=7.6, 2.0 Hz, 1H), 7.10 (td, J=7.6, 1.2 Hz, 1H), 6.57 (s, 1H), 3.74 (m, 4H), 3.35 (m, 2H), 2.70 (m, 2H), 2.64 (q, J=7.6 Hz, 2H), 1.33 (s, 9H), 1.17 (t, J=7.6 Hz, 3H).

Example 288

1-(5-tert-Butyl-3-(5-oxo-1,4-diazepane-1-carbonyl) thiophen-2-yl)-3-o-tolylurea

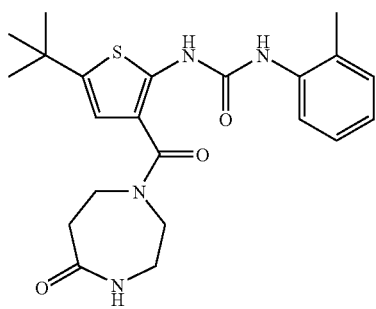

The compound of this example was prepared using a procedure analogous to the procedure described in Example 58. ¹H NMR (400 MHz, CD₃OD) δ (ppm) 7.51 (dd, J=8.0, 1.2 Hz, 1H), 7.18 (m, 1H), 7.14 (m, 1H), 7.04 (td, J=7.6, 1.2 Hz, 1H), 6.58 (s, 1H), 3.74 (td, J=7.6, 1.2 Hz, 1H), 3.35 (m, 2H), 2.72 (m, 2H), 2.25 (s, 3H), 1.34 (s, 9H).

Example 289

1-(2-Bromophenyl)-3-(5-tert-butyl-3-(5-oxo-1,4-diazepane-1-carbonyl)thiophen-2-yl)urea

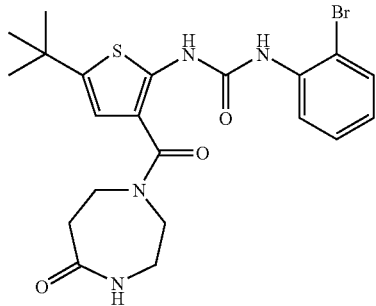

The compound of this example was prepared using a procedure analogous to the procedure described in Example 58. ¹H NMR (400 MHz, CD₃OD) δ (ppm) 7.89 (dd, J=8.4, 1.6 Hz, 1H), 7.55 (dd, J=8.0, 2.0 Hz, 1H), 7.30 (m, 1H), 6.99 (m, 1H), 6.59 (s, 1H), 3.75 (m, 4H), 3.34 (m, 2H), 2.71 (m, 2H), 1.33 (s, 9H).

Example 290

1-(5-tert-Butyl-3-(5-oxo-1,4-diazepane-1-carbonyl) thiophen-2-yl)-3-(2-isopropylphenyl)urea

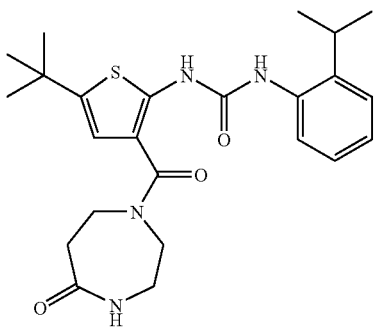

The compound of this example was prepared using a procedure analogous to the procedure described in Example 58. ¹H NMR (400 MHz, CD₃OD) δ (ppm) 7.38 (m, 1H), 7.31 (m, 1H), 7.19-7.15 (2H), 6.58 (s, 1H), 3.74 (m, 4H), 3.35 (m, 4H), 3.17 (hept, J=6.8 Hz, 1H), 2.71 (m, 2H), 1.34 (s, 9H), 1.20 (d, J=6.8 Hz, 6H).

Example 291

1-(5-tert-Butyl-3-(5-oxo-1,4-diazepane-1-carbonyl) thiophen-2-yl)-3-(2-(trifluoromethoxy)phenyl)urea

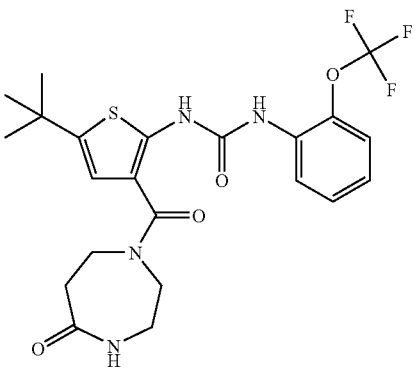

The compound of this example was prepared using the procedure described in Example 160 except that 2-trifluoromethoxyphenyl isocyanate was used instead of 2,3-dichloro-4-fluorophenyl isocyanate. ¹H NMR (400 MHz, CD₃OD) δ (ppm) 8.14 (dd, J=8.4, 1.6 Hz, 1H), 7.31-7.27 (2H), 7.10 (m, 1H), 6.59 (s, 1H), 3.76 (m, 1H), 3.36 (m, 2H), 2.72 (m, 2H), 1.35 (s, 9H).

Example 292

1-(5-tert-Butyl-3-(5-oxo-1,4-diazepane-1-carbonyl)thiophen-2-yl)-3-(2-iodophenyl)urea

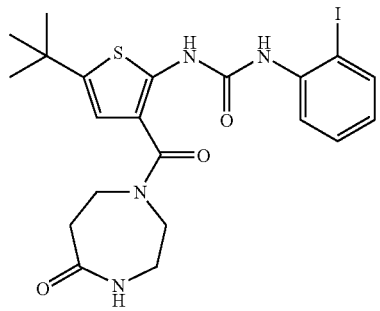

The compound of this example was prepared using the procedure described in Example 160 except that 2-iodophenylisocyanate was used instead of 2,3-dichloro-4-fluorophenyl isocyanate. $^1$H NMR (400 MHz, CD$_3$OD) δ (ppm) 7.82 (dd, J=8.0, 1.2 Hz, 1H), 7.65 (dd, J=8.0, 1.2 Hz, 1H), 7.34 (m, 1H), 6.88 (m, 1H), 6.59 (s, 1H), 3.74 (m, 4H), 3.36 (m, 2H), 2.72 (m, 2H), 1.33 (s, 9H).

Example 293

1-(5-tert-Butyl-3-(5-oxo-1,4-diazepane-1-carbonyl)thiophen-2-yl)-3-(2-chlorophenyl)urea

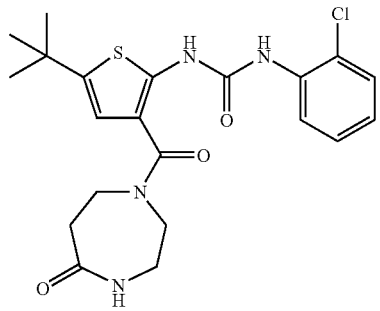

The compound of this example was prepared using the procedure described in Example 160 except that 2-chlorophenylisocyanate was used instead of 2,3-dichloro-4-fluoro-phenylisocyanate. $^1$H NMR (400 MHz, CD$_3$OD) δ (ppm) 7.98 (dd, J=8.4, 1.6 Hz, 1H), 7.38 (dd, J=8.0, 1.2 Hz, 1H), 7.26 (m, 1H), 7.04 (m, 1H), 6.59 (s, 1H), 3.76 (m, 4H), 3.35 (m, 2H), 2.71 (m, 2H), 1.34 (s, 9H).

Example 294

1-(5-tert-Butyl-3-(5-oxo-1,4-diazepane-1-carbonyl)thiophen-2-yl)-3-(2-(trifluoromethyl)phenyl)urea

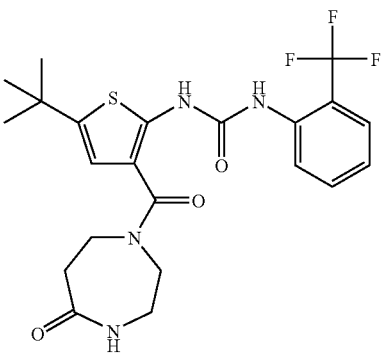

The compound of this example was prepared using the procedure described in Example 160 except that 2-trifluorophenylisocyanate was used instead of 2,3-dichloro-4-fluorophenylisocyanate. $^1$H NMR (400 MHz, CD$_3$OD) δ (ppm) 7.82 (d, J=8.0, 1H), 7.64 (m, 1H), 7.58 (m, 1H), 7.28 (m, 1H), 6.59 (s, 1H), 3.76 (m, 4H), 3.35 (m, 2H), 2.72 (m, 2H), 1.35 (s, 9H).

Example 295

1-(5-tert-Butyl-3-(2,2-dimethyl-3-oxopiperazine-1-carbonyl)thiophen-2-yl)-3-(2-chlorophenyl)urea

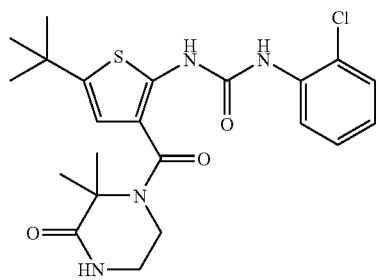

The compound of this example was prepared using the procedure described in Example 136 except that 2-chlorophenyl isocyanate was used instead of 2,3-dichlorophenyl isocyanate. $^1$H NMR (400 MHz, CD$_3$OD) δ (ppm) 7.94 (dd, J=8.4, 1.6 Hz, 1H), 7.39 (dd, J=8.0, 1.6 Hz, 1H), 7.26 (m, 1H), 7.06 (m, 1H), 6.56 (s, 1H), 3.66 (m, 2H), 3.40 (m, 2H), 1.80 (s, 6H), 1.34 (s, 9H).

Example 296

1-(5-tert-Butyl-3-(1-(2-(dimethylamino)ethyl)-3,3-dimethyl-2-oxopiperazine-4-carbonyl)thiophen-2-yl)-3-(2-tert-butylphenyl)urea

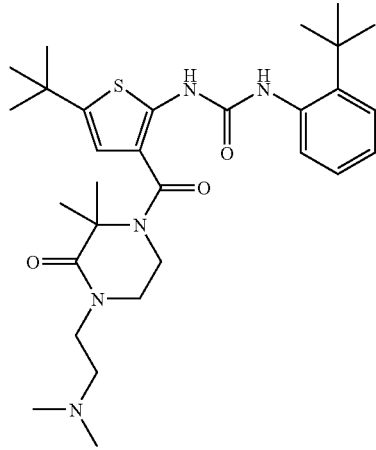

The compound of this example was prepared using the procedure described in Example 173 except that 2-tert-butylphenyl isocyanate was used instead of 2,3-dichloro-phenyl isocyanate. ¹H NMR (400 MHz, CD₃OD) δ (ppm) 7.43 (m, 1H), 7.25-7.19 (2H), 7.17 (m, 1H), 6.55 (s, 1H), 3.68 (m, 2H), 3.54 (m, 2H), 2.54 (t, J=7.2 Hz, 2H), 2.29 (s, 6H), 1.73 (s, 6H), 1.38 (s, 9H), 1.33 (s, 9H).

Example 297

1-(5-tert-Butyl-3-(1-(2-(dimethylamino)ethyl)-3,3-dimethyl-2-oxopiperazine-4-carbonyl)thiophen-2-yl)-3-ortho-tolylurea

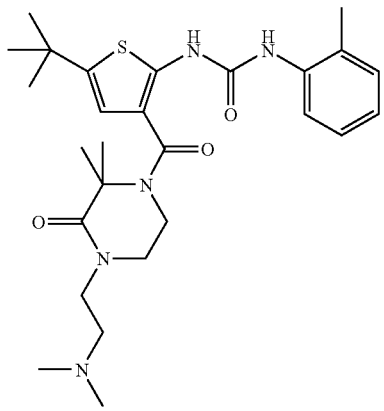

The compound of this example was prepared using the procedure described in Example 207 except that 2-methylphenyl isocyanate was used instead of 2-chloro-4-fluorophenyl isocyanate. ¹H NMR (400 MHz, CD₃OD) δ (ppm) 7.47 (dd, J=8.0, 0.8 Hz, 1H), 7.20 (m, 1H), 7.16 (m, 1H), 7.06 (td, J=7.6, 1.2 Hz, 1H), 6.56 (s, 1H), 3.70 (m, 2H), 3.54 (m, 4H), 2.54 (t, J=7.2 Hz, 2H), 2.29 (s, 6H), 2.26 (s, 3H), 1.76 (s, 6H), 1.34 (s, 9H).

Example 298

1-(5-tert-Butyl-3-(1-(2-(dimethylamino)ethyl)-3,3-dimethyl-2-oxopiperazine-4-carbonyl)thiophen-2-yl)-3-(2-ethylphenyl)urea

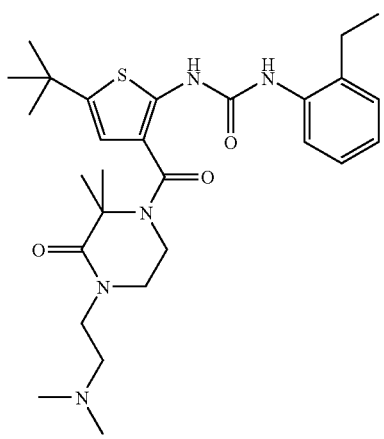

The compound of this example was prepared using the procedure described in Example 207 except that 2-ethylphenylisocyanate was used instead of 2-chloro-4-fluorophenyl isocyanate. ¹H NMR (400 MHz, CD₃OD) δ (ppm) 7.43 (dd, J=8.0, 1.6 Hz, 1H), 7.23 (dd, J=6.1, 1.6 Hz, 1H), 7.17 (m, 1H), 7.12 (m, 1H), 6.56 (s, 1H), 3.70 (m, 2H), 3.54 (m, 4H), 2.64 (q, J=7.2 Hz, 2H), 2.53 (t, J=7.2 Hz, 2H), 2.29 (s, J=6H), 1.76 (s, 6H), 1.34 (s, 9H), 1.19 (t, J=7.2 Hz, 3H).

Example 299

1-(5-tert-Butyl-3-(1-(2-(dimethylamino)ethyl)-3,3-dimethyl-2-oxopiperazine-4-carbonyl)thiophen-2-yl)-3-(2-(trifluoromethyl)phenyl)urea

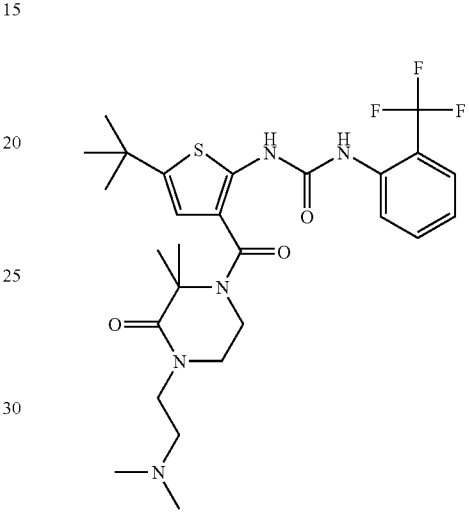

The compound of this example was prepared using the procedure described in Example 207 except that 2-trifluorophenyl isocyanate was used instead of 2-chloro-4-fluorophenyl isocyanate. ¹H NMR (400 MHz, CD₃OD) δ (ppm) 7.93 (d, J=8.0 Hz, 1H), 7.59 (d, J=7.6 Hz, 1H), 7.53 (m, 1H), 7.23 (m, 1H), 6.41 (s, 1H), 3.72 (m, 2H), 3.51 (m, 4H), 2.48 (t, J=6.4 Hz, 2H), 2.24 (s, 6H), 1.76 (s, 6H), 1.32 (s, 9H).

Example 300

1-(5-tert-Butyl-3-(1-(2-(dimethylamino)ethyl)-3,3-dimethyl-2-oxopiperazine-4-carbonyl)thiophen-2-yl)-3-(2-methoxyphenyl)urea

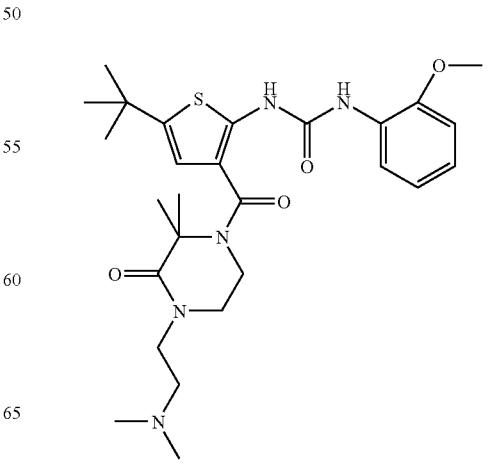

The compound of this example was prepared using the procedure described in Example 207 except that 2-methoxyphenyl isocyanate was used instead of 2-chloro-4-fluorophenyl isocyanate. $^1$H NMR (400 MHz, CD$_3$OD) δ (ppm) 7.95 (dd, J=8.0, 1.6 Hz, 1H), 7.01 (m, 1H), 6.97 (m, 1H), 6.88 (m, 1H), 6.56 (s, 1H), 3.87 (s, 3H), 3.68 (m, 2H), 3.53 (m, 4H), 2.52 (t, J=7.6 Hz, 2H), 2.27 (s, 6H), 1.79 (s, 6H), 1.34 (s, 9H).

Example 301

1-(5-tert-Butyl-3-(1-(2-(dimethylamino)ethyl)-7-oxo-1,4-diazepane-4-carbonyl)thiophen-2-yl)-3-ortho-tolylurea

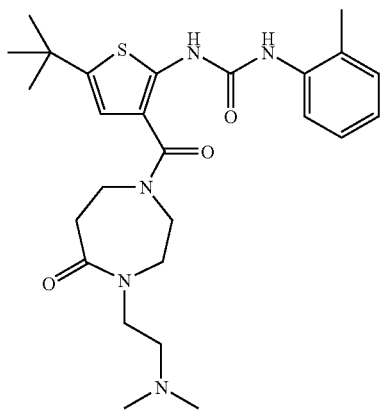

The compound of this example was prepared using the procedure described in Example 213 except that 2-methylphenyl isocyanate was used instead of 2-chloro-4-flurophenyl isocyanate. $^1$H NMR (400 MHz, CD$_3$OD) δ (ppm) 7.51 (m, 1H), 7.19 (m, 1H), 7.15 (m, 1H), 7.04 (td, J=7.6, 1.2 Hz, 1H), 6.58 (s, 1H), 3.78 (m, 2H), 3.71 (m, 2H), 3.61 (m, 2H), 3.49 (t, J=6.0 Hz, 2H), 2.81 (t, J=6.0 Hz, 2H), 2.38 (t, J=6.0 Hz, 2H), 2.26 (s, 3H), 2.21 (s, 6H), 1.34 (s, 9H).

Example 302

1-(5-tert-Butyl-3-(1-(2-(dimethylamino)ethyl)-7-oxo-1,4-diazepane-4-carbonyl)thiophen-2-yl)-3-(2-ethylphenyl)urea

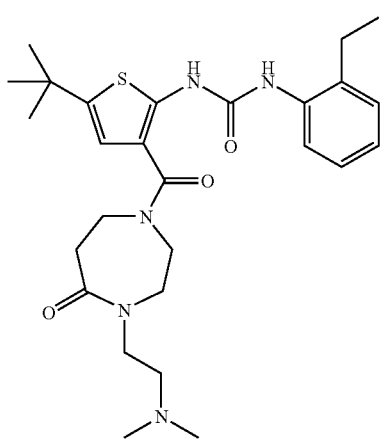

The compound of this example was prepared using the procedure described in Example 213 except that 2-ethylphenyl isocyanate was used instead of 2-chloro-4-fluorophenyl isocyanate. $^1$H NMR (400 MHz, CD$_3$OD) δ (ppm) 7.47 (dd, J=8.0, 1.6 Hz, 1H), 7.22 (m, 1H), 7.17 (m, 1H), 7.11 (td, J=7.6, 1.6 Hz, 1H), 6.57 (s, 1H), 3.77 (m, 2H), 3.71 (t, J=6.0 Hz, 2H), 3.61 (m, 2H), 3.49 (t, J=6.8 Hz, 2H), 2.81 (t, J=6.0 Hz, 2H), 2.64 (q, J=7.6 Hz, 2H), 2.22 (s, 6H), 1.34 (s, 9H), 1.18 (t, J=7.6 Hz, 3H).

Example 303

1-(5-tert-Butyl-3-(1-(2-(dimethylamino)ethyl)-7-oxo-1,4-diazepane-4-carbonyl)thiophen-2-yl)-3-(2-tert-butylphenyl)urea

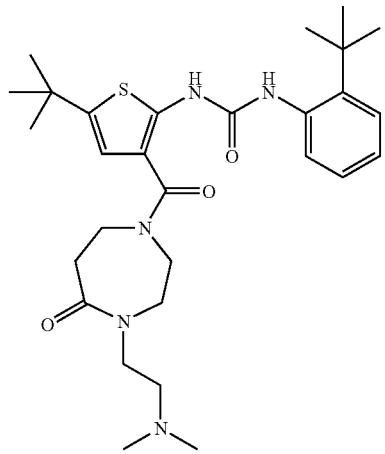

The compound of this example was prepared using the procedure described in Example 213 except that 2-tert-butylphenyl isocyanate was used instead of 2-chloro-4-fluorophenyl isocyanate. $^1$H NMR (400 MHz, CD$_3$OD) δ (ppm) 7.44 (m, 1H), 7.23-7.16 (3H), 6.56 (s, 1H), 3.77 (m, 2H), 3.70 (t, J=6.0 Hz, 2H), 3.60 (m, 2H), 3.50 (t, J=6.8 Hz, 2H), 2.79 (t, J=6.0 Hz, 2H), 2.40 (t, J=6.8 Hz, 2H), 2.23 (s, 6H), 1.38 (s, 9H), 1.33 (s, 9H).

Example 304

1-(5-tert-Butyl-3-(1-(2-(dimethylamino)ethyl)-7-oxo-1,4-diazepane-4-carbonyl)thiophen-2-yl)-3-(2-methoxyphenyl)urea

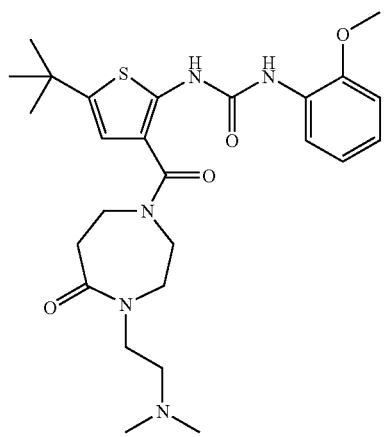

The compound of this example was prepared using the procedure described in Example 213 except that 2-methoxyphenyl isocyanate was used instead of 2-chloro-4-fluorophenyl isocyanate. ¹H NMR (400 MHz, CD₃OD) δ (ppm) 7.97 (dd, J=8.0, 1.6 Hz, 1H), 7.01 (m, 1H), 6.96 (m, 1H), 6.89 (m, 1H), 6.57 (s, 1H), 3.87 (s, 3H), 3.77 (m, 2H), 3.73 (t, J=6.0 Hz, 2H), 3.60 (m, 2H), 3.50 (t, J=6.8 Hz, 2H), 2.80 (t, J=6.0 Hz, 2H), 2.40 (t, J=6.8 Hz, 2H), 2.22 (s, 6H), 1.35 (s, 9H).

Example 305

1-(5-tert-Butyl-3-(1-(2-(dimethylamino)ethyl)-7-oxo-1,4-diazepane-4-carbonyl)thiophen-2-yl)-3-(2-chlorophenyl)urea

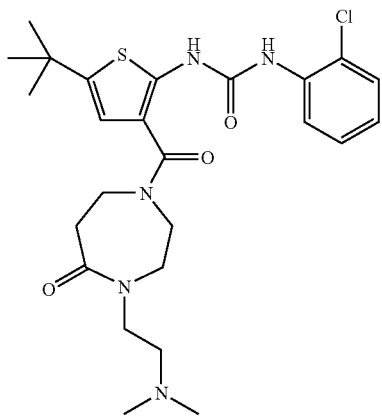

The compound of this example was prepared using the procedure described in Example 213 except that 2-chlorophenylisocyanate was used instead of 2-chloro-4-fluorophenyl isocyanate. ¹H NMR (400 MHz, CD₃OD) δ (ppm) 7.97 (dd, J=8.0, 1.6 Hz, 1H), 7.39 (m, 1H), 7.26 (m, 1H), 7.05 (m, 1H), 6.59 (s, 1H), 3.78 (m, 2H), 3.73 (t, J=6.0 Hz, 2H), 3.61 (m, 2H), 3.50 (t, J=6.8 Hz, 2H), 2.80 (t, J=6.0 Hz, 2H), 2.39 (t, J=6.8 Hz, 2H), 2.22 (s, 6H), 1.35 (s, 9H).

Example 306

1-(5-tert-Butyl-3-(1-(2-(dimethylamino)ethyl)-7-oxo-1,4-diazepane-4-carbonyl)thiophen-2-yl)-3-(2-(trifluoromethyl)phenyl)urea

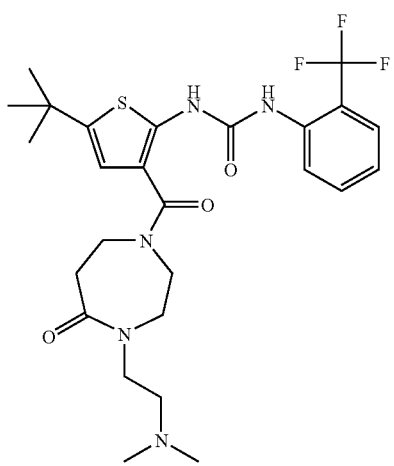

The compound of this example was prepared using the procedure described in Example 213 except that 2-trifluorophenyl isocyanate was used instead of 2-chloro-4-fluoroisocyanate. ¹H NMR (400 MHz, CD₃OD) δ (ppm) 7.76 (d, J=8.0 Hz, 1H), 7.66 (m, 1H), 7.60 (m, 1H), 7.32 (t, J=8.0 Hz, 1H), 6.59 (s, 1H), 3.78 (m, 2H), 3.73 (m, 2H), 3.61 (m, 2H), 3.50 (t, J=6.8 Hz, 2H), 2.80 (t, J=6.0 Hz, 2H), 2.39 (t, J=6.8 Hz, 2H), 2.22 (s, 6H), 1.35 (s, 9H).

Example 307

1-(5-tert-Butyl-3-(1-(methylsulfonyl)piperazine-4-carbonyl)thiophen-2-yl)-3-(2,3-dichlorophenyl)urea

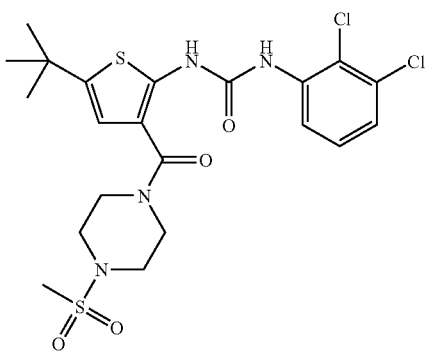

The compound of this example was prepared using the procedure described in Example 138 except that 1-(methylsultone)-piperazine was used instead of piperazin-2-one. ¹H NMR (400 MHz, CDCl₃): δ (ppm) 10.20 (s, 1H), 8.19 (dd, J=7.0, 2.7 Hz, 1H), 7.23-7.18 (m, 3H), 6.48 (s, 1H), 3.85-3.77 (m, 4H), 3.32-3.25 (m, 4H), 2.81 (s, 3H), 1.36 (s, 9H).

Example 308

1-(3-(1-Acetylpiperazine-4-carbonyl)-5-tert-butylthiophen-2-yl)-3-(2,3-dichlorophenyl)urea

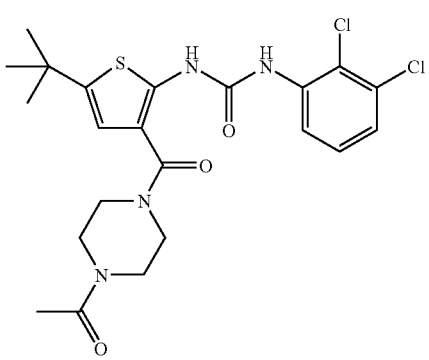

The compound of this example was prepared using the procedure described in Example 138 except that 1-(piperazin-1-yl)ethanone was used instead of piperazin-2-one. ¹H NMR (400 MHz, CDCl₃): δ (ppm) 10.30 (d, J=41.6 Hz, 1H), 8.19 (dd, J=7.4, 2.5 Hz, 1H), 7.32 (s, 1H), 7.22-7.15 (m, 2H), 6.49 (s, 1H), 3.77-3.65 (m, 6H), 3.58-3.52 (m, 2H), 2.14 (s, 3H), 1.35 (s, 9H).

Example 309

1-(3-(1-Acetyl-1,4-diazepane-4-carbonyl)-5-tert-butylthiophen-2-yl)-3-(2,3-dichlorophenyl)urea

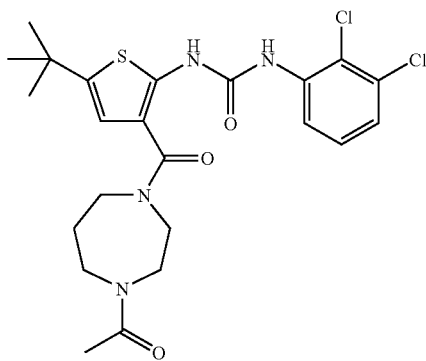

The compound of this example was prepared using the procedure described in Example 138 except that 1-(1,4-diazepan-1-yl)ethanone was used instead of piperazin-2-one. ¹H NMR (400 MHz, CDCl₃): δ (ppm) 10.00 (s, 1H), 8.20 (d, J=7.7 Hz, 1H), 7.72 (s, 1H), 7.20-7.12 (m, 2H), 6.51 (d, J=13.8 Hz, 1H), 3.85-3.75 (m, 3H), 3.73-3.62 (m, 4H), 3.56 (t, J=6.0 Hz, 1H), 2.14 (s, 3H), 1.91 (s, 2H), 1.33 (s, 9H).

Example 310

1-(5-tert-Butyl-3-(1-(methylsulfonyl)-1,4-diazepane-4-carbonyl)thiophen-2-yl)-3-(2,3-dichlorophenyl)urea

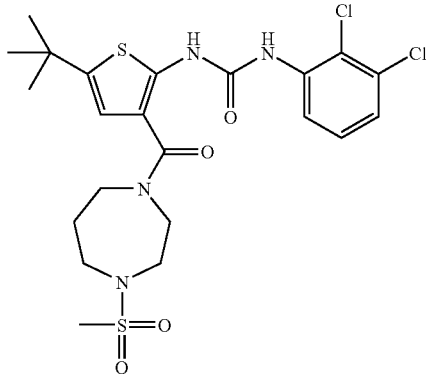

The compound of this example was prepared using the procedure described in Example 138 except that 1-(methylsulfonyl)-1,4-diazepane was used instead of piperazin-2-one. ¹H-NMR (400 MHz, CDCl₃): δ (ppm) 9.88 (s, 1H), 8.22 (dd, J=7.6, 2.2 Hz, 1H), 7.47 (s, 1H), 7.21-7.09 (m, 2H), 6.52 (s, 1H), 3.83 (t, J=5.5 Hz, 1H), 3.76-3.69 (m, 3H), 3.59 (s, 1H), 3.50-3.39 (m, 3H), 2.86 (d, J=7.4 Hz, 3H), 2.16-2.09 (m, 1H), 1.96 (s, 1H), 1.34 (s, 9H).

Example 311

1-(5-tert-Butyl-3-(3-ethyl-3-methyl-1-(2-(2-morpholinoethylamino)-2-oxoethyl)-2-oxopiperazine-4-carbonyl)thiophen-2-yl)-3-(2,3-dichlorophenyl)urea

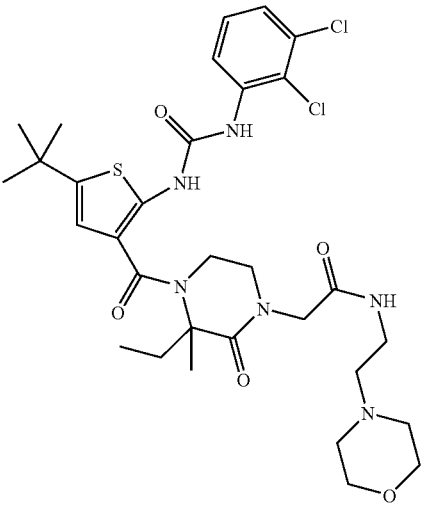

The compound of this example was prepared using the procedure described in Example 179 except that 2-(3-ethyl-3-methyl-2-oxopiperazin-1-yl)-N-(2-morpholinoethyl)acetamide was used instead of 3-ethyl-3-methylpiperazin-2-one. ¹H-NMR (400 MHz, CD₂Cl₂): δ (ppm) 10.12 (s, 1H), 8.14 (dd, J=7.9, 1.8 Hz, 1H), 8.00 (s, 1H), 7.23-7.14 (m, 2H), 6.48 (m+s, 2H), 4.10-3.98 (m, 3H), 3.69-3.62 (m, 6H), 3.48-3.33 (m 3H), 2.76-2.65 (m, 1H), 2.47-2.39 (m, 6H), 2.13-1.95 (m, 1H), 1.74 (s, 3H), 1.36 (s, 9H), 0.78 (m, 3H).

Example 312

1-(5-tert-Butyl-3-(1-(2-(2-(dimethylamino)ethylamino)-2-oxoethyl)-3-ethyl-3-methyl-2-oxopiperazine-4-carbonyl)thiophen-2-yl)-3-(2,3-dichloro-4-fluorophenyl)urea

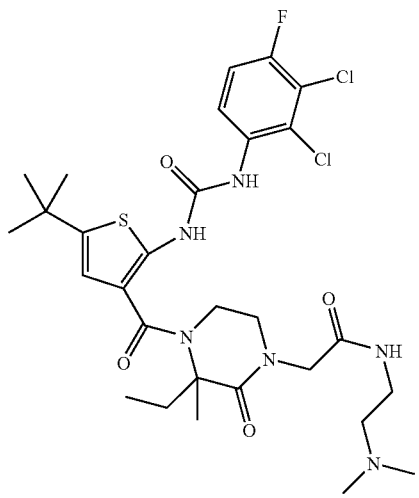

The compound of this example was prepared using the procedure described in Example 281 except that 2,3-dichloro-4-fluorophenyl)isocyanate was used instead of 2,3-dichlorophenylisocyanate. $^1$H-NMR (400 MHz, CD$_2$Cl$_2$): δ (ppm) 10.09 (s, 1H), 8.11-8.05 (m, 1H), 7.99 (s, 1H), 7.16-7.06 (m, 1H), 6.68 (s, 1H), 6.49-6.47 (m, 1H), 4.11-3.98 (m, 3H), 3.71-3.62 (m, 2H), 3.48-3.41 (m, 1H), 3.32 (q, J=5.2 Hz, 2H), 2.73-2.61 (m, 1H), 2.45 (t, J=5.4 Hz, 2H), 2.25 (s, 6H), 2.12-2.00 (m, 1H), 1.75 (s, 3H), 1.31 (3, 9H), 0.77 (t, J=7.0 Hz, 3H).

Example 313

1-(5-tert-Butyl-2-(2-methyl-1,1-dioxy-1-thia-2,5-diazepan-1-one-5-carbonyl)furan-3-yl)-3-(2,3-dichlorophenyl)urea

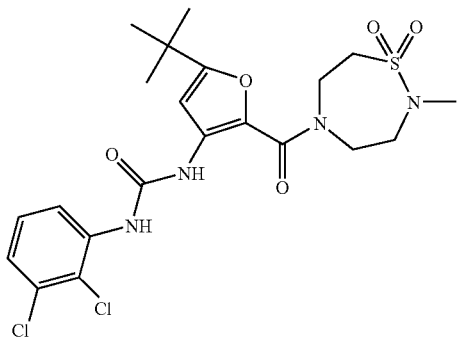

The compound of this example was prepared using the procedure described in Example 276 except that 2-methyl-1,2,5-thiadiazapan-1,1-dioxide was used instead of 3,3-dimethylpiperazin-2-one. $^1$H-NMR (400 MHz, CDCl$_3$) δ 1.24 (s, 9H), 2.81 (s, 3H), 3.36 (m, 2H) 3.47 (t, J=8.0 Hz, 2H), 3.88-4.25 (d brd, 4H), 7.02 (s, 1H), 7.14 (m, 2H), 8.06 (d, J=6.8 Hz, 1H), 9.71 (s, 1H).

Example 314

1-(5-tert-Butyl-3-(1-(2-(2-(dimethylamino)ethylamino)-2-oxoethyl)-3,3-dimethyl-2-oxopiperazine-4-carbonyl)thiophen-2-yl)-3-(2,3-dichlorophenyl)urea

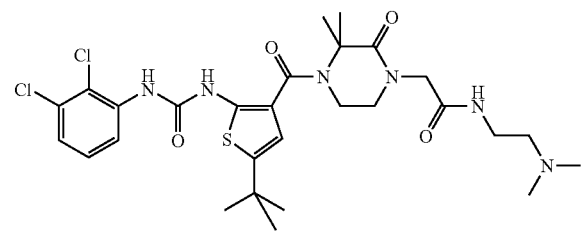

The compound of this example was made by taking the compound of Example 184 and reacting it with N,N-dimethylamino ethyl amine at 60° C. The crude product was concentrated and purified on preparative thin layer chromatography using as solvent a 10:1 dichloromethane:methanol mixture. $^1$H-NMR (400 MHz, CDCl$_3$): δ (ppm) 10.12 (s, 1H), 8.07 (dd, J=7.9, 2.0 Hz, 1H), 7.98 (s, 1H), 7.15-7.04 (m, 2H), 6.57 (t, J=4.7 Hz, 1H), 6.39 (s, 1H), 3.94 (s, 2H), 3.72 (t, J=4.9 Hz, 2H), 3.49 (t, J=4.8 Hz, 2H), 3.22 (q, J=5.5 Hz, 2H), 2.34 (t, J=6.0 Hz, 2H), 2.13 (s, 6H), 1.69 (s, 6H), 1.27 (s, 9H).

Example 315

1-(5-tert-Butyl-3-(1-(2-(2-(dimethylamino)ethylamino)-2-oxoethyl)-3,3-dimethyl-2-oxopiperazine-4-carbonyl)thiophen-2-yl)-3-(2,3-dichloro-4-fluorophenyl)urea

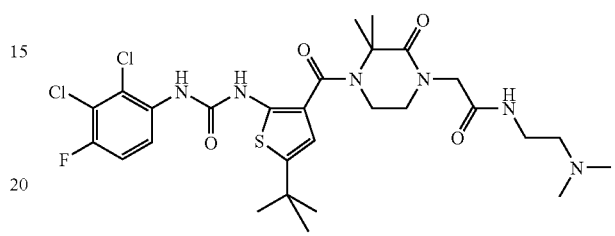

The compound of this example was prepared using the procedure described in Example 313 except that 2,3-dichloro-4-fluorophenylisocyanate was used instead of 2,3-dichlorophenylisocyanate. $^1$H-NMR (400 MHz, CDCl$_3$): δ (ppm) 10.08 (s, 1H), 8.02 (q, J=5.0 Hz, 1H), 7.85 (s, 1H), 7.02 (dd, J=9.3, 8.2 Hz, 1H), 6.56 (t, J=4.5 Hz, 1H), 6.39 (s, 1H), 3.94 (s, 2H), 3.72 (t, J=4.9 Hz, 2H), 3.49 (t, J=4.9 Hz, 2H), 3.23 (q, J=5.5 Hz, 2H), 2.35 (t, J=5.9 Hz, 2H), 2.15 (s, 6H), 1.69 (s, 6H), 1.27 (s, 9H).

Example 316

1-(5-tert-Butyl-3-(3-ethyl-3-methyl-2-oxo-1-(2-oxo-2-(2-(pyrrolidin-1-yl)ethylamino)ethyl)piperazine-4-carbonyl)thiophen-2-yl)-3-(2,3-dichlorophenyl)urea

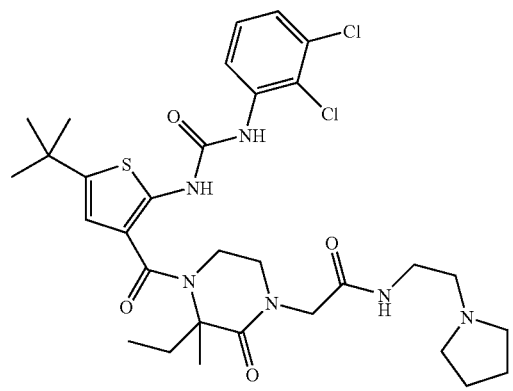

The compound of this example was prepared using the procedure described in Example 179 except that 2-(3-ethyl-3-methyl-2-oxopiperazin-1-yl)-N-(2-(pyrrolidin-1-yl)ethyl) acetamide was used instead of 3-ethyl-3-methypiperazin-2-one. $^1$H-NMR (400 MHz, CD$_2$Cl$_2$): δ (ppm) 10.01 (br s, 1H), 8.14 (d, J=7.8 Hz, 1H), 7.91 (s, 1H), 7.25-7.14 (m, 2H), 6.56-6.45 (m, 2H), 4.12-3.97 (m, 3H), 3.72-3.60 (m, 2H), 3.48-3.27 (m, 2H), 2.75-2.64 (m, 1H), 2.59 (t, J=7.2 Hz, 2H), 2.45 (br s, 4H), 2.13-2.00 (m, 1H), 1.74 (br s, 7H), 1.34 (m, 9H), 0.78 (t, J=7.3 Hz, 3H).

Example 317

1-(5-tert-Butyl-3-(3-ethyl-3-methyl-1-(2-(4-meth-ylpiperazin-1-yl)-2-oxoethyl)-2-oxopiperazine-4-carbonyl)thiophen-2-yl)-3-(2,3-dichlorophenyl)urea

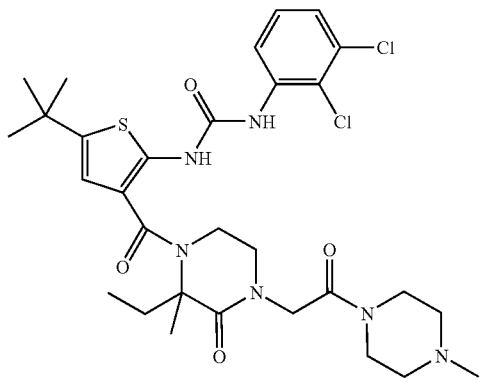

The compound of this example was prepared using the procedure described in Example 179 except that 3-ethyl-3-methyl-1-(2-(4-methylpiperazin-1-yl)-2-oxoethyl)piperazin-2-one was used instead of 3-ethyl-3-methylpiperazin-2-one. $^1$H-NMR (400 MHz, CD$_2$Cl$_2$): δ (ppm) 10.14 (s, 1H), 8.16 (q, J=3.3 Hz, 2H), 7.61 (s, 1H), 7.20 (m, 2H), 6.46 (s, 1H), 4.18-4.00 (m, 3H), 3.62-3.40 (m, 7H), 2.73-2.70 (m, 1H), 2.43-2.40 (m, 4H), 2.25 (s, 3H), 2.16-2.21 (m, 1H), 1.76 (s, 3H), 1.31 (s, 9H), 0.84 (t, J=7.3 Hz, 3H).

Example 318

Ethyl 1-(2-tert-butyl-5-(3-(2,3-dichlorophenyl)ureido)thiophene-4-carbonyl)-2-methyl-3-oxopiperazine-2-carboxylate

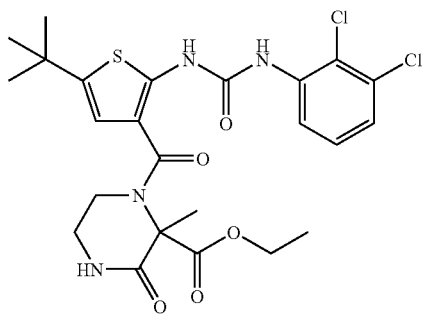

The compound of this example was prepared using the procedure described in Example 179 except that ethyl-2-methyl-3-oxopiperazine-2-carboxylate was used instead of 3,3-dimethylpiperazin-2-one. $^1$H-NMR (400 MHz, CD$_3$OD): δ (ppm) 7.98-7.92 (m, 1H), 7.19-7.15 (m, 2H), 6.51 (s, 1H), 4.18 (q, J=7.2 Hz, 2H), 4.10-4.01 (m, 1H), 3.68-3.55 (m, 2H), 3.42-3.32 (m, 1H), 1.82 (s, 3H), 1.33 (s, 9H), 1.22 (t, J=7.1 Hz, 3H).

Example 319

1-(3-(1-(3-(Bis(2-hydroxyethyl)amino)-3-oxopropyl)-3,3-dimethyl-2-oxopiperazine-4-carbonyl)-5-tert-butylthiophen-2-yl)-3-(2,3-dichlorophenyl)urea

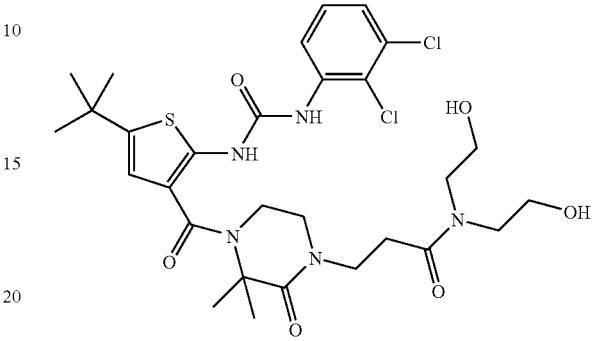

The compound of this example was prepared using the procedure described in Example 179 except that 2-(2,3-dimethyl-2-oxopiperazin-1-yl)-N-(2-hydroxyethyl)-N-(3-hydroxypropyl)acetamide was used instead of 3-ethyl-3-methylpiperazin-2-one. $^1$H-NMR (400 MHz, CD$_2$Cl$_2$) δ (ppm) 10.15 (s, 1H), 8.13-8.10 (m, 1H), 8.06 (s, 1H), 7.20-7.16 (m, 2H), 6.49 (s, 1H), 3.78-3.50 (m, 14H), 2.72 (t, J=6.3 Hz, 2H), 1.76 (s, 6H), 1.47 (m, 9H).

Example 320

2-(4-{5-tert-Butyl-2-[3-(2-chloro-4-fluorophenyl)ureido]thiophene-3-carbonyl}-7-oxo-[1,4]diazepan-1-yl)-N-methoxy-N-methylacetamide

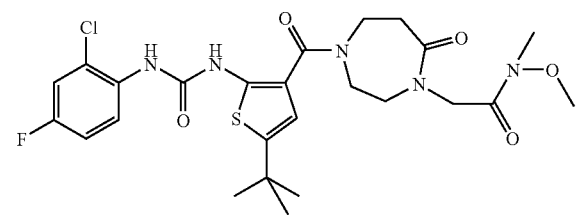

The compound of this example was prepared using a procedure analogous to the procedure described in Example 263. $^1$H-NMR (400 MHz, CDCl$_3$): δ (ppm) 10.01 (s, 1H), 8.12 (dd, J=9.2, 5.7 Hz, 1H), 7.73 (s, 1H), 7.06 (dd, J=8.0, 2.9 Hz, 1H), 6.98-6.91 (m, 1H), 6.41 (s, 1H), 4.36 (s, 2H), 4.01-3.96 (m, 2H), 3.85-3.79 (m, 2H), 3.73 (s, 3H), 3.60-3.54 (m, 2H), 3.16 (s, 3H), 2.85-2.78 (m, 2H), 1.31 (s, 9H).

Example 321

2-(4-{5-tert-Butyl-2-[3-(2-chloro-3,4-difluorophenyl)ureido]thiophene-3-carbonyl}-7-oxo-[1,4]diazepan-1-yl)-N-methoxy-N-methylacetamide

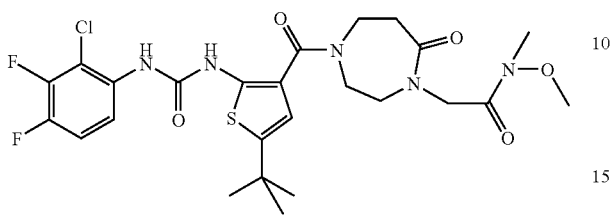

The compound of this example was prepared using a procedure analogous to the procedure described in Example 263.
$^1$H NMR (400 MHz, CDCl$_3$): δ (ppm) 9.98 (s, 1H), 7.93-7.88 (m, 1H), 7.82 (s, 1H), 6.99 (q, J=9.0 Hz, 1H), 6.37 (s, 1H), 4.31 (s, 2H), 3.96-3.91 (m, 2H), 3.79-3.74 (m, 2H), 3.68 (s, 3H), 3.56-3.50 (m, 2H), 3.11 (s, 3H), 2.81-2.75 (m, 2H), 1.26 (s, 9H).

Example 322

2-(4-{5-tert-Butyl-2-[3-(2-chloro-3,4-difluorophenyl)ureido]thiophene-3-carbonyl}-7-oxo-[1,4]diazepan-1-yl)-N-(2-dimethylaminoethyl)acetamide

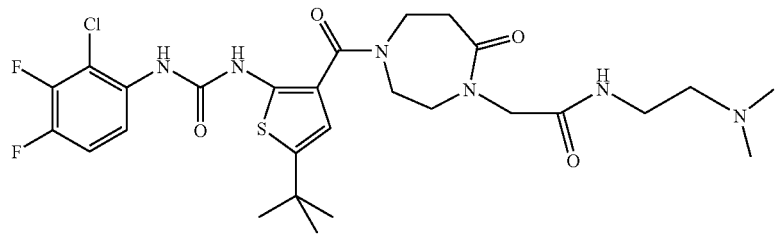

The compound of this example was prepared using a procedure analogous to the procedure described in Example 179.

$^1$H NMR (400 MHz, CDCl$_3$): δ (ppm) 7.85-7.78 (m, 1H), 7.22 (q, J=9.3 Hz, 1H), 6.59 (s, 1H), 4.09 (s, 2H), 3.89-3.84 (m, 2H), 3.79 (t, J=5.6 Hz, 2H), 3.70-3.64 (m, 2H), 3.38-3.33 (m, 2H), 2.84 (t, J=5.5 Hz, 2H), 2.57 (t, J=6.5 Hz, 2H), 2.35 (s, 6H), 1.35 (s, 9H).

Example 323

1-(5-tert-Butyl-3-(1-(2-(dimethylamino)ethyl)-3,3-dimethyl-2-oxopiperazine-4-carbonyl)thiophen-2-yl)-3-(2-chloropyridin-3-yl)urea

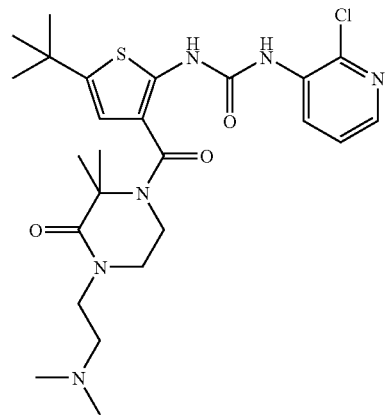

The compound of this example was prepared using the procedure described in Example 206 except that 3-chloro-4-isocyanatopyridine was used instead of 2,3-dichlorophenylisocyanate. $^1$H NMR (400 MHz, CD$_3$OD) δ (ppm) 8.49 (dd, J=8.0, 1.2 Hz, 1H), 8.04 (dd, J=4.8, 1.2 Hz, 1H), 7.35 (dd, J=8.0, 1.2 Hz, 1H), 6.60 (s, 1H), 3.70 (t, J=4.4 Hz, 2H), 3.56 (m, 4H), 2.61 (t, 2H), 2.34 (s, 6H), 1.80 (s, 6H), 1.36 (s, 9H).

Example 324

1-(5-tert-Butyl-3-(1-(2-(dimethylamino)ethyl)-7-oxo-1,4-diazepane-4-carbonyl)thiophen-2-yl)-3-(2-chloropyridin-3-yl)urea

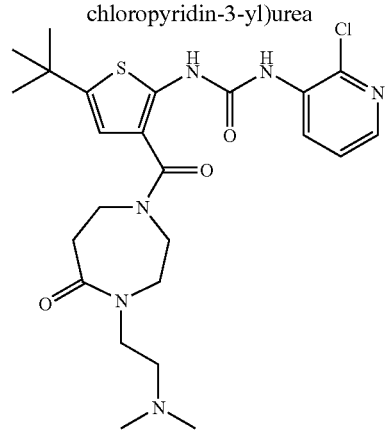

The compound of this example was prepared using the procedure described in Example 212 except that 3-chloro-4-isocyanatopyridine was used instead of 2,3-dichlorophenyl-isocyanate. $^1$H NMR (400 MHz, CD$_3$OD) δ (ppm) 8.51 (dd, J=8.0, 1.2 Hz, 1H), 8.04 (dd, J=4.8, 1.2 Hz,), 7.35 (dd, J=8.0, 4.8 Hz, 1H), 6.60 (s, 1H), 3.78 (m, 2H), 3.74 (t, J=6.0 Hz, 2H), 3.62 (m, 2H), 3.52 (t, J=6.8 Hz, 2H), 2.81 (m, 2H), 2.45 (m, 2H), 2.26 (s, 6H), 1.36 (s, 9H).

Example 325

1-(5-tert-Butyl-3-(1-(2-(dimethylamino)ethyl)-3,3-dimethyl-2-oxopiperazine-4-carbonyl)thiophen-2-yl)-3-(2-chloro-3-methylphenyl)urea

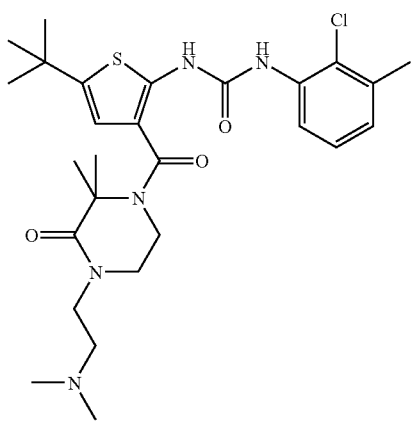

The compound of this example was prepared using the procedure described in Example 206 except that 2-chloro-3-methyl phenylisocyanate was used instead of 2,3-dichlorophenylisocyanate. $^1$H NMR (400 MHz, CD$_3$OD) δ (ppm) 7.45 (dd, J=8.0, 1.2 Hz, 1H), 7.15 (m, 1H), 7.03 (m, 1H), 6.58 (s, 1H), 3.68 (m, 2H), 3.53 (m, 4H), 2.57 (t, J=8.8 Hz, 2H), 2.32 (s, 3H), 2.31 (s, 6H), 1.78 (s, 6H), 1.34 (s, 9H).

Example 326

1-(5-tert-Butyl-3-(1-(2-(dimethylamino)ethyl)-7-oxo-1,4-diazepane-4-carbonyl)thiophen-2-yl)-3-(2-chloro-3-methylphenyl)urea

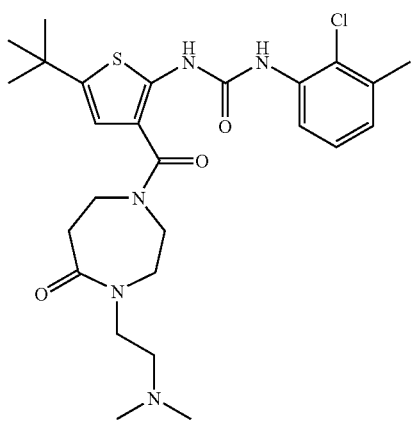

The compound of this example was prepared using the procedure described in Example 212 except that 2-chloro-3-methylphenyl isocyanate was used instead of 2,3-dichlorophenyl isocyanate. $^1$H NMR (400 MHz, CD$_3$OD) δ (ppm) 7.78 (m, 1H), 7.15 (t, J=8.0 Hz, 1H), 7.01 (m, 1H), 6.58 (s, 1H), 3.78 (m, 2H), 3.73 (m, 2H), 3.61 (m, 2H), 3.52 (t, J=6.8 Hz, 2H), 2.81 (t, J=6.0 Hz, 2H), 2.49 (t, J=6.4 Hz, 2H), 2.36 (s, 3H), 2.29 (s, 6H), 1.34 (s, 9H).

Example 327

1-(5-tert-butyl-3-(2,2-dimethyl-3-oxopiperazine-1-carbonyl)thiophen-2-yl)-3-o-tolylurea

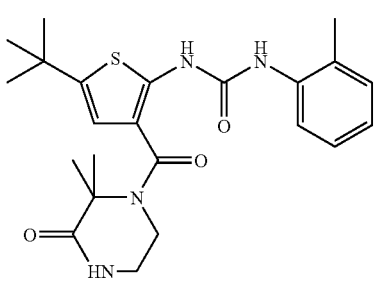

The compound of this example was prepared using the procedure described in Example 179 except that 2-methylphenyl isocyanate was used instead of 2,3-dichlorophenyl-isocyanate. $^1$H NMR (400 MHz, acetone-d$_6$) δ (ppm) 9.84 (s, 1H), 8.57 (s, 1H), 7.74 (d, J=8.0 Hz, 1H), 7.21-7.17 (m, 1H), 7.04 (m, 1H), 6.63 (s, 1H), 3.76 (t, J=4.8 Hz, 2H), 3.54 (m, 2H), 2.26 (s, 3H), 1.72 (s, 6H), 1.35 (s, 9H).

Example 328

1-(5-tert-butyl-3-(2,2-dimethyl-3-oxopiperazine-1-carbonyl)thiophen-2-yl)-3-(2-ethylphenyl)urea

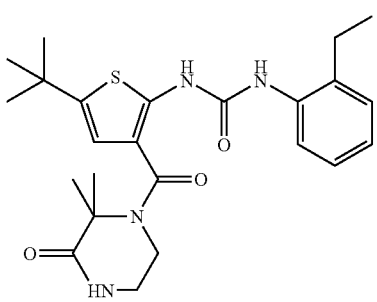

The compound of this example was prepared using the procedure described in Example 179 except that 2-ethylphenylisocyanate was used instead of 2,3-dichlorophenylisocyanate. $^1$H NMR (400 MHz, acetone-d$_6$) δ (ppm) 9.83 (s, 1H), 8.54 (s, 1H), 7.68 (d, J=8.0 Hz, 1H), 7.24 (d, J=8.0 Hz, 1H), 7.20 (m, 1H), 7.15 (s, 1H), 7.11 (m, 1H), 6.63 (s, 1H), 3.75 (t, J=4.8 Hz, 2H), 3.53 (m, 2H), 2.67 (q, J=7.6 Hz, 2H), 1.71 (s, 6H), 1.35 (s, 9H), 1.18 (t, J=7.6 Hz, 3H).

Example 329

1-(5-tert-Butyl-3-(2,2-dimethyl-3-oxopiperazine-1-carbonyl)thiophen-2-yl)-3-(2-tert-butylphenyl)urea

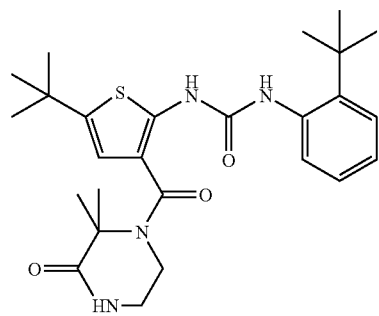

The compound of this example was prepared using the procedure described in Example 179 except that 2-tert-butylphenyl isocyanate was used instead of 2,3-dichlorophenylisocyanate. $^1$H NMR (400 MHz, Acetone-$d_6$) δ (ppm) 9.79 (s, 1H), 8.20 (s, 1H), 7.48 (m, 1H), 7.28-7.23 (3H), 7.17 (s, 1H), 6.61 (s, 1H), 3.74 (t, J=4.8 Hz, 2H), 3.52 (m, 2H), 1.68 (s, 9H), 1.35 (s, 9H).

Example 330

1-(5-tert-Butyl-3-(1-(2-(dimethylamino)ethyl)-3,3-dimethyl-2-oxopiperazine-4-carbonyl)thiophen-2-yl)-3-(2-chloro-3-methoxyphenyl)urea

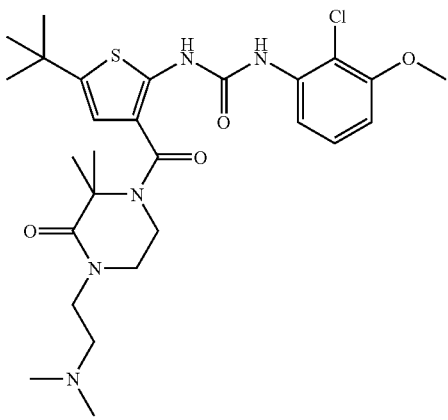

The compound of this example was prepared using the procedure described in Example 206 except that 2-chloro-3-methoxyphenyl isocyanate was used instead of 2-chloro-4-fluorophenylisocyanate. $^1$H NMR (400 MHz, CD$_3$OD) δ (ppm) 7.67 (d, J=6.8 Hz, 1H), 7.24 (d, J=8.8 Hz, 1H), 6.63 (dd, J=8.8, 3.2 Hz, 1H), 6.58 (s, 1H), 3.77 (s, 3H), 3.68 (m, 2H), 3.55 (m, 4H), 2.58 (t, J=6.8 Hz, 2H), 2.32 (s, 6H), 1.79 (s, 6H), 1.34 (s, 9H).

Example 331

1-(5-tert-Butyl-3-(1-(2-(dimethylamino)ethyl)-7-oxo-1,4-diazepane-4-carbonyl)thiophen-2-yl)-3-(2-chloro-3-methoxyphenyl)urea

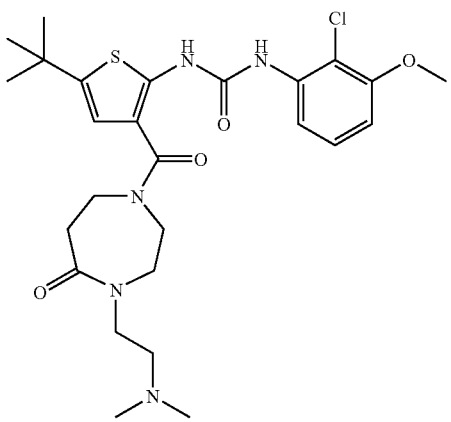

The compound of this example was prepared using the procedure described in Example 212 except that 2-chloro-3-methoxyl phenylisocyanate was used instead of 2-chloro-4-fluorophenylisocyanate. $^1$H NMR (400 MHz, CD$_3$OD) δ (ppm) 7.70 (d, J=7.2 Hz, 1H), 7.25 (d, J=8.8 Hz, 1H), 6.62 (dd, J=8.8, 3.2 Hz, 1H), 6.58 (s, 1H), 3.78 (t, J=6.0 Hz, 2H), 3.77 (s, 3H), 3.73 (t, J=6.0 Hz, 2H), 3.61 (m, 2H), 3.52 (t, J=6.8 Hz, 2H), 2.80 (t, J=5.6 Hz, 2H), 2.45 (t, J=6.8 Hz, 2H), 2.26 (s, 6H), 1.35 (s, 9H).

Example 332

1-(5-tert-Butyl-3-(1-(2-((2,2-dimethyl-1,3-dioxolan-4-yl)methylamino)-2-oxoethyl)-3,3-dimethyl-2-oxopiperazine-4-carbonyl)thiophen-2-yl)-3-(2,3-dichlorophenyl)urea

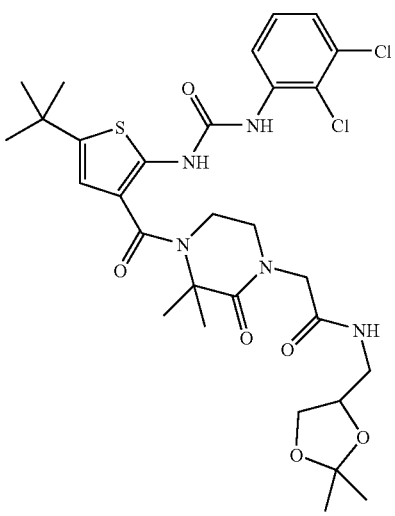

The compound of this example was prepared using the procedure described in Example 179 except that N-(2,2-dimethyl-1,3-dioxolan-4-yl)methyl)-2-(3-ethyl-3-methyl-2-oxopiperazin-1-yl)acetamide was used instead of 3,3-methylethylpiperazin-2-one. $^1$H NMR (400 MHz, CD$_2$Cl$_2$): δ (ppm) 10.18 (s, 1H), 8.14 (d, J=8.1 Hz, 1H), 7.51 (s, 1H), 7.26-7.20 (m, 2H), 6.50 (s, 1H), 6.33 (br s, 1H), 4.21 (q, J=3.3 Hz, 1H), 4.06-4.00 (m, 4H), 3.80 (t, J=4.3 Hz, 2H), 3.63-3.59 (m, 2H), 3.50-3.48 (m, 1H), 3.33-3.30 (m, 1H), 1.78 (s, 6H), 1.59 (s, 6H), 1.35 (s, 9H).

Example 333

1-(5-tert-Butyl-3-(1-(2-(2,3-dihydroxypropylamino)-2-oxoethyl)-3,3-dimethyl-2-oxopiperazine-4-carbonyl)thiophen-2-yl)-3-(2,3-dichlorophenyl)urea

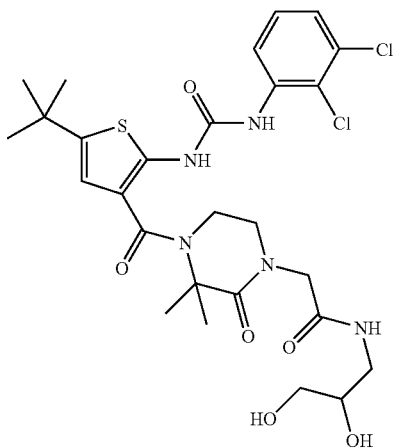

The compound of this example was prepared using the compound of Example 331 in dichloromethane and treating it with trifluoroacetic acid and stirring for 1 h. The reaction was then quenched with saturated aqueous sodium bicarbonate. The crude was concentrated and taken up in methanol, loaded in silicagel. The compound was eluted with a 10:1 dichloromethane:methanol mixture to yield the expected compound. $^1$H NMR (400 MHz, CD$_2$Cl$_2$): δ (ppm) 10.18 (s, 1H), 8.60 (s, 1H), 8.24 (d, J=8.2 Hz, 1H), 7.51 (s, 1H), 7.26-7.20 (m, 2H), 6.48 (s, 1H), 4.12-3.30 (m, 11H), 1.78 (s, 6H), 1.35 (s, 9H).

Example 334

1-(5-tert-Butyl-2-(1-(2-(2-(dimethylamino)ethylamino)-2-oxoethyl)-3-ethyl-3-methyl-2-oxopiperazine-4-carbonyl)thiophen-3-yl)-3-(2,3-dichlorophenyl)urea

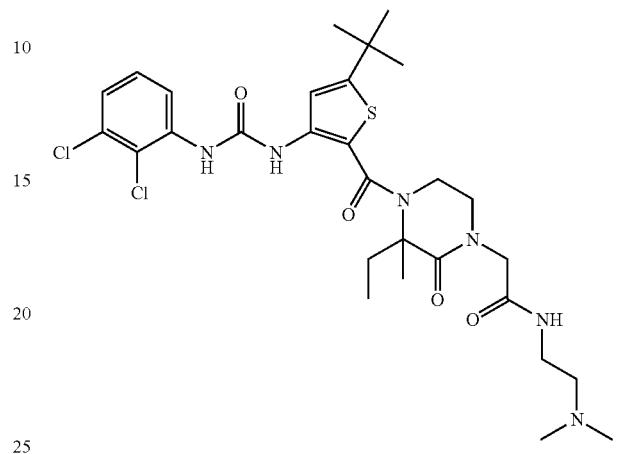

The compound of this example was prepared using the procedure described in Example 183 except that N-(2-dimethylamino)ethyl)-2-(3-ethyl-3-methyl-2-oxopiperazin-1-yl)acetamide was used instead of 3-ethyl-3-methylpiperazin-2-one. $^1$H NMR (400 MHz, DMSO-d$_6$): δ (ppm) 9.50 (bs, 1H); 9.27 (bs, 1H); 7.90 (m, 1H); 7.80 (m, 1H); 7.39 (s, 1H); 7.28 (m, 1H); 4.00 (m, 5H); 3.80 (d, 1H); 3.58 (m, 2H); 2.61 (m, 1H); 2.45 (d, 6H); 2.25 (t, 2H); 2.12 (s, 3H); 1.90 (m, 1H); 1.30 (s, 9H); 0.70 (t, 3H).

Example 335

1-(5-tert-Butyl-2-(1-(2-(2-(dimethylamino)ethylamino)-2-oxoethyl)-3,3-dimethyl-2-oxopiperazine-4-carbonyl)thiophen-3-yl)-3-(2,3-dichlorophenyl)urea

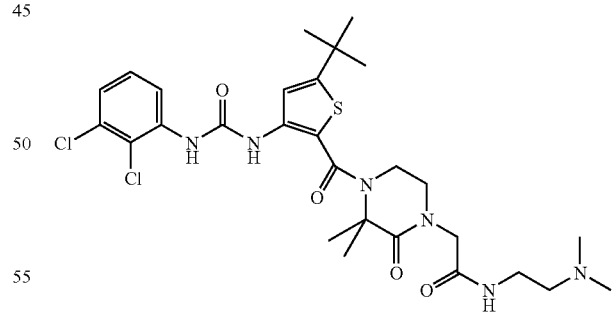

The compound of this example was prepared using the procedure described in Example 183 except that 2-(3,3-dimethyl-2-oxopiperazin-1-yl)-N-(2-dimethylamino)ethyl)acetamide was used instead of 3-ethyl-3-methylpiperazin-2-one. $^1$H NMR (400 MHz, CD$_2$Cl$_2$): δ (ppm) 9.75 (bs, 1H); 8.02 (d, 1H); 7.61 (s, 1H); 7.13 (m, 3H); 6.42 (t, 1H); 3.92 (m, 4H); 3.53 (m, 2H); 3.20 (m, 2H); 2.30 (m, 2H); 2.12 (s, 6H); 1.67 (s, 6H); 1.30 (s, 9H).

Example 336

1-(5-tert-Butyl-3-(3,3-dimethyl-2-oxo-1-(2-oxo-2-(propylamino)ethyl)piperazine-4-carbonyl)thiophen-2-yl)-3-(2,3-dichlorophenyl)urea

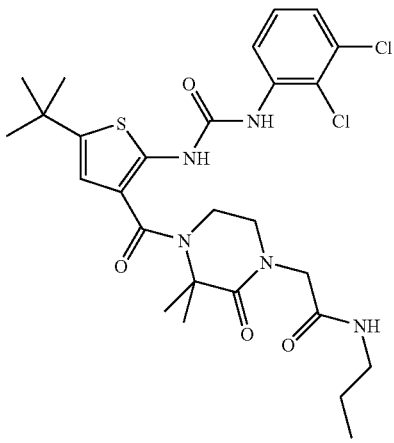

The compound of this example was prepared using the procedure described in Example 179 except that 2-(3,3-dimethyl-2-oxopiperazin-1-yl)-N-propylacetamide was used instead of 3-ethyl-3-methylpiperazin-2-one. $^1$H NMR (400 MHz, CD$_2$Cl$_2$): δ 10.19 (s, 1H), 8.16 (dd, J=7.9, 1.9 Hz, 1H), 7.89 (s, 1H), 7.24-7.14 (m, 2H), 6.48 (s, 1H), 6.14 (s, 1H), 4.03 (s, 2H), 3.79 (t, J=4.9 Hz, 2H), 3.60 (t, J=4.9 Hz, 2H), 3.18 (q, J=6.6 Hz, 2H), 1.74 (s, 6H), 1.54-1.46 (m, 2H), 1.37 (s, 9H), 0.92 (t, J=4.9 Hz, 3H).

Example 337

1-(5-tert-Butyl-3-(1-(2-(methoxymethoxy)ethyl)-3,3-dimethyl-2-oxopiperazine-4-carbonyl)thiophen-2-yl)-3-(2,3-dichlorophenyl)urea

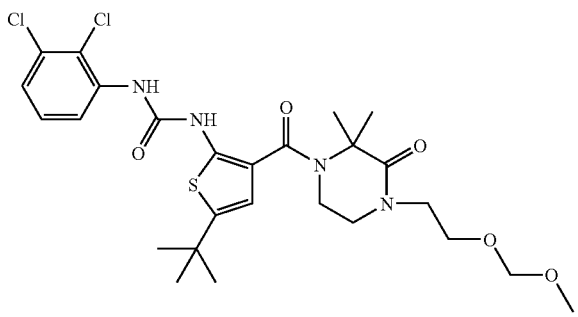

The compound of this example was prepared using the procedure described in Example 179 except that 1-(2-(methoxylmethyl)ethyl)-3,3-dimethylpiperazin-2-one was used instead of 3-ethyl-3-methylpiperazin-2-one. $^1$H NMR (400 MHz, CDCl$_3$): δ (ppm) 10.16 (s, 1H), 8.11 (q, J=3.3 Hz, 1H), 7.46 (s, 1H), 7.13-7.08 (m, 2H), 6.38 (s, 1H), 4.56 (s, 2H), 3.73-3.63 (m, 4H), 3.61-3.53 (m, 4H), 3.30 (s, 3H), 1.74 (s, 6H), 1.29 (s, 9H).

Example 338

1-(5-tert-Butyl-3-(1-(2-hydroxyethyl)-3,3-dimethyl-2-oxopiperazine-4-carbonyl)thiophen-2-yl)-3-(2,3-dichlorophenyl)urea

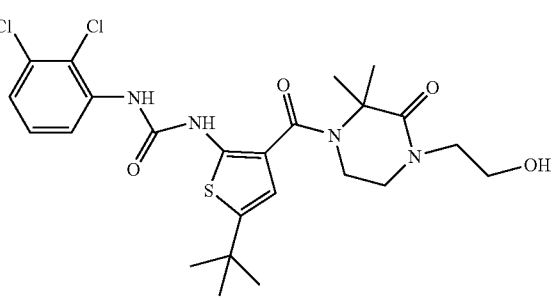

The compound of this example was prepared using the procedure described in Example 179 except that 1-(2-hydroxyethyl)-3,3-dimethyl-piperazin-2-one was used instead of 3-ethyl-3-methylpiperazin-2-one. $^1$H NMR (400 MHz, CDCl$_3$): δ (ppm) 10.19 (s, 1H), 8.08 (s, 1H), 7.13-7.08 (m, 2H), 6.38 (s, 1H), 3.81-3.67 (m, 4H), 3.59-3.50 (m, 4H), 1.75 (s, 6H), 1.29 (s, 9H).

Example 339

1-(5-tert-Butyl-3-(1,3,3-trimethylpiperazine-4-carbonyl)thiophen-2-yl)-3-(2,3-dichlorophenyl)urea

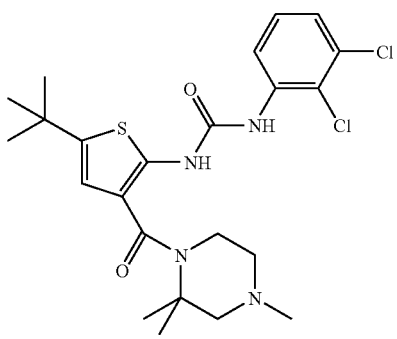

The compound of this example was prepared using the procedure described in Example 179 except that 1,3,3-trimethylpiperazin-2-one was used instead of 3-ethyl-3-methylpiperazin-2-one. $^1$H NMR (400 MHz, CD$_2$Cl$_2$): δ (ppm) 10.48 (s, 1H), 8.24 (d, J=8.1 Hz, 1H), 8.12 (s, 1H), 7.20-7.09 (m, 2H), 6.50 (s, 1H), 3.58 (t, J=4.9 Hz, 2H), 2.45 (t, J=4.8 Hz, 2H), 2.33 (s, 2H), 2.23 (s, 3H), 1.46 (s, 6H), 1.37 (s, 9H).

Example 340

1-(5-tert-butyl-3-(5-oxo-1,4-diazepane-1-carbonyl)thiophen-2-yl)-3-(3,5-dichloropyridin-4-yl)urea

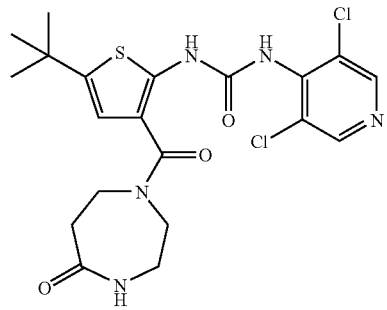

$^1$H NMR (400 MHz, CD$_3$OD) δ (ppm) 8.53 (s, 2H), 6.62 (s, 1H), 3.77 (m, 4H), 3.38 (m, 2H), 2.74 (m, 2H), 1.34 (s, 9H).

Example 341

1-(5-tert-butyl-3-(1-(2-(2-(dimethylamino)ethylamino)-2-oxoethyl)piperazine-4-carbonyl)thiophen-2-yl)-3-(2,3-dichlorophenyl)urea

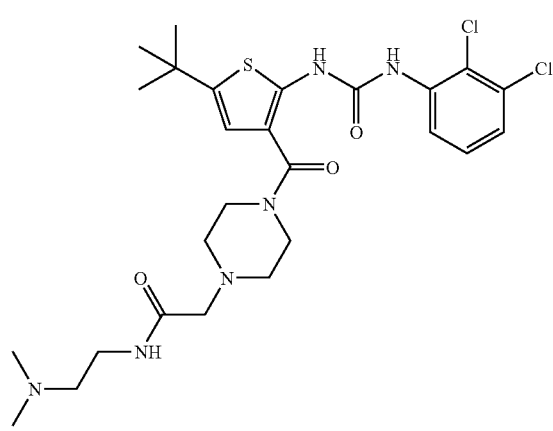

$^1$H NMR (400 MHz, CD$_3$OD) δ 8.01 (ddd, J=6.0, 3.2, 0.8 Hz, 1H), 7.24 (dd, J=4.4, 0.8 Hz, 1H), 7.23 (m, 1H), 6.57 (s, 1H), 3.70 (m, 4H), 3.35 (t, J=6.8 Hz, 2H), 3.04 (s, 2H), 2.55 (m, 4H), 2.44 (t, J=6.8 Hz, 2H), 2.25 (s, 6H), 1.34 (s, 9H).

Example 342

1-(2-tert-butyl-4-(2,2-dimethyl-3-oxopiperazine-1-carbonyl)thiazol-5-yl)-3-(2,3-dichlorophenyl)urea

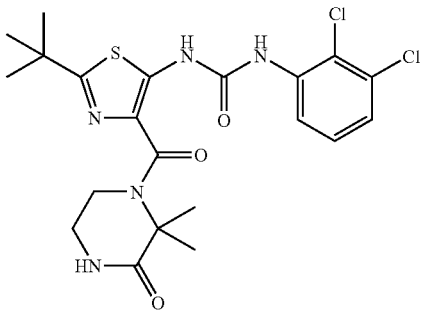

$^1$H NMR (400 MHz, dmso-d$_6$): δ (ppm) 10.65 (s, 1H), 9.95 (s, 1H), 8.00 (br s, 1H), 7.86 (dd, J=8.0, 1.8 Hz, 1H), 7.35 (dd, J=8.1, 1.9 Hz, 1H), 7.31 (t, J=8.1 Hz, 1H), 3.77 (t, J=4.6 Hz, 2H), 3.38-3.31 (m, 2H), 1.68 (s, 6H), 1.32 (s, 9H)

Example 343

1-(5-tert-butyl-3-(1-(2-(3-(dimethylamino)propylamino)-2-oxoethyl)-3,3-dimethyl-2-oxopiperazine-4-carbonyl)thiophen-2-yl)-3-(2,3-dichlorophenyl)urea

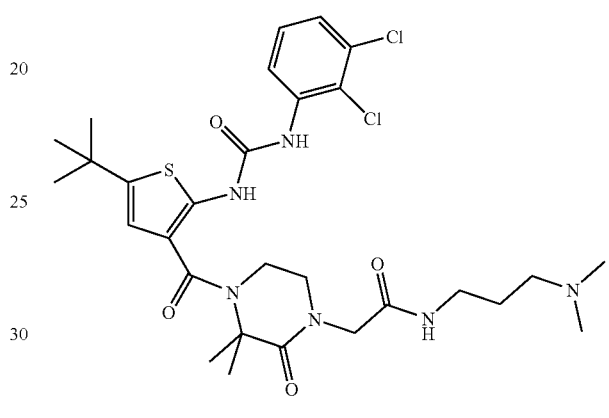

$^1$H NMR (400 MHz, CD$_6$SO): δ (ppm) 10.48 (s, 1H), 10.03 (s, 1H), 9.56 (s, 1H), 7.88-7.82 (m, 2H), 7.25 (s, 1H), 6.48 (s, 1H), 3.87 (s, 2H), 3.59-2.55 (m, 2H), 3.46-3.42 (m, 2H), 3.06-3.03 (m, 2H), 2.38-2.34 (m, 2H), 2.21 (s, 6H), 1.64 (s, 6H), 1.55 (t, J=10.3 Hz, 2H), 1.21 (s, 9H).

Example 344

1-(5-tert-butyl-3-(5-oxo-1,4-diazepane-1-carbonyl)-1H-pyrrol-2-yl)-3-(2,3-dichlorophenyl)urea

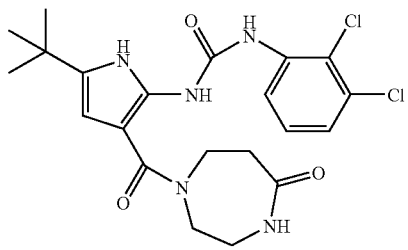

$^1$H NMR (400 MHz, CDCl$_3$): δ (ppm) 10.45 (s, 1H), 10.24 (s, 1H), 8.03 (d, J=7.8 Hz, 1H), 7.80 (s, 1H), 7.28-7.23 (m, 2H), 6.40 (s, 1H), 5.70 (d, J=2.9 Hz, 1H), 3.90-3.85 (m, 4H), 3.43-3.37 (m, 2H), 2.78-2.72 (m, 2H), 1.26 (s, 9H).

Example 345

2-(4-{5-tert-Butyl-2-[3-(2-chloro-4-fluoro-phenyl)-ureido]-thiophene-3-carbonyl}-3,3-dimethyl-2-oxo-piperazin-1-yl)-N-(2-dimethylamino-ethyl)-acetamide

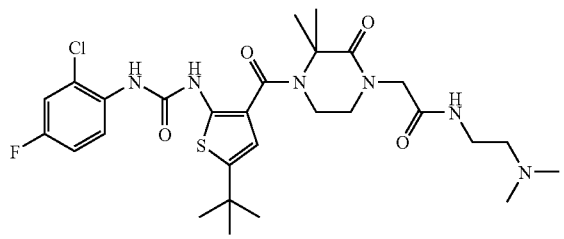

$^1$H NMR (400 MHz, CDCl$_3$): δ (ppm) (ppm) 10.05 (s, 1H), 8.07 (dd, J=9.1, 5.6 Hz, 1H), 7.93 (s, 1H), 7.51 (t, J=5.4 Hz, 1H), 6.99 (dd, J=8.1, 3.0 Hz, 1H), 6.93-6.86 (m, 1H), 6.39 (s, 1H), 3.99 (s, 2H), 3.77 (t, J=4.8 Hz, 2H), 3.55 (t, J=4.8 Hz, 2H), 3.46 (q, J=5.5 Hz, 2H), 2.79 (t, J=5.6 Hz, 2H), 2.49 (s, 6H), 1.73 (s, 6H), 1.27 (s, 9H).

Example 346

Methyl 2-(4-(2-tert-butyl-5-(3-(2,3-dichlorophenyl)ureido)thiazole-4-carbonyl)-3,3-dimethyl-2-oxopiperazin-1-yl)acetate

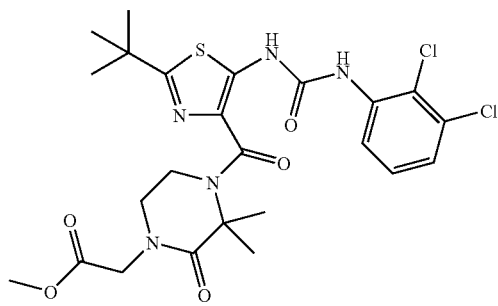

$^1$H NMR (400 MHz, dmso-d$_6$): δ (ppm) 10.67 (s, 1H), 9.97 (s, 1H), 7.86 (dd, J=8.0, 1.8 Hz, 1H), 7.36 (dd, J=8.0, 1.8 Hz, 1H), 7.31 (t, J=8.0 Hz, 1H), 4.14 (s, 2H), 3.88 (t, J=4.5 Hz, 2H), 3.64 (s, 3H), 3.59 (t, J=4.5 Hz, 2H), 1.70 (s, 6H), 1.33 (s, 9H).

Example 347

Methyl 4-(3-(5-tert-butyl-2-(2,2-dimethyl-3-oxopiperazine-1-carbonyl)thiophen-3-yl)ureido)-3-chlorobenzoate

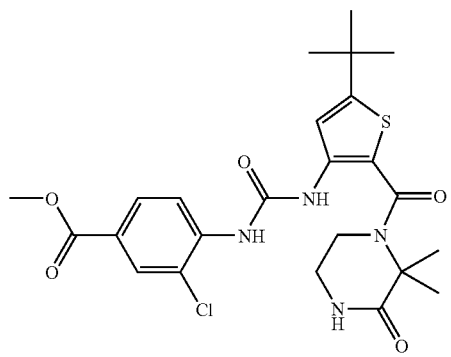

$^1$H NMR (400 MHz, CDCl$_3$) δ (ppm) 1.37 (s, 9H), 1.78 (s, 6H), 3.54 (m, 2H), 3.88 (s, 3H), 3.94 (m, 2H), 6.26 (s br, 1H), 7.41 (s, 1H), 7.72 (s, 1H), 7.91 (d, J=9.4 Hz, 1H), 8.03 (s, 1H), 8.33 (d, J=9.4 Hz, 1H), 9.97 (s, 1H).

Example 348

(2-(4-{5-tert-Butyl-3-[3-(2-chloro-3,4-difluoro-phenyl)-ureido]-thiophene-2-carbonyl}-3,3-dimethyl-2-oxo-piperazin-1-yl)-N-(2-dimethylamino-ethyl)-acetamide)

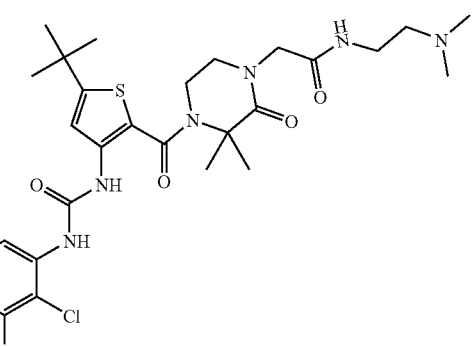

$^1$H NMR (400 MHz, CD$_2$Cl$_2$): δ (ppm) 9.80 (bs, 1H); 8.00 (m, 1H); 7.65 (s, 1H); 7.21 (bs, 1H); 7.15 (t, 1H); 6.66 (bs, 1H); 4.00 (s, 1H); 3.97 (m, 2H); 3.60 (m, 2H); 3.33 (q, 2H); 2.44 (t, 2H); 2.22 (s, 6H); 1.76 (s, 6H); 1.39 (s, 9H).

Example 349

2-(4-{5-tert-Butyl-3-[3-(2,3-dichloro-pyridin-4-yl)-ureido]-thiophene-2-carbonyl}-3,3-dimethyl-2-oxo-piperazin-1-yl)-N-(2-dimethylamino-ethyl)-acetamide

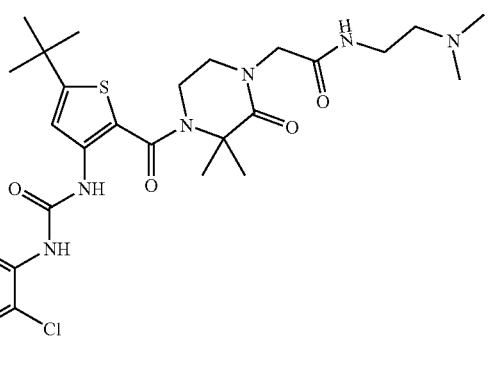

¹H NMR (400 MHz, CD2Cl2): δ (ppm) 10.00 (bs, 1H); 8.25 (d, 1H); 8.15 (d, 1H); 7.68 (s, 1H); 7.60 (bs, 1H); 6.63 (bs, 1H); 4.00 (s, 1H); 3.97 (m, 2H); 3.60 (m, 2H); 3.33 (q, 2H); 2.43 (t, 2H); 2.22 (s, 6H); 1.77 (s, 6H); 1.39 (s, 9H).

Example 350

1-(5-tert-butyl-2-(2,2-dimethyl-3-oxopiperazine-1-carbonyl)thiophen-3-yl)-3-(2-chloro-6-methylphenyl)urea

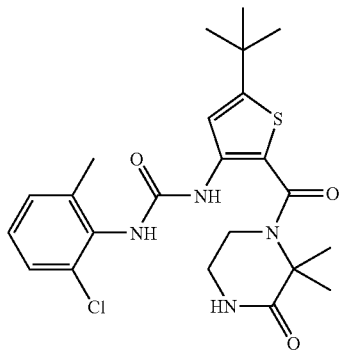

¹H NMR (400 MHz, CD3OD) δ (ppm) 1.36 (s, 9H), 1.73 (s, 6H), 2.32 (s, 3H), 3.43 (m, 2H), 3.85 (m, 2H), 7.23-7.14 (m, 2H), 7.31 (d, J=8.0 Hz, 1H), 7.48 (s, 1H).

Example 351

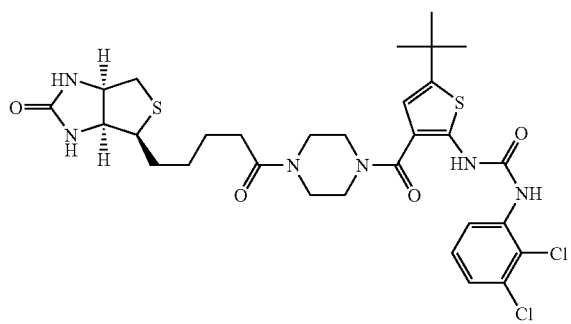

¹H NMR (400 MHz, CDCl3): δ (ppm) 10.21 (s, 1H), 8.50 (s, 1H), 8.17 (dd, J=8.0, 1.8 Hz, 1H), 7.07-7.15 (m, 2H), 6.41 (s, 1H), 6.39 (s, 1H), 5.74 (s, 1H), 4.43-4.47 (m, 1H), 4.24-4.29 (m, 1H), 3.45-3.69 (m, 8H), 3.11 (q, J=6.2 Hz, 1H), 2.85 (dd, J=12.8, 4.8 Hz, 1H), 2.69 (d, J=12.7 Hz, 1H), 2.35 (t, J=7.1 Hz, 2H), 1.56-1.76 (m, 4H), 1.38-1.47 (m, 2H), 1.30 (s, 9H).

Example 352

1-(5-tert-Butyl-3-(1-(3-(4-methoxyphenyl)propanoyl)piperazine-4-carbonyl)thiophen-2-yl)-3-(2,3-dichlorophenyl)urea

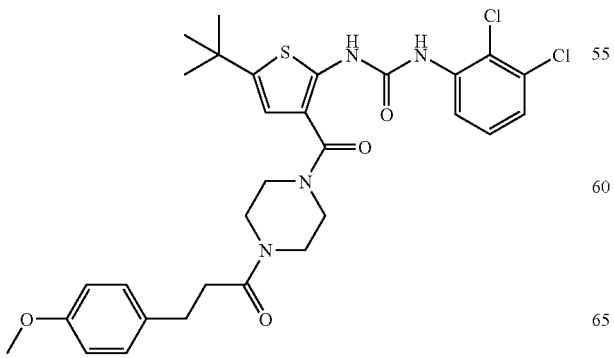

¹H NMR (400 MHz, CDCl3): δ (ppm) 10.16 (s, 1H), 8.15 (dd, J=7.6, 2.1 Hz, 1H), 8.04 (s, 1H), 7.09-7.14 (m, 4H), 6.81 (d, J=8.6 Hz, 2H), 6.37 (s, 1H), 3.76 (s, 3H), 3.60-3.67 (m, 4H), 3.52 (s, 2H), 3.41 (s, 2H), 2.91 (t, J=7.6 Hz, 2H), 2.60 (t, J=7.6 Hz, 2H), 1.28 (s, 9H).

Example 353

1-(5-tert-Butyl-3-(1-(2-(4-methoxyphenyl)acetyl)piperazine-4-carbonyl)thiophen-2-yl)-3-(2,3-dichlorophenyl)urea

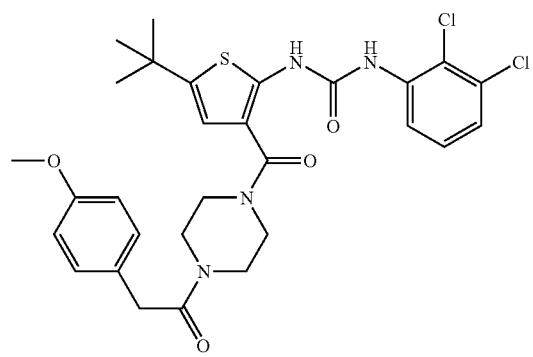

¹H NMR (400 MHz, CDCl3): δ (ppm) 10.11 (s, 1H), 8.13 (dd, J=7.4, 2.1 Hz, 1H), 8.01 (s, 1H), 7.08-7.16 (m, 4H), 6.84 (d, J=8.4 Hz, 2H), 6.35 (s, 1H), 3.76 (s, 3H), 3.69 (s, 2H), 3.66 (s, 2H), 3.62 (s, 2H), 3.46 (s, 4H), 1.27 (s, 9H).

Example 354 tert-Butyl 4-(2-tert-butyl-5-(3-(2,3-dichlorophenyl)ureido)thiophene-4-carbonyl)piperazine-1-carboxylate

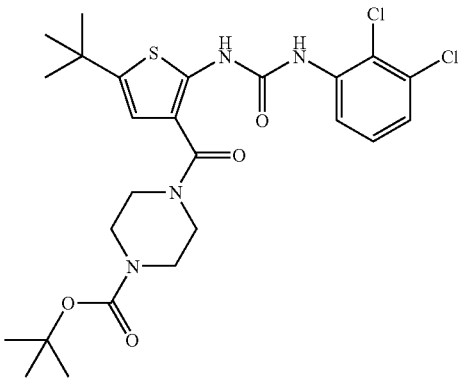

¹H NMR (400 MHz, CDCl₃): δ (ppm) 10.23 (s, 1H), 8.17 (dd, J=7.9, 2.0 Hz, 1H), 8.14 (s, 1H), 7.07-7.15 (m, 2H), 6.40 (s, 1H), 3.63-3.66 (m, 4H), 3.46-3.49 (m, 4H), 1.46 (s, 9H), 1.29 (s, 9H).

Example 355 tert-Butyl 4-(2-tert-butyl-5-(3-(2,3-dichlorophenyl)ureido)thiophene-4-carbonyl)-3,3-dimethylpiperazine-1-carboxylate

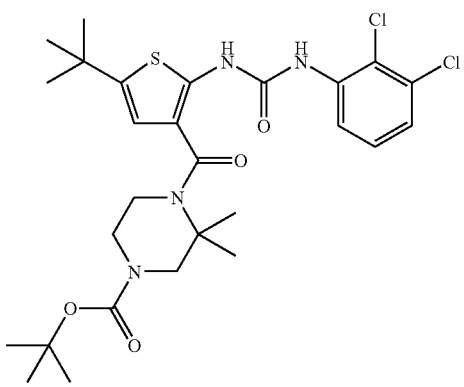

¹H NMR (400 MHz, CDCl₃): δ (ppm) 10.35 (s, 1H), 8.21 (d, J=7.8 Hz, 1H), 8.04 (s, 1H), 7.08-7.15 (m, 2H), 6.42 (s, 1H), 3.71-3.75 (m, 2H), 3.52 (s, 2H), 3.44 (s, 2H), 1.46 (s, 9H), 1.45 (s, 6H), 1.33 (s, 9H).

Example 356

1-(5-tert-Butyl-3-(piperazine-4-carbonyl)thiophen-2-yl)-3-(2,3-dichlorophenyl)urea

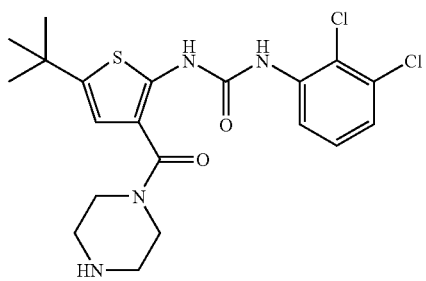

¹H NMR (400 MHz, methanol-d₄): δ (ppm) 7.95-8.00 (m, 1H), 7.22-7.28 (m, 2H), 6.64 (s, 1H), 3.90 (t, J=5.3 Hz, 4H), 3.29 (t, J=5.1 Hz, 4H), 1.36 (s, 9H).

Example 357

Methyl 2-(4-(2-tert-butyl-5-(3-(2,3-dichlorophenyl)ureido)thiophene-4-carbonyl)piperazin-1-yl)acetate

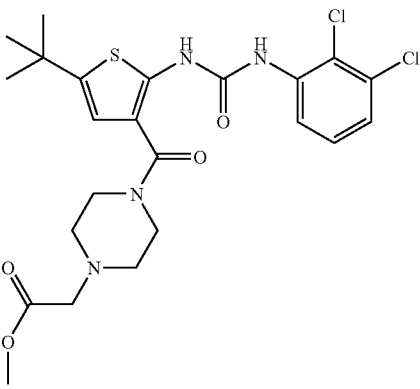

¹H NMR (400 MHz, methanol-d₄): δ (ppm) 8.03 (dd, J=7.2, 2.5 Hz, 1H), 7.09-7.15 (m, 2H), 6.43 (s, 1H), 3.66-3.70 (m, 7H), 3.25 (s, 2H), 2.60 (t, J=4.6 Hz, 4H), 1.28 (s, 9H).

Example 358

1-(5-tert-butyl-3-(1-(2-(2-(diethylamino)ethylamino)-2-oxoethyl)-3,3-dimethyl-2-oxopiperazine-4-carbonyl)thiophen-2-yl)-3-(2,3-dichlorophenyl)urea

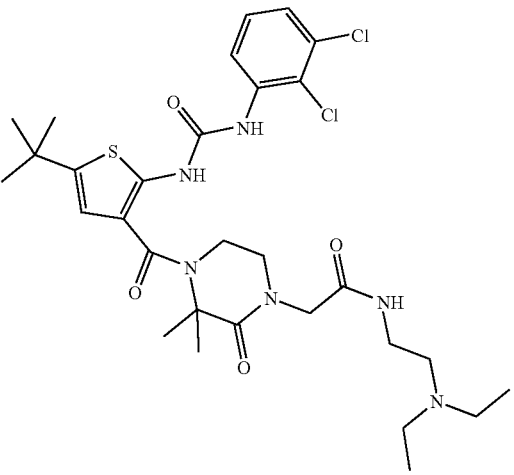

¹H NMR (400 MHz, CDCl₃): δ (ppm) 10.32 (s, 1H), 8.16 (dd, J=7.5, 2.4 Hz, 1H), 8.02 (s, 1H), 7.60 (br s, 1H), 7.20-7.13 (m, 2H), 6.50 (s, 1H), 4.06 (s, 2H), 3.81 (t, J=5.1 Hz, 2H), 3.66-3.61 (m, 2H), 3.43 (q, J=5.5 Hz, 2H), 2.79-2.69 (m, 6H), 1.81 (s, 6H), 1.34 (s, 9H), 1.11 (t, J=7.2 Hz, 6H).

Example 359

1-(5-tert-butyl-3-(1-(2-((2-(dimethylamino)ethyl)(methyl)amino)-2-oxoethyl)-3,3-dimethyl-2-oxopiperazine-4-carbonyl)thiophen-2-yl)-3-(2,3-dichlorophenyl)urea

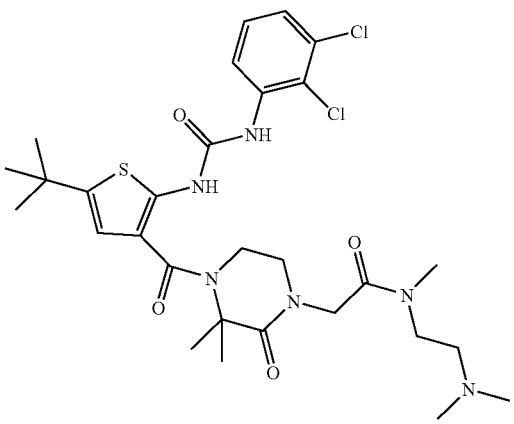

$^1$H NMR (400 MHz, CDCl$_3$): δ (ppm) 10.19 (s, 1H), 8.13 (dd, J=7.6, 2.5 Hz, 1H), 7.67 (s, 1H), 7.14-7.07 (m, 2H), 6.41 (s, 1H), 4.25 (s, 2H), 3.82-3.75 (m, 2H), 3.67-3.55 (m, 4H), 3.03 (s, 3H), 2.84 (t, J=6.1 Hz, 2H), 2.57 (s, 6H), 1.76 (s, 6H), 1.29 (s, 9H).

Example 360

1-(5-tert-butyl-3-(1-(2-(cyclopropylmethylamino)-2-oxoethyl)-3,3-dimethyl-2-oxopiperazine-4-carbonyl)thiophen-2-yl)-3-(2,3-dichlorophenyl)urea

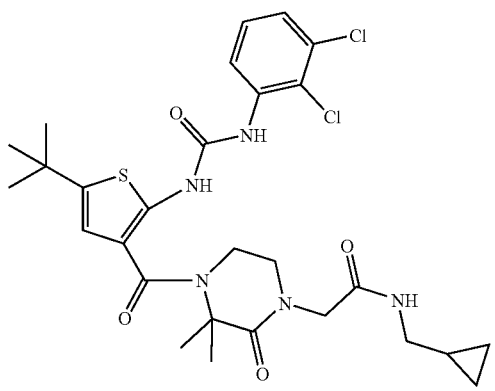

$^1$H NMR (400 MHz, CD$_3$OD): δ (ppm) 7.81 (t, J=4.9 Hz, 1H), 7.03-7.00 (m, 2H), 6.33 (s, 1H), 3.88 (s, 2H), 3.59 (t, J=5.0 Hz, 2H), 3.38 (t, J=4.9 Hz, 2H), 2.88 (d, J=7.0 Hz, 2H), 1.65 (s, 6H), 1.16 (s, 9H), 0.77 (s, 1H), 0.33-0.28 (m, 2H), 0.01 (t, J=5.3 Hz, 2H).

Example 361

1-(2-tert-butyl-4-(1-(2-(2-(dimethylamino)ethylamino)-2-oxoethyl)-3,3-dimethyl-2-oxopiperazine-4-carbonyl)thiazol-5-yl)-3-(2,3-dichlorophenyl)urea

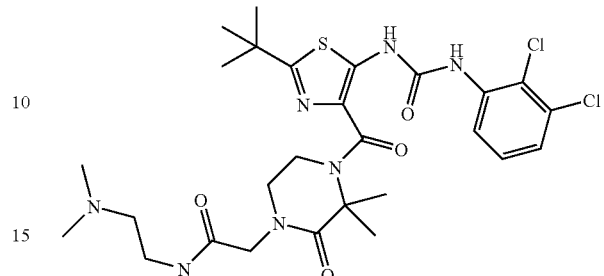

$^1$H NMR (400 MHz, CD$_3$OD/CDCl$_3$): δ (ppm) 7.91 (dd, J=6.8, 2.9 Hz, 1H), 7.20-7.13 (m, 2H), 4.06 (t, J=4.4 Hz, 2H), 4.03 (s, 2H), 3.67 (t, J=4.5 Hz, 2H), 3.36 (t, J=6.2 Hz, 2H), 2.58 (t, J=6.2 Hz, 2H), 2.35 (s, 6H), 1.80 (s, 6H), 1.35 (s, 9H).

Example 362

1-(5-tert-butyl-3-((2,2,2-trifluoroethyl)carbamoyl)thiophen-2-yl)-3-(2,3-dichlorophenyl)urea

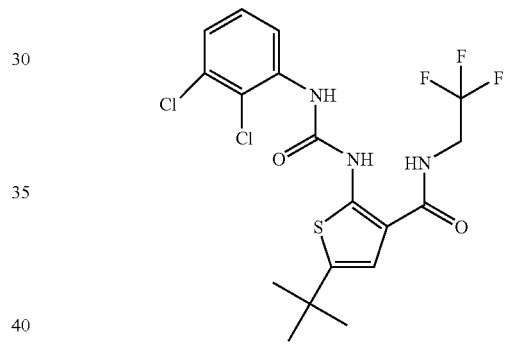

$^1$H NMR (400 MHz, CD$_2$Cl$_2$): δ (ppm) 11.31 (s, 1H), 8.12 (dd, J=7.1, 3.1 Hz, 1H), 7.42 (s, 1H), 7.26-7.20 (m, 2H), 6.67 (s, 1H), 6.27 (s, 1H), 4.13-4.03 (m, 2H 1.36 (s, 9H).

Example 363

1-(5-tert-butyl-3-(1-(5-(dimethylamino)pentyl)-3,3-dimethyl-2-oxopiperazine-4-carbonyl)thiophen-2-yl)-3-(2,3-dichlorophenyl)urea

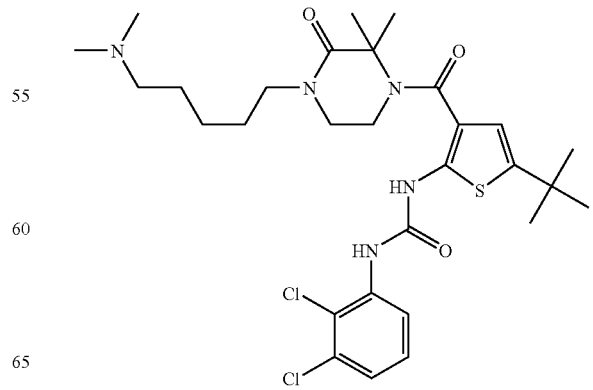

¹H NMR (400 MHz, CDCl₃): δ (ppm) 10.22 (s, 1H), 8.18 (dd, J=7.4, 2.6 Hz, 1H), 7.85 (s, 1H), 7.20-7.12 (m, 2H), 6.45 (s, 1H), 3.73 (t, J=4.8 Hz, 2H), 3.49-3.45 (m, 4H), 2.83 (t, J=7.9 Hz, 2H), 2.66 (s, 6H), 1.78 (s, 6H), 1.67-1.58 (m, 2H), 1.40-1.30 (s+m, 13H).

Example 364

1-(5-tert-butyl-3-(3,3-dimethyl-2-oxo-1-(2-oxo-2-(2,2,2-trifluoroethylamino)ethyl)piperazine-4-carbonyl)thiophen-2-yl)-3-(2,3-dichlorophenyl)urea

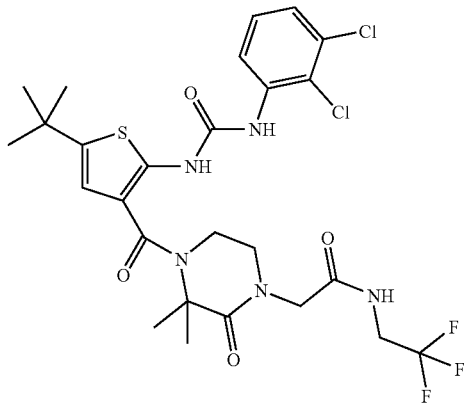

¹H NMR (400 MHz, CDCl₃): δ (ppm) 10.18 (s, 1H), 8.16 (dd, J=7.3, 2.7 Hz, 1H), 7.80 (s, 1H), 7.18-7.12 (m, 2H), 7.01 (t, J=6.3 Hz, 1H), 6.41 (s, 1H), 4.08 (s, 2H), 3.92-3.73 (m, 4H), 3.63 (t, J=4.8 Hz, 2H), 1.78 (s, 6H), 1.31 (s, 9H).

Example 365

1-(5-tert-butyl-2-(2,2-dimethyl-3-oxopiperazine-1-carbonyl)thiophen-3-yl)-3-(2-chloro-5-methoxyphenyl)urea

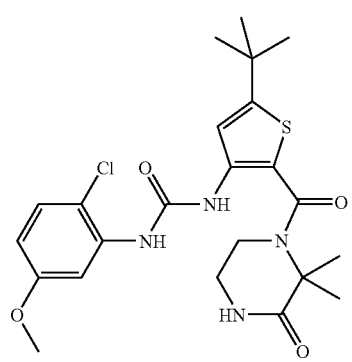

¹H NMR (400 MHz, DMSO-d₆) δ (ppm) 1.32 (s, 9H), 1.63 (s, 6H), 3.26 (m, 2H), 3.62 (m, 2H), 3.96 (s, 3H), 6.63 (dd, J=9.6 Hz, J=4.0 Hz, 1H), 7.26 (s, 1H), 7.31 (d, J=9.6 Hz, 1H), 7.61 (d, J=4.0 Hz, 1H), 8.05 (s, 1H), 8.92 (s, 1H), 9.40 (s, 1H).

Example 366

2-(4-{5-tert-Butyl-3-[3-(2,3-dichloro-4-fluoro-phenyl)-ureido]-thiophene-2-carbonyl}-3,3-dimethyl-2-oxo-piperazin-1-yl)-N-(2-dimethylamino-ethyl)-acetamide

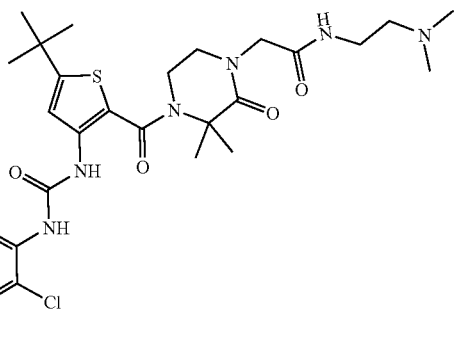

¹H NMR (400 MHz, CD2Cl2): δ (ppm) 9.80 (bs, 1H); 8.00 (m, 1H); 7.67 (s, 1H); 7.21 (bs, 1H); 7.15 (t, 1H); 6.67 (bs, 1H); 4.00 (s, 1H); 3.97 (m, 2H); 3.60 (m, 2H); 3.33 (q, 2H); 2.44 (t, 2H); 2.23 (s, 6H); 1.76 (s, 6H); 1.39 (s, 9H).

Example 367

1-(5-tert-Butyl-3-(2,2-dimethyl-3-oxopiperazine-1-carbonyl)thiophen-2-yl)-3-(3,5-dichloropyridin-4-yl)urea

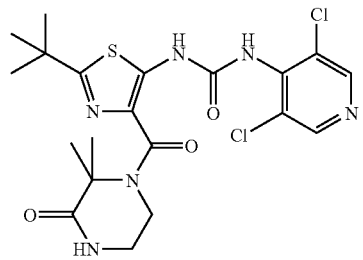

¹H NMR (400 MHz, CD₃OD) δ (ppm) 8.54 (s, 2H), 6.59 (s, 1H), 3.69 (t, J=4.8 Hz, 2H), 3.42 (t, J=4.8 Hz, 2H), 1.79 (s, 6H), 1.34 (s, 9H).

Example 368

1-(5-tert-Butyl-3-(2,2-dimethyl-3-oxopiperazine-1-carbonyl)thiophen-2-yl)-3-(3-chloropyridin-4-yl)urea

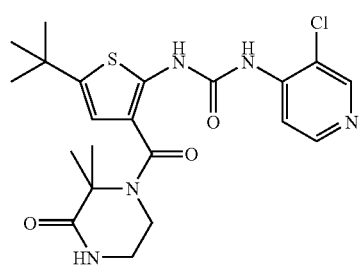

¹H NMR (400 MHz, CD₃OD) δ (ppm) 8.14 (dd, J=10.8, 6.0 Hz, 1H), 7.68 (m, 1H), 7.37 (dt, J=6.0, 2.0 Hz, 1H), 6.59 (s, 1H), 3.70 (m, 2H), 3.43 (m, 2H), 1.79 (s, 6H), 1.36 (s, 9H).

Example 369

1-(5-tert-Butyl-3-(1-(2-(dimethylamino)ethyl)-3,3-dimethyl-2-oxopiperazine-4-carbonyl)thiophen-2-yl)-3-(3-chloropyridin-4-yl)urea

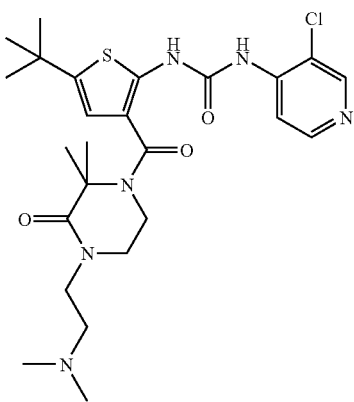

¹H NMR (400 MHz, CD₃OD) δ (ppm) 8.12 (d, J=6.0 Hz, 1H), 7.67 (d, J=2.0 Hz, 1H), 7.36 (m, 1H), 6.61 (s, 1H), 3.72 (m, 2H), 3.57 (m, 2H), 3.55 (m, 2H), 2.55 (t, J=7.8 Hz, 2H), 2.30 (s, 6H), 1.78 (s, 6H), 1.37 (s, 9H).

Example 370

1-(5-tert-Butyl-3-(2,2-dimethyl-3-oxopiperazine-1-carbonyl)thiophen-2-yl)-3-(2-chloro-3-methylphenyl)urea

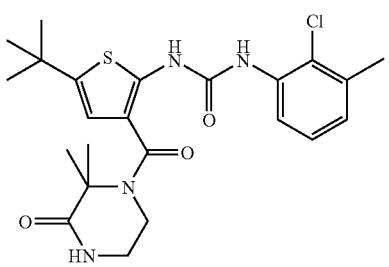

¹H NMR (400 MHz, CD₃OD) δ (ppm) 7.74 (dd, J=8.0, 1.6 Hz, 1H), 7.16 (t, J=8.0 Hz, 1H), 7.03 (d, J=8.0 Hz, 1H), 6.56 (s, 1H), 3.66 (m, 2H), 3.40 (m, 2H), 2.37 (s, 3H), 1.79 (s, 6H), 1.34 (s, 9H).

Example 371

1-(5-tert-Butyl-3-(1-(2-(2-(dimethylamino)ethylamino)-2-oxoethyl)-3-ethyl-3-methyl-2-oxopiperazine-4-carbonyl)thiophen-2-yl)-3-(2-chloro-4-fluorophenyl)urea

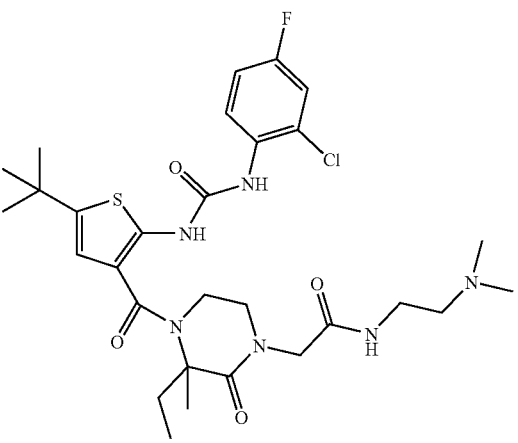

¹H NMR (400 MHz, CD₂Cl₂): δ (ppm) 10.01 (s, 1H), 8.07 (dd, J=9.0, 5.7 Hz, 1H), 7.27 (s, 1H), 7.15 (dd, J=8.3, 2.7 Hz, 1H), 7.06-7.00 (m, 1H), 6.67 (s, 1H), 6.48 (s, 1H), 4.09-3.96 (m, 3H), 3.66 (t, J=8.7 Hz, 2H), 3.47-3.29 (m, 3H), 2.76-2.65 (m, 1H), 2.47 (t, J=5.8 Hz, 2H), 2.27 (s, 6H), 2.15-2.02 (m, 1H), 1.74 (s, 3H), 1.39 (s, 9H), 0.83 (t, J=5.8 Hz, 3H).

Example 372

1-(5-tert-Butyl-3-(1-(2-(2-(dimethylamino)ethylamino)-2-oxoethyl)-3-ethyl-3-methyl-2-oxopiperazine-4-carbonyl)thiophen-2-yl)-3-(2-(trifluoromethyl)phenyl)urea

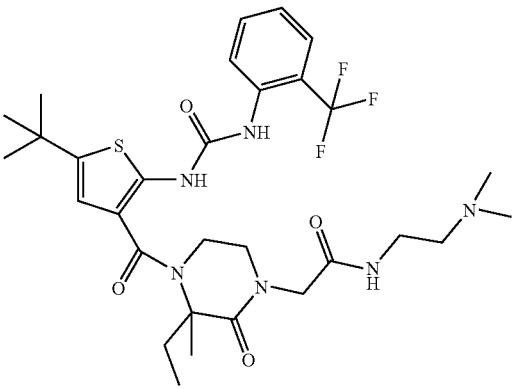

¹H NMR (400 MHz, CD₂Cl₂): δ (ppm) 7.87 (d, J=8.2 Hz, 1H), 7.66-7.56 (m, 2H), 7.30 (t, J=7.6 Hz, 1H), 6.53 (s, 1H), 6.45 (s, 1H), 4.08 (s, 2H), 4.00-3.93 (m, 1H), 3.70-3.57 (m, 2H), 3.45-3.39 (m, 1H), 3.28 (q, J=5.2 Hz, 2H), 2.75-2.65 (m, 1H), 2.37 (t, J=6.0 Hz, 2H), 2.19 (s, 6H), 2.10-2.01 (m, 1H), 1.70 (s, 3H), 1.34 (s, 9H), 0.79 (t, J=7.4 Hz, 3H).

Example 373

1-(5-tert-Butyl-3-(1-(2-(2-(dimethylamino)ethylamino)-2-oxoethyl)-3,3-dimethyl-2-oxopiperazine-4-carbonyl)-1H-pyrrol-2-yl)-3-(2,3-dichlorophenyl)urea

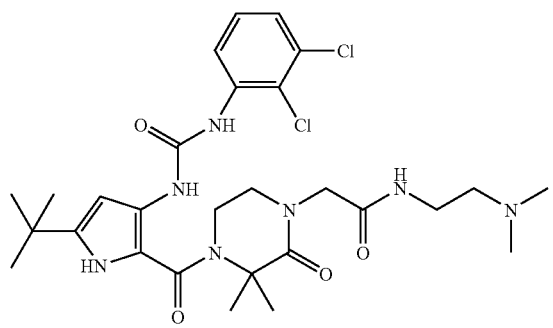

$^1$H NMR (400 MHz, CD$_3$OD): δ (ppm) 8.54 (s, 1H), 8.03 (dd, J=7.8, 2.0 Hz, 1H), 7.25-7.18 (m, 2H), 6.22 (s, 1H), 4.04 (s, 2H), 3.76 (t, J=5.1 Hz, 2H), 3.63 (s, 1H), 3.59-3.55 (m, 2H), 3.33 (t, J=6.7 Hz, 2H), 2.45 (t, J=6.7 Hz, 2H), 2.25 (s, 6H), 1.79 (s, 6H), 1.30 (s, 9H).

Example 374

Methyl 4-(2-tert-butyl-5-(3-(2,3-dichlorophenyl)ureido)thiophene-4-carbonyl)piperazine-1-carboxylate

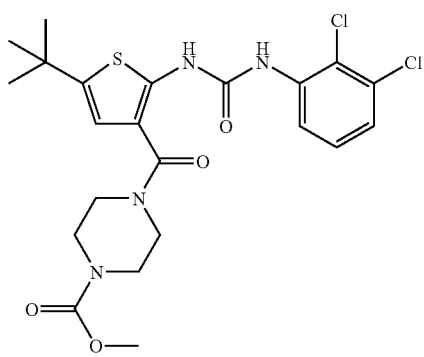

$^1$H NMR (400 MHz, CDCl$_3$): δ (ppm) 10.17 (s, 1H), 8.13-8.16 (m, 2H), 7.07-7.14 (m, 2H), 6.38 (s, 1H), 3.71 (s, 3H), 3.63-3.67 (m, 4H), 3.50-3.54 (m, 4H), 1.27 (s, 9H).

Example 375

1-(5-tert-Butyl-3-(1-(dimethylcarbamoyl)piperazine-4-carbonyl)thiophen-2-yl)-3-(2,3-dichlorophenyl)urea

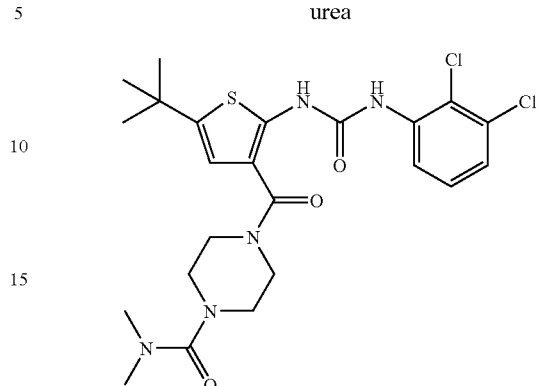

$^1$H NMR (400 MHz, CDCl$_3$): δ (ppm) 10.20 (s, 1H), 8.30 (s, 1H), 8.16 (dd, J=7.9, 1.9 Hz, 1H), 7.05-7.13 (m, 2H), 6.39 (s, 1H), 3.66-3.70 (m, 4H), 3.23-3.27 (m, 4H), 2.83 (s, 6H), 1.27 (s, 9H).

Example 376

1-(5-tert-Butyl-3-(1-(morpholine-4-carbonyl)piperazine-4-carbonyl)thiophen-2-yl)-3-(2,3-dichlorophenyl)urea

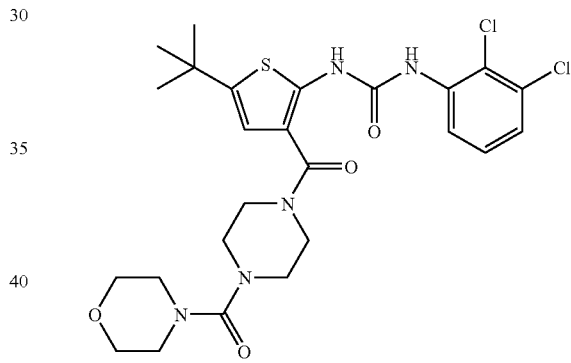

$^1$H NMR (400 MHz, methanol-d$_4$): δ (ppm) 8.02-8.07 (m, 1H), 7.08-7.15 (m, 2H), 6.41 (s, 1H), 3.62-3.65 (m, 8H), 3.23-3.28 (m, 8H), 1.28 (s, 9H).

Example 377

N-(5-tert-Butyl-3-(thiomorpholine-1,1-dioxide-4-carbonyl)thiophen-2-yl)-2-(2,3-dichlorophenyl)acetamide

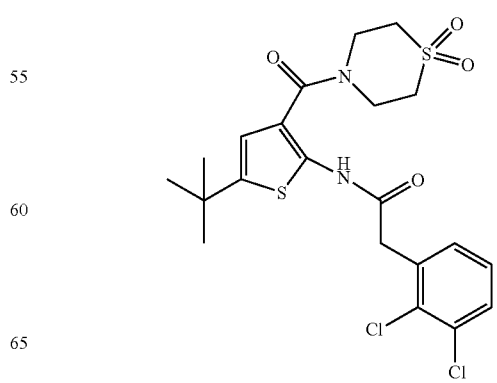

¹H NMR NMR (400 MHz, CDCl₃): δ (ppm) 10.39 (s, 1H), 7.47 (d, J=1.7 Hz, 1H), 7.45 (d, J=1.7 Hz, 1H), 7.31 (d, J=1.7 Hz, 1H), 7.29 (d, J=1.6 Hz, 1H), 6.46 (s, 1H), 4.12-4.08 (m, 4H), 3.94 (s, 2H), 3.06 (t, J=5.4 Hz, 4H), 1.33 (s, 9H).

Example 378

1-(5-tert-Butyl-3-(2,2-dimethyl-3-oxopiperazine-1-carbonyl)thiophen-2-yl)-3-(2-chloropyridin-3-yl)urea

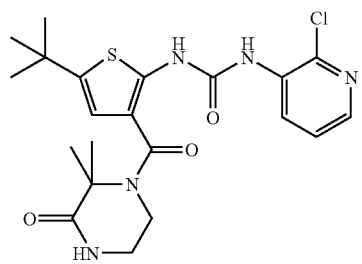

¹H NMR (400 MHz, DMSO-d₆) δ (ppm) 10.06 (s, 1H), 9.58 (s, 1H), 8.34 (dd, J=8.0, 1.2 Hz, 1H), 8.07 (dd, J=4.8, 1.2 Hz, 1H), 8.04 (bs, 1H), 7.37 (dd, J=8.0, 4.8 Hz, 1H), 6.56 (s, 1H), 3.51 (m, 2H), 1.68 (s, 6H), 1.28 (s, 9H).

Example 379

1-(5-tert-Butyl-3-(5-oxo-1,4-diazepane-1-carbonyl)thiophen-2-yl)-3-(2-chloropyridin-3-yl)urea

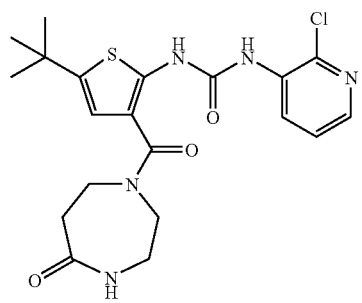

¹H NMR (400 MHz, DMSO-d₆) δ (ppm) 10.02 (s, 1H), 9.33 (s, 1H), 8.33 (dd, J=8.0, 1.2 Hz, 1H), 7.99 (dd, J=4.8, 1.2 Hz, 1H), 7.62 (m, 1H), 7.31 (dd, J=8.0, 4.8 Hz, 1H), 6.50 (s, 1H), 3.54 (m, 4H), 3.17 (m, 2H), 2.49 (m, 2H), 1.23 (s, 9H).

Example 380

1-(5-tert-Butyl-3-(1-(2-(dimethylamino)ethyl)-3,3-dimethyl-2-oxopiperazine-4-carbonyl)thiophen-2-yl)-3-(3,5-dichloropyridin-4-yl)urea

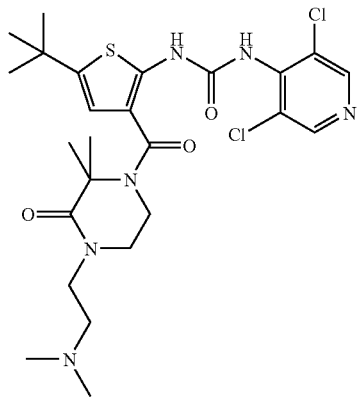

¹H NMR (400 MHz, CD₃OD) δ (ppm) 8.54 (s, 2H), 6.60 (s, 1H), 3.72 (m, 2H), 3.56 (m, 4H), 2.59 (t, J=6.8 Hz, 2H), 2.32 (s, 6H), 1.79 (s, 6H), 1.34 (s, 9H).

Example 381

1-(5-tert-Butyl-3-(1-(2-(dimethylamino)ethyl)-7-oxo-1,4-diazepane-4-carbonyl)thiophen-2-yl)-3-(3,5-dichloropyridin-4-yl)urea

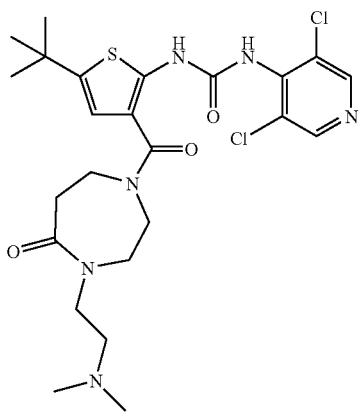

¹H NMR (400 MHz, CD₃OD) δ (ppm) 8.54 (s, 2H), 6.62 (s, 1H), 3.81 (m, 2H), 3.74 (t, J=6.0 Hz, 2H), 3.64 (m, 2H), 3.53 (t, J=6.8 Hz, 2H), 2.84 (t, J=6.0 Hz, 2H), 2.48 (t, J=6.4 Hz, 2H), 2.29 (s, 6H), 1.34 (s, 9H).

Example 382

Biological Activity of the Compounds

Human non-activated p38 kinase (MW=43 kDa) was purified according to the protocol described herein. Chemicals were purchased from Calbiochem. Fluorescence characterizations were conducted using a Cary Eclipse (Varian Analytical Instruments, Walnut Creek, Calif.). Research-grade CM5 sensor chips and coupling reagents (N-ethyl-N'-dimethylaminopropylcarbodiimide (EDC) N-hydroxysuccinimide (NHS), and 1 M ethanolamine HCl, pH 8.5) were purchased from Biacore AB (Uppsala, Sweden). The biosensor analyses were conducted using a Biacore 3000 SPR instrument. The kinetic analyses were carried on a Molecular Devices spectrophotometer (Molecular Devices Corporation, CA, USA).

Thermal Stability of Non-activated p38 kinase by Fluorescence.

Prior to the analysis, approximately 1 µM non-activated p38 kinase was mixed either with inhibitor or an equal amount of DMSO and then allowed to equilibrate for 5 min at room temperature. The reactions were carried using 25 mM sodium phosphate buffer containing 150 mM NaCl, 1.0 mM EDTA, 0.005% P-20, 5% DMSO. The intrinsic fluorescence was monitored at an absorption maximum of 280 nm and an emission maximum of 340 nm, with 5 nm width slits. Temperature dependent analyses were conducted in parallel by slowly increasing the temperature at the rate 1° C./min from 20° C. to 80° C., while monitoring the intrinsic fluorescence traces.

Biosensor Analysis.

Immobilization of Non-activated p38 Kinase. Initially, CM5 sensor chips were docked into the instrument and pre-conditioned in water at 100 µL/min by applying two consecutive 50 µL pulses of 50 mM NaOH and 1M NaCl, followed by 10 mM HCl, 0.1% SDS and water. P38 kinase surfaces were prepared by standard amine coupling via exposed primary amines on p38 kinase in the presence of saturating concentration of SB-203580 (5 µM) to preserve binding activity. Immobilizations were conducted at 25° C. in the 25 mM sodium phosphate buffer containing 150 mM NaCl, 1.0 mM EDTA, 0.005% P-20, 5% DMSO at a flow rate of 10 µL/min. Typical immobilization levels ranged from 2000-5000 RU. Nonderivatized flow cells served as reference surfaces.

High-resolution p38 kinase/Inhibitor interaction studies. Interaction analyses of inhibitor binding to non-activated p38 kinase surfaces were performed at 25° C. Prior to each binding study, the instrument was primed five times with the immobilization buffer. All assays were conducted at a flow rate of 100 µL/min and a typical data collection rate of either 2.5 or 5.0 Hz. All experiments were repeated 3-5 times on newly immobilized p38 kinase surfaces.

ATPase Assay. The ATPase activity of activated p38 was characterized using the EnzCheck phosphate assay kit (Molecular Probe). The phosphate that was generated by the hydrolysis reaction was quantitated using the nucleoside phosphorylation reaction. The reactions were carried out at 30° C. in 0.1 M Hepes buffer, pH 7.6, containing 10 mM $MgCl_2$, 10% Glycerol, 1 unit/mL nucleoside phosphorylase and 200 µM nucleoside substrate (MESG). Unless otherwise indicated, the p38 concentrations were maintained at 200 nM. The kinetic analyses were conducted in a 96-well plate on a Molecular Devices spectrophotometer.

Protein Kinase Assay. The protein kinase activity of p38 was determined by measuring the incorporation of $^{33}P$ from $\gamma$-[$^{33}P$]ATP into the GST-ATF-2 substrate, amino acids 19-96 (Upstate, NY USA). The reactions were carried out in a final volume of 50 µL of 24 mM Tris-HCl buffer, pH 7.5, containing 13 mM $MgCl_2$, 12% Glycerol, 2% DMSO, 2 mM DTT, 2.5 Ci of $\gamma$-[$^{33}P$]ATP (1000 Ci/mmol; 1 Ci=37 GBq) (AmershamBiosciense), 10 M ATP (AmershamBiosciense), and 2 M GST-ATF2. Compounds were preincubated with 10 nM p38 for 20 min at 30° C.; the reactions were initiated by the addition of GST-ATF2 and ATP and incubated for 70 min at 30° C. before being stopped by the addition of 10 µL of 600 mM phosphoric acid. The phosphorylated substrate was captured on phosphocellulose 96-well plate (Millipore MAPH-NOB 10), washed with 100 mM phosphoric acid, and counted in a BeckmenCoulter LS6500 liquid scintillation counter.

Activation Kinetics. The activation of p38 by upstream kinase MKK6 (Sigma) was characterized using ELISA kit p38MAPK [pTpY180/182] (Biosource International). The reactions were carried out at 25° C. in a final volume of 50 µL of 28 mM Tris-HCl buffer, pH 7.5, containing 15.3 mM $MgCl_2$, 14% glycerol (w/v), and 2 mM DTT. Compounds were preincubated for 40 min with 120 nM of p38 kinase. Reactions were initiated by the addition of 3 nM MKK6 and 10 µM ATP and incubated for 25 min before being stopped by addition of 2 µL of 0.5 M EDTA. The reactions were transferred into 96-well plate and a capture ELISA was performed as described by the manufacturer.

Lipopolysaccharide (LPS) mediated TNFα secretion. The human monocytic cell line THP-1 cells (ATCC, TIB-202) were used to assess the effects of p38 inhibitors on LPS-mediated TNFα secretion. THP-1 cells were grown in suspension and maintained in RPMI 1640 media containing 10% fetal bovine serum and 2 mM glutamine. HeLa cells (human cervical cells; ATCC#: CCL-2) were used to assess toxicity potential of selected p38 inhibitors. These cells were grown and maintained in EMEM media containing 10% fetal bovine serum.

Test Compound Evaluation. Cells were plated at a density of $0.5-1 \times 10^5$ cells/well in a volume of 200 µL in a 96 well plate format. Test compounds were diluted in cell culture media and added to the culture wells at concentrations ranging from 0.1 to 60 µM. Twenty minutes after test compound addition, LPS (2 ng/mL; Serotype 055:B5; SigmaAldrich) was added to the well for 2 hrs. After LPS exposure, 100 µL of culture media were assessed for TNFα levels by a commercially available ELISA (BD Biosciences; OptEIA Human TNF-α ELISA kit II;). Test compounds were evaluated for their ability to inhibit LPS-mediated TNFα secretion. The amount of TNFα secreted into the culture media in the presence of test compounds was compared to the amount secreted in the absence of compound. Data are expressed as $IC_{50}$ values. $IC_{50}$ values were determined by non-linear regression analysis using Graphpad PRISM graphing and curve fitting program.

Cell Viability Assays. The effects of the test compounds on THP-1 cell viability were evaluated at the end of the incubation period. The cells remaining in the culture wells were assessed for cell viability using a WST-1 cell viability assay (Quick Cell Proliferation Assay Kit: Biovision). WST-1 solution (10 µL) was added to the remaining cells and incubated at 37° C. for 30 to 120 minutes. Absorbance was read at 450 nm. Increased absorbance was proportional to cell viability. Cell viability was determined by comparing viability in treated cells were compared to cell viability in untreated cells. $LD_{50}$ values were determined by non-linear regression analysis using Graphpad PRISM graphing and curve fitting program.

HeLa Cell Viability. In some cases, HeLa cell viability was assessed as a determinant of general toxicity potential of test compounds. HeLa cells were plated in 96-well format at a density of $2-5 \times 10^4$ cells/well in a volume of 100 µL in EMEM media containing 10% fetal bovine serum. After 24 hours, test compounds were added to the culture media at concentrations ranging from 0.1 to 60 µM. Twenty-four hours after compound addition, cells were assessed for cell viability using the WST-1 cell viability assay (see above). Cell viability was determined by comparing viability in treated cells were compared to cell viability in untreated cells. $LD_{50}$ values were determined by non-linear regression analysis using Graphpad PRISM graphing and curve fitting program.

TABLE 1

| Example No. | Protein Kinase (% Inhibition at 10 μM) | |
|---|---|---|
| 1 | 76-100 | |
| 2 | 76-100 | |
| 3 | 76-100 | |
| 4 | 76-100 | |
| 5 | 76-100 | |
| 6 | 76-100 | |
| 7 | 51-75 | |
| 8 | 76-100 | |
| 9 | 51-75 | |
| 10 | 76-100 | |
| 11 | 76-100 | |
| 12 | 76-100 | |
| 13 | 26-50 | |
| 14 | 0-25 | |
| 15 | 51-75 | |
| 16 | 26-50 | |
| 17 | 76-100 | |
| 18 | 51-75 | |
| 19 | 51-75 | |
| 20 | 0-25 | |
| 21 | 76-100 | |
| 22 | 26-50 | |
| 23 | 26-50 | |
| 24 | 76-100 | |
| 25 | 76-100 | |
| 26 | 51-75 | |
| 27 | 51-76 | (0.5 μM) |
| 28 | 0-25 | |
| 29 | 0-25 | |
| 30 | 51-75 | |
| 31 | 51-75 | |
| 32 | 26-50 | |
| 33 | 0-25 | |
| 34 | 76-100 | |
| 35 | 51-75 | |
| 36 | 76-100 | |
| 37 | 51-75 | (3 μM) |
| 38 | 76-100 | (3 μM) |
| 39 | 76-100 | (3 μM) |
| 40 | 76-100 | (3 μM) |
| 41 | 76-100 | (3 μM) |
| 42 | 76-100 | (3 μM) |
| 43 | 76-100 | (3 μM) |
| 44 | 76-100 | |

TABLE 2

| Example No. | Protein Kinase (% Inhibition at 3 μM) |
|---|---|
| 45 | 76-100 |
| 46 | 76-100 |
| 47 | 76-100 |
| 48 | 76-100 |
| 49 | 51-75 |
| 50 | 76-100 |
| 51 | 76-100 |
| 52 | 76-100 |
| 53 | 76-100 |
| 54 | 76-100 |
| 55 | 76-100 |
| 56 | 76-100 |
| 57 | 76-100 |
| 58 | 76-100 |
| 59 | 76-100 |
| 60 | 76-100 |
| 61 | 76-100 |
| 62 | 76-100 |
| 63 | 76-100 |

TABLE 2-continued

| Example No. | Protein Kinase (% Inhibition at 3 μM) |
|---|---|
| 64 | 51-75 |
| 65 | 26-50 |
| 66 | 0-25 |
| 67 | 76-100 |
| 68 | 76-100 |
| 69 | 0-25 |
| 70 | 26-50 |
| 71 | 76-100 |
| 72 | 76-100 |
| 73 | 76-100 |
| 74 | 76-100 |
| 75 | 76-100 |
| 76 | 76-100 |
| 77 | 26-50 |
| 78 | 76-100 |
| 79 | 76-100 |
| 80 | 76-100 |
| 81 | 0-25 |
| 82 | 76-100 |
| 83 | 76-100 |
| 84 | 76-100 |
| 85 | 26-50 |
| 86 | 76-100 |
| 87 | 76-100 |
| 88 | 76-100 |
| 89 | 76-100 |
| 90 | 76-100 |
| 91 | 76-100 |
| 92 | 76-100 |
| 93 | 76-100 |
| 94 | 76-100 |
| 95 | 76-100 |
| 96 | 76-100 |

The compounds of Examples 98, 99, 101-103, 105-108, 112-119, 121, and 123-129 displayed protein kinase inhibition of 76-100% when tested at 3 μM according to the procedure described above. The compounds of Examples 97, 111, and 122 displayed protein kinase inhibition of 51-75% when tested according to the same procedure. The compounds of Examples 100, 104, 109 and 110 displayed protein kinase inhibition of 26-50% when tested according to the same procedure. The compound of Example 120 displayed protein kinase inhibition of 0-25% when tested according to the same procedure. The compounds of Examples 130-136 displayed protein kinase inhibition of 76-100% when tested according to the same procedure at 0.5 μM.

Additional exemplified compounds showed kinase activity having an $IC_{50}$ of less then 5 μM.

Having now fully described this invention, it will be understood by those of ordinary skill in the art that the same can be performed within a wide and equivalent range of conditions, formulations and other parameters without affecting the scope of the invention or any embodiment thereof. All patents and publications cited herein are fully incorporated by reference herein in their entirety.

What is claimed is:

1. A compound of Formula I:

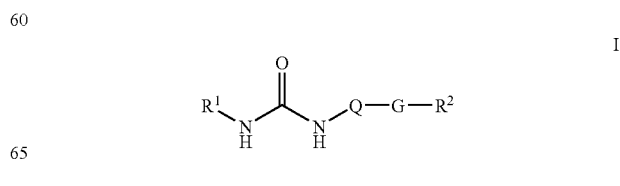

I or a pharmaceutically acceptable salt thereof, wherein $R^1$ is an aryl group, which is optionally substituted with one or more $R^3$ groups;

Q is thienyl which is substituted with one or more of $R^4$ or $R^5$;

G is —C(O)—;

$R^2$ is

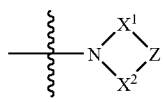

—wherein $X^1$ and $X^2$ are independently $(CR^6R^7)_n$, wherein n is independently at each occurrence 1, 2, or 3; and Z is —$NR^8$—S(O)$_2$—, —$NR^8$C(O)—, —S—, —S(O)—, —S(O)$_2$—, or —C(O)—; or $R^2$ is heteroarylamino, or heteroarylalkylamino, each of which is optionally substituted with 1, 2, or 3 substituents selected from $R^6$;

each $R^3$ is independently $C_{1-4}$ alkyl, halogen, hydroxy, alkoxy, amino, $C_{1-4}$ alkylamino, di($C_{1-4}$)alkylamino, optionally substituted phenyl, ar($C_{1-3}$)alkyl, optionally substituted phenoxy, $C_{1-4}$ haloalkyl, $CONR^aR^b$, or $COOR^a$, wherein $R^a$ and $R^b$ are independently H or $C_{1-4}$ alkyl;

each $R^4$ is independently $C_{3-10}$ alkyl or $C_{3-10}$ haloalkyl, each of which is optionally substituted with one to three phenyl groups; $C_{3-7}$ cycloalkyl, which is optionally substituted with one or more $C_{1-3}$ alkyl, halogen, hydroxy, oxo, or thioketo; optionally substituted $C_{3-10}$ cycloheteroalkyl; $C_{3-10}$ branched alkenyl which is optionally partially or fully halogenated, and which is optionally substituted with one to three $C_{1-5}$ alkyl or a phenyl group; $C_{5-7}$ cycloalkenyl optionally substituted with one to three $C_{1-3}$ alkyl groups; cyano; or $C_{1-4}$ alkoxycarbonyl;

each $R^5$ is independently hydrogen, alkyl, halogen, hydroxy, alkoxy, amino, alkylamino, dialkylamino, phenyl, or substituted phenyl;

each $R^6$ and $R^7$ are independently hydrogen, $C_{1-4}$ alkyl, halogen, amino, $C_{1-4}$ alkylamino, $C_{1-4}$ hydroxyalkyl, NH—CO—($C_{1-4}$)alkyl, —COO—($C_{1-4}$)alkyl, —CONH$_2$, —CONH—($C_{1-4}$)alkyl, —CH$_2$NH$_2$, —CH$_2$NH—($C_{1-4}$)alkyl, CH$_2$NH—CO—($C_{1-4}$)alkyl, CH$_2$COOH, CH$_2$COO—($C_{1-4}$)alkyl, —$C_{1-4}$alkyl ($C_{6-10}$) aryl, or —$C_{1-4}$alkyl(5-6 membered)heteroaryl;

or $R^6$ and $R^7$ together form a $C_{3-5}$ cycloalkyl group or an oxo group; and $R^8$ is hydrogen, $C_{1-6}$ alkyl, $C_{2-4}$ alkenyl, $C_{2-4}$ alkynyl, optionally substituted with one or more of hydroxyl, halogen, cyano, amino, mono($C_{1-6}$)alkylamino, di($C_{1-6}$) alkylamino, $C_{1-6}$ alkoxy, aminocarbonyl, $C_{1-6}$ alkylaminocarbonyl, $C_{6-10}$ arylaminocarbonyl, aralkylaminocarbonyl, $C_{1-6}$ alkylcarbonylamino, arylcarbonylamino, aralkylcarbonylamino, $C_{1-6}$ cycloalkyl, 3-7 membered cycloheteroalkyl, hydroxy($C_{1-6}$)alkyl, nitro, aminoalkyl, monoalkylaminoalkyl, dialkylaminoalkyl, formylamino, ($C_{1-6}$)alkylcarbonylamino, carboxy, ($C_{1-6}$) alkoxycarbonyl, aminocarbonyl, mono($C_{1-6}$) alkylaminocarbonyl, di($C_{1-6}$)alkylaminocarbonyl, carboxy($C_{1-6}$)alkyl, ($C_{1-6}$)alkoxycarbonyl($C_{1-6}$)alkyl, aminocarbonyl($C_{1-6}$)alkyl, mono($C_{1-6}$)alkylaminocarbonyl ($C_{1-6}$)alkyl, di($C_{1-6}$)alkylaminocarbonylalkyl ($C_{1-6}$), sulfonylamino, ($C_{1-6}$)alkylsulfonylamino, aminosulfonyl, mono($C_{1-6}$)alkylaminosulfonyl, (di($C_{1-6}$) alkylaminosulfonyl, ($C_{1-6}$)alkoxycarbonylamino, aminocarbonylamino, mono($C_{1-6}$) alkylaminocarbonylamino, di($C_{1-6}$) alkylaminocarbonylamino, $C_{6-10}$ aryl, 5-10 membered heteroaryl, N-hydroxyaminocarbonyl, N-alkoxyaminocarbonyl, and N-alkoxy-N-alkylaminocarbonyl.

2. The compound according to claim 1, wherein $R^1$ is selected from the group consisting of phenyl, and naphthyl, each optionally substituted with one or more $R^3$ groups.

3. The compound according to claim 1, wherein Q is substituted with a straight or branched chain $C_{1-5}$ alkyl group.

4. The compound according to claim 1, wherein $R^2$ is

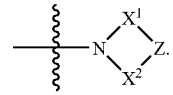

5. The compound according to claim 1, wherein $R^2$ is selected from the group consisting of thiomorpholin-4-yl, 1-oxothiomorpholin-4-yl, 1,1-dioxothiomorpholin-4-yl, 3-oxopiperazin-1-yl, 5-oxo-1,4-diazepan-1-yl, and 1,1-dioxo[1,2,5]thiadiazepan-5-yl.

6. The compound according to claim 1, wherein $R^2$ is selected from the group consisting of thiomorpholinyl, oxothiomorpholinyl, dioxothiomorpholinyl, oxopiperazinyl, oxodiazepanyl, and dioxothiadiazepanyl.

7. The compound according to claim 1, wherein $X^1$ and $X^2$ are methylene, ethylene, or propylene.

8. The compound according to claim 1, wherein $R^1$ is phenyl substituted with one or more halogens.

9. The compound according to claim 1, wherein $R^1$ is selected from the group consisting of 4-chlorophenyl, 4-phenoxyphenyl, 2,3-dichlorophenyl, 2,3-dichloro-4-fluorophenyl, 2-chloro-3,4-difluorophenyl, 2-chloro-3-fluorophenyl, 1-naphthyl, and 2-naphthyl.

10. The compound according to claim 1, wherein said thienyl is substituted at the 5-position with a straight or branched chain $C_{1-5}$ alkyl group.

11. The compound according to claim 1, wherein $R^1$ is phenyl optionally substituted with 1-3 of $C_{1-4}$ alkyl, halogen, amino, hydroxy, $C_{1-4}$ haloalkyl, and $C_{1-4}$ alkoxy.

12. A compound selected from the group consisting of
1-[5-tert-butyl-3-(1,1-dioxo-1λ$^6$-thiomorpholine-4-carbonyl)thiophen-2-yl]-3-(4-chlorophenyl)urea;
1-[5-tert-butyl-3-(1,1-dioxo-1λ$^6$-thiomorpholine-4-carbonyl)thiophen-2-yl]-3-naphthalen-1-ylurea;
1-[5-tert-butyl-3-(1,1-dioxo-1λ$^6$-thiomorpholine-4-carbonyl)thiophen-2-yl]-3-naphthalen-2-ylurea;
1-[5-tert-butyl-2-(1,1-dioxo-1λ$^6$-thiomorpholine-4-carbonyl)thiophen-3-yl]-3-(4-chlorophenyl)urea;
1-[5-tert-butyl-2-(1,1-dioxo-1λ$^6$-thiomorpholine-4-carbonyl)thiophen-3-yl]-3-naphthalen-1-ylurea;
1-[5-tert-butyl-2-(1,1-dioxo-1λ$^6$-thiomorpholine-4-carbonyl)thiophen-3-yl]-3-naphthalen-2-ylurea;
1-[5-tert-butyl-3-(thiomorpholine-4-carbonyl)thiophen-2-yl]-3-naphthalen-1-ylurea;

1-[5-tert-butyl-3-(1-oxo-$\lambda^4$-thiomorpholine-4-carbonyl)thiophen-2-yl]-3-naphthalen-1-ylurea;

1-[5-tert-butyl-3-(1,1-dioxo-1$\lambda^6$-thiomorpholine-4-carbonyl)thiophen-2-yl]-3-(4-phenoxyphenyl)urea;

1-[5-tert-butyl-3-(1,1-dioxo-1$\lambda^6$-thiomorpholine-4-carbonyl)thiophen-2-yl]-3-(4-hydroxynaphthalen-1-yl)urea;

1-[5-tert-butyl-3-(3-oxopiperazine-1-carbonyl)thiophen-2-yl]-3-naphthalen-1-ylurea;

1-[5-tert-butyl-3-(5-oxo[1,4]diazepane-1-carbonyl)thiophen-2-yl]-3-naphthalen-1-yl-urea;

1-[5-tert-butyl-3-(1,1-dioxo-1$\lambda^6$-[1,2,5]thiadiazepane-5-carbonyl)-thiophen-2-yl]-3-naphthalen-1-ylurea;

1-[5-tert-butyl-3-(1,1-dioxo-1$\lambda^6$-[1,2,5]thiadiazepane-5-carbonyl)-thiophen-2-yl]-3-naphthalen-2-ylurea;

1-[5-tert-butyl-3-(1,1-dioxo-1$\lambda^6$-[1,2,5]thiadiazepane-5-carbonyl)-thiophen-2-yl]-3-(4-chlorophenyl)urea;

1-(4-bromonaphthalen-1-yl)-3-[5-tert-butyl-3-(1,1-dioxo-1$\lambda^6$-thiomorpholine-4-carbonyl)thiophen-2-yl]urea;

1-[5-tert-butyl-3-(1,1-dioxo-1$\lambda^6$-thiomorpholine-4-carbonyl)thiophen-2-yl]-3-(4-chloronaphthalen-1-yl)urea;

1-[5-tert-butyl-3-(5-oxo[1,4]diazepane-1-carbonyl)thiophen-2-yl]-3-naphthalen-2-ylurea;

1-[5-tert-butyl-3-(5-oxo-[1,4]diazepane-1-carbonyl)thiophen-2-yl]-3-(4-chlorophenyl)urea;

1-[5-tert-butyl-3-(3-oxopiperazine-1-carbonyl)thiophen-2-yl]-3-(4-chlorophenyl)urea;

1-[5-tert-butyl-3-(3-oxopiperazine-1-carbonyl)thiophen-2-yl]-3-(2-naphthyl)urea;

1-[5-tert-butyl-2-(5-oxo-[1,4]diazepane-1-carbonyl)thiophen-3-yl]-3-naphthalen-1-ylurea;

1-[5-tert-butyl-2-(1,1-dioxo-1$\lambda^6$-[1,2,5]thiadiazepane-5-carbonyl)thiophen-3-yl]-3-naphthalen-1-ylurea;

1-[5-tert-butyl-2-(3-oxopiperazine-1-carbonyl)thiophen-3-yl]-3-naphthalen-1-ylurea;

1-[5-tert-butyl-3-(5-oxo-[1,4]diazepane-1-carbonyl)thiophen-2-yl]-3-(2,3-dichlorophenyl)urea;

1-[5-tert-butyl-3-(5-oxo-[1,4]diazepane-1-carbonyl)thiophen-2-yl]-3-(3-chlorophenyl)urea;

1-[5-tert-butyl-3-(1,1-dioxo-1$\lambda^6$-thiomorpholine-4-carbonyl)thiophen-2-yl]-3-(2,3-dichlorophenyl)urea;

1-[5-tert-butyl-3-(1,1-dioxo-1$\lambda^6$-thiomorpholine-4-carbonyl)thiophen-2-yl]-3-(3-chlorophenyl)urea;

1-[5-tert-butyl-3-(1,1-dioxo-1$\lambda^6$-thiomorpholine-4-carbonyl)thiophen-2-yl]-3-(3-chloro-4-methoxyphenyl)urea;

1-[5-tert-butyl-3-(1,1-dioxo-1$\lambda^6$-thiomorpholine-4-carbonyl)thiophen-2-yl]-3-(3,4-dichlorophenyl)urea;

1-[5-tert-butyl-3-(1,1-dioxo-1$\lambda^6$-thiomorpholine-4-carbonyl)thiophen-2-yl]-3-(3-tolyl)urea;

1-[5-tert-butyl-3-(1,1-dioxo-1$\lambda^6$-thiomorpholine-4-carbonyl)thiophen-2-yl]-3-(3,5-dichlorophenyl)urea;

1-(3-(pyridin-3-ylcarbamoyl)-5-tert-butylthiophen-2-yl)-3-(4-chloro-phenyl)urea;

1-[5-tert-butyl-3-(2-methyl-3-oxopiperazine-1-carbonyl)thiophen-2-yl]-3-(4-chlorophenyl)urea;

1-[5-tert-butyl-3-(2-methyl-3-oxopiperazine-1-carbonyl)thiophen-2-yl]-3-naphthalen-1-ylurea;

{1-[5-tert-butyl-2-(3-naphthalen-1-ylureido)thiophene-3-carbonyl]-3-oxopiperazin-2-yl}acetic acid methyl ester;

1-[5-tert-butyl-3-(1,1-dioxo-1$\lambda^6$-[1,2,5]thiadiazepane-5-carbonyl)-thiophen-2-yl]-3-(3-chloro-4-methoxyphenyl)urea;

1-[5-tert-butyl-3-(1,1-dioxo-1$\lambda^6$-[1,2,5]thiadiazepane-5-carbonyl)-thiophen-2-yl]-3-(3,4-dichlorophenyl)urea;

1-[5-tert-butyl-3-(1,1-dioxo-1$\lambda^6$-[1,2,5]thiadiazepane-5-carbonyl)-thiophen-2-yl]-3-(3-tolyl)urea;

1-[5-tert-butyl-3-(1,1-dioxo-1$\lambda^6$-[1,2,5]thiadiazepane-5-carbonyl)-thiophen-2-yl]-3-(3,5-dichlorophenyl)urea;

1-[5-tert-butyl-3-(5-oxo-[1,4]diazepane-1-carbonyl)thiophen-2-yl]-3-(3-chloro-4-methoxyphenyl)urea;

; and

1-[5-tert-butyl-2-(5-oxo-[1,4]diazepane-1-carbonyl)thiophen-3-yl]-3-(3,4-dichloro-phenyl)urea.

13. The compound according to claim 1, wherein $R^4$ is $C_{3-5}$ alkyl and $R^5$ is hydrogen.

14. The compound according to claim 1, wherein $R^4$ is tert-butyl and $R^5$ is hydrogen.

15. The compound according to claim 1, wherein Q is substituted at position 5 with a $C_{1-5}$ alkyl.

16. The compound according to claim 1, wherein Q is substituted at position 5 with a tert-butyl.

17. The compound according to claim 1, wherein the urea is bonded at position 2 of Q and G is bonded at position 3 of Q.

18. The compound according to claim 1, wherein the urea is bonded at position 3 of Q and G is bonded at position 2 of Q.

19. A compound which is 1-(5-tert-butyl-(2-(1-(2-(2-(dimethylamino)ethylamino)-2-oxoethyl)-3,3-dimethyl-2-oxopiperazine-4-carbonyl)thiophen-3-yl)-3-(2,3-dichlorophenyl)urea, or a pharmaceutically acceptable salt thereof.

* * * * *